US011793812B2

(12) United States Patent
Johnson et al.

(10) Patent No.: US 11,793,812 B2
(45) Date of Patent: Oct. 24, 2023

(54) METHODS OF TREATING ENDOMETRIOSIS

(71) Applicants: Sumitomo Pharma Switzerland GmbH, Basel (CH); Takeda Pharmaceutical Company Limited, Osaka (JP)

(72) Inventors: Brendan Mark Johnson, Chapel Hill, NC (US); Lynn Seely, San Mateo, CA (US); Paul N. Mudd, Jr., Cary, NC (US); Susan Wollowitz, Lafayette, CA (US); Mark Hibberd, Hampshire (GB); Masataka Tanimoto, Osaka (JP); Vijaykumar Reddy Rajasekhar, Apple Valley, CA (US); Mayukh Vasant Sukhatme, Mamaroneck, NY (US)

(73) Assignees: Sumitomo Pharma Switzerland GmbH, Basel (CH); Takeda Pharmaceutical Company Limited, Osaka (JP)

( * ) Notice: Subject to any disclaimer, the term of this patent is extended or adjusted under 35 U.S.C. 154(b) by 216 days.

(21) Appl. No.: 17/317,769

(22) Filed: May 11, 2021

(65) Prior Publication Data
US 2021/0401841 A1 Dec. 30, 2021

Related U.S. Application Data

(60) Division of application No. 16/370,299, filed on Mar. 29, 2019, now Pat. No. 11,033,551, which is a continuation of application No. PCT/EP2017/074907, filed on Sep. 29, 2017.

(60) Provisional application No. 62/528,409, filed on Jul. 3, 2017, provisional application No. 62/492,839, filed on May 1, 2017, provisional application No. 62/402,034, filed on Sep. 30, 2016, provisional application No. 62/402,055, filed on Sep. 30, 2016, provisional application No. 62/402,150, filed on Sep. 30, 2016.

(51) Int. Cl.
*A61K 31/519* (2006.01)
*A61K 31/565* (2006.01)
*A61K 31/57* (2006.01)
*A61P 5/00* (2006.01)
*A61P 15/00* (2006.01)
*A61K 31/513* (2006.01)
*A61K 9/00* (2006.01)

(52) U.S. Cl.
CPC .......... *A61K 31/519* (2013.01); *A61K 31/513* (2013.01); *A61P 15/00* (2018.01); *A61K 9/0053* (2013.01); *A61K 31/565* (2013.01); *A61K 31/57* (2013.01)

(58) Field of Classification Search
CPC .... A61K 31/519; A61K 31/565; A61K 31/57; A61P 15/00
See application file for complete search history.

(56) References Cited

U.S. PATENT DOCUMENTS

| | | | |
|---|---|---|---|
| 6,265,393 B1* | 7/2001 | Heinrichs | A61K 45/06 514/800 |
| 6,297,379 B1 | 10/2001 | Furuya et al. | |
| 6,340,686 B1 | 1/2002 | Furuya et al. | |
| 6,849,738 B2 | 2/2005 | Fukuoka et al. | |
| 7,056,927 B2 | 6/2006 | Guo et al. | |
| 7,176,211 B2 | 2/2007 | Guo et al. | |
| 7,300,935 B2 | 11/2007 | Cho et al. | |
| 7,419,983 B2 | 9/2008 | Guo et al. | |
| 7,569,570 B2 | 8/2009 | Furuya et al. | |
| 8,058,280 B2 | 11/2011 | Cho et al. | |
| 8,735,401 B2 | 5/2014 | Cho et al. | |
| 8,765,948 B2 | 7/2014 | Gallagher et al. | |
| 9,346,822 B2 | 5/2016 | Cho et al. | |

(Continued)

FOREIGN PATENT DOCUMENTS

| | | |
|---|---|---|
| EC | SP-96-1635 A | 6/1997 |
| EC | SP-97-1998 A | 4/1998 |

(Continued)

OTHER PUBLICATIONS

Bulun et al. Endocrine reviews 2019, 40, 1048-1079.*
Becker, C.M. et al. (2017). "Revaluating response and failure of medical treatment of endometriosis: A systemic review," Fertility and Sterility 108:125-136.
Johnson, N.P. et al. (2013). "Consensus on current management of endometriosis," Human Reproduction 28:1552-1568.
Johnson, N.P. et al. (2017). "World endometriosis society consensus on the classification of endometriosis," Human Reproduction 32:315-324.

(Continued)

*Primary Examiner* — Irina Neagu
(74) *Attorney, Agent, or Firm* — Cooley LLP

(57) ABSTRACT

Methods for treating uterine fibroids, endometriosis, adenomyosis, or heavy menstrual bleeding in a subject, which include administering to the subject from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg per day of a hormone replacement medicament. The present disclosure has methods for reducing menstrual bleeding in a subject, reducing bone mineral density loss in a subject caused by administering a GnRH antagonist to the subject, suppressing sex hormones in a subject, reducing vasomotor symptoms or hot flashes in a subject, and reducing symptoms of decreased libido in a subject having uterine fibroids, endometriosis, or adenomyosis. Further provided are methods of maintaining blood glucose profile, maintaining lipid profile, and/or maintaining bone mineral density in a pre-menopausal woman being treated for one or more conditions or symptoms of endometriosis, adenomyosis, uterine fibroids, or heavy menstrual bleeding; and methods of contraception and treating infertility.

4 Claims, 224 Drawing Sheets

(56) References Cited

U.S. PATENT DOCUMENTS

| | | |
|---|---|---|
| 9,382,214 B2 | 7/2016 | Gallagher et al. |
| 9,422,310 B2 | 8/2016 | Beaton et al. |
| 9,427,418 B2 | 8/2016 | Dalton et al. |
| 9,624,161 B2 | 4/2017 | Dalton et al. |
| 9,758,528 B2 | 9/2017 | Fukuoka et al. |
| 9,949,974 B2 | 4/2018 | Goss et al. |
| 10,150,778 B2 | 12/2018 | Miwa |
| 10,350,170 B2 | 7/2019 | Yamane et al. |
| 10,449,191 B2 | 10/2019 | Rajasekhar et al. |
| 10,464,945 B2 | 11/2019 | Miwa |
| 10,544,160 B2 | 1/2020 | Miwa |
| 10,786,501 B2 | 9/2020 | Rajasekhar et al. |
| 11,033,551 B2 | 6/2021 | Johnson |
| 11,053,257 B2 | 7/2021 | Miwa |
| 11,583,526 B2 | 2/2023 | Rajasekhar et al. |
| 2006/0160829 A1 | 7/2006 | Cho et al. |
| 2008/0108623 A1 | 5/2008 | Cho et al. |
| 2009/0048273 A1 | 2/2009 | Furuya et al. |
| 2010/0331520 A1 | 12/2010 | Asami et al. |
| 2011/0172249 A1 | 7/2011 | Kamikawa et al. |
| 2014/0288031 A1 | 9/2014 | Chwalisz et al. |
| 2017/0320836 A1 | 11/2017 | Gallagher et al. |
| 2020/0000730 A1 | 1/2020 | Yamane et al. |
| 2020/0138819 A1 | 5/2020 | Loumaye et al. |
| 2021/0205303 A1 | 7/2021 | Rajasekhar et al. |
| 2022/0135585 A1 | 5/2022 | Miwa |
| 2022/0204525 A1 | 6/2022 | Fukuoka et al. |
| 2022/0370462 A1 | 11/2022 | Johnson et al. |
| 2022/0372044 A1 | 11/2022 | Jagusch et al. |
| 2022/0396582 A1 | 12/2022 | Brandl et al. |
| 2022/0401443 A1 | 12/2022 | Rajasekhar et al. |
| 2023/0165800 A1 | 6/2023 | Alonzo et al. |

FOREIGN PATENT DOCUMENTS

| | | |
|---|---|---|
| EC | SP-06-6999 A | 12/2006 |
| EP | 0 748 190 A1 | 12/1996 |
| EP | 1 066 041 A1 | 1/2001 |
| JP | 2012-077020 A | 4/2012 |
| WO | WO-2004/067535 A1 | 8/2004 |
| WO | WO-2005/105103 A2 | 11/2005 |
| WO | WO-2005/105103 A3 | 11/2005 |
| WO | WO-2011/156908 A1 | 12/2011 |
| WO | WO-2014/051164 | 4/2014 |
| WO | WO-2014/143669 A1 | 9/2014 |
| WO | WO-2018/060463 | 4/2018 |
| WO | WO-2018/060501 A2 | 4/2018 |
| WO | WO-2018/060501 A3 | 4/2018 |
| WO | WO-2021/239917 A1 | 12/2021 |
| WO | WO-2022/101303 A1 | 5/2022 |
| WO | WO-2023/066941 A1 | 4/2023 |

OTHER PUBLICATIONS

Kuznetsov, L. et al. (2017). "Diagnosis and management of endometriosis: Summary of NICE guidance," BMJ 358:33935.

Batzer, F.R. (2006). "GnRH agonist and antagonist: Options for endometriosis pain treatment," Thomas Jefferson University, Department of Obstetrics and Gynecology Faculty Papers, pp. 1-20.

ClinicalTrials.gov (2016). History of Changes for Study NCT02655237, first posted on Jan. 13, 2016, 14 total pages.

ClinicalTrials.gov (2016). History of Changes for Study NCT02655224, first posted on Jan. 13, 2016, 12 total pages.

ClinicalTrials.gov (2017). History of Changes for Study NCT03204318, last update submitted Jun. 28, 2017, and posted on Jul. 2, 2017, 10 total pages.

ClinicalTrials.gov (2017). History of Changes for Study NCT03204331, last update submitted Jun. 28, 2017, and posted on Jul. 2, 2017, 8 total pages.

Form S-1 Registration Statement under the Securities Act of 1933, Myovant Sciences Ltd., Sep. 30, 2016, pp. 1-209, filing details located at https://www.sec.gov/Archives/edgar/data/1679082/000119312516727309/0001193125-16-727309-index.htm, 209 total pages.

Gonzales, M. et al. (2012). "Patients with adenomyosis are more likely to have deep endometriosis," Gynecol. Surg. 9:259-264.

Lukes et al., "Pharmacokinetics, pharmacodynamics, and safety of relugolix, a potent oral once-daily gonadotropin-releasing hormone (GnRH) receptor antagonist, as monotherapy and in combination with estradiol/norethindrone acetate add-back therapy," Human Reproduction 32: i267-i268, 2017 (abstr).

Myovant Sciences (2017). Press Release: "Myovant Sciences Announces Presentation of Positive Phase 2 Data for Relugolix in Women with Heavy Menstrual Bleeding and Uterine Fibroids at the Annual Meeting of the American Congress of Obstetricians and Gynecologists," 2 total pages.

Opposition filed by Sandoz AG on Dec. 15, 2022, against EP Application No. 17 823 018.1, Myovant Sciences GmbH et al., 42 total pages.

PCT Request for Application No. PCT/EP2017/074907, filed on Sep. 29, 2017, 6 total pages.

United States Securities and Exchange Commission, Form 10-Q, Quarterly Report Pursuant to Section 13 or 15(d) of the Securities Exchange Act of 1934, Myovant Sciences, Feb. 13, 2017, pp. 1-68, filing details located at https://www.sec.gov/Archives/edgar/data/1679082/000167908217000005/0001679082-17-000005- index.htm.

U.S. Appl. No. 62/402,150, filed Sep. 30, 2016, by Ditzier, 195 total pages.

U.S. Appl. No. 62/528,409, filed Jul. 3, 2017, by Ditzler, 23 total pages.

U.S. Appl. No. 62/492,839, filed May 1, 2017, by Rajasekhar et al., 515 total pages.

U.S. Appl. No. 62/402,055, filed Sep. 30, 2016, by Rajasekhar et al., 268 total pages.

U.S. Appl. No. 62/402,034, filed Sep. 30, 2016, by Rajasekhar et al., 212 total pages.

Jayasena, C.N. et al. (2014). "Kisspeptin-54 triggers egg maturation in women undergoing in vitro fertilization," J. Clin. Invest. 124:3667-3677.

International Search Report dated Sep. 9, 2021, for PCT Application No. PCT/EP2021/064280, filed on May 27, 2021, 3 pages.

Melis, G.B. et al. (2016). "Overview of elagolix for the treatment of endometriosis," Expert Opin. Drug Metab. Toxicol. 12:581-588.

Myovant Sciences Press Release (2020). "Myovant Sciences and Gedeon Richter enter into exclusive license agreement to commercialize Relugolix combination tablet for uterine fibroids and endometriosis in certain territories outside the U.S.," located at https://investors.myovant.com/news-releases/news-release-details/myovant-sciences-and-gedeon-richter-enter-exclusive-license, 2 total pages.

Myovant Sciences Press Release (2020). "Myovant Sciences announces 88% one-year response rate in positive phase 3 Liberty extension study of once-daily Relugolix combination therapy in women with uterine fibroids," located at https://investors.myovant.com/news-releases/news-release-details/myovant-sciences-announces-88-one-year-response-rate-positive, 2 total pages.

Myovant Sciences Press Release (2020). "Myovant Sciences announces positive results from Phase 3 SPIRIT 2 study evaluating once-daily Relugolix combination therapy in women with Endometriosis and from ovulation inhibition study," located https://investors.myovant.com/news-releases/news-release-details/myovant-sciences-announces-positive-results-phase-3-spirit-2/, 3 total pages.

Rowe, R.C. et al. (2009). "Mannitol," in Academy of Pharmaceutical Sciences and Royal Pharmaceutical Society of Great Britain. Handbook of Pharmaceutical Excipients $6^{th}$ Edition, Washington, D.C: American Pharmaceutical Association, p. 424.

Written Opinion of the International Searching Authority dated Sep. 9, 2021, for PCT Application No. PCT/EP2021/064280, filed on May 27, 2021, 8 pages.

AbbVie Pressroom (2016). AbbVie announces positive top-line results from second phase 3 study investigating Elagolix in patients with endometriosis, 3 total pages.

(56) References Cited

OTHER PUBLICATIONS

Ács, N. et al. (2015). "Treatment of endometriosis-associated pain with elagolix, an oral GnRH antagonist: Results from a phase 2, randomized controlled study," *J. Endometri. Pelvic Pain Disorders* 7:56-62.
Ács, N. et al. (2015). 703 Supplemental Material, 3 total pages.
Ács, N. et al. (2015). 703 Supplemental Figures and Tables, 9 total pages.
Activella Application No. NDA 20-970 (1998). Center for drug evaluation and research. Chemistry Reviews, 63 total pages.
Activella ® Highlights of Prescribing Information (2013). 10 total pages.
Al-Azemi, M. et al. (2009). "Immediate and delayed add-back hormonal replacement therapy during ultra long GnRH agonist treatment of chronic cyclical pelvic pain," *BJOG* 116:1646-1656.
Al-Hendy, A. et al. (2017). "Uterine fibroids: Burden and unmet medical need," Semin. Reprod. Med. 35:473-480.
Al-Hendy, A. et al. (2019). "Treatment of symptomatic uterine fibroids with Relugolix combination therapy—Efficacy and safety results from two double-blind, randomized, placebo-controlled phase 3 clinical trials," ASRM Presentation, 23 total pages.
Al-Hendy, A. et al. (2020). "LIBERTY: Long-term extension study demonstrating one-year efficacy and safety of Relugolix combination therapy in women with symptomatic uterine fibroids," ASRM Presentation, 18 total pages.
Al-Hendy, A. et al. (2019). "Treatment of symptoms of uterine fibroids with relugolix combination therapy: efficacy and safety; results from the Phase 3 LIBERTY 1 clinical trial," Fertility and Sterility 112:E434.
Al-Hendy, A. et al. (2020). "Quality of life improvement with Relugolix combination therapy in patients with heavy menstrual bleeding associated with uterine fibroids: Results from the liberty Phase 3 program," Fertility and Sterility 114:e85, O-205 presented at ASRM 2020.
American Society for Reproductive Medicine (2011). "Noncontraceptive benefits of birth control pills," 1 total page.
Archer, D.F. et al. (2015). "Elagolix for the management of heavy menstrual bleeding associated with uterine fibroids: Results from a Phase 2A proof-of-concept study," 19 total pages.
Archer, D.F. et al. (2017). "Elagolix for the management of heavy menstrual bleeding associated with uterine fibroids: Results from a phase 2a proof-of-concept study," Fertility and Sterility 108:152-160, with Supplemental Figures 1-3 and Materials, 28 total pages.
Archer, D.F. et al. (2020). "Elagolix suppresses ovulation in a dose-dependent mnner: Results from a 3-month, randomized study in ovulatory women," J. Clin. Endocrinol. Metab. 105:821-832.
As-Sanie, S. et al. (2020). "Efficacy and safety of Relugolix combination therapy in women with endometriosis-Associated pain: Phase 3 randomized, double-blind, placebo-controlled study (SPIRIT (2)," Fertility and Sterility 114:e77, O-187 presented at 76th American Society for Reproductive Medicine Virtual Scientific Congress & Expo.
Barbieri, R.L. (1992). "Hormone treatment of endometriosis: the estrogen threshold hypothesis," *Am. J. Obstet. Gynecol.* 166:740-745.
Becker, C.M. et al. (2021). "The effect of time since surgical diagnosis of endometriosis on treatment outcomes with Relugolix combination therapy in women with Endometriosis-associated pain: SPIRIT Program," Presented at the European Society of Human Reproduction and Embryology (ESHRE), 37th Annual Meeting, Jun.-Jul. 2021, 13 total pages.
Bedaiwy, M.A et al. (2006). "Treatment with leuprolide acetate and hormonal add-back for up to 10 years in stage IV endometriosis patients with chronic pelvic pain," Fertil. Steril. 86:220-222.
Bulun, S.E. (2013). "Uterine fibroids," *N. Engl. J. Med.* 369:1344-1355.
Carr, B. et al. (2013). "Elagolix, an oral GnRH antagonist for endometriosis-associated pain: A randomized controlled study," *J. Endometrio. Pelvic Pain Dis.* 5:105-115.
Carr, B. et al. (2014). "Elagolix, an oral GnRH antagonist, versus subcutaneous depot medroxyprogesterone acetate for the treatment of endometriosis: effects on bone mineral density," *Reprod. Sci.* 21:1341-1351.
Carr, B. et al. (2014). "Elagolix, an oral GnRH antagonist, versus subcutaneous depot medroxyprogesterone acetate for the treatment of endometriosis: effects on bone mineral density," *Reprod. Sci.* 21:1341-1351, Supplemental Material.
Center for Drug Evaluation and Research (2018). Application No. 210450Orig1s000, Elagolix Ovulation Rate.
Chen, C. et al. (2008). "Discovery of sodium R-(+)-4-{2-[5-(2-fluoro-3-methoxyphenyl)-3-(2-fluoro-6- [trifluoromethyl]benzyl)-4-methyl-2,6-dioxo-3,6-dihydro-2H-pyrimidin-1-yl]-1-phenylethylamino}butyrate (elagolix), a potent and orally available nonpeptide antagonist of the human gonadotropin-releasing hormone receptor," *J. Med. Chem.* 51:7478-7485.
ClinicalTrials.gov (2016). Bioavailability and Effect of Food on TAK-385 Tablet Formulations in Healthy Participants—Study Results—ClinicalTrials.gov, located at https://www.clinicaltrials.gov/ct2/show/results/NCT02396147?term=relugolix&rank=9, 14 total pages.
ClinicalTrials.gov. (2017). LIBERTY 1: Efficacy & safety study of Relugolix in women with heavy menstrual bleeding associated with uterine fibroids. Identifier NCT03049735, 6 total pages.
ClinicalTrials.gov. (2017). LIBERTY 2: Efficacy & safety study of Relugolix in women with heavy menstrual bleeding associated with uterine fibroids. Identifier NCT03103087, 6 total pages.
ClinicalTrials.gov. (2017). SPIRIT 1: Efficacy and safety study of Relugolix in women with Endometriosis-associated pain. Identifier NCT03204318, 6 total pages.
ClinicalTrials.gov. (2017). SPIRIT 2: Efficacy and safety study of Relugolix in women with Endometriosis-associated pain. Identifier NCT03204331, 6 total pages.
ClinicalTrials.gov. (2013). Efficacy and safety of TAK-385 in the treatment of uterine fibroids. Identifier NCT01452659, 8 total pages.
ClinicalTrials.gov. (2016). A placebo-controlled, phase 3 study of TAK-385 40 mg in the treatment of pain symptoms associated with uterine fibroids. Identifier NCT02655224, 6 total pages.
ClinicalTrials.gov. (2014). Efficacy and safety of TAK-385 in the treatment of endometriosis. Identifier NCT01458301, 7 total pages.
ClinicalTrials.gov. (2014). A long-term extension study of TAK-385 in the treatment of endometriosis. Identifier NCT01452685, 6 total pages.
ClinicalTrials.gov. (2016). A phase 3 study to evaluate the efficacy and safety of TAK-385 40 mg compared with leuprorelin in the treatment of uterine fibroids. Identifier NCT02655237, 8 total pages.
ClinicalTrials.gov. (2014). Safety and efficacy pre-menopausal women with heavy uterine bleeding and uterine fibroids. Identifier NCT01441635, 10 total pages.
ClinicalTrials.gov. (2018). LIBERTY Extension: Efficacy and safety extension study of Relugolix in women with heavy menstrual bleeding associated with uterine fibroids, Identifier NCT03412890, 9 total pages.
ClinicalTrials.gov. (2018). SPIRIT Extension: Efficacy and safety extension study of Relugolix in women with endometriosis-associated pain, Identifier NCT03654274, 10 total pages.
ClinicalTrials.gov. (2020). LIBERTY 1: Efficacy & safety study of Relugolix in women with heavy menstrual bleeding associated with uterine fibroids. Identifier NCT03049735, 12 total pages.
ClinicalTrials.gov. (2020). LIBERTY 2: Efficacy & safety study of Relugolix in women with heavy menstrual bleeding associated with uterine fibroids. Identifier NCT03103087, 12 total pages.
Cramer, D.W. et al. (2002). "Determinants of early follicular phase gonadotrophin and estradiol concentrations in women of late reproductive age," Hum. Reprod. 17:221-227.
Diamond, M.P. et al. (2014). "Elagolix treatment for endometriosis-associated pain: results from a phase 2, randomized, double-blind, placebo-controlled study," Reprod. Sci. 21:363-371.
Duijkers, I. et al. (2020). "Characterization of pituitary and ovarian hormone concentration during treatment with Relugolix combination therapy," ASRM Presentation, 12 total pages.

(56) References Cited

OTHER PUBLICATIONS

Duijkers, I.J.M. et al. (2020). "Inhibition of ovulation during co-administration of the once-daily, oral gonadotropin-releasing hormone receptor antagonist, Relugolix, with estradiol and norethindrone acetate in healthy premenopausal women," Presentation Poster, 1 total page.
Dunselman, G.A.J. et al. (2014). "ESHRE guideline: management of women with endometriosis," *Hum. Reprod.* 29:400-412.
Ehlers, K. et al. (2013). "Gonadotropin-releasing hormone (GnRH) and the GnRH receptor (GnRHR)," The Global library of women's medicine, 7 total pages.
Ettinger, B. et al. (2012). "The effect of Elagolix, a novel, orally active GnRH antagonist, on bone mineral density (BMD) in women with endometriosis," The Endocrine Society's 94$^{th}$ Annual Meeting and Expo, Jun. 23-26, 2012, Houston, TX., 1 total page.
FemHRT™ (1999). Center for drug evaluation and research. Application No. 21-065. Clinical pharmacology and biopharmaceutics review(s), 44 total pages.
FemHRT™ (1999). Center for drug evaluation and research. Application No. 21-065. Medical review(s), 46 total pages.
Fernandez, H. et al. (2004). "One year comparison between two add-back therapies in patients treated with a GnRH agonist for symptomatic endometriosis: A randomized double-blind trial," *Human Reprod.* 19:1465-1471.
Finkelstein, J.S. et al. (2008). "Bone mineral density changes during the menopause transition in a multiethnic cohort of women," *J. Clin. Endocrinol. Metab.* 93:861-868.
Friedman, A.J. et al. (1993). "A prospective, randomized trial of gonadotropin-releasing hormone agonist plus estrogen-progestin or progestin "add-back" regimens for women with leiomyomata uteri," *J. Clin. Endocrinol. Metab.* 76:1439-1445.
Friedman, A.J. et al. (1994). "Long-term medical therapy for leiomyomata uteri: a prospective, randomized study of leuprolide acetate depot plus either oestrogen-progestin or progestin 'add-back' for 2 years," *Hum. Reprod.* 9:1618-1625.
Friedman, A.J. et al. (1990). "Efficacy and safety considerations in women with uterine leiomyomas treated with gonadotropin-releasing hormone agonists: The estrogen threshold hypothesis," Am. J. Obstet. Gynecol. 163:1114-1119.
Fuldeore, M.J. et al. (2010). "Add-back therapy use and its impact on LA persistence in patients with endometriosis," *Curr. Med. Res. Opin.* 26:729-736.
Grundy, J. et al. (2008). "The pharmacokinetics (PK) and pharmacodynamics (PD) of an orally activegonadotropin-releasing hormone (GNRH) antagonist (NBI-56418) with once daily and sipping dose regimens in healthy premenopausal women," Abstract PIII-72, 83(Suppl. 1):S94.
Hornstein, M.D. et al. (1998). "Leuprolide acetate depot and hormonal add-back in endometriosis: a 12-month study. Lupron Add-Back Study Group," *Obstet. Gynecol.* 91:16-24.
Hoshiai, H. et al. (2017). "Phase 2 study of Relugolix vs placebo in heavy menstrual bleeding associated with uterine fibroids," Presented at ACOG. *Obstet. Gynecol.* 87S:29.
Imani, R. et al. (2009). "Petal study: Safety, tolerability and effectiveness of elagolix, an oral GNRH antagonist for endometriosis," *Fertility & Sterility* P-81, p. S111.
International Search Report dated Apr. 4, 2018, for PCT Application No. PCT/EP2017/074907, filed on Sep. 29, 2017, 6 pages.
Kim, N.Y. et al. (2010). "The efficacy and tolerability of short-term low-dose estrogen-only add-back therapy during post-operative GnRH agonist treatment for endometriosis," *Eur. J. Obstet. Gynecol. Reprod. Biol.* 154:85-89.
Kuhnz, W. et al. (1997). "In vivo conversion of norethisterone and norethisterone acetate to ethinyl estradiol in postmenopausal women," *Contraception* 56:379-385.
KUSM-W Department of Obstetrics and Gynecology (2016). Research and QI Update, vol. 1, Issue 1, 4 total pages.
KUSM-W (2015). "Research, quality improvement, and clinical research update," Presentation slides, 37 total pages.
Lee, J.Y. et al. (2015). "Effects of Hormone Therapy on Serum Lipid Levels in Postmenopausal Korean Women," *J. Menopausal Med.* 21:104-111.
Lee, D.Y. et al. (2016). "Effects of different add-back regimens on hypoestrogenic problems by postoperative gonadotropin-releasing hormone agonist treatment in endometriosis," *Obstet. Gynecol. Sci.* 59:32-38.
Lukes, A. et al. (2021). "Once-daily Relugolix combination therapy results in sustained reduction in symptoms and improved quality of life in women with uterine fibroids treated over 52 weeks," Presented at the European Society of Human Reproduction and Embryology (ESHRE) 2021, 37th Annual Meeting, Jun. 26-Jul. 1, 2021, 15 total pages.
Lupron Medical Review Part 1 (2001). Application No. 20-708/S-011 Medical reviews. NDA 20-011/S021 and NDA 20-708/s011, 43 total pages.
Lupron Medical Review Part 2 (2001). NDA 20-011/s021 & NDA 20-708/s011, 42 total pages.
Lupron Medical Review Part 3 (2001). NDA 20-011/s021 & NDA 20-708/s011, 42 total pages.
McLaren, J.S. et al. (2012). "Gonadotrophin receptor hormone analogues in combination with add-back therapy: an update," Menopause International 18:68-72.
Mizutani, T. e al. (2005). "Effect of steroid add-back therapy on the proliferative activity of uterine leiomyoma cells under gonadotropin-releasing hormone agonist therapy," *Gynecol. Endocrinol.* 20:80-83.
Miwa, K. et al. (2011). "Discovery of 1-{4-[1-(2,6-difluorobenzyl)-5-[(dimethylamino)methyl]-3-(6-methoxypyridazin-3-yl)-2,4-dioxo-1,2,3,4-tetrahydrothieno[2,3-d]pyrimidin-6-yl]phenyl}-3-methoxyurea (TAK-385) as a potent, orally active, non-peptide antagonist of the human gonadotropin-releasing hormone receptor," *J. Med. Chem.* 54:4998-5012.
Moroni, R.M. et al. (2015). "Add-back therapy with GnRH analogues for uterine fibroids (review)," Cochrane Library, 78 total pages.
Myovant Sciences (2019). Press Release: "Myovant Sciences announces positive results from second phase 3 study evaluating one-daily Religolix combination therapy in women with uterine fibroids and positive results from Bioequivalence study," 3 total pages.
Myovant Sciences (2019). Press Release: "Myovant Sciences announces late-breaking oral presentation of phase 3 LIBERTY 1 & 2 study results at 2019 American Society for reproductive medicine scientific congress," 2 total pages.
Myovant Sciences (2021). Press Release: "Myovant Sciences and Pfizer announce positive one-year data from phase 3 SPITIT extension study of once-daily Relugolix combination therapy in Women with Endometriosis," 3 total pages.
Nakata, D. et al. (2014). "Suppression of the hypothalamic-pituitary-gonadal axis by TAK-385 (relugolix), a novel, investigational, orally active, small molecule gonadotropin-releasing hormone (GnRH) antagonist: studies in human GnRH receptor knock-in mice," *Eurp. J. Pharmacol.* 723:167-174.
Ng, J.W. et al. (2016). "Dose-dependent suppression of gonadotropins and ovarian hormones by elagolix in healthy premenopausal females," S-200, 2 total pages.
Notice of Allowance dated Mar. 31, 2021, for U.S. Appl. No. 16/370,299, filed Mar. 29, 2019, 18 pages.
Oral and Transdermal estrogen dose equivalents (2012), 1 total page.
Osuga, Y. et al. (2020). "Relugolix, an oral gonadotropin-releasing hormone receptor antagonist, reduces endometriosis-associated pain in a dose-response manner: a randomized, double-blind, placebo-controlled study," Fertil. Steril. 7:S0015-0282(20)30716-0, 8 total pages.
Perez-Lopez, F.R. et al. (2014). "EMAS position statement: Management of uterine fibroids," Maturitas 79:106-116.
PR Newswire (2014). Endometriosis opportunity analysis and forecasts to 2017, located at https://www.prnewswire.com/news-releases/opportunityanalyzer-endometriosis---opportunity-analysis-and-forecasts-to-2017-244856221.html, 4 total pages.

(56) References Cited

OTHER PUBLICATIONS

Practice Committee of the American Society for Reproductive Medicine (2014). "Treatment of pelvic pain associated with endometriosis: A committee opinion," *Fertility & Sterility* 101:927-935.
Riggs, M.M. et al. (2012). "Integrated pharmacometrics and systems pharmacology model-based analyses to guide GnRH receptor modulator development for management of endometriosis," *CPT Pharmacometrics Syst. Pharmacol.* 1:e11.
Riggs, M.M. et al. (2011). "Application of a multiscale physiologically-based bone and calcium systems model to guide the development of GnRH receptor modulators for the management of endometriosis," American Conference on Pharmacometrics Poster, Apr. 3-7, 2011, San Diego, CA., 1 total page.
Speroff, L. et al. (2000). "The effect of varying low-dose combinations of norethindrone acetate and ethinyl estradiol (femhrt) on the frequency and intensity of vasomotor symptoms," *Menopause* 7:383-390.
Streuli, I. et al. (2012). "New treatment strategies and emerging drugs in endometriosis," Expert Opinion on Emerging Drugs 17:83-104.
Sriprasert, I. et al. (2017). "Heavy menstrual bleeding diagnosis and medical management," Contraception and Reproductive Medicine 2:20, 8 total pages.
Stricker, R. et al. (2006). "Establishment of detailed reference values for luteinizing hormone, follicle stimulating hormone, estradiol, and progesterone during different phases of the menstrual cycle on the Abbott ARCHITECT® analyzer," Clin. Chem. Lab. Med. 44:883-887.
Struthers, R.S. et al. (2009). "Suppression of gonadotropins and estradiol in premenopausal women by oral administration of the nonpeptide gonadotropin-releasing hormone antagonist elagolix," *J. Clin. Endocrinol. Metab.* 94:545-551.
Takeda Press Release. (2016). Roivant sciences and Takeda launch Myovant Sciences to development innovative therapeutics for women's health and prostate cancer, located at https://www.takeda.com/newsroom/newsreleases/2016/roivant-sciences-and-takeda-launch-myovant-sciences-to-develop-innovative-therapeutics-for-womens-health-and-prostate-cancer/, 2 total pages.
Tanaka, A. et al. (2009). "Pharmacological profile of TAK-385, an orally active gonadotropin releasing hormone (GNRH) antagonist," *Fertility & Sterility* P-86, p. S113.
Taylor, H.S. et al. (2017). "Treatment of endometriosis-associated pain with elagolix, an oral GnRH antagonist," N. Engl. J. Med. 377:28-40.
Todd, T. et al. (2007). "Newly diagnosed iron deficiency anaemia in a premenopausal woman," BMJ 334:259.
Wessler, J.D. et al. (2013). "The P-glycoprotein transport system and cardiovascular drugs," *J. Am. Coll. Cardiol.* 61:2495-2502.
Wise, L.A. et al. (2016). "Epidemiology of uterine fibroids—from menarche to menopause," Clin. Obstet. Gynecol. 59:2-24.

Written Opinion of the International Searching Authority dated Apr. 4, 2018, for PCT Application No. PCT/EP2017/074907, filed on Sep. 29, 2017, 14 pages.
Wu, D. et al. (2014). "Clinical efficacy of add-back therapy in treatment of endometriosis: a meta-analysis," *Arch. Gynecol. Obstet.* 290:513-523.
U.S. Appl. No. 17/349,584, filed Jun. 16, 2021, by Fukuoka et al.
Al-Hendy, A. et al. (2021). "Treatment of uterine fibroid symptoms with relugolix combination therapy," N. Engl. J. Med. 384:630-642.
As-Sanie et al., O-1, ASRM 2022 Genes, Gametes, and Genetics, Oct. 22-26, 2022, Scientific Abstracts to be presented at the 78th Scientific Congress of the American Society for Reproductive Medicine, Oct. 22-26, 2022, Anaheim, California, p. e1.
Becker et al., Session 62, Abstracts of the 38th Hybrid Annual Meeting of the ESHRE, Jul. 3-6, 2022, page i1 10.
Duijkers et al., P-287, Abstracts of the 36th Annual Meeting of the ESHRE, Jul. 5-8, 2020, p. i268-i269.
Giudice et al., "Once daily oral relugolix combination therapy versus placebo in patients with endometriosis-associated pain: two replicate phase 3, randomised, double-blind, studies (SPIRIT 1 and 2)". Lancet (2022) 399:2267-2279, published Aug. 25, 2022.
Harding, GH. et al. (2008). "The responsiveness of the uterine fibroid symptom and health-related quality of life questionnaire (UFS-QOL)," Health of Quality of Life Outcomes 6:99, 8 total pages.
Multi-Disciplinary Review and Evaluation of Orilissa (Elagolix Sodium) by the Center for Drug Evalation and Research; https://www.accessdata.fda.gov/drugsatfda_docs/nda/2018/210450Orig1s000MultiD.pdf; p. 262, published Jul. 3, 2018.
MYFEMBREE U.S Prescribing Information, Jan. 2023, 41 pages.
Myovant Sciences, "Myovant Sciences and Pfizer announce publication in The Lancet of Phase 3 Spirit 1 and Spirit 2 studies of once-daily relugolix combination therapy in women with endometriosis-associated pain", published Jun. 17, 2022.
Negre, J.M.S. (Date Unknown). "New galenic contributions to methods of administration," Continuing Education for Hospital Pharmacists, 57 total pages (with English Translation).
Response to Opposition filed by Myovant Sciences, Inc. on May 15, 2023, to Opposition against EP Patent No. 3518933, filed by Sandoz AG, 50 total pages.
RYEQO EPAR Product Information, Jul. 2022, 35 pages.
UCLA Health (2019). Uterine fibroid symptom & health-related quality of life questionnaire (UFS-QOL), located at https://www.uclahealth.org/sites/default/files/documents/Fibroid-Questionnaire-2019.pdf, 3 total pages.
Wikipedia Article (2022). "Form S-1," located at https://en.wikipedia.org/wiki/Form_S-1, 1 total page.
Wikipedia Article (2023). "Medication," located at https://en.wikipedia.org/wiki/Medication, 19 total pages.
Non-Final Office Action dated Jul. 14, 2023, for U.S. Appl. No. 17/866,201, filed Jul. 15, 2022, 20 pages.

\* cited by examiner

Month: _____

| Date | Pads | | | Tampons | | | Clots | | Flooding | Score |
|---|---|---|---|---|---|---|---|---|---|---|
| | Light (1 pt each) | Medium (5 pts each) | Heavy (10 pts each) | Light (1 pt each) | Medium (5 pts each) | Heavy (10 pts each) | 5 cent size (1 pt each) | 50 cent size (5 pts each) | 5 pt each episode | |
| 1 | | | | | | | | | | |
| 2 | | | | | | | | | | |
| 3 | | | | | | | | | | |
| 4 | | | | | | | | | | |
| 5 | | | | | | | | | | |
| 6 | | | | | | | | | | |
| 7 | | | | | | | | | | |
| 8 | | | | | | | | | | |
| 9 | | | | | | | | | | |
| 10 | | | | | | | | | | |
| 11 | | | | | | | | | | |
| 12 | | | | | | | | | | |
| 13 | | | | | | | | | | |
| 14 | | | | | | | | | | |
| 15 | | | | | | | | | | |
| 16 | | | | | | | | | | |
| 17 | | | | | | | | | | |
| 18 | | | | | | | | | | |
| 19 | | | | | | | | | | |
| 20 | | | | | | | | | | |
| 21 | | | | | | | | | | |
| 22 | | | | | | | | | | |
| 23 | | | | | | | | | | |
| 24 | | | | | | | | | | |
| 25 | | | | | | | | | | |
| 26 | | | | | | | | | | |
| 27 | | | | | | | | | | |
| 28 | | | | | | | | | | |
| 29 | | | | | | | | | | |
| 30 | | | | | | | | | | |
| 31 | | | | | | | | | | |
| | | | | | | | | | Total | |

Count the number of sanitary pads and/or tampons you use each day (24 hour period).
Calculate a score for each day, then add up the score at the end of the month.

FIG. 1

Uterine Fibroid Pain

Using the scale below with 0 being "No Pain" and 10 being the "Worst Pain Possible", please circle the number that represents the amount of pain caused by your uterine fibroids today:

```
|----|----|----|----|----|----|----|----|----|----|
0    1    2    3    4    5    6    7    8    9    10
No Pain                                    Worst Pain Possible
```

FIG. 2

| | During the previous month, how distressed were you by... | Not at all | A little bit | Some what | A great deal | A very great deal |
|---|---|---|---|---|---|---|
| 1 | Heavy bleeding during your menstrual period | ☐ | ☐ | ☐ | ☐ | ☐ |
| 2 | Passing blood clots during your menstrual period | ☐ | ☐ | ☐ | ☐ | ☐ |
| 3 | Fluctuation in the duration of your menstrual period compared to your previous cycle | ☐ | ☐ | ☐ | ☐ | ☐ |
| 4 | Fluctuation in the length of your monthly cycle compared to your previous cycle | ☐ | ☐ | ☐ | ☐ | ☐ |
| 5 | Feeling tightness or pressure in your pelvic area | ☐ | ☐ | ☐ | ☐ | ☐ |
| 6 | Frequent urination during the daytime hours | ☐ | ☐ | ☐ | ☐ | ☐ |
| 7 | Frequent nighttime urination | ☐ | ☐ | ☐ | ☐ | ☐ |
| 8 | Feeling fatigued | ☐ | ☐ | ☐ | ☐ | ☐ |

FIG. 3A

| | During the previous month, how often have your symptoms related to uterine fibroids... | None of the time | A little of the time | Some of the time | Most of the time | All of the time |
|---|---|---|---|---|---|---|
| 9 | Made you feel anxious about the unpredictable onset or duration of your periods? | ☐ | ☐ | ☐ | ☐ | ☐ |
| 10 | Made you anxious about traveling? | ☐ | ☐ | ☐ | ☐ | ☐ |
| 11 | Interfered with your physical activities? | ☐ | ☐ | ☐ | ☐ | ☐ |
| 12 | Caused you to feel tired or worn out? | ☐ | ☐ | ☐ | ☐ | ☐ |
| 13 | Made you decrease the amount of time you spent on exercise or other physical activities? | ☐ | ☐ | ☐ | ☐ | ☐ |
| 14 | Made you feel as if you are not in control of your life? | ☐ | ☐ | ☐ | ☐ | ☐ |
| 15 | Made you concerned about soiling underclothes? | ☐ | ☐ | ☐ | ☐ | ☐ |
| 16 | Made you feel less productive? | ☐ | ☐ | ☐ | ☐ | ☐ |
| 17 | Caused you to feel drowsy or sleepy during the day? | ☐ | ☐ | ☐ | ☐ | ☐ |
| 18 | Made you feel self-conscious of weight gain? | ☐ | ☐ | ☐ | ☐ | ☐ |
| 19 | Made you feel that it was difficult to carry out your usual activities? | ☐ | ☐ | ☐ | ☐ | ☐ |
| 20 | Interfered with your social activities? | ☐ | ☐ | ☐ | ☐ | ☐ |
| 21 | Made you feel conscious about the size and appearance of your stomach? | ☐ | ☐ | ☐ | ☐ | ☐ |
| 22 | Made you concerned about soiling bed linen? | ☐ | ☐ | ☐ | ☐ | ☐ |
| 23 | Made you feel sad, discouraged, or hopeless? | ☐ | ☐ | ☐ | ☐ | ☐ |

FIG. 3B

| | During the previous month, how often have your symptoms related to uterine fibroids... | None of the time | A little of the time | Some of the time | Most of the time | All of the time |
|---|---|---|---|---|---|---|
| 24 | Made you feel down hearted and blue? | ☐ | ☐ | ☐ | ☐ | ☐ |
| 25 | Made you feel wiped out? | ☐ | ☐ | ☐ | ☐ | ☐ |
| 26 | Caused you to be concerned or worried about your health? | ☐ | ☐ | ☐ | ☐ | ☐ |
| 27 | Caused you to plan activities more carefully? | ☐ | ☐ | ☐ | ☐ | ☐ |
| 28 | Made you feel inconvenienced about always carrying extra pads, tampons, and clothing to avoid accidents? | ☐ | ☐ | ☐ | ☐ | ☐ |
| 29 | Caused you embarrassment? | ☐ | ☐ | ☐ | ☐ | ☐ |
| 30 | Made you feel uncertain about your future? | ☐ | ☐ | ☐ | ☐ | ☐ |
| 31 | Made you feel irritable? | ☐ | ☐ | ☐ | ☐ | ☐ |
| 32 | Made you concerned about soiling outer clothes? | ☐ | ☐ | ☐ | ☐ | ☐ |
| 33 | Affected the size of clothing you wear during your periods? | ☐ | ☐ | ☐ | ☐ | ☐ |
| 34 | Made you feel that you are not in control of your health? | ☐ | ☐ | ☐ | ☐ | ☐ |
| 35 | Made you feel weak as if energy was drained from your body? | ☐ | ☐ | ☐ | ☐ | ☐ |
| 36 | Diminished your sexual desire? | ☐ | ☐ | ☐ | ☐ | ☐ |
| 37 | Caused you to avoid sexual relations? | ☐ | ☐ | ☐ | ☐ | ☐ |

FIG. 3C

| Cohort | Placebo | SRD 1.0 mg Fasted | SRD 5.0 mg Fasted | SRD 10 mg Fasted | SRD 20 mg Fasted | SRD 40 mg Fasted | SRD 80 mg Fasted | Food Effect 40 mg or one-half MTD Fed/Fasted | MRD 10 mg QD Fasted | MRD 20 mg QD Fasted | MRD 40 mg QD Fasted |
|---|---|---|---|---|---|---|---|---|---|---|---|
| | Fasted | | | | | | | | | | |
| 1 a/b | 2 | 10 | | | | | | | | | |
| 2 | 2 | | 10 | | | | | | | | |
| 3 | 2 | | | 10 | | | | | | | |
| 4 | 2 | | | | 10 | | | | | | |
| 5 | 2 | | | | | 10 | | | | | |
| 6 | 2 | | | | | | 10 | | | | |
| 7 | 0 | | | | | | | 12 | | | |
| 8 | 3 | | | | | | | | 9 | | |
| 9 | 3 | | | | | | | | | 9 | |
| 10 | 3 | | | | | | | | | | 9 |

FIG. 4

| Parameter | Statistics | 1.0 mg (N=10) | 5.0 mg (N=10) | 10 mg (N=10) | 20 mg (N=10) | 40 mg (N=10) | 80 mg (N=10) |
|---|---|---|---|---|---|---|---|
| AUC (0-t lqc) (ng*hr/mL) | N | 10 | 10 | 10 | 10 | 10 | 10 |
| | Mean | 0.945 | 7.404 | 15.528 | 40.992 | 93.351 | 319.338 |
| | SD | 0.3131 | 2.5783 | 3.9677 | 20.9865 | 43.2431 | 220.9533 |
| | Geometric Mean | 0.907 | 6.965 | 14.904 | 34.488 | 84.406 | 258.790 |
| | %CV | 33.1300 | 34.8300 | 25.5500 | 51.2000 | 46.3200 | 69.1900 |
| | Median | 0.849 | 7.728 | 16.579 | 40.903 | 93.638 | 262.356 |
| | Minimum | 0.69 | 3.82 | 6.39 | 6.51 | 42.17 | 99.59 |
| | Maximum | 1.72 | 11.37 | 20.68 | 75.03 | 168.16 | 739.19 |
| AUC (0-inf) (ng*hr/mL) | N | 10 | 10 | 10 | 10 | 10 | 10 |
| | Mean | 1.072 | 8.046 | 16.956 | 45.162 | 103.684 | 348.096 |
| | SD | 0.3395 | 2.7729 | 3.9843 | 23.0727 | 47.8892 | 238.0285 |
| | Geometric Mean | 1.032 | 7.575 | 16.406 | 38.035 | 93.557 | 283.225 |
| | %CV | 31.6700 | 34.4600 | 23.5000 | 51.0900 | 46.1900 | 68.3800 |
| | Median | 0.969 | 8.443 | 18.045 | 45.249 | 107.666 | 293.453 |
| | Minimum | 0.78 | 4.19 | 7.83 | 7.27 | 45.84 | 110.01 |
| | Maximum | 1.88 | 12.05 | 22.32 | 82.79 | 186.03 | 809.55 |

FIG. 5A

| Parameter | Statistics | 1.0 mg (N=10) | 5.0 mg (N=10) | 10 mg (N=10) | 20 mg (N=10) | 40 mg (N=10) | 80 mg (N=10) |
|---|---|---|---|---|---|---|---|
| Cmax (ng/mL) | N | 10 | 10 | 10 | 10 | 10 | 10 |
| | Mean | 0.1424 | 0.6132 | 1.9032 | 4.4462 | 11.4330 | 51.4120 |
| | SD | 0.06242 | 0.21943 | 1.13706 | 2.81666 | 7.73259 | 66.66872 |
| | Geometric Mean | 0.1325 | 0.5793 | 1.6270 | 3.4981 | 9.3630 | 31.6081 |
| | %CV | 43.82000 | 35.79000 | 59.74000 | 63.35000 | 67.63000 | 129.68000 |
| | Median | 0.1245 | 0.5605 | 1.6100 | 3.7350 | 9.4600 | 32.9000 |
| | Minimum | 0.087 | 0.297 | 0.467 | 0.502 | 4.170 | 8.720 |
| | Maximum | 0.270 | 1.040 | 4.540 | 9.740 | 27.500 | 232.000 |
| Tmax (hr) | N | 10 | 10 | 10 | 10 | 10 | 10 |
| | Mean | 0.810 | 1.946 | 1.711 | 2.098 | 1.898 | 3.796 |
| | SD | 0.3376 | 1.9670 | 1.8243 | 1.3922 | 1.5591 | 1.9478 |
| | Median | 0.775 | 0.990 | 1.015 | 1.750 | 1.500 | 4.000 |
| | Minimum | 0.50 | 0.48 | 0.50 | 0.50 | 0.48 | 0.48 |
| | Maximum | 1.50 | 6.00 | 6.00 | 4.00 | 4.00 | 6.00 |
| Lambda_z (1/hr) | N | 10 | 10 | 10 | 10 | 10 | 10 |
| | Mean | 0.11590 | 0.04807 | 0.04543 | 0.04307 | 0.04412 | 0.04430 |
| | SD | 0.029194 | 0.004674 | 0.006672 | 0.002277 | 0.007171 | 0.004705 |
| | Median | 0.10512 | 0.04887 | 0.04575 | 0.04272 | 0.04204 | 0.04434 |
| | Minimum | 0.0812 | 0.0404 | 0.0325 | 0.0395 | 0.0318 | 0.0368 |
| | Maximum | 0.1609 | 0.0572 | 0.0571 | 0.0468 | 0.0573 | 0.0499 |

FIG. 5B

| Parameter | Statistics | 1.0 mg (N=10) | 5.0 mg (N=10) | 10 mg (N=10) | 20 mg (N=10) | 40 mg (N=10) | 80 mg (N=10) |
|---|---|---|---|---|---|---|---|
| T1/2 (hr) | N | 10 | 10 | 10 | 10 | 10 | 10 |
| | Mean | 6.3215 | 14.5419 | 15.5803 | 16.1307 | 16.0930 | 15.8132 |
| | SD | 1.52713 | 1.42534 | 2.51796 | 0.84847 | 2.67703 | 1.75965 |
| | Median | 6.5951 | 14.1812 | 15.1491 | 16.2250 | 16.4865 | 15.6371 |
| | Minimum | 4.308 | 12.128 | 12.144 | 14.828 | 12.108 | 13.883 |
| | Maximum | 8.541 | 17.172 | 21.363 | 17.556 | 21.820 | 18.821 |
| CL/F (L/hr) | N | 10 | 10 | 10 | 10 | 10 | 10 |
| | Mean | 1001.8 | 705.7 | 637.7 | 702.2 | 475.6 | 342.6 |
| | SD | 251.67 | 283.12 | 237.91 | 745.76 | 231.02 | 212.49 |
| | Median | 1032.9 | 596.7 | 554.2 | 442.8 | 371.5 | 288.1 |
| | Minimum | 532 | 415 | 448 | 242 | 215 | 99 |
| | Maximum | 1284 | 1194 | 1278 | 2749 | 873 | 727 |
| Vz/F (L) | N | 10 | 10 | 10 | 10 | 10 | 10 |
| | Mean | 8790.4 | 14949.1 | 14997.6 | 16301.1 | 10699.4 | 7870.3 |
| | SD | 1781.31 | 6804.03 | 8956.43 | 17440.73 | 4515.97 | 4919.31 |
| | Median | 9122.9 | 12847.5 | 11682.9 | 10758.8 | 10001.0 | 6856.2 |
| | Minimum | 5138 | 8437 | 9709 | 5918 | 4919 | 2295 |
| | Maximum | 10995 | 27250 | 39383 | 64360 | 17102 | 16737 |

FIG. 5C

| Parameter | Statistics | 40 mg Fed (N=12) | 40 mg Fasted (N=11) |
|---|---|---|---|
| AUC (0-tlqc) (ng*hr/mL) | N<br>Mean<br>SD<br>Geometric Mean<br>%CV<br>Median<br>Minimum<br>Maximum | 12<br>55.792<br>21.7076<br>51.833<br>38.9100<br>51.938<br>25.71<br>94.13 | 11<br>110.782<br>69.4023<br>93.722<br>62.6500<br>99.967<br>35.08<br>266.07 |
| AUC (0-inf) (ng*hr/mL) | N<br>Mean<br>SD<br>Geometric Mean<br>%CV<br>Median<br>Minimum<br>Maximum | 12<br>63.437<br>25.3950<br>58.674<br>40.0300<br>60.478<br>29.39<br>107.31 | 11<br>125.275<br>80.1066<br>105.501<br>63.9400<br>110.506<br>39.20<br>302.41 |
| Cmax (ng/mL) | N<br>Mean<br>SD<br>Geometric Mean<br>%CV<br>Median<br>Minimum<br>Maximum | 12<br>4.5908<br>1.69972<br>4.2890<br>37.02000<br>4.4000<br>1.570<br>8.770 | 11<br>13.8709<br>12.00958<br>10.1753<br>86.58000<br>7.9100<br>3.870<br>38.500 |

FIG. 6A

| Parameter | Statistics | 40 mg Fed (N=12) | 40 mg Fasted (N=11) |
|---|---|---|---|
| Tmax (hr) | N<br>Mean<br>SD<br>Median<br>Minimum<br>Maximum | 12<br>3.040<br>1.8565<br>3.005<br>1.00<br>6.00 | 11<br>3.226<br>2.0564<br>3.980<br>0.50<br>6.03 |
| Lambda_z (1/hr) | N<br>Mean<br>SD<br>Median<br>Minimum<br>Maximum | 12<br>0.04147<br>0.005761<br>0.04089<br>0.0319<br>0.0552 | 11<br>0.04013<br>0.006275<br>0.04125<br>0.0284<br>0.0511 |
| T1/2 (hr) | N<br>Mean<br>SD<br>Median<br>Minimum<br>Maximum | 12<br>16.9911<br>2.23051<br>16.9499<br>12.558<br>21.738 | 11<br>17.6896<br>3.00630<br>16.7998<br>13.577<br>24.384 |

FIG. 6B

| Parameter | Statistics | 40 mg Fed (N=12) | 40 mg Fasted (N=11) |
|---|---|---|---|
| CL/F (L/hr) | N<br>Mean<br>SD<br>Median<br>Minimum<br>Maximum | 12<br>739.7<br>315.95<br>674.3<br>373<br>1361 | 11<br>445.4<br>260.68<br>362.0<br>132<br>1020 |
| Vz/F (L) | N<br>Mean<br>SD<br>Median<br>Minimum<br>Maximum | 12<br>17932.0<br>7702.13<br>16569.7<br>9028<br>33876 | 11<br>11042.3<br>6343.34<br>8974.3<br>3534<br>24731 |

FIG. 6C

| Parameter | Statistics | 10 mg (N=9) | 20 mg (N=9) | 40 mg (N=9) |
|---|---|---|---|---|
| Cmax (ng/mL) | N | 9 | 9 | 9 |
| | Mean | 1.3902 | 8.0944 | 17.8356 |
| | SD | 0.43020 | 7.36850 | 8.45057 |
| | Geometric Mean | 1.3185 | 5.6302 | 15.7495 |
| | %CV | 30.94000 | 91.03000 | 47.38000 |
| | Median | 1.3400 | 5.0600 | 19.0000 |
| | Minimum | 0.582 | 1.750 | 6.010 |
| | Maximum | 1.960 | 21.800 | 29.500 |

FIG. 7A

| Parameter | Statistics | 10 mg (N=9) | 20 mg (N=9) | 40 mg (N=9) |
|---|---|---|---|---|
| Tmax (hr) | N | 9 | 9 | 9 |
| | Mean | 0.996 | 1.181 | 1.274 |
| | SD | 0.5026 | 0.4548 | 0.4540 |
| | Median | 1.000 | 1.000 | 1.480 |
| | Minimum | 0.48 | 0.50 | 0.48 |
| | Maximum | 2.00 | 2.00 | 2.00 |
| CL/F (L/hr) | N | 9 | 9 | 9 |
| | Mean | 1244.5 | 959.7 | 697.6 |
| | SD | 454.88 | 525.52 | 323.29 |
| | Median | 1063.8 | 1101.1 | 682.1 |
| | Minimum | 661 | 262 | 346 |
| | Maximum | 2102 | 1918 | 1288 |
| Vz/F (L) | N | 9 | 9 | 9 |
| | Mean | 9626.8 | 6442.1 | 4486.4 |
| | SD | 3217.84 | 4182.91 | 2246.21 |
| | Median | 9241.1 | 6475.1 | 4138.9 |
| | Minimum | 6102 | 1862 | 2240 |
| | Maximum | 16861 | 14546 | 8325 |

FIG. 7B

| Parameter | Statistics | 10 mg (N=9) | 20 mg (N=9) | 40 mg (N=9) |
|---|---|---|---|---|
| AUC (0-tau) (ng*hr/mL) | N<br>Mean<br>SD<br>Geometric Mean<br>%CV<br>Median<br>Minimum<br>Maximum | 9<br>9.001<br>3.1805<br>8.510<br>35.3400<br>9.400<br>4.76<br>15.12 | 9<br>30.368<br>22.3518<br>24.658<br>73.6000<br>18.164<br>10.42<br>76.27 | 9<br>68.591<br>29.0593<br>62.885<br>42.3700<br>58.646<br>31.06<br>115.69 |

FIG. 7C

| Parameter | Statistics | 10 mg (N=9) | 20 mg (N=9) | 40 mg (N=9) |
|---|---|---|---|---|
| Cmax (ng/mL) | N<br>Mean<br>SD<br>Geometric Mean<br>%CV<br>Median<br>Minimum<br>Maximum | 9<br>2.3456<br>1.06976<br>2.1309<br>45.61000<br>2.0500<br>0.970<br>4.230 | 9<br>10.8400<br>9.40906<br>7.7140<br>86.80000<br>8.2000<br>1.920<br>30.800 | 9<br>19.3289<br>8.71450<br>17.2746<br>45.09000<br>21.8000<br>7.560<br>30.300 |
| Tmax (hr) | N<br>Mean<br>SD<br>Median<br>Minimum<br>Maximum | 9<br>0.903<br>0.4794<br>0.980<br>0.48<br>2.02 | 9<br>1.382<br>0.4817<br>1.480<br>0.50<br>2.00 | 9<br>1.149<br>0.3524<br>1.000<br>0.48<br>1.48 |

FIG. 7D

| Parameter | Statistics | 10 mg (N=9) | 20 mg (N=9) | 40 mg (N=9) |
|---|---|---|---|---|
| CL/F (L/hr) | N | 9 | 9 | 9 |
| | Mean | 569.7 | 436.3 | 373.4 |
| | SD | 276.44 | 237.41 | 104.75 |
| | Median | 510.1 | 340.8 | 336.0 |
| | Minimum | 307 | 172 | 240 |
| | Maximum | 1141 | 965 | 552 |
| Cmin (ng/mL) | N | 9 | 9 | 9 |
| | Mean | 0.4322 | 0.9477 | 2.3778 |
| | SD | 0.17211 | 0.31134 | 0.65001 |
| | Median | 0.4630 | 0.9650 | 2.2600 |
| | Minimum | 0.154 | 0.586 | 1.500 |
| | Maximum | 0.650 | 1.570 | 3.430 |
| Vz/F (L) | N | 9 | 9 | 9 |
| | Mean | 5041.8 | 3618.3 | 3086.5 |
| | SD | 2361.55 | 2399.69 | 1018.38 |
| | Median | 4437.0 | 2591.5 | 2491.0 |
| | Minimum | 2756 | 1161 | 2088 |
| | Maximum | 10231 | 8998 | 5034 |

FIG. 7E

| Parameter | Statistics | 10 mg (N=9) | 20 mg (N=9) | 40 mg (N=9) |
|---|---|---|---|---|
| AUC (0-tau) (ng*hr/mL) | N | 9 | 9 | 9 |
| | Mean | 20.626 | 57.102 | 114.497 |
| | SD | 7.7049 | 27.5719 | 30.4617 |
| | Geometric Mean | 19.166 | 51.408 | 110.819 |
| | %CV | 37.3500 | 48.2900 | 26.6000 |
| | Median | 19.603 | 58.679 | 119.044 |
| | Minimum | 8.76 | 20.72 | 72.50 |
| | Maximum | 32.62 | 116.42 | 166.48 |

FIG. 7F

| Parameter | Statistic | 1 mg Cohort 1 N=10 | 5 mg Cohort 2 N=10 | 10 mg Cohort 3 N=10 | 20 mg Cohort 4 N=10 | 40 mg Cohort 5 N=10 | 80 mg Cohort 6 N=10 |
|---|---|---|---|---|---|---|---|
| AUC(0-tlqc) (ng.hr/mL) | Mean | 0.95 | 7.40 | 15.5 | 41.0 | 93.4 | 319.3 |
| | %CV | 33.1 | 34.8 | 25.6 | 51.2 | 46.3 | 69.2 |
| AUC(0-inf) (ng.hr/mL) | Mean | 1.07 | 8.05 | 17.0 | 45.2 | 103.7 | 348.1 |
| | %CV | 31.7 | 34.5 | 23.5 | 51.1 | 46.2 | 68.4 |
| Cmax (ng/mL) | Mean | 0.14 | 0.61 | 1.90 | 4.45 | 11.4 | 51.4 |
| | %CV | 43.8 | 35.8 | 59.7 | 63.4 | 67.6 | 129.7 |
| Tmax (hr) | Median | 0.78 | 0.99 | 1.02 | 1.75 | 1.50 | 4.00 |
| | Min | 0.50 | 0.48 | 0.50 | 0.50 | 0.48 | 0.48 |
| | Max | 1.50 | 6.00 | 6.00 | 4.00 | 4.00 | 6.00 |
| T1/2 (hr) | Mean | 6.32 | 14.5 | 15.6 | 16.1 | 16.1 | 15.8 |
| | %CV | 24.2 | 9.80 | 16.2 | 5.26 | 16.6 | 11.1 |
| CL/F (L/hr) | Mean | 1001.8 | 705.7 | 637.7 | 702.2 | 475.6 | 342.6 |
| | %CV | 25.1 | 40.1 | 37.3 | 106.2 | 48.6 | 62.0 |
| Vz/F (L) | Mean | 8790.4 | 14949.1 | 14997.6 | 16301.1 | 10699.4 | 7870.3 |
| | %CV | 20.3 | 45.5 | 59.7 | 107.0 | 42.2 | 62.5 |
| CLr (L/hr) | Mean | 8.35 | 5.82 | 7.05 | 6.43 | 5.71 | 6.59 |
| | SD | 1.95 | 0.60 | 0.86 | 1.11 | 1.45 | 1.95 |
| Ae(0-48) (ng) | Mean | 8552.4 | 46234.2 | 121193.8 | 282502.9 | 586432.1 | 2086264.8 |
| | SD | 1787.3 | 14778.5 | 37096.4 | 144612.2 | 331076.2 | 1263075.1 |
| Fe (%) | Mean | 0.86 | 0.93 | 1.21 | 1.41 | 1.47 | 2.61 |
| | SD | 0.18 | 0.30 | 0.37 | 0.72 | 0.83 | 1.58 |

FIG. 8

| Parameter | Statistic | 40 mg (Fed) Cohort 7 N=12 | 40 mg (Fasted) Cohort 7 N=11 |
|---|---|---|---|
| AUC(0-tlqc) (ng.hr/mL) | Mean %CV | 55.8 38.9 | 110.8 62.7 |
| AUC(0-inf) (ng.hr/mL) | Mean %CV | 63.4 40.0 | 125.3 63.9 |
| Cmax (ng/mL) | Mean %CV | 4.59 37.0 | 13.9 86.6 |
| Tmax (hr) | Median Min Max | 3.01 1.00 6.00 | 3.98 0.50 6.03 |
| T1/2 (hr) | Mean %CV | 17.0 13.1 | 17.7 17.0 |
| CL/F (L/hr) | Mean %CV | 739.7 42.7 | 445.4 58.5 |
| Vz/F (L) | Mean %CV | 17932.0 43.0 | 11042.3 57.5 |
| CLr (L/hr) | Mean SD | 6.10 2.28 | 6.76 2.66 |
| Ae (0-48) (ng) | Mean SD | 367437.3 157501.3 | 785231.9 498301.5 |
| Fe (%) | Mean SD | 0.92 0.39 | 1.96 1.25 |

FIG. 9

| Parameter | Statistics | 40 mg Fed (N=12) | 40 mg Fasted (N=11) |
|---|---|---|---|
| Ae (0-24) (ng) | N<br>Mean<br>SD<br>Median<br>Minimum<br>Maximum | 12<br>298277.78<br>123149.878<br>264198.25<br>107834.3<br>484530.0 | 11<br>668810.00<br>431829.921<br>526155.00<br>237740.0<br>1679920.0 |
| Ae (0-48) (ng) | N<br>Mean<br>SD<br>Median<br>Minimum<br>Maximum | 12<br>367437.28<br>157501.262<br>327290.50<br>119894.3<br>622980.0 | 11<br>785231.91<br>498301.527<br>613642.00<br>269940.0<br>1947570.0 |
| CLr (L/hr) | N<br>Mean<br>SD<br>Median<br>Minimum<br>Maximum | 12<br>6.1047<br>2.2763<br>5.9197<br>2.901<br>9.763 | 11<br>6.7583<br>2.6624<br>6.0225<br>3.529<br>12.006 |
| Fe (%) | N<br>Mean<br>SD<br>Median<br>Minimum<br>Maximum | 12<br>0.919<br>0.3938<br>0.818<br>0.30<br>1.56 | 11<br>1.963<br>1.2458<br>1.534<br>0.67<br>4.87 |

FIG. 10

| Parameter | Statistic | 10 mg QD Cohort 8 N=9 | | 20 mg QD Cohort 9 N=9 | | 40 mg QD Cohort 10 N=9 | |
|---|---|---|---|---|---|---|---|
| Day | | 1 | 14 | 1 | 14 | 1 | 14 |
| AUC(0-tau) (ng.hr/mL) | Mean | 9.00 | 20.6 | 30.4 | 57.1 | 68.6 | 114.5 |
| | %CV | 35.3 | 37.4 | 73.6 | 48.3 | 42.4 | 26.6 |
| Cmax (ng/mL) | Mean | 1.39 | 2.35 | 8.09 | 10.8 | 17.8 | 19.3 |
| | %CV | 30.9 | 45.6 | 91.0 | 86.8 | 47.4 | 45.1 |
| Cmin (ng/mL) | Mean | nc | 0.43 | nc | 0.95 | nc | 2.38 |
| | %CV | | 39.8 | | 32.9 | | 27.3 |
| Tmax (hr) | Median | 1.00 | 0.98 | 1.00 | 1.48 | 1.48 | 1.00 |
| | Min | 0.48 | 0.48 | 0.50 | 0.50 | 0.48 | 0.48 |
| | Max | 2.00 | 2.02 | 2.00 | 2.00 | 2.00 | 1.48 |
| CL/F (L/hr) | Mean | 1244.5 | 569.7 | 959.7 | 436.3 | 697.6 | 373.4 |
| | %CV | 36.6 | 48.5 | 54.8 | 54.4 | 46.3 | 28.1 |
| Vz/F (L) | Mean | 9626.8 | 5041.8 | 6442.1 | 3618.3 | 4486.4 | 3086.5 |
| | %CV | 33.4 | 46.8 | 64.9 | 66.3 | 50.1 | 33.0 |
| CLr (L/hr) | Mean | 7.16 | 6.48 | 6.73 | 6.80 | 7.72 | 6.88 |
| | SD | 1.22 | 1.09 | 1.40 | 1.51 | 2.37 | 1.05 |
| Ae (0-24) (ng) | Mean | 63908.3 | 133516.4 | 187501.2 | 386014.5 | 483564.9 | 781916.1 |
| | SD | 22517.1 | 54251.2 | 125602.1 | 221641.6 | 166529.9 | 229873.0 |
| Fe (%) | Mean | 0.64 | 1.34 | 0.94 | 1.93 | 1.21 | 1.96 |
| | SD | 0.23 | 0.54 | 0.63 | 1.11 | 0.42 | 0.57 |

FIG. 11

| Parameter | Statistics | 10 mg (N=9) | 20 mg (N=9) | 40 mg (N=9) |
|---|---|---|---|---|
| Ae (0-24) (ng) | N<br>Mean<br>SD<br>Median<br>Minimum<br>Maximum | 9<br>63908.26<br>22517.082<br>61001.50<br>32778.3<br>102080.0 | 9<br>187501.17<br>125602.099<br>144746.00<br>83845.5<br>491438.5 | 9<br>483564.94<br>166529.865<br>446106.00<br>244794.0<br>752790.0 |
| CLr (L/hr) | N<br>Mean<br>SD<br>Median<br>Minimum<br>Maximum | 9<br>7.1595<br>1.2178<br>6.8909<br>5.466<br>9.251 | 9<br>6.7303<br>1.3971<br>6.5351<br>3.715<br>8.300 | 9<br>7.7148<br>2.3694<br>7.8814<br>2.774<br>10.448 |
| Fe (%) | N<br>Mean<br>SD<br>Median<br>Minimum<br>Maximum | 9<br>0.639<br>0.2252<br>0.610<br>0.33<br>1.02 | 9<br>0.938<br>0.6280<br>0.724<br>0.42<br>2.46 | 9<br>1.209<br>0.4163<br>1.115<br>0.61<br>1.88 |

FIG. 12

| Parameter | Statistics | 10 mg (N=9) | 20 mg (N=9) | 40 mg (N=9) |
|---|---|---|---|---|
| Ae (0-24) (ng) | N<br>Mean<br>SD<br>Median<br>Minimum<br>Maximum | 9<br>133516.44<br>54251.164<br>141057.00<br>57301.0<br>213979.5 | 9<br>386014.50<br>221641.558<br>333928.00<br>136682.5<br>924280.0 | 9<br>781916.11<br>229873.004<br>702690.00<br>550720.0<br>1235100.0 |
| CLr (L/hr) | N<br>Mean<br>SD<br>Median<br>Minimum<br>Maximum | 9<br>6.4821<br>1.0869<br>6.5597<br>4.933<br>7.834 | 9<br>6.7992<br>1.5060<br>6.5966<br>4.728<br>9.988 | 9<br>6.8776<br>1.0524<br>6.5485<br>5.699<br>8.825 |
| Fe (%) | N<br>Mean<br>SD<br>Median<br>Minimum<br>Maximum | 9<br>1.335<br>0.5425<br>1.411<br>0.57<br>2.14 | 9<br>1.930<br>1.1082<br>1.670<br>0.68<br>4.62 | 9<br>1.955<br>0.5747<br>1.757<br>1.38<br>3.09 |

FIG. 13

| Parameter | LS Mean Ratio (%) Fed/Fasted | 90% CI |
|---|---|---|
| AUC(0-tlqc) (ng·hr/mL) | 55.25 | 43.30, 70.49 |
| AUC(0-inf) (ng·hr/mL) | 55.49 | 43.23, 71.22 |
| Cmax (ng/mL) | 40.96 | 25.78, 65.08 |

FIG. 14

| Dose | N | Day | Geometric Mean (a) | Contrast | % Ratio (b) | 90% Confidence Interval of Ratio (c) |
|---|---|---|---|---|---|---|
| Cohort 8 TAK-385 10 mg | 9 | 4 | 0.21824 | Average of Days 5 to 15 vs Day 4 | 163.92 | (148.86, 180.50) |
| | 9 | 5 | 0.28130 | Average of Days 6 to 15 vs Day 5 | 130.26 | (118.25, 143.50) |
| | 9 | 6 | 0.35238 | Average of Days 7 to 15 vs Day 6 | 104.44 | (94.76, 115.11) |
| | 9 | 7 | 0.38417 | Average of Days 8 to 15 vs Day 7 | 95.28 | (86.40, 105.08) |
| | 9 | 8 | 0.36925 | Average of Days 9 to 15 vs Day 8 | 99.01 | (89.71, 109.27) |
| | 9 | 9 | 0.33428 | Average of Days 10 to 15 vs Day 9 | 111.01 | (100.48, 122.65) |
| | 9 | 10 | 0.33648 | Average of Days 11 to 15 vs Day 10 | 112.47 | (101.66, 124.43) |
| | 9 | 11 | 0.30524 | Average of Days 12 to 15 vs Day 11 | 130.82 | (118.00, 145.04) |
| | 9 | 12 | 0.34917 | Average of Days 13 to 15 vs Day 12 | 119.60 | (107.51, 133.04) |
| | 9 | 13 | 0.42355 | Average of Days 14 to 15 vs Day 13 | 97.90 | (87.44, 109.61) |
| | 9 | 14 | 0.42336 | Day 15 vs Day 14 | 95.93 | (84.19, 109.30) |
| | 9 | 15 | 0.40612 | | | |
| Cohort 9 TAK-385 20 mg | 9 | 4 | 0.50550 | Average of Days 5 to 15 vs Day 4 | 172.20 | (156.54, 189.43) |
| | 9 | 5 | 0.57901 | Average of Days 6 to 15 vs Day 5 | 156.59 | (142.30, 172.33) |
| | 9 | 6 | 1.00968 | Average of Days 7 to 15 vs Day 6 | 88.73 | (80.59, 97.70) |
| | 9 | 7 | 0.95455 | Average of Days 8 to 15 vs Day 7 | 93.12 | (84.52, 102.58) |
| | 9 | 8 | 0.81713 | Average of Days 9 to 15 vs Day 8 | 110.09 | (99.86, 121.38) |
| | 9 | 9 | 0.74287 | Average of Days 10 to 15 vs Day 9 | 125.02 | (113.29, 137.98) |
| | 9 | 10 | 0.95968 | Average of Days 11 to 15 vs Day 10 | 96.15 | (87.00, 106.26) |
| | 9 | 11 | 0.83939 | Average of Days 12 to 15 vs Day 11 | 112.56 | (101.64, 124.65) |
| | 9 | 12 | 0.81200 | Average of Days 13 to 15 vs Day 12 | 122.38 | (110.14, 135.98) |

| Dose | N | Day | Geometric Mean (a) | Contrast | % Ratio (b) | 90% Confidence Interval of Ratio (c) |
|---|---|---|---|---|---|---|
| | 9 | 13 | 1.08388 | Average of Days 14 to 15 vs Day 13 | 87.78 | (78.50, 98.17) |
| | 9 | 14 | 1.02922 | Day 15 vs Day 14 | 85.46 | (75.11, 97.24) |
| | 9 | 15 | 0.87962 | | | |
| Cohort 10 TAK-385 40 mg | 9 | 4 | 1.51622 | Average of Days 6,8,10,12,14, and 15 vs Day 4 | 142.80 | (125.87, 162.02) |
| | 9 | 6 | 2.06631 | Average of Days 8,10,12,14, and 15 vs Day 6 | 105.77 | (93.06, 120.22) |
| | 9 | 8 | 2.28925 | Average of Days 10,12,14, and 15 vs Day 8 | 94.37 | (82.81, 107.54) |
| | 9 | 10 | 2.03910 | Average of Days 12,14, and 15 vs Day 10 | 108.01 | (94.37, 123.61) |
| | 9 | 12 | 2.05625 | Average of Days 14, and 15 vs Day 12 | 110.84 | (96.06, 127.90) |
| | 9 | 14 | 2.60288 | Day 15 vs Day 14 | 76.68 | (65.00, 90.46) |
| | 9 | 15 | 1.99581 | | | |

FIG. 16

| Dose (mg) | LS Mean | | % Ratio | 90% CI |
|---|---|---|---|---|
| | AUC(0-inf) (ng.hr/mL) Day 1 (Ref) | AUC(0-tau) (ng.hr/mL) Day 14 (Test) | | |
| 10 | 16.4 | 19.2 | 116.8 | 87.4, 156.1 |
| 20 | 38.0 | 51.4 | 135.2 | 82.5, 221.4 |
| 40 | 93.6 | 110.8 | 118.5 | 85.9, 163.3 |

|  | Placebo (N=57) | 10mg (N=48) | 20mg (N=56) | 40mg (N=55) | Total (N=216) |
|---|---|---|---|---|---|
| Age (years) (N[%]) | | | | | |
| 20<=-<30 | 1 (1.8) | 1 (2.1) | 2 (3.6) | 1 (1.8) | 5 (2.3) |
| 30<=-<40 | 12 (21.1) | 10 (20.8) | 10 (17.9) | 16 (29.1) | 48 (22.2) |
| 40<=-<50 | 42 (73.7) | 35 (72.9) | 41 (73.2) | 38 (69.1) | 156 (72.2) |
| 50<=-<=Max | 2 (3.5) | 2 (4.2) | 3 (5.4) | 0 (0.0) | 7 (3.2) |
| Age (years) | | | | | |
| N | 57 | 48 | 56 | 55 | 216 |
| Mean | 42.4 | 42.7 | 42.6 | 41.1 | 42.2 |
| SD | 5.05 | 4.59 | 5.32 | 4.37 | 4.87 |
| Minimum | 29 | 28 | 27 | 28 | 27 |
| Q1 | 40.0 | 40.5 | 40.0 | 39.0 | 40.0 |
| Median | 43.0 | 44.0 | 42.5 | 42.0 | 43.0 |
| Q3 | 46.0 | 45.5 | 47.0 | 44.0 | 45.5 |
| Maximum | 51 | 51 | 53 | 49 | 53 |
| Height (cm) (N[%]) | | | | | |
| Min<=-<150 | 1 (1.8) | 5 (10.4) | 0 (0.0) | 2 (3.6) | 8 (3.7) |
| 150<=-<160 | 29 (50.9) | 17 (35.4) | 36 (64.3) | 24 (43.6) | 106 (49.1) |
| 160<=-<170 | 26 (45.6) | 25 (52.1) | 20 (35.7) | 28 (50.9) | 99 (45.8) |
| 170<=-<=Max | 1 (1.8) | 1 (2.1) | 0 (0.0) | 1 (1.8) | 3 (1.4) |
| Height (cm) | | | | | |
| N | 57 | 48 | 56 | 55 | 216 |
| Mean | 159.5 | 158.8 | 157.9 | 160.1 | 159.1 |
| SD | 4.84 | 5.77 | 4.37 | 5.75 | 5.22 |
| Minimum | 149 | 146 | 150 | 148 | 146 |
| Q1 | 156.0 | 155.5 | 154.0 | 157.0 | 155.0 |
| Median | 159.0 | 160.0 | 158.0 | 160.0 | 159.0 |
| Q3 | 163.0 | 163.0 | 162.0 | 165.0 | 163.0 |
| Maximum | 171 | 170 | 165 | 174 | 174 |
| Weight (kg) at Baseline (N[%]) | | | | | |
| Min<=-<50 | 12 (21.1) | 4 (8.3) | 14 (25.0) | 7 (12.7) | 37 (17.1) |
| 50<=-<60 | 17 (29.8) | 30 (62.5) | 31 (55.4) | 32 (58.2) | 110 (50.9) |
| 60<=-<70 | 16 (28.1) | 10 (20.8) | 10 (17.9) | 13 (23.6) | 49 (22.7) |
| 70<=-<80 | 8 (14.0) | 4 (8.3) | 0 (0.0) | 3 (5.5) | 15 (6.9) |
| 80<=-<=Max | 4 (7.0) | 0 (0.0) | 1 (1.8) | 0 (0.0) | 5 (2.3) |

FIG. 30A

|  | Placebo (N=57) | 10mg (N=48) | 20mg (N=56) | 40mg (N=55) | Total (N=216) |
|---|---|---|---|---|---|
| Weight (kg) at Baseline | | | | | |
| N | 57 | 48 | 56 | 55 | 216 |
| Mean | 60.73 | 57.85 | 54.68 | 57.29 | 57.65 |
| SD | 11.759 | 7.781 | 7.660 | 7.136 | 9.050 |
| Minimum | 44.3 | 41.4 | 41.3 | 43.0 | 41.3 |
| Q1 | 50.40 | 52.90 | 49.80 | 52.80 | 51.55 |
| Median | 59.20 | 57.15 | 53.90 | 56.00 | 56.15 |
| Q3 | 69.60 | 62.25 | 58.95 | 61.60 | 62.30 |
| Maximum | 85.6 | 77.8 | 83.0 | 78.2 | 85.6 |
| Body Mass Index ($kg/m^2$) at Baseline (N[%]) | | | | | |
| Min<=-<18.5 | 6 (10.5) | 1 (2.1) | 3 (5.4) | 3 (5.5) | 13 (6.0) |
| 18.5<=-<25.0 | 30 (52.6) | 36 (75.0) | 48 (85.7) | 41 (74.5) | 155 (71.8) |
| 25.0<=-<Max | 21 (36.8) | 11 (22.9) | 5 (8.9) | 11 (20.0) | 48 (22.2) |
| Body Mass Index ($kg/m^2$) at Baseline | | | | | |
| N | 57 | 48 | 56 | 55 | 216 |
| Mean | 23.81 | 22.93 | 21.90 | 22.39 | 22.76 |
| SD | 4.243 | 2.715 | 2.831 | 2.806 | 3.295 |
| Minimum | 17.2 | 17.7 | 17.4 | 15.8 | 15.8 |
| Q1 | 20.50 | 21.15 | 19.95 | 20.50 | 20.40 |
| Median | 22.80 | 22.55 | 21.80 | 21.90 | 22.20 |
| Q3 | 26.30 | 24.20 | 23.25 | 23.70 | 24.40 |
| Maximum | 34.9 | 30.4 | 33.2 | 29.4 | 34.9 |
| Smoking Classification (N[%]) | | | | | |
| Never Smoked | 39 (68.4) | 35 (72.9) | 38 (67.9) | 38 (69.1) | 150 (69.4) |
| Current Smoker | 9 (15.8) | 4 (8.3) | 9 (16.1) | 7 (12.7) | 29 (13.4) |
| Ex-Smoker | 9 (15.8) | 9 (18.8) | 9 (16.1) | 10 (18.2) | 37 (17.1) |
| Birth Experience (N[%]) | | | | | |
| Yes | 30 (52.6) | 25 (52.1) | 29 (51.8) | 20 (36.4) | 104 (48.1) |
| No | 27 (47.4) | 23 (47.9) | 27 (48.2) | 35 (63.6) | 112 (51.9) |
| Disease Duration (year) (N[%]) | | | | | |
| Min<=-<=1 | 21 (36.8) | 16 (33.3) | 16 (28.6) | 21 (38.2) | 74 (34.3) |
| 1<-<=3 | 12 (21.1) | 9 (18.8) | 10 (17.9) | 14 (25.5) | 45 (20.8) |
| 3<-<=5 | 5 (8.8) | 6 (12.5) | 8 (14.3) | 7 (12.7) | 26 (12.0) |
| 5<-<=10 | 11 (19.3) | 11 (22.9) | 14 (25.0) | 9 (16.4) | 45 (20.8) |
| 10<-<=Max | 8 (14.0) | 6 (12.5) | 8 (14.3) | 4 (7.3) | 26 (12.0) |

FIG. 30B

|  | Placebo (N=57) | 10mg (N=48) | 20mg (N=56) | 40mg (N=55) | Total (N=216) |
|---|---|---|---|---|---|
| Disease Duration (year) | | | | | |
| N | 57 | 48 | 56 | 55 | 216 |
| Mean | 3.90 | 4.15 | 4.90 | 2.99 | 3.98 |
| SD | 4.347 | 4.344 | 4.868 | 3.523 | 4.325 |
| Minimum | 0.0 | 0.0 | 0.0 | 0.0 | 0.0 |
| Q1 | 0.20 | 0.50 | 0.60 | 0.30 | 0.40 |
| Median | 2.30 | 3.00 | 3.80 | 1.50 | 2.30 |
| Q3 | 6.20 | 6.20 | 8.30 | 4.50 | 6.00 |
| Maximum | 16.9 | 19.0 | 17.1 | 14.8 | 19.0 |
| Type of Uterine Fibroid | | | | | |
| Subserosal Fibroid (N[%]) | 23 (40.4) | 22 (45.8) | 25 (44.6) | 17 (30.9) | 87 (40.3) |
| Intramural Fibroid (N[%]) | 42 (73.7) | 39 (81.3) | 44 (78.6) | 45 (81.8) | 170 (78.7) |
| Submucosal Fibroid (N[%]) | 12 (21.1) | 11 (22.9) | 11 (19.6) | 11 (20.0) | 45 (20.8) |
| Cervical Fibroid (N[%]) | 1 (1.8) | 1 (2.1) | 1 (1.8) | 2 (3.6) | 5 (2.3) |
| Other Fibroid (N[%]) | 0 (0.0) | 0 (0.0) | 0 (0.0) | 0 (0.0) | 0 (0.0) |
| Stopped Any Medications for Uterine Fibroids (N[%]) | | | | | |
| Yes | 18 (31.6) | 9 (18.8) | 21 (37.5) | 13 (23.6) | 61 (28.2) |
| No | 39 (68.4) | 39 (81.3) | 35 (62.5) | 42 (76.4) | 155 (71.8) |
| Type of Medication for Uterine Fibroid | | | | | |
| GnRH Agonist (N[%]) | 9 (15.8) | 4 (8.3) | 13 (23.2) | 4 (7.3) | 30 (13.9) |
| Herbal Medicine (N[%]) | 9 (15.8) | 4 (8.3) | 6 (10.7) | 7 (12.7) | 26 (12.0) |
| Other Medicines for Uterine Firbroids (N[%]) | 5 (8.8) | 2 (4.2) | 3 (5.4) | 5 (9.1) | 15 (6.9) |
| Any Surgery for Uterine Fibroids (N[%]) | | | | | |
| Yes | 5 (8.8) | 3 (6.3) | 10 (17.9) | 2 (3.6) | 20 (9.3) |
| No | 52 (91.2) | 45 (93.8) | 46 (82.1) | 53 (96.4) | 196 (90.7) |
| Volume of Myoma at Baseline (cm³) (N[%]) | | | | | |
| Min<=-<=28 | 9 (16.1) | 11 (22.9) | 14 (25.5) | 14 (25.9) | 48 (22.5) |
| 28<-<=170 | 36 (64.3) | 25 (52.1) | 27 (49.1) | 27 (50.0) | 115 (54.0) |
| 170<-<=700 | 11 (19.6) | 12 (25.0) | 14 (25.5) | 11 (20.4) | 48 (22.5) |
| 700<-<=Max | 0 (0.0) | 0 (0.0) | 0 (0.0) | 2 (3.7) | 2 (0.9) |
| Volume of Myoma at Baseline (cm³) | | | | | |
| N | 56 | 48 | 55 | 54 | 213 |
| Mean | 136.13 | 115.57 | 118.68 | 138.00 | 127.46 |
| SD | 159.111 | 127.396 | 117.364 | 199.758 | 154.112 |
| Minimum | 10.1 | 9.4 | 8.1 | 14.5 | 8.1 |
| Q1 | 43.55 | 30.65 | 27.10 | 27.20 | 33.60 |
| Median | 82.00 | 61.60 | 72.10 | 68.20 | 69.10 |
| Q3 | 141.25 | 170.85 | 173.60 | 167.00 | 160.90 |
| Maximum | 688.1 | 653.8 | 446.5 | 1040.1 | 1040.1 |

FIG. 30C

| | Placebo (N=57) | 10mg (N=48) | 20mg (N=56) | 40mg (N=55) | Total (N=216) |
|---|---|---|---|---|---|
| Volume of Uterus at Baseline (cm$^3$) (N[%]) | | | | | |
| Min<=-<=28 | 0 (0.0) | 0 (0.0) | 0 (0.0) | 0 (0.0) | 0 (0.0) |
| 28<-<=170 | 16 (28.6) | 16 (33.3) | 13 (23.6) | 16 (29.6) | 61 (28.6) |
| 170<-<=700 | 32 (57.1) | 26 (54.2) | 36 (65.5) | 30 (55.6) | 124 (58.2) |
| 700<-<=Max | 8 (14.3) | 6 (12.5) | 6 (10.9) | 8 (14.8) | 28 (13.1) |
| Volume of Uterus at Baseline (cm$^3$) | | | | | |
| N | 56 | 48 | 55 | 54 | 213 |
| Mean | 366.51 | 322.12 | 363.33 | 406.63 | 365.86 |
| SD | 276.607 | 285.002 | 304.622 | 361.814 | 308.350 |
| Minimum | 47.0 | 37.1 | 54.5 | 36.1 | 36.1 |
| Q1 | 157.00 | 161.05 | 172.70 | 145.00 | 160.90 |
| Median | 262.95 | 212.00 | 271.70 | 290.95 | 251.70 |
| Q3 | 482.60 | 383.75 | 427.50 | 557.60 | 452.80 |
| Maximum | 1281.6 | 1479.1 | 1577.4 | 1929.4 | 1929.4 |
| PBAC Score at Baseline (N[%]) | | | | | |
| 120<=-<200 | 20 (35.1) | 23 (47.9) | 27 (48.2) | 27 (49.1) | 97 (44.9) |
| 200<=-<500 | 27 (47.4) | 20 (41.7) | 21 (37.5) | 26 (47.3) | 94 (43.5) |
| 500<=-<=Max | 10 (17.5) | 5 (10.4) | 8 (14.3) | 2 (3.6) | 25 (11.6) |
| PBAC Score at Baseline | | | | | |
| N | 57 | 48 | 56 | 55 | 216 |
| Mean | 327.9 | 269.4 | 276.5 | 259.9 | 284.3 |
| SD | 292.05 | 160.80 | 165.89 | 190.51 | 211.53 |
| Minimum | 120 | 120 | 123 | 120 | 120 |
| Q1 | 165.0 | 139.0 | 155.0 | 159.0 | 156.5 |
| Median | 232.0 | 211.0 | 214.0 | 219.0 | 222.5 |
| Q3 | 351.0 | 364.5 | 331.0 | 302.0 | 332.5 |
| Maximum | 1838 | 740 | 735 | 1378 | 1838 |
| NRS Score at Baseline (N[%]) | | | | | |
| Min<=-<4 | 57(100.0) | 47 (97.9) | 55 (98.2) | 55(100.0) | 214 (99.1) |
| 4<=-<7 | 0 (0.0) | 1 (2.1) | 1 (1.8) | 0 (0.0) | 2 (0.9) |
| 7<=-<=Max | 0 (0.0) | 0 (0.0) | 0 (0.0) | 0 (0.0) | 0 (0.0) |
| NRS Score at Baseline | | | | | |
| N | 57 | 48 | 56 | 55 | 216 |
| Mean | 0.80 | 0.71 | 0.75 | 0.60 | 0.72 |
| SD | 0.802 | 1.130 | 0.931 | 0.600 | 0.874 |
| Minimum | 0.0 | 0.0 | 0.0 | 0.0 | 0.0 |
| Q1 | 0.20 | 0.20 | 0.15 | 0.10 | 0.20 |
| Median | 0.50 | 0.35 | 0.40 | 0.40 | 0.40 |
| Q3 | 1.10 | 0.80 | 1.00 | 0.90 | 1.00 |
| Maximum | 2.9 | 6.7 | 4.3 | 2.6 | 6.7 |

FIG. 30D

|  | Placebo (N=57) | 10mg (N=48) | 20mg (N=56) | 40mg (N=55) | Total (N=216) |
|---|---|---|---|---|---|
| UFS-QOL Score at Baseline | | | | | |
| Symptom Severity (N[%]) | | | | | |
| Min<=-<=25 | 32 (56.1) | 23 (47.9) | 30 (53.6) | 28 (50.9) | 113 (52.3) |
| 25<-<=50 | 19 (33.3) | 19 (39.6) | 25 (44.6) | 26 (47.3) | 89 (41.2) |
| 50<-<=75 | 5 (8.8) | 6 (12.5) | 1 (1.8) | 1 (1.8) | 13 (6.0) |
| 75<-<=Max | 1 (1.8) | 0 (0.0) | 0 (0.0) | 0 (0.0) | 1 (0.5) |
| Symptom Severity | | | | | |
| N | 57 | 48 | 56 | 55 | 216 |
| Mean | 27.64 | 29.31 | 25.84 | 25.29 | 26.95 |
| SD | 17.726 | 17.291 | 14.431 | 13.989 | 15.875 |
| Minimum | 0.0 | 0.0 | 0.0 | 0.0 | 0.0 |
| Q1 | 12.50 | 18.80 | 15.60 | 12.50 | 15.60 |
| Median | 25.00 | 28.10 | 25.00 | 25.00 | 25.00 |
| Q3 | 40.60 | 39.05 | 40.60 | 34.40 | 40.60 |
| Maximum | 81.3 | 68.8 | 56.3 | 53.1 | 81.3 |
| Concern (N[%]) | | | | | |
| Min<=-<=25 | 42 (73.7) | 33 (68.8) | 39 (69.6) | 42 (76.4) | 156 (72.2) |
| 25<-<=50 | 8 (14.0) | 9 (18.8) | 14 (25.0) | 8 (14.5) | 39 (18.1) |
| 50<-<=75 | 6 (10.5) | 4 (8.3) | 2 (3.6) | 4 (7.3) | 16 (7.4) |
| 75<-<=Max | 1 (1.8) | 2 (4.2) | 1 (1.8) | 1 (1.8) | 5 (2.3) |
| Concern | | | | | |
| N | 57 | 48 | 56 | 55 | 216 |
| Mean | 19.56 | 22.50 | 19.11 | 19.45 | 20.07 |
| SD | 23.362 | 24.145 | 18.417 | 21.119 | 21.682 |
| Minimum | 0.0 | 0.0 | 0.0 | 0.0 | 0.0 |
| Q1 | 5.00 | 5.00 | 5.00 | 0.00 | 5.00 |
| Median | 10.00 | 15.00 | 15.00 | 15.00 | 15.00 |
| Q3 | 30.00 | 32.50 | 30.00 | 25.00 | 30.00 |
| Maximum | 100.00 | 95.0 | 80.0 | 85.00 | 100.0 |
| Activities (N[%]) | | | | | |
| Min<=-<=25 | 47 (82.5) | 44 (91.7) | 52 (92.9) | 47 (85.5) | 190 (88.0) |
| 25<-<=50 | 7 (12.3) | 4 (8.3) | 4 (7.1) | 7 (12.7) | 22 (10.2) |
| 50<-<=75 | 2 (3.5) | 0 (0.0) | 0 (0.0) | 0 (0.0) | 2 (0.9) |
| 75<-<=Max | 1 (1.8) | 0 (0.0) | 0 (0.0) | 1 (1.8) | 2 (0.9) |

FIG. 30E

|  | Placebo (N=57) | 10mg (N=48) | 20mg (N=56) | 40mg (N=55) | Total (N=216) |
|---|---|---|---|---|---|
| Activities | | | | | |
| N | 57 | 48 | 56 | 55 | 216 |
| Mean | 11.03 | 9.75 | 8.61 | 9.49 | 9.72 |
| SD | 17.461 | 11.522 | 11.576 | 14.924 | 14.122 |
| Minimum | 0.0 | 0.0 | 0.0 | 0.0 | 0.0 |
| Q1 | 0.00 | 0.00 | 0.00 | 0.00 | 0.00 |
| Median | 3.60 | 5.35 | 3.60 | 3.60 | 3.60 |
| Q3 | 14.30 | 17.90 | 12.50 | 10.70 | 14.30 |
| Maximum | 82.1 | 46.4 | 50.0 | 78.6 | 82.1 |
| Energy/Mood (N[%]) | | | | | |
| Min<=-<=25 | 45 (78.9) | 41 (85.4) | 45 (80.4) | 46 (83.6) | 177 (81.9) |
| 25<-<=50 | 5 (8.8) | 6 (12.5) | 9 (16.1) | 6 (10.9) | 26 (12.0) |
| 50<-<=75 | 5 (8.8) | 1 (2.1) | 2 (3.6) | 2 (3.6) | 10 (4.6) |
| 75<-<=Max | 2 (3.5) | 0 (0.0) | 0 (0.0) | 1 (1.8) | 3 (1.4) |
| Energy/Mood | | | | | |
| N | 57 | 48 | 56 | 55 | 216 |
| Mean | 17.73 | 13.76 | 13.40 | 15.26 | 15.10 |
| SD | 22.167 | 13.219 | 15.003 | 18.465 | 17.675 |
| Minimum | 0.0 | 0.0 | 0.0 | 0.0 | 0.0 |
| Q1 | 3.60 | 3.60 | 0.00 | 3.60 | 3.60 |
| Median | 10.70 | 8.90 | 10.70 | 7.10 | 7.10 |
| Q3 | 21.40 | 21.40 | 17.90 | 21.40 | 21.40 |
| Maximum | 100.0 | 53.6 | 53.6 | 78.6 | 100.0 |
| Control (N[%]) | | | | | |
| Min<=-<=25 | 45 (78.9) | 41 (85.4) | 52 (92.9) | 45 (81.8) | 183 (84.7) |
| 25<-<=50 | 5 (8.8) | 7 (14.6) | 3 (5.4) | 7 (12.7) | 22 (10.2) |
| 50<-<=75 | 6 (10.5) | 0 (0.0) | 1 (1.8) | 3 (5.5) | 10 (4.6) |
| 75<-<=Max | 1 (1.8) | 0 (0.0) | 0 (0.0) | 0 (0.0) | 1 (0.5) |
| Control | | | | | |
| N | 57 | 48 | 56 | 55 | 216 |
| Mean | 17.63 | 12.71 | 10.45 | 15.18 | 14.05 |
| SD | 21.694 | 13.247 | 11.881 | 18.104 | 16.938 |
| Minimum | 0.0 | 0.0 | 0.0 | 0.0 | 0.0 |
| Q1 | 0.00 | 5.00 | 0.00 | 5.00 | 0.00 |
| Median | 10.00 | 10.00 | 5.00 | 10.00 | 10.00 |
| Q3 | 25.00 | 20.00 | 15.00 | 25.00 | 20.00 |
| Maximum | 95.0 | 50.0 | 55.0 | 75.0 | 95.0 |
| Self-consciousness (N[%]) | | | | | |
| Min<=-<=25 | 47 (82.5) | 38 (79.2) | 46 (82.1) | 38 (69.1) | 169 (78.2) |
| 25<-<=50 | 6 (10.5) | 10 (20.8) | 7 (12.5) | 14 (25.5) | 37 (17.1) |
| 50<-<=75 | 3 (5.3) | 0 (0.0) | 3 (5.4) | 1 (1.8) | 7 (3.2) |
| 75<-<=Max | 1 (1.8) | 0 (0.0) | 0 (0.0) | 2 (3.6) | 3 (1.4) |

FIG. 30F

|  | Placebo (N=57) | 10mg (N=48) | 20mg (N=56) | 40mg (N=55) | Total (N=216) |
|---|---|---|---|---|---|
| Self-consciousness | | | | | |
| N | 57 | 48 | 56 | 55 | 216 |
| Mean | 13.89 | 14.76 | 14.72 | 18.78 | 15.54 |
| SD | 20.437 | 15.493 | 16.739 | 22.406 | 19.046 |
| Minimum | 0.0 | 0.0 | 0.0 | 0.0 | 0.0 |
| Q1 | 0.00 | 0.00 | 0.00 | 0.00 | 0.00 |
| Median | 8.30 | 12.50 | 8.30 | 8.30 | 8.30 |
| Q3 | 16.70 | 25.00 | 25.00 | 33.30 | 25.00 |
| Maximum | 91.7 | 50.0 | 58.3 | 100.0 | 100.0 |
| Sexual Function (N[%]) | | | | | |
| Min<=-<=25 | 45 (78.9) | 40 (83.3) | 48 (85.7) | 42 (76.4) | 175 (81.0) |
| 25<-<=50 | 3 (5.3) | 4 (8.3) | 7 (12.5) | 8 (14.5) | 22 (10.2) |
| 50<-<=75 | 4 (7.0) | 3 (6.3) | 0 (0.0) | 3 (5.5) | 10 (4.6) |
| 75<-<=Max | 5 (8.8) | 1 (2.1) | 1 (1.8) | 2 (3.6) | 9 (4.2) |
| Sexual Function | | | | | |
| N | 57 | 48 | 56 | 55 | 216 |
| Mean | 18.42 | 15.63 | 12.50 | 16.82 | 15.86 |
| SD | 30.990 | 23.843 | 21.052 | 25.025 | 25.495 |
| Minimum | 0.0 | 0.0 | 0.0 | 0.0 | 0.0 |
| Q1 | 0.00 | 0.00 | 0.00 | 0.00 | 0.00 |
| Median | 0.00 | 0.00 | 0.00 | 0.00 | 0.00 |
| Q3 | 25.00 | 25.00 | 25.00 | 25.00 | 25.00 |
| Maximum | 100.0 | 100.0 | 100.0 | 100.0 | 100.0 |
| HRQL Total (N[%]) | | | | | |
| Min<=-<=25 | 45 (78.9) | 37 (77.1) | 46 (82.1) | 44 (80.0) | 172 (79.6) |
| 25<-<=50 | 8 (14.0) | 11 (22.9) | 10 (17.9) | 8 (14.5) | 37 (17.1) |
| 50<-<=75 | 3 (5.3) | 0 (0.0) | 0 (0.0) | 2 (3.6) | 5 (2.3) |
| 75<-<=Max | 1 (1.8) | 0 (0.0) | 0 (0.0) | 1 (1.8) | 2 (0.9) |
| HRQL Total | | | | | |
| N | 57 | 48 | 56 | 55 | 216 |
| Mean | 16.06 | 14.35 | 12.79 | 15.04 | 14.57 |
| SD | 18.797 | 11.914 | 11.510 | 15.536 | 14.801 |
| Minimum | 0.0 | 0.0 | 0.0 | 0.0 | 0.0 |
| Q1 | 3.40 | 4.75 | 3.40 | 6.00 | 3.85 |
| Median | 7.80 | 9.90 | 9.05 | 9.50 | 9.05 |
| Q3 | 20.70 | 23.70 | 18.10 | 20.70 | 21.15 |
| Maximum | 80.2 | 41.4 | 45.7 | 77.6 | 80.2 |
| Hemoglobin at Baseline (g/dL) (N[%]) | | | | | |
| Min<=-<10 | 4 (7.0) | 0 (0.0) | 5 (8.9) | 7 (12.7) | 16 (7.4) |
| 10<=-<12 | 23 (40.4) | 21 (43.8) | 17 (30.4) | 18 (32.7) | 79 (36.6) |
| 12<=-<=Max | 30 (52.6) | 27 (56.3) | 34 (60.7) | 30 (54.5) | 121 (56.0) |

FIG. 30G

|  | Placebo (N=57) | 10mg (N=48) | 20mg (N=56) | 40mg (N=55) | Total (N=216) |
|---|---|---|---|---|---|
| Hemoglobin at Baseline (g/dL) | | | | | |
| N | 57 | 48 | 56 | 55 | 216 |
| Mean | 12.11 | 12.18 | 12.15 | 11.99 | 12.11 |
| SD | 1.504 | 1.159 | 1.407 | 1.699 | 1.456 |
| Minimum | 7.5 | 10.0 | 9.0 | 7.7 | 7.5 |
| Q1 | 11.10 | 11.15 | 11.05 | 10.70 | 11.10 |
| Median | 12.30 | 12.15 | 12.30 | 12.40 | 12.30 |
| Q3 | 13.10 | 12.95 | 13.20 | 13.10 | 13.10 |
| Maximum | 14.9 | 14.7 | 14.8 | 15.0 | 15.0 |
| Hematocrit at Baseline (%) | | | | | |
| N | 57 | 48 | 56 | 55 | 216 |
| Mean | 38.36 | 38.50 | 38.30 | 38.06 | 38.30 |
| SD | 3.739 | 3.128 | 3.882 | 4.275 | 3.775 |
| Minimum | 26.6 | 32.0 | 28.7 | 28.2 | 26.6 |
| Q1 | 36.00 | 36.40 | 35.80 | 35.40 | 35.90 |
| Median | 38.50 | 38.60 | 38.75 | 38.80 | 38.60 |
| Q3 | 41.10 | 41.05 | 40.65 | 41.10 | 41.05 |
| Maximum | 45.3 | 45.2 | 46.7 | 45.3 | 46.7 |
| Serum Iron at Baseline (µg/dL) | | | | | |
| N | 57 | 48 | 56 | 55 | 216 |
| Mean | 64.0 | 63.8 | 62.6 | 56.5 | 61.7 |
| SD | 45.85 | 40.05 | 43.00 | 34.85 | 41.06 |
| Minimum | 10 | 11 | 13 | 9 | 9 |
| Q1 | 27.0 | 33.5 | 31.5 | 28.0 | 31.0 |
| Median | 52.0 | 53.5 | 52.5 | 52.0 | 52.5 |
| Q3 | 87.0 | 84.5 | 83.0 | 81.0 | 84.5 |
| Maximum | 209 | 180 | 208 | 139 | 209 |
| Ferritin at Baseline (ng/mL) | | | | | |
| N | 57 | 48 | 56 | 55 | 216 |
| Mean | 13.93 | 13.17 | 14.79 | 12.94 | 13.73 |
| SD | 12.463 | 12.217 | 11.396 | 12.384 | 12.057 |
| Minimum | 1.2 | 2.6 | 2.1 | 1.2 | 1.2 |
| Q1 | 5.10 | 4.45 | 4.20 | 4.70 | 4.65 |
| Median | 10.00 | 7.65 | 13.85 | 9.70 | 10.00 |
| Q3 | 18.20 | 16.90 | 20.95 | 16.70 | 18.35 |
| Maximum | 55.6 | 57.6 | 47.1 | 67.4 | 67.4 |

FIG. 30H

| Statistics | Placebo (N=57) | 10mg (N=48) | 20mg (N=56) | 40mg (N=55) |
|---|---|---|---|---|
| N | 57 | 48 | 55 | 55 |
| Mean | 405.2 | 268.0 | 126.0 | 21.3 |
| SD | 353.71 | 276.37 | 188.55 | 56.11 |
| Minimum | 53 | 0 | 0 | 0 |
| Q1 | 146.0 | 80.5 | 0.0 | 0.0 |
| Median | 301.0 | 180.0 | 29.0 | 0.0 |
| Q3 | 545.0 | 423.0 | 185.0 | 3.0 |
| Maximun | 2056 | 1392 | 922 | 235 |

FIG. 31

| Statistics | Placebo (N=57) | 10mg (N=48) | 20mg (N=56) | 40mg (N=55) |
|---|---|---|---|---|
| N | 57 | 48 | 55 | 55 |
| Mean | 77.3 | -1.4 | -153.0 | -238.7 |
| SD | 255.54 | 222.94 | 194.83 | 203.34 |
| Minimum | -961 | -406 | -621 | -1378 |
| Q1 | -42.0 | -126.5 | -217.0 | -295.0 |
| Median | 64.0 | -15.5 | -141.0 | -190.0 |
| Q3 | 218.0 | 105.5 | -9.0 | -130.0 |
| Maximun | 533 | 652 | 187 | 26 |

FIG. 32

( ): Percent

|  |  | Treatment | Yes | No | Total |
|---|---|---|---|---|---|
| <Volume of Uterus at Baseline (cm³)> | Min<=-<=28 | Placebo | 0 (0.0) | 0 (0.0) | 0 |
|  |  | 10 mg | 0 (0.0) | 0 (0.0) | 0 |
|  |  | 20 mg | 0 (0.0) | 0 (0.0) | 0 |
|  |  | 40 mg | 0 (0.0) | 0 (0.0) | 0 |
|  | 28<=-<=170 | Placebo | 0 (0.0) | 16 (100) | 16 |
|  |  | 10 mg | 5 (31.3) | 11 (68.8) | 16 |
|  |  | 20 mg | 4 (30.8) | 9 (69.2) | 13 |
|  |  | 40 mg | 12 (75.0) | 4 (25.0) | 16 |
|  | 170<=-<=700 | Placebo | 0 (0.0) | 32 (100) | 32 |
|  |  | 10 mg | 4 (15.4) | 22 (84.6) | 26 |
|  |  | 20 mg | 18 (50.0) | 18 (50.0) | 36 |
|  |  | 40 mg | 26 (86.7) | 4 (13.3) | 30 |
|  | 700<=-<=Max | Placebo | 0 (0.0) | 8 (100) | 8 |
|  |  | 10 mg | 1 (16.7) | 5 (83.3) | 6 |
|  |  | 20 mg | 1 (20.0) | 4 (80.0) | 5 |
|  |  | 40 mg | 7 (87.5) | 1 (12.5) | 8 |

FIG. 33

|  | Placebo (N=57) | | 10mg (N=48) | | 20mg (N=56) | | 40mg (N=55) | |
|---|---|---|---|---|---|---|---|---|
| Visit / Statistics | Observed Value at Visit | Percent Change from Baseline | Observed Value at Visit | Percent Change from Baseline | Observed Value at Visit | Percent Change from Baseline | Observed Value at Visit | Percent Change from Baseline |
| Week 0 | | | | | | | | |
| N | 56 | | 48 | | 55 | | 54 | |
| Mean | 136.13 | | 115.57 | | 118.68 | | 138.00 | |
| SD | 159.111 | | 127.396 | | 117.364 | | 199.758 | |
| Minimum | 10.1 | | 9.4 | | 8.1 | | 14.5 | |
| Q1 | 43.55 | | 30.65 | | 27.10 | | 27.20 | |
| Median | 82.00 | | 61.60 | | 72.10 | | 68.20 | |
| Q3 | 141.25 | | 170.85 | | 173.60 | | 167.00 | |
| Maximum | 688.1 | | 653.8 | | 446.5 | | 1040.1 | |
| Week 2 | | | | | | | | |
| N | 56 | 56 | 48 | 48 | 56 | 55 | 55 | 54 |
| Mean | 134.42 | 8.72 | 116.68 | -4.10 | 98.63 | -16.12 | 109.29 | -16.29 |
| SD | 140.559 | 40.964 | 152.833 | 31.837 | 112.118 | 30.992 | 132.534 | 33.769 |
| Minimum | 7.9 | -76.4 | 2.1 | -89.4 | 4.0 | -71.1 | 3.5 | -79.8 |
| Q1 | 38.50 | -15.10 | 30.55 | -18.05 | 22.35 | -39.90 | 25.60 | -38.30 |
| Median | 87.65 | 2.40 | 64.50 | -2.85 | 53.05 | -17.00 | 55.00 | -16.60 |
| Q3 | 169.55 | 21.65 | 129.25 | 14.50 | 131.05 | 6.20 | 155.90 | -3.80 |
| Maximum | 554.9 | 154.7 | 830.1 | 115.0 | 477.9 | 78.1 | 581.3 | 103.4 |
| Week 4 | | | | | | | | |
| N | 56 | 56 | 47 | 47 | 56 | 55 | 55 | 54 |
| Mean | 136.44 | 2.10 | 90.89 | -16.20 | 101.51 | -15.81 | 100.04 | -27.23 |
| SD | 159.095 | 36.518 | 108.009 | 24.106 | 132.419 | 42.560 | 139.060 | 30.949 |
| Minimum | 6.9 | -67.9 | 4.8 | -75.3 | 2.5 | -81.9 | 3.3 | -80.9 |
| Q1 | 30.80 | -18.15 | 26.70 | -28.80 | 19.60 | -50.60 | 23.00 | -50.40 |
| Median | 77.90 | 3.20 | 54.20 | -14.10 | 46.10 | -21.10 | 45.50 | -29.25 |
| Q3 | 146.15 | 14.75 | 93.20 | -2.20 | 119.70 | 4.80 | 128.50 | -11.70 |
| Maximum | 692.4 | 129.4 | 521.8 | 29.9 | 599.4 | 98.5 | 716.0 | 59.6 |
| Week 8 | | | | | | | | |
| N | 56 | 55 | 47 | 47 | 54 | 53 | 55 | 54 |
| Mean | 132.79 | 7.43 | 97.47 | -17.47 | 86.34 | -27.51 | 86.01 | -37.58 |
| SD | 140.825 | 35.436 | 117.339 | 32.559 | 103.084 | 34.276 | 120.639 | 27.719 |
| Minimum | 8.4 | -79.4 | 4.8 | -74.7 | 2.1 | -83.1 | 1.3 | -92.5 |
| Q1 | 41.90 | -16.40 | 22.40 | -37.10 | 16.40 | -54.60 | 19.20 | -56.50 |
| Median | 89.50 | 4.80 | 51.40 | -19.60 | 39.20 | -25.20 | 40.60 | -35.25 |
| Q3 | 151.65 | 22.50 | 124.20 | 3.70 | 117.50 | -2.50 | 103.40 | -23.50 |
| Maximum | 695.6 | 99.0 | 531.2 | 59.9 | 413.6 | 76.0 | 649.1 | 35.9 |
| Week 12 | | | | | | | | |
| N | 55 | 54 | 47 | 47 | 54 | 53 | 55 | 54 |
| Mean | 128.26 | 10.19 | 97.09 | -22.63 | 75.09 | -36.69 | 77.88 | -38.59 |
| SD | 130.414 | 47.159 | 126.578 | 29.539 | 89.699 | 32.631 | 110.873 | 34.197 |
| Minimum | 11.3 | -72.6 | 2.4 | -79.8 | 1.5 | -87.1 | 2.3 | -88.7 |
| Q1 | 33.50 | -17.10 | 23.80 | -41.70 | 14.20 | -64.30 | 16.50 | -61.50 |
| Median | 86.60 | -0.10 | 44.30 | -22.60 | 33.70 | -38.80 | 45.10 | -40.25 |
| Q3 | 161.10 | 31.30 | 119.80 | 1.60 | 112.60 | -16.00 | 100.70 | -24.60 |
| Maximum | 690.8 | 145.9 | 626.2 | 44.3 | 400.3 | 51.6 | 649.9 | 107.4 |

FIG. 34 (cm³)

| Visit / Statistics | Placebo (N=57) | | 10mg (N=48) | | 20mg (N=56) | | 40mg (N=55) | |
|---|---|---|---|---|---|---|---|---|
| | Observed Value at Visit | Percent Change from Baseline | Observed Value at Visit | Percent Change from Baseline | Observed Value at Visit | Percent Change from Baseline | Observed Value at Visit | Percent Change from Baseline |
| Week 0 | | | | | | | | |
| N | 56 | | 48 | | 55 | | 54 | |
| Mean | 366.51 | | 322.12 | | 363.33 | | 406.63 | |
| SD | 276.607 | | 285.002 | | 304.622 | | 361.814 | |
| Minimum | 47.0 | | 37.1 | | 54.5 | | 36.1 | |
| Q1 | 157.00 | | 161.05 | | 172.70 | | 145.00 | |
| Median | 262.95 | | 212.00 | | 271.70 | | 290.95 | |
| Q3 | 482.60 | | 383.75 | | 427.50 | | 557.60 | |
| Maximum | 1281.6 | | 1479.1 | | 1577.4 | | 1929.4 | |
| Week 2 | | | | | | | | |
| N | 56 | 56 | 48 | 48 | 56 | 55 | 55 | 54 |
| Mean | 384.88 | 7.36 | 305.07 | -2.35 | 294.81 | -14.45 | 293.51 | -21.64 |
| SD | 313.354 | 42.244 | 265.810 | 25.628 | 269.990 | 29.022 | 288.596 | 29.350 |
| Minimum | 31.7 | -64.8 | 33.0 | -50.7 | 37.7 | -64.4 | 47.2 | -86.4 |
| Q1 | 154.75 | -15.80 | 160.05 | -16.60 | 137.95 | -32.00 | 134.70 | -39.10 |
| Median | 295.70 | 0.45 | 203.00 | -4.05 | 208.65 | -20.90 | 204.00 | -25.80 |
| Q3 | 487.25 | 18.30 | 340.95 | 5.15 | 371.15 | -2.20 | 363.90 | -9.50 |
| Maximum | 1353.2 | 220.9 | 1219.2 | 96.2 | 1727.2 | 127.8 | 1746.1 | 92.5 |
| Week 4 | | | | | | | | |
| N | 56 | 56 | 47 | 47 | 56 | 55 | 55 | 54 |
| Mean | 381.17 | 8.98 | 258.10 | -9.69 | 291.73 | -19.50 | 267.74 | -28.05 |
| SD | 298.220 | 46.900 | 171.703 | 26.951 | 327.844 | 30.159 | 275.256 | 33.402 |
| Minimum | 44.2 | -54.2 | 21.4 | -64.1 | 20.9 | -86.3 | 35.1 | -70.9 |
| Q1 | 161.70 | -17.10 | 159.50 | -32.50 | 128.10 | -40.50 | 115.30 | -49.30 |
| Median | 298.70 | -0.55 | 220.70 | -10.50 | 208.55 | -26.60 | 175.30 | -35.85 |
| Q3 | 490.15 | 15.80 | 284.60 | 6.50 | 322.25 | -1.20 | 301.60 | -17.60 |
| Maximum | 1334.5 | 238.0 | 789.5 | 45.6 | 1896.3 | 81.4 | 1646.8 | 108.3 |
| Week 8 | | | | | | | | |
| N | 56 | 55 | 47 | 47 | 54 | 53 | 55 | 54 |
| Mean | 380.19 | 4.28 | 259.64 | -10.66 | 290.93 | -23.00 | 224.91 | -37.91 |
| SD | 289.302 | 40.100 | 190.452 | 32.130 | 413.549 | 33.724 | 227.442 | 31.819 |
| Minimum | 31.3 | -51.5 | 19.3 | -67.6 | 22.6 | -82.1 | 28.6 | -86.3 |
| Q1 | 165.50 | -17.40 | 153.00 | -33.60 | 111.40 | -50.00 | 94.30 | -59.80 |
| Median | 247.10 | 0.10 | 195.10 | -8.00 | 174.60 | -24.20 | 161.30 | -43.60 |
| Q3 | 516.70 | 15.30 | 313.50 | 5.60 | 311.20 | -6.80 | 271.50 | -30.60 |
| Maximum | 1341.6 | 225.7 | 836.9 | 78.5 | 2274.4 | 60.2 | 1404.7 | 85.3 |
| Week 12 | | | | | | | | |
| N | 55 | 54 | 47 | 47 | 54 | 53 | 55 | 54 |
| Mean | 379.38 | 9.75 | 252.93 | -12.10 | 259.44 | -27.70 | 208.03 | -40.90 |
| SD | 300.058 | 57.946 | 175.064 | 29.936 | 322.759 | 28.787 | 209.312 | 37.233 |
| Minimum | 47.5 | -51.0 | 40.3 | -65.7 | 21.6 | -81.8 | 26.7 | -83.5 |
| Q1 | 168.40 | -27.10 | 125.60 | -34.00 | 99.20 | -49.10 | 85.40 | -62.70 |
| Median | 248.10 | 1.20 | 205.60 | -18.60 | 178.85 | -31.30 | 161.90 | -48.85 |
| Q3 | 498.40 | 18.10 | 305.80 | 6.40 | 308.00 | -10.30 | 238.50 | -36.80 |
| Maximum | 1377.9 | 281.5 | 695.3 | 76.9 | 2155.7 | 64.3 | 1207.6 | 111.6 |

FIG. 35 (cm$^3$)

| Analyte/ Treatment | Statistics | Visit | | | | | | | | | | | |
|---|---|---|---|---|---|---|---|---|---|---|---|---|---|
| | | Week 0: 0.5-1.5hr | Week 0: 2-5hr | Week 2: Predose | Week 2: 0.5-1.5hr | Week 2: 2-5hr | Week 4: Predose | Week 4: 0.5-1.5hr | Week 4: 2-5hr | Week 8: Predose | Week 8: 0.5-1.5hr | Week 8: 2-5hr | Week 12 |
| (ng/mL) 10 mg | N | 23 | 15 | 48 | 28 | 17 | 48 | 25 | 19 | 47 | 24 | 18 | 46 |
| | Mean | 1.319 | 0.6589 | 0.2971 | 1.365 | 0.9201 | 0.3137 | 1.350 | 0.8376 | 1.3588 | 1.309 | 1.036 | 0.3163 |
| | SD | 1.7911 | 0.39447 | 0.14874 | 1.1756 | 0.45834 | 0.16146 | 1.0676 | 0.35916 | 0.23052 | 0.69842 | 0.46983 | 0.20811 |
| | Minimum | 0.00 | 0.238 | 0.936 | 0.229 | 0.396 | 0.119 | 0.330 | 0.236 | 0.116 | 0.527 | 0.366 | 0.917 |
| | Q1 | 0.2510 | 0.3960 | 0.1870 | 0.6580 | 0.5930 | 0.2065 | .07550 | 0.6480 | 0.1956 | 0.7230 | 0.7180 | 0.180 |
| | Median | 0.7660 | 0.4820 | 0.2605 | 1.080 | 0.7640 | .02740 | 1.130 | 0.7880 | 0.2780 | 1.130 | 1.025 | 0.2505 |
| | Q3 | 1.480 | 1.100 | 0.3775 | 1.365 | 1.080 | .03810 | 1.520 | 1.080 | 0.4430 | 1.715 | 1.220 | 1.3660 |
| | Maximum | 8.27 | 1.51 | 0.810 | 5.51 | 2.04 | 0.748 | 4.99 | 1.68 | 1.22 | 2.91 | 1.98 | 1.22 |
| 20 mg | N | 32 | 21 | 56 | 36 | 22 | 55 | 35 | 22 | 54 | 36 | 22 | 54 |
| | Mean | 2.346 | 1.855 | 0.6963 | 3.488 | 2.791 | 0.7609 | 3.034 | 2.400 | 0.8073 | 3.049 | 2.580 | 0.7491 |
| | SD | 1.9670 | 1.2762 | 0.33665 | 2.4991 | 1.7543 | 0.32471 | 1.4465 | 1.7940 | 0.61029 | 1.7723 | 1.8209 | 0.41487 |
| | Minimum | 0.210 | 0.288 | 0.00 | 0.912 | 0.856 | 0.264 | 0.988 | 0.731 | 0.273 | 0.782 | 0.979 | 0.0361 |
| | Q1 | 0.5965 | 09350 | 0.4685 | 2.015 | 1.520 | 0.5030 | 1.780 | 1.440 | 0.5520 | 1.825 | 1.490 | 0.5090 |
| | Median | 1.930 | 1.650 | 0.6180 | 2.520 | 2.295 | 0.7120 | 3.070 | 1.850 | 0.6230 | 2.730 | 1.880 | 0.6930 |
| | Q3 | 3.425 | 2.470 | 0.8705 | 4.640 | 3.350 | 1.000 | 4.040 | 2.750 | 0.8650 | 4.115 | 3.060 | 0.8810 |
| | Maximum | 8.05 | 4.96 | 1.82 | 12.1 | 6.88 | 1.69 | 6.33 | 7.45 | 4.23 | 8.60 | 7.37 | 2.66 |
| 40 mg | N | 25 | 15 | 55 | 30 | 17 | 54 | 31 | 20 | 55 | 32 | 20 | 54 |
| | Mean | 4.985 | 3.350 | 1.839 | 7.334 | 6.179 | 1.926 | 6.145 | 4.777 | 1.668 | 7.588 | 6.713 | 1.603 |
| | SD | 4.4498 | 3.1580 | 1.6126 | 5.0789 | 5.4690 | 1.4695 | 3.5320 | 2.7861 | 0.81689 | 7.4398 | 6.0820 | 0.78773 |
| | Minimum | 0.00 | 0.00 | 0.00 | 0.976 | 1.97 | 0.00 | 1.06 | 1.86 | 0.00 | 2.07 | 0.947 | 0.00 |
| | Q1 | 2.600 | 1.340 | 1.060 | 4.420 | 2.960 | 1.040 | 3.110 | 2.645 | 1.040 | 2.930 | 2.220 | 1.040 |
| | Median | 3.780 | 2.070 | 1.580 | 5.805 | 3.860 | 1.520 | 5.480 | 4.225 | 1.520 | 4.965 | 4.730 | 1.390 |
| | Q3 | 7.330 | 3.970 | 2.080 | 10.00 | 7.430 | 2.220 | 8.410 | 6.415 | 2.320 | 8.660 | 9.405 | 2.030 |
| | Maximum | 20.7 | 10.9 | 11.4 | 22.4 | 23.8 | 8.47 | 16.8 | 11.9 | 4.44 | 36.1 | 31.0 | 4.05 |

FIG. 37

| Analyte/Treatment | Statistics | Visit | | | | | | | | | | | |
|---|---|---|---|---|---|---|---|---|---|---|---|---|---|
| | | Week 0: 0.5-1.5hr | Week 0: 2-5hr | Week 2: Predose | Week 2: 0.5-1.5hr | Week 2: 2-5hr | Week 4: Predose | Week 4: 0.5-1.5hr | Week 4: 2-5hr | Week 8: Predose | Week 8: 0.5-1.5hr | Week 8: 2-5hr | Week 12 |
| (ng/mL) 10 mg | N | 22 | 14 | 47 | 27 | 16 | 48 | 23 | 18 | 47 | 22 | 16 | 46 |
| | Mean | 1.368 | 0.6889 | 0.3014 | 1.391 | 0.9327 | 0.3137 | 1.371 | 0.8091 | 0.3588 | 1.306 | 1.089 | 0.3163 |
| | SD | 1.8177 | 0.39113 | 0.14726 | 1.1899 | 0.47031 | 0.16146 | 1.0939 | 0.34682 | 0.23052 | 0.68704 | 0.46894 | 0.20811 |
| | Minimum | 0.00 | 0.271 | 0.0987 | 0.229 | 0.396 | 0.119 | 0.330 | 0.236 | 0.116 | 0.527 | 0.366 | 0.0917 |
| | Q1 | 0.3660 | 0.4250 | 0.1880 | 0.6460 | 0.5585 | 0.2065 | 0.7550 | 0.6480 | 0.1950 | 0.730 | 0.7670 | 0.1870 |
| | Median | 0.8020 | 0.4965 | 0.2610 | 1.080 | 0.8140 | 0.2740 | 1.130 | 0.7820 | 0.2780 | 1.130 | 1.075 | 0.2505 |
| | Q3 | 1.480 | 1.100 | 0.3920 | 1.380 | 1.140 | 0.3810 | 1.520 | 0.8770 | 0.4430 | 1.690 | 1.330 | 0.3660 |
| | Maximum | 8.27 | 1.51 | 0.810 | 5.51 | 2.04 | 0.748 | 4.99 | 1.68 | 1.22 | 2.91 | 1.98 | 1.22 |
| 20 mg | N | 31 | 20 | 56 | 34 | 20 | 55 | 34 | 21 | 53 | 34 | 21 | 54 |
| | Mean | 2.162 | 1.863 | 0.6963 | 3.576 | 2.788 | 0.7609 | 2.952 | 2.435 | 0.8145 | 3.010 | 2.589 | 0.7491 |
| | SD | 1.6966 | 1.3087 | 0.33665 | 2.5338 | 1.8311 | 0.32471 | 1.3827 | 1.8304 | 0.61385 | 1.7997 | 1.8653 | 0.41487 |
| | Minimum | 0.210 | 0.288 | 0.00 | 0.912 | 0.856 | 0.264 | 0.988 | 0.731 | 0.273 | 0.782 | 0.979 | 0.0361 |
| | Q1 | 0.5770 | 0.9210 | 0.4685 | 2.030 | 1.510 | 0.5030 | 1.780 | 1.440 | 0.5560 | 1.770 | 1.490 | 0.5090 |
| | Median | 1.870 | 1.510 | 0.6180 | 2.520 | 2.295 | 0.7120 | 2.960 | 1.870 | 0.6230 | 2.580 | 1.760 | 0.6930 |
| | Q3 | 3.360 | 2.645 | 0.8705 | 4.650 | 3.335 | 1.000 | 3.820 | 2.750 | 0.8650 | 3.800 | 3.060 | 0.8810 |
| | Maximum | 6.14 | 4.96 | 1.82 | 12.1 | 6.88 | 1.69 | 6.33 | 7.45 | 4.23 | 8.60 | 7.37 | 2.66 |
| 40 mg | N | 24 | 14 | 55 | 28 | 15 | 54 | 28 | 18 | 55 | 31 | 20 | 54 |
| | Mean | 5.141 | 3.355 | 1.839 | 7.552 | 6.264 | 1.926 | 6.292 | 4.840 | 1.668 | 7.760 | 6.713 | 1.603 |
| | SD | 4.4751 | 3.2771 | 1.6126 | 5.1144 | 5.7974 | 1.4695 | 3.5866 | 2.8937 | 0.81689 | 7.4981 | 6.0820 | 0.78773 |
| | Minimum | 0.00 | 0.00 | 0.00 | 1.91 | 1.97 | 0.00 | 2.45 | 1.86 | 0.00 | 2.07 | 0.947 | 0.00 |
| | Q1 | 2.665 | 1.340 | 1.060 | 4.520 | 2.730 | 1.040 | 3.265 | 2.570 | 1.040 | 3.030 | 2.220 | 1.040 |
| | Median | 3.790 | 1.955 | 1.580 | 5.805 | 3.860 | 1.520 | 5.190 | 4.225 | 1.520 | 5.050 | 4.730 | 1.390 |
| | Q3 | 7.435 | 3.970 | 2.080 | 10.10 | 7.710 | 2.220 | 8.530 | 7.140 | 2.320 | 9.710 | 9.405 | 2.030 |
| | Maximum | 20.7 | 10.9 | 11.4 | 22.4 | 23.8 | 8.47 | 16.8 | 11.9 | 4.44 | 36.1 | 31.0 | 4.05 |

FIG. 39

| Analyte/Treatment | Statistics | Visit | | | | | | | | | | | |
|---|---|---|---|---|---|---|---|---|---|---|---|---|---|
| | | Week 0: 0.5-1.5hr | Week 0: 2-5hr | Week 2: Predose | Week 2: 0.5-1.5hr | Week 2: 2-5hr | Week 4: Predose | Week 4: 0.5-1.5hr | Week 4: 2-5hr | Week 8: Predose | Week 8: 0.5-1.5hr | Week 8: 2-5hr | Week 12 |
| (ng/mL) | | | | | | | | | | | | | |
| 10 mg | N | 1 | 1 | 1 | 1 | 1 | 0 | 2 | 1 | 0 | 2 | 2 | 0 |
| | Mean | 0.2510 | 0.2380 | 0.09360 | 0.6700 | 0.7180 | | 1.109 | 1.350 | | 1.343 | 0.6160 | |
| | SD | | | | | | | 0.94964 | | | 1.1420 | 0.23900 | |
| | Minimum | 0.251 | 0.238 | 0.0936 | 0.670 | 0.718 | | 0.437 | 1.35 | | 0.535 | 0.447 | |
| | Q1 | 0.2510 | 0.2380 | 0.09360 | 0.6700 | 0.7180 | | 0.4370 | 1.350 | | 0.5350 | 0.4470 | |
| | Median | 0.2510 | 0.2380 | 0.09360 | 0.6700 | 0.7180 | | 1.109 | 1.350 | | 1.343 | 0.6160 | |
| | Q3 | 0.2510 | 0.2380 | 0.09360 | 0.6700 | 0.7180 | | 1.780 | 1.350 | | 2.150 | 0.7850 | |
| | Maximum | 0.251 | 0.238 | 0.0936 | 0.670 | 0.718 | | 1.78 | 1.35 | | 2.15 | 0.785 | |
| 20 mg | N | 1 | 1 | 0 | 2 | 2 | 0 | 1 | 1 | 0 | 2 | 2 | 0 |
| | Mean | 8.050 | 1.680 | | 1.989 | 2.820 | | 5.830 | 1.660 | 0.4290 | 3.710 | 2.370 | |
| | SD | | | | 1.4022 | 0.96167 | | | | | 1.4566 | | |
| | Minimum | 8.05 | 1.68 | | 0.997 | 2.14 | | 5.83 | 1.66 | 0.429 | 2.68 | 2.37 | |
| | Q1 | 8.050 | 1.680 | | 0.9970 | 2.140 | | 5.830 | 1.660 | 0.4290 | 2.680 | 2.370 | |
| | Median | 8.050 | 1.680 | | 1.989 | 2.820 | | 5.830 | 1.660 | 0.4290 | 3.710 | 2.370 | |
| | Q3 | 8.050 | 1.680 | | 2.980 | 3.500 | | 5.830 | 1.660 | 0.4290 | 4.740 | 2.370 | |
| | Maximum | 8.05 | 1.68 | | 2.98 | 3.50 | | 5.83 | 1.66 | 0.429 | 4.74 | 2.37 | |
| 40 mg | N | 1 | 1 | 0 | 2 | 2 | 0 | 3 | 2 | 0 | 1 | 0 | 0 |
| | Mean | 1.240 | 3.280 | | 4.283 | 5.545 | | 4.770 | 4.205 | | 2.270 | | |
| | SD | | | | 4.6768 | 2.6658 | | 3.2133 | 2.1001 | | | | |
| | Minimum | 1.24 | 3.28 | | 0.976 | 3.66 | | 1.06 | 2.72 | | 2.27 | | |
| | Q1 | 1.240 | 3.280 | | 0.9760 | 3.660 | | 1.030 | 2.720 | | 2.270 | | |
| | Median | 1.240 | 3.280 | | 4.283 | 5.545 | | 6.580 | 4.205 | | 2.270 | | |
| | Q3 | 1.240 | 3.280 | | 7.590 | 7.430 | | 6.670 | 5.690 | | 2.270 | | |
| | Maximum | 1.24 | 3.28 | | 7.59 | 7.43 | | 6.67 | 5.69 | | 2.27 | | |

FIG. 40

| Visit / Statistics | Placebo (N=57) | 10mg (N=48) | 20mg (N=56) | 40mg (N=55) |
|---|---|---|---|---|
| Week 6 to 12 | | | | |
| N | 57 | 48 | 55 | 55 |
| Mean | 0.82 | 0.61 | 0.35 | 0.25 |
| SD | 0.989 | 1.235 | 0.618 | 0.542 |
| Minimum | 0.0 | 0.0 | 0.0 | 0.0 |
| Q1 | 0.20 | 0.00 | 0.00 | 0.00 |
| Median | 0.40 | 0.20 | 0.00 | 0.00 |
| Q3 | 1.00 | 0.60 | 0.50 | 0.20 |
| Maximum | 3.8 | 6.5 | 2.9 | 2.5 |
| Week 2 to 6 | | | | |
| N | 57 | 48 | 56 | 55 |
| Mean | 0.82 | 0.67 | 0.48 | 0.29 |
| SD | 1.045 | 1.228 | 0.970 | 0.564 |
| Minimum | 0.0 | 0.0 | 0.0 | 0.0 |
| Q1 | 0.10 | 0.00 | 0.00 | 0.00 |
| Median | 0.40 | 0.20 | 0.10 | 0.00 |
| Q3 | 1.20 | 0.95 | 0.40 | 0.30 |
| Maximum | 3.9 | 6.5 | 4.4 | 2.6 |
| Week 2 to 12 | | | | |
| N | 57 | 48 | 56 | 55 |
| Mean | 0.82 | 0.63 | 0.44 | 0.27 |
| SD | 0.992 | 1.217 | 0.855 | 0.535 |
| Minimum | 0.0 | 0.0 | 0.0 | 0.0 |
| Q1 | 0.10 | 0.00 | 0.00 | 0.00 |
| Median | 0.40 | 0.20 | 0.10 | 0.00 |
| Q3 | 0.90 | 0.65 | 0.30 | 0.20 |
| Maximum | 3.8 | 6.5 | 4.4 | 2.6 |

FIG. 41

|  | Placebo (N=57) | | 10mg (N=48) | | 20mg (N=56) | | 40mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 27.64 | | 29.31 | | 25.84 | | 25.29 | |
| SD | 17.726 | | 17.291 | | 14.431 | | 13.989 | |
| Minimum | 0.0 | | 0.0 | | 0.0 | | 0.0 | |
| Q1 | 12.50 | | 18.80 | | 15.60 | | 12.50 | |
| Median | 25.00 | | 28.10 | | 25.00 | | 25.00 | |
| Q3 | 40.60 | | 39.05 | | 40.60 | | 34.40 | |
| Maximum | 81.3 | | 68.8 | | 56.3 | | 53.1 | |
| Week 4 | | | | | | | | |
| N | 57 | 57 | 48 | 48 | 56 | 56 | 55 | 55 |
| Mean | 25.01 | -2.64 | 23.78 | -5.53 | 23.12 | -2.73 | 24.10 | -1.19 |
| SD | 16.990 | 14.165 | 14.736 | 13.765 | 14.327 | 13.501 | 16.141 | 13.821 |
| Minimum | 0.0 | -37.5 | 0.0 | -34.4 | 0.0 | -34.4 | 0.0 | -34.4 |
| Q1 | 12.50 | -12.50 | 10.95 | -12.50 | 10.95 | -12.50 | 12.50 | -9.30 |
| Median | 18.80 | -3.10 | 21.60 | -6.20 | 23.45 | -6.20 | 18.80 | 0.00 |
| Q3 | 34.40 | 6.20 | 35.95 | 3.10 | 34.40 | 3.10 | 31.30 | 6.20 |
| Maximum | 68.8 | 37.5 | 59.4 | 25.0 | 56.3 | 56.3 | 71.9 | 34.4 |
| Week 8 | | | | | | | | |
| N | 56 | 56 | 47 | 47 | 54 | 54 | 55 | 55 |
| Mean | 25.68 | -1.67 | 24.55 | -5.25 | 18.53 | -7.00 | 18.08 | -7.21 |
| SD | 17.291 | 12.683 | 16.105 | 16.722 | 13.304 | 16.747 | 15.187 | 14.979 |
| Minimum | 0.0 | -31.3 | 0.0 | -53.2 | 0.0 | -56.3 | 0.0 | -40.6 |
| Q1 | 12.50 | -6.30 | 12.50 | -12.50 | 6.30 | -21.90 | 3.10 | -18.70 |
| Median | 25.00 | 0.00 | 18.80 | -3.10 | 18.80 | -4.70 | 18.80 | -9.40 |
| Q3 | 34.40 | 3.20 | 34.40 | 3.20 | 25.00 | 3.10 | 28.10 | 0.00 |
| Maximum | 84.4 | 21.9 | 65.6 | 37.5 | 59.4 | 31.3 | 53.1 | 25.0 |
| Week 12 | | | | | | | | |
| N | 55 | 55 | 47 | 47 | 54 | 54 | 55 | 55 |
| Mean | 23.48 | -3.58 | 23.28 | -6.51 | 16.53 | -8.97 | 14.05 | -11.25 |
| SD | 17.226 | 13.325 | 16.053 | 18.122 | 14.024 | 15.530 | 15.272 | 17.274 |
| Minimum | 0.0 | -37.5 | 0.0 | -40.7 | 0.0 | -43.8 | 0.0 | -40.6 |
| Q1 | 9.40 | -12.50 | 12.50 | -21.90 | 6.30 | -21.90 | 0.00 | -25.00 |
| Median | 21.90 | -3.10 | 21.90 | -3.10 | 12.50 | -7.80 | 9.40 | -12.50 |
| Q3 | 31.30 | 3.20 | 31.30 | 6.30 | 28.10 | 0.00 | 25.00 | 0.00 |
| Maximum | 71.9 | 31.3 | 62.5 | 28.1 | 50.0 | 28.1 | 65.6 | 43.7 |

FIG. 42

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 16.06 | | 14.35 | | 12.79 | | 15.04 | |
| SD | 18.797 | | 11.914 | | 11.510 | | 15.536 | |
| Minimum | 0.0 | | 0.0 | | 0.0 | | 0.0 | |
| Q1 | 3.40 | | 4.75 | | 3.40 | | 6.00 | |
| Median | 7.80 | | 9.90 | | 9.05 | | 9.50 | |
| Q3 | 20.70 | | 23.70 | | 18.10 | | 2.70 | |
| Maximum | 80.2 | | 41.4 | | 45.7 | | 77.6 | |
| Week 4 | | | | | | | | |
| N | 57 | 57 | 48 | 48 | 56 | 56 | 55 | 55 |
| Mean | 14.19 | -1.88 | 11.28 | -3.07 | 11.10 | -1.69 | 11.31 | -3.73 |
| SD | 17.284 | 10.649 | 10.342 | 8.124 | 13.829 | 8.087 | 12.082 | 9.464 |
| Minimum | 0.0 | -33.7 | 0.0 | -27.6 | 0.0 | -33.6 | 0.0 | -37.9 |
| Q1 | 1.70 | -5.10 | 4.30 | -7.35 | 2.60 | -5.60 | 2.60 | -6.00 |
| Median | 6.90 | -0.90 | 7.80 | -2.15 | 6.00 | -1.70 | 6.90 | -1.70 |
| Q3 | 19.00 | 1.70 | 16.35 | 2.55 | 13.80 | 1.30 | 15.50 | 1.70 |
| Maximum | 75.0 | 28.4 | 36.2 | 16.4 | 67.2 | 21.5 | 56.9 | 21.6 |
| Week 8 | | | | | | | | |
| N | 56 | 56 | 47 | 47 | 54 | 54 | 55 | 55 |
| Mean | 13.32 | -2.91 | 13.39 | -1.23 | 9.54 | -2.21 | 11.20 | -3.84 |
| SD | 18.601 | 14.795 | 13.179 | 9.990 | 10.904 | 8.430 | 12.279 | 14.719 |
| Minimum | 0.0 | -78.5 | 0.0 | -16.4 | 0.0 | -33.6 | 0.0 | -68.1 |
| Q1 | 1.70 | -5.15 | 2.60 | -6.90 | 2.60 | -5.20 | 2.60 | -8.60 |
| Median | 4.30 | -2.60 | 9.50 | -0.90 | 6.90 | -1.70 | 6.90 | -3.40 |
| Q3 | 16.40 | 0.00 | 21.60 | 2.60 | 12.10 | 0.90 | 14.70 | 1.70 |
| Maximum | 74.1 | 31.9 | 50.0 | 37.1 | 56.0 | 19.8 | 53.4 | 37.9 |
| Week 12 | | | | | | | | |
| N | 55 | 55 | 47 | 47 | 54 | 54 | 55 | 55 |
| Mean | 14.19 | -2.20 | 13.01 | -1.61 | 9.63 | -2.11 | 9.52 | -5.52 |
| SD | 18.797 | 11.555 | 13.270 | 10.586 | 12.735 | 10.529 | 10885 | 15.871 |
| Minimum | 0.0 | -33.6 | 0.0 | -26.7 | 0.0 | -32.7 | 0.0 | -73.3 |
| Q1 | 1.70 | -6.90 | 3.40 | -7.80 | 1.70 | -6.10 | 1.70 | -10.40 |
| Median | 6.00 | -2.60 | 7.80 | -0.90 | 5.60 | -1.70 | 5.20 | -2.60 |
| Q3 | 20.70 | 1.70 | 19.80 | 1.80 | 12.90 | 0.90 | 13.80 | 1.80 |
| Maximum | 76.7 | 56.0 | 56.0 | 43.0 | 53.4 | 35.4 | 47.4 | 31.9 |

FIG. 43

| Visit / Statistics | Placebo (N=57) Observed Value at Visit | Change from Baseline | 10mg (N=48) Observed Value at Visit | Change from Baseline | 20mg (N=56) Observed Value at Visit | Change from Baseline | 40mg (N=55) Observed Value at Visit | Change from Baseline |
|---|---|---|---|---|---|---|---|---|
| Week 0 | | | | | | | | |
| N | 57 | | 48 | | 56 | | 55 | |
| Mean | 19.56 | | 22.50 | | 19.11 | | 19.45 | |
| SD | 23.362 | | 24.145 | | 18.417 | | 21.119 | |
| Minimum | 0.0 | | 0.0 | | 0.0 | | 0.0 | |
| Q1 | 5.00 | | 5.00 | | 5.00 | | 0.00 | |
| Median | 10.00 | | 15.00 | | 15.00 | | 15.00 | |
| Q3 | 30.00 | | 32.50 | | 30.00 | | 25.00 | |
| Maximum | 100.0 | | 95.0 | | 80.0 | | 85.0 | |
| Week 4 | | | | | | | | |
| N | 57 | 57 | 48 | 48 | 56 | 56 | 55 | 55 |
| Mean | 14.30 | -5.26 | 14.48 | -8.02 | 16.16 | -2.95 | 15.18 | -4.27 |
| SD | 19.398 | 15.992 | 17.692 | 17.587 | 18.141 | 12.569 | 16.100 | 13.382 |
| Minimum | 0.0 | -60.0 | 0.0 | -65.0 | 0.0 | -45.0 | 0.0 | -35.0 |
| Q1 | 0.00 | -10.00 | 0.00 | -10.00 | 0.00 | -7.50 | 0.00 | -15.00 |
| Median | 5.00 | 0.00 | 10.00 | 0.00 | 10.00 | 0.00 | 10.00 | 0.00 |
| Q3 | 20.00 | 0.00 | 20.00 | 0.00 | 22.50 | 2.50 | 25.00 | 5.00 |
| Maximum | 75.0 | 35.0 | 90.0 | 25.0 | 90.0 | 20.0 | 60.0 | 35.0 |
| Week 8 | | | | | | | | |
| N | 56 | 56 | 47 | 47 | 54 | 54 | 55 | 55 |
| Mean | 15.89 | -3.75 | 21.17 | -1.81 | 14.44 | -3.98 | 13.64 | -5.82 |
| SD | 21.786 | 16.875 | 25.264 | 16.662 | 18.725 | 19.556 | 14.828 | 20.944 |
| Minimum | 0.0 | -75.0 | 0.0 | -50.0 | 0.0 | -55.0 | 0.0 | -80.0 |
| Q1 | 0.00 | -10.00 | 0.00 | -5.00 | 0.00 | -10.00 | 0.00 | -15.00 |
| Median | 5.00 | -5.00 | 15.00 | 0.00 | 7.50 | 0.00 | 10.00 | 0.00 |
| Q3 | 25.00 | 5.00 | 30.00 | 5.00 | 20.00 | 0.00 | 20.00 | 5.00 |
| Maximum | 85.0 | 30.0 | 95.0 | 55.0 | 80.0 | 55.0 | 60.0 | 40.0 |
| Week 12 | | | | | | | | |
| N | 55 | 55 | 47 | 47 | 54 | 54 | 55 | 55 |
| Mean | 15.45 | -4.27 | 21.70 | -1.28 | 14.81 | -3.61 | 9.18 | -10.27 |
| SD | 23.180 | 12.451 | 25.158 | 18.693 | 21.390 | 16.963 | 12.163 | 22.698 |
| Minimum | 0.0 | -30.0 | 0.0 | -65.0 | 0.0 | -55.0 | 0.0 | -85.0 |
| Q1 | 0.00 | -10.00 | 0.00 | -5.00 | 0.00 | -15.00 | 0.00 | -20.00 |
| Median | 0.00 | -5.00 | 15.00 | 0.00 | 5.00 | 0.00 | 0.00 | -5.00 |
| Q3 | 20.00 | 0.00 | 25.00 | 5.00 | 25.00 | 5.00 | 20.00 | 0.00 |
| Maximum | 85.0 | 35.0 | 95.0 | 45.0 | 90.0 | 50.0 | 40.0 | 35.0 |

FIG. 44

|  | Placebo (N=57) | | 10mg (N=48) | | 20mg (N=56) | | 40mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 11.03 | | 9.75 | | 8.61 | | 9.49 | |
| SD | 17.461 | | 11.522 | | 11.576 | | 14.924 | |
| Minimum | 0.0 | | 0.0 | | 0.0 | | 0.0 | |
| Q1 | 0.00 | | 0.00 | | 0.00 | | 0.00 | |
| Median | 3.60 | | 5.35 | | 3.60 | | 3.60 | |
| Q3 | 14.30 | | 17.90 | | 12.50 | | 10.70 | |
| Maximum | 82.1 | | 46.4 | | 50.0 | | 78.6 | |
| Week 4 | | | | | | | | |
| N | 57 | 57 | 48 | 48 | 56 | 56 | 55 | 55 |
| Mean | 10.33 | -0.69 | 7.00 | -2.75 | 7.53 | -1.08 | 6.23 | -3.25 |
| SD | 15.878 | 12.302 | 8.895 | 9.174 | 13.953 | 9.983 | 10.156 | 10.011 |
| Minimum | 0.0 | -46.5 | 0.0 | -32.1 | 0.0 | -46.4 | 0.0 | -35.7 |
| Q1 | 0.00 | -3.60 | 0.00 | -7.10 | 0.00 | -5.35 | 0.00 | -3.60 |
| Median | 3.60 | 0.00 | 3.60 | 0.00 | 0.00 | 0.00 | 0.00 | 0.00 |
| Q3 | 14.30 | 3.50 | 10.70 | 3.55 | 3.55 | 1.75 | 7.10 | 0.00 |
| Maximum | 71.4 | 42.8 | 35.7 | 21.4 | 21.4 | 25.0 | 42.9 | 21.4 |
| Week 8 | | | | | | | | |
| N | 56 | 56 | 47 | 47 | 54 | 54 | 55 | 55 |
| Mean | 10.27 | -0.95 | 9.65 | -10.30 | 6.05 | -1.99 | 5.58 | -3.90 |
| SD | 18.957 | 16.973 | 13.730 | 10.291 | 11.621 | 10.300 | 10.091 | 15.588 |
| Minimum | 0.0 | -82.1 | 0.0 | -25.0 | 0.0 | -46.4 | 0.0 | -75.0 |
| Q1 | 0.00 | -7.10 | 0.00 | -3.60 | 0.00 | -7.10 | 0.00 | -3.60 |
| Median | 0.00 | 0.00 | 0.00 | 0.00 | 3.60 | 0.00 | 0.00 | 0.00 |
| Q3 | 10.70 | 0.00 | 21.40 | 0.00 | 7.10 | 0.00 | 7.10 | 0.00 |
| Maximum | 64.3 | 50.0 | 53.6 | 32.2 | 71.4 | 28.5 | 35.7 | 32.1 |
| Week 12 | | | | | | | | |
| N | 55 | 55 | 47 | 47 | 54 | 54 | 55 | 55 |
| Mean | 10.52 | -0.85 | 7.37 | -2.59 | 6.41 | -1.59 | 4.68 | -4.81 |
| SD | 18.422 | 13.487 | 8.698 | 9.288 | 12.378 | 11.269 | 8.845 | 15.981 |
| Minimum | 0.0 | -25.0 | 0.0 | -39.3 | 0.0 | -42.9 | 0.0 | -78.6 |
| Q1 | 0.00 | -7.10 | 0.00 | -7.10 | 0.00 | -3.60 | 0.00 | -7.10 |
| Median | 0.00 | 0.00 | 3.60 | 0.00 | 0.00 | 0.00 | 0.00 | 0.00 |
| Q3 | 10.70 | 0.00 | 14.30 | 3.50 | 7.10 | 0.00 | 3.60 | 0.00 |
| Maximum | 75.0 | 67.9 | 28.6 | 25.0 | 57.1 | 39.3 | 35.7 | 28.6 |

FIG. 45

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 17.73 | | 13.76 | | 13.40 | | 15.26 | |
| SD | 22.167 | | 13.219 | | 15.003 | | 18.465 | |
| Minimum | 0.0 | | 0.0 | | 0.0 | | 0.0 | |
| Q1 | 3.60 | | 3.60 | | 0.00 | | 3.60 | |
| Median | 10.70 | | 8.90 | | 10.70 | | 7.10 | |
| Q3 | 21.40 | | 21.40 | | 17.90 | | 21.40 | |
| Maximum | 100.0 | | 53.6 | | 53.6 | | 78.6 | |
| Week 4 | | | | | | | | |
| N | 57 | 57 | 48 | 48 | 56 | 56 | 55 | 55 |
| Mean | 16.50 | -1.18 | 12.13 | -1.64 | 10.84 | -2.56 | 12.40 | -2.86 |
| SD | 19.171 | 15.066 | 12.754 | 9.381 | 15.421 | 9.594 | 15.510 | 12.616 |
| Minimum | 0.0 | -46.4 | 0.0 | -21.5 | 0.0 | -32.1 | 0.0 | -50.0 |
| Q1 | 3.60 | -3.60 | 3.60 | -7.20 | 0.00 | -7.20 | 0.00 | -7.10 |
| Median | 10.70 | 0.00 | 8.90 | 0.00 | 3.60 | -1.75 | 7.10 | 0.00 |
| Q3 | 25.00 | 3.60 | 17.90 | 3.55 | 14.30 | 3.60 | 17.90 | 3.60 |
| Maximum | 85.7 | 28.6 | 60.7 | 17.9 | 75.0 | 21.4 | 67.9 | 32.1 |
| Week 8 | | | | | | | | |
| N | 56 | 56 | 47 | 47 | 54 | 54 | 55 | 55 |
| Mean | 14.80 | -3.06 | 13.23 | -0.75 | 9.93 | -1.98 | 12.92 | -2.34 |
| SD | 20.723 | 19.288 | 14.963 | 12.480 | 12.362 | 11.139 | 17.262 | 19.706 |
| Minimum | 0.0 | -96.4 | 0.0 | -28.6 | 0.0 | -39.3 | 0.0 | -71.5 |
| Q1 | 0.00 | -7.10 | 0.00 | -7.10 | 0.00 | -7.10 | 0.00 | -7.10 |
| Median | 3.60 | -3.50 | 7.10 | 0.00 | 3.60 | 0.00 | 7.10 | 0.00 |
| Q3 | 25.00 | 3.60 | 21.40 | 3.50 | 17.90 | 3.60 | 17.90 | 3.60 |
| Maximum | 82.1 | 35.7 | 60.7 | 39.3 | 46.4 | 25.0 | 75.0 | 57.1 |
| Week 12 | | | | | | | | |
| N | 55 | 55 | 47 | 47 | 54 | 54 | 55 | 55 |
| Mean | 15.72 | -2.40 | 12.31 | -1.67 | 9.39 | -2.52 | 9.93 | -5.33 |
| SD | 21.798 | 18.736 | 15.310 | 12.024 | 13.672 | 12.644 | 13.949 | 18.597 |
| Minimum | 0.0 | -60.7 | 0.0 | -32.1 | 0.0 | -35.8 | 0.0 | -71.5 |
| Q1 | 0.00 | -7.20 | 0.00 | -7.10 | 0.00 | -7.20 | 0.00 | -10.70 |
| Median | 10.70 | -3.50 | 7.10 | 0.00 | 3.60 | 0.00 | 3.60 | -3.60 |
| Q3 | 21.40 | 7.10 | 21.40 | 3.60 | 14.30 | 0.00 | 14.30 | 0.00 |
| Maximum | 92.9 | 78.6 | 64.3 | 42.9 | 50.0 | 42.9 | 64.3 | 46.4 |

FIG. 46

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 17.63 | | 12.71 | | 10.45 | | 15.18 | |
| SD | 21.694 | | 13.247 | | 11.881 | | 18.104 | |
| Minimum | 0.0 | | 0.0 | | 0.0 | | 0.0 | |
| Q1 | 0.00 | | 5.00 | | 0.00 | | 5.00 | |
| Median | 10.00 | | 10.00 | | 5.00 | | 10.00 | |
| Q3 | 25.00 | | 20.00 | | 15.00 | | 25.00 | |
| Maximum | 95.0 | | 50.0 | | 55.0 | | 75.0 | |
| Week 4 | | | | | | | | |
| N | 57 | 57 | 48 | 48 | 56 | 56 | 55 | 55 |
| Mean | 14.30 | -3.33 | 11.98 | -0.73 | 10.98 | 0.54 | 10.73 | -4.45 |
| SD | 21.701 | 11.739 | 11.928 | 10.964 | 15.475 | 9.519 | 14.318 | 9.985 |
| Minimum | 0.0 | -30.0 | 0.0 | -20.0 | 0.0 | -20.0 | 0.0 | -45.0 |
| Q1 | 0.00 | -10.00 | 0.00 | -7.50 | 0.00 | -5.00 | 0.00 | -10.00 |
| Median | 5.00 | 0.00 | 10.00 | 0.00 | 5.00 | 0.00 | 5.00 | -5.00 |
| Q3 | 15.00 | 0.00 | 20.00 | 5.00 | 12.50 | 2.50 | 15.00 | 0.00 |
| Maximum | 100.0 | 40.0 | 45.0 | 40.0 | 75.0 | 35.0 | 70.0 | 15.0 |
| Week 8 | | | | | | | | |
| N | 56 | 56 | 47 | 47 | 54 | 54 | 55 | 55 |
| Mean | 12.95 | -4.91 | 11.17 | -1.70 | 9.07 | -0.19 | 12.64 | -2.55 |
| SD | 19.135 | 17.149 | 12.520 | 11.716 | 12.998 | 10.987 | 17.765 | 17.766 |
| Minimum | 0.0 | -90.0 | 0.0 | -25.0 | 0.0 | -20.0 | 0.0 | -65.0 |
| Q1 | 0.00 | -10.00 | 5.00 | -5.00 | 0.00 | -5.00 | 0.00 | -10.00 |
| Median | 5.00 | 0.00 | 5.00 | 0.00 | 5.00 | 0.00 | 5.00 | 0.00 |
| Q3 | 17.50 | 0.00 | 15.00 | 0.00 | 15.00 | 0.00 | 15.00 | 0.00 |
| Maximum | 85.0 | 35.0 | 55.0 | 45.0 | 50.0 | 45.0 | 80.0 | 65.0 |
| Week 12 | | | | | | | | |
| N | 55 | 55 | 47 | 47 | 54 | 54 | 55 | 55 |
| Mean | 15.27 | -2.73 | 11.17 | -1.70 | 8.24 | -1.02 | 11.09 | -4.09 |
| SD | 21.909 | 14.524 | 14.265 | 12.652 | 13.073 | 11.508 | 14.773 | 17.562 |
| Minimum | 0.0 | -50.0 | 0.0 | -30.0 | 0.0 | -20.0 | 0.0 | -70.0 |
| Q1 | 0.00 | -10.0 | 0.00 | -5.00 | 0.00 | -5.00 | 0.00 | -5.00 |
| Median | 5.00 | 0.00 | 5.00 | -5.00 | 5.00 | 0.00 | 5.00 | 0.00 |
| Q3 | 25.00 | 0.00 | 20.00 | 0.00 | 10.00 | 0.00 | 15.00 | 0.00 |
| Maximum | 100.0 | 70.0 | 55.0 | 45.0 | 50.0 | 45.0 | 60.0 | 45.0 |

FIG. 47

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 13.89 | | 14.76 | | 14.72 | | 18.78 | |
| SD | 20.437 | | 15.493 | | 16.739 | | 22.046 | |
| Minimum | 0.0 | | 0.0 | | 0.0 | | 0.0 | |
| Q1 | 0.00 | | 0.00 | | 0.00 | | 0.00 | |
| Median | 8.30 | | 12.50 | | 8.30 | | 8.30 | |
| Q3 | 16.70 | | 25.00 | | 25.00 | | 33.30 | |
| Maximum | 91.7 | | 50.0 | | 58.3 | | 100.0 | |
| Week 4 | | | | | | | | |
| N | 57 | 57 | 48 | 48 | 56 | 56 | 55 | 55 |
| Mean | 15.93 | 2.04 | 11.11 | -3.65 | 11.75 | -2.97 | 10.29 | -8.48 |
| SD | 25.646 | 13.097 | 13.021 | 10.010 | 17.027 | 13.147 | 11.995 | 16.553 |
| Minimum | 0.0 | -25.0 | 0.0 | -41.7 | 0.0 | -33.3 | 0.0 | -66.7 |
| Q1 | 0.00 | 0.00 | 0.00 | -8.30 | 0.00 | -8.30 | 0.00 | -16.70 |
| Median | 0.00 | 0.00 | 8.30 | 0.00 | 8.30 | 0.00 | 8.30 | 0.00 |
| Q3 | 25.00 | 8.30 | 16.70 | 0.00 | 16.70 | 0.00 | 16.70 | 0.00 |
| Maximum | 100.0 | 58.3 | 41.7 | 16.7 | 66.7 | 33.4 | 41.7 | 25.0 |
| Week 8 | | | | | | | | |
| N | 56 | 56 | 47 | 47 | 54 | 54 | 55 | 55 |
| Mean | 14.88 | 0.90 | 13.29 | -1.78 | 8.48 | -5.09 | 9.85 | -8.93 |
| SD | 26.007 | 15.460 | 15.412 | 12.758 | 13.098 | 11.833 | 16.129 | 18.479 |
| Minimum | 0.0 | -50.0 | 0.0 | -25.0 | 0.0 | -25.0 | 0.0 | -83.3 |
| Q1 | 0.00 | 0.00 | 0.00 | -8.40 | 0.00 | -8.40 | 0.00 | -16.60 |
| Median | 0.00 | 0.00 | 8.30 | 0.00 | 0.00 | -4.15 | 0.00 | 0.00 |
| Q3 | 16.70 | 0.00 | 25.00 | 0.00 | 16.70 | 0.00 | 16.70 | 0.00 |
| Maximum | 100.0 | 58.3 | 50.0 | 33.3 | 50.0 | 41.7 | 66.7 | 25.0 |
| Week 12 | | | | | | | | |
| N | 55 | 55 | 47 | 47 | 54 | 54 | 55 | 55 |
| Mean | 16.21 | 2.11 | 14.89 | -0.18 | 10.34 | -3.24 | 9.99 | -8.79 |
| SD | 25.176 | 12.746 | 18.049 | 14.896 | 14.199 | 11.027 | 15.831 | 21.060 |
| Minimum | 0.0 | -25.0 | 0.0 | -41.7 | 0.0 | -25.0 | 0.0 | -83.3 |
| Q1 | 0.00 | 0.00 | 0.00 | -8.30 | 0.00 | -8.30 | 0.00 | -25.00 |
| Median | 8.30 | 0.00 | 8.30 | 0.00 | 0.00 | 0.00 | 8.30 | 0.00 |
| Q3 | 25.00 | 8.30 | 25.00 | 8.30 | 16.70 | 0.00 | 8.30 | 0.00 |
| Maximum | 100.0 | 58.3 | 83.3 | 58.3 | 50.0 | 33.3 | 66.7 | 33.4 |

FIG. 48

|  | Placebo (N=57) | | 10mg (N=48) | | 20mg (N=56) | | 40mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 18.42 | | 15.63 | | 12.50 | | 16.82 | |
| SD | 30.990 | | 23.843 | | 21.052 | | 25.025 | |
| Minimum | 0.0 | | 0.0 | | 0.0 | | 0.0 | |
| Q1 | 0.00 | | 0.00 | | 0.00 | | 0.00 | |
| Median | 0.00 | | 0.00 | | 0.00 | | 0.00 | |
| Q3 | 25.00 | | 25.00 | | 25.00 | | 25.00 | |
| Maximum | 100.0 | | 100.0 | | 100.0 | | 100.0 | |
| Week 4 | | | | | | | | |
| N | 57 | 57 | 48 | 48 | 56 | 56 | 55 | 55 |
| Mean | 16.23 | -2.19 | 13.80 | -1.82 | 11.16 | -1.34 | 18.64 | 1.82 |
| SD | 30.706 | 24.677 | 20.986 | 16.709 | 22.320 | 14.632 | 26.557 | 20.330 |
| Minimum | 0.0 | -100.0 | 0.0 | -37.5 | 0.0 | -50.0 | 0.0 | -62.5 |
| Q1 | 0.00 | 0.00 | 0.00 | 0.00 | 0.00 | 0.00 | 0.00 | 0.00 |
| Median | 0.00 | 0.00 | 0.00 | 0.00 | 0.00 | 0.00 | 0.00 | 0.00 |
| Q3 | 25.00 | 0.00 | 25.00 | 0.00 | 12.50 | 0.00 | 37.50 | 0.00 |
| Maximum | 100.0 | 100.0 | 75.0 | 50.0 | 100.0 | 37.5 | 100.0 | 100.0 |
| Week 8 | | | | | | | | |
| N | 56 | 56 | 47 | 47 | 54 | 54 | 55 | 55 |
| Mean | 10.94 | -7.81 | 13.30 | -2.66 | 10.88 | -0.23 | 17.27 | 0.45 |
| SD | 25.457 | 26.281 | 20.590 | 20.346 | 23.797 | 23.226 | 25.740 | 20.828 |
| Minimum | 0.0 | -100.0 | 0.0 | -62.5 | 0.0 | -50.0 | 0.0 | -75.0 |
| Q1 | 0.00 | -6.25 | 0.00 | -12.5 | 0.00 | 0.00 | 0.00 | 0.00 |
| Median | 0.00 | 0.00 | 0.00 | 0.00 | 0.00 | 0.00 | 0.00 | 0.00 |
| Q3 | 0.00 | 0.00 | 25.00 | 0.00 | 12.50 | 0.00 | 25.00 | 0.00 |
| Maximum | 100.0 | 50.0 | 75.0 | 75.0 | 100.0 | 100.0 | 100.0 | 62.5 |
| Week 12 | | | | | | | | |
| N | 55 | 55 | 47 | 47 | 54 | 54 | 55 | 55 |
| Mean | 12.73 | -6.15 | 15.16 | -0.80 | 11.11 | 0.00 | 21.14 | 4.32 |
| SD | 26.624 | 22.932 | 26.572 | 22.931 | 26.115 | 24.160 | 31.629 | 26.045 |
| Minimum | 0.0 | -100.0 | 0.0 | -62.5 | 0.0 | -50.0 | 0.0 | -50.0 |
| Q1 | 0.00 | 0.00 | 0.00 | -12.50 | 0.00 | 0.00 | 0.00 | 0.00 |
| Median | 0.00 | 0.00 | 0.00 | 0.00 | 0.00 | 0.00 | 0.00 | 0.00 |
| Q3 | 0.00 | 0.00 | 25.00 | 0.00 | 12.50 | 0.00 | 25.0 | 12.50 |
| Maximum | 100.0 | 37.5 | 100.0 | 75.0 | 100.0 | 75.0 | 100.0 | 100.0 |

FIG. 49

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 12.11 | | 12.18 | | 12.15 | | 11.99 | |
| SD | 1.504 | | 1.159 | | 1.407 | | 1.699 | |
| Minimum | 7.5 | | 10.0 | | 9.0 | | 7.7 | |
| Q1 | 11.10 | | 11.15 | | 11.05 | | 10.70 | |
| Median | 12.30 | | 12.15 | | 12.30 | | 12.40 | |
| Q3 | 13.10 | | 12.95 | | 13.20 | | 13.10 | |
| Maximum | 14.9 | | 14.7 | | 14.8 | | 15.0 | |
| Week 4 | | | | | | | | |
| N | 57 | 57 | 48 | 48 | 56 | 56 | 55 | 55 |
| Mean | 12.15 | 0.03 | 12.56 | 0.38 | 12.79 | 0.64 | 12.45 | 0.47 |
| SD | 1.518 | 0.983 | 1.191 | 0.888 | 1.495 | 0.946 | 1.644 | 0.823 |
| Minimum | 8.5 | -2.5 | 9.4 | -1.1 | 9.6 | -1.6 | 8.2 | -1.1 |
| Q1 | 11.00 | -0.30 | 11.90 | -0.30 | 11.75 | 0.20 | 11.40 | -0.10 |
| Median | 12.20 | 0.00 | 12.50 | 0.25 | 13.00 | 0.20 | 12.80 | 0.40 |
| Q3 | 13.30 | 0.50 | 13.40 | 0.85 | 13.80 | 1.20 | 13.70 | 1.00 |
| Maximum | 14.5 | 2.9 | 14.9 | 3.2 | 16.0 | 3.1 | 15.1 | 2.9 |
| Week 8 | | | | | | | | |
| N | 56 | 56 | 47 | 47 | 54 | 54 | 55 | 55 |
| Mean | 12.33 | 0.13 | 12.55 | 0.34 | 12.88 | 0.77 | 12.81 | 0.83 |
| SD | 1.554 | 1.174 | 1.164 | 0.847 | 1.379 | 1.028 | 1.543 | 0.974 |
| Minimum | 6.5 | -4.6 | 9.7 | -1.6 | 9.2 | -1.5 | 8.8 | -0.8 |
| Q1 | 11.30 | -0.55 | 11.60 | -0.30 | 12.40 | 0.20 | 12.10 | 0.10 |
| Median | 12.70 | 0.05 | 12.50 | 0.40 | 13.10 | 0.65 | 13.30 | 0.80 |
| Q3 | 13.35 | 0.85 | 13.40 | 1.00 | 13.70 | 1.20 | 13.80 | 1.10 |
| Maximum | 15.2 | 3.6 | 14.9 | 2.1 | 15.8 | 4.7 | 15.2 | 4.4 |
| Week 12 | | | | | | | | |
| N | 55 | 55 | 47 | 47 | 54 | 54 | 55 | 55 |
| Mean | 12.42 | 0.20 | 12.55 | 0.35 | 12.94 | 0.83 | 12.91 | 0.92 |
| SD | 1.353 | 1.003 | 1.350 | 1.055 | 1.225 | 1.161 | 1.380 | 1.183 |
| Minimum | 8.6 | -2.3 | 8.08 | -2.2 | 9.3 | -2.8 | 9.4 | -1.1 |
| Q1 | 11.60 | -0.40 | 11.70 | -0.20 | 12.50 | 0.10 | 12.30 | 0.00 |
| Median | 12.50 | 0.00 | 12.80 | 0.20 | 13.10 | 0.70 | 13.20 | 0.80 |
| Q3 | 13.50 | 0.80 | 13.30 | 1.00 | 13.90 | 1.50 | 14.10 | 1.40 |
| Maximum | 15.1 | 2.7 | 15.3 | 2.8 | 15.6 | 3.6 | 15.1 | 4.8 |
| Follow-up | | | | | | | | |
| N | 57 | 57 | 48 | 48 | 56 | 56 | 55 | 55 |
| Mean | 12.04 | -0.08 | 12.15 | -0.03 | 12.52 | 0.37 | 12.62 | 0.63 |
| SD | 1.521 | 1.067 | 1.232 | 0.936 | 1.276 | 1.318 | 1.199 | 1.280 |
| Minimum | 7.8 | -4.0 | 8.9 | -2.1 | 8.9 | -4.7 | 9.4 | -1.6 |
| Q1 | 11.00 | -0.60 | 11.45 | -0.65 | 11.75 | -0.30 | 12.10 | -0.20 |
| Median | 12.20 | 0.00 | 12.20 | -0.05 | 12.70 | 0.20 | 12.90 | 0.40 |
| Q3 | 13.20 | 0.40 | 13.00 | 0.40 | 13.45 | 1.05 | 13.60 | 1.30 |
| Maximum | 15.4 | 2.6 | 15.1 | 2.7 | 14.6 | 3.7 | 14.5 | 5.6 |

FIG. 50 (g/dL)

| | Placebo (N=19) | | 10mg (N=14) | | 20mg (N=22) | | 40mg (N=12) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 19 | | 14 | | 22 | | 12 | |
| Mean | 11.45 | | 11.93 | | 12.19 | | 11.48 | |
| SD | 1.713 | | 0.934 | | 1.340 | | 2.276 | |
| Minimum | 7.5 | | 10.6 | | 9.5 | | 7.7 | |
| Q1 | 11.00 | | 11.20 | | 11.60 | | 9.85 | |
| Median | 11.60 | | 11.85 | | 12.30 | | 11.65 | |
| Q3 | 12.80 | | 12.80 | | 12.70 | | 13.05 | |
| Maximum | 14.0 | | 13.9 | | 14.8 | | 15.0 | |
| Week 4 | | | | | | | | |
| N | 19 | 19 | 14 | 14 | 22 | 22 | 12 | 12 |
| Mean | 12.06 | 0.61 | 13.26 | 1.34 | 13.36 | 1.17 | 12.56 | 1.08 |
| SD | 1.828 | 1.058 | 0.928 | 0.771 | 1.221 | 1.040 | 2.128 | 1.161 |
| Minimum | 8.5 | -2.1 | 11.4 | 0.4 | 11.2 | -0.9 | 8.2 | -0.9 |
| Q1 | 10.60 | 0.00 | 12.50 | 0.40 | 12.80 | 0.60 | 12.05 | 0.30 |
| Median | 12.20 | 0.70 | 13.30 | 1.35 | 13.00 | 1.05 | 13.05 | 1.05 |
| Q3 | 13.30 | 1.20 | 13.80 | 1.80 | 14.00 | 1.40 | 13.95 | 2.00 |
| Maximum | 14.5 | 2.9 | 14.9 | 3.2 | 16.0 | 3.4 | 15.1 | 2.9 |
| Week 8 | | | | | | | | |
| N | 18 | 18 | 14 | 14 | 22 | 22 | 12 | 12 |
| Mean | 12.87 | 1.19 | 13.04 | 1.11 | 13.42 | 1.23 | 13.12 | 1.63 |
| SD | 1.270 | 0.953 | 0.987 | 0.555 | 1.199 | 1.357 | 1.862 | 1.418 |
| Minimum | 10.6 | -0.6 | 11.5 | 0.4 | 11.2 | -1.5 | 8.8 | -0.2 |
| Q1 | 12.20 | 0.60 | 12.20 | 0.80 | 12.80 | 0.40 | 12.70 | 0.75 |
| Median | 12.90 | 1.15 | 13.15 | 0.95 | 13.35 | 1.20 | 13.75 | 1.10 |
| Q3 | 13.60 | 1.90 | 13.60 | 1.60 | 14.20 | 1.80 | 14.35 | 2.65 |
| Maximum | 15.2 | 3.6 | 14.9 | 2.1 | 15.8 | 4.7 | 14.8 | 4.4 |
| Week 12 | | | | | | | | |
| N | 18 | 18 | 14 | 14 | 22 | 22 | 12 | 12 |
| Mean | 12.66 | 0.99 | 12.99 | 1.06 | 13.47 | 1.28 | 13.28 | 1.80 |
| SD | 1.542 | 1.002 | 1.574 | 1.336 | 1.048 | 1.491 | 1.605 | 1.684 |
| Minimum | 8.6 | -0.9 | 8.8 | -2.2 | 11.1 | -2.8 | 9.4 | -0.8 |
| Q1 | 11.80 | 0.30 | 12.40 | 0.30 | 13.00 | 0.40 | 12.50 | 0.40 |
| Median | 12.65 | 1.10 | 13.15 | 1.10 | 13.45 | 1.35 | 13.90 | 1.85 |
| Q3 | 13.90 | 1.50 | 14.00 | 2.10 | 14.10 | 2.10 | 14.30 | 3.00 |
| Maximum | 15.1 | 2.7 | 15.3 | 2.8 | 15.6 | 3.6 | 14.9 | 4.8 |
| Follow-up | | | | | | | | |
| N | 19 | 19 | 14 | 14 | 22 | 22 | 12 | 12 |
| Mean | 11.77 | 0.32 | 12.21 | 0.29 | 12.79 | 0.60 | 12.74 | 1.26 |
| SD | 1.849 | 1.488 | 1.494 | 1.130 | 1.342 | 1.759 | 1.282 | 1.991 |
| Minimum | 7.8 | -4.0 | 8.9 | -2.1 | 9.2 | -4.7 | 9.5 | -1.6 |
| Q1 | 10.70 | -0.40 | 11.50 | -0.40 | 11.90 | 0.20 | 12.35 | -0.10 |
| Median | 12.10 | 0.60 | 12.55 | 0.35 | 12.95 | 0.60 | 13.05 | 1.25 |
| Q3 | 13.20 | 1.30 | 13.20 | 0.70 | 13.90 | 1.60 | 13.65 | 2.30 |
| Maximum | 15.4 | 2.6 | 14.5 | 2.7 | 14.6 | 3.7 | 14.0 | 5.6 |

Note: Iron drug concomitant Medications that started prior to and were ongoing at Baseline.

FIG. 51

|  | Placebo (N=38) | | 10mg (N=34) | | 20mg (N=34) | | 40mg (N=43) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 38 | | 34 | | 34 | | 43 | |
| Mean | 12.44 | | 12.28 | | 12.13 | | 12.13 | |
| SD | 1.287 | | 1.238 | | 1.469 | | 1.504 | |
| Minimum | 10.6 | | 10.0 | | 9.0 | | 8.6 | |
| Q1 | 11.20 | | 11.10 | | 10.90 | | 11.10 | |
| Median | 12.45 | | 12.40 | | 12.40 | | 12.60 | |
| Q3 | 13.60 | | 13.20 | | 13.30 | | 13.10 | |
| Maximum | 14.9 | | 14.7 | | 14.7 | | 14.6 | |
| Week 4 | | | | | | | | |
| N | 38 | 38 | 34 | 34 | 34 | 34 | 43 | 43 |
| Mean | 12.19 | -0.26 | 12.26 | -0.1 | 12.42 | 0.29 | 12.42 | 0.30 |
| SD | 1.362 | 0.812 | 1.176 | 0.538 | 1.556 | 0.701 | 1.512 | 0.618 |
| Minimum | 8.6 | -2.5 | 9.4 | -1.1 | 9.6 | -1.6 | 8.7 | -1.1 |
| Q1 | 11.00 | -0.60 | 11.70 | -0.30 | 11.20 | -0.20 | 11.40 | -0.10 |
| Median | 12.25 | -0.20 | 12.45 | 0.00 | 12.90 | 0.30 | 12.80 | 0.30 |
| Q3 | 13.30 | 0.10 | 12.90 | 0.30 | 13.10 | 0.60 | 13.70 | 0.70 |
| Maximum | 14.3 | 2.6 | 14.6 | 1.6 | 15.2 | 1.9 | 15.1 | 1.6 |
| Week 8 | | | | | | | | |
| N | 38 | 38 | 33 | 33 | 32 | 32 | 43 | 43 |
| Mean | 12.07 | -0.38 | 12.35 | 0.02 | 12.51 | 0.46 | 12.73 | 0.60 |
| SD | 1.625 | 0.905 | 1.186 | 0.737 | 1.389 | 0.559 | 1.455 | 0.674 |
| Minimum | 6.5 | -4.6 | 9.7 | -1.6 | 9.2 | -0.7 | 9.3 | -0.8 |
| Q1 | 10.70 | -0.70 | 11.50 | -0.30 | 11.60 | 0.05 | 12.00 | 0.10 |
| Median | 12.50 | -0.30 | 12.30 | -0.20 | 12.60 | 0.50 | 13.10 | 0.60 |
| Q3 | 13.20 | 0.10 | 13.30 | 0.50 | 13.55 | 0.90 | 13.70 | 0.90 |
| Maximum | 14.8 | 1.0 | 14.4 | 1.6 | 14.8 | 1.4 | 15.2 | 2.0 |
| Week 12 | | | | | | | | |
| N | 37 | 37 | 33 | 33 | 32 | 32 | 43 | 43 |
| Mean | 12.60 | -0.18 | 12.37 | 0.05 | 12.57 | 0.52 | 12.80 | 0.67 |
| SD | 1.256 | 0.756 | 1.223 | 0.748 | 1.217 | 0.744 | 1.313 | 0.879 |
| Minimum | 9.8 | -2.3 | 9.6 | -1.9 | 9.3 | -1.3 | 9.5 | -1.1 |
| Q1 | 11.50 | -0.50 | 11.60 | -0.30 | 12.10 | 0.10 | 12.10 | -0.10 |
| Median | 12.40 | -0.20 | 12.70 | 0.00 | 12.65 | 0.55 | 12.90 | 0.70 |
| Q3 | 13.30 | 0.40 | 13.20 | 0.50 | 13.40 | 0.95 | 13.90 | 1.20 |
| Maximum | 14.9 | 1.3 | 14.7 | 1.6 | 14.3 | 2.2 | 15.1 | 2.9 |
| Follow-up | | | | | | | | |
| N | 38 | 38 | 34 | 34 | 34 | 34 | 43 | 43 |
| Mean | 12.17 | -0.27 | 12.16 | -0.15 | 12.35 | 0.22 | 12.58 | 0.45 |
| SD | 1.336 | 0.725 | 1.131 | 0.829 | 1.220 | 0.931 | 1.189 | 0.961 |
| Minimum | 9.5 | -2.2 | 9.9 | -1.8 | 8.9 | -1.7 | 9.4 | -1.3 |
| Q1 | 11.10 | -0.60 | 11.40 | -0.70 | 11.60 | -0.30 | 11.70 | -0.20 |
| Median | 12.25 | -0.20 | 12.10 | -0.15 | 12.55 | 0.00 | 12.90 | 0.30 |
| Q3 | 13.30 | 0.10 | 12.90 | 0.40 | 13.30 | 0.80 | 13.30 | 1.20 |
| Maximum | 14.7 | 1.5 | 15.1 | 1.9 | 14.2 | 2.7 | 14.5 | 2.7 |

Note: Iron drug concomitant Medications that started prior to and were ongoing at Baseline.

FIG. 52

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 38.36 | | 38.50 | | 38.30 | | 38.06 | |
| SD | 3.739 | | 3.128 | | 3.882 | | 4.275 | |
| Minimum | 26.6 | | 32.0 | | 28.7 | | 28.2 | |
| Q1 | 36.00 | | 36.40 | | 35.80 | | 35.40 | |
| Median | 38.50 | | 38.60 | | 38.75 | | 38.80 | |
| Q3 | 41.10 | | 41.05 | | 40.65 | | 41.10 | |
| Maximum | 45.3 | | 45.2 | | 46.7 | | 45.3 | |
| Week 4 | | | | | | | | |
| N | 57 | 57 | 48 | 48 | 56 | 56 | 55 | 55 |
| Mean | 38.31 | -0.05 | 39.48 | 0.97 | 40.06 | 1.76 | 39.44 | 1.37 |
| SD | 3.985 | 2.738 | 3.327 | 2.346 | 3.773 | 2.572 | 4.012 | 2.551 |
| Minimum | 28.9 | -7.2 | 29.7 | -2.9 | 31.0 | -4.1 | 28.9 | -3.5 |
| Q1 | 35.70 | -1.4 | 38.00 | -0.60 | 37.70 | 0.35 | 37.90 | -0.60 |
| Median | 38.50 | 0.00 | 38.95 | 0.80 | 40.30 | 1.40 | 40.10 | 1.10 |
| Q3 | 42.10 | 1.50 | 42.60 | 2.25 | 42.20 | 2.85 | 42.00 | 2.90 |
| Maximum | 44.9 | 8.9 | 47.3 | 9.0 | 47.8 | 10.9 | 45.6 | 9.8 |
| Week 8 | | | | | | | | |
| N | 56 | 56 | 47 | 47 | 54 | 54 | 55 | 55 |
| Mean | 38.79 | 0.22 | 39.43 | 0.84 | 4.39 | 2.16 | 40.23 | 2.17 |
| SD | 3.932 | 3.140 | 3.154 | 2.225 | 3.389 | 2.874 | 3.620 | 2.832 |
| Minimum | 23.3 | -12.3 | 31.8 | -4.6 | 29.7 | -5.6 | 32.7 | -2.6 |
| Q1 | 36.60 | -1.35 | 37.30 | -0.60 | 39.20 | 0.70 | 38.00 | 0.10 |
| Median | 39.25 | 0.05 | 39.30 | 0.70 | 40.80 | 2.00 | 40.90 | 1.50 |
| Q3 | 41.15 | 1.70 | 41.90 | 2.30 | 42.00 | 3.60 | 43.10 | 3.80 |
| Maximum | 47.3 | 10.6 | 47.0 | 6.5 | 48.1 | 14.1 | 46.9 | 12.1 |
| Week 12 | | | | | | | | |
| N | 55 | 55 | 47 | 47 | 54 | 54 | 55 | 55 |
| Mean | 39.13 | 0.51 | 39.37 | 0.77 | 40.54 | 2.31 | 40.53 | 2.46 |
| SD | 3.324 | 2.583 | 3.639 | 2.792 | 3.003 | 3.522 | 3.307 | 3.455 |
| Minimum | 29.5 | -6.0 | 29.3 | -8.5 | 32.8 | -8.0 | 33.2 | -4.4 |
| Q1 | 37.00 | -1.10 | 37.60 | -0.90 | 39.30 | 0.30 | 38.20 | 0.40 |
| Median | 39.50 | 0.30 | 39.70 | 0.80 | 40.60 | 2.15 | 40.80 | 1.80 |
| Q3 | 41.20 | 2.00 | 41.20 | 2.60 | 42.40 | 3.50 | 43.20 | 4.50 |
| Maximum | 45.4 | 9.5 | 48.2 | 7.7 | 49.0 | 11.5 | 46.3 | 12.6 |
| Follow-up | | | | | | | | |
| N | 57 | 57 | 48 | 48 | 56 | 56 | 55 | 55 |
| Mean | 38.09 | -0.27 | 38.15 | -0.35 | 39.11 | 0.81 | 39.45 | 1.39 |
| SD | 3.625 | 2.959 | 3.311 | 2.391 | 3.085 | 3.753 | 2.923 | 3.560 |
| Minimum | 28.8 | -13.0 | 30.7 | -7.1 | 30.9 | -14.4 | 33.4 | -4.6 |
| Q1 | 36.20 | -1.30 | 36.30 | -1.90 | 37.70 | -0.95 | 37.10 | -1.00 |
| Median | 38.40 | 0.10 | 38.20 | -0.40 | 39.25 | 0.20 | 40.20 | 1.00 |
| Q3 | 40.30 | 1.00 | 40.55 | 0.85 | 41.15 | 3.05 | 40.70 | 3.30 |
| Maximum | 46.1 | 8.5 | 45.6 | 6.0 | 44.9 | 11.3 | 44.3 | 14.2 |

FIG. 53

| Visit / Statistics | Placebo (N=57) Observed Value at Visit | Placebo (N=57) Change from Baseline | 10mg (N=48) Observed Value at Visit | 10mg (N=48) Change from Baseline | 20mg (N=56) Observed Value at Visit | 20mg (N=56) Change from Baseline | 40mg (N=55) Observed Value at Visit | 40mg (N=55) Change from Baseline |
|---|---|---|---|---|---|---|---|---|
| Week 0 | | | | | | | | |
| N | 57 | | 48 | | 56 | | 55 | |
| Mean | 64.0 | | 63.8 | | 62.6 | | 56.5 | |
| SD | 45.85 | | 40.05 | | 43.00 | | 34.85 | |
| Minimum | 10 | | 11 | | 13 | | 9 | |
| Q1 | 27.0 | | 33.5 | | 31.5 | | 28.0 | |
| Median | 52.0 | | 53.5 | | 52.5 | | 52.0 | |
| Q3 | 87.0 | | 84.5 | | 83.0 | | 81.0 | |
| Maximum | 209 | | 180 | | 208 | | 139 | |
| Week 4 | | | | | | | | |
| N | 57 | 57 | 48 | 48 | 56 | 56 | 55 | 55 |
| Mean | 68.1 | 4.1 | 72.8 | 9.0 | 77.4 | 14.8 | 77.6 | 21.1 |
| SD | 55.53 | 48.48 | 40.58 | 44.95 | 49.74 | 55.47 | 44.81 | 41.36 |
| Minimum | 13 | -118 | 18 | -113 | 18 | -167 | 10 | -78 |
| Q1 | 37.0 | -16.0 | 42.5 | -3.0 | 40.0 | -5.5 | 40.0 | -4.0 |
| Median | 50.0 | -1.0 | 66.5 | 11.0 | 64.5 | 13.5 | 74.0 | 18.0 |
| Q3 | 76.0 | 14.0 | 93.5 | 23.5 | 101.0 | 41.5 | 114.0 | 48.0 |
| Maximum | 316 | 212 | 204 | 164 | 206 | 176 | 187 | 168 |
| Week 8 | | | | | | | | |
| N | 56 | 56 | 47 | 47 | 54 | 54 | 55 | 55 |
| Mean | 68.3 | 3.3 | 67.3 | 3.0 | 84.2 | 23.2 | 78.2 | 21.7 |
| SD | 54.24 | 43.57 | 34.74 | 37.99 | 49.42 | 45.36 | 41.91 | 37.30 |
| Minimum | 14 | -96 | 17 | -125 | 17 | -94 | 18 | -43 |
| Q1 | 32.0 | -19.5 | 38.0 | -20.0 | 45.0 | -4.0 | 49.0 | -3.0 |
| Median | 55.0 | -1.5 | 58.0 | 3.0 | 82.0 | 21.5 | 77.0 | 15.0 |
| Q3 | 92.0 | 23.0 | 92.0 | 26.0 | 107.0 | 44.0 | 101.0 | 47.0 |
| Maximum | 311 | 114 | 146 | 76 | 276 | 201 | 185 | 133 |
| Week 12 | | | | | | | | |
| N | 55 | 55 | 47 | 47 | 54 | 54 | 55 | 55 |
| Mean | 68.1 | 2.3 | 75.3 | 11.0 | 85.7 | 24.7 | 82.0 | 25.5 |
| SD | 49.17 | 57.87 | 16.94 | 42.94 | 44.40 | 53.53 | 36.93 | 44.43 |
| Minimum | 11 | -190 | 12 | -86 | 19 | -95 | 15 | -70 |
| Q1 | 27.0 | -28.0 | 35.0 | -9.0 | 58.0 | 2.0 | 55.0 | 3.0 |
| Median | 65.0 | 1.0 | 61.0 | 11.0 | 82.5 | 24.5 | 78.0 | 24.0 |
| Q3 | 88.0 | 29.0 | 108.0 | 39.0 | 102.0 | 53.0 | 103.5 | 43.0 |
| Maximum | 244 | 186 | 204 | 101 | 260 | 185 | 177 | 143 |
| Follow-up | | | | | | | | |
| N | 57 | 57 | 48 | 48 | 56 | 56 | 55 | 55 |
| Mean | 70.4 | 6.4 | 68.9 | 5.1 | 80.9 | 18.3 | 78.8 | 22.3 |
| SD | 49.09 | 4.82 | 44.66 | 49.58 | 54.16 | 59.45 | 43.80 | 42.49 |
| Minimum | 7 | -99 | 14 | -141 | 10 | -126 | 15 | -41 |
| Q1 | 29.0 | -1.0 | 36.5 | -13.5 | 44.0 | -80.5 | 43.0 | -6.0 |
| Median | 61.0 | 3.0 | 63.5 | 0.0 | 71.0 | 16.0 | 80.0 | 16.0 |
| Q3 | 100.0 | 26.0 | 92.5 | 25.5 | 103.5 | 41.5 | 107.0 | 46.0 |
| Maximum | 238 | 152 | 251 | 196 | 286 | 211 | 223 | 134 |

FIG. 54

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 13.93 | | 13.17 | | 14.79 | | 12.94 | |
| SD | 12.463 | | 12.217 | | 11.396 | | 12.384 | |
| Minimum | 1.2 | | 2.6 | | 2.1 | | 1.2 | |
| Q1 | 5.10 | | 4.45 | | 4.20 | | 4.70 | |
| Median | 10.00 | | 7.65 | | 13.85 | | 9.70 | |
| Q3 | 18.20 | | 16.90 | | 20.95 | | 16.70 | |
| Maximum | 55.6 | | 57.6 | | 47.1 | | 67.4 | |
| Week 4 | | | | | | | | |
| N | 57 | 57 | 48 | 48 | 56 | 56 | 55 | 55 |
| Mean | 11.37 | -2.56 | 14.71 | 1.54 | 14.77 | -0.02 | 15.15 | 2.21 |
| SD | 9.325 | 5.106 | 16.372 | 9.133 | 11.536 | 8.471 | 15.133 | 7.042 |
| Minimum | 1.7 | -26.5 | 1.7 | -16.1 | 2.2 | -26.7 | 1.1 | -21.9 |
| Q1 | 5.10 | -4.20 | 4.10 | -1.80 | 4.05 | -2.75 | 4.40 | -0.50 |
| Median | 7.50 | -1.40 | 7.60 | 0.25 | 12.35 | 0.20 | 11.70 | 0.80 |
| Q3 | 15.40 | 0.10 | 17.05 | 2.25 | 19.95 | 2.30 | 19.40 | 5.40 |
| Maximum | 42.3 | 5.6 | 81.5 | 38.4 | 44.8 | 19.8 | 73.6 | 23.5 |
| Week 8 | | | | | | | | |
| N | 56 | 56 | 47 | 47 | 54 | 54 | 55 | 55 |
| Mean | 11.37 | -2.78 | 12.43 | -0.95 | 16.34 | 1.81 | 18.10 | 5.16 |
| SD | 8.497 | 8.446 | 11.117 | 4.763 | 15.659 | 11.703 | 16.177 | 8.646 |
| Minimum | 1.1 | -32.9 | 2.5 | -13.9 | 2.3 | -23.4 | 2.1 | -14.4 |
| Q1 | 4.75 | -4.40 | 4.10 | -1.80 | 4.00 | -2.90 | 4.90 | -0.10 |
| Median | 8.50 | -0.95 | 9.80 | -0.10 | 14.50 | 0.10 | 14.80 | 2.60 |
| Q3 | 17.20 | 0.75 | 17.90 | 1.10 | 23.90 | 6.00 | 24.60 | 8.00 |
| Maximum | 35.5 | 19.7 | 52.8 | 13.0 | 87.9 | 47.5 | 72.7 | 32.4 |
| Week 12 | | | | | | | | |
| N | 55 | 55 | 47 | 47 | 54 | 54 | 55 | 55 |
| Mean | 11.01 | -3.30 | 10.81 | -2.56 | 18.03 | 3.50 | 21.84 | 8.91 |
| SD | 9.349 | 7.110 | 9.489 | 6.833 | 14.427 | 10.229 | 21.509 | 13.131 |
| Minimum | 1.6 | -28.0 | 2.4 | -20.1 | 1.9 | -17.4 | 1.6 | -13.6 |
| Q1 | 4.20 | -7.00 | 4.00 | -6.90 | 5.20 | -1.20 | 6.20 | 0.90 |
| Median | 8.40 | -1.40 | 7.20 | -0.40 | 15.60 | 1.00 | 13.40 | 4.80 |
| Q3 | 15.50 | 0.00 | 15.70 | 0.30 | 27.70 | 8.80 | 28.30 | 12.80 |
| Maximum | 40.4 | 22.7 | 43.4 | 14.0 | 61.6 | 29.0 | 88.9 | 54.5 |
| Follow-up | | | | | | | | |
| N | 57 | 57 | 48 | 48 | 56 | 56 | 55 | 55 |
| Mean | 11.34 | -2.59 | 10.79 | -2.38 | 17.81 | 3.02 | 16.79 | 3.85 |
| SD | 12.785 | 12.953 | 9.252 | 7.432 | 17.367 | 14.410 | 15.048 | 8.559 |
| Minimum | 1.4 | -30.9 | 2.1 | -25.8 | 2.1 | -24.6 | 1.4 | -13.8 |
| Q1 | 3.80 | -8.60 | 4.15 | -3.45 | 5.35 | -3.00 | 5.10 | -0.20 |
| Median | 7.30 | -1.30 | 6.80 | -0.20 | 13.00 | 0.60 | 12.00 | 1.60 |
| Q3 | 12.70 | 1.00 | 15.30 | 1.50 | 23.45 | 5.25 | 22.20 | 6.40 |
| Maximum | 81.2 | 76.0 | 38.7 | 7.9 | 83.2 | 57.6 | 60.0 | 35.0 |

FIG. 55

|  | Placebo (N=57) | | 10 mg (N=48) | | 20 mg (N=56) | | 40 mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 3.675 | | 4.139 | | 4.524 | | 3.762 | |
| SD | 1.6512 | | 2.8170 | | 2.9313 | | 2.1693 | |
| Minimum | 1.55 | | 0.90 | | 0.00 | | 0.80 | |
| Q1 | 2.430 | | 2.400 | | 2.640 | | 2.220 | |
| Median | 3.280 | | 3.480 | | 3.485 | | 3.520 | |
| Q3 | 4.480 | | 4.930 | | 5.230 | | 4.230 | |
| Maximum | 8.82 | | 16.31 | | 13.85 | | 13.91 | |
| Week 2 | | | | | | | | |
| N | 57 | 57 | 48 | 48 | 56 | 56 | 55 | 55 |
| Mean | 6.805 | 3.130 | 5.897 | 1.758 | 3.029 | -1.495 | 1.467 | -2.296 |
| SD | 8.1723 | 8.1934 | 6.1026 | 6.8703 | 2.8767 | 4.4337 | 1.7612 | 2.2667 |
| Minimum | 0.63 | -6.16 | 0.44 | -15.45 | 0.15 | -12.83 | 0.00 | -7.04 |
| Q1 | 2.470 | -0.820 | 2.020 | -1.625 | 1.220 | -2.875 | 0.430 | -3.630 |
| Median | 4.530 | 0.790 | 3.815 | 0.990 | 2.520 | -1.005 | 0.720 | -2.610 |
| Q3 | 7.310 | 3.780 | 6.550 | 3.275 | 3.725 | 0.035 | 1.630 | -0.800 |
| Maximum | 44.06 | 41.63 | 29.22 | 26.26 | 19.58 | 17.39 | 8.21 | 4.74 |
| Week 4 | | | | | | | | |
| N | 57 | 57 | 48 | 48 | 56 | 56 | 55 | 55 |
| Mean | 4.121 | 0.446 | 3.808 | -0.332 | 3.210 | -1.314 | 1.263 | -2.499 |
| SD | 2.5260 | 2.1496 | 3.8253 | 5.0298 | 8.6339 | 9.0577 | 1.7096 | 2.7978 |
| Minimum | 1.42 | -4.20 | 0.74 | -12.77 | 0.13 | -12.43 | 0.00 | -13.64 |
| Q1 | 2.580 | -0.440 | 1.750 | -2.570 | 0.840 | -3.510 | 0.270 | -3.790 |
| Median | 3.600 | 0.110 | 2.565 | -0.860 | 1.750 | -1.705 | 0.550 | -2.870 |
| Q3 | 4.670 | 0.900 | 4.810 | 1.315 | 2.780 | -0.730 | 1.310 | -0.910 |
| Maximum | 14.43 | 9.25 | 24.28 | 22.70 | 65.42 | 59.73 | 6.66 | 4.54 |

FIG. 57

|  | Placebo (N=57) | | 10 mg (N=48) | | 20 mg (N=56) | | 40 mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 8 | | | | | | | | |
| N | 56 | 56 | 47 | 47 | 54 | 54 | 55 | 55 |
| Mean | 6.695 | 3.063 | 5.953 | 1.817 | 3.091 | -1.301 | 1.555 | -2.207 |
| SD | 15.2870 | 14.7377 | 8.6143 | 8.9287 | 2.9400 | 4.3215 | 3.3988 | 3.9825 |
| Minimum | 0.95 | -4.15 | 0.79 | -13.80 | 0.11 | -12.45 | 0.00 | -13.34 |
| Q1 | 2.290 | -1.040 | 2.180 | -1.250 | 1.090 | -3.030 | 0.330 | -3.610 |
| Median | 3.565 | 0.115 | 3.460 | -0.040 | 2.260 | -1.025 | 0.570 | -2.920 |
| Q3 | 5.585 | 1.990 | 5.370 | 3.270 | 4.000 | 1.140 | 1.120 | -1.100 |
| Maximum | 115.40 | 107.39 | 53.80 | 47.47 | 14.17 | 8.43 | 24.07 | 20.62 |
| Week 12 | | | | | | | | |
| N | 55 | 55 | 47 | 47 | 54 | 54 | 55 | 55 |
| Mean | 5.308 | 1.665 | 5.054 | 0.918 | 3.703 | -0.690 | 1.757 | -2.005 |
| SD | 4.2232 | 4.4314 | 5.9127 | 6.4867 | 5.5331 | 6.7558 | 3.4673 | 4.1533 |
| Minimum | 0.86 | -7.15 | 0.61 | -15.05 | 0.14 | -12.90 | 0.00 | -13.04 |
| Q1 | 2.570 | -0.160 | 1.850 | -0.960 | 1.270 | -3.070 | 0.350 | -3.490 |
| Median | 4.130 | 0.590 | 3.550 | 0.420 | 2.685 | -0.895 | 0.650 | -2.760 |
| Q3 | 5.750 | 2.510 | 5.870 | 1.920 | 4.190 | 1.120 | 1.850 | -1.080 |
| Maximum | 21.11 | 19.05 | 36.55 | 29.70 | 39.99 | 37.43 | 24.60 | 21.96 |
| Follow-up | | | | | | | | |
| N | 57 | 57 | 48 | 48 | 56 | 56 | 55 | 55 |
| Mean | 6.630 | 2.955 | 5.837 | 1.697 | 6.470 | 1.946 | 6.806 | 3.044 |
| SD | 8.7266 | 8.4124 | 5.7110 | 5.6417 | 8.5785 | 8.0722 | 9.9265 | 9.8358 |
| Minimum | 0.66 | -4.84 | 0.68 | -11.58 | 1.05 | -6.45 | 1.02 | -4.05 |
| Q1 | 2.750 | -0.270 | 1.965 | -1.105 | 3.045 | -1.120 | 2.770 | -0.890 |
| Median | 4.360 | 0.670 | 3.860 | 0.415 | 4.255 | 0.745 | 3.930 | 0.570 |
| Q3 | 5.540 | 2.600 | 7.390 | 1.900 | 5.340 | 1.915 | 6.650 | 3.330 |
| Maximum | 58.98 | 53.56 | 27.31 | 20.46 | 53.35 | 51.35 | 64.34 | 60.37 |

FIG. 57 (Cont.)

|  | Placebo (N=57) | | 10mg (N=48) | | 20mg (N=56) | | 40mg (N=55) | |
|---|---|---|---|---|---|---|---|---|
| Visit / Statistics | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 7.645 | | 8.086 | | 8.391 | | 7.760 | |
| SD | 3.4048 | | 5.7335 | | 7.1619 | | 4.8656 | |
| Minimum | 3.18 | | 2.56 | | 1.49 | | 3.50 | |
| Q1 | 5.410 | | 5.190 | | 5.005 | | 4.630 | |
| Median | 6.580 | | 6.645 | | 6.125 | | 6.140 | |
| Q3 | 8.560 | | 9.000 | | 8.380 | | 8.880 | |
| Maximum | 19.09 | | 35.25 | | 38.21 | | 29.85 | |
| Week 2 | | | | | | | | |
| N | 57 | 57 | 48 | 48 | 56 | 56 | 55 | 55 |
| Mean | 5.152 | -2.493 | 6.426 | -1.660 | 6.241 | -2.150 | 4.931 | -2.829 |
| SD | 6.2489 | 5.7479 | 3.4331 | 6.0057 | 2.8654 | 6.8712 | 2.7708 | 5.5737 |
| Minimum | 1.52 | -13.10 | 1.74 | -30.40 | 2.08 | -29.14 | 1.04 | -25.89 |
| Q1 | 2.750 | -4.310 | 4.215 | -2.735 | 4.295 | -2.625 | 3.370 | -4.650 |
| Median | 3.570 | -2.740 | 5.990 | -0.615 | 5.705 | -0.675 | 4.280 | -2.140 |
| Q3 | 5.240 | -1.130 | 7.860 | 0.935 | 7.465 | 0.900 | 6.290 | -0.200 |
| Maximum | 46.40 | 32.79 | 18.57 | 8.81 | 16.18 | 9.15 | 17.08 | 13.52 |
| Week 4 | | | | | | | | |
| N | 57 | 57 | 48 | 48 | 56 | 56 | 55 | 55 |
| Mean | 6.349 | -1.296 | 5.613 | -2.474 | 5.115 | -3.276 | 3.837 | -3.923 |
| SD | 4.7191 | 4.391 | 3.1100 | 5.7228 | 3.3136 | 7.4297 | 2.1475 | 4.9573 |
| Minimum | 1.69 | -13.47 | 1.24 | -32.70 | 1.72 | -30.39 | 0.62 | -26.61 |
| Q1 | 4.020 | -3.480 | 2.940 | -4.635 | 3.075 | -4.440 | 1.970 | -5.450 |
| Median | 5.280 | -1.140 | 5.225 | -0.765 | 4.660 | -1.420 | 3.710 | -2.960 |
| Q3 | 6.780 | 0.010 | 7.125 | 0.640 | 5.910 | 0.165 | 5.660 | -1.240 |
| Maximum | 31.55 | 15.78 | 14.11 | 3.97 | 23.22 | 14.59 | 9.27 | 3.85 |
| Week 8 | | | | | | | | |
| N | 56 | 56 | 47 | 47 | 54 | 54 | 55 | 55 |
| Mean | 7.447 | -0.241 | 6.241 | -1.885 | 5.098 | -3.423 | 3.631 | -4.130 |
| SD | 8.9223 | 7.8464 | 3.0392 | 6.7324 | 2.2181 | 7.8873 | 2.1796 | 4.6422 |
| Minimum | 1.39 | -12.86 | 1.54 | -33.43 | 1.26 | -36.40 | 0.71 | -25.62 |
| Q1 | 3.555 | -3.060 | 4.160 | -2.430 | 3.070 | -4.490 | 1.910 | -5.800 |
| Median | 5.080 | -1.620 | 6.150 | -0.180 | 4.840 | -0.875 | 3.210 | -3.200 |
| Q3 | 7.745 | 0.495 | 7.720 | 1.340 | 6.890 | 0.920 | 4.930 | -1.570 |
| Maximum | 49.96 | 34.19 | 16.31 | 8.54 | 10.62 | 4.76 | 10.09 | 3.28 |
| Week 12 | | | | | | | | |
| N | 55 | 55 | 47 | 47 | 54 | 54 | 55 | 55 |
| Mean | 6.999 | -0.660 | 6.065 | -2.061 | 5.526 | -2.995 | 3.970 | -3.790 |
| SD | 6.8985 | 5.4495 | 3.1520 | 6.2541 | 2.0815 | 7.7752 | 3.0045 | 5.0147 |
| Minimum | 1.01 | -13.01 | 1.24 | -33.05 | 1.24 | -30.90 | 0.68 | -25.77 |
| Q1 | 3.420 | -3.120 | 3.020 | -3.370 | 4.270 | -3.730 | 2.020 | -5.900 |
| Median | 5.140 | -1.040 | 6.200 | -1.060 | 5.710 | -0.720 | 2.950 | -3.180 |
| Q3 | 6.770 | 0.370 | 7.580 | 1.540 | 7.360 | 1.190 | 6.090 | -1.680 |
| Maximum | 39.76 | 26.15 | 15.70 | 5.47 | 9.02 | 4.34 | 18.77 | 12.78 |

FIG. 59

| Follow-up | | | | | | | | |
|---|---|---|---|---|---|---|---|---|
| N | 57 | 57 | 48 | 48 | 56 | 56 | 55 | 55 |
| Mean | 6.445 | -1.200 | 6.940 | -1.146 | 6.733 | -1.659 | 5.669 | -2.091 |
| SD | 5.2518 | 4.7664 | 6.8303 | 7.4756 | 7.8938 | 8.1339 | 6.4089 | 7.0762 |
| Minimum | 1.46 | -11.15 | 0.00 | -28.49 | 0.76 | -34.32 | 1.21 | -15.50 |
| Q1 | 3.720 | -3.050 | 2.810 | -3.535 | 2.460 | -4.230 | 2.260 | -4.040 |
| Median | 5.030 | -1.500 | 5.365 | -1.035 | 4.830 | -1.540 | 3.890 | -2.550 |
| Q3 | 7.190 | -0.060 | 7.270 | 1.165 | 6.930 | 1.460 | 6.090 | -1.130 |
| Maximum | 33.67 | 20.06 | 35.76 | 23.38 | 49.80 | 21.70 | 34.36 | 30.80 |

(mIU/mL)

FIG. 59 (Cont.)

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 52.7 | | 65.3 | | 74.6 | | 55.1 | |
| SD | 41.84 | | 54.56 | | 118.12 | | 50.95 | |
| Minimum | 0 | | 0 | | 0 | | 0 | |
| Q1 | 31.0 | | 31.0 | | 28.0 | | 31.0 | |
| Median | 41.0 | | 46.5 | | 44.0 | | 40.0 | |
| Q3 | 71.0 | | 83.5 | | 65.6 | | 59.0 | |
| Maximum | 275 | | 284 | | 684 | | 294 | |
| Week 2 | | | | | | | | |
| N | 57 | 57 | 48 | 48 | 56 | 56 | 55 | 55 |
| Mean | 186.1 | 133.4 | 121.9 | 56.5 | 80.8 | 6.1 | 20.4 | -34.7 |
| SD | 135.66 | 132.49 | 136.59 | 147.12 | 135.31 | 182.94 | 59.46 | 75.91 |
| Minimum | 18 | 0 | 0 | -214 | 0 | -667 | 0 | -294 |
| Q1 | 95.0 | 54.0 | 29.5 | -13.0 | 0.0 | -38.5 | 0.0 | -47.0 |
| Median | 142.0 | 104.0 | 82.5 | 11.0 | 25.0 | -14.5 | 0.0 | -34.0 |
| Q3 | 223.0 | 168.0 | 138.5 | 85.5 | 58.0 | 13.5 | 19.0 | -21.0 |
| Maximum | 781 | 743 | 571 | 515 | 544 | 522 | 407 | 369 |
| Week 4 | | | | | | | | |
| N | 57 | 57 | 48 | 48 | 56 | 56 | 55 | 55 |
| Mean | 77.8 | 25.1 | 94.7 | 29.3 | 45.8 | -28.8 | 11.3 | -43.8 |
| SD | 60.29 | 61.02 | 173.48 | 181.53 | 65.44 | 128.50 | 37.39 | 58.25 |
| Minimum | 0 | -199 | 0 | -222 | 0 | -656 | 0 | -294 |
| Q1 | 37.0 | -7.0 | 22.5 | -42.5 | 0.0 | -42.0 | 0.0 | -55.0 |
| Median | 55.0 | 13.0 | 58.0 | -9.0 | 23.5 | -15.0 | 0.0 | -35.0 |
| Q3 | 102.0 | 67.0 | 91.0 | 39.0 | 66.0 | 11.5 | 0.0 | -124.0 |
| Maximum | 242 | 170 | 1120 | 1054 | 317 | 265 | 246 | 141 |
| Week 8 | | | | | | | | |
| N | 56 | 56 | 47 | 47 | 54 | 54 | 55 | 55 |
| Mean | 149.3 | 97.0 | 94.9 | 28.8 | 46.7 | -23.0 | 13.9 | -41.2 |
| SD | 149.27 | 148.04 | 122.88 | 128.25 | 61.63 | 117.98 | 59.56 | 78.67 |
| Minimum | 0 | -119 | 0 | -211 | 0 | -594 | 0 | -294 |
| Q1 | 42.5 | 4.5 | 23.0 | -26.0 | 0.0 | -45.0 | 0.0 | -55.0 |
| Median | 91.5 | 37.5 | 52.0 | -1.0 | 16.0 | -23.0 | 0.0 | -38.0 |
| Q3 | 196.0 | 136.5 | 107.0 | 48.0 | 83.0 | 21.0 | 0.0 | -23.0 |
| Maximum | 721 | 636 | 576 | 544 | 221 | 159 | 433 | 391 |
| Week 12 | | | | | | | | |
| N | 55 | 55 | 47 | 47 | 54 | 54 | 55 | 55 |
| Mean | 145.2 | 92.5 | 77.5 | 11.4 | 40.6 | -29.1 | 8.8 | -46.3 |
| SD | 138.53 | 131.74 | 78.01 | 92.41 | 92.80 | 148.74 | 25.37 | 55.53 |
| Minimum | 0 | -179 | 0 | -203 | 0 | -684 | 0 | -294 |
| Q1 | 43.0 | 6.0 | 25.0 | -42.0 | 0.0 | -45.0 | 0.0 | -55.0 |
| Median | 110.0 | 59.0 | 57.0 | 0.0 | 13.0 | -18.5 | 0.0 | -35.0 |
| Q3 | 228.0 | 167.0 | 103.0 | 54.0 | 54.0 | 1.0 | 0.0 | -24.0 |
| Maximum | 681 | 596 | 344 | 278 | 576 | 506 | 153 | 74 |

FIG. 61

| Follow-up | | | | | | | | |
|---|---|---|---|---|---|---|---|---|
| N | 57 | 57 | 48 | 48 | 56 | 56 | 55 | 55 |
| Mean | 164.7 | 112.1 | 220.4 | 155.1 | 145.6 | 71.0 | 190.8 | 135.7 |
| SD | 175.65 | 162.49 | 630.74 | 637.63 | 129.08 | 172.34 | 152.81 | 164.12 |
| Minimum | 0 | -70 | 12 | -170 | 0 | -535 | 0 | -174 |
| Q1 | 53.0 | 16.0 | 48.0 | -6.0 | 45.5 | -11.0 | 87.0 | 18.0 |
| Median | 106.0 | 69.0 | 110.5 | 23.5 | 115.0 | 45.0 | 168.0 | 121.0 |
| Q3 | 187.0 | 149.0 | 178.0 | 134.5 | 200.0 | 153.5 | 265.0 | 221.0 |
| Maximum | 937 | 891 | 4420 | 4392 | 539 | 512 | 872 | 828 |

| Visit / Statistics | Placebo (N=57) | | 10mg (N=48) | | 20mg (N=56) | | 40mg (N=55) | |
|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline |
| Week 0 | | | | | | | | |
| N | 57 | | 48 | | 56 | | 55 | |
| Mean | 0.418 | | 0.335 | | 0.644 | | 0.571 | |
| SD | 0.9331 | | 0.5285 | | 1.2669 | | 1.8142 | |
| Minimum | 0.00 | | 0.00 | | 0.00 | | 0.08 | |
| Q1 | 0.210 | | 0.140 | | 0.220 | | 0.190 | |
| Median | 0.290 | | 0.270 | | 0.325 | | 0.300 | |
| Q3 | 0.380 | | 0.400 | | 0.425 | | 0.390 | |
| Maximum | 7.26 | | 3.79 | | 6.75 | | 13.70 | |
| Week 2 | | | | | | | | |
| N | 57 | 57 | 48 | 48 | 56 | 56 | 55 | 55 |
| Mean | 8.354 | 7.937 | 2.796 | 2.461 | 0.598 | -0.046 | 0.299 | -0.271 |
| SD | 6.9286 | 7.1320 | 5.5397 | 5.5927 | 2.6713 | 2.9958 | 0.2706 | 1.8091 |
| Minimum | 0.16 | 6.99 | 0.00 | -3.38 | 0.00 | -6.53 | 0.06 | -13.32 |
| Q1 | 1.400 | 1.270 | 0.185 | -0.035 | 0.140 | -0.170 | 0.160 | -0.110 |
| Median | 7.740 | 7.400 | 0.315 | 0.040 | 0.235 | -0.070 | 0.230 | -0.050 |
| Q3 | 13.300 | 12.930 | 0.660 | 0.265 | 0.315 | -0.010 | 0.350 | 0.030 |
| Maximum | 22.20 | 21.93 | 22.80 | 22.72 | 20.20 | 19.88 | 1.77 | 1.22 |
| Week 4 | | | | | | | | |
| N | 57 | 57 | 48 | 48 | 56 | 56 | 55 | 55 |
| Mean | 1.057 | 0.639 | 3.449 | 3.114 | 2.292 | 1.648 | 0.320 | -0.251 |
| SD | 2.7048 | 2.5000 | 4.9653 | 4.8588 | 4.1845 | 4.2533 | 0.3146 | 1.8377 |
| Minimum | 0.00 | -0.19 | 0.00 | -0.23 | 0.00 | -6.57 | 0.00 | -13.39 |
| Q1 | 0.150 | -0.070 | 0.180 | -0.025 | 0.190 | -0.140 | 0.170 | -0.130 |
| Median | 0.320 | -0.010 | 0.440 | 0.080 | 0.270 | -0.045 | 0.240 | -0.050 |
| Q3 | 0.490 | 0.170 | 6.130 | 5.915 | 2.510 | 1.715 | 0.350 | 0.010 |
| Maximum | 15.90 | 15.58 | 17.10 | 16.70 | 20.40 | 19.95 | 1.83 | 1.75 |
| Week 8 | | | | | | | | |
| N | 56 | 56 | 47 | 47 | 54 | 54 | 55 | 55 |
| Mean | 2.480 | 2.0159 | 2.277 | 1.943 | 1.303 | 0.647 | 0.245 | -0.326 |
| SD | 5.1106 | 4.9623 | 4.5311 | 4.5186 | 2.5023 | 2.8018 | 0.1421 | 1.7990 |
| Minimum | 0.00 | -0.28 | 0.00 | -1.10 | 0.00 | -6.54 | 0.04 | -13.38 |
| Q1 | 0.180 | -0.080 | 0.190 | -0.020 | 0.160 | -0.160 | 0.150 | -0.140 |
| Median | 0.300 | -0.010 | 0.360 | 0.040 | 0.250 | -0.035 | 0.220 | -0.060 |
| Q3 | 1.035 | 0.605 | 1.300 | 0.710 | 0.380 | 0.060 | 0.320 | -0.010 |
| Maximum | 19.60 | 19.27 | 22.90 | 22.39 | 10.40 | 9.98 | 0.77 | 0.11 |
| Week 12 | | | | | | | | |
| N | 55 | 55 | 47 | 47 | 54 | 54 | 55 | 55 |
| Mean | 2.793 | 2.367 | 3.430 | 3.096 | 0.862 | 0.206 | 0.432 | -0.139 |
| SD | 5.2660 | 5.1833 | 5.7878 | 5.6113 | 2.3095 | 2.0388 | 1.1059 | 0.7549 |
| Minimum | 0.07 | -0.33 | 0.04 | -0.31 | 0.00 | -6.56 | 0.00 | -5.39 |
| Q1 | 0.230 | -0.040 | 0.130 | -0.040 | 0.140 | -0.180 | 0.160 | -0.120 |
| Median | 0.360 | 0.050 | 0.410 | 0.080 | 0.250 | -0.090 | 0.250 | -0.060 |
| Q3 | 1.170 | 0.910 | 3.170 | 3.010 | 0.370 | 0.040 | 0.350 | 0.020 |
| Maximum | 21.30 | 21.05 | 22.30 | 21.80 | 13.90 | 7.73 | 8.31 | 1.21 |

FIG. 63

| Follow-up | | | | | | | | |
|---|---|---|---|---|---|---|---|---|
| N | 57 | 57 | 48 | 48 | 56 | 56 | 55 | 55 |
| Mean | 3.011 | 2.594 | 4.970 | 4.636 | 5.566 | 4.922 | 9.207 | 8.636 |
| SD | 4.9158 | 4.9385 | 8.1503 | 8.1333 | 7.4073 | 7.5263 | 8.1727 | 8.6304 |
| Minimum | 0.06 | -1.78 | 0.08 | -0.30 | 0.00 | -3.91 | 0.09 | -13.13 |
| Q1 | 0.270 | -0.040 | 0.230 | 0.000 | 0.310 | -0.025 | 1.240 | 0.900 |
| Median | 0.500 | 0.070 | 0.450 | 0.170 | 1.115 | 0.520 | 9.590 | 8.890 |
| Q3 | 2.430 | 1.980 | 7.010 | 6.330 | 10.095 | 8.855 | 15.000 | 14.610 |
| Maximum | 19.80 | 19.46 | 38.70 | 38.33 | 29.20 | 28.83 | 31.70 | 31.52 |

| | Placebo (N=57) | 10mg (N=48) | 20mg (N=56) | 40mg (N=55) |
|---|---|---|---|---|
| Duration of Menstruation Recovery (Days) | | | | |
| N | 57 | 47 | 55 | 52 |
| Mean | 18.6 | 19.8 | 31.0 | 36.4 |
| SD | 8.75 | 9.26 | 17.65 | 7.63 |
| Minimum | 1 | 3 | 5 | 6 |
| Median | 19.0 | 22.0 | 28.0 | 37.0 |
| Maximum | 52 | 40 | 113 | 54 |

FIG. 64

Clinical Trial Medication

1. Did you take your dose of study Treatment <u>today</u>?

☐ Yes

If Yes, please provide

Date: dd - MMM - yyyy

Time: HH:MM [AM/PM]

☐ No

2 Did you take your dose of study treatment while <u>on an empty stomach</u>? (i.e., at least 1 hour before or 2 hours after a meal)

☐ Yes

Menstrual Bleeding

1. Did you experience any menstrual bleeding today?

☐ Yes (this includes spotting as well as bleeding) *[Q2 Option - Categorize Bleeding vs. Spotting]*

☐ No

2. Did you use a menstrual product today? (i.e., pads, tampons, panty liners)?

☐ Yes

Use of Pain Medication (Analgesics) and Supplements

1. Did you take any medication today to treat pain caused by your uterine fibroids?

☐ Yes

Name of the medication _____ (generic or trade name)

[Total amount of the medication _____ ]

☐ No

2. Did you take your Calcium/Vitamin D Tablet?

☐ Yes

The following questions ask about the effect of your health problems on your ability to work and perform regular activities. By health problems we mean any physical or emotional problem or symptom. *Please fill in the blanks or circle a number, as indicated.*

1. Are you currently employed (working for pay)? _____ NO _____ YES
   *If NO, tick "NO" and skip to question 6.*

The next questions are about the past seven days, not including today.

2. During the past seven days, how many hours did you miss from work because of your health problems? Include hours you missed on sick days, times you went in late, left early, etc., because of your health problems. Do not include time you missed to participate in this study.

_____ HOURS

3. During the past seven days, how many hours did you miss from work because of any other reason, such as vacation, holidays, time off to participate in this study?

_____ HOURS

4. During the past seven days, how many hours did you actually work?

_____ HOURS *(If "0", skip to question 6.)*

FIG. 66A

5. During the past seven days, how much did your health problems affect your productivity while you were working? Think about days you were limited in the amount or kind of work you could do, days you accomplished less than you would like, or days you could not do your work as carefully as usual. If health problems affected your work only a little, choose a low number. Choose a high number if health problems affected your work a great deal.

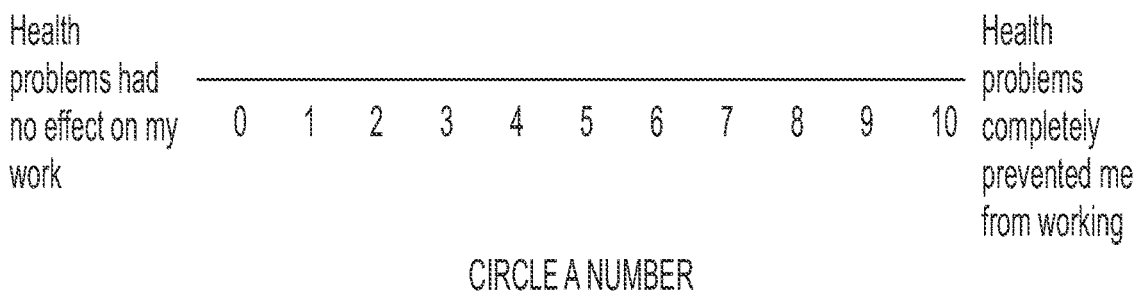

6. During the past seven days, how much did your health problems affect your ability to do your regular daily activities, other than work at a job? By regular activities, we mean the usual activities you do, such as work around the house, shopping, childcare, exercising, studying, etc. Think about times you were limited in the amount or kind of activities you could do and times you accomplished less than you would like. If health problems affected your activities only a little, choose a low number. Choose a high number if health problems affected your activities a great deal.

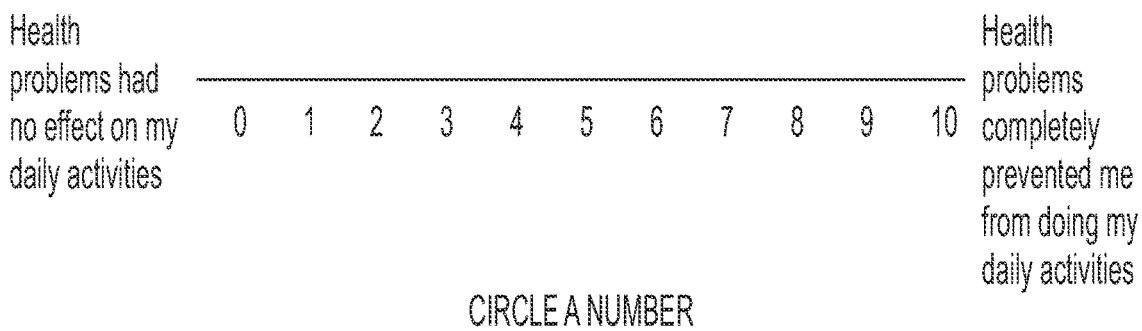

FIG. 66B

We would like to find out if there have been any changes in your uterine fibroid symptoms since you started taking your study treatment.
Please complete the following.

1. Has there been any change in your uterine fibroid symptoms since you started taking your study treatment? Please indicate if there has been any change in your symptoms by choosing one of the following options:
   - ☐ Worse (Go to Question 2)
   - ☐ About the same
   - ☐ Better (Go to Question 3)

2. How much worse would you say your uterine fibroid symptoms have been since you started taking your study treatment? Please choose one of the options below:
   - ☐ Almost the same, hardly worse at all
   - ☐ A little worse
   - ☐ Somewhat worse
   - ☐ Moderately worse
   - ☐ A good deal worse
   - ☐ A great deal worse
   - ☐ A very great deal worse 3. How much better would you say your uterine fibroid symptoms have been since you started taking your study treatment? Please choose one of the options below:
   - ☐ Almost the same, hardly better at all
   - ☐ A little better
   - ☐ Somewhat better
   - ☐ Moderately worse
   - ☐ A good deal better
   - ☐ A great deal better
   - ☐ A very great deal better Participant Initials: _____

FIG. 67

The lower limit of quantification of estradiol was 10 pg/ml.

| Analyte / Treatment | Statistics | Week 0: 0.5-1.5hr | Week 0: 2-5hr | Week 2: Predose | Week 2: 0.5-1.5hr | Week 2: 2-5hr | Week 4: Predose | Week 4: 0.5-1.5hr | Week 4: 2-5hr | Week 8: Predose | Week 8: 0.5-1.5hr | Week 8: 2-5hr | Week 12 | Week 16: Predose | Week 20: Predose | Week 24 |
|---|---|---|---|---|---|---|---|---|---|---|---|---|---|---|---|---|
| Compound 1 (ng/mL) | | | | | | | | | | | | | | | | |
| Compound 1 10 mg | N | 50 | 33 | 102 | 58 | 39 | 103 | 54 | 35 | 101 | 58 | 34 | 100 | 83 | 79 | 77 |
| | Mean | 0.8288 | 0.5841 | 0.3079 | 1.273 | 0.8893 | 0.3356 | 1.229 | 0.9502 | 0.3380 | 1.354 | 0.8445 | 0.2900 | 0.3230 | 0.3138 | 0.2811 |
| | SD | 0.94599 | 0.40905 | 0.16377 | 0.72473 | 0.43347 | 0.21682 | 0.84650 | 0.64644 | 0.21226 | 0.91596 | 0.36815 | 0.19348 | 0.22403 | 0.19052 | 0.13437 |
| | Minimum | 0.0342 | 0.113 | 0.0263 | 0.196 | 0.167 | 0.0540 | 0.269 | 0.187 | 0.0754 | 0.283 | 0.273 | 0.00 | 0.00 | 0.0277 | 0.00 |
| | Q1 | 0.3720 | 0.2990 | 0.1980 | 0.7700 | 0.5950 | 0.2060 | 0.6900 | 0.5370 | 0.2220 | 0.6720 | 0.5320 | 0.1830 | 0.2040 | 0.1920 | 0.2020 |
| | Median | 0.5290 | 0.4470 | 0.2715 | 1.205 | 0.8030 | 0.2660 | 0.9680 | 0.7920 | 0.2830 | 1.030 | 0.7065 | 0.2500 | 0.2680 | 0.2660 | 0.2510 |
| | Q3 | 1.030 | 0.7060 | 0.3680 | 1.610 | 1.150 | 0.3970 | 1.510 | 1.160 | 0.3780 | 1.580 | 1.200 | 0.3320 | 0.3600 | 0.3560 | 0.3840 |
| | Maximum | 6.18 | 2.12 | 1.16 | 3.34 | 2.26 | 1.35 | 4.81 | 3.27 | 1.28 | 3.73 | 1.74 | 1.46 | 1.26 | 0.947 | 0.782 |
| Compound 1 20 mg | N | 45 | 26 | 100 | 50 | 31 | 97 | 49 | 26 | 92 | 48 | 30 | 90 | 77 | 77 | 73 |
| | Mean | 2.891 | 2.154 | 0.8022 | 2.912 | 2.981 | 0.8162 | 3.515 | 3.567 | 0.7982 | 3.437 | 2.643 | 0.6936 | 0.6885 | 0.7131 | 0.6722 |
| | SD | 2.7706 | 2.0639 | 0.56366 | 1.6750 | 4.4730 | 0.50431 | 3.2291 | 4.3676 | 0.66000 | 3.8334 | 2.0642 | 0.35405 | 0.46006 | 0.40900 | 0.31166 |
| | Minimum | 0.131 | 0.437 | 0.122 | 0.447 | 0.640 | 0.170 | 0.453 | 0.828 | 0.212 | 0.198 | 0.619 | 0.185 | 0.0149 | 0.00 | 0.00 |
| | Q1 | 1.360 | 0.9180 | 0.4765 | 1.480 | 1.370 | 0.4640 | 2.240 | 1.695 | 0.4815 | 1.670 | 1.370 | 0.4140 | 0.4440 | 0.4610 | 0.4480 |
| | Median | 1.990 | 1.605 | 0.6465 | 2.575 | 2.100 | 0.6600 | 2.710 | 2.170 | 0.6440 | 2.450 | 2.230 | 0.6460 | 0.6280 | 0.5740 | 0.6330 |
| | Q3 | 3.530 | 2.460 | 0.9055 | 4.260 | 3.120 | 0.9840 | 3.980 | 2.785 | 0.8990 | 3.870 | 3.050 | 0.8290 | 0.7770 | 0.8610 | 0.8180 |
| | Maximum | 15.9 | 10.0 | 3.47 | 7.14 | 26.5 | 3.22 | 22.4 | 19.2 | 5.13 | 25.9 | 11.5 | 1.86 | 3.78 | 2.55 | 1.72 |
| Compound 1 40 mg | N | 57 | 37 | 103 | 66 | 37 | 100 | 60 | 32 | 100 | 57 | 30 | 101 | 89 | 87 | 84 |
| | Mean | 7.424 | 7.680 | 2.383 | 9.210 | 7.550 | 2.315 | 11.61 | 8.479 | 2.287 | 10.29 | 11.20 | 1.982 | 1.995 | 2.240 | 1.908 |
| | SD | 7.1719 | 8.7934 | 3.7299 | 9.6488 | 6.8462 | 3.5245 | 16.720 | 7.8284 | 3.0492 | 10.096 | 16.227 | 2.7931 | 1.6474 | 2.6029 | 2.0047 |
| | Minimum | 0.00 | 0.727 | 0.603 | 1.57 | 0.820 | 0.118 | 1.86 | 1.03 | 0.201 | 1.27 | 1.87 | 0.0216 | 0.0222 | 0.00 | 0.448 |
| | Q1 | 2.900 | 2.830 | 1.170 | 3.840 | 3.320 | 1.150 | 3.960 | 3.480 | 1.255 | 3.500 | 3.260 | 1.060 | 1.130 | 1.130 | 1.140 |
| | Median | 4.990 | 4.520 | 1.560 | 5.890 | 5.820 | 1.725 | 6.760 | 5.310 | 1.685 | 6.520 | 6.245 | 1.540 | 1.790 | 1.660 | 1.490 |
| | Q3 | 8.810 | 10.40 | 2.460 | 10.60 | 8.680 | 2.380 | 11.45 | 11.65 | 2.520 | 13.00 | 9.890 | 2.220 | 2.280 | 2.300 | 2.060 |
| | Maximum | 35.0 | 39.9 | 29.9 | 53.1 | 30.5 | 32.9 | 108 | 34.6 | 29.9 | 58.0 | 82.3 | 28.1 | 14.1 | 20.4 | 17.5 |

Note: Due to an error in the drug assignment procedure at the investigational site, Subject ID 2096-005, originally randomized to Compound 1 40mg group, was administered placebo treatment throughout the treatment period. Based on this, PK samples were measured at Visit 4,5,6 and Visit 7/Discontinued, but the concentration of Compound 1 were <0.01 ng/mL (lower limit of quanitation) at all visits.

FIG. 71

| Analyte / Treatment | Statistics | Week 0: 0.5-1.5hr | Week 0: 2.5hr | Week 2: Predose | Week 2: 0.5-1.5hr | Week 2: 2.5hr | Week 4: Predose | Week 4: 0.5-1.5hr | Week 4: 2.5hr | Week 8: Predose | Week 8: 0.5-1.5hr | Week 8: 2.5hr | Week 12 | Week 16: Predose | Week 20: Predose | Week 24 |
|---|---|---|---|---|---|---|---|---|---|---|---|---|---|---|---|---|
| Compound 1 (ng/mL) | | | | | | | | | | | | | | | | |
| Compound 1 10 mg | N | 50 | 33 | 101 | 57 | 38 | 101 | 52 | 34 | 100 | 56 | 33 | 98 | 82 | 79 | 77 |
| | Mean | 0.8288 | 0.5641 | 0.3100 | 1.278 | 0.8909 | 0.3385 | 1.241 | 0.9672 | 0.3406 | 1.324 | 0.8301 | 0.2783 | 0.3251 | 0.3138 | 0.2811 |
| | SD | 0.94599 | 0.40905 | 0.16312 | 0.73015 | 0.43917 | 0.21771 | 0.85247 | 0.64817 | 0.21168 | 0.88090 | 0.38482 | 0.15475 | 0.22458 | 0.19052 | 0.13437 |
| | Minimum | 0.0342 | 0.113 | 0.0263 | 0.198 | 0.167 | 0.0540 | 0.269 | 0.187 | 0.0789 | 0.283 | 0.273 | 0.00 | 0.00 | 0.0277 | 0.00 |
| | Q1 | 0.3720 | 0.2990 | 0.2080 | 0.7700 | 0.5950 | 0.2100 | 0.6960 | 0.5420 | 0.2325 | 0.6620 | 0.5320 | 0.1810 | 0.2060 | 0.1920 | 0.2020 |
| | Median | 0.5290 | 0.4170 | 0.2740 | 1.210 | 0.8025 | 0.2670 | 0.9680 | 0.8375 | 0.2865 | 1.030 | 0.6800 | 0.2475 | 0.2885 | 0.2660 | 0.2510 |
| | Q3 | 1.030 | 0.7060 | 0.3680 | 1.610 | 1.150 | 0.3970 | 1.550 | 1.160 | 0.3805 | 1.580 | 1.170 | 0.3310 | 0.3600 | 0.3560 | 0.3840 |
| | Maximum | 6.18 | 2.12 | 1.16 | 3.34 | 2.26 | 1.35 | 4.81 | 3.27 | 1.28 | 3.73 | 1.74 | 0.937 | 1.26 | 0.947 | 0.782 |
| Compound 1 20 mg | N | 44 | 26 | 98 | 50 | 31 | 96 | 49 | 28 | 91 | 48 | 30 | 88 | 77 | 77 | 72 |
| | Mean | 2.784 | 2.154 | 0.8002 | 2.912 | 2.961 | 0.8206 | 3.515 | 3.567 | 0.6032 | 3.437 | 2.643 | 0.6904 | 0.6885 | 0.7132 | 0.6712 |
| | SD | 2.7061 | 2.0639 | 0.56335 | 1.6750 | 4.4730 | 0.55503 | 3.2291 | 4.3676 | 0.66186 | 3.8334 | 2.0642 | 0.35234 | 0.46006 | 0.40900 | 0.31374 |
| | Minimum | 0.131 | 0.437 | 0.122 | 0.447 | 0.640 | 0.170 | 0.453 | 0.828 | 0.212 | 0.198 | 0.619 | 0.185 | 0.0149 | 0.00 | 0.00 |
| | Q1 | 1.355 | 0.9180 | 0.4790 | 1.480 | 1.370 | 0.4680 | 2.240 | 1.695 | 0.4840 | 1.670 | 1.370 | 0.4125 | 0.4440 | 0.4610 | 0.4425 |
| | Median | 1.990 | 1.605 | 0.6465 | 2.575 | 2.100 | 0.6640 | 2.710 | 2.170 | 0.6450 | 2.450 | 2.230 | 0.6460 | 0.6280 | 0.5740 | 0.6320 |
| | Q3 | 3.500 | 2.460 | 0.8910 | 4.260 | 3.120 | 0.9905 | 3.980 | 2.785 | 0.9110 | 3.870 | 3.050 | 0.8260 | 0.7770 | 0.8610 | 0.8190 |
| | Maximum | 15.9 | 10.0 | 3.47 | 7.14 | 26.5 | 3.22 | 22.4 | 19.2 | 5.13 | 25.9 | 11.5 | 1.86 | 3.78 | 2.55 | 1.72 |
| Compound 1 40 mg | N | 57 | 37 | 103 | 66 | 37 | 100 | 60 | 32 | 96 | 57 | 30 | 100 | 89 | 87 | 84 |
| | Mean | 7.424 | 7.680 | 2.383 | 9.210 | 7.550 | 2.315 | 11.61 | 8.479 | 2.233 | 10.29 | 11.20 | 1.987 | 1.995 | 2.240 | 1.908 |
| | SD | 7.1719 | 8.7934 | 3.7299 | 9.6488 | 6.8462 | 3.5245 | 16.720 | 7.8284 | 3.0509 | 10.096 | 16.227 | 2.8068 | 1.6474 | 2.6029 | 2.0047 |
| | Minimum | 0.00 | 0.727 | 0.603 | 1.57 | 0.820 | 0.118 | 1.86 | 1.03 | 0.201 | 1.27 | 1.87 | 0.0216 | 0.0222 | 0.00 | 0.448 |
| | Q1 | 2.900 | 2.830 | 1.170 | 3.840 | 3.320 | 1.150 | 3.960 | 3.480 | 1.245 | 3.500 | 3.260 | 1.050 | 1.130 | 1.130 | 1.140 |
| | Median | 4.990 | 4.520 | 1.560 | 5.890 | 5.820 | 1.725 | 6.780 | 5.310 | 1.680 | 6.520 | 6.215 | 1.540 | 1.790 | 1.660 | 1.490 |
| | Q3 | 8.810 | 10.40 | 2.460 | 10.60 | 8.680 | 2.380 | 11.45 | 11.65 | 2.510 | 13.00 | 9.690 | 2.220 | 2.280 | 2.300 | 2.060 |
| | Maximum | 35.0 | 39.9 | 29.9 | 53.1 | 30.5 | 32.9 | 108 | 34.6 | 29.9 | 58.0 | 82.3 | 28.1 | 14.1 | 20.4 | 17.5 |

FIG. 73

| Analyte / Treatment | Statistics | Visit | | | | | | | | | | | | |
|---|---|---|---|---|---|---|---|---|---|---|---|---|---|---|
| | | Week 0: 0.5-1.5hr | Week 0: 2.5hr | Week 2: Predose | Week 2: 0.5-1.5hr | Week 2: 2.5hr | Week 4: Predose | Week 4: 0.5-1.5hr | Week 4: 2.5hr | Week 6: Predose | Week 8: 0.5-1.5hr | Week 8: 2.5hr | Week 12 | Week 16: Predose | Week 20: Predose | Week 24 |
| Compound 1 (ng/mL) | | | | | | | | | | | | | | | | |
| Compound 1 10 mg | N | 0 | 0 | 1 | 1 | 1 | 2 | 2 | 1 | 1 | 2 | 1 | 2 | 1 | 0 | 0 |
| | Mean | | | 0.08980 | 0.9860 | 0.8260 | 0.1890 | 0.9140 | 0.3720 | 0.0754 | 2.192 | 1.320 | 0.8620 | 0.1500 | | |
| | SD | | | | | | 0.10465 | 0.84287 | | | 1.9205 | | 0.84570 | | | |
| | Minimum | | | 0.0898 | 0.986 | 0.828 | 0.114 | 0.318 | 0.372 | 0.0754 | 0.834 | 1.32 | 0.264 | 0.150 | | |
| | Q1 | | | 0.08980 | 0.9860 | 0.8280 | 0.1140 | 0.3180 | 0.3720 | 0.07540 | 0.8340 | 1.320 | 0.2640 | 0.1500 | | |
| | Median | | | 0.08980 | 0.9860 | 0.8280 | 0.1890 | 0.9140 | 0.3720 | 0.07540 | 2.192 | 1.320 | 0.8620 | 0.1500 | | |
| | Q3 | | | 0.08980 | 0.9860 | 0.8280 | 0.2620 | 1.510 | 0.3720 | 0.07540 | 3.550 | 1.320 | 1.460 | 0.1500 | | |
| | Maximum | | | 0.0898 | 0.986 | 0.828 | 0.262 | 1.51 | 0.372 | 0.0754 | 3.55 | 1.32 | 1.46 | 0.150 | | |
| Compound 1 20 mg | N | 1 | 0 | 2 | 0 | 0 | 1 | 0 | 0 | 1 | 0 | 0 | 2 | 0 | 1 | 0 |
| | Mean | 7.570 | | 0.8990 | | | 0.3880 | | | 0.3380 | | | 0.8320 | | 0.7470 | |
| | SD | | | 0.80752 | | | | | | | | | 0.56286 | | | |
| | Minimum | 7.57 | | 0.328 | | | 0.388 | | | 0.338 | | | 0.434 | | 0.747 | |
| | Q1 | 7.570 | | 0.3280 | | | 0.3880 | | | 0.3380 | | | 0.4340 | | 0.7470 | |
| | Median | 7.570 | | 0.8990 | | | 0.3880 | | | 0.3380 | | | 0.8320 | | 0.7470 | |
| | Q3 | 7.570 | | 1.470 | | | 0.3880 | | | 0.3380 | | | 1.230 | | 0.7470 | |
| | Maximum | 7.57 | | 1.47 | | | 0.388 | | | 0.338 | | | 1.23 | | 0.747 | |
| Compound 1 40 mg | N | 0 | 0 | 0 | 0 | 0 | 0 | 0 | 0 | 4 | 0 | 0 | 1 | 0 | 0 | 0 |
| | Mean | | | | | | | | | 3.580 | | | 1.520 | | | |
| | SD | | | | | | | | | 3.1222 | | | | | | |
| | Minimum | | | | | | | | | 1.62 | | | 1.52 | | | |
| | Q1 | | | | | | | | | 1.785 | | | 1.520 | | | |
| | Median | | | | | | | | | 2.235 | | | 1.520 | | | |
| | Q3 | | | | | | | | | 5.375 | | | 1.520 | | | |
| | Maximum | | | | | | | | | 8.23 | | | 1.52 | | | |

FIG. 75

| | Placebo (N=77) | Compound 1 10mg (N=84) | Compound 1 20mg (N=78) | Compound 1 40mg (N=89) | Leuprorelin (N=69) | Total (N=397) |
|---|---|---|---|---|---|---|
| Age (years) | | | | | | |
| N | 77 | 84 | 78 | 89 | 69 | 397 |
| Mean | 35.9 | 35.3 | 35.3 | 35.4 | 36.6 | 35.7 |
| SD | 5.99 | 6.41 | 7.01 | 6.15 | 6.14 | 6.34 |
| Height (cm) | | | | | | |
| N | 77 | 84 | 78 | 89 | 69 | 397 |
| Mean | 159.7 | 159.6 | 158.4 | 159.6 | 160.7 | 159.6 |
| SD | 5.21 | 4.82 | 5.85 | 5.08 | 4.48 | 5.14 |
| Weight (kg) at Baseline | | | | | | |
| N | 77 | 84 | 78 | 89 | 69 | 397 |
| Mean | 54.00 | 54.03 | 51.47 | 54.83 | 56.11 | 54.06 |
| SD | 7.864 | 8.073 | 6.530 | 8.624 | 8.826 | 8.119 |
| BMI (kg/m$^2$) at Baseline | | | | | | |
| N | 77 | 84 | 78 | 89 | 69 | 397 |
| Mean | 21.17 | 21.22 | 20.53 | 21.52 | 21.74 | 21.23 |
| SD | 2.880 | 3.082 | 2.542 | 3.179 | 3.339 | 3.027 |
| Smoking Classification (N[%]) | | | | | | |
| Never Smoked | 57 (74.0) | 61 (72.6) | 55 (70.5) | 54 (60.7) | 43 (62.3) | 270 (68.0) |
| Current Smoker | 14 (18.2) | 8 (9.5) | 13 (16.7) | 16 (18.0) | 13 (18.8) | 64 (16.1) |
| Ex-Smoker | 6 (7.8) | 15 (17.9) | 10 (12.8) | 19 (21.3) | 13 (18.8) | 63 (15.9) |
| Birth Experience (N[%]) | | | | | | |
| Yes | 28 (36.4) | 34 (40.5) | 30 (38.5) | 32 (36.0) | 28 (40.6) | 152 (38.3) |
| No | 49 (63.6) | 50 (59.5) | 48 (61.5) | 57 (64.0) | 41 (59.4) | 245 (61.7) |

FIG. 76A

|  | Placebo (N=77) | Compound 1 10mg (N=84) | Compound 1 20mg (N=78) | Compound 1 40mg (N=89) | Leuprorelin (N=69) | Total (N=397) |
|---|---|---|---|---|---|---|
| Disease Duration (Years) | | | | | | |
| N | 77 | 84 | 78 | 89 | 69 | 397 |
| Mean | 3.80 | 3.64 | 3.42 | 4.14 | 3.06 | 3.64 |
| SD | 4.694 | 5.037 | 3.945 | 5.348 | 3.968 | 4.665 |
| Any Surgery for Endometriosis (N[%]) | | | | | | |
| Yes | 21 (27.3) | 20 (23.8) | 17 (21.8) | 18 (20.2) | 19 (27.5) | 95 (23.9) |
| No | 56 (72.7) | 64 (76.2) | 61 (78.2) | 71 (79.8) | 50 (72.5) | 302 (76.1) |
| Stopped Any Medications for Endometriosis (N[%]) | | | | | | |
| Yes | 58 (75.3) | 57 (67.9) | 64 (82.1) | 61 (68.5) | 51 (73.9) | 291 (73.3) |
| No | 19 (24.7) | 27 (32.1) | 14 (17.9) | 28 (31.5) | 18 (26.1) | 106 (26.7) |
| Mean of VAS Score[1]) (mm) at Baseline | | | | | | |
| *Pelvic Pain* | | | | | | |
| N | 77 | 84 | 78 | 89 | 69 | 397 |
| Mean | 15.035 | 14.623 | 14.808 | 15.839 | 16.003 | 15.251 |
| SD | 13.9226 | 12.7215 | 13.9933 | 12.4982 | 15.8823 | 13.6942 |
| *Dysmenorrhea* | | | | | | |
| N | 77 | 84 | 78 | 89 | 69 | 397 |
| Mean | 28.082 | 26.860 | 26.630 | 31.572 | 28.446 | 28.384 |
| SD | 15.9511 | 17.1543 | 18.6387 | 17.4390 | 20.3506 | 17.8930 |
| *Dyspareunia* | | | | | | |
| N | 31 | 36 | 38 | 33 | 22 | 160 |
| Mean | 12.551 | 8.141 | 13.519 | 9.162 | 10.447 | 10.800 |
| SD | 15.2080 | 15.2022 | 17.0608 | 14.2543 | 11.2510 | 14.9798 |
| Mean of M-B&B Score[2]) at Baseline | | | | | | |
| *Pelvic Pain* | | | | | | |
| N | 77 | 84 | 78 | 89 | 69 | 397 |
| Mean | 0.619 | 0.656 | 0.624 | 0.673 | 0.715 | 0.657 |
| SD | 0.4555 | 0.4807 | 0.4547 | 0.4521 | 0.5608 | 0.4786 |
| *Dysmenorrhea* | | | | | | |
| N | 77 | 84 | 78 | 89 | 69 | 397 |
| Mean | 1.148 | 1.140 | 1.154 | 1.238 | 1.209 | 1.178 |
| SD | 0.4485 | 0.4520 | 0.4866 | 0.4691 | 0.4800 | 0.4664 |
| *Deep Dyspareunia* | | | | | | |
| N | 31 | 36 | 38 | 33 | 22 | 160 |
| Mean | 0.626 | 0.509 | 0.683 | 0.550 | 0.614 | 0.596 |
| SD | 0.4316 | 0.6013 | 0.5684 | 0.4668 | 0.4377 | 0.5131 |
| B&B Score[3]) at Baseline | | | | | | |
| *Dysmenorrhea* | | | | | | |
| N | 77 | 84 | 78 | 89 | 69 | 397 |
| Mean | 2.0 | 2.1 | 2.1 | 2.1 | 2.1 | 2.1 |
| SD | 0.38 | 0.46 | 0.47 | 0.46 | 0.48 | 0.45 |
| *Dyspareunia* | | | | | | |
| N | 31 | 37 | 40 | 33 | 22 | 163 |
| Mean | 0.9 | 0.7 | 1.0 | 0.6 | 0.9 | 0.8 |
| SD | 0.68 | 0.67 | 0.73 | 0.55 | 0.75 | 0.69 |

FIG. 76B

|  | Placebo (N=77) | Compound 1 10mg (N=84) | Compound 1 20mg (N=78) | Compound 1 40mg (N=89) | Leuprorelin (N=69) | Total (N=397) |
|---|---|---|---|---|---|---|
| Pelvic Pain | | | | | | |
| N | 77 | 84 | 78 | 89 | 69 | 397 |
| Mean | 1.6 | 1.7 | 1.6 | 1.5 | 1.6 | 1.6 |
| SD | 0.55 | 0.68 | 0.63 | 0.59 | 0.57 | 0.61 |
| Pelvic Tenderness | | | | | | |
| N | 77 | 84 | 78 | 89 | 69 | 397 |
| Mean | 1.6 | 1.5 | 1.6 | 1.5 | 1.4 | 1.5 |
| SD | 0.72 | 0.83 | 0.74 | 0.81 | 0.74 | 0.77 |
| Induration | | | | | | |
| N | 77 | 84 | 78 | 89 | 69 | 397 |
| Mean | 1.4 | 1.3 | 1.4 | 1.3 | 1.1 | 1.3 |
| SD | 0.75 | 0.95 | 0.85 | 0.88 | 0.86 | 0.86 |
| Scale Score of EHP-30[4]) (mm) at Baseline | | | | | | |
| Pain | | | | | | |
| N | 77 | 84 | 78 | 89 | 69 | 397 |
| Mean | 23.73 | 27.33 | 27.30 | 29.01 | 26.98 | 26.94 |
| SD | 18.772 | 20.988 | 19.434 | 20.124 | 20.154 | 19.904 |
| Control & Powerlessness | | | | | | |
| N | 77 | 84 | 78 | 89 | 69 | 397 |
| Mean | 25.11 | 25.00 | 30.40 | 26.59 | 28.93 | 27.12 |
| SD | 21.730 | 21.778 | 23.567 | 21.998 | 24.061 | 22.571 |
| Emotional well-being | | | | | | |
| N | 77 | 84 | 78 | 89 | 69 | 397 |
| Mean | 21.86 | 20.69 | 25.27 | 20.97 | 21.38 | 22.00 |
| SD | 20.427 | 20.282 | 19.715 | 18.252 | 20.076 | 19.695 |
| Social Support | | | | | | |
| N | 77 | 84 | 78 | 89 | 69 | 397 |
| Mean | 16.90 | 16.09 | 21.82 | 15.75 | 16.86 | 17.43 |
| SD | 20.535 | 17.418 | 21.834 | 18.710 | 21.424 | 19.968 |
| Self Image | | | | | | |
| N | 77 | 84 | 78 | 89 | 69 | 397 |
| Mean | 19.15 | 15.48 | 17.95 | 14.79 | 16.30 | 16.66 |
| SD | 22.218 | 16.626 | 19.236 | 17.979 | 21.931 | 19.536 |
| Proportion of Days with Usage of Pain Killer (%) at Baseline | | | | | | |
| N | 77 | 84 | 78 | 89 | 69 | 397 |
| Mean | 10.71 | 12.51 | 13.03 | 12.63 | 12.43 | 12.28 |
| SD | 12.431 | 12.398 | 16.096 | 15.034 | 14.638 | 14.139 |
| Mean of Amount of Bleeding at Baseline | | | | | | |
| N | 77 | 84 | 78 | 89 | 69 | 397 |
| Mean | 2.283 | 2.250 | 2.290 | 2.421 | 2.392 | 2.327 |
| SD | 0.5440 | 0.5032 | 0.5600 | 0.5459 | 0.5862 | 0.5483 |
| CA125 (U/mL) at Baseline | | | | | | |
| N | 77 | 84 | 78 | 89 | 69 | 397 |
| Mean | 62.49 | 93.48 | 69.79 | 89.31 | 70.43 | 77.87 |
| SD | 50.297 | 162.990 | 88.388 | 111.715 | 87.305 | 108.649 |

FIG. 76C

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Baseline | | | | | | | | | | |
| N | 97 | | 103 | | 100 | | 103 | | 81 | |
| Mean | 3.940 | | 3.789 | | 3.819 | | 3.994 | | 3.724 | |
| SD | 2.5105 | | 1.6048 | | 2.0763 | | 2.8043 | | 1.7718 | |
| Minimum | 0.96 | | 1.35 | | 0.81 | | 0.94 | | 0.43 | |
| Median | 3.650 | | 3.670 | | 3.590 | | 3.370 | | 3.460 | |
| Maximum | 19.99 | | 12.57 | | 19.04 | | 26.80 | | 10.61 | |
| Week 2 | | | | | | | | | | |
| N | 97 | 97 | 103 | 103 | 100 | 100 | 103 | 103 | 81 | 81 |
| Mean | 7.851 | 3.911 | 8.107 | 4.318 | 4.542 | 0.723 | 1.266 | -2.729 | 2.526 | -1.198 |
| SD | 9.6551 | 9.6834 | 9.0974 | 8.9196 | 8.4291 | 8.6710 | 3.4478 | 4.4552 | 1.4462 | 2.0110 |
| Minimum | 0.75 | -13.94 | 1.05 | -4.37 | 0.11 | -14.87 | 0.00 | -26.50 | 0.77 | -6.66 |
| Median | 4.600 | 1.380 | 5.250 | 1.610 | 3.125 | -0.600 | 0.360 | -2.860 | 2.200 | -1.150 |
| Maximum | 66.30 | 61.64 | 48.95 | 45.41 | 55.54 | 51.09 | 33.47 | 30.38 | 11.31 | 9.51 |
| Week 4 | | | | | | | | | | |
| N | 96 | 96 | 103 | 103 | 99 | 99 | 101 | 101 | 80 | 80 |
| Mean | 5.759 | 1.801 | 4.316 | 0.527 | 2.949 | -0.879 | 1.188 | -2.838 | 0.627 | -3.099 |
| SD | 8.4572 | 7.5006 | 4.3789 | 4.1967 | 2.5558 | 3.1952 | 3.3008 | 4.3098 | 0.2783 | 1.7750 |
| Minimum | 1.21 | -12.63 | 0.67 | -5.23 | 0.00 | -15.20 | 0.00 | -26.32 | 0.26 | -10.01 |
| Median | 3.900 | 0.395 | 2.980 | -0.450 | 2.230 | -1.520 | 0.290 | -2.910 | 0.560 | -2.755 |
| Maximum | 67.25 | 49.19 | 27.23 | 23.55 | 14.76 | 9.98 | 30.23 | 25.16 | 1.87 | 0.05 |
| Week 8 | | | | | | | | | | |
| N | 95 | 95 | 103 | 103 | 96 | 96 | 101 | 101 | 79 | 79 |
| Mean | 6.575 | 2.601 | 4.882 | 1.093 | 3.353 | -0.484 | 0.957 | -3.068 | 0.280 | -3.435 |
| SD | 10.3306 | 10.1759 | 5.9970 | 6.2454 | 2.7942 | 3.5179 | 1.3395 | 3.1283 | 0.1980 | 1.8058 |
| Minimum | 0.85 | -4.35 | 0.66 | -5.69 | 0.17 | -16.46 | 0.00 | -26.13 | 0.00 | -10.45 |
| Median | 3.920 | 0.420 | 3.550 | -0.060 | 2.575 | -1.235 | 0.390 | -2.800 | 0.240 | -3.190 |
| Maximum | 80.66 | 76.48 | 43.95 | 42.06 | 12.82 | 10.03 | 5.92 | 2.47 | 1.45 | -0.29 |
| Week 12 | | | | | | | | | | |
| N | 93 | 93 | 101 | 101 | 92 | 92 | 101 | 101 | 76 | 76 |
| Mean | 6.425 | 2.467 | 5.838 | 2.042 | 5.493 | 1.692 | 1.301 | -2.724 | 0.237 | -3.525 |
| SD | 8.2179 | 8.5329 | 7.6968 | 7.8405 | 10.9445 | 10.9277 | 2.4863 | 3.7540 | 0.1380 | 1.7906 |
| Minimum | 0.96 | -13.86 | 0.47 | -4.09 | 0.18 | -17.35 | 0.00 | -25.81 | 0.00 | -10.42 |
| Median | 4.240 | 0.630 | 4.050 | 0.750 | 2.780 | -0.870 | 0.530 | -2.700 | 0.205 | -3.300 |
| Maximum | 50.57 | 46.41 | 64.40 | 61.23 | 83.13 | 78.68 | 21.35 | 17.21 | 0.71 | -0.29 |

FIG. 78A

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Week 16 | | | | | | | | | | |
| N | 75 | 75 | 84 | 84 | 78 | 78 | 89 | 89 | 69 | 69 |
| Mean | 6.628 | 2.495 | 6.978 | 3.186 | 5.550 | 1.692 | 1.364 | -2.643 | 0.208 | -3.521 |
| SD | 8.5115 | 8.7861 | 9.3092 | 9.1207 | 10.2887 | 10.4251 | 2.4363 | 3.7229 | 0.1308 | 1.8180 |
| Minimum | 0.51 | -12.64 | 0.35 | -4.35 | 0.17 | -17.70 | 0.00 | -25.97 | 0.00 | -10.43 |
| Median | 3.900 | 0.370 | 4.140 | 0.760 | 3.350 | 0.255 | 0.700 | -2.590 | 0.200 | -3.350 |
| Maximum | 58.23 | 51.55 | 54.44 | 48.43 | 85.59 | 81.14 | 19.04 | 13.97 | 0.62 | -0.26 |
| Week 20 | | | | | | | | | | |
| N | 74 | 74 | 81 | 81 | 77 | 77 | 87 | 87 | 64 | 64 |
| Mean | 7.315 | 3.182 | 7.566 | 3.771 | 4.822 | 0.946 | 1.294 | -2.766 | 0.212 | -3.488 |
| SD | 8.9251 | 9.4121 | 13.4823 | 13.3110 | 9.8074 | 10.1956 | 1.5747 | 3.2894 | 0.1579 | 1.8610 |
| Minimum | 1.29 | -12.65 | 0.57 | -5.28 | 0.17 | -17.00 | 0.00 | -25.95 | 0.00 | -10.61 |
| Median | 5.075 | 0.830 | 4.230 | 0.500 | 3.560 | -0.420 | 0.730 | -2.540 | 0.185 | -3.260 |
| Maximum | 67.85 | 63.99 | 78.03 | 73.71 | 86.97 | 84.15 | 8.55 | 5.35 | 0.75 | -0.25 |
| Week 24 | | | | | | | | | | |
| N | 68 | 68 | 79 | 79 | 74 | 74 | 87 | 87 | 61 | 61 |
| Mean | 6.188 | 2.281 | 5.668 | 1.893 | 3.670 | -0.207 | 1.352 | -2.672 | 0.192 | -3.489 |
| SD | 6.6334 | 6.8009 | 6.1118 | 5.7256 | 2.9395 | 3.6364 | 1.5916 | 3.2403 | 0.1468 | 1.8984 |
| Minimum | 0.93 | -10.71 | 0.14 | -4.65 | 0.21 | -17.60 | 0.00 | -25.25 | 0.00 | -10.61 |
| Median | 4.240 | 0.945 | 3.600 | 0.300 | 2.790 | -0.785 | 0.880 | -2.480 | 0.180 | -3.140 |
| Maximum | 41.71 | 37.73 | 38.30 | 35.82 | 13.36 | 8.58 | 8.11 | 3.97 | 0.65 | -0.30 |
| Follow-up | | | | | | | | | | |
| N | 77 | 77 | 83 | 83 | 77 | 77 | 89 | 89 | 69 | 69 |
| Mean | 6.264 | 2.156 | 7.543 | 3.779 | 6.447 | 2.575 | 6.590 | 2.583 | 0.870 | -2.858 |
| SD | 6.1913 | 6.4505 | 9.1424 | 9.1983 | 8.6445 | 8.9157 | 8.9079 | 8.9640 | 1.3407 | 2.2122 |
| Minimum | 0.39 | -12.16 | 0.87 | -4.57 | 0.12 | -13.81 | 0.57 | -15.11 | 0.00 | -10.38 |
| Median | 4.380 | 0.610 | 4.960 | 1.540 | 4.520 | 0.590 | 4.470 | 0.630 | 0.300 | -2.420 |
| Maximum | 32.36 | 26.60 | 68.94 | 64.28 | 61.02 | 57.48 | 60.76 | 55.84 | 7.19 | 2.72 |

(mIU/mL)

FIG. 78B

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Baseline | | | | | | | | | | |
| N | 97 | | 103 | | 100 | | 103 | | 81 | |
| Mean | 6.433 | | 7.101 | | 7.353 | | 7.518 | | 7.234 | |
| SD | 1.9662 | | 2.7828 | | 4.5689 | | 5.9428 | | 3.5726 | |
| Minimum | 1.58 | | 2.54 | | 1.33 | | 3.05 | | 3.08 | |
| Median | 6.240 | | 6.640 | | 6.025 | | 6.240 | | 6.410 | |
| Maximum | 13.06 | | 21.20 | | 30.18 | | 52.98 | | 22.48 | |
| Week 2 | | | | | | | | | | |
| N | 97 | 97 | 103 | 103 | 100 | 100 | 103 | 103 | 81 | 81 |
| Mean | 4.843 | -1.590 | 6.549 | -0.552 | 6.181 | -1.173 | 3.800 | -3.718 | 1.927 | -5.307 |
| SD | 4.2961 | 4.3405 | 2.8633 | 3.5922 | 3.3981 | 4.8390 | 1.9227 | 5.9567 | 1.4846 | 3.8511 |
| Minimum | 1.36 | -9.21 | 1.80 | -14.73 | 1.77 | -21.60 | 0.60 | -49.59 | 0.21 | -21.53 |
| Median | 3.800 | -2.330 | 5.930 | -0.290 | 5.875 | -0.610 | 3.390 | -2.550 | 1.660 | -4.480 |
| Maximum | 40.39 | 31.49 | 21.95 | 15.95 | 25.14 | 15.62 | 9.07 | 4.67 | 6.07 | 0.50 |
| Week 4 | | | | | | | | | | |
| N | 96 | 96 | 103 | 103 | 99 | 99 | 101 | 101 | 80 | 80 |
| Mean | 6.474 | 0.056 | 5.540 | -1.560 | 5.076 | -2.290 | 3.121 | -4.394 | 2.198 | -5.059 |
| SD | 4.3629 | 3.8596 | 2.9462 | 3.5549 | 2.7136 | 4.4859 | 2.3970 | 6.2362 | 1.2708 | 3.8044 |
| Minimum | 1.16 | -6.89 | 1.16 | -12.68 | 1.21 | -21.85 | 0.38 | -49.47 | 0.55 | -20.56 |
| Median | 5.650 | -0.235 | 5.090 | -1.120 | 4.720 | -1.690 | 2.320 | -3.740 | 1.935 | -4.285 |
| Maximum | 30.97 | 21.22 | 23.71 | 16.07 | 14.31 | 4.60 | 14.71 | 10.80 | 6.48 | 1.33 |
| Week 8 | | | | | | | | | | |
| N | 95 | 95 | 103 | 103 | 96 | 96 | 101 | 101 | 79 | 79 |
| Mean | 6.197 | -0.232 | 5.572 | -1.529 | 5.097 | -2.322 | 2.757 | -4.758 | 3.209 | -4.062 |
| SD | 5.7041 | 5.3020 | 2.7445 | 3.7307 | 2.3862 | 4.5041 | 1.9080 | 5.9827 | 1.4897 | 3.8714 |
| Minimum | 1.18 | -7.74 | 1.26 | -15.39 | 0.68 | -20.50 | 0.36 | -49.02 | 0.82 | -19.72 |
| Median | 5.190 | -1.240 | 5.340 | -1.260 | 4.635 | -1.655 | 2.250 | -3.830 | 3.030 | -3.380 |
| Maximum | 33.96 | 27.87 | 19.46 | 12.49 | 12.21 | 3.94 | 8.95 | 2.32 | 8.06 | 3.05 |
| Week 12 | | | | | | | | | | |
| N | 93 | 93 | 101 | 101 | 92 | 92 | 101 | 101 | 76 | 76 |
| Mean | 5.533 | -0.917 | 6.056 | -1.037 | 5.859 | -1.595 | 2.806 | -4.710 | 3.614 | -3.729 |
| SD | 2.9936 | 2.5433 | 3.7250 | 3.9115 | 4.9502 | 5.1730 | 1.8637 | 5.9563 | 1.4384 | 3.8085 |
| Minimum | 0.66 | -7.59 | 1.21 | -18.94 | 0.82 | -20.95 | 0.17 | -48.91 | 1.00 | -18.31 |
| Median | 5.190 | -1.190 | 5.510 | -1.020 | 4.805 | -0.960 | 2.390 | -3.760 | 3.355 | -2.925 |
| Maximum | 15.93 | 5.48 | 25.78 | 17.97 | 32.08 | 19.92 | 9.28 | 1.64 | 8.10 | 5.02 |

FIG. 80A

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Week 16 | | | | | | | | | | |
| N | 75 | 75 | 84 | 84 | 78 | 78 | 89 | 89 | 69 | 69 |
| Mean | 5.405 | -1.153 | 5.889 | -0.959 | 6.213 | -1.613 | 2.922 | -4.462 | 3.719 | -3.685 |
| SD | 4.7732 | 4.6310 | 2.9180 | 3.6358 | 4.9984 | 6.1769 | 1.9871 | 5.8759 | 1.4623 | 3.7537 |
| Minimum | 1.33 | -7.86 | 0.79 | -11.21 | 1.15 | -21.24 | 0.18 | -48.73 | 0.97 | -18.13 |
| Median | 4.390 | -1.390 | 5.360 | -0.680 | 5.300 | -1.285 | 2.580 | -3.660 | 3.660 | -2.840 |
| Maximum | 39.34 | 30.44 | 15.27 | 9.19 | 38.73 | 26.57 | 8.68 | 3.46 | 8.01 | 1.63 |
| Week 20 | | | | | | | | | | |
| N | 74 | 74 | 81 | 81 | 77 | 77 | 87 | 87 | 64 | 64 |
| Mean | 5.571 | -0.987 | 6.147 | -0.747 | 6.122 | -1.738 | 2.978 | -4.482 | 3.927 | -3.504 |
| SD | 3.1388 | 3.1512 | 3.9377 | 4.2252 | 5.6231 | 6.8834 | 2.0633 | 5.9161 | 1.3854 | 3.9422 |
| Minimum | 1.21 | -7.71 | 0.74 | -10.03 | 1.13 | -25.00 | 0.20 | -49.04 | 1.52 | -18.69 |
| Median | 4.860 | -0.945 | 5.350 | -0.990 | 5.680 | -1.180 | 2.380 | -3.650 | 3.890 | -2.935 |
| Maximum | 21.84 | 14.42 | 23.70 | 14.65 | 49.55 | 36.49 | 9.34 | 1.85 | 7.57 | 4.49 |
| Week 24 | | | | | | | | | | |
| N | 68 | 68 | 79 | 79 | 74 | 74 | 87 | 87 | 61 | 61 |
| Mean | 5.751 | -0.871 | 5.807 | -1.131 | 5.229 | -2.532 | 3.003 | -4.467 | 4.018 | -3.428 |
| SD | 3.3327 | 3.4772 | 2.4162 | 2.8207 | 2.1699 | 4.9399 | 2.0197 | 5.7857 | 1.5223 | 3.7910 |
| Minimum | 1.21 | -8.19 | 1.02 | -8.25 | 1.02 | -22.31 | 0.24 | -48.06 | 1.50 | -17.57 |
| Median | 5.030 | -0.985 | 5.740 | -0.630 | 5.525 | -0.990 | 2.500 | -3.550 | 3.790 | -2.730 |
| Maximum | 18.84 | 11.98 | 12.23 | 8.34 | 10.96 | 4.33 | 9.67 | 2.39 | 7.94 | 3.58 |
| Follow-up | | | | | | | | | | |
| N | 77 | 77 | 83 | 83 | 77 | 77 | 89 | 89 | 69 | 69 |
| Mean | 5.306 | -1.174 | 5.650 | -1.215 | 5.431 | -2.444 | 5.161 | -2.223 | 5.442 | -1.962 |
| SD | 3.6079 | 3.5195 | 3.9525 | 4.3882 | 5.7715 | 6.4303 | 6.3417 | 6.5751 | 2.1984 | 3.7938 |
| Minimum | 1.17 | -8.26 | 0.98 | -14.37 | 0.54 | -23.68 | 0.69 | -23.85 | 0.80 | -16.34 |
| Median | 4.850 | -1.330 | 4.630 | -1.380 | 4.410 | -2.510 | 3.670 | -2.500 | 4.990 | -1.420 |
| Maximum | 22.84 | 14.60 | 26.47 | 17.29 | 43.19 | 30.30 | 51.09 | 45.83 | 13.28 | 6.02 |

(mIU/mL)

FIG. 80B

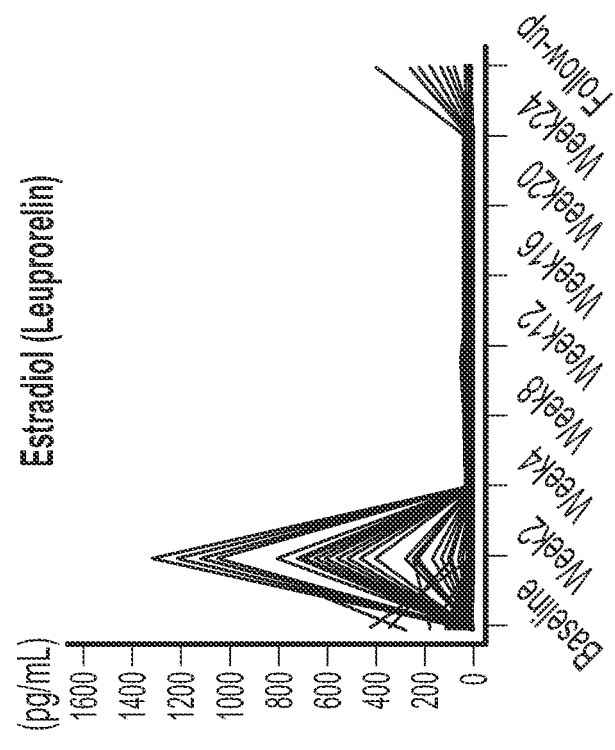
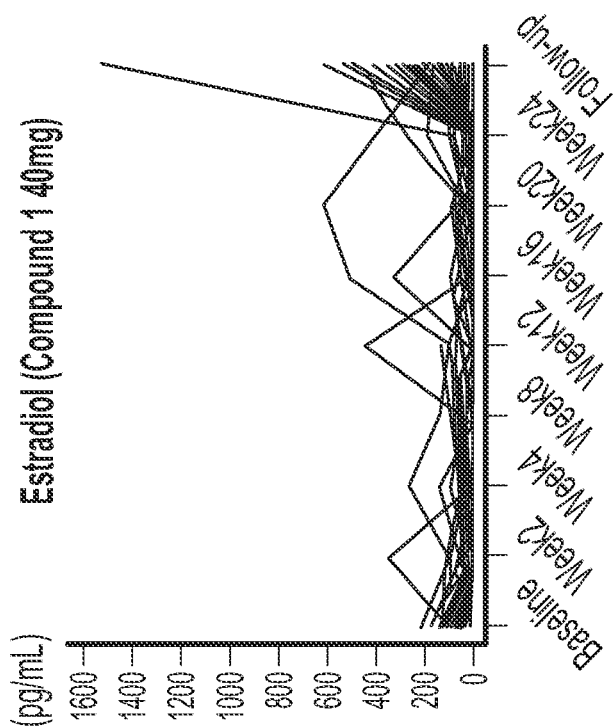
FIG. 81 (Cont.)

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Baseline | | | | | | | | | | |
| N | 97 | | 103 | | 100 | | 103 | | 81 | |
| Mean | 54.3 | | 57.1 | | 55.6 | | 52.5 | | 60.1 | |
| SD | 59.80 | | 53.40 | | 71.72 | | 35.34 | | 65.72 | |
| Minimum | 12 | | 20 | | 0 | | 13 | | 0 | |
| Median | 41.0 | | 45.0 | | 41.0 | | 44.0 | | 42.0 | |
| Maximum | 533 | | 460 | | 691 | | 220 | | 419 | |
| Week 2 | | | | | | | | | | |
| N | 97 | 97 | 103 | 103 | 100 | 100 | 103 | 103 | 81 | 81 |
| Mean | 205.4 | 151.1 | 130.1 | 73.0 | 58.1 | 2.5 | 12.7 | -39.8 | 204.0 | 143.9 |
| SD | 139.90 | 150.78 | 154.02 | 160.40 | 101.31 | 117.87 | 39.18 | 42.45 | 341.69 | 342.04 |
| Minimum | 0 | -337 | 0 | -365 | 0 | -642 | 0 | -170 | 0 | -407 |
| Median | 170.0 | 110.0 | 56.0 | 11.0 | 26.5 | -14.0 | 0.0 | -36.0 | 12.0 | -18.0 |
| Maximum | 683 | 606 | 699 | 652 | 746 | 665 | 354 | 258 | 1320 | 1281 |
| Week 4 | | | | | | | | | | |
| N | 96 | 96 | 103 | 103 | 99 | 99 | 101 | 101 | 80 | 80 |
| Mean | 90.6 | 36.3 | 81.3 | 24.1 | 43.2 | -12.4 | 11.2 | -41.3 | 2.0 | -58.5 |
| SD | 85.88 | 95.47 | 105.13 | 120.67 | 61.03 | 92.42 | 33.39 | 36.80 | 5.24 | 64.98 |
| Minimum | 15 | -468 | 0 | -436 | 0 | -645 | 0 | -170 | 0 | -401 |
| Median | 56.0 | 14.0 | 48.0 | 3.0 | 24.0 | -19.0 | 0.0 | -36.0 | 0.0 | -42.0 |
| Maximum | 451 | 404 | 616 | 576 | 351 | 312 | 264 | 90 | 22 | 0 |
| Week 8 | | | | | | | | | | |
| N | 95 | 95 | 103 | 103 | 96 | 96 | 101 | 101 | 79 | 79 |
| Mean | 121.1 | 66.5 | 70.9 | 13.8 | 52.2 | -3.5 | 8.2 | -44.4 | 3.1 | -57.7 |
| SD | 106.79 | 108.94 | 66.28 | 84.08 | 88.11 | 112.72 | 20.64 | 33.02 | 7.74 | 65.76 |
| Minimum | 19 | -253 | 0 | -398 | 0 | -665 | 0 | -170 | 0 | -397 |
| Median | 94.0 | 41.0 | 50.0 | -3.0 | 25.0 | -16.5 | 0.0 | -37.0 | 0.0 | -40.0 |
| Maximum | 807 | 646 | 294 | 272 | 556 | 522 | 134 | 48 | 30 | 0 |
| Week 12 | | | | | | | | | | |
| N | 93 | 93 | 101 | 101 | 92 | 92 | 101 | 101 | 76 | 76 |
| Mean | 149.8 | 95.1 | 90.1 | 32.9 | 72.1 | 16.0 | 13.3 | -39.2 | 3.8 | -57.6 |
| SD | 123.91 | 141.67 | 98.14 | 112.97 | 139.84 | 161.96 | 49.29 | 58.15 | 10.14 | 69.21 |
| Minimum | 13 | -478 | 0 | -436 | 0 | -673 | 0 | -170 | 0 | -419 |
| Median | 112.0 | 62.0 | 62.0 | 19.0 | 24.5 | -19.5 | 0.0 | -41.0 | 0.0 | -40.0 |
| Maximum | 602 | 576 | 672 | 641 | 836 | 817 | 443 | 387 | 50 | 21 |

FIG. 82A

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Week 16 | | | | | | | | | | |
| N | 75 | 75 | 84 | 84 | 78 | 78 | 89 | 89 | 69 | 69 |
| Mean | 165.5 | 114.1 | 99.5 | 40.2 | 60.8 | 4.4 | 15.4 | -38.6 | 4.6 | -57.4 |
| SD | 127.20 | 129.86 | 120.47 | 129.34 | 103.14 | 129.80 | 65.07 | 56.97 | 8.91 | 68.71 |
| Minimum | 0 | -113 | 0 | -403 | 0 | -671 | 0 | -170 | 0 | -383 |
| Median | 132.0 | 82.0 | 51.0 | 7.0 | 23.5 | -13.5 | 0.0 | -40.0 | 0.0 | -39.0 |
| Maximum | 593 | 566 | 586 | 547 | 456 | 423 | 509 | 289 | 36 | 3 |
| Week 20 | | | | | | | | | | |
| N | 74 | 74 | 81 | 81 | 77 | 77 | 87 | 87 | 64 | 64 |
| Mean | 166.4 | 115.6 | 91.5 | 32.1 | 47.2 | -9.5 | 14.6 | -39.9 | 4.3 | -58.1 |
| SD | 161.32 | 154.69 | 103.25 | 115.44 | 57.05 | 89.54 | 67.35 | 58.16 | 8.53 | 73.66 |
| Minimum | 14 | -120 | 0 | -386 | 0 | -560 | 0 | -170 | 0 | -419 |
| Median | 110.5 | 66.5 | 61.0 | 13.0 | 23.0 | -17.0 | 0.0 | -40.0 | 0.0 | -35.5 |
| Maximum | 773 | 647 | 483 | 437 | 256 | 213 | 615 | 395 | 31 | 14 |
| Week 24 | | | | | | | | | | |
| N | 68 | 68 | 79 | 79 | 74 | 74 | 87 | 87 | 61 | 61 |
| Mean | 158.4 | 106.7 | 84.5 | 25.5 | 52.3 | -4.9 | 11.7 | -40.6 | 3.9 | -59.9 |
| SD | 161.01 | 161.32 | 109.67 | 117.16 | 71.85 | 107.43 | 37.61 | 46.18 | 8.63 | 72.23 |
| Minimum | 0 | -118 | 0 | -410 | 0 | -663 | 0 | -170 | 0 | -380 |
| Median | 94.0 | 56.0 | 39.0 | 1.0 | 26.5 | -9.0 | 0.0 | -39.0 | 0.0 | -40.0 |
| Maximum | 934 | 887 | 517 | 432 | 408 | 345 | 267 | 187 | 39 | 33 |
| Follow-up | | | | | | | | | | |
| N | 77 | 77 | 83 | 83 | 77 | 77 | 89 | 89 | 69 | 69 |
| Mean | 150.2 | 92.7 | 129.1 | 69.8 | 144.9 | 88.1 | 178.6 | 124.6 | 30.5 | -31.5 |
| SD | 117.97 | 126.72 | 126.68 | 129.83 | 142.61 | 167.35 | 190.85 | 191.38 | 67.43 | 104.95 |
| Minimum | 0 | -341 | 0 | -409 | 0 | -655 | 0 | -109 | 0 | -408 |
| Median | 122.0 | 66.0 | 88.0 | 35.0 | 107.0 | 45.0 | 137.0 | 89.0 | 11.0 | -28.0 |
| Maximum | 608 | 502 | 651 | 556 | 765 | 712 | 1510 | 1459 | 392 | 374 |

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Baseline | | | | | | | | | | |
| N | 97 | | 103 | | 100 | | 103 | | 81 | |
| Mean | 0.367 | | 0.444 | | 0.348 | | 0.434 | | 0.338 | |
| SD | 0.2374 | | 0.4848 | | 0.2043 | | 0.8914 | | 0.1675 | |
| Minimum | 0.00 | | 0.04 | | 0.00 | | 0.00 | | 0.07 | |
| Median | 0.340 | | 0.350 | | 0.285 | | 0.330 | | 0.330 | |
| Maximum | 1.41 | | 3.68 | | 1.36 | | 9.18 | | 1.28 | |
| Week 2 | | | | | | | | | | |
| N | 97 | 97 | 103 | 103 | 100 | 100 | 103 | 103 | 81 | 81 |
| Mean | 8.219 | 7.852 | 1.778 | 1.334 | 0.655 | 0.306 | 0.600 | 0.167 | 0.511 | 0.173 |
| SD | 8.1673 | 8.2238 | 4.0191 | 4.0886 | 1.7395 | 1.7721 | 2.2123 | 2.3900 | 1.3763 | 1.3791 |
| Minimum | 0.07 | -0.52 | 0.00 | -3.52 | 0.00 | -0.94 | 0.00 | -8.87 | 0.00 | -0.91 |
| Median | 5.450 | 5.210 | 0.340 | -0.020 | 0.270 | -0.035 | 0.250 | -0.060 | 0.290 | -0.020 |
| Maximum | 43.00 | 42.32 | 21.50 | 21.42 | 13.60 | 13.50 | 20.70 | 20.40 | 12.30 | 11.94 |
| Week 4 | | | | | | | | | | |
| N | 96 | 96 | 103 | 103 | 99 | 99 | 101 | 101 | 80 | 80 |
| Mean | 1.969 | 1.604 | 2.556 | 2.112 | 1.687 | 1.339 | 0.502 | 0.069 | 0.254 | -0.084 |
| SD | 4.3210 | 4.3189 | 4.1054 | 4.1367 | 3.4741 | 3.4736 | 1.3777 | 1.6452 | 0.1395 | 0.1348 |
| Minimum | 0.00 | -0.87 | 0.00 | -3.52 | 0.00 | -0.29 | 0.00 | -8.88 | 0.00 | -0.88 |
| Median | 0.375 | 0.030 | 0.440 | 0.040 | 0.350 | 0.010 | 0.260 | -0.060 | 0.240 | -0.065 |
| Maximum | 24.70 | 24.56 | 20.30 | 20.07 | 20.90 | 20.31 | 9.43 | 9.37 | 0.62 | 0.11 |
| Week 8 | | | | | | | | | | |
| N | 95 | 95 | 103 | 103 | 96 | 96 | 101 | 101 | 79 | 79 |
| Mean | 3.865 | 3.497 | 2.870 | 2.426 | 1.484 | 1.134 | 0.352 | -0.081 | 0.265 | -0.075 |
| SD | 6.0154 | 5.9917 | 4.6452 | 4.7227 | 2.9854 | 2.9929 | 0.7703 | 1.1699 | 0.1386 | 0.1276 |
| Minimum | 0.00 | -0.25 | 0.07 | -3.50 | 0.00 | -0.40 | 0.00 | -8.88 | 0.00 | -0.73 |
| Median | 0.680 | 0.120 | 0.490 | 0.080 | 0.295 | -0.020 | 0.240 | -0.070 | 0.270 | -0.060 |
| Maximum | 23.40 | 23.19 | 22.50 | 22.03 | 16.60 | 16.25 | 7.60 | 7.32 | 0.60 | 0.16 |
| Week 12 | | | | | | | | | | |
| N | 93 | 93 | 101 | 101 | 92 | 92 | 101 | 101 | 76 | 76 |
| Mean | 4.224 | 3.854 | 2.883 | 2.435 | 1.510 | 1.159 | 0.345 | -0.088 | 0.247 | -0.093 |
| SD | 6.6269 | 6.6161 | 5.2326 | 5.2948 | 3.5727 | 3.5874 | 0.6684 | 1.1004 | 0.1269 | 0.1361 |
| Minimum | 0.00 | -1.10 | 0.00 | -3.45 | 0.00 | -0.40 | 0.00 | -8.83 | 0.00 | -0.83 |
| Median | 0.580 | 0.170 | 0.390 | 0.020 | 0.355 | -0.020 | 0.240 | -0.090 | 0.240 | -0.070 |
| Maximum | 31.20 | 31.06 | 26.50 | 26.03 | 16.70 | 16.46 | 6.38 | 6.10 | 0.53 | 0.12 |

FIG. 84A

| Visit / Statistics | Placebo (N=97) | | Compound 1 10 mg (N=103) | | Compound 1 20 mg (N=100) | | Compound 1 40 mg (N=103) | | Leuprorelin (N=81) | |
|---|---|---|---|---|---|---|---|---|---|---|
| | Observed Value at Visit | Change from Baseline | Observed Value at Visit | Change from Baseline | Observed Value at Visit | Change from Baseline | Observed Value at Visit | Change from Baseline | Observed Value at Visit | Change from Baseline |
| Week 16 | | | | | | | | | | |
| N | 75 | 75 | 84 | 84 | 78 | 78 | 89 | 89 | 69 | 69 |
| Mean | 4.837 | 4.460 | 2.473 | 2.001 | 1.468 | 1.128 | 0.522 | 0.076 | 0.247 | -0.091 |
| SD | 7.0789 | 7.0809 | 4.8197 | 4.8924 | 4.1143 | 4.1127 | 1.7533 | 2.0108 | 0.1267 | 0.1525 |
| Minimum | 0.00 | -1.11 | 0.06 | -3.44 | 0.00 | -0.40 | 0.00 | -8.92 | 0.00 | -0.91 |
| Median | 1.010 | 0.470 | 0.400 | 0.020 | 0.275 | -0.050 | 0.220 | -0.070 | 0.230 | -0.060 |
| Maximum | 34.10 | 34.10 | 23.50 | 23.10 | 27.30 | 26.69 | 12.50 | 12.31 | 0.57 | 0.13 |
| Week 20 | | | | | | | | | | |
| N | 74 | 74 | 81 | 81 | 77 | 77 | 87 | 87 | 64 | 64 |
| Mean | 3.487 | 3.109 | 2.372 | 1.892 | 1.525 | 1.193 | 0.339 | -0.100 | 0.264 | -0.076 |
| SD | 5.9037 | 5.9008 | 4.9131 | 4.9933 | 3.6715 | 3.6901 | 0.6027 | 1.1140 | 0.1283 | 0.1487 |
| Minimum | 0.00 | -1.01 | 0.08 | -3.45 | 0.00 | -0.32 | 0.00 | -8.86 | 0.00 | -0.86 |
| Median | 0.515 | 0.075 | 0.390 | -0.010 | 0.280 | -0.030 | 0.210 | -0.080 | 0.260 | -0.050 |
| Maximum | 29.40 | 28.75 | 26.70 | 26.46 | 17.30 | 17.24 | 4.61 | 4.14 | 0.56 | 0.13 |
| Week 24 | | | | | | | | | | |
| N | 68 | 68 | 79 | 79 | 74 | 74 | 87 | 87 | 61 | 61 |
| Mean | 4.029 | 3.642 | 2.125 | 1.645 | 2.363 | 2.032 | 0.580 | 0.143 | 0.248 | -0.099 |
| SD | 6.1053 | 6.1163 | 3.7671 | 3.8558 | 4.3576 | 4.3484 | 2.2138 | 2.4249 | 0.1171 | 0.1560 |
| Minimum | 0.00 | -0.78 | 0.06 | -3.51 | 0.00 | -0.41 | 0.00 | -8.86 | 0.00 | -0.96 |
| Median | 0.530 | 0.110 | 0.400 | 0.000 | 0.340 | 0.005 | 0.220 | -0.080 | 0.270 | -0.070 |
| Maximum | 23.40 | 23.26 | 15.90 | 15.53 | 16.80 | 16.27 | 17.30 | 17.24 | 0.51 | 0.10 |
| Follow-up | | | | | | | | | | |
| N | 77 | 77 | 83 | 83 | 77 | 77 | 89 | 89 | 69 | 69 |
| Mean | 4.780 | 4.402 | 4.455 | 3.983 | 4.807 | 4.468 | 8.301 | 7.856 | 0.882 | 0.545 |
| SD | 7.7944 | 7.7892 | 6.0513 | 6.0515 | 7.5004 | 7.5100 | 8.3767 | 8.5456 | 3.7114 | 3.7152 |
| Minimum | 0.00 | -0.84 | 0.06 | -3.42 | 0.08 | -0.39 | 0.00 | -7.92 | 0.00 | -0.71 |
| Median | 0.540 | 0.260 | 0.800 | 0.410 | 1.010 | 0.760 | 6.240 | 5.890 | 0.280 | -0.030 |
| Maximum | 37.90 | 37.22 | 23.90 | 23.22 | 41.90 | 41.29 | 28.60 | 28.39 | 27.50 | 27.10 |

| Variable / Visit | | Treatment | Summary Statistics | | | | | |
|---|---|---|---|---|---|---|---|---|
| | | | N | Mean | SD | Min | Median | Max |
| Biochemical Endometriosis Marker (CA125) (U/mL) | Baseline | Placebo | 97 | 58.42 | 48.650 | 7.9 | 47.00 | 288.0 |
| | | Compound 1 10mg | 103 | 85.33 | 149.891 | 6.9 | 38.10 | 1070.0 |
| | | Compound 1 20mg | 100 | 67.44 | 83.191 | 8.3 | 44.95 | 589.0 |
| | | Compound 1 40mg | 103 | 85.93 | 105.800 | 7.1 | 43.40 | 586.0 |
| | | Leuprorelin | 81 | 67.96 | 83.523 | 7.5 | 32.90 | 417.0 |
| | Week 12 | Placebo | 94 | 46.63 | 56.804 | 5.9 | 32.50 | 450.0 |
| | | Compound 1 10mg | 103 | 36.89 | 56.927 | 4.2 | 21.30 | 509.0 |
| | | Compound 1 20mg | 98 | 24.87 | 24.313 | 4.7 | 17.80 | 182.0 |
| | | Compound 1 40mg | 102 | 21.27 | 21.048 | 3.6 | 13.85 | 124.0 |
| | | Leuprorelin | 80 | 21.24 | 30.846 | 3.7 | 12.50 | 194.0 |
| | Week 24 | Placebo | 73 | 44.13 | 38.729 | 7.3 | 31.50 | 230.0 |
| | | Compound 1 10mg | 81 | 37.50 | 48.743 | 5.5 | 22.10 | 319.0 |
| | | Compound 1 20mg | 74 | 25.55 | 23.720 | 5.4 | 18.20 | 140.0 |
| | | Compound 1 40mg | 87 | 20.18 | 21.616 | 4.0 | 12.70 | 113.0 |
| | | Leuprorelin | 63 | 20.11 | 27.151 | 3.9 | 11.20 | 143.0 |

FIG. 85

| Variable / Visit | | Treatment | Summary Statistics | | | | | |
|---|---|---|---|---|---|---|---|---|
| | | | N | Mean | SD | Min | Median | Max |
| Percent Change from Baseline in Biochemical Endometriosis Marker (CA125) (%) | Week 12 | Placebo | 94 | -16.46 | 38.785 | -78.5 | -20.40 | 135.0 |
| | | Compound 1 10mg | 103 | -34.04 | 87.314 | -95.7 | -47.10 | 793.0 |
| | | Compound 1 20mg | 98 | -46.08 | 36.418 | -98.6 | -51.10 | 112.2 |
| | | Compound 1 40mg | 102 | -55.67 | 35.898 | -97.8 | -62.95 | 109.3 |
| | | Leuprorelin | 80 | -54.95 | 36.069 | -94.4 | -60.50 | 149.5 |
| | Week 24 | Placebo | 73 | -14.01 | 55.858 | -83.3 | -24.00 | 273.6 |
| | | Compound 1 10mg | 81 | -39.08 | 41.893 | -93.3 | -47.60 | 145.0 |
| | | Compound 1 20mg | 74 | -46.24 | 33.099 | -98.5 | -51.25 | 47.8 |
| | | Compound 1 40mg | 87 | -56.69 | 45.139 | -98.0 | -65.50 | 179.2 |
| | | Leuprorelin | 63 | -54.15 | 46.359 | -92.8 | -60.30 | 201.8 |

FIG. 86

| Variable / Visit | | Treatment | Summary Statistics | | | | | | 95% CI | |
|---|---|---|---|---|---|---|---|---|---|---|
| | | | N | Mean | SD | Min | Median | Max | Lower | Upper |
| Mean of VAS Score for Pelvic Pain (mm) | Baseline | Placebo | 97 | 15.610 | 14.3204 | 0.82 | 11.330 | 64.96 | 12.7235 | 18.4959 |
| | | Compound 1 10mg | 103 | 14.595 | 11.9866 | 0.30 | 12.000 | 69.26 | 12.2520 | 16.9373 |
| | | Compound 1 20mg | 100 | 15.589 | 15.0569 | 0.48 | 11.090 | 69.85 | 12.6014 | 18.5766 |
| | | Compound 1 40mg | 103 | 15.259 | 11.9932 | 1.86 | 12.190 | 81.23 | 12.9150 | 17.6029 |
| | | Leuprorelin | 81 | 15.181 | 15.1029 | 0.08 | 11.000 | 76.39 | 11.8413 | 18.5204 |
| | Day 1 - 28 | Placebo | 97 | 13.315 | 13.1953 | 0.00 | 8.750 | 57.93 | 10.6560 | 15.9749 |
| | | Compound 1 10mg | 103 | 9.988 | 10.3249 | 0.00 | 6.640 | 43.25 | 7.9705 | 12.0062 |
| | | Compound 1 20mg | 100 | 11.627 | 14.7324 | 0.00 | 6.320 | 63.36 | 8.7041 | 14.5505 |
| | | Compound 1 40mg | 103 | 11.498 | 13.2341 | 0.00 | 7.000 | 82.57 | 8.9119 | 14.0848 |
| | | Leuprorelin | 81 | 10.899 | 14.8866 | 0.00 | 6.000 | 76.82 | 7.6076 | 14.1910 |
| | Day 29 - 56 | Placebo | 96 | 12.041 | 12.3114 | 0.00 | 6.750 | 45.57 | 9.5464 | 14.5355 |
| | | Compound 1 10mg | 103 | 8.858 | 9.6429 | 0.00 | 5.750 | 52.11 | 6.9737 | 10.7430 |
| | | Compound 1 20mg | 99 | 8.324 | 12.2852 | 0.00 | 3.820 | 58.61 | 5.8738 | 1.7743 |
| | | Compound 1 40mg | 101 | 6.362 | 10.4401 | 0.00 | 2.320 | 49.86 | 4.3010 | 8.4230 |
| | | Leuprorelin | 79 | 6.873 | 14.2302 | 0.00 | 1.320 | 77.00 | 3.6859 | 10.0607 |
| | Day 57 - 84 | Placebo | 95 | 11.776 | 13.5443 | 0.00 | 6.890 | 73.67 | 9.0166 | 14.5348 |
| | | Compound 1 10mg | 101 | 8.400 | 10.1329 | 0.00 | 4.930 | 50.75 | 6.3992 | 10.4000 |
| | | Compound 1 20mg | 94 | 6.675 | 10.8072 | 0.00 | 2.520 | 65.14 | 4.4614 | 8.8884 |
| | | Compound 1 40mg | 101 | 4.785 | 8.9162 | 0.00 | 0.790 | 53.93 | 3.0249 | 6.5452 |
| | | Leuprorelin | 78 | 5.013 | 12.0454 | 0.00 | 0.195 | 65.86 | 2.2970 | 7.7286 |
| | Day 85 - 112 | Placebo | 77 | 11.175 | 12.9918 | 0.00 | 5.890 | 53.21 | 8.2263 | 14.1238 |
| | | Compound 1 10mg | 84 | 7.895 | 10.2362 | 0.00 | 3.860 | 50.36 | 5.6738 | 10.1166 |
| | | Compound 1 20mg | 78 | 6.280 | 9.2399 | 0.00 | 3.340 | 48.61 | 4.1963 | 8.3629 |
| | | Compound 1 40mg | 89 | 3.364 | 6.3640 | 0.00 | 0.460 | 38.36 | 2.0233 | 4.7045 |
| | | Leuprorelin | 69 | 3.418 | 10.0341 | 0.00 | 0.070 | 68.79 | 1.0080 | 5.8289 |
| | Day 113 - 140 | Placebo | 75 | 10.694 | 13.0408 | 0.00 | 5.570 | 49.89 | 7.6937 | 13.6945 |
| | | Compound 1 10mg | 84 | 7.111 | 8.5152 | 0.00 | 3.810 | 48.68 | 5.2627 | 8.9585 |
| | | Compound 1 20mg | 77 | 6.011 | 9.2439 | 0.00 | 1.820 | 55.82 | 3.9131 | 8.1093 |
| | | Compound 1 40mg | 89 | 3.733 | 8.3028 | 0.00 | 0.040 | 40.86 | 1.9840 | 5.4820 |
| | | Leuprorelin | 68 | 2.848 | 7.2362 | 0.00 | 0.000 | 50.14 | 0.7329 | 4.2359 |
| | Day 141 - 168 | Placebo | 71 | 10.444 | 12.3696 | 0.00 | 5.500 | 49.19 | 7.5164 | 13.3721 |
| | | Compound 1 10mg | 80 | 6.861 | 9.2099 | 0.00 | 3.105 | 49.93 | 4.8113 | 8.9104 |
| | | Compound 1 20mg | 77 | 5.486 | 9.1562 | 0.00 | 2.180 | 42.04 | 3.4080 | 7.5644 |
| | | Compound 1 40mg | 88 | 2.979 | 6.1704 | 0.00 | 0.000 | 39.43 | 1.6717 | 4.2865 |
| | | Leuprorelin | 63 | 2.167 | 5.1999 | 0.00 | 0.000 | 23.46 | 0.8572 | 3.4764 |
| | End of Treatment Period | Placebo | 97 | 12.387 | 12.7540 | 0.11 | 7.210 | 50.00 | 9.8168 | 14.9578 |
| | | Compound 1 10mg | 103 | 7.746 | 9.0900 | 0.00 | 4.360 | 49.93 | 5.9692 | 9.5223 |
| | | Compound 1 20mg | 100 | 6.557 | 11.2902 | 0.00 | 2.535 | 62.25 | 4.3166 | 8.7970 |
| | | Compound 1 40mg | 103 | 3.335 | 6.4059 | 0.00 | 0.040 | 37.68 | 2.0833 | 4.5872 |
| | | Leuprorelin | 81 | 2.629 | 5.5783 | 0.00 | 0.000 | 25.39 | 1.3958 | 3.8627 |

FIG. 88

| Variable / Visit | Visit | Treatment | Summary Statistics | | | | | | 95% CI | |
|---|---|---|---|---|---|---|---|---|---|---|
| | | | N | Mean | SD | Min | Median | Max | Lower | Upper |
| Change from Baseline in Mean of VAS Score for Pelvic Pain (mm) | Day 1 - 28 | Placebo | 97 | -2.294 | 8.9903 | -34.17 | -2.680 | 23.64 | -4.1062 | -0.4823 |
| | | Compound 1 10mg | 103 | -4.606 | 7.1304 | -33.87 | -3.570 | 12.29 | -5.9999 | -3.2127 |
| | | Compound 1 20mg | 100 | -3.962 | 6.6751 | -24.94 | -3.395 | 11.64 | -5.2862 | -2.6372 |
| | | Compound 1 40mg | 103 | -3.761 | 7.8831 | -29.95 | -2.920 | 30.97 | -5.3012 | -2.2199 |
| | | Leuprorelin | 81 | -4.282 | 7.3628 | -36.98 | -2.820 | 14.52 | -5.9096 | -2.6536 |
| | Day 29 - 56 | Placebo | 96 | -3.604 | 10.1906 | -30.81 | -3.360 | 29.21 | -5.6688 | -1.5392 |
| | | Compound 1 10mg | 103 | -5.736 | 9.8576 | -60.69 | -3.780 | 13.54 | -7.6629 | -3.8098 |
| | | Compound 1 20mg | 99 | -6.787 | 9.3858 | -41.71 | -5.750 | 21.35 | -8.6594 | -4.9155 |
| | | Compound 1 40mg | 101 | -8.960 | 9.8226 | -44.66 | -8.110 | 24.61 | -10.8990 | -7.0208 |
| | | Leuprorelin | 79 | -8.618 | 9.9690 | -52.37 | -6.410 | 23.93 | -10.8513 | -6.3854 |
| | Day 57 - 84 | Placebo | 95 | -3.945 | 10.7499 | -45.96 | -3.660 | 36.64 | -6.1353 | -1.7556 |
| | | Compound 1 10mg | 101 | -6.282 | 9.1659 | -50.65 | -4.540 | 10.23 | -8.0914 | -4.4725 |
| | | Compound 1 20mg | 94 | -8.547 | 13.8568 | -64.33 | -5.795 | 36.40 | -11.3851 | -5.7088 |
| | | Compound 1 40mg | 101 | -10.537 | 11.0516 | -63.05 | -9.200 | 28.68 | -12.7185 | -8.3551 |
| | | Leuprorelin | 78 | -10.364 | 10.4428 | -54.59 | -7.885 | 14.70 | -12.7183 | -8.0094 |
| | Day 85 - 112 | Placebo | 77 | -3.860 | 11.5776 | -41.25 | -3.320 | 41.53 | -6.4877 | -1.2321 |
| | | Compound 1 10mg | 84 | -6.727 | 10.4187 | -62.26 | -4.260 | 14.32 | -8.9883 | -4.4663 |
| | | Compound 1 20mg | 78 | -8.528 | 13.2829 | -64.33 | -5.465 | 14.87 | -11.5228 | -5.5331 |
| | | Compound 1 40mg | 89 | -12.475 | 10.9347 | -69.73 | -10.000 | 15.74 | -14.7780 | -10.1712 |
| | | Leuprorelin | 69 | -12.585 | 10.8106 | -55.12 | -9.140 | 0.24 | -15.1816 | -9.9877 |
| | Day 113 - 140 | Placebo | 75 | -4.407 | 11.8397 | -48.39 | -4.390 | 31.71 | -7.1306 | -1.6825 |
| | | Compound 1 10mg | 84 | -7.512 | 10.5832 | -57.72 | -5.070 | 15.97 | -9.8086 | -5.2152 |
| | | Compound 1 20mg | 77 | -8.153 | 10.8432 | -48.89 | -6.350 | 17.53 | -10.6144 | -5.6921 |
| | | Compound 1 40mg | 89 | -12.106 | 12.3644 | -75.66 | -9.880 | 28.65 | -14.7101 | -9.5009 |
| | | Leuprorelin | 68 | -13.681 | 11.8045 | -55.41 | -10.290 | 2.70 | -16.5386 | -10.8240 |
| | Day 141 - 168 | Placebo | 71 | -4.866 | 12.4477 | -56.08 | -3.210 | 20.89 | -7.8120 | -1.9193 |
| | | Compound 1 10mg | 80 | -7.872 | 11.2457 | -57.94 | -5.390 | 17.22 | -10.3746 | -5.3694 |
| | | Compound 1 20mg | 77 | -8.678 | 10.6479 | -57.49 | -6.000 | 17.32 | -11.0949 | -6.2614 |
| | | Compound 1 40mg | 88 | -12.919 | 11.8210 | -76.87 | -9.960 | 7.74 | -15.4234 | -10.4141 |
| | | Leuprorelin | 63 | -13.804 | 12.8288 | -63.71 | -10.260 | -0.08 | -17.0347 | -10.5729 |
| | End of Treatment Period | Placebo | 97 | -3.222 | 12.1616 | -56.03 | -3.020 | 36.03 | -5.6735 | -0.7713 |
| | | Compound 1 10mg | 103 | -6.849 | 10.5616 | -57.94 | -4.820 | 17.22 | -8.9131 | -4.7848 |
| | | Compound 1 20mg | 100 | -9.032 | 11.8432 | -64.33 | -5.970 | 17.32 | -11.3821 | -6.6823 |
| | | Compound 1 40mg | 103 | -11.924 | 11.2609 | -76.80 | -9.700 | 8.53 | -14.1245 | -9.7229 |
| | | Leuprorelin | 81 | -12.552 | 12.5609 | -63.71 | -9.020 | 3.33 | -15.3290 | -9.7742 |

FIG. 90

| Variable / Visit | | | Diff | 95% CI | |
|---|---|---|---|---|---|
| | | | | Lower | Upper |
| Change from Baseline in Mean of VAS Score for Pelvic Pain (mm) | Day 1 - 28 | Compound 1 10mg- Leuprorelin | -0.325 | -2.4442 | 1.7948 |
| | | Compound 1 20mg- Leuprorelin | 0.320 | -1.7422 | 2.3830 |
| | | Compound 1 40mg- Leuprorelin | 0.521 | -1.7231 | 2.7652 |
| | Day 29 - 56 | Compound 1 10mg- Leuprorelin | 2.882 | -0.0413 | 5.8054 |
| | | Compound 1 20mg- Leuprorelin | 1.831 | -1.0418 | 4.7036 |
| | | Compound 1 40mg- Leuprorelin | -0.342 | -3.2720 | 2.5889 |
| | Day 57 - 84 | Compound 1 10mg- Leuprorelin | 4.082 | 1.1839 | 6.9798 |
| | | Compound 1 20mg- Leuprorelin | 1.817 | -1.9404 | 5.5742 |
| | | Compound 1 40mg- Leuprorelin | -0.173 | -3.3830 | 3.0370 |
| | Day 85 - 112 | Compound 1 10mg- Leuprorelin | 5.857 | 2.4556 | 9.2592 |
| | | Compound 1 20mg- Leuprorelin | 4.057 | 0.0762 | 8.0372 |
| | | Compound 1 40mg- Leuprorelin | 0.110 | -3.3374 | 3.5575 |
| | Day 113 - 140 | Compound 1 10mg- Leuprorelin | 6.169 | 2.5770 | 9.7618 |
| | | Compound 1 20mg- Leuprorelin | 5.528 | 1.8098 | 9.2464 |
| | | Compound 1 40mg- Leuprorelin | 1.576 | -2.2821 | 5.4338 |
| | Day 141 - 168 | Compound 1 10mg- Leuprorelin | 5.932 | 1.9466 | 9.9170 |
| | | Compound 1 20mg- Leuprorelin | 5.126 | 1.2028 | 9.0484 |
| | | Compound 1 40mg- Leuprorelin | 0.885 | -3.1100 | 4.8801 |
| | End of Treatment Period | Compound 1 10mg- Leuprorelin | 5.703 | 2.3389 | 9.0675 |
| | | Compound 1 20mg- Leuprorelin | 3.519 | -0.0702 | 7.1091 |
| | | Compound 1 40mg- Leuprorelin | 0.628 | -2.8443 | 4.1001 |

FIG. 91

| Variable / Visit | Treatment | Summary Statistics | | | | | | 95% CI | |
|---|---|---|---|---|---|---|---|---|---|
| | | N | Mean | SD | Min | Median | Max | Lower | Upper |
| Mean of VAS Score for Dyspareunia (mm) | Baseline | | | | | | | | |
| | Placebo | 41 | 11.046 | 14.2483 | 0.00 | 4.00 | 60.00 | 6.5490 | 15.5437 |
| | Compound 1 10mg | 46 | 8.822 | 14.2407 | 0.00 | 1.550 | 72.00 | 4.5934 | 13.0514 |
| | Compound 1 20mg | 47 | 12.470 | 16.4833 | 0.00 | 4.500 | 60.00 | 7.6301 | 17.3095 |
| | Compound 1 40mg | 44 | 9.389 | 15.4208 | 0.00 | 2.800 | 64.67 | 4.7005 | 14.0772 |
| | Leuprorelin | 26 | 9.455 | 10.7051 | 0.00 | 6.250 | 44.00 | 5.1315 | 13.7793 |
| | Day 1 - 28 | | | | | | | | |
| | Placebo | 44 | 10.676 | 16.5317 | 0.00 | 4.750 | 81.00 | 5.6496 | 15.7018 |
| | Compound 1 10mg | 50 | 9.608 | 15.4027 | 0.00 | 2.735 | 75.00 | 5.2302 | 13.9850 |
| | Compound 1 20mg | 44 | 10.809 | 15.5738 | 0.00 | 2.625 | 53.50 | 6.0738 | 15.5435 |
| | Compound 1 40mg | 42 | 9.522 | 13.6408 | 0.00 | 2.065 | 53.00 | 5.2714 | 13.7729 |
| | Leuprorelin | 25 | 7.288 | 16.2960 | 0.00 | 0.860 | 67.00 | 0.5609 | 14.0143 |
| | Day 29 - 56 | | | | | | | | |
| | Placebo | 38 | 9.115 | 10.4655 | 0.00 | 4.800 | 40.40 | 5.6748 | 12.5546 |
| | Compound 1 10mg | 48 | 9.751 | 18.2336 | 0.00 | 1.915 | 78.00 | 4.4570 | 15.0459 |
| | Compound 1 20mg | 49 | 11.660 | 19.4615 | 0.00 | 1.750 | 68.00 | 6.0698 | 17.2498 |
| | Compound 1 40mg | 39 | 6.711 | 12.6281 | 0.00 | 1.000 | 64.00 | 2.6172 | 10.8043 |
| | Leuprorelin | 24 | 3.440 | 6.8993 | 0.00 | 0.000 | 27.00 | 0.5263 | 6.3529 |
| | Day 57 - 84 | | | | | | | | |
| | Placebo | 36 | 11.445 | 15.5573 | 0.00 | 4.165 | 58.00 | 6.1814 | 16.7091 |
| | Compound 1 10mg | 50 | 10.110 | 18.5404 | 0.00 | 1.550 | 73.00 | 4.8405 | 15.3787 |
| | Compound 1 20mg | 35 | 9.229 | 16.6530 | 0.00 | 0.830 | 72.00 | 3.5081 | 14.9491 |
| | Compound 1 40mg | 40 | 4.126 | 7.9652 | 0.00 | 0.125 | 33.00 | 1.5789 | 6.6736 |
| | Leuprorelin | 24 | 5.478 | 10.7612 | 0.00 | 0.000 | 41.75 | 0.9343 | 10.0224 |
| | Day 85 - 112 | | | | | | | | |
| | Placebo | 27 | 9.226 | 16.1421 | 0.00 | 5.500 | 70.00 | 2.8400 | 15.6111 |
| | Compound 1 10mg | 35 | 4.574 | 8.8940 | 0.00 | 0.000 | 38.00 | 1.5191 | 7.6295 |
| | Compound 1 20mg | 31 | 8.927 | 16.1695 | 0.00 | 0.500 | 57.00 | 2.9958 | 14.8578 |
| | Compound 1 40mg | 31 | 9.564 | 17.7291 | 0.00 | 1.800 | 62.00 | 3.0608 | 16.0669 |
| | Leuprorelin | 23 | 3.484 | 5.6895 | 0.00 | 0.000 | 18.00 | 1.0236 | 5.9442 |
| | Day 113 - 140 | | | | | | | | |
| | Placebo | 33 | 9.305 | 13.4358 | 0.00 | 2.500 | 47.00 | 4.5413 | 14.0696 |
| | Compound 1 10mg | 38 | 3.804 | 8.4116 | 0.00 | 0.000 | 47.50 | 1.0397 | 6.5693 |
| | Compound 1 20mg | 30 | 8.789 | 16.0423 | 0.00 | 0.500 | 52.00 | 2.7984 | 14.7789 |
| | Compound 1 40mg | 34 | 5.410 | 11.3459 | 0.00 | 0.000 | 47.00 | 1.4515 | 9.3691 |
| | Leuprorelin | 15 | 2.522 | 3.8630 | 0.00 | 0.000 | 11.00 | 0.3827 | 4.6613 |
| | Day 141 - 168 | | | | | | | | |
| | Placebo | 20 | 9.192 | 12.7469 | 0.00 | 2.915 | 42.00 | 3.2258 | 15.1572 |
| | Compound 1 10mg | 36 | 5.550 | 11.1157 | 0.00 | 0.000 | 46.00 | 1.7893 | 9.3113 |
| | Compound 1 20mg | 29 | 3.806 | 8.9781 | 0.00 | 0.000 | 35.00 | 0.3911 | 7.2213 |
| | Compound 1 40mg | 31 | 3.531 | 9.6053 | 0.00 | 0.000 | 51.00 | 0.0074 | 7.0539 |
| | Leuprorelin | 18 | 5.565 | 12.5556 | 0.00 | 0.000 | 47.00 | -0.6788 | 11.8088 |
| | End of Treatment Period | | | | | | | | |
| | Placebo | 36 | 11.318 | 15.7393 | 0.00 | 3.875 | 58.00 | 5.9924 | 16.6432 |
| | Compound 1 10mg | 50 | 6.218 | 10.6280 | 0.00 | 0.290 | 46.00 | 3.1976 | 9.2384 |
| | Compound 1 20mg | 40 | 6.363 | 13.1847 | 0.00 | 0.585 | 53.00 | 2.1461 | 10.5794 |
| | Compound 1 40mg | 39 | 4.842 | 9.1145 | 0.00 | 0.170 | 33.00 | 1.8870 | 7.7961 |
| | Leuprorelin | 23 | 4.913 | 10.6249 | 0.00 | 0.000 | 47.00 | 0.3185 | 9.5076 |

FIG. 93

| Variable / Visit | Treatment | | Summary Statistics | | | | | 95% CI | |
|---|---|---|---|---|---|---|---|---|---|
| | | N | Mean | SD | Min | Median | Max | Lower | Upper |
| Change from Baseline in Mean of VAS Score for Dyspareunia (mm) | Day 1 - 28 Placebo | 37 | -1.464 | 6.1084 | -17.50 | 0.000 | 8.25 | -3.5007 | 0.5726 |
| | Compound 1 10mg | 39 | 1.642 | 10.6212 | -38.00 | 0.000 | 26.50 | -1.8007 | 5.0853 |
| | Compound 1 20mg | 39 | 0.953 | 12.3795 | -32.67 | 0.000 | 50.00 | -3.0599 | 4.9661 |
| | Compound 1 40mg | 33 | 2.995 | 9.7916 | -21.67 | 0.000 | 35.00 | -0.4774 | 6.4665 |
| | Leuprorelin | 21 | -3.126 | 17.0520 | -31.00 | -3.500 | 45.00 | -10.8882 | 4.6358 |
| | Day 29 - 56 Placebo | 31 | -6.324 | 13.7901 | -53.00 | -3.250 | 22.90 | -11.3821 | -1.2656 |
| | Compound 1 10mg | 40 | 0.700 | 17.1416 | -41.00 | 0.000 | 67.50 | -4.7824 | 6.1819 |
| | Compound 1 20mg | 40 | -0.358 | 13.4556 | -34.24 | 0.000 | 36.00 | -4.6616 | 3.9451 |
| | Compound 1 40mg | 32 | -1.085 | 9.2912 | -30.50 | 0.000 | 23.00 | -4.4349 | 2.2649 |
| | Leuprorelin | 17 | -5.988 | 8.9457 | -25.00 | -4.670 | 13.00 | -10.5871 | -1.3882 |
| | Day 57 - 84 Placebo | 30 | -5.018 | 14.8372 | -55.00 | 0.000 | 13.50 | -10.5583 | 0.5223 |
| | Compound 1 10mg | 41 | -1.033 | 12.2047 | -25.00 | 0.000 | 59.50 | -4.8852 | 2.8194 |
| | Compound 1 20mg | 33 | -0.191 | 10.6032 | -35.67 | 0.000 | 29.50 | -3.9503 | 3.5691 |
| | Compound 1 40mg | 33 | -1.860 | 10.3161 | 31.67 | 0.000 | 22.00 | -5.5182 | 1.7976 |
| | Leuprorelin | 18 | -6.752 | 10.5824 | -26.00 | -5.770 | 16.75 | -12.0142 | -1.4891 |
| | Day 85 - 112 Placebo | 22 | -0.715 | 20.9133 | -32.50 | -1.050 | 66.00 | -9.9879 | 8.5570 |
| | Compound 1 10mg | 28 | -3.865 | 7.9514 | -34.00 | -0.155 | 4.18 | -6.9486 | -0.7821 |
| | Compound 1 20mg | 28 | -1.911 | 14.4995 | -35.67 | -1.800 | 43.80 | -7.5330 | 3.7116 |
| | Compound 1 40mg | 22 | 0.265 | 13.2572 | -32.50 | 0.000 | 34.00 | -5.6125 | 6.1434 |
| | Leuprorelin | 19 | -6.915 | 9.4608 | -33.00 | -4.000 | 1.30 | -11.4747 | -2.3548 |
| | Day 113 - 140 Placebo | 26 | -2.913 | 10.8470 | -30.00 | -0.500 | 15.83 | -7.2946 | 1.4677 |
| | Compound 1 10mg | 28 | -4.879 | 12.8937 | -60.00 | -0.070 | 6.28 | -9.8786 | 0.1207 |
| | Compound 1 20mg | 26 | -1.778 | 13.6186 | -35.04 | -1.495 | 38.80 | -7.2787 | 3.7226 |
| | Compound 1 40mg | 25 | -1.063 | 11.3013 | -34.00 | 0.000 | 32.00 | -5.7282 | 3.6018 |
| | Leuprorelin | 13 | -7.552 | 11.1102 | -37.00 | -4.670 | 5.00 | -14.2661 | -0.8385 |
| | Day 141 - 168 Placebo | 16 | -3.256 | 15.8951 | -45.00 | 0.000 | 16.00 | -11.7261 | 5.2136 |
| | Compound 1 10mg | 28 | -4.124 | 10.5641 | -46.50 | -0.070 | 15.60 | -8.2206 | -0.0279 |
| | Compound 1 20mg | 26 | -4.012 | 12.5050 | -33.47 | -1.250 | 35.00 | -9.0628 | 1.0390 |
| | Compound 1 40mg | 22 | -0.830 | 13.6774 | -35.00 | 0.000 | 48.00 | -6.8947 | 5.2338 |
| | Leuprorelin | 14 | -4.953 | 16.9523 | -40.50 | -3.000 | 36.33 | -14.7408 | 4.8351 |
| | End of Treatment Period Placebo | 29 | -1.145 | 12.6625 | -45.00 | 0.000 | 16.00 | -5.9617 | 3.6715 |
| | Compound 1 10mg | 40 | -3.454 | 10.8509 | -46.50 | -0.500 | 29.00 | -6.9238 | 0.0168 |
| | Compound 1 20mg | 34 | -3.553 | 11.5544 | -33.47 | -0.965 | 35.00 | -7.5848 | 0.4783 |
| | Compound 1 40mg | 31 | -0.925 | 12.0373 | -35.00 | 0.000 | 29.00 | -5.3398 | 3.4908 |
| | Leuprorelin | 18 | -4.593 | 15.0878 | -40.50 | -3.250 | 36.33 | -12.0963 | 2.9096 |

FIG. 95

| Variable / Visit | | | Diff | 95% CI | |
|---|---|---|---|---|---|
| | | | | Lower | Upper |
| Change from Baseline in Mean of VAS Score for Dyspareunia (mm) | Day 1 - 28 | Compound 1 10mg- Leuprorelin | 4.768 | -2.3819 | 11.9189 |
| | | Compound 1 20mg- Leuprorelin | 4.079 | -3.5958 | 11.7543 |
| | | Compound 1 40mg- Leuprorelin | 6.121 | -1.2006 | 13.4421 |
| | Day 29 - 56 | Compound 1 10mg- Leuprorelin | 6.687 | -2.1433 | 15.5181 |
| | | Compound 1 20mg- Leuprorelin | 5.629 | -1.5161 | 12.7749 |
| | | Compound 1 40mg- Leuprorelin | 4.903 | -0.6370 | 10.4423 |
| | Day 57 - 84 | Compound 1 10mg- Leuprorelin | 5.719 | -0.9308 | 12.3683 |
| | | Compound 1 20mg- Leuprorelin | 6.561 | 0.3217 | 12.8004 |
| | | Compound 1 40mg- Leuprorelin | 4.891 | -1.2380 | 11.0208 |
| | Day 85 - 112 | Compound 1 10mg- Leuprorelin | 3.049 | -2.0913 | 8.1900 |
| | | Compound 1 20mg- Leuprorelin | 5.004 | -2.6143 | 12.6223 |
| | | Compound 1 40mg- Leuprorelin | 7.180 | -0.2060 | 14.5663 |
| | Day 113 - 140 | Compound 1 10mg- Leuprorelin | 2.673 | -5.7255 | 11.0723 |
| | | Compound 1 20mg- Leuprorelin | 5.774 | -3.0760 | 14.6245 |
| | | Compound 1 40mg- Leuprorelin | 6.489 | -1.3043 | 14.2825 |
| | Day 141 - 168 | Compound 1 10mg- Leuprorelin | 0.829 | -7.7647 | 9.4219 |
| | | Compound 1 20mg- Leuprorelin | 0.941 | -8.5778 | 10.4597 |
| | | Compound 1 40mg- Leuprorelin | 4.122 | -6.3092 | 14.5540 |
| | End of Treatment Period | Compound 1 10mg- Leuprorelin | 1.140 | -5.8492 | 8.1289 |
| | | Compound 1 20mg- Leuprorelin | 1.040 | -6.4921 | 8.5723 |
| | | Compound 1 40mg- Leuprorelin | 3.669 | -4.2135 | 11.5512 |

FIG. 96

| Variable / Visit | | Treatment | Summary Statistics | | | | | | 95% CI | |
|---|---|---|---|---|---|---|---|---|---|---|
| | | | N | Mean | SD | Min | Median | Max | Lower | Upper |
| Mean of VAS Score for Dysmenorrhea (mm) | Baseline | Placebo | 97 | 28.379 | 16.5910 | 0.00 | 24.600 | 74.50 | 25.0349 | 31.7226 |
| | | Compound 1 10mg | 103 | 28.213 | 17.6370 | 0.00 | 25.140 | 70.67 | 24.7663 | 31.6603 |
| | | Compound 1 20mg | 100 | 27.703 | 18.9350 | 0.00 | 25.365 | 80.00 | 23.9458 | 31.4600 |
| | | Compound 1 40mg | 103 | 30.430 | 17.0426 | 5.25 | 30.090 | 82.00 | 27.0995 | 33.7611 |
| | | Leuprorelin | 81 | 27.118 | 19.7795 | 0.00 | 21.500 | 92.80 | 22.7448 | 31.4920 |
| | Day 1 - 28 | Placebo | 97 | 23.832 | 17.8381 | 0.00 | 20.250 | 73.40 | 20.2367 | 27.4270 |
| | | Compound 1 10mg | 103 | 17.556 | 17.0427 | 0.00 | 12.250 | 73.56 | 14.2256 | 20.8872 |
| | | Compound 1 20mg | 100 | 18.545 | 19.2141 | 0.00 | 11.875 | 73.50 | 14.7323 | 22.3573 |
| | | Compound 1 40mg | 103 | 19.452 | 19.1065 | 0.00 | 14.500 | 86.00 | 15.7176 | 23.1859 |
| | | Leuprorelin | 81 | 17.133 | 19.4179 | 0.00 | 10.750 | 86.33 | 12.8397 | 21.4270 |
| | Day 29 - 56 | Placebo | 96 | 21.718 | 17.0320 | 0.00 | 18.200 | 82.00 | 18.2670 | 25.1690 |
| | | Compound 1 10mg | 103 | 15.394 | 15.9513 | 0.00 | 11.200 | 72.00 | 12.2764 | 18.5114 |
| | | Compound 1 20mg | 99 | 7.433 | 12.7505 | 0.00 | 0.000 | 63.33 | 4.8901 | 9.9762 |
| | | Compound 1 40mg | 101 | 1.032 | 4.5411 | 0.00 | 0.000 | 29.25 | 0.1352 | 1.9281 |
| | | Leuprorelin | 79 | 0.972 | 6.3180 | 0.00 | 0.000 | 55.00 | -0.4430 | 2.3873 |
| | Day 57 - 84 | Placebo | 95 | 21.728 | 18.3520 | 0.00 | 17.170 | 73.67 | 17.9891 | 25.4661 |
| | | Compound 1 10mg | 101 | 13.568 | 15.5954 | 0.00 | 8.000 | 66.00 | 10.4890 | 16.6465 |
| | | Compound 1 20mg | 94 | 6.626 | 13.5146 | 0.00 | 0.000 | 93.00 | 3.8581 | 9.3942 |
| | | Compound 1 40mg | 101 | 0.569 | 2.5367 | 0.00 | 0.000 | 14.67 | 0.0679 | 1.0695 |
| | | Leuprorelin | 78 | 0.000 | 0.0000 | 0.00 | 0.000 | 0.00 | 0.0000 | 0.0000 |
| | Day 85 - 112 | Placebo | 77 | 19.419 | 15.4500 | 0.00 | 16.400 | 70.40 | 15.9121 | 22.9256 |
| | | Compound 1 10mg | 84 | 11.943 | 14.8590 | 0.00 | 6.580 | 62.50 | 8.7187 | 15.1679 |
| | | Compound 1 20mg | 78 | 7.616 | 13.6165 | 0.00 | 0.000 | 66.00 | 4.5460 | 10.6861 |
| | | Compound 1 40mg | 89 | 1.039 | 5.9676 | 0.00 | 0.000 | 51.40 | -0.2179 | 2.2963 |
| | | Leuprorelin | 69 | 0.000 | 0.0000 | 0.00 | 0.000 | 0.00 | 0.0000 | 0.0000 |
| | Day 113 - 140 | Placebo | 75 | 21.299 | 17.3486 | 0.00 | 19.170 | 67.00 | 17.3071 | 25.2902 |
| | | Compound 1 10mg | 84 | 10.769 | 14.0906 | 0.00 | 5.300 | 60.57 | 7.7110 | 13.8267 |
| | | Compound 1 20mg | 77 | 8.040 | 13.8727 | 0.00 | 0.000 | 56.60 | 4.8912 | 11.1886 |
| | | Compound 1 40mg | 89 | 0.390 | 2.0190 | 0.00 | 0.000 | 15.00 | -0.0354 | 0.8152 |
| | | Leuprorelin | 68 | 0.000 | 0.0000 | 0.00 | 0.000 | 0.00 | 0.0000 | 0.0000 |
| | Day 141 - 168 | Placebo | 71 | 18.797 | 14.8825 | 0.00 | 16.200 | 55.20 | 15.2748 | 22.3201 |
| | | Compound 1 10mg | 80 | 11.758 | 15.4431 | 0.00 | 4.540 | 56.83 | 8.3208 | 15.1942 |
| | | Compound 1 20mg | 77 | 6.132 | 13.2012 | 0.00 | 0.000 | 56.50 | 3.1359 | 9.1285 |
| | | Compound 1 40mg | 88 | 0.430 | 2.3141 | 0.00 | 0.000 | 19.67 | -0.0604 | 0.9202 |
| | | Leuprorelin | 63 | 0.000 | 0.0000 | 0.00 | 0.000 | 0.00 | 0.0000 | 0.0000 |
| | End of Treatment Period | Placebo | 97 | 22.607 | 17.5557 | 0.00 | 19.000 | 82.00 | 19.0683 | 26.1449 |
| | | Compound 1 10mg | 103 | 12.857 | 15.0429 | 0.00 | 7.710 | 56.83 | 9.9173 | 15.7973 |
| | | Compound 1 20mg | 100 | 7.878 | 14.2406 | 0.00 | 0.000 | 64.06 | 5.0521 | 10.7035 |
| | | Compound 1 40mg | 103 | 0.918 | 4.3438 | 0.00 | 0.000 | 30.00 | 0.0688 | 1.7667 |
| | | Leuprorelin | 81 | 0.174 | 1.1623 | 0.00 | 0.000 | 9.38 | -0.0826 | 0.4315 |

FIG. 98

| Variable / Visit | | Treatment | Summary Statistics | | | | | 95% CI | |
|---|---|---|---|---|---|---|---|---|---|
| | | | N | Mean | SD | Min | Median | Max | Lower | Upper |
| Change from Baseline in Mean of VAS Score for Dysmenorrhea (mm) | Day 1 - 28 | Placebo | 97 | -4.547 | 16.4741 | -54.25 | -5.120 | 48.00 | -7.8672 | -1.2266 |
| | | Compound 1 10mg | 103 | -10.657 | 17.0824 | -70.67 | -9.310 | 21.86 | -13.9955 | -7.3183 |
| | | Compound 1 20mg | 100 | -9.158 | 16.6375 | -80.00 | -7.045 | 29.86 | -12.4593 | -5.8569 |
| | | Compound 1 40mg | 103 | -10.979 | 14.8545 | -43.30 | -10.600 | 34.60 | -13.8817 | -8.0754 |
| | | Leuprorelin | 81 | -9.985 | 15.7027 | -45.98 | -8.420 | 24.76 | -13.4572 | -6.5129 |
| | Day 29 - 56 | Placebo | 96 | -6.693 | 15.5192 | -50.00 | -5.815 | 32.70 | -9.8378 | -3.5488 |
| | | Compound 1 10mg | 103 | -12.819 | 17.4978 | -58.14 | -9.530 | 18.37 | -16.2392 | -9.3997 |
| | | Compound 1 20mg | 99 | -19.880 | 19.6246 | -80.00 | -17.310 | 18.90 | -23.7945 | -15.9663 |
| | | Compound 1 40mg | 101 | -29.631 | 18.1588 | -82.00 | -30.090 | 22.25 | -33.2154 | -26.0458 |
| | | Leuprorelin | 79 | -26.506 | 20.3326 | -92.80 | -21.200 | 12.00 | -31.0601 | -21.9516 |
| | Day 57 - 84 | Placebo | 95 | -6.857 | 15.8099 | -46.14 | -9.280 | 36.13 | -10.0772 | -3.6359 |
| | | Compound 1 10mg | 101 | -14.747 | 16.8648 | -63.27 | -12.250 | 18.15 | -18.0765 | -11.4179 |
| | | Compound 1 20mg | 94 | -20.689 | 21.4387 | -80.00 | -17.675 | 52.00 | -25.0805 | -16.2984 |
| | | Compound 1 40mg | 101 | -30.094 | 17.2623 | -82.00 | -29.880 | -5.25 | -33.5014 | -26.6858 |
| | | Leuprorelin | 78 | -27.558 | 19.9878 | -92.80 | -23.145 | 0.00 | -32.0650 | -23.0519 |
| | Day 85 - 112 | Placebo | 77 | -8.663 | 14.1539 | -38.83 | -10.430 | 34.83 | -11.8759 | -5.4508 |
| | | Compound 1 10mg | 84 | -14.917 | 17.1865 | -58.14 | -10.035 | 24.29 | -18.6462 | -11.1869 |
| | | Compound 1 20mg | 78 | -19.014 | 21.1116 | -80.00 | -14.790 | 25.63 | -23.7738 | -14.2539 |
| | | Compound 1 40mg | 89 | -30.532 | 16.8634 | -82.00 | -30.000 | -0.11 | -34.0848 | -26.9802 |
| | | Leuprorelin | 69 | -28.446 | 20.3506 | -92.80 | -24.140 | 0.00 | -33.3344 | -23.5569 |
| | Day 113 - 140 | Placebo | 75 | -6.735 | 16.6093 | -44.00 | -7.200 | 45.20 | -10.5561 | -2.9132 |
| | | Compound 1 10mg | 84 | -16.091 | 17.4065 | -58.14 | -14.080 | 38.67 | -19.8685 | -12.3136 |
| | | Compound 1 20mg | 77 | -17.953 | 21.0936 | -78.67 | -15.620 | 53.86 | -22.7404 | -13.1651 |
| | | Compound 1 40mg | 89 | -31.182 | 17.2889 | -82.00 | -30.600 | 1.57 | -34.8238 | -27.5398 |
| | | Leuprorelin | 68 | -28.666 | 20.4184 | -92.80 | -25.070 | 0.00 | -33.6088 | -23.7242 |
| | Day 141 - 168 | Placebo | 71 | -8.676 | 16.4615 | -58.50 | -7.110 | 25.75 | -12.5724 | -4.7797 |
| | | Compound 1 10mg | 80 | -15.191 | 17.6754 | -70.33 | -14.010 | 30.69 | -19.1245 | -11.2575 |
| | | Compound 1 20mg | 77 | -19.860 | 19.1617 | -80.00 | -16.920 | 14.64 | -24.2096 | -15.5112 |
| | | Compound 1 40mg | 88 | -31.210 | 17.7668 | -82.00 | -30.750 | -5.71 | -34.9741 | -27.4452 |
| | | Leuprorelin | 63 | -28.373 | 20.7287 | -92.80 | -24.140 | 0.00 | -33.5935 | -23.1526 |
| | End of Treatment Period | Placebo | 97 | -5.772 | 17.1295 | -58.50 | -6.710 | 45.20 | -9.2245 | -2.3198 |
| | | Compound 1 10mg | 103 | -15.356 | 18.0506 | -63.27 | -13.820 | 30.69 | -18.8838 | -11.8282 |
| | | Compound 1 20mg | 100 | -19.825 | 20.4332 | -80.00 | -16.795 | 20.53 | -23.8795 | -15.7707 |
| | | Compound 1 40mg | 103 | -29.513 | 17.5379 | -82.00 | -29.880 | -2.86 | -32.9401 | -26.0849 |
| | | Leuprorelin | 81 | -26.944 | 19.9212 | -92.80 | -21.500 | 0.00 | -31.3489 | -22.5390 |

FIG. 100

| Variable / Visit | | | Diff | 95% CI | |
|---|---|---|---|---|---|
| | | | | Lower | Upper |
| Change from Baseline in Mean of VAS Score for Dysmenorrhea (mm) | Day 1 - 28 | Compound 1 10mg- Leuprorelin | -0.672 | -5.5037 | 4.1601 |
| | | Compound 1 20mg- Leuprorelin | 0.827 | -3.9595 | 5.6134 |
| | | Compound 1 40mg- Leuprorelin | -0.993 | -5.4571 | 3.4701 |
| | Day 29 - 56 | Compound 1 10mg- Leuprorelin | 13.686 | 8.1446 | 19.2282 |
| | | Compound 1 20mg- Leuprorelin | 6.625 | 0.6882 | 12.5626 |
| | | Compound 1 40mg- Leuprorelin | -3.125 | -8.7983 | 2.5488 |
| | Day 57 - 84 | Compound 1 10mg- Leuprorelin | 12.811 | 7.3708 | 18.2517 |
| | | Compound 1 20mg- Leuprorelin | 6.869 | 0.5820 | 13.1560 |
| | | Compound 1 40mg- Leuprorelin | -2.535 | -8.0376 | 2.9674 |
| | Day 85 - 112 | Compound 1 10mg- Leuprorelin | 13.529 | 7.5333 | 19.5250 |
| | | Compound 1 20mg- Leuprorelin | 9.432 | 2.6513 | 16.2123 |
| | | Compound 1 40mg- Leuprorelin | -2.087 | -7.9371 | 3.7635 |
| | Day 113 - 140 | Compound 1 10mg- Leuprorelin | 12.575 | 6.5120 | 18.6388 |
| | | Compound 1 20mg- Leuprorelin | 10.714 | 3.8783 | 17.5492 |
| | | Compound 1 40mg- Leuprorelin | -2.515 | -8.4669 | 3.4363 |
| | Day 141 - 168 | Compound 1 10mg- Leuprorelin | 13.182 | 6.8290 | 19.5351 |
| | | Compound 1 20mg- Leuprorelin | 8.513 | 1.8344 | 15.1908 |
| | | Compound 1 40mg- Leuprorelin | -2.837 | -9.0508 | 3.3775 |
| | End of Treatment Period | Compound 1 10mg- Leuprorelin | 11.588 | 6.0512 | 17.1247 |
| | | Compound 1 20mg- Leuprorelin | 7.119 | 1.1585 | 13.0792 |
| | | Compound 1 40mg- Leuprorelin | -2.569 | -8.0255 | 2.8883 |

FIG. 101

| Variable / Visit | Treatment | Summary Statistics | | | | | |
|---|---|---|---|---|---|---|---|
| | | N | Mean | SD | Min | Median | Max |
| Mean of M-B&B Score for Pelvic Pain | Baseline | | | | | | |
| | Placebo | 97 | 0.648 | 0.4536 | 0.00 | 0.620 | 1.85 |
| | Compound 1 10mg | 103 | 0.656 | 0.4615 | 0.00 | 0.620 | 2.14 |
| | Compound 1 20mg | 100 | 0.626 | 0.4749 | 0.00 | 0.530 | 1.88 |
| | Compound 1 40mg | 103 | 0.654 | 0.4410 | 0.00 | 0.630 | 2.31 |
| | Leuprorelin | 81 | 0.675 | 0.5451 | 0.00 | 0.570 | 2.48 |
| | Day 1 - 28 | | | | | | |
| | Placebo | 97 | 0.529 | 0.4418 | 0.00 | 0.420 | 2.00 |
| | Compound 1 10mg | 103 | 0.527 | 0.4333 | 0.00 | 0.450 | 1.83 |
| | Compound 1 20mg | 100 | 0.524 | 0.5050 | 0.00 | 0.390 | 2.25 |
| | Compound 1 40mg | 102 | 0.538 | 0.4747 | 0.00 | 0.470 | 2.24 |
| | Leuprorelin | 80 | 0.493 | 0.4920 | 0.00 | 0.340 | 2.58 |
| | Day 29 - 56 | | | | | | |
| | Placebo | 96 | 0.495 | 0.4803 | 0.00 | 0.280 | 2.05 |
| | Compound 1 10mg | 103 | 0.476 | 0.4320 | 0.00 | 0.360 | 1.52 |
| | Compound 1 20mg | 99 | 0.434 | 0.4457 | 0.00 | 0.290 | 1.57 |
| | Compound 1 40mg | 101 | 0.400 | 0.4328 | 0.00 | 0.250 | 1.61 |
| | Leuprorelin | 79 | 0.378 | 0.4919 | 0.00 | 0.180 | 2.57 |
| | Day 57 - 84 | | | | | | |
| | Placebo | 94 | 0.453 | 0.4786 | 0.00 | 0.290 | 2.00 |
| | Compound 1 10mg | 101 | 0.446 | 0.4511 | 0.00 | 0.320 | 1.64 |
| | Compound 1 20mg | 94 | 0.381 | 0.4399 | 0.00 | 0.185 | 1.76 |
| | Compound 1 40mg | 101 | 0.324 | 0.4420 | 0.00 | 0.070 | 1.75 |
| | Leuprorelin | 78 | 0.287 | 0.4847 | 0.00 | 0.040 | 2.36 |
| | Day 85 - 112 | | | | | | |
| | Placebo | 77 | 0.449 | 0.4816 | 0.00 | 0.240 | 2.09 |
| | Compound 1 10mg | 84 | 0.418 | 0.4082 | 0.00 | 0.310 | 1.36 |
| | Compound 1 20mg | 78 | 0.386 | 0.4397 | 0.00 | 0.185 | 1.59 |
| | Compound 1 40mg | 89 | 0253 | 0.3714 | 0.00 | 0.040 | 1.43 |
| | Leuprorelin | 69 | 0.230 | 0.4442 | 0.00 | 0.000 | 2.57 |
| | Day 113 - 140 | | | | | | |
| | Placebo | 75 | 0.407 | 0.4814 | 0.00 | 0.200 | 2.00 |
| | Compound 1 10mg | 84 | 0.411 | 0.4148 | 0.00 | 0.270 | 1.33 |
| | Compound 1 20mg | 77 | 0.341 | 0.4308 | 0.00 | 0.110 | 1.65 |
| | Compound 1 40mg | 89 | 0.256 | 0.4379 | 0.00 | 0.000 | 1.86 |
| | Leuprorelin | 68 | 0.194 | 0.3908 | 0.00 | 0.000 | 2.04 |
| | Day 141 - 168 | | | | | | |
| | Placebo | 71 | 0.390 | 0.4729 | 0.00 | 0.170 | 2.00 |
| | Compound 1 10mg | 80 | 0.354 | 0.4131 | 0.00 | 0.140 | 1.22 |
| | Compound 1 20mg | 77 | 0.343 | 0.4161 | 0.00 | 0.120 | 1.22 |
| | Compound 1 40mg | 88 | 0.229 | 0.3597 | 0.00 | 0.000 | 1.21 |
| | Leuprorelin | 63 | 0.171 | 0.3444 | 0.00 | 0.000 | 1.32 |
| | End of Treatment Period | | | | | | |
| | Placebo | 97 | 0.476 | 0.4820 | 0.00 | 0.350 | 2.00 |
| | Compound 1 10mg | 103 | 0.396 | 0.4208 | 0.00 | 0.230 | 1.43 |
| | Compound 1 20mg | 100 | 0.358 | 0.4376 | 0.00 | 0.180 | 2.00 |
| | Compound 1 40mg | 103 | 0.254 | 0.3767 | 0.00 | 0.000 | 1.29 |
| | Leuprorelin | 80 | 0.199 | 0.3632 | 0.00 | 0.000 | 1.36 |

FIG. 102

| Variable / Visit | Treatment | | Summary Statistics | | | | |
|---|---|---|---|---|---|---|---|
| | | N | Mean | SD | Min | Median | Max |
| Mean of M-B&B Score for Dysmenorrhea | Baseline Placebo | 97 | 1.164 | 0.4412 | 0.00 | 1.170 | 2.14 |
| | Compound 1 10mg | 103 | 1.187 | 0.4739 | 0.00 | 1.170 | 2.33 |
| | Compound 1 20mg | 100 | 1.174 | 0.4812 | 0.00 | 1.200 | 2.44 |
| | Compound 1 40mg | 103 | 1.207 | 0.4652 | 0.00 | 1.220 | 2.50 |
| | Leuprorelin | 81 | 1.171 | 0.4681 | 0.00 | 1.140 | 2.60 |
| | Day 1 - 28 Placebo | 97 | 1.011 | 0.4948 | 0.00 | 1.000 | 2.33 |
| | Compound 1 10mg | 103 | 0.872 | 0.5226 | 0.00 | 1.000 | 2.67 |
| | Compound 1 20mg | 100 | 0.810 | 0.5753 | 0.00 | 0.830 | 2.75 |
| | Compound 1 40mg | 103 | 0.830 | 0.5809 | 0.00 | 1.000 | 2.29 |
| | Leuprorelin | 81 | 0.835 | 0.5893 | 0.00 | 1.000 | 2.11 |
| | Day 29 - 56 Placebo | 96 | 0.982 | 0.5027 | 0.00 | 1.000 | 2.25 |
| | Compound 1 10mg | 103 | 0.760 | 0.5726 | 0.00 | 0.860 | 2.25 |
| | Compound 1 20mg | 99 | 0.399 | 0.5611 | 0.00 | 0.000 | 2.50 |
| | Compound 1 40mg | 101 | 0.055 | 0.2209 | 0.00 | 0.000 | 1.38 |
| | Leuprorelin | 79 | 0.033 | 0.1886 | 0.00 | 0.000 | 1.50 |
| | Day 57 - 84 Placebo | 95 | 0.943 | 0.5684 | 0.00 | 1.000 | 2.38 |
| | Compound 1 10mg | 101 | 0.679 | 0.6044 | 0.00 | 0.710 | 2.00 |
| | Compound 1 20mg | 94 | 0.339 | 0.5354 | 0.00 | 0.000 | 2.57 |
| | Compound 1 40mg | 101 | 0.040 | 0.1669 | 0.00 | 0.000 | 1.00 |
| | Leuprorelin | 78 | 0.000 | 0.0000 | 0.00 | 0.000 | 0.00 |
| | Day 85 - 112 Placebo | 77 | 0.905 | 0.4661 | 0.00 | 0.900 | 2.00 |
| | Compound 1 10mg | 84 | 0.624 | 0.5699 | 0.00 | 0.670 | 2.00 |
| | Compound 1 20mg | 78 | 0.420 | 0.5583 | 0.00 | 0.000 | 1.83 |
| | Compound 1 40mg | 89 | 0.049 | 0.2486 | 0.00 | 0.000 | 2.00 |
| | Leuprorelin | 69 | 0.000 | 0.0000 | 0.00 | 0.000 | 0.00 |
| | Day 113 - 140 Placebo | 75 | 0.945 | 0.5395 | 0.00 | 1.000 | 2.10 |
| | Compound 1 10mg | 84 | 0.581 | 0.5570 | 0.00 | 0.500 | 2.00 |
| | Compound 1 20mg | 77 | 0.404 | 0.5358 | 0.00 | 0.000 | 1.80 |
| | Compound 1 40mg | 89 | 0.033 | 0.1564 | 0.00 | 0.000 | 1.00 |
| | Leuprorelin | 68 | 0.000 | 0.0000 | 0.00 | 0.000 | 0.00 |
| | Day 141 - 168 Placebo | 71 | 0.907 | 0.5197 | 0.00 | 0.860 | 2.17 |
| | Compound 1 10mg | 80 | 0.622 | 0.6103 | 0.00 | 0.470 | 2.20 |
| | Compound 1 20mg | 77 | 0.298 | 0.5433 | 0.00 | 0.000 | 2.00 |
| | Compound 1 40mg | 88 | 0.047 | 0.2070 | 0.00 | 0.000 | 1.17 |
| | Leuprorelin | 63 | 0.000 | 0.0000 | 0.00 | 0.000 | 0.00 |
| | End of Treatment Period Placebo | 97 | 0.979 | 0.5462 | 0.00 | 1.000 | 2.14 |
| | Compound 1 10mg | 103 | 0.679 | 0.5781 | 0.00 | 0.600 | 2.20 |
| | Compound 1 20mg | 100 | 0.380 | 0.5660 | 0.00 | 0.000 | 2.11 |
| | Compound 1 40mg | 103 | 0.063 | 0.2525 | 0.00 | 0.000 | 1.50 |
| | Leuprorelin | 81 | 0.011 | 0.0750 | 0.00 | 0.000 | 0.63 |

FIG. 103

| Variable / Visit | Visit | Treatment | Summary Statistics | | | | | |
|---|---|---|---|---|---|---|---|---|
| | | | N | Mean | SD | Min | Median | Max |
| Mean of M-B&B Score for Deep Dyspareunia | Baseline | Placebo | 41 | 0.554 | 0.4475 | 0.00 | 0.670 | 1.00 |
| | | Compound 1 10mg | 46 | 0.562 | 0.6029 | 0.00 | 0.330 | 2.00 |
| | | Compound 1 20mg | 47 | 0.636 | 0.5483 | 0.00 | 0.670 | 2.00 |
| | | Compound 1 40mg | 44 | 0.546 | 0.4836 | 0.00 | 0.500 | 1.33 |
| | | Leuprorelin | 26 | 0.596 | 0.4502 | 0.00 | 0.835 | 1.00 |
| | Day 1 - 28 | Placebo | 44 | 0.514 | 0.5123 | 0.00 | 0.415 | 2.00 |
| | | Compound 1 10mg | 50 | 0.565 | 0.5236 | 0.00 | 0.515 | 2.00 |
| | | Compound 1 20mg | 44 | 0.607 | 0.5606 | 0.00 | 0.535 | 2.00 |
| | | Compound 1 40mg | 42 | 0.573 | 0.6264 | 0.00 | 0.500 | 2.00 |
| | | Leuprorelin | 25 | 0.405 | 0.5533 | 0.00 | 0.000 | 2.00 |
| | Day 29 - 56 | Placebo | 38 | 0.594 | 0.4779 | 0.00 | 0.750 | 1.60 |
| | | Compound 1 10mg | 48 | 0.524 | 0.6284 | 0.00 | 0.125 | 2.00 |
| | | Compound 1 20mg | 49 | 0.641 | 0.6839 | 0.00 | 0.500 | 2.00 |
| | | Compound 1 40mg | 39 | 0.440 | 0.5178 | 0.00 | 0.130 | 2.00 |
| | | Leuprorelin | 24 | 0.318 | 0.4556 | 0.00 | 0.000 | 1.00 |
| | Day 57 - 84 | Placebo | 36 | 0.647 | 0.6063 | 0.00 | 0.930 | 2.00 |
| | | Compound 1 10mg | 50 | 0.527 | 0.5964 | 0.00 | 0.270 | 2.00 |
| | | Compound 1 20mg | 35 | 0.453 | 0.5538 | 0.00 | 0.000 | 2.00 |
| | | Compound 1 40mg | 40 | 0.360 | 0.4517 | 0.00 | 0.000 | 1.33 |
| | | Leuprorelin | 24 | 0.357 | 0.4568 | 0.00 | 0.000 | 1.00 |
| | Day 85 - 112 | Placebo | 27 | 0.526 | 0.5729 | 0.00 | 0.330 | 2.00 |
| | | Compound 1 10mg | 35 | 0.315 | 0.4306 | 0.00 | 0.000 | 1.00 |
| | | Compound 1 20mg | 31 | 0.494 | 0.6231 | 0.00 | 0.000 | 2.00 |
| | | Compound 1 40mg | 31 | 0.556 | 0.7068 | 0.00 | 0.250 | 3.00 |
| | | Leuprorelin | 23 | 0.333 | 0.4715 | 0.00 | 0.000 | 1.00 |
| | Day 113 - 140 | Placebo | 33 | 0.509 | 0.4825 | 0.00 | 0.500 | 1.17 |
| | | Compound 1 10mg | 38 | 0.325 | 0.4415 | 0.00 | 0.000 | 1.20 |
| | | Compound 1 20mg | 30 | 0.436 | 0.5664 | 0.00 | 0.065 | 2.00 |
| | | Compound 1 40mg | 34 | 0.314 | 0.4404 | 0.00 | 0.000 | 1.15 |
| | | Leuprorelin | 15 | 0.311 | 0.4492 | 0.00 | 0.000 | 1.00 |
| | Day 141 - 168 | Placebo | 20 | 0.513 | 0.5185 | 0.00 | 0.460 | 1.33 |
| | | Compound 1 10mg | 36 | 0.320 | 0.4626 | 0.00 | 0.000 | 1.40 |
| | | Compound 1 20mg | 29 | 0.337 | 0.5127 | 0.00 | 0.000 | 2.00 |
| | | Compound 1 40mg | 31 | 0.287 | 0.4126 | 0.00 | 0.000 | 1.00 |
| | | Leuprorelin | 18 | 0.407 | 0.6913 | 0.00 | 0.000 | 2.00 |
| | End of Treatment Period | Placebo | 36 | 0.591 | 0.5682 | 0.00 | 0.585 | 2.00 |
| | | Compound 1 10mg | 50 | 0.368 | 0.4740 | 0.00 | 0.000 | 1.40 |
| | | Compound 1 20mg | 40 | 0.378 | 0.5079 | 0.00 | 0.000 | 2.00 |
| | | Compound 1 40mg | 39 | 0.366 | 0.4503 | 0.00 | 0.000 | 1.00 |
| | | Leuprorelin | 23 | 0.388 | 0.5457 | 0.00 | 0.000 | 2.00 |

FIG. 104

| Variable / Visit | Treatment | | Summary Statistics | | | | |
|---|---|---|---|---|---|---|---|
| | | N | Mean | SD | Min | Median | Max |
| Change from Baseline in Mean of M-B&B Score for Pelvic Pain | Day 1 - 28 Placebo | 97 | -0.119 | 0.3283 | -1.03 | -0.070 | 0.77 |
| | Compound 1 10mg | 103 | -0.130 | 0.2526 | -0.90 | -0.120 | 0.48 |
| | Compound 1 20mg | 100 | -0.101 | 0.3347 | -1.27 | -0.050 | 0.66 |
| | Compound 1 40mg | 102 | -0.122 | 0.2962 | -1.11 | -0.095 | 0.89 |
| | Leuprorelin | 80 | -0.189 | 0.3365 | -1.32 | -0.105 | 0.38 |
| | Day 29 - 56 Placebo | 96 | -0.152 | 0.3785 | -1.19 | -0.125 | 1.43 |
| | Compound 1 10mg | 103 | -0.181 | 0.3111 | -1.56 | -0.150 | 0.53 |
| | Compound 1 20mg | 99 | -0.178 | 0.3540 | -1.30 | -0.120 | 0.74 |
| | Compound 1 40mg | 101 | -0.256 | 0.3457 | -1.31 | -0.240 | 0.61 |
| | Leuprorelin | 79 | -0.312 | 0.4436 | -1.50 | -0.170 | 1.09 |
| | Day 57 - 84 Placebo | 94 | -0.187 | 0.3512 | -1.27 | -0.150 | 0.94 |
| | Compound 1 10mg | 101 | -0.218 | 0.3014 | -1.09 | -0.170 | 0.47 |
| | Compound 1 20mg | 94 | -0.239 | 0.4548 | -1.52 | -0.195 | 0.76 |
| | Compound 1 40mg | 101 | -0.332 | 0.4026 | -1.36 | -0.270 | 0.71 |
| | Leuprorelin | 78 | -0.399 | 0.4625 | -1.67 | -0.285 | 0.67 |
| | Day 85 - 112 Placebo | 77 | -0.170 | 0.3957 | -1.28 | -0.160 | 1.54 |
| | Compound 1 10mg | 84 | -0.239 | 0.3380 | -1.40 | -0.175 | 0.45 |
| | Compound 1 20mg | 78 | -0.237 | 0.4251 | -1.52 | -0.210 | 0.75 |
| | Compound 1 40mg | 89 | -0.420 | 0.3867 | -1.45 | -0.350 | 0.39 |
| | Leuprorelin | 69 | -0.485 | 0.4304 | -1.77 | -0.350 | 0.24 |
| | Day 113 - 140 Placebo | 75 | -0.213 | 0.3819 | -1.37 | -0.190 | 1.20 |
| | Compound 1 10mg | 84 | -0.245 | 0.3647 | -1.41 | -0.190 | 0.42 |
| | Compound 1 20mg | 77 | -0.272 | 0.3845 | -1.38 | -0.210 | 0.59 |
| | Compound 1 40mg | 89 | -0.418 | 0.4921 | -2.31 | -0.360 | 1.70 |
| | Leuprorelin | 68 | -0.524 | 0.4510 | -1.81 | -0.395 | 0.28 |
| | Day 141 - 168 Placebo | 71 | -0.235 | 0.3632 | -1.37 | -0.190 | 0.65 |
| | Compound 1 10mg | 80 | -0.314 | 0.3654 | -1.45 | -0.195 | 0.37 |
| | Compound 1 20mg | 77 | -0.269 | 0.3918 | -1.38 | -0.210 | 0.74 |
| | Compound 1 40mg | 88 | -0.448 | 0.4511 | -2.31 | -0.390 | 0.45 |
| | Leuprorelin | 63 | -0.537 | 0.4599 | -1.81 | -0.360 | 0.00 |
| | End of Treatment Period Placebo | 97 | -0.172 | 0.3851 | -1.37 | -0.150 | 1.40 |
| | Compound 1 10mg | 103 | -0.260 | 0.3624 | -1.45 | -0.170 | 0.53 |
| | Compound 1 20mg | 100 | -0.268 | 0.3913 | -1.52 | -0.180 | 0.73 |
| | Compound 1 40mg | 103 | -0.400 | 0.4491 | -2.31 | -0.340 | 0.57 |
| | Leuprorelin | 80 | -0.483 | 0.4860 | -1.81 | -0.340 | 0.64 |

FIG. 105

| Variable / Visit | Treatment | Summary Statistics ||||||
|---|---|---|---|---|---|---|---|
| | | N | Mean | SD | Min | Median | Max |
| Change from Baseline in Mean of M-B&B Score for Dysmenorrhea | Day 1 - 28 Placebo | 97 | -0.153 | 0.4546 | -1.40 | -0.170 | 1.14 |
| | Compound 1 10mg | 103 | -0.315 | 0.5008 | -2.33 | -0.400 | 0.89 |
| | Compound 1 20mg | 100 | -0.365 | 0.5306 | -1.63 | -0.400 | 1.25 |
| | Compound 1 40mg | 103 | -0.378 | 0.5247 | -1.50 | -0.430 | 1.20 |
| | Leuprorelin | 81 | -0.336 | 0.5442 | -1.67 | -0.350 | 0.87 |
| | Day 29 - 56 Placebo | 96 | -0.181 | 0.4806 | -1.43 | -0.215 | 1.00 |
| | Compound 1 10mg | 103 | -0.427 | 0.6105 | -2.25 | -0.380 | 1.20 |
| | Compound 1 20mg | 99 | -0.770 | 0.6751 | -2.10 | -0.770 | 1.00 |
| | Compound 1 40mg | 101 | -1.157 | 0.5022 | -2.50 | -1.200 | 0.38 |
| | Leuprorelin | 79 | -1.147 | 0.5106 | -2.60 | -1.170 | 0.36 |
| | Day 57 - 84 Placebo | 94 | -0.220 | 0.4977 | -1.83 | -0.200 | 0.85 |
| | Compound 1 10mg | 101 | -0.518 | 0.6568 | -2.25 | -0.430 | 1.00 |
| | Compound 1 20mg | 94 | -0.830 | 0.6575 | -2.44 | -0.900 | 1.10 |
| | Compound 1 40mg | 101 | -1.172 | 0.4778 | -2.50 | -1.200 | 0.00 |
| | Leuprorelin | 78 | -1.179 | 0.4732 | -2.60 | -1.155 | 0.00 |
| | Day 85 - 112 Placebo | 77 | -0.243 | 0.5029 | -1.83 | -0.250 | 1.14 |
| | Compound 1 10mg | 84 | -0.515 | 0.6519 | -2.25 | -0.440 | 1.00 |
| | Compound 1 20mg | 78 | -0.735 | 0.6649 | -2.44 | -0.640 | 0.71 |
| | Compound 1 40mg | 89 | -1.189 | 0.4690 | -2.50 | -1.220 | 0.00 |
| | Leuprorelin | 69 | -1.209 | 0.4800 | -2.60 | -1.170 | 0.00 |
| | Day 113 - 140 Placebo | 75 | -0.196 | 0.5257 | -1.50 | -0.220 | 1.20 |
| | Compound 1 10mg | 84 | -0.559 | 0.6840 | -2.25 | -0.555 | 1.50 |
| | Compound 1 20mg | 77 | -0.738 | 0.6426 | -2.44 | -0.700 | 1.25 |
| | Compound 1 40mg | 89 | -1.205 | 0.4542 | -2.50 | -1.250 | 0.00 |
| | Leuprorelin | 68 | -1.214 | 0.4817 | -2.60 | -1.170 | 0.00 |
| | Day 141 - 168 Placebo | 71 | -0.217 | 0.5172 | -1.43 | -0.210 | 0.83 |
| | Compound 1 10mg | 80 | -0.525 | 0.6922 | -2.33 | -0.500 | 1.49 |
| | Compound 1 20mg | 77 | -0.844 | 0.6089 | -2.00 | -1.000 | 0.83 |
| | Compound 1 40mg | 88 | -1.198 | 0.4754 | -2.50 | -1.220 | 0.00 |
| | Leuprorelin | 63 | -1.210 | 0.4946 | -2.60 | -1.170 | 0.00 |
| | End of Treatment Period Placebo | 97 | -0.185 | 0.5491 | -1.83 | -0.200 | 1.20 |
| | Compound 1 10mg | 103 | -0.509 | 0.6675 | -2.25 | -0.430 | 1.49 |
| | Compound 1 20mg | 100 | -0.795 | 0.6490 | -2.10 | -0.750 | 1.10 |
| | Compound 1 40mg | 103 | -1.144 | 0.5014 | -2.50 | -1.200 | 0.14 |
| | Leuprorelin | 81 | -1.160 | 0.4802 | -2.60 | -1.140 | 0.00 |

FIG. 106

| Variable / Visit | Treatment | | Summary Statistics | | | | |
|---|---|---|---|---|---|---|---|
| | | N | Mean | SD | Min | Median | Max |
| Change from Baseline in Mean of M-B&B Score for Deep Dyspareunia | Day 1 - 28 Placebo | 37 | -0.056 | 0.3395 | -1.00 | 0.000 | 1.00 |
| | Compound 1 10mg | 39 | 0.062 | 0.4084 | -1.00 | 0.000 | 1.00 |
| | Compound 1 20mg | 39 | 0.064 | 0.5602 | -1.00 | 0.000 | 2.00 |
| | Compound 1 40mg | 33 | 0.053 | 0.4618 | -1.00 | 0.000 | 1.00 |
| | Leuprorelin | 21 | -0.209 | 0.6311 | -1.00 | 0.000 | 1.33 |
| | Day 29 - 56 Placebo | 31 | -0.101 | 0.4087 | -1.00 | 0.000 | 0.85 |
| | Compound 1 10mg | 40 | 0.021 | 0.5106 | -1.00 | 0.000 | 1.75 |
| | Compound 1 20mg | 40 | -0.027 | 0.6317 | -1.19 | 0.000 | 2.00 |
| | Compound 1 40mg | 32 | -0.072 | 0.4321 | -1.00 | 0.000 | 1.00 |
| | Leuprorelin | 17 | -0.199 | 0.4568 | -1.00 | 0.000 | 0.50 |
| | Day 57 - 84 Placebo | 30 | -0.075 | 0.3370 | -1.00 | 0.000 | 0.50 |
| | Compound 1 10mg | 41 | -0.077 | 0.4927 | -1.50 | 0.000 | 1.00 |
| | Compound 1 20mg | 33 | -0.079 | 0.5723 | -1.33 | 0.000 | 1.00 |
| | Compound 1 40mg | 33 | -0.098 | 0.5080 | -1.00 | 0.000 | 1.00 |
| | Leuprorelin | 18 | -0.339 | 0.5202 | -1.00 | -0.165 | 0.50 |
| | Day 85 - 112 Placebo | 22 | -0.007 | 0.4329 | -1.00 | 0.000 | 1.00 |
| | Compound 1 10mg | 28 | -0.178 | 0.3531 | -1.00 | 0.000 | 0.45 |
| | Compound 1 20mg | 28 | -0.208 | 0.5875 | -1.33 | -0.225 | 1.40 |
| | Compound 1 40mg | 22 | -0.051 | 0.5484 | -0.80 | 0.000 | 2.00 |
| | Leuprorelin | 19 | -0.202 | 0.4500 | -1.00 | 0.000 | 0.50 |
| | Day 113 - 140 Placebo | 26 | -0.109 | 0.3042 | -1.00 | 0.000 | 0.36 |
| | Compound 1 10mg | 28 | -0.191 | 0.4146 | -1.00 | 0.000 | 0.50 |
| | Compound 1 20mg | 26 | -0.194 | 0.5121 | -1.20 | -0.015 | 1.00 |
| | Compound 1 40mg | 25 | -0.204 | 0.3203 | -1.00 | 0.000 | 0.17 |
| | Leuprorelin | 13 | -0.256 | 0.5118 | -1.00 | 0.000 | 0.50 |
| | Day 141 - 168 Placebo | 16 | -0.038 | 0.4199 | -1.00 | 0.000 | 0.58 |
| | Compound 1 10mg | 28 | -0.204 | 0.4235 | -1.00 | 0.000 | 0.40 |
| | Compound 1 20mg | 26 | -0.222 | 0.5360 | -1.13 | -0.100 | 1.00 |
| | Compound 1 40mg | 22 | -0.171 | 0.3178 | -1.00 | 0.000 | 0.20 |
| | Leuprorelin | 14 | -0.191 | 0.5545 | -1.00 | 0.000 | 1.00 |
| | End of Treatment Period Placebo | 29 | 0.003 | 0.3796 | -1.00 | 0.000 | 0.58 |
| | Compound 1 10mg | 40 | -0.171 | 0.4683 | -1.00 | 0.000 | 1.08 |
| | Compound 1 20mg | 34 | -0.210 | 0.4936 | -1.13 | -0.015 | 1.00 |
| | Compound 1 40mg | 31 | -0.097 | 0.4325 | -1.00 | 0.000 | 1.00 |
| | Leuprorelin | 18 | -0.208 | 0.5604 | -1.00 | 0.000 | 1.00 |

FIG. 107

| Variable / Visit | | | Diff | 95% CI | |
|---|---|---|---|---|---|
| | | | | Lower | Upper |
| Change from Baseline in Mean of M-B&B Score for Pelvic Pain | Day 1 - 28 | Compound 1 10mg- Leuprorelin | 0.059 | -0.0269 | 0.1449 |
| | | Compound 1 20mg- Leuprorelin | 0.087 | -0.0120 | 0.1866 |
| | | Compound 1 40mg- Leuprorelin | 0.066 | -0.0267 | 0.1588 |
| | Day 29 - 56 | Compound 1 10mg- Leuprorelin | 0.131 | 0.0206 | 0.2415 |
| | | Compound 1 20mg- Leuprorelin | 0.133 | 0.0153 | 0.2512 |
| | | Compound 1 40mg- Leuprorelin | 0.056 | -0.0605 | 0.1717 |
| | Day 57 - 84 | Compound 1 10mg- Leuprorelin | 0.181 | 0.0675 | 0.2936 |
| | | Compound 1 20mg- Leuprorelin | 0.160 | 0.0214 | 0.2985 |
| | | Compound 1 40mg- Leuprorelin | 0.067 | -0.0612 | 0.1944 |
| | Day 85 - 112 | Compound 1 10mg- Leuprorelin | 0.247 | 0.1238 | 0.3693 |
| | | Compound 1 20mg- Leuprorelin | 0.248 | 0.1081 | 0.3875 |
| | | Compound 1 40mg- Leuprorelin | 0.065 | -0.0635 | 0.1940 |
| | Day 113 - 140 | Compound 1 10mg- Leuprorelin | 0.279 | 0.1482 | 0.4096 |
| | | Compound 1 20mg- Leuprorelin | 0.252 | 0.1150 | 0.3893 |
| | | Compound 1 40mg- Leuprorelin | 0.106 | -0.0452 | 0.2569 |
| | Day 141 - 168 | Compound 1 10mg- Leuprorelin | 0.224 | 0.0872 | 0.3600 |
| | | Compound 1 20mg- Leuprorelin | 0.268 | 0.1255 | 0.4101 |
| | | Compound 1 40mg- Leuprorelin | 0.089 | -0.0590 | 0.2376 |
| | End of Treatment Period | Compound 1 10mg- Leuprorelin | 0.223 | 0.0989 | 0.3464 |
| | | Compound 1 20mg- Leuprorelin | 0.215 | 0.0859 | 0.3440 |
| | | Compound 1 40mg- Leuprorelin | 0.083 | -0.0543 | 0.2195 |

FIG. 108

| Variable / Visit | | | Diff | 95% CI | |
|---|---|---|---|---|---|
| | | | | Lower | Upper |
| Change from Baseline in Mean of M-B&B Score for Dysmenorrhea | Day 1 - 28 | Compound 1 10mg- Leuprorelin | 0.021 | -0.1317 | 0.1733 |
| | | Compound 1 20mg- Leuprorelin | -0.028 | -0.1868 | 0.1299 |
| | | Compound 1 40mg- Leuprorelin | -0.042 | -0.1981 | 0.1145 |
| | Day 29 - 56 | Compound 1 10mg- Leuprorelin | 0.720 | 0.5520 | 0.8881 |
| | | Compound 1 20mg- Leuprorelin | 0.377 | 0.1960 | 0.5579 |
| | | Compound 1 40mg- Leuprorelin | -0.010 | -0.1604 | 0.1395 |
| | Day 57 - 84 | Compound 1 10mg- Leuprorelin | 0.661 | 0.4875 | 0.8350 |
| | | Compound 1 20mg- Leuprorelin | 0.349 | 0.1733 | 0.5249 |
| | | Compound 1 40mg- Leuprorelin | 0.007 | -0.1347 | 0.1484 |
| | Day 85 - 112 | Compound 1 10mg- Leuprorelin | 0.694 | 0.5072 | 0.8801 |
| | | Compound 1 20mg- Leuprorelin | 0.474 | 0.2830 | 0.6655 |
| | | Compound 1 40mg- Leuprorelin | 0.020 | -0.1299 | 0.1704 |
| | Day 113 - 140 | Compound 1 10mg- Leuprorelin | 0.656 | 0.4615 | 0.8496 |
| | | Compound 1 20mg- Leuprorelin | 0.476 | 0.2878 | 0.6646 |
| | | Compound 1 40mg- Leuprorelin | 0.009 | -0.1392 | 0.1575 |
| | Day 141 - 168 | Compound 1 10mg- Leuprorelin | 0.685 | 0.4811 | 0.8895 |
| | | Compound 1 20mg- Leuprorelin | 0.366 | 0.1778 | 0.5543 |
| | | Compound 1 40mg- Leuprorelin | 0.013 | -0.1450 | 0.1704 |
| | End of Treatment Period | Compound 1 10mg- Leuprorelin | 0.651 | 0.4777 | 0.8250 |
| | | Compound 1 20mg- Leuprorelin | 0.366 | 0.1945 | 0.5365 |
| | | Compound 1 40mg- Leuprorelin | 0.016 | -0.1283 | 0.1601 |

FIG. 109

| Variable / Visit | | | Diff | 95% CI | |
|---|---|---|---|---|---|
| | | | | Lower | Upper |
| Change from Baseline in Mean of M-B&B Score for Deep Dyspareunia | Day 1 - 28 | Compound 1 10mg- Leuprorelin | 0.271 | 0.0016 | 0.5397 |
| | | Compound 1 20mg- Leuprorelin | 0.273 | -0.0446 | 0.5899 |
| | | Compound 1 40mg- Leuprorelin | 0.262 | -0.0368 | 0.5607 |
| | Day 29 - 56 | Compound 1 10mg- Leuprorelin | 0.220 | -0.0680 | 0.5071 |
| | | Compound 1 20mg- Leuprorelin | 0.172 | -0.1680 | 0.5122 |
| | | Compound 1 40mg- Leuprorelin | 0.127 | -0.1394 | 0.3927 |
| | Day 57 - 84 | Compound 1 10mg- Leuprorelin | 0.262 | -0.0214 | 0.5460 |
| | | Compound 1 20mg- Leuprorelin | 0.260 | -0.0666 | 0.5868 |
| | | Compound 1 40mg- Leuprorelin | 0.241 | -0.0603 | 0.5430 |
| | Day 85 - 112 | Compound 1 10mg- Leuprorelin | 0.024 | -0.2122 | 0.2604 |
| | | Compound 1 20mg- Leuprorelin | -0.007 | -0.3280 | 0.3147 |
| | | Compound 1 40mg- Leuprorelin | 0.150 | -0.1699 | 0.4704 |
| | Day 113 - 140 | Compound 1 10mg- Leuprorelin | 0.065 | -0.2386 | 0.3680 |
| | | Compound 1 20mg- Leuprorelin | 0.062 | -0.2905 | 0.4143 |
| | | Compound 1 40mg- Leuprorelin | 0.052 | -0.2219 | 0.3254 |
| | Day 141 - 168 | Compound 1 10mg- Leuprorelin | -0.013 | -0.3242 | 0.2978 |
| | | Compound 1 20mg- Leuprorelin | -0.031 | -0.3952 | 0.3328 |
| | | Compound 1 40mg- Leuprorelin | 0.019 | -0.2754 | 0.3141 |
| | End of Treatment Period | Compound 1 10mg- Leuprorelin | 0.037 | -0.2459 | 0.3205 |
| | | Compound 1 20mg- Leuprorelin | -0.001 | -0.3042 | 0.3015 |
| | | Compound 1 40mg- Leuprorelin | 0.111 | -0.1768 | 0.3987 |

FIG. 110

| Variable / Visit | Treatment | | Summary Statistics | | | | | |
|---|---|---|---|---|---|---|---|---|
| | | | N | Mean | SD | Min | Median | Max |
| B & B Score for Dysmenorrhea | Baseline | Placebo | 97 | 2.0 | 0.37 | 1 | 2.0 | 3 |
| | | Compound 1 10mg | 103 | 2.1 | 0.48 | 1 | 2.0 | 3 |
| | | Compound 1 20mg | 100 | 2.1 | 0.43 | 1 | 2.0 | 3 |
| | | Compound 1 40mg | 103 | 2.1 | 0.47 | 1 | 2.0 | 3 |
| | | Leuprorelin | 81 | 2.1 | 0.49 | 1 | 2.0 | 3 |
| | Week 4 | Placebo | 96 | 1.7 | 0.70 | 0 | 2.0 | 3 |
| | | Compound 1 10mg | 103 | 1.4 | 0.82 | 0 | 1.0 | 3 |
| | | Compound 1 20mg | 99 | 1.3 | 0.80 | 0 | 1.0 | 3 |
| | | Compound 1 40mg | 102 | 1.3 | 0.90 | 0 | 1.0 | 3 |
| | | Leuprorelin | 81 | 1.1 | 0.80 | 0 | 1.0 | 3 |
| | Week 8 | Placebo | 95 | 1.6 | 0.75 | 0 | 2.0 | 3 |
| | | Compound 1 10mg | 103 | 1.1 | 0.88 | 0 | 1.0 | 3 |
| | | Compound 1 20mg | 96 | 0.6 | 0.79 | 0 | 0.0 | 2 |
| | | Compound 1 40mg | 101 | 0.1 | 0.44 | 0 | 0.0 | 2 |
| | | Leuprorelin | 79 | 0.0 | 0.19 | 0 | 0.0 | 1 |
| | Week 12 | Placebo | 93 | 1.6 | 0.76 | 0 | 2.0 | 3 |
| | | Compound 1 10mg | 101 | 1.1 | 0.86 | 0 | 1.0 | 3 |
| | | Compound 1 20mg | 92 | 0.6 | 0.81 | 0 | 0.0 | 3 |
| | | Compound 1 40mg | 101 | 0.1 | 0.24 | 0 | 0.0 | 1 |
| | | Leuprorelin | 76 | 0.0 | 0.00 | 0 | 0.0 | 0 |
| | Week 16 | Placebo | 75 | 1.5 | 0.66 | 0 | 2.0 | 3 |
| | | Compound 1 10mg | 84 | 0.9 | 0.81 | 0 | 1.0 | 3 |
| | | Compound 1 20mg | 78 | 0.5 | 0.75 | 0 | 0.0 | 3 |
| | | Compound 1 40mg | 89 | 0.1 | 0.38 | 0 | 0.0 | 3 |
| | | Leuprorelin | 69 | 0.0 | 0.00 | 0 | 0.0 | 0 |
| | Week 20 | Placebo | 74 | 1.6 | 0.80 | 0 | 2.0 | 3 |
| | | Compound 1 10mg | 81 | 1.0 | 0.85 | 0 | 1.0 | 3 |
| | | Compound 1 20mg | 77 | 0.7 | 0.83 | 0 | 0.0 | 2 |
| | | Compound 1 40mg | 87 | 0.1 | 0.33 | 0 | 0.0 | 2 |
| | | Leuprorelin | 64 | 0.0 | 0.00 | 0 | 0.0 | 0 |
| | Week 24 | Placebo | 68 | 1.7 | 0.62 | 0 | 2.0 | 3 |
| | | Compound 1 10mg | 79 | 1.0 | 0.80 | 0 | 1.0 | 3 |
| | | Compound 1 20mg | 74 | 0.5 | 0.81 | 0 | 0.0 | 3 |
| | | Compound 1 40mg | 87 | 0.1 | 0.39 | 0 | 0.0 | 2 |
| | | Leuprorelin | 61 | 0.0 | 0.00 | 0 | 0.0 | 0 |

FIG. 111

| Variable / Visit | Treatment | | Summary Statistics | | | | |
|---|---|---|---|---|---|---|---|
| | | N | Mean | SD | Min | Median | Max |
| B & B Score for Dyspareunia | Baseline Placebo | 41 | 0.9 | 0.73 | 0 | 1.0 | 3 |
| | Compound 1 10mg | 47 | 0.7 | 0.71 | 0 | 1.0 | 2 |
| | Compound 1 20mg | 49 | 0.9 | 0.72 | 0 | 1.0 | 3 |
| | Compound 1 40mg | 44 | 0.7 | 0.61 | 0 | 1.0 | 2 |
| | Leuprorelin | 26 | 0.8 | 0.73 | 0 | 1.0 | 3 |
| | Week 4 Placebo | 43 | 0.7 | 0.67 | 0 | 1.0 | 2 |
| | Compound 1 10mg | 50 | 0.7 | 0.69 | 0 | 1.0 | 2 |
| | Compound 1 20mg | 43 | 0.8 | 0.59 | 0 | 1.0 | 2 |
| | Compound 1 40mg | 42 | 0.6 | 0.66 | 0 | 1.0 | 2 |
| | Leuprorelin | 27 | 0.5 | 0.75 | 0 | 0.0 | 3 |
| | Week 8 Placebo | 37 | 0.8 | 0.63 | 0 | 1.0 | 3 |
| | Compound 1 10mg | 46 | 0.6 | 0.65 | 0 | 0.0 | 2 |
| | Compound 1 20mg | 49 | 0.7 | 0.71 | 0 | 1.0 | 2 |
| | Compound 1 40mg | 38 | 0.6 | 0.60 | 0 | 0.5 | 2 |
| | Leuprorelin | 24 | 0.4 | 0.58 | 0 | 0.0 | 2 |
| | Week 12 Placebo | 37 | 0.8 | 0.65 | 0 | 1.0 | 2 |
| | Compound 1 10mg | 50 | 0.6 | 0.72 | 0 | 1.0 | 3 |
| | Compound 1 20mg | 37 | 0.6 | 0.69 | 0 | 0.0 | 2 |
| | Compound 1 40mg | 40 | 0.5 | 0.55 | 0 | 0.0 | 2 |
| | Leuprorelin | 24 | 0.3 | 0.56 | 0 | 0.0 | 2 |
| | Week 16 Placebo | 28 | 0.8 | 0.86 | 0 | 1.0 | 3 |
| | Compound 1 10mg | 37 | 0.4 | 0.50 | 0 | 0.0 | 1 |
| | Compound 1 20mg | 33 | 0.6 | 0.70 | 0 | 0.0 | 2 |
| | Compound 1 40mg | 32 | 0.6 | 0.71 | 0 | 0.5 | 3 |
| | Leuprorelin | 23 | 0.3 | 0.49 | 0 | 0.0 | 1 |
| | Week 20 Placebo | 32 | 0.7 | 0.59 | 0 | 1.0 | 2 |
| | Compound 1 10mg | 36 | 0.4 | 0.60 | 0 | 0.0 | 2 |
| | Compound 1 20mg | 30 | 0.5 | 0.57 | 0 | 0.0 | 2 |
| | Compound 1 40mg | 33 | 0.5 | 0.56 | 0 | 0.0 | 2 |
| | Leuprorelin | 17 | 0.3 | 0.47 | 0 | 0.0 | 1 |
| | Week 24 Placebo | 21 | 0.7 | 0.66 | 0 | 1.0 | 2 |
| | Compound 1 10mg | 36 | 0.4 | 0.55 | 0 | 0.0 | 2 |
| | Compound 1 20mg | 28 | 0.5 | 0.58 | 0 | 0.0 | 2 |
| | Compound 1 40mg | 30 | 0.4 | 0.50 | 0 | 0.0 | 1 |
| | Leuprorelin | 17 | 0.4 | 0.71 | 0 | 0.0 | 2 |

FIG. 112

| Variable / Visit | Treatment | | Summary Statistics | | | | |
|---|---|---|---|---|---|---|---|
| | | N | Mean | SD | Min | Median | Max |
| B & B Score for Pelvic Pain | Baseline Placebo | 97 | 1.5 | 0.54 | 1 | 2.0 | 3 |
| | Compound 1 10mg | 103 | 1.7 | 0.67 | 1 | 2.0 | 3 |
| | Compound 1 20mg | 100 | 1.6 | 0.62 | 1 | 2.0 | 3 |
| | Compound 1 40mg | 103 | 1.5 | 0.61 | 1 | 1.0 | 3 |
| | Leuprorelin | 81 | 1.6 | 0.56 | 1 | 2.0 | 3 |
| | Week 4 Placebo | 95 | 1.2 | 0.69 | 0 | 1.0 | 2 |
| | Compound 1 10mg | 103 | 1.2 | 0.61 | 0 | 1.0 | 3 |
| | Compound 1 20mg | 99 | 1.1 | 0.69 | 0 | 1.0 | 3 |
| | Compound 1 40mg | 102 | 1.0 | 0.65 | 0 | 1.0 | 3 |
| | Leuprorelin | 81 | 1.0 | 0.61 | 0 | 1.0 | 2 |
| | Week 8 Placebo | 95 | 1.1 | 0.62 | 0 | 1.0 | 2 |
| | Compound 1 10mg | 103 | 1.0 | 0.75 | 0 | 1.0 | 3 |
| | Compound 1 20mg | 96 | 1.0 | 0.68 | 0 | 1.0 | 3 |
| | Compound 1 40mg | 101 | 0.9 | 0.65 | 0 | 1.0 | 3 |
| | Leuprorelin | 79 | 0.8 | 0.67 | 0 | 1.0 | 2 |
| | Week 12 Placebo | 93 | 1.1 | 0.64 | 0 | 1.0 | 3 |
| | Compound 1 10mg | 101 | 1.0 | 0.77 | 0 | 1.0 | 3 |
| | Compound 1 20mg | 92 | 0.8 | 0.73 | 0 | 1.0 | 3 |
| | Compound 1 40mg | 101 | 0.6 | 0.60 | 0 | 1.0 | 2 |
| | Leuprorelin | 76 | 0.5 | 0.62 | 0 | 0.0 | 2 |
| | Week 16 Placebo | 75 | 1.0 | 0.71 | 0 | 1.0 | 3 |
| | Compound 1 10mg | 84 | 1.0 | 0.77 | 0 | 1.0 | 3 |
| | Compound 1 20mg | 78 | 0.7 | 0.63 | 0 | 1.0 | 2 |
| | Compound 1 40mg | 89 | 0.5 | 0.60 | 0 | 0.0 | 2 |
| | Leuprorelin | 69 | 0.4 | 0.55 | 0 | 0.0 | 2 |
| | Week 20 Placebo | 74 | 1.0 | 0.80 | 0 | 1.0 | 3 |
| | Compound 1 10mg | 81 | 0.9 | 0.68 | 0 | 1.0 | 3 |
| | Compound 1 20mg | 77 | 0.8 | 0.71 | 0 | 1.0 | 3 |
| | Compound 1 40mg | 87 | 0.5 | 0.64 | 0 | 0.0 | 3 |
| | Leuprorelin | 64 | 0.4 | 0.59 | 0 | 0.0 | 2 |
| | Week 24 Placebo | 68 | 1.0 | 0.80 | 0 | 1.0 | 3 |
| | Compound 1 10mg | 79 | 0.8 | 0.67 | 0 | 1.0 | 3 |
| | Compound 1 20mg | 74 | 0.7 | 0.65 | 0 | 1.0 | 2 |
| | Compound 1 40mg | 87 | 0.5 | 0.64 | 0 | 0.0 | 3 |
| | Leuprorelin | 61 | 0.4 | 0.58 | 0 | 0.0 | 2 |

FIG. 113

| Variable / Visit | Treatment | | Summary Statistics | | | | | |
|---|---|---|---|---|---|---|---|---|
| | | | N | Mean | SD | Min | Median | Max |
| B & B Score for Pelvic Tenderness | Baseline | Placebo | 97 | 1.6 | 0.71 | 0 | 2.0 | 3 |
| | | Compound 1 10mg | 103 | 1.5 | 0.80 | 0 | 2.0 | 3 |
| | | Compound 1 20mg | 100 | 1.5 | 0.78 | 0 | 2.0 | 3 |
| | | Compound 1 40mg | 103 | 1.6 | 0.81 | 0 | 2.0 | 3 |
| | | Leuprorelin | 81 | 1.4 | 0.72 | 0 | 2.0 | 3 |
| | Week 4 | Placebo | 96 | 1.3 | 0.82 | 0 | 1.0 | 3 |
| | | Compound 1 10mg | 103 | 1.2 | 0.83 | 0 | 1.0 | 3 |
| | | Compound 1 20mg | 99 | 1.1 | 0.85 | 0 | 1.0 | 3 |
| | | Compound 1 40mg | 102 | 1.2 | 0.80 | 0 | 1.0 | 3 |
| | | Leuprorelin | 81 | 1.0 | 0.76 | 0 | 1.0 | 2 |
| | Week 8 | Placebo | 95 | 1.2 | 0.82 | 0 | 1.0 | 3 |
| | | Compound 1 10mg | 103 | 1.1 | 0.79 | 0 | 1.0 | 3 |
| | | Compound 1 20mg | 96 | 0.9 | 0.74 | 0 | 1.0 | 3 |
| | | Compound 1 40mg | 101 | 0.9 | 0.69 | 0 | 1.0 | 3 |
| | | Leuprorelin | 79 | 0.7 | 0.63 | 0 | 1.0 | 2 |
| | Week 12 | Placebo | 93 | 1.2 | 0.85 | 0 | 1.0 | 3 |
| | | Compound 1 10mg | 101 | 1.0 | 0.81 | 0 | 1.0 | 3 |
| | | Compound 1 20mg | 92 | 0.8 | 0.75 | 0 | 1.0 | 3 |
| | | Compound 1 40mg | 101 | 0.7 | 0.67 | 0 | 1.0 | 3 |
| | | Leuprorelin | 76 | 0.7 | 0.70 | 0 | 1.0 | 3 |
| | Week 16 | Placebo | 75 | 1.1 | 0.79 | 0 | 1.0 | 3 |
| | | Compound 1 10mg | 84 | 0.8 | 0.79 | 0 | 1.0 | 3 |
| | | Compound 1 20mg | 78 | 0.9 | 0.76 | 0 | 1.0 | 3 |
| | | Compound 1 40mg | 89 | 0.7 | 0.69 | 0 | 1.0 | 3 |
| | | Leuprorelin | 69 | 0.4 | 0.61 | 0 | 0.0 | 2 |
| | Week 20 | Placebo | 74 | 1.0 | 0.78 | 0 | 1.0 | 2 |
| | | Compound 1 10mg | 81 | 0.8 | 0.75 | 0 | 1.0 | 3 |
| | | Compound 1 20mg | 77 | 0.8 | 0.74 | 0 | 1.0 | 3 |
| | | Compound 1 40mg | 87 | 0.5 | 0.66 | 0 | 0.0 | 3 |
| | | Leuprorelin | 64 | 0.4 | 0.61 | 0 | 0.0 | 2 |
| | Week 24 | Placebo | 68 | 1.0 | 0.82 | 0 | 1.0 | 3 |
| | | Compound 1 10mg | 79 | 0.8 | 0.74 | 0 | 1.0 | 3 |
| | | Compound 1 20mg | 74 | 0.8 | 0.74 | 0 | 1.0 | 3 |
| | | Compound 1 40mg | 87 | 0.5 | 0.66 | 0 | 0.0 | 3 |
| | | Leuprorelin | 61 | 0.3 | 0.50 | 0 | 0.0 | 2 |

FIG. 114

| Variable / Visit | Treatment | | Summary Statistics | | | | |
|---|---|---|---|---|---|---|---|
| | | N | Mean | SD | Min | Median | Max |
| B & B Score for Induration | Baseline Placebo | 97 | 1.4 | 0.72 | 0 | 2.0 | 3 |
| | Compound 1 10mg | 103 | 1.2 | 0.92 | 0 | 1.0 | 3 |
| | Compound 1 20mg | 100 | 1.4 | 0.83 | 0 | 1.0 | 3 |
| | Compound 1 40mg | 103 | 1.3 | 0.86 | 0 | 2.0 | 3 |
| | Leuprorelin | 81 | 1.1 | 0.85 | 0 | 1.0 | 3 |
| | Week 4 Placebo | 96 | 1.3 | 0.77 | 0 | 1.0 | 3 |
| | Compound 1 10mg | 103 | 1.0 | 0.88 | 0 | 1.0 | 3 |
| | Compound 1 20mg | 99 | 0.9 | 0.77 | 0 | 1.0 | 3 |
| | Compound 1 40mg | 102 | 1.1 | 0.85 | 0 | 1.0 | 3 |
| | Leuprorelin | 81 | 0.9 | 0.79 | 0 | 1.0 | 2 |
| | Week 8 Placebo | 95 | 1.2 | 0.81 | 0 | 1.0 | 3 |
| | Compound 1 10mg | 103 | 0.8 | 0.78 | 0 | 1.0 | 3 |
| | Compound 1 20mg | 96 | 0.9 | 0.79 | 0 | 1.0 | 3 |
| | Compound 1 40mg | 101 | 0.8 | 0.73 | 0 | 1.0 | 3 |
| | Leuprorelin | 79 | 0.6 | 0.67 | 0 | 1.0 | 2 |
| | Week 12 Placebo | 93 | 1.0 | 0.78 | 0 | 1.0 | 3 |
| | Compound 1 10mg | 101 | 0.7 | 0.74 | 0 | 1.0 | 3 |
| | Compound 1 20mg | 92 | 0.8 | 0.76 | 0 | 1.0 | 3 |
| | Compound 1 40mg | 101 | 0.7 | 0.68 | 0 | 1.0 | 2 |
| | Leuprorelin | 76 | 0.4 | 0.62 | 0 | 0.0 | 2 |
| | Week 16 Placebo | 75 | 1.0 | 0.73 | 0 | 1.0 | 3 |
| | Compound 1 10mg | 84 | 0.7 | 0.72 | 0 | 1.0 | 3 |
| | Compound 1 20mg | 78 | 0.8 | 0.78 | 0 | 1.0 | 3 |
| | Compound 1 40mg | 89 | 0.6 | 0.71 | 0 | 1.0 | 3 |
| | Leuprorelin | 69 | 0.3 | 0.56 | 0 | 0.0 | 2 |
| | Week 20 Placebo | 74 | 1.0 | 0.83 | 0 | 1.0 | 3 |
| | Compound 1 10mg | 81 | 0.6 | 0.69 | 0 | 1.0 | 3 |
| | Compound 1 20mg | 77 | 0.7 | 0.78 | 0 | 1.0 | 3 |
| | Compound 1 40mg | 87 | 0.5 | 0.68 | 0 | 0.0 | 3 |
| | Leuprorelin | 64 | 0.3 | 0.50 | 0 | 0.0 | 2 |
| | Week 24 Placebo | 68 | 0.9 | 0.86 | 0 | 1.0 | 3 |
| | Compound 1 10mg | 79 | 0.6 | 0.79 | 0 | 0.0 | 3 |
| | Compound 1 20mg | 74 | 0.7 | 0.78 | 0 | 1.0 | 3 |
| | Compound 1 40mg | 87 | 0.5 | 0.68 | 0 | 0.0 | 3 |
| | Leuprorelin | 61 | 0.3 | 0.56 | 0 | 0.0 | 2 |

FIG. 115

| Variable / Visit | Treatment | | Summary Statistics | | | | |
|---|---|---|---|---|---|---|---|
| | | N | Mean | SD | Min | Median | Max |
| Change from Baseline in B & B Score for Dysmenorrhea | Week 4 Placebo | 96 | -0.3 | 0.64 | -2 | 0.0 | 1 |
| | Compound 1 10mg | 103 | -0.7 | 0.85 | -3 | -1.0 | 1 |
| | Compound 1 20mg | 99 | -0.8 | 0.86 | -3 | -1.0 | 1 |
| | Compound 1 40mg | 102 | -0.7 | 0.90 | -3 | -1.0 | 1 |
| | Leuprorelin | 81 | -1.0 | 0.84 | -3 | -1.0 | 1 |
| | Week 8 Placebo | 95 | -0.4 | 0.71 | -2 | 0.0 | 1 |
| | Compound 1 10mg | 103 | -1.0 | 0.92 | -3 | -1.0 | 1 |
| | Compound 1 20mg | 96 | -1.5 | 0.87 | -3 | -2.0 | 0 |
| | Compound 1 40mg | 101 | -2.0 | 0.64 | -3 | -2.0 | 0 |
| | Leuprorelin | 79 | -2.0 | 0.56 | -3 | -2.0 | 0 |
| | Week 12 Placebo | 93 | -0.4 | 0.76 | -2 | 0.0 | 1 |
| | Compound 1 10mg | 101 | -1.0 | 0.93 | -3 | -1.0 | 1 |
| | Compound 1 20mg | 92 | -1.5 | 0.91 | -3 | -2.0 | 1 |
| | Compound 1 40mg | 101 | -2.0 | 0.51 | -3 | -2.0 | -1 |
| | Leuprorelin | 76 | -2.1 | 0.49 | -3 | -2.0 | -1 |
| | Week 16 Placebo | 75 | -0.4 | 0.70 | -2 | 0.0 | 1 |
| | Compound 1 10mg | 84 | -1.1 | 0.90 | -3 | -1.0 | 0 |
| | Compound 1 20mg | 78 | -1.5 | 0.91 | -3 | -2.0 | 1 |
| | Compound 1 40mg | 89 | -2.0 | 0.54 | -3 | -2.0 | 0 |
| | Leuprorelin | 69 | -2.1 | 0.48 | -3 | -2.0 | -1 |
| | Week 20 Placebo | 74 | -0.4 | 0.82 | -3 | 0.0 | 1 |
| | Compound 1 10mg | 81 | -1.1 | 0.91 | -3 | -1.0 | 1 |
| | Compound 1 20mg | 77 | -1.4 | 0.94 | -3 | -2.0 | 1 |
| | Compound 1 40mg | 87 | -2.0 | 0.56 | -3 | -2.0 | 0 |
| | Leuprorelin | 64 | -2.1 | 0.48 | -3 | -2.0 | -1 |
| | Week 24 Placebo | 68 | -0.3 | 0.64 | -2 | 0.0 | 1 |
| | Compound 1 10mg | 79 | -1.0 | 0.87 | -3 | -1.0 | 1 |
| | Compound 1 20mg | 74 | -1.5 | 0.94 | -3 | -2.0 | 1 |
| | Compound 1 40mg | 87 | -2.0 | 0.61 | -3 | -2.0 | 0 |
| | Leuprorelin | 61 | -2.1 | 0.49 | -3 | -2.0 | -1 |

FIG. 116

| Variable / Visit | Treatment | | Summary Statistics | | | | |
|---|---|---|---|---|---|---|---|
| | | N | Mean | SD | Min | Median | Max |
| Change from Baseline in B & B Score for Dyspareunia | Week 4 Placebo | 36 | -0.2 | 0.71 | -3 | 0.0 | 1 |
| | Compound 1 10mg | 39 | 0.1 | 0.65 | -2 | 0.0 | 1 |
| | Compound 1 20mg | 38 | 0.0 | 0.68 | -1 | 0.0 | 2 |
| | Compound 1 40mg | 33 | 0.0 | 0.53 | -1 | 0.0 | 1 |
| | Leuprorelin | 22 | -0.5 | 0.86 | -2 | 0.0 | 1 |
| | Week 8 Placebo | 30 | -0.3 | 0.69 | -2 | 0.0 | 2 |
| | Compound 1 10mg | 39 | -0.1 | 0.70 | -1 | 0.0 | 2 |
| | Compound 1 20mg | 41 | -0.2 | 0.77 | -2 | 0.0 | 2 |
| | Compound 1 40mg | 31 | 0.0 | 0.60 | -1 | 0.0 | 2 |
| | Leuprorelin | 17 | -0.5 | 0.87 | -2 | 0.0 | 1 |
| | Week 12 Placebo | 31 | -0.2 | 0.72 | -3 | 0.0 | 1 |
| | Compound 1 10mg | 41 | -0.2 | 0.68 | -2 | 0.0 | 1 |
| | Compound 1 20mg | 35 | -0.2 | 0.81 | -2 | 0.0 | 1 |
| | Compound 1 40mg | 33 | -0.1 | 0.60 | -1 | 0.0 | 1 |
| | Leuprorelin | 19 | -0.6 | 0.68 | -2 | -1.0 | 0 |
| | Week 16 Placebo | 23 | 0.0 | 0.60 | -1 | 0.0 | 1 |
| | Compound 1 10mg | 30 | -0.2 | 0.57 | -2 | 0.0 | 1 |
| | Compound 1 20mg | 29 | -0.4 | 0.68 | -2 | 0.0 | 1 |
| | Compound 1 40mg | 23 | -0.1 | 0.67 | -1 | 0.0 | 2 |
| | Leuprorelin | 19 | -0.5 | 0.77 | -2 | 0.0 | 0 |
| | Week 20 Placebo | 25 | -0.2 | 0.72 | -3 | 0.0 | 1 |
| | Compound 1 10mg | 27 | -0.3 | 0.66 | -2 | 0.0 | 1 |
| | Compound 1 20mg | 26 | -0.5 | 0.58 | -1 | -0.5 | 1 |
| | Compound 1 40mg | 25 | -0.2 | 0.55 | -1 | 0.0 | 1 |
| | Leuprorelin | 14 | -0.6 | 0.65 | -2 | -0.5 | 0 |
| | Week 24 Placebo | 17 | -0.2 | 0.83 | -2 | 0.0 | 1 |
| | Compound 1 10mg | 28 | -0.3 | 0.67 | -2 | 0.0 | 1 |
| | Compound 1 20mg | 25 | -0.4 | 0.70 | -2 | 0.0 | 1 |
| | Compound 1 40mg | 22 | -0.1 | 0.43 | -1 | 0.0 | 1 |
| | Leuprorelin | 13 | -0.5 | 0.88 | -2 | 0.0 | 1 |

FIG. 117

| Variable / Visit | Treatment | | Summary Statistics | | | | | |
|---|---|---|---|---|---|---|---|---|
| | | | N | Mean | SD | Min | Median | Max |
| Change from Baseline in B & B Score for Pelvic Pain | Week 4 | Placebo | 96 | -0.3 | 0.79 | -2 | 0.0 | 1 |
| | | Compound 1 10mg | 103 | -0.5 | 0.79 | -3 | 0.0 | 2 |
| | | Compound 1 20mg | 99 | -0.5 | 0.84 | -3 | 0.0 | 2 |
| | | Compound 1 40mg | 102 | -0.5 | 0.78 | -3 | 0.0 | 1 |
| | | Leuprorelin | 81 | -0.7 | 0.76 | -2 | -1.0 | 1 |
| | Week 8 | Placebo | 95 | -0.5 | 0.78 | -2 | -1.0 | 1 |
| | | Compound 1 10mg | 103 | -0.6 | 0.88 | -3 | -1.0 | 2 |
| | | Compound 1 20mg | 96 | -0.6 | 0.84 | -3 | -1.0 | 1 |
| | | Compound 1 40mg | 101 | -0.7 | 0.88 | -3 | -1.0 | 2 |
| | | Leuprorelin | 79 | -0.8 | 0.81 | -2 | -1.0 | 1 |
| | Week 12 | Placebo | 93 | -0.5 | 0.75 | -2 | -1.0 | 2 |
| | | Compound 1 10mg | 101 | -0.6 | 0.76 | -3 | -1.0 | 1 |
| | | Compound 1 20mg | 92 | -0.8 | 0.94 | -3 | -1.0 | 2 |
| | | Compound 1 40mg | 101 | -0.9 | 0.84 | -3 | -1.0 | 1 |
| | | Leuprorelin | 76 | -1.1 | 0.73 | -3 | -1.0 | 1 |
| | Week 16 | Placebo | 75 | -0.6 | 0.78 | -2 | -1.0 | 2 |
| | | Compound 1 10mg | 84 | -0.7 | 0.83 | -3 | -1.0 | 1 |
| | | Compound 1 20mg | 78 | -0.9 | 0.80 | -3 | -1.0 | 1 |
| | | Compound 1 40mg | 89 | -1.0 | 0.78 | -3 | -1.0 | 0 |
| | | Leuprorelin | 69 | -1.2 | 0.71 | -3 | -1.0 | 0 |
| | Week 20 | Placebo | 74 | -0.6 | 0.81 | -2 | -1.0 | 2 |
| | | Compound 1 10mg | 81 | -0.7 | 0.78 | -3 | -1.0 | 1 |
| | | Compound 1 20mg | 77 | -0.8 | 0.83 | -3 | -1.0 | 1 |
| | | Compound 1 40mg | 87 | -1.0 | 0.84 | -3 | -1.0 | 2 |
| | | Leuprorelin | 64 | -1.2 | 0.69 | -3 | -1.0 | 0 |
| | Week 24 | Placebo | 68 | -0.6 | 0.85 | -2 | -1.0 | 1 |
| | | Compound 1 10mg | 79 | -0.8 | 0.79 | -3 | -1.0 | 1 |
| | | Compound 1 20mg | 74 | -0.9 | 0.85 | -3 | -1.0 | 1 |
| | | Compound 1 40mg | 87 | -1.0 | 0.86 | -3 | -1.0 | 2 |
| | | Leuprorelin | 61 | -1.2 | 0.72 | -3 | -1.0 | 0 |

FIG. 118

| Variable / Visit | Treatment | | Summary Statistics | | | | | |
|---|---|---|---|---|---|---|---|---|
| | | | N | Mean | SD | Min | Median | Max |
| Change from Baseline in B & B Score for Pelvic Tenderness | Week 4 | Placebo | 96 | -0.3 | 0.63 | -2 | 0.0 | 1 |
| | | Compound 1 10mg | 103 | -0.3 | 0.74 | -2 | 0.0 | 2 |
| | | Compound 1 20mg | 99 | -0.4 | 0.77 | -3 | 0.0 | 2 |
| | | Compound 1 40mg | 102 | -0.4 | 0.69 | -3 | 0.0 | 1 |
| | | Leuprorelin | 81 | -0.5 | 0.74 | -2 | 0.0 | 2 |
| | Week 8 | Placebo | 95 | -0.4 | 0.69 | -2 | 0.0 | 1 |
| | | Compound 1 10mg | 103 | -0.4 | 0.75 | -2 | 0.0 | 1 |
| | | Compound 1 20mg | 96 | -0.6 | 0.78 | -3 | -1.0 | 1 |
| | | Compound 1 40mg | 101 | -0.7 | 0.81 | -3 | -1.0 | 1 |
| | | Leuprorelin | 79 | -0.7 | 0.67 | -2 | -1.0 | 1 |
| | Week 12 | Placebo | 93 | -0.5 | 0.80 | -3 | 0.0 | 2 |
| | | Compound 1 10mg | 101 | -0.5 | 0.73 | -2 | 0.0 | 1 |
| | | Compound 1 20mg | 92 | -0.7 | 0.79 | -3 | -1.0 | 1 |
| | | Compound 1 40mg | 101 | -0.9 | 0.89 | -3 | -1.0 | 1 |
| | | Leuprorelin | 76 | -0.8 | 0.77 | -2 | -1.0 | 1 |
| | Week 16 | Placebo | 75 | -0.5 | 0.68 | -2 | 0.0 | 1 |
| | | Compound 1 10mg | 84 | -0.6 | 0.83 | -2 | -1.0 | 1 |
| | | Compound 1 20mg | 78 | -0.7 | 0.84 | -3 | -1.0 | 1 |
| | | Compound 1 40mg | 89 | -0.8 | 0.78 | -3 | -1.0 | 1 |
| | | Leuprorelin | 69 | -1.0 | 0.80 | -3 | -1.0 | 1 |
| | Week 20 | Placebo | 74 | -0.6 | 0.78 | -3 | -0.5 | 1 |
| | | Compound 1 10mg | 81 | -0.6 | 0.83 | -3 | -1.0 | 1 |
| | | Compound 1 20mg | 77 | -0.8 | 0.83 | -3 | -1.0 | 1 |
| | | Compound 1 40mg | 87 | -1.0 | 0.87 | -3 | -1.0 | 1 |
| | | Leuprorelin | 64 | -1.0 | 0.82 | -2 | -1.0 | 1 |
| | Week 24 | Placebo | 68 | -0.6 | 0.74 | -2 | -1.0 | 1 |
| | | Compound 1 10mg | 79 | -0.7 | 0.83 | -2 | -1.0 | 1 |
| | | Compound 1 20mg | 74 | -0.8 | 0.79 | -3 | -1.0 | 1 |
| | | Compound 1 40mg | 87 | -1.0 | 0.92 | -3 | -1.0 | 1 |
| | | Leuprorelin | 61 | -1.1 | 0.78 | -3 | -1.0 | 0 |

FIG. 119

| Variable / Visit | Treatment | | Summary Statistics | | | | | |
|---|---|---|---|---|---|---|---|---|
| | | | N | Mean | SD | Min | Median | Max |
| Change from Baseline in B & B Score for Induration | Week 4 | Placebo | 96 | -0.2 | 0.50 | -2 | 0.0 | 1 |
| | | Compound 1 10mg | 103 | -0.2 | 0.66 | -2 | 0.0 | 1 |
| | | Compound 1 20mg | 99 | -0.4 | 0.72 | -3 | 0.0 | 1 |
| | | Compound 1 40mg | 102 | -0.2 | 0.63 | -2 | 0.0 | 2 |
| | | Leuprorelin | 81 | -0.2 | 0.56 | -2 | 0.0 | 1 |
| | Week 8 | Placebo | 95 | -0.3 | 0.56 | -2 | 0.0 | 1 |
| | | Compound 1 10mg | 103 | -0.4 | 0.64 | -2 | 0.0 | 1 |
| | | Compound 1 20mg | 96 | -0.6 | 0.81 | -3 | 0.0 | 1 |
| | | Compound 1 40mg | 101 | -0.6 | 0.80 | -3 | -1.0 | 2 |
| | | Leuprorelin | 79 | -0.5 | 0.78 | -2 | 0.0 | 1 |
| | Week 12 | Placebo | 93 | -0.4 | 0.65 | -2 | 0.0 | 1 |
| | | Compound 1 10mg | 101 | -0.5 | 0.69 | -2 | 0.0 | 1 |
| | | Compound 1 20mg | 92 | -0.6 | 0.79 | -3 | -0.5 | 1 |
| | | Compound 1 40mg | 101 | -0.7 | 0.82 | -3 | -1.0 | 2 |
| | | Leuprorelin | 76 | -0.7 | 0.82 | -3 | -1.0 | 1 |
| | Week 16 | Placebo | 75 | -0.5 | 0.60 | -2 | 0.0 | 1 |
| | | Compound 1 10mg | 84 | -0.6 | 0.78 | -2 | -1.0 | 1 |
| | | Compound 1 20mg | 78 | -0.7 | 0.81 | -3 | -1.0 | 1 |
| | | Compound 1 40mg | 89 | -0.7 | 0.82 | -3 | -1.0 | 2 |
| | | Leuprorelin | 69 | -0.8 | 0.79 | -3 | -1.0 | 0 |
| | Week 20 | Placebo | 74 | -0.4 | 0.72 | -2 | 0.0 | 1 |
| | | Compound 1 10mg | 81 | -0.6 | 0.77 | -2 | -1.0 | 1 |
| | | Compound 1 20mg | 77 | -0.7 | 0.86 | -3 | -1.0 | 1 |
| | | Compound 1 40mg | 87 | -0.8 | 0.82 | -3 | -1.0 | 1 |
| | | Leuprorelin | 64 | -0.8 | 0.80 | -3 | -1.0 | 0 |
| | Week 24 | Placebo | 68 | -0.5 | 0.72 | -2 | -1.0 | 1 |
| | | Compound 1 10mg | 79 | -0.6 | 0.81 | -3 | -1.0 | 1 |
| | | Compound 1 20mg | 74 | -0.7 | 0.85 | -3 | -1.0 | 2 |
| | | Compound 1 40mg | 87 | -0.8 | 0.81 | -3 | -1.0 | 1 |
| | | Leuprorelin | 61 | -0.8 | 0.82 | -3 | -1.0 | 1 |

FIG. 120

| Variable / Visit | Treatment | | Summary Statistics | | | | | |
|---|---|---|---|---|---|---|---|---|
| | | | N | Mean | SD | Min | Median | Max |
| Proportion of Days with Usage of Pain Killer (%) | Baseline | Placebo | 97 | 10.02 | 11.549 | 0.0 | 7.10 | 57.1 |
| | | Compound 1 10mg | 103 | 12.52 | 12.323 | 0.0 | 8.60 | 50.0 |
| | | Compound 1 20mg | 100 | 13.25 | 16.426 | 0.0 | 8.00 | 76.9 |
| | | Compound 1 40mg | 103 | 11.98 | 14.528 | 0.0 | 8.00 | 67.5 |
| | | Leuprorelin | 81 | 11.61 | 13.836 | 0.0 | 8.00 | 85.7 |
| | Day 1 - 28 | Placebo | 97 | 8.95 | 11.842 | 0.0 | 7.10 | 64.3 |
| | | Compound 1 10mg | 103 | 6.03 | 9.026 | 0.0 | 3.60 | 46.4 |
| | | Compound 1 20mg | 100 | 8.86 | 14.744 | 0.0 | 3.60 | 75.0 |
| | | Compound 1 40mg | 103 | 7.14 | 12.612 | 0.0 | 3.60 | 75.0 |
| | | Leuprorelin | 81 | 7.72 | 14.086 | 0.0 | 3.60 | 82.1 |
| | Day 29 - 56 | Placebo | 96 | 8.59 | 11.170 | 0.0 | 7.10 | 78.6 |
| | | Compound 1 10mg | 103 | 6.56 | 9.748 | 0.0 | 3.60 | 60.7 |
| | | Compound 1 20mg | 99 | 5.93 | 12.661 | 0.0 | 0.00 | 81.8 |
| | | Compound 1 40mg | 101 | 1.94 | 5.565 | 0.0 | 0.00 | 32.1 |
| | | Leuprorelin | 79 | 4.21 | 14.812 | 0.0 | 0.00 | 89.3 |
| | Day 57 - 84 | Placebo | 95 | 7.97 | 9.569 | 0.0 | 7.10 | 50.0 |
| | | Compound 1 10mg | 101 | 5.82 | 9.143 | 0.0 | 3.60 | 60.7 |
| | | Compound 1 20mg | 94 | 5.90 | 12.963 | 0.0 | 0.00 | 60.7 |
| | | Compound 1 40mg | 101 | 1.96 | 7.145 | 0.0 | 0.00 | 53.6 |
| | | Leuprorelin | 78 | 3.72 | 15.744 | 0.0 | 0.00 | 100.0 |
| | Day 85 - 112 | Placebo | 77 | 8.86 | 12.037 | 0.0 | 3.60 | 53.6 |
| | | Compound 1 10mg | 84 | 5.82 | 7.869 | 0.0 | 3.60 | 46.4 |
| | | Compound 1 20mg | 78 | 5.13 | 12.149 | 0.0 | 0.00 | 64.3 |
| | | Compound 1 40mg | 89 | 1.29 | 3.742 | 0.0 | 0.00 | 17.9 |
| | | Leuprorelin | 69 | 2.23 | 13.379 | 0.0 | 0.00 | 100.0 |
| | Day 113 - 140 | Placebo | 75 | 8.79 | 11.461 | 0.0 | 7.10 | 57.1 |
| | | Compound 1 10mg | 84 | 6.04 | 8.033 | 0.0 | 3.60 | 46.4 |
| | | Compound 1 20mg | 77 | 5.52 | 13.289 | 0.0 | 0.00 | 82.1 |
| | | Compound 1 40mg | 89 | 2.17 | 9.335 | 0.0 | 0.00 | 75.0 |
| | | Leuprorelin | 68 | 2.38 | 12.641 | 0.0 | 0.00 | 92.9 |
| | Day 141 - 168 | Placebo | 71 | 9.21 | 12.620 | 0.0 | 7.10 | 71.4 |
| | | Compound 1 10mg | 80 | 5.72 | 8.630 | 0.0 | 1.80 | 46.4 |
| | | Compound 1 20mg | 77 | 5.11 | 15.208 | 0.0 | 0.00 | 89.3 |
| | | Compound 1 40mg | 88 | 1.83 | 8.001 | 0.0 | 0.00 | 59.3 |
| | | Leuprorelin | 63 | 1.08 | 5.470 | 0.0 | 0.00 | 39.3 |
| | End of Treatment Period | Placebo | 97 | 9.42 | 11.614 | 0.0 | 7.10 | 71.4 |
| | | Compound 1 10mg | 103 | 6.20 | 8.786 | 0.0 | 3.60 | 46.4 |
| | | Compound 1 20mg | 100 | 5.89 | 14.644 | 0.0 | 0.00 | 89.3 |
| | | Compound 1 40mg | 103 | 2.03 | 7.791 | 0.0 | 0.00 | 60.7 |
| | | Leuprorelin | 81 | 1.55 | 6.539 | 0.0 | 0.00 | 39.3 |

FIG. 121

| Variable / Visit | Treatment | | Summary Statistics | | | | | |
|---|---|---|---|---|---|---|---|---|
| | | | N | Mean | SD | Min | Median | Max |
| Change from Baseline in Proportion of Days with Usage of Pain Killer (%) | Day 1 - 28 | Placebo | 97 | -1.07 | 10.313 | -41.7 | 0.00 | 42.2 |
| | | Compound 1 10mg | 103 | -6.49 | 9.041 | -32.9 | -4.10 | 14.3 |
| | | Compound 1 20mg | 100 | -4.40 | 10.721 | -39.1 | -3.15 | 28.2 |
| | | Compound 1 40mg | 103 | -4.84 | 11.803 | -54.7 | -3.60 | 50.0 |
| | | Leuprorelin | 81 | -3.89 | 9.637 | -33.7 | -3.50 | 32.4 |
| | Day 29 - 56 | Placebo | 96 | -1.49 | 12.865 | -39.3 | 0.00 | 69.5 |
| | | Compound 1 10mg | 103 | -5.97 | 10.516 | -46.4 | -3.50 | 17.7 |
| | | Compound 1 20mg | 99 | -7.46 | 12.299 | -62.6 | -3.80 | 18.6 |
| | | Compound 1 40mg | 101 | -10.27 | 12.569 | -58.3 | -6.90 | 10.7 |
| | | Leuprorelin | 79 | -7.61 | 12.404 | -52.0 | -7.70 | 39.5 |
| | Day 57 - 84 | Placebo | 95 | -2.22 | 10.670 | -50.0 | 0.00 | 32.1 |
| | | Compound 1 10mg | 101 | -6.81 | 11.102 | -46.4 | -3.80 | 21.3 |
| | | Compound 1 20mg | 94 | -7.16 | 14.939 | -76.9 | -3.85 | 24.5 |
| | | Compound 1 40mg | 101 | -10.26 | 13.483 | -64.3 | -6.90 | 23.8 |
| | | Leuprorelin | 78 | -8.24 | 13.636 | -52.0 | -7.85 | 53.8 |
| | Day 85 - 112 | Placebo | 77 | -1.85 | 12.678 | -35.7 | -1.80 | 45.8 |
| | | Compound 1 10mg | 84 | -6.69 | 11.923 | -50.0 | -3.50 | 21.4 |
| | | Compound 1 20mg | 78 | -7.91 | 13.836 | -66.2 | -4.20 | 35.2 |
| | | Compound 1 40mg | 89 | -11.35 | 14.427 | -67.5 | -7.40 | 6.0 |
| | | Leuprorelin | 69 | -10.20 | 11.376 | -52.0 | -8.00 | 14.3 |
| | Day 113 - 140 | Placebo | 75 | -1.83 | 12.356 | -46.4 | -1.20 | 32.1 |
| | | Compound 1 10mg | 84 | -6.47 | 11.210 | -39.3 | -3.50 | 13.7 |
| | | Compound 1 20mg | 77 | -7.39 | 13.625 | -76.9 | -3.90 | 15.6 |
| | | Compound 1 40mg | 89 | -10.47 | 15.980 | -67.5 | -7.10 | 60.7 |
| | | Leuprorelin | 68 | -10.06 | 12.997 | -52.0 | -7.70 | 37.1 |
| | Day 141 - 168 | Placebo | 71 | -1.45 | 10.920 | -46.4 | 0.00 | 25.0 |
| | | Compound 1 10mg | 80 | -6.92 | 10.391 | -42.8 | -4.40 | 12.5 |
| | | Compound 1 20mg | 77 | -7.80 | 15.187 | -76.9 | -5.40 | 46.4 |
| | | Compound 1 40mg | 88 | -10.82 | 14.941 | -67.5 | -7.25 | 25.0 |
| | | Leuprorelin | 63 | -11.94 | 13.331 | -67.8 | -8.30 | 7.1 |
| | End of Treatment Period | Placebo | 97 | -0.60 | 10.251 | -50.0 | 0.00 | 37.3 |
| | | Compound 1 10mg | 103 | -6.32 | 9.817 | -42.8 | -3.60 | 13.7 |
| | | Compound 1 20mg | 100 | -7.36 | 14.585 | -76.9 | -4.00 | 28.5 |
| | | Compound 1 40mg | 103 | -9.95 | 14.214 | -67.5 | -6.50 | 21.4 |
| | | Leuprorelin | 81 | -10.06 | 13.063 | -67.8 | -7.70 | 28.6 |

FIG. 122

| Variable / Visit | | | Diff | 95% CI | |
|---|---|---|---|---|---|
| | | | | Lower | Upper |
| Change from Baseline in Proportion of Days with Usage of Pain Killer (%) | Day 1 - 28 | Compound 1 10mg- Leuprorelin | -2.60 | -5.326 | 0.128 |
| | | Compound 1 20mg- Leuprorelin | -0.51 | -3.532 | 2.515 |
| | | Compound 1 40mg- Leuprorelin | -0.96 | -4.152 | 2.238 |
| | Day 29 - 56 | Compound 1 10mg- Leuprorelin | 1.64 | -1.713 | 4.999 |
| | | Compound 1 20mg- Leuprorelin | 0.15 | -3.527 | 3.824 |
| | | Compound 1 40mg- Leuprorelin | -2.67 | -6.369 | 1.039 |
| | Day 57 - 84 | Compound 1 10mg- Leuprorelin | 1.43 | -2.221 | 5.079 |
| | | Compound 1 20mg- Leuprorelin | 1.08 | -3.267 | 5.419 |
| | | Compound 1 40mg- Leuprorelin | -2.02 | -6.048 | 2.013 |
| | Day 85 - 112 | Compound 1 10mg- Leuprorelin | 3.51 | -0.235 | 7.264 |
| | | Compound 1 20mg- Leuprorelin | 2.29 | -1.868 | 6.456 |
| | | Compound 1 40mg- Leuprorelin | -1.15 | -5.323 | 3.032 |
| | Day 113 - 140 | Compound 1 10mg- Leuprorelin | 3.59 | -0.291 | 7.471 |
| | | Compound 1 20mg- Leuprorelin | 2.67 | -1.713 | 7.060 |
| | | Compound 1 40mg- Leuprorelin | -0.40 | -5.103 | 4.293 |
| | Day 141 - 168 | Compound 1 10mg- Leuprorelin | 5.03 | 1.105 | 8.947 |
| | | Compound 1 20mg- Leuprorelin | 4.15 | -0.686 | 8.977 |
| | | Compound 1 40mg- Leuprorelin | 1.12 | -3.540 | 5.782 |
| | End of Treatment Period | Compound 1 10mg- Leuprorelin | 3.75 | 0.419 | 7.076 |
| | | Compound 1 20mg- Leuprorelin | 2.70 | -1.403 | 6.812 |
| | | Compound 1 40mg- Leuprorelin | 0.12 | -3.904 | 4.137 |

FIG. 123

| Variable / Visit | Treatment | | Summary Statistics | | | | | |
|---|---|---|---|---|---|---|---|---|
| | | | N | Mean | SD | Min | Median | Max |
| Mean of Amount of Bleeding | Baseline | Placebo | 97 | 2.286 | 0.5371 | 1.00 | 2.330 | 3.33 |
| | | Compound 1 10mg | 103 | 2.296 | 0.5265 | 1.00 | 2.380 | 3.60 |
| | | Compound 1 20mg | 100 | 2.310 | 0.5541 | 1.00 | 2.310 | 4.50 |
| | | Compound 1 40mg | 103 | 2.407 | 0.5405 | 1.00 | 2.400 | 4.50 |
| | | Leuprorelin | 81 | 2.371 | 0.5723 | 1.00 | 2.380 | 4.00 |
| | Day 1 - 28 | Placebo | 97 | 2.170 | 0.5485 | 0.00 | 2.170 | 3.75 |
| | | Compound 1 10mg | 103 | 1.846 | 0.6232 | 0.00 | 2.000 | 3.67 |
| | | Compound 1 20mg | 100 | 1.781 | 0.6576 | 0.00 | 1.730 | 3.50 |
| | | Compound 1 40mg | 103 | 1.828 | 0.6987 | 0.00 | 1.710 | 4.00 |
| | | Leuprorelin | 81 | 1.859 | 0.7876 | 0.00 | 1.750 | 4.11 |
| | Day 29 - 56 | Placebo | 96 | 2.216 | 0.6140 | 0.00 | 2.250 | 4.25 |
| | | Compound 1 10mg | 103 | 1.860 | 1.0702 | 0.00 | 2.140 | 4.00 |
| | | Compound 1 20mg | 99 | 1.012 | 1.1788 | 0.00 | 0.000 | 3.75 |
| | | Compound 1 40mg | 101 | 0.181 | 0.5754 | 0.00 | 0.000 | 2.60 |
| | | Leuprorelin | 79 | 0.176 | 0.4935 | 0.00 | 0.000 | 3.33 |
| | Day 57 - 84 | Placebo | 95 | 2.259 | 0.6244 | 0.00 | 2.330 | 3.80 |
| | | Compound 1 10mg | 101 | 1.638 | 1.1519 | 0.00 | 2.000 | 4.00 |
| | | Compound 1 20mg | 94 | 0.904 | 1.1664 | 0.00 | 0.000 | 3.50 |
| | | Compound 1 40mg | 101 | 0.139 | 0.5740 | 0.00 | 0.000 | 3.50 |
| | | Leuprorelin | 78 | 0.000 | 0.0000 | 0.00 | 0.000 | 0.00 |
| | Day 85 - 112 | Placebo | 77 | 2.184 | 0.5654 | 0.00 | 2.200 | 3.17 |
| | | Compound 1 10mg | 84 | 1.700 | 1.1043 | 0.00 | 2.000 | 3.57 |
| | | Compound 1 20mg | 78 | 1.071 | 1.2284 | 0.00 | 0.000 | 3.33 |
| | | Compound 1 40mg | 89 | 0.151 | 0.5872 | 0.00 | 0.000 | 3.18 |
| | | Leuprorelin | 69 | 0.000 | 0.0000 | 0.00 | 0.000 | 0.00 |
| | Day 113 - 140 | Placebo | 75 | 2.295 | 0.5662 | 0.00 | 2.330 | 3.50 |
| | | Compound 1 10mg | 84 | 1.540 | 1.1674 | 0.00 | 2.000 | 4.50 |
| | | Compound 1 20mg | 77 | 1.226 | 1.3331 | 0.00 | 0.000 | 4.00 |
| | | Compound 1 40mg | 89 | 0.137 | 0.5491 | 0.00 | 0.000 | 2.88 |
| | | Leuprorelin | 68 | 0.000 | 0.0000 | 0.00 | 0.000 | 0.00 |
| | Day 141 - 168 | Placebo | 71 | 2.198 | 0.6388 | 0.00 | 2.290 | 3.50 |
| | | Compound 1 10mg | 80 | 1.639 | 1.1442 | 0.00 | 2.000 | 3.50 |
| | | Compound 1 20mg | 77 | 0.873 | 1.1896 | 0.00 | 0.000 | 3.50 |
| | | Compound 1 40mg | 88 | 0.172 | 0.6565 | 0.00 | 0.000 | 3.50 |
| | | Leuprorelin | 63 | 0.000 | 0.0000 | 0.00 | 0.000 | 0.00 |
| | End of Treatment Period | Placebo | 97 | 2.230 | 0.6437 | 0.00 | 2.290 | 4.25 |
| | | Compound 1 10mg | 103 | 1.767 | 1.0709 | 0.00 | 2.110 | 3.75 |
| | | Compound 1 20mg | 100 | 1.046 | 1.2174 | 0.00 | 0.000 | 3.50 |
| | | Compound 1 40mg | 103 | 0.200 | 0.6837 | 0.00 | 0.000 | 3.41 |
| | | Leuprorelin | 81 | 0.051 | 0.3297 | 0.00 | 0.000 | 2.50 |

FIG. 124

| Variable / Visit | Treatment | | Summary Statistics | | | | | |
|---|---|---|---|---|---|---|---|---|
| | | | N | Mean | SD | Min | Median | Max |
| Change from Baseline in Mean of Amount of Bleeding | Day 1 - 28 | Placebo | 97 | -0.116 | 0.6741 | -2.00 | -0.100 | 1.64 |
| | | Compound 1 10mg | 103 | -0.450 | 0.8425 | -3.00 | -0.450 | 1.75 |
| | | Compound 1 20mg | 100 | -0.528 | 0.8755 | -3.17 | -0.500 | 1.57 |
| | | Compound 1 40mg | 103 | -0.580 | 0.7151 | -2.00 | -0.620 | 1.64 |
| | | Leuprorelin | 81 | -0.512 | 0.7953 | -2.83 | -0.580 | 1.50 |
| | Day 29 - 56 | Placebo | 96 | -0.076 | 0.7273 | -1.60 | -0.155 | 2.65 |
| | | Compound 1 10mg | 103 | -0.436 | 1.1223 | -3.60 | -0.190 | 1.60 |
| | | Compound 1 20mg | 99 | -1.291 | 1.2438 | -3.40 | -1.690 | 2.00 |
| | | Compound 1 40mg | 101 | -2.242 | 0.7077 | -4.50 | -2.300 | -0.07 |
| | | Leuprorelin | 79 | -2.215 | 0.6799 | -4.00 | -2.250 | 0.47 |
| | Day 57 - 84 | Placebo | 95 | -0.038 | 0.7185 | -1.83 | -0.130 | 2.42 |
| | | Compound 1 10mg | 101 | -0.661 | 1.2117 | -3.43 | -0.330 | 1.50 |
| | | Compound 1 20mg | 94 | -1.405 | 1.1435 | -3.25 | -1.800 | 1.21 |
| | | Compound 1 40mg | 101 | -2.284 | 0.6812 | -4.50 | -2.330 | -0.07 |
| | | Leuprorelin | 78 | -2.393 | 0.5608 | -4.00 | -2.415 | -1.00 |
| | Day 85 - 112 | Placebo | 77 | -0.099 | 0.6799 | -2.38 | -0.140 | 1.80 |
| | | Compound 1 10mg | 84 | -0.551 | 1.1531 | -2.86 | -0.310 | 1.64 |
| | | Compound 1 20mg | 78 | -1.219 | 1.2592 | -3.00 | -1.585 | 1.58 |
| | | Compound 1 40mg | 89 | -2.270 | 0.7254 | -4.50 | -2.330 | 0.20 |
| | | Leuprorelin | 69 | -2.392 | 0.5862 | -4.00 | -2.430 | -1.00 |
| | Day 113 - 140 | Placebo | 75 | -0.007 | 0.6710 | -1.60 | 0.000 | 1.50 |
| | | Compound 1 10mg | 84 | -0.710 | 1.2643 | -3.60 | -0.465 | 2.12 |
| | | Compound 1 20mg | 77 | -1.055 | 1.3914 | -3.00 | -1.500 | 2.37 |
| | | Compound 1 40mg | 89 | -2.284 | 0.6952 | -4.50 | -2.330 | 0.28 |
| | | Leuprorelin | 68 | -2.388 | 0.5893 | -4.00 | -2.415 | -1.00 |
| | Day 141 - 168 | Placebo | 71 | -0.102 | 0.7294 | -2.50 | -0.130 | 1.37 |
| | | Compound 1 10mg | 80 | -0.587 | 1.2463 | -3.20 | -0.225 | 2.00 |
| | | Compound 1 20mg | 77 | -1.408 | 1.2903 | -3.50 | -1.830 | 2.10 |
| | | Compound 1 40mg | 88 | -2.251 | 0.7503 | -4.50 | -2.330 | 0.33 |
| | | Leuprorelin | 63 | -2.395 | 0.6032 | -4.00 | -2.430 | -1.00 |
| | End of Treatment Period | Placebo | 97 | -0.056 | 0.7274 | -2.38 | -0.110 | 2.65 |
| | | Compound 1 10mg | 103 | -0.529 | 1.2185 | -3.60 | -0.210 | 1.75 |
| | | Compound 1 20mg | 100 | -1.264 | 1.3280 | -3.50 | -1.680 | 2.10 |
| | | Compound 1 40mg | 103 | -2.207 | 0.8149 | -4.50 | -2.330 | 0.67 |
| | | Leuprorelin | 81 | -2.320 | 0.7281 | -4.00 | -2.380 | 1.50 |

FIG. 125

| Variable / Visit | | | Diff | 95% CI | |
|---|---|---|---|---|---|
| | | | | Lower | Upper |
| Change from Baseline in Mean of Amount of Bleeding | Day 1 - 28 | Compound 1 10mg- Leuprorelin | 0.062 | -0.1793 | 0.3025 |
| | | Compound 1 20mg- Leuprorelin | -0.016 | -0.2643 | 0.2316 |
| | | Compound 1 40mg- Leuprorelin | -0.068 | -0.2880 | 0.1523 |
| | Day 29 - 56 | Compound 1 10mg- Leuprorelin | 1.779 | 1.4966 | 2.0609 |
| | | Compound 1 20mg- Leuprorelin | 0.924 | 0.6163 | 1.2312 |
| | | Compound 1 40mg- Leuprorelin | -0.028 | -0.2337 | 0.1787 |
| | Day 57- 84 | Compound 1 10mg- Leuprorelin | 1.732 | 1.4400 | 2.0249 |
| | | Compound 1 20mg- Leuprorelin | 0.989 | 0.7086 | 1.2687 |
| | | Compound 1 40mg- Leuprorelin | 0.109 | -0.0785 | 0.2973 |
| | Day 85 - 112 | Compound 1 10mg- Leuprorelin | 1.842 | 1.5395 | 2.1437 |
| | | Compound 1 20mg- Leuprorelin | 1.174 | 0.8464 | 1.5008 |
| | | Compound 1 40mg- Leuprorelin | 0.123 | -0.0891 | 0.3344 |
| | Day 113 - 140 | Compound 1 10mg- Leuprorelin | 1.677 | 1.3485 | 2.0058 |
| | | Compound 1 20mg- Leuprorelin | 1.333 | 0.9740 | 1.6922 |
| | | Compound 1 40mg- Leuprorelin | 0.104 | -0.1036 | 0.3110 |
| | Day 141 - 168 | Compound 1 10mg- Leuprorelin | 1.808 | 1.4698 | 2.1458 |
| | | Compound 1 20mg- Leuprorelin | 0.987 | 0.6378 | 1.3361 |
| | | Compound 1 40mg- Leuprorelin | 0.144 | -0.0821 | 0.3698 |
| | End of Treatment Period | Compound 1 10mg- Leuprorelin | 1.791 | 1.4884 | 2.0932 |
| | | Compound 1 20mg- Leuprorelin | 1.056 | 0.7313 | 1.3809 |
| | | Compound 1 40mg- Leuprorelin | 0.113 | -0.1149 | 0.3410 |

FIG. 126

| Variable / Visit | | Treatment | | Yes | No | Total |
|---|---|---|---|---|---|---|
| Subject Who Achieved Amenorrhea (%) | Day 1 - 28 | Placebo | | 1 (1.0) | 96 (99.0) | 97 |
| | | Compound 1 | 10mg | 2 (1.9) | 101 (98.1) | 103 |
| | | Compound 1 | 20mg | 2 (2.0) | 98 (98.0) | 100 |
| | | Compound 1 | 40mg | 1 (1.0) | 102 (99.0) | 103 |
| | | Leuprorelin | | 3 (3.7) | 78 (96.3) | 81 |
| | Day 29 - 56 | Placebo | | 1 (1.0) | 95 (99.0) | 96 |
| | | Compound 1 | 10mg | 20 (19.4) | 83 (80.6) | 103 |
| | | Compound 1 | 20mg | 54 (54.5) | 45 (45.5) | 99 |
| | | Compound 1 | 40mg | 91 (90.1) | 10 (9.9) | 101 |
| | | Leuprorelin | | 67 (84.8) | 12 (15.2) | 79 |
| | Day 57 - 84 | Placebo | | 3 (3.2) | 92 (96.8) | 95 |
| | | Compound 1 | 10mg | 28 (27.7) | 73 (72.3) | 101 |
| | | Compound 1 | 20mg | 56 (59.6) | 38 (40.4) | 94 |
| | | Compound 1 | 40mg | 95 (94.1) | 6 (5.9) | 101 |
| | | Leuprorelin | | 78 (100) | 0 (0.0) | 78 |
| | Day 85 - 112 | Placebo | | 3 (3.9) | 74 (96.1) | 77 |
| | | Compound 1 | 10mg | 21 (25.0) | 63 (75.0) | 84 |
| | | Compound 1 | 20mg | 43 (55.1) | 35 (44.9) | 78 |
| | | Compound 1 | 40mg | 83 (93.3) | 6 (6.7) | 89 |
| | | Leuprorelin | | 69 (100) | 0 (0.0) | 69 |

FIG. 127A

| Variable / Visit | Treatment | | Yes | No | Total |
|---|---|---|---|---|---|
| Day 113 - 140 | Placebo | | 2 (2.7) | 73 (97.3) | 75 |
| | Compound 1 | 10mg | 26 (31.0) | 58 (69.0) | 84 |
| | Compound 1 | 20mg | 40 (51.9) | 37 (48.1) | 77 |
| | Compound 1 | 40mg | 83 (93.3) | 6 (6.7) | 89 |
| | Leuprorelin | | 68 (100) | 0 (0.0) | 68 |
| Day 141 - 168 | Placebo | | 3 (4.2) | 68 (95.8) | 71 |
| | Compound 1 | 10mg | 23 (28.8) | 57 (71.3) | 80 |
| | Compound 1 | 20mg | 47 (61.0) | 30 (39.0) | 77 |
| | Compound 1 | 40mg | 82 (93.2) | 6 (6.8) | 88 |
| | Leuprorelin | | 63 (100) | 0 (0.0) | 63 |
| End of Treatment Period | Placebo | | 4 (4.1) | 93 (95.9) | 97 |
| | Compound 1 | 10mg | 23 (22.3) | 80 (77.7) | 103 |
| | Compound 1 | 20mg | 54 (54.0) | 46 (46.0) | 100 |
| | Compound 1 | 40mg | 94 (91.3) | 9 (8.7) | 103 |
| | Leuprorelin | | 79 (97.5) | 2 (2.5) | 81 |

FIG. 127B

| Variable | | | Estimate | 95% CI | |
|---|---|---|---|---|---|
| | | | | Lower | Upper |
| Proportion of Subject Who Achieved Amenorrhea (%) | Day 1 - 28 | Compound 1 10mg- Leuprorelin | -1.8 | -6.663 | 3.139 |
| | | Compound 1 20mg- Leuprorelin | -1.7 | -6.648 | 3.240 |
| | | Compound 1 40mg- Leuprorelin | -2.7 | -7.261 | 1.795 |
| | Day 29 - 56 | Compound 1 10mg- Leuprorelin | -65.4 | -76.393 | -54.393 |
| | | Compound 1 20mg- Leuprorelin | -30.3 | -42.868 | -17.661 |
| | | Compound 1 40mg- Leuprorelin | 5.3 | -4.538 | 15.116 |
| | Day 57 - 84 | Compound 1 10mg- Leuprorelin | -72.3 | -81.007 | -63.547 |
| | | Compound 1 20mg- Leuprorelin | -40.4 | -50.346 | -30.505 |
| | | Compound 1 40mg- Leuprorelin | -5.9 | -10.551 | -1.331 |
| | Day 85 - 112 | Compound 1 10mg- Leuprorelin | -75.0 | -84.260 | -65.740 |
| | | Compound 1 20mg- Leuprorelin | -44.9 | -55.909 | -33.834 |
| | | Compound 1 40mg- Leuprorelin | -6.7 | -11.951 | -1.532 |
| | Day 113 - 140 | Compound 1 10mg- Leuprorelin | -69.0 | -78.934 | -59.161 |
| | | Compound 1 20mg- Leuprorelin | -48.1 | -59.211 | -36.892 |
| | | Compound 1 40mg- Leuprorelin | -6.7 | -11.951 | -1.532 |
| | Day 141 - 168 | Compound 1 10mg- Leuprorelin | -71.3 | -81.168 | -61.332 |
| | | Compound 1 20mg- Leuprorelin | -39.0 | -49.853 | -28.069 |
| | | Compound 1 40mg- Leuprorelin | -6.8 | -12.084 | -1.552 |
| | End of Treatment Period | Compound 1 10mg- Leuprorelin | -75.2 | -83.925 | -66.477 |
| | | Compound 1 20mg- Leuprorelin | -43.5 | -53.867 | -33.194 |
| | | Compound 1 40mg- Leuprorelin | -6.3 | -12.684 | 0.147 |

FIG. 128

| Variable / Visit | | Treatment | Summary Statistics | | | | | |
|---|---|---|---|---|---|---|---|---|
| | | | N | Mean | SD | Min | Median | Max |
| Pain | Baseline | Placebo | 97 | 24.84 | 20.022 | 0.0 | 20.50 | 97.7 |
| | | Compound 1 10mg | 103 | 28.58 | 21.806 | 0.0 | 22.70 | 93.2 |
| | | Compound 1 20mg | 100 | 26.73 | 18.610 | 0.0 | 23.85 | 72.7 |
| | | Compound 1 40mg | 103 | 28.93 | 20.148 | 0.0 | 25.00 | 75.0 |
| | | Leuprorelin | 81 | 26.52 | 19.592 | 0.0 | 22.70 | 86.4 |
| | Week 4 | Placebo | 96 | 22.99 | 19.709 | 0.0 | 19.35 | 97.7 |
| | | Compound 1 10mg | 103 | 17.74 | 19.520 | 0.0 | 11.40 | 90.9 |
| | | Compound 1 20mg | 99 | 15.11 | 17.042 | 0.0 | 9.10 | 79.5 |
| | | Compound 1 40mg | 102 | 14.44 | 17.771 | 0.0 | 9.10 | 81.8 |
| | | Leuprorelin | 81 | 16.10 | 18.740 | 0.0 | 9.10 | 90.9 |
| | Week 8 | Placebo | 95 | 19.93 | 18.735 | 0.0 | 15.90 | 97.7 |
| | | Compound 1 10mg | 103 | 13.83 | 17.348 | 0.0 | 9.10 | 93.2 |
| | | Compound 1 20mg | 96 | 8.24 | 11.376 | 0.0 | 4.50 | 52.3 |
| | | Compound 1 40mg | 101 | 4.86 | 10.129 | 0.0 | 0.00 | 47.7 |
| | | Leuprorelin | 79 | 6.85 | 11.940 | 0.0 | 0.00 | 52.3 |
| | Week 12 | Placebo | 93 | 19.35 | 21.539 | 0.0 | 13.60 | 88.6 |
| | | Compound 1 10mg | 101 | 10.53 | 13.845 | 0.0 | 4.50 | 61.4 |
| | | Compound 1 20mg | 92 | 8.99 | 15.187 | 0.0 | 0.00 | 61.4 |
| | | Compound 1 40mg | 101 | 3.26 | 9.343 | 0.0 | 0.00 | 47.7 |
| | | Leuprorelin | 76 | 3.83 | 9.401 | 0.0 | 0.00 | 52.3 |
| | Week 16 | Placebo | 75 | 16.79 | 14.857 | 0.0 | 15.90 | 61.4 |
| | | Compound 1 10mg | 84 | 9.69 | 12.436 | 0.0 | 4.50 | 56.8 |
| | | Compound 1 20mg | 78 | 7.66 | 13.069 | 0.0 | 0.0 | 70.5 |
| | | Compound 1 40mg | 89 | 3.12 | 7.758 | 0.0 | 0.0 | 34.1 |
| | | Leuprorelin | 69 | 3.03 | 8.204 | 0.0 | 0.0 | 45.5 |
| | Week 20 | Placebo | 74 | 19.65 | 18.911 | 0.0 | 13.60 | 75.0 |
| | | Compound 1 10mg | 81 | 10.38 | 12.709 | 0.0 | 6.80 | 65.9 |
| | | Compound 1 20mg | 77 | 6.97 | 11.889 | 0.0 | 0.00 | 50.0 |
| | | Compound 1 40mg | 87 | 3.19 | 10.918 | 0.0 | 0.00 | 77.3 |
| | | Leuprorelin | 64 | 1.70 | 5.665 | 0.0 | 0.00 | 29.5 |
| | Week 24 | Placebo | 68 | 18.85 | 18.389 | 0.0 | 13.60 | 77.3 |
| | | Compound 1 10mg | 79 | 10.38 | 15.386 | 0.0 | 4.50 | 75.0 |
| | | Compound 1 20mg | 74 | 6.42 | 11.181 | 0.0 | 0.00 | 52.3 |
| | | Compound 1 40mg | 87 | 2.43 | 6.292 | 0.0 | 0.00 | 29.5 |
| | | Leuprorelin | 61 | 1.23 | 4.223 | 0.0 | 0.00 | 27.3 |

FIG. 129

| Variable / Visit | | Treatment | Summary Statistics | | | | | |
|---|---|---|---|---|---|---|---|---|
| | | | N | Mean | SD | Min | Median | Max |
| Control & Powerlessness | Baseline | Placebo | 97 | 25.77 | 20.815 | 0.0 | 20.80 | 91.7 |
| | | Compound 1 10mg | 103 | 27.43 | 23.010 | 0.0 | 20.80 | 91.7 |
| | | Compound 1 20mg | 100 | 28.63 | 22.530 | 0.0 | 25.00 | 100.0 |
| | | Compound 1 40mg | 103 | 25.85 | 21.239 | 0.0 | 20.80 | 91.7 |
| | | Leuprorelin | 81 | 27.83 | 22.904 | 0.0 | 20.80 | 100.0 |
| | Week 4 | Placebo | 96 | 21.18 | 19.592 | 0.0 | 16.70 | 95.8 |
| | | Compound 1 10mg | 103 | 18.94 | 19.949 | 0.0 | 12.50 | 91.7 |
| | | Compound 1 20mg | 99 | 20.75 | 22.674 | 0.0 | 12.50 | 100.0 |
| | | Compound 1 40mg | 102 | 17.48 | 18.537 | 0.0 | 8.30 | 87.5 |
| | | Leuprorelin | 81 | 18.42 | 20.687 | 0.0 | 12.50 | 91.7 |
| | Week 8 | Placebo | 95 | 18.60 | 17.984 | 0.0 | 12.50 | 66.7 |
| | | Compound 1 10mg | 103 | 16.43 | 20.952 | 0.0 | 8.30 | 100.0 |
| | | Compound 1 20mg | 96 | 14.46 | 17.038 | 0.0 | 8.30 | 66.7 |
| | | Compound 1 40mg | 101 | 9.78 | 14.515 | 0.0 | 4.20 | 70.8 |
| | | Leuprorelin | 79 | 12.03 | 17.227 | 0.0 | 4.20 | 79.2 |
| | Week 12 | Placebo | 93 | 17.70 | 18.076 | 0.0 | 12.50 | 79.2 |
| | | Compound 1 10mg | 101 | 13.62 | 16.733 | 0.0 | 8.30 | 70.8 |
| | | Compound 1 20mg | 92 | 14.54 | 18.719 | 0.0 | 8.30 | 75.0 |
| | | Compound 1 40mg | 101 | 8.46 | 14.121 | 0.0 | 4.20 | 75.0 |
| | | Leuprorelin | 76 | 9.10 | 14.793 | 0.0 | 4.20 | 75.0 |
| | Week 16 | Placebo | 75 | 16.06 | 16.772 | 0.0 | 8.30 | 75.0 |
| | | Compound 1 10mg | 84 | 11.91 | 15.241 | 0.0 | 4.20 | 75.0 |
| | | Compound 1 20mg | 78 | 11.97 | 15.622 | 0.0 | 4.20 | 79.2 |
| | | Compound 1 40mg | 89 | 6.32 | 9.887 | 0.0 | 0.00 | 37.5 |
| | | Leuprorelin | 69 | 9.73 | 14.618 | 0.0 | 4.20 | 70.8 |
| | Week 20 | Placebo | 74 | 20.16 | 20.495 | 0.0 | 12.50 | 91.7 |
| | | Compound 1 10mg | 81 | 11.94 | 14.987 | 0.0 | 4.20 | 70.8 |
| | | Compound 1 20mg | 77 | 8.61 | 12.564 | 0.0 | 4.20 | 66.7 |
| | | Compound 1 40mg | 87 | 6.52 | 13.063 | 0.0 | 0.00 | 66.7 |
| | | Leuprorelin | 64 | 6.64 | 10.799 | 0.0 | 0.00 | 50.0 |
| | Week 24 | Placebo | 68 | 18.87 | 20.457 | 0.0 | 12.50 | 75.0 |
| | | Compound 1 10mg | 79 | 11.35 | 15.428 | 0.0 | 4.20 | 66.7 |
| | | Compound 1 20mg | 74 | 10.53 | 13.777 | 0.0 | 4.20 | 50.0 |
| | | Compound 1 40mg | 87 | 5.61 | 9.672 | 0.0 | 0.00 | 41.7 |
| | | Leuprorelin | 61 | 5.60 | 10.698 | 0.0 | 0.00 | 50.0 |

FIG. 130

| Variable / Visit | Treatment | | Summary Statistics | | | | | |
|---|---|---|---|---|---|---|---|---|
| | | | N | Mean | SD | Min | Median | Max |
| Emotional Well-being | Baseline | Placebo | 97 | 22.98 | 19.976 | 0.0 | 16.70 | 83.3 |
| | | Compound 1 10mg | 103 | 21.81 | 20.092 | 0.0 | 16.70 | 87.5 |
| | | Compound 1 20mg | 100 | 23.75 | 19.336 | 0.0 | 20.80 | 75.0 |
| | | Compound 1 40mg | 103 | 20.39 | 17.502 | 0.0 | 16.70 | 100.0 |
| | | Leuprorelin | 81 | 21.19 | 19.056 | 0.0 | 16.70 | 95.8 |
| | Week 4 | Placebo | 96 | 21.06 | 20.584 | 0.0 | 16.70 | 91.7 |
| | | Compound 1 10mg | 103 | 15.54 | 17.592 | 0.0 | 8.30 | 75.0 |
| | | Compound 1 20mg | 99 | 20.03 | 19.487 | 0.0 | 16.70 | 87.5 |
| | | Compound 1 40mg | 102 | 15.28 | 16.338 | 0.0 | 12.50 | 87.5 |
| | | Leuprorelin | 81 | 15.28 | 17.840 | 0.0 | 8.30 | 91.7 |
| | Week 8 | Placebo | 95 | 18.42 | 20.070 | 0.0 | 12.50 | 87.5 |
| | | Compound 1 10mg | 103 | 14.41 | 17.245 | 0.0 | 8.30 | 66.7 |
| | | Compound 1 20mg | 96 | 15.54 | 16.770 | 0.0 | 12.50 | 79.2 |
| | | Compound 1 40mg | 101 | 11.10 | 14.652 | 0.0 | 4.20 | 58.3 |
| | | Leuprorelin | 79 | 14.25 | 19.114 | 0.0 | 8.30 | 91.7 |
| | Week 12 | Placebo | 93 | 16.40 | 19.568 | 0.0 | 8.30 | 87.5 |
| | | Compound 1 10mg | 101 | 13.66 | 16.183 | 0.0 | 8.30 | 62.5 |
| | | Compound 1 20mg | 92 | 15.40 | 18.695 | 0.0 | 8.30 | 87.5 |
| | | Compound 1 40mg | 101 | 10.23 | 13.708 | 0.0 | 4.20 | 58.3 |
| | | Leuprorelin | 76 | 12.89 | 18.744 | 0.0 | 4.20 | 83.3 |
| | Week 16 | Placebo | 75 | 16.89 | 19.884 | 0.0 | 8.30 | 87.5 |
| | | Compound 1 10mg | 84 | 12.00 | 15.632 | 0.0 | 4.20 | 66.7 |
| | | Compound 1 20mg | 78 | 13.14 | 16.101 | 0.0 | 8.30 | 83.3 |
| | | Compound 1 40mg | 89 | 8.62 | 13.218 | 0.0 | 0.00 | 54.2 |
| | | Leuprorelin | 69 | 12.02 | 17.804 | 0.0 | 4.20 | 91.7 |
| | Week 20 | Placebo | 74 | 17.46 | 20.340 | 0.0 | 8.30 | 91.7 |
| | | Compound 1 10mg | 81 | 12.24 | 14.438 | 0.0 | 8.30 | 54.2 |
| | | Compound 1 20mg | 77 | 10.34 | 12.177 | 0.0 | 4.20 | 50.0 |
| | | Compound 1 40mg | 87 | 8.14 | 12.581 | 0.0 | 0.00 | 54.2 |
| | | Leuprorelin | 64 | 9.05 | 15.117 | 0.0 | 0.00 | 66.7 |
| | Week 24 | Placebo | 68 | 15.93 | 18.377 | 0.0 | 10.40 | 62.5 |
| | | Compound 1 10mg | 79 | 12.56 | 16.913 | 0.0 | 4.20 | 58.3 |
| | | Compound 1 20mg | 74 | 10.19 | 12.900 | 0.0 | 4.20 | 50.0 |
| | | Compound 1 40mg | 87 | 7.86 | 13.104 | 0.0 | 0.00 | 58.3 |
| | | Leuprorelin | 61 | 9.43 | 16.316 | 0.0 | 0.00 | 66.7 |

FIG. 131

| Variable / Visit | Treatment | | Summary Statistics | | | | | |
|---|---|---|---|---|---|---|---|---|
| | | | N | Mean | SD | Min | Median | Max |
| Social Support | Baseline | Placebo | 97 | 17.67 | 19.993 | 0.0 | 12.50 | 100.0 |
| | | Compound 1 10mg | 103 | 16.52 | 17.697 | 0.0 | 12.50 | 62.5 |
| | | Compound 1 20mg | 100 | 19.96 | 20.622 | 0.0 | 12.50 | 81.3 |
| | | Compound 1 40mg | 103 | 15.73 | 18.689 | 0.0 | 12.50 | 75.0 |
| | | Leuprorelin | 81 | 17.07 | 20.306 | 0.0 | 12.50 | 81.3 |
| | Week 4 | Placebo | 96 | 17.59 | 20.491 | 0.0 | 20.50 | 75.0 |
| | | Compound 1 10mg | 103 | 12.70 | 16.129 | 0.0 | 6.30 | 62.5 |
| | | Compound 1 20mg | 99 | 15.61 | 20.416 | 0.0 | 6.30 | 81.3 |
| | | Compound 1 40mg | 102 | 12.89 | 17.832 | 0.0 | 6.30 | 93.8 |
| | | Leuprorelin | 81 | 13.98 | 19.071 | 0.0 | 6.30 | 81.3 |
| | Week 8 | Placebo | 95 | 14.75 | 18.309 | 0.0 | 6.30 | 68.8 |
| | | Compound 1 10mg | 103 | 11.85 | 17.043 | 0.0 | 6.30 | 81.3 |
| | | Compound 1 20mg | 96 | 13.04 | 18.654 | 0.0 | 0.00 | 81.3 |
| | | Compound 1 40mg | 101 | 9.91 | 16.142 | 0.0 | 0.00 | 68.8 |
| | | Leuprorelin | 79 | 13.38 | 21.156 | 0.0 | 0.00 | 100.0 |
| | Week 12 | Placebo | 93 | 14.33 | 19.740 | 0.0 | 6.30 | 75.0 |
| | | Compound 1 10mg | 101 | 9.67 | 14.895 | 0.0 | 0.00 | 56.3 |
| | | Compound 1 20mg | 92 | 11.50 | 18.360 | 0.0 | 6.30 | 93.8 |
| | | Compound 1 40mg | 101 | 8.92 | 14.297 | 0.0 | 0.00 | 81.3 |
| | | Leuprorelin | 76 | 10.62 | 17.658 | 0.0 | 0.00 | 68.8 |
| | Week 16 | Placebo | 75 | 13.43 | 19.381 | 0.0 | 6.30 | 75.0 |
| | | Compound 1 10mg | 84 | 8.87 | 14.438 | 0.0 | 0.00 | 75.0 |
| | | Compound 1 20mg | 78 | 11.79 | 19.119 | 0.0 | 0.00 | 81.3 |
| | | Compound 1 40mg | 89 | 6.40 | 12.823 | 0.0 | 0.00 | 62.5 |
| | | Leuprorelin | 69 | 10.43 | 19.792 | 0.0 | 0.00 | 93.8 |
| | Week 20 | Placebo | 74 | 13.19 | 19.348 | 0.0 | 6.30 | 81.3 |
| | | Compound 1 10mg | 81 | 8.58 | 14.448 | 0.0 | 0.00 | 68.8 |
| | | Compound 1 20mg | 77 | 9.51 | 16.344 | 0.0 | 0.00 | 75.0 |
| | | Compound 1 40mg | 87 | 6.12 | 11.952 | 0.0 | 0.00 | 62.5 |
| | | Leuprorelin | 64 | 8.02 | 14.507 | 0.0 | 0.00 | 56.3 |
| | Week 24 | Placebo | 68 | 15.00 | 21.532 | 0.0 | 6.30 | 81.3 |
| | | Compound 1 10mg | 79 | 8.79 | 14.252 | 0.0 | 0.00 | 62.5 |
| | | Compound 1 20mg | 74 | 8.71 | 14.960 | 0.0 | 0.00 | 68.8 |
| | | Compound 1 40mg | 87 | 5.69 | 11.472 | 0.0 | 0.00 | 68.8 |
| | | Leuprorelin | 61 | 7.80 | 15.134 | 0.0 | 0.00 | 56.3 |

FIG. 132

| Variable / Visit | Treatment | | Summary Statistics | | | | |
|---|---|---|---|---|---|---|---|
| | | N | Mean | SD | Min | Median | Max |
| Self Image | Baseline Placebo | 97 | 19.41 | 22.203 | 0.0 | 8.30 | 100.0 |
| | Compound 1 10mg | 103 | 15.86 | 16.690 | 0.0 | 16.70 | 75.0 |
| | Compound 1 20mg | 100 | 15.66 | 18.133 | 0.0 | 8.30 | 83.3 |
| | Compound 1 40mg | 103 | 14.97 | 18.686 | 0.0 | 8.30 | 75.0 |
| | Leuprorelin | 81 | 16.25 | 21.886 | 0.0 | 8.30 | 100.0 |
| | Week 4 Placebo | 96 | 18.75 | 21.864 | 0.0 | 8.30 | 83.3 |
| | Compound 1 10mg | 103 | 12.62 | 15.650 | 0.0 | 8.30 | 66.7 |
| | Compound 1 20mg | 99 | 11.86 | 16.838 | 0.0 | 8.30 | 83.3 |
| | Compound 1 40mg | 102 | 11.76 | 15.968 | 0.0 | 8.30 | 75.0 |
| | Leuprorelin | 81 | 13.06 | 20.324 | 0.0 | 8.30 | 100.0 |
| | Week 8 Placebo | 95 | 15.43 | 20.306 | 0.0 | 8.30 | 91.7 |
| | Compound 1 10mg | 103 | 10.60 | 14.300 | 0.0 | 0.00 | 83.3 |
| | Compound 1 20mg | 96 | 9.03 | 15.040 | 0.0 | 0.00 | 91.7 |
| | Compound 1 40mg | 101 | 8.25 | 15.609 | 0.0 | 0.00 | 83.3 |
| | Leuprorelin | 79 | 11.49 | 19.124 | 0.0 | 0.00 | 100.0 |
| | Week 12 Placebo | 93 | 15.59 | 20.897 | 0.0 | 8.30 | 91.7 |
| | Compound 1 10mg | 101 | 10.40 | 14.502 | 0.0 | 0.00 | 58.3 |
| | Compound 1 20mg | 92 | 9.87 | 15.720 | 0.0 | 0.00 | 75.0 |
| | Compound 1 40mg | 101 | 6.76 | 13.626 | 0.0 | 0.00 | 83.3 |
| | Leuprorelin | 76 | 10.74 | 18.554 | 0.0 | 0.00 | 100.0 |
| | Week 16 Placebo | 75 | 15.22 | 20.061 | 0.0 | 8.30 | 83.3 |
| | Compound 1 10mg | 84 | 8.93 | 12.990 | 0.0 | 0.00 | 50.0 |
| | Compound 1 20mg | 78 | 9.08 | 15.329 | 0.0 | 0.00 | 75.0 |
| | Compound 1 40mg | 89 | 4.68 | 10.432 | 0.0 | 0.00 | 58.3 |
| | Leuprorelin | 69 | 9.90 | 18.813 | 0.0 | 0.00 | 83.3 |
| | Week 20 Placebo | 74 | 15.20 | 20.243 | 0.0 | 8.30 | 75.0 |
| | Compound 1 10mg | 81 | 9.26 | 14.196 | 0.0 | 0.00 | 66.7 |
| | Compound 1 20mg | 77 | 7.14 | 12.662 | 0.0 | 0.00 | 50.0 |
| | Compound 1 40mg | 87 | 5.26 | 10.639 | 0.0 | 0.00 | 58.3 |
| | Leuprorelin | 64 | 9.11 | 19.287 | 0.0 | 0.00 | 100.0 |
| | Week 24 Placebo | 68 | 14.95 | 19.074 | 0.0 | 8.30 | 75.0 |
| | Compound 1 10mg | 79 | 9.81 | 14.045 | 0.0 | 0.00 | 58.3 |
| | Compound 1 20mg | 74 | 7.21 | 12.288 | 0.0 | 0.00 | 50.0 |
| | Compound 1 40mg | 87 | 5.17 | 11.094 | 0.0 | 0.00 | 58.3 |
| | Leuprorelin | 61 | 7.92 | 17.576 | 0.0 | 0.00 | 100.0 |

FIG. 133

| Variable / Visit | Treatment | | Summary Statistics | | | | | |
|---|---|---|---|---|---|---|---|---|
| | | | N | Mean | SD | Min | Median | Max |
| Change from Baseline in Pain | Week 4 | Placebo | 96 | -1.85 | 17.661 | -63.6 | -2.30 | 47.7 |
| | | Compound 1 10mg | 103 | -10.83 | 16.514 | -72.8 | -9.10 | 45.4 |
| | | Compound 1 20mg | 99 | -11.75 | 17.853 | -70.5 | -11.40 | 43.2 |
| | | Compound 1 40mg | 102 | -14.60 | 17.987 | -68.2 | -11.40 | 31.8 |
| | | Leuprorelin | 81 | -10.41 | 16.720 | -84.1 | -9.10 | 27.2 |
| | Week 8 | Placebo | 95 | -4.86 | 16.816 | -68.2 | -4.50 | 43.2 |
| | | Compound 1 10mg | 103 | -14.74 | 19.705 | -75.0 | -13.60 | 27.2 |
| | | Compound 1 20mg | 96 | -18.18 | 18.264 | -72.7 | -15.90 | 15.9 |
| | | Compound 1 40mg | 101 | -23.74 | 20.122 | -72.7 | -22.70 | 22.7 |
| | | Leuprorelin | 79 | -19.91 | 19.952 | -84.1 | -15.90 | 22.8 |
| | Week 12 | Placebo | 93 | -5.58 | 18.988 | -54.5 | -6.80 | 88.6 |
| | | Compound 1 10mg | 101 | -18.32 | 19.758 | -90.9 | -13.70 | 22.8 |
| | | Compound 1 20mg | 92 | -17.76 | 20.355 | -72.7 | -15.90 | 45.4 |
| | | Compound 1 40mg | 101 | -25.34 | 20.865 | -75.0 | -22.70 | 40.9 |
| | | Leuprorelin | 76 | -23.15 | 20.410 | -86.4 | -18.20 | 9.1 |
| | Week 16 | Placebo | 75 | -7.39 | 14.857 | -36.4 | -6.80 | 34.1 |
| | | Compound 1 10mg | 84 | -17.64 | 20.071 | -81.8 | -14.75 | 36.4 |
| | | Compound 1 20mg | 78 | -19.64 | 18.587 | -72.7 | -15.90 | 4.6 |
| | | Compound 1 40mg | 89 | -25.89 | 20.561 | -72.7 | -22.70 | 18.2 |
| | | Leuprorelin | 69 | -23.95 | 20.089 | -86.4 | -18.20 | 6.8 |
| | Week 20 | Placebo | 74 | -4.58 | 21.259 | -61.3 | -4.60 | 63.6 |
| | | Compound 1 10mg | 81 | -16.67 | 19.786 | -75.0 | -15.90 | 25.0 |
| | | Compound 1 20mg | 77 | -19.77 | 18.717 | -72.7 | -18.20 | 18.2 |
| | | Compound 1 40mg | 87 | -25.58 | 22.338 | -75.0 | -22.70 | 65.9 |
| | | Leuprorelin | 64 | -25.32 | 20.816 | -86.4 | -19.35 | 4.5 |
| | Week 24 | Placebo | 68 | -5.41 | 18.421 | -65.9 | -6.80 | 61.4 |
| | | Compound 1 10mg | 79 | -16.98 | 20.286 | -81.8 | -15.90 | 38.6 |
| | | Compound 1 20mg | 74 | -20.58 | 19.650 | -72.7 | -17.00 | 25.0 |
| | | Compound 1 40mg | 87 | -25.94 | 19.902 | -75.0 | -22.70 | 2.3 |
| | | Leuprorelin | 61 | -26.38 | 20.341 | -86.4 | -20.50 | 0.0 |

FIG. 134

| Variable / Visit | Treatment | | Summary Statistics | | | | |
|---|---|---|---|---|---|---|---|
| | | N | Mean | SD | Min | Median | Max |
| Change from Baseline in Control & Powerlessness | Week 4 Placebo | 96 | -4.60 | 17.712 | -75.0 | -4.20 | 45.9 |
| | Compound 1 10mg | 103 | -8.49 | 14.523 | -58.3 | -8.30 | 25.0 |
| | Compound 1 20mg | 99 | -8.08 | 18.647 | -70.8 | -8.30 | 50.0 |
| | Compound 1 40mg | 102 | -8.54 | 14.986 | -58.3 | -4.20 | 20.8 |
| | Leuprorelin | 81 | -9.41 | 16.384 | -95.8 | -8.30 | 25.0 |
| | Week 8 Placebo | 95 | -7.14 | 16.600 | -54.1 | -4.20 | 54.1 |
| | Compound 1 10mg | 103 | -11.00 | 19.477 | -70.8 | -8.30 | 41.7 |
| | Compound 1 20mg | 96 | -14.41 | 21.804 | -91.7 | -12.50 | 37.5 |
| | Compound 1 40mg | 101 | -15.92 | 21.883 | -83.4 | -12.50 | 29.2 |
| | Leuprorelin | 79 | -16.30 | 24.343 | -95.8 | -16.70 | 54.2 |
| | Week 12 Placebo | 93 | -8.20 | 18.740 | -75.0 | -8.30 | 66.7 |
| | Compound 1 10mg | 101 | -13.70 | 18.709 | -87.5 | -8.30 | 20.8 |
| | Compound 1 20mg | 92 | -14.58 | 23.593 | -95.8 | -10.45 | 33.3 |
| | Compound 1 40mg | 101 | -17.24 | 22.478 | -83.4 | -12.50 | 41.7 |
| | Leuprorelin | 76 | -19.58 | 23.265 | -95.8 | -16.70 | 45.9 |
| | Week 16 Placebo | 75 | -9.28 | 17.040 | -83.4 | -8.30 | 33.4 |
| | Compound 1 10mg | 84 | -13.09 | 17.510 | -66.7 | -8.40 | 45.8 |
| | Compound 1 20mg | 78 | -18.42 | 22.581 | -91.7 | -12.50 | 33.3 |
| | Compound 1 40mg | 89 | -20.27 | 21.542 | -91.7 | -12.50 | 12.5 |
| | Leuprorelin | 69 | -19.20 | 23.100 | -95.8 | -16.70 | 41.6 |
| | Week 20 Placebo | 74 | -5.29 | 17.976 | -50.0 | -4.20 | 41.7 |
| | Compound 1 10mg | 81 | -12.96 | 16.668 | -66.7 | -8.30 | 16.6 |
| | Compound 1 20mg | 77 | -21.31 | 21.081 | -91.7 | -16.70 | 8.4 |
| | Compound 1 40mg | 87 | -20.35 | 23.908 | -83.4 | -16.70 | 66.7 |
| | Leuprorelin | 64 | -22.99 | 21.734 | -91.7 | -16.70 | 8.3 |
| | Week 24 Placebo | 68 | -6.92 | 15.848 | -54.2 | -8.30 | 37.5 |
| | Compound 1 10mg | 79 | -13.97 | 17.502 | -66.7 | -8.30 | 29.1 |
| | Compound 1 20mg | 74 | -20.04 | 21.880 | -91.7 | -14.55 | 16.7 |
| | Compound 1 40mg | 87 | -20.88 | 21.676 | -83.4 | -12.50 | 12.5 |
| | Leuprorelin | 61 | -24.80 | 23.839 | -95.8 | -16.70 | 8.3 |

FIG. 135

| Variable / Visit | Treatment | | Summary Statistics | | | | | |
|---|---|---|---|---|---|---|---|---|
| | | | N | Mean | SD | Min | Median | Max |
| Change from Baseline in Emotional Well-being | Week 4 | Placebo | 96 | -1.99 | 15.074 | -37.5 | -4.10 | 75.0 |
| | | Compound 1 10mg | 103 | -6.27 | 11.503 | -54.2 | -4.20 | 16.7 |
| | | Compound 1 20mg | 99 | -3.79 | 14.697 | -58.3 | -4.10 | 29.2 |
| | | Compound 1 40mg | 102 | -5.14 | 13.415 | -62.5 | -4.15 | 29.2 |
| | | Leuprorelin | 81 | -5.91 | 14.628 | -87.5 | -4.20 | 25.0 |
| | Week 8 | Placebo | 95 | -4.65 | 13.617 | -54.1 | -4.10 | 29.2 |
| | | Compound 1 10mg | 103 | -7.40 | 15.725 | -54.2 | -4.20 | 50.0 |
| | | Compound 1 20mg | 96 | -8.55 | 15.224 | -54.1 | -8.30 | 25.0 |
| | | Compound 1 40mg | 101 | -9.48 | 17.230 | -100.0 | -4.20 | 25.0 |
| | | Leuprorelin | 79 | -7.33 | 16.324 | -70.8 | -4.20 | 41.7 |
| | Week 12 | Placebo | 93 | -6.27 | 14.482 | -75.0 | -4.20 | 20.9 |
| | | Compound 1 10mg | 101 | -8.29 | 16.442 | -58.3 | -4.20 | 33.3 |
| | | Compound 1 20mg | 92 | -8.88 | 18.620 | -58.3 | -4.20 | 41.7 |
| | | Compound 1 40mg | 101 | -10.35 | 17.767 | -95.8 | -8.30 | 33.3 |
| | | Leuprorelin | 76 | -8.77 | 17.253 | -83.3 | -8.30 | 45.8 |
| | Week 16 | Placebo | 75 | -5.33 | 16.004 | -54.1 | -4.20 | 45.8 |
| | | Compound 1 10mg | 84 | -8.68 | 15.495 | -58.3 | -4.20 | 37.5 |
| | | Compound 1 20mg | 78 | -12.13 | 18.008 | -66.7 | -8.30 | 16.7 |
| | | Compound 1 40mg | 89 | -12.35 | 16.716 | -83.3 | -8.30 | 12.5 |
| | | Leuprorelin | 69 | -9.36 | 15.774 | -79.2 | -8.30 | 29.2 |
| | Week 20 | Placebo | 74 | -4.84 | 16.949 | -54.1 | -4.20 | 45.8 |
| | | Compound 1 10mg | 81 | -8.29 | 14.396 | -50.0 | -4.20 | 29.1 |
| | | Compound 1 20mg | 77 | -14.34 | 15.825 | -58.3 | -8.40 | 20.8 |
| | | Compound 1 40mg | 87 | -13.17 | 16.899 | -75.0 | -8.30 | 33.3 |
| | | Leuprorelin | 64 | -12.18 | 16.646 | -70.8 | -8.30 | 33.3 |
| | Week 24 | Placebo | 68 | -6.74 | 17.669 | -58.4 | -4.20 | 45.8 |
| | | Compound 1 10mg | 79 | -8.38 | 15.918 | -58.3 | -4.20 | 41.6 |
| | | Compound 1 20mg | 74 | -15.37 | 17.858 | -66.6 | -12.50 | 20.8 |
| | | Compound 1 40mg | 87 | -13.26 | 16.316 | -62.5 | -8.30 | 16.7 |
| | | Leuprorelin | 61 | -12.37 | 18.332 | -87.5 | -8.30 | 29.2 |

FIG. 136

| Variable / Visit | Treatment | | Summary Statistics | | | | | |
|---|---|---|---|---|---|---|---|---|
| | | | N | Mean | SD | Min | Median | Max |
| Change from Baseline in Social Support | Week 4 | Placebo | 96 | -0.26 | 15.253 | -50.0 | 0.00 | 75.0 |
| | | Compound 1 10mg | 103 | -3.82 | 12.010 | -37.5 | 0.00 | 37.5 |
| | | Compound 1 20mg | 99 | -4.11 | 16.006 | -62.5 | 0.00 | 56.2 |
| | | Compound 1 40mg | 102 | -2.76 | 12.273 | -37.5 | 0.00 | 37.5 |
| | | Leuprorelin | 81 | -3.09 | 12.346 | -62.5 | 0.00 | 31.3 |
| | Week 8 | Placebo | 95 | -3.09 | 13.426 | -56.2 | 0.00 | 37.5 |
| | | Compound 1 10mg | 103 | -4.68 | 11.640 | -37.5 | 0.00 | 31.3 |
| | | Compound 1 20mg | 96 | -6.77 | 15.255 | -43.8 | -6.25 | 43.8 |
| | | Compound 1 40mg | 101 | -5.82 | 13.621 | -56.3 | 0.00 | 18.7 |
| | | Leuprorelin | 79 | -3.96 | 17.624 | -62.5 | 0.00 | 62.5 |
| | Week 12 | Placebo | 93 | -3.23 | 14.591 | -50.0 | 0.00 | 43.8 |
| | | Compound 1 10mg | 101 | -6.57 | 10.290 | -43.7 | -6.30 | 18.8 |
| | | Compound 1 20mg | 92 | -8.43 | 16.950 | -43.8 | -6.30 | 31.3 |
| | | Compound 1 40mg | 101 | -6.81 | 15.189 | -56.3 | 0.00 | 18.8 |
| | | Leuprorelin | 76 | -6.75 | 16.355 | -62.5 | 0.00 | 25.0 |
| | Week 16 | Placebo | 75 | -3.92 | 13.587 | -50.0 | 0.00 | 37.5 |
| | | Compound 1 10mg | 84 | -7.23 | 10.829 | -37.5 | -6.30 | 25.0 |
| | | Compound 1 20mg | 78 | -10.02 | 16.746 | -50.0 | -6.30 | 31.3 |
| | | Compound 1 40mg | 89 | -9.35 | 17.433 | -62.5 | -6.20 | 31.3 |
| | | Leuprorelin | 69 | -6.44 | 16.778 | -62.5 | 0.00 | 25.0 |
| | Week 20 | Placebo | 74 | -4.14 | 15.603 | -62.5 | 0.00 | 43.8 |
| | | Compound 1 10mg | 81 | -7.34 | 11.304 | -37.5 | -6.30 | 18.8 |
| | | Compound 1 20mg | 77 | -11.94 | 16.479 | -56.3 | -6.30 | 18.7 |
| | | Compound 1 40mg | 87 | -9.92 | 15.826 | -62.5 | -6.20 | 18.8 |
| | | Leuprorelin | 64 | -9.38 | 16.709 | -62.5 | 0.00 | 6.3 |
| | Week 24 | Placebo | 68 | -3.21 | 16.612 | -62.5 | 0.00 | 43.8 |
| | | Compound 1 10mg | 79 | -7.52 | 10.840 | -43.7 | -6.30 | 12.5 |
| | | Compound 1 20mg | 74 | -13.44 | 17.055 | -62.5 | -6.30 | 25.0 |
| | | Compound 1 40mg | 87 | -10.28 | 17.109 | -75.0 | -6.20 | 25.0 |
| | | Leuprorelin | 61 | -10.46 | 17.923 | -62.5 | -6.30 | 25.0 |

FIG. 137

| Variable / Visit | Treatment | | Summary Statistics | | | | | |
|---|---|---|---|---|---|---|---|---|
| | | | N | Mean | SD | Min | Median | Max |
| Change from Baseline in Self Image | Week 4 | Placebo | 96 | -0.78 | 14.099 | -58.3 | 0.00 | 50.0 |
| | | Compound 1 10mg | 103 | -3.24 | 11.509 | -33.4 | 0.00 | 41.7 |
| | | Compound 1 20mg | 99 | -3.54 | 11.550 | -41.7 | 0.00 | 33.3 |
| | | Compound 1 40mg | 102 | -3.27 | 12.750 | -58.3 | 0.00 | 25.0 |
| | | Leuprorelin | 81 | -3.19 | 12.940 | -50.0 | 0.00 | 25.0 |
| | Week 8 | Placebo | 95 | -4.12 | 14.837 | -75.0 | 0.00 | 33.4 |
| | | Compound 1 10mg | 103 | -5.26 | 10.881 | -33.4 | 0.00 | 16.7 |
| | | Compound 1 20mg | 96 | -6.77 | 13.911 | -75.0 | 0.00 | 16.7 |
| | | Compound 1 40mg | 101 | -6.94 | 17.082 | -66.7 | 0.00 | 33.3 |
| | | Leuprorelin | 79 | -5.17 | 15.113 | -58.3 | 0.00 | 25.0 |
| | Week 12 | Placebo | 93 | -3.94 | 16.421 | -75.0 | 0.00 | 41.7 |
| | | Compound 1 10mg | 101 | -5.53 | 11.562 | -33.4 | 0.00 | 25.0 |
| | | Compound 1 20mg | 92 | -6.34 | 14.895 | -58.3 | -4.15 | 41.7 |
| | | Compound 1 40mg | 101 | -8.42 | 16.184 | -66.7 | 0.00 | 33.3 |
| | | Leuprorelin | 76 | -6.14 | 16.350 | -58.3 | 0.00 | 50.0 |
| | Week 16 | Placebo | 75 | -4.22 | 14.519 | -75.0 | 0.00 | 33.3 |
| | | Compound 1 10mg | 84 | -6.55 | 11.059 | -33.4 | 0.00 | 25.0 |
| | | Compound 1 20mg | 78 | -8.87 | 16.080 | -75.0 | -8.30 | 25.0 |
| | | Compound 1 40mg | 89 | -10.12 | 18.098 | -66.7 | 0.00 | 25.0 |
| | | Leuprorelin | 69 | -6.40 | 15.997 | -66.7 | 0.00 | 33.4 |
| | Week 20 | Placebo | 74 | -4.39 | 15.674 | -83.3 | 0.00 | 33.3 |
| | | Compound 1 10mg | 81 | -6.07 | 11.933 | -33.4 | 0.00 | 50.0 |
| | | Compound 1 20mg | 77 | -10.07 | 16.017 | -75.0 | -8.30 | 16.7 |
| | | Compound 1 40mg | 87 | -9.87 | 17.679 | -75.0 | -8.30 | 25.0 |
| | | Leuprorelin | 64 | -7.81 | 16.659 | -75.0 | 0.00 | 25.0 |
| | Week 24 | Placebo | 68 | -5.39 | 15.421 | -83.3 | 0.00 | 33.3 |
| | | Compound 1 10mg | 79 | -5.91 | 12.811 | -41.7 | 0.00 | 41.6 |
| | | Compound 1 20mg | 74 | -10.59 | 15.256 | -75.0 | -8.30 | 16.7 |
| | | Compound 1 40mg | 87 | -9.68 | 17.744 | -75.0 | 0.00 | 25.0 |
| | | Leuprorelin | 61 | -9.42 | 15.553 | -58.3 | 0.00 | 25.0 |

FIG. 138

| Variable / Visit | | | Diff | 95% CI | |
|---|---|---|---|---|---|
| | | | | Lower | Upper |
| Change from Baseline in Pain | Week 4 | Compound 1 10mg- Leuprorelin | -0.42 | -5.286 | 4.445 |
| | | Compound 1 20mg- Leuprorelin | -1.34 | -6.467 | 3.794 |
| | | Compound 1 40mg- Leuprorelin | -4.18 | -9.303 | 0.939 |
| | Week 8 | Compound 1 10mg- Leuprorelin | 5.17 | -0.679 | 11.015 |
| | | Compound 1 20mg- Leuprorelin | 1.73 | -3.980 | 7.439 |
| | | Compound 1 40mg- Leuprorelin | -3.83 | -9.774 | 2.110 |
| | Week 12 | Compound 1 10mg- Leuprorelin | 4.83 | -1.173 | 10.838 |
| | | Compound 1 20mg- Leuprorelin | 5.39 | -0.847 | 11.627 |
| | | Compound 1 40mg- Leuprorelin | -2.19 | -8.383 | 4.007 |
| | Week 16 | Compound 1 10mg- Leuprorelin | 6.31 | -0.139 | 12.752 |
| | | Compound 1 20mg- Leuprorelin | 4.31 | -1.993 | 1.620 |
| | | Compound 1 40mg- Leuprorelin | -1.94 | -8.393 | 4.506 |
| | Week 20 | Compound 1 10mg- Leuprorelin | 8.66 | 1.962 | 15.349 |
| | | Compound 1 20mg- Leuprorelin | 5.55 | -1.0.7 | 12.138 |
| | | Compound 1 40mg- Leuprorelin | -0.25 | -7.317 | 6.810 |
| | Week 24 | Compound 1 10mg- Leuprorelin | 9.40 | 2.557 | 16.247 |
| | | Compound 1 20mg- Leuprorelin | 5.80 | -1.024 | 12.634 |
| | | Compound 1 40mg- Leuprorelin | 0.44 | -6.190 | 7.067 |

FIG. 139

| Variable / Visit | | | Diff | 95% CI | |
|---|---|---|---|---|---|
| | | | | Lower | Upper |
| Change from Baseline in Control & Powerlessness | Week 4 | Compound 1 10mg-Leuprorelin | 0.93 | -3.578 | 5.429 |
| | | Compound 1 20mg-Leuprorelin | 1.33 | -3.890 | 6.556 |
| | | Compound 1 40mg-Leuprorelin | 0.88 | -3.709 | 5.464 |
| | Week 8 | Compound 1 10mg-Leuprorelin | 5.30 | -1.114 | 11.706 |
| | | Compound 1 20mg-Leuprorelin | 1.89 | -5.001 | 8.781 |
| | | Compound 1 40mg-Leuprorelin | 0.38 | -6.438 | 7.192 |
| | Week 12 | Compound 1 10mg-Leuprorelin | 5.88 | -0.346 | 12.112 |
| | | Compound 1 20mg-Leuprorelin | 5.00 | -2.177 | 12.174 |
| | | Compound 1 40mg-Leuprorelin | 2.34 | -4.496 | 9.181 |
| | Week 16 | Compound 1 10mg-Leuprorelin | 6.11 | -0.382 | 12.599 |
| | | Compound 1 20mg-Leuprorelin | 0.78 | -6.678 | 8.234 |
| | | Compound 1 40mg-Leuprorelin | -1.07 | -8.116 | 5.973 |
| | Week 20 | Compound 1 10mg-Leuprorelin | 10.03 | 3.723 | 16.329 |
| | | Compound 1 20mg-Leuprorelin | 1.67 | -5.477 | 8.823 |
| | | Compound 1 40mg-Leuprorelin | 2.64 | -4.852 | 10.126 |
| | Week 24 | Compound 1 10mg-Leuprorelin | 10.83 | 3.918 | 17.735 |
| | | Compound 1 20mg-Leuprorelin | 4.76 | -3.037 | 12.551 |
| | | Compound 1 40mg-Leuprorelin | 3.92 | -3.531 | 11.380 |

FIG. 140

| Variable / Visit | | | Diff | 95% CI | |
|---|---|---|---|---|---|
| | | | | Lower | Upper |
| Change from Baseline in Emotional Well-being | Week 4 | Compound 1 10mg- Leuprorelin | -0.36 | -4.158 | 3.443 |
| | | Compound 1 20mg- Leuprorelin | 2.12 | -2.212 | 6.460 |
| | | Compound 1 40mg- Leuprorelin | 0.77 | -3.329 | 4.872 |
| | Week 8 | Compound 1 10mg- Leuprorelin | -0.08 | -4.793 | 4.643 |
| | | Compound 1 20mg- Leuprorelin | -1.22 | -5.937 | 3.495 |
| | | Compound 1 40mg- Leuprorelin | -2.16 | -7.147 | 2.835 |
| | Week 12 | Compound 1 10mg- Leuprorelin | 0.48 | -4.556 | 5.510 |
| | | Compound 1 20mg- Leuprorelin | -0.11 | -5.620 | 5.407 |
| | | Compound 1 40mg- Leuprorelin | -1.58 | -6.843 | 3.675 |
| | Week 16 | Compound 1 10mg- Leuprorelin | 0.67 | -4.341 | 5.688 |
| | | Compound 1 20mg- Leuprorelin | -2.77 | -8.320 | 2.784 |
| | | Compound 1 40mg- Leuprorelin | -3.00 | -8.164 | 2.172 |
| | Week 20 | Compound 1 10mg- Leuprorelin | 3.89 | -1.212 | 8.989 |
| | | Compound 1 20mg- Leuprorelin | -2.16 | -7.581 | 3.256 |
| | | Compound 1 40mg- Leuprorelin | -0.99 | -6.457 | 4.472 |
| | Week 24 | Compound 1 10mg- Leuprorelin | 3.98 | -1.752 | 9.713 |
| | | Compound 1 20mg- Leuprorelin | -3.00 | -9.187 | 3.178 |
| | | Compound 1 40mg- Leuprorelin | -0.90 | -6.567 | 4.769 |

FIG. 141

| Variable / Visit | | | Diff | 95% CI | |
|---|---|---|---|---|---|
| | | | | Lower | Upper |
| Change from Baseline in Social Support | Week 4 | Compound 1 10mg- Leuprorelin | -0.74 | -4.298 | 2.827 |
| | | Compound 1 20mg- Leuprorelin | -1.02 | -5.298 | 3.262 |
| | | Compound 1 40mg- Leuprorelin | 0.33 | -3.282 | 3.945 |
| | Week 8 | Compound 1 10mg- Leuprorelin | -0.72 | -5.006 | 3.575 |
| | | Compound 1 20mg- Leuprorelin | -2.81 | -7.720 | 2.094 |
| | | Compound 1 40mg- Leuprorelin | -1.86 | -6.456 | 2.734 |
| | Week 12 | Compound 1 10mg- Leuprorelin | 0.18 | -3.786 | 4.147 |
| | | Compound 1 20mg- Leuprorelin | -1.68 | -6.786 | 3.426 |
| | | Compound 1 40mg- Leuprorelin | -0.06 | -4.769 | 4.641 |
| | Week 16 | Compound 1 10mg- Leuprorelin | -0.79 | -5.228 | 3.650 |
| | | Compound 1 20mg- Leuprorelin | -3.59 | -9.062 | 1.888 |
| | | Compound 1 40mg- Leuprorelin | -2.91 | -8.345 | 2.523 |
| | Week 20 | Compound 1 10mg- Leuprorelin | 2.04 | -2.568 | 6.653 |
| | | Compound 1 20mg- Leuprorelin | -2.56 | -8.108 | 2.984 |
| | | Compound 1 40mg- Leuprorelin | -0.54 | -5.813 | 4.733 |
| | Week 24 | Compound 1 10mg- Leuprorelin | 2.93 | -1.905 | 7.772 |
| | | Compound 1 20mg- Leuprorelin | -2.98 | -8.950 | 2.989 |
| | | Compound 1 40mg- Leuprorelin | 0.18 | -5.581 | 5.937 |

FIG. 142

| Variable / Visit | | | Diff | 95% CI | |
|---|---|---|---|---|---|
| | | | | Lower | Upper |
| Change from Baseline in Self Image | Week 4 | Compound 1 10mg- Leuprorelin | -0.05 | -3.612 | 3.513 |
| | | Compound 1 20mg- Leuprorelin | -0.35 | -3.953 | 3.258 |
| | | Compound 1 40mg- Leuprorelin | -0.08 | -3.851 | 3.688 |
| | Week 8 | Compound 1 10mg- Leuprorelin | -0.09 | -3.896 | 3.711 |
| | | Compound 1 20mg- Leuprorelin | -1.60 | -5.938 | 2.736 |
| | | Compound 1 40mg- Leuprorelin | -1.77 | -6.582 | 3.050 |
| | Week 12 | Compound 1 10mg- Leuprorelin | 0.61 | -3.532 | 4.751 |
| | | Compound 1 20mg- Leuprorelin | -0.20 | -4.969 | 4.561 |
| | | Compound 1 40mg- Leuprorelin | -2.28 | -7.154 | 2.589 |
| | Week 16 | Compound 1 10mg- Leuprorelin | -0.15 | -4.482 | 4.190 |
| | | Compound 1 20mg- Leuprorelin | -2.47 | -7.705 | 2.775 |
| | | Compound 1 40mg- Leuprorelin | -3.71 | -9.167 | 1.741 |
| | Week 20 | Compound 1 10mg- Leuprorelin | 1.74 | -2.957 | 6.438 |
| | | Compound 1 20mg- Leuprorelin | -2.26 | -7.712 | 3.198 |
| | | Compound 1 40mg- Leuprorelin | -2.06 | -7.674 | 3.556 |
| | Week 24 | Compound 1 10mg- Leuprorelin | 3.52 | -1.226 | 8.257 |
| | | Compound 1 20mg- Leuprorelin | -1.16 | -6.425 | 4.104 |
| | | Compound 1 40mg- Leuprorelin | -0.25 | -5.825 | 5.316 |

FIG. 143

Endometriosis Pain Questionnaire

Please rate your pain by circling the one number that best describes your endometriosis pain on average in the last month.

0   1   2   3   4   5   6   7   8   9   10

No pain                                                   Pain as bad as you can imagine

FIG. 144

Modified Biberoglu and Behrman Grading Scale

For each of the following three symptoms, please mark the circle that best describes your experience over the past 24 hours.

| | | Degree | Description |
|---|---|---|---|
| 1. Dysmenorrhea | $O_3$ | Severe | In bed all day, incapacitation |
| | $O_2$ | Moderate | In bed part of day, some loss of work efficiency |
| | $O_1$ | Mild | Some loss of work efficiency |
| | $O_0$ | No pain | No pain associated with menstruation during past 24 hours |
| | $O_9$ | No menstruation | No menstruation during past 4 hours |

| | | Degree | Description |
|---|---|---|---|
| 2. Pelvic Pain | $O_3$ | Severe | Requires strong analgesics |
| | $O_2$ | Moderate | Noticeable pelvic pain |
| | $O_1$ | Mild | Occasional pelvic pain |
| | $O_0$ | No pain | No pelvic pain during past 24 hours |

| | | Degree | Description |
|---|---|---|---|
| 3. Deep dyspareunia | $O_3$ | Severe | Avoids intercourse because of pain |
| | $O_2$ | Moderate | Intercourse painful to the point of causing interruption |
| | $O_1$ | Mild | Tolerated pain |
| | $O_0$ | No pain | No pain during intercourse |
| | $O_9$ | No intercourse | No intercourse for other reasons |

FIG. 145

Symptoms of Endometriosis Scale

> For the following question, please circle one number to rate your pelvic pain (unrelated to your menstrual period) in the past 24 hours.

1. How would you rate your pelvic pain in the past 24 hours? Pelvic pain is defined as localized pain in the lower abdomen unrelated to the menstrual cycle.

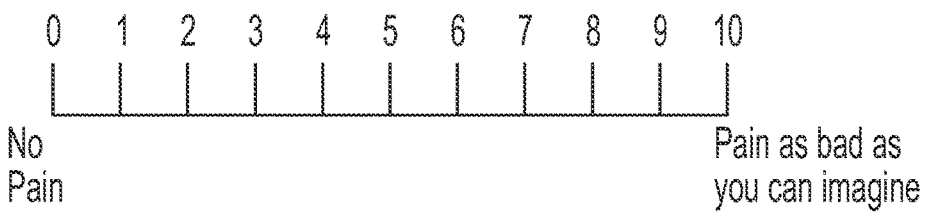

2. In the past 24 hours, did you menstruate?
   ☐ Yes    ☐ No

If the response to question 2 is "NO", please skip to question 5.

3. How would you describe the amount of bleeding in the past 24 hours compared to a normal menstrual Period?
   ☐ Spotting    ☐ Light    ☐ Moderate    ☐ Heavy > For the following question, please circle one number to rate your pelvic pain related to menstruation in the past 24 hours.

4. How would you rate your pelvic pain due to menstruation in the past 24 hours?

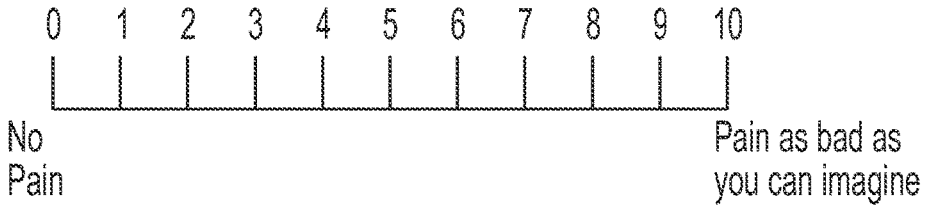

5. In the past 24 hours, did you have or attempt to have vaginal sexual intercourse?
   ☐ Yes    ☐ No If the response to question 5 is "NO", please skip to question 7.

FIG. 146A

For the following question, please circle one number to rate your pelvic pain during vaginal sexual intercourse.

6. How would you rate your pelvic pain during vaginal sexual intercourse? Please limit your rating to sexual encounters in the past 24 hours?

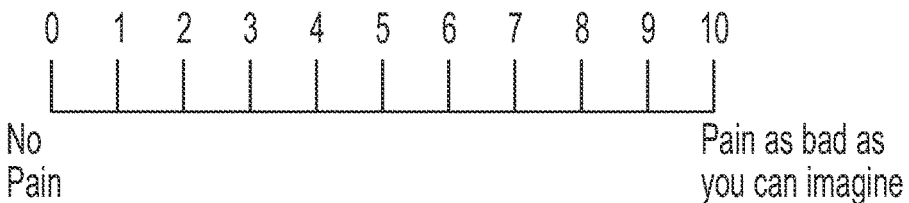

No Pain            Pain as bad as you can imagine

Please skip to question 8.

7. In the past 24 hours, have you avoided vaginal sexual intercourse because you expected it to be painful?

☐ Yes      ☐ No

8. Did you take any medications to relieve your endometriosis pain over the last 24 hours?

☐ Yes      ☐ No

If the response to question 8 is "NO", skip to question 10.

9. Please record the medications that you took to relieve endometriosis pain in the past 24 hours. Medications may include over the counter medications, herbal remedies, vitamins or supplements.

> For the following question, please place a vertical mark on the line to show how you would rate your pelvic pain (unrelated to your menstrual period) in the past 24 hours.

10. How would you rate your pelvic pain in the past 24 hours? Pelvic pain is defined as localized pain in the lower abdomen unrelated to the menstrual cycle.

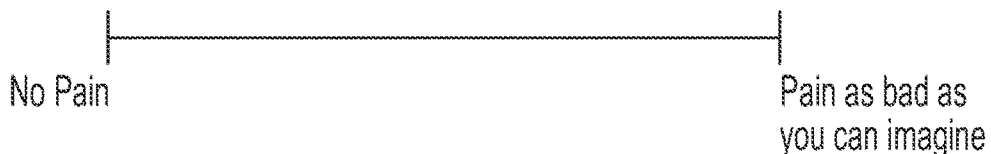

> For the following question, please place a vertical mark on the line to show how you would rate your pelvic pain related to the menses in the past 24 hours.

11. How would you rate your pelvic pain due to menstruation in the past 24 hours?

> For the following question, please place a vertical mark on the line to show how you would rate your pelvic pain during sexual intercourse, if applicable.

12. How would you rate your pelvic pain during vaginal sexual intercourse? Please limit your rating to sexual encounters in the past 24 hours?

FIG. 146C

Assignment 1

PHT firsthand knowledge
LogPad   Build: 0.01T
UBC
A2-7208

[Test] [Assign LogPad]

Assignment 2

Enter Site Access Code
****
1 2 3   * #
4 5 6   . .
7 8 9
CE 0 C
←

Assignment 3

Enter Site Access Code
****
1 2 3   * #
4 5 6   . .
7 8 9
CE 0 C
←   →

Assignment 4

DialingSetup
Please select the country you are dialing from:

▼

←

Assignment 5

DialingSetup
Please select the country you are dialing from:

▼ United States

←

Assignment 6

Verify Correct Time and Date!
On the next screen
1. SELECT your time zone.
2. VERIFY that the local time and date are correct.
3. If the local time and date are NOT correct, touch the Time Check button to perform a time synchronization.

←   →

Assignment 7

Select Your Time Zone
(-8:00) US/CA - Pacific Time
(-7:00) US/CA - Mountain Time
(-6:00) US/CA - Central Time
(-5:00) US/CA - Eastern Time
(-11:00) Pacific/Apia; Samaa
(-10:00) Pacific/Honolulu
(-10:00) America/Aleutian Islands
(-9:00) America/Anchorage

←   ✓

Assignment 8

Select Your Time Zone
(-8:00) US/CA - Pacific Time
(-7:00) US/CA - Mountain Time
(-6:00) US/CA - Central Time
(-5:00) US/CA - Eastern Time
(-11:00) Pacific/Apia; Samaa
(-10:00) Pacific/Honolulu
(-10:00) America/Aleutian Islands
(-9:00) America/Anchorage Local Time:
07-Aug-2008 09:40 AM

←   ✓   →

Assignment 9

Enrollment
Has the Subject previously received a LogPad for this study?
☐ No
☐ Yes

Assignment 19

Keypad abc

```
1 2 3 4 5 6 7 8 9 0
q w e r t y u i o p
a s d f g h j k l
z x c v b n m , .
Caps    Space    Shift
```

Assignment 20

Site Personnel Selection

Please select your name from the list below as the person responsible for current data entry. If your name does not appear, select NEW NAME and carefully enter your complete (first and last) name.

abc

NEW NAME

Assignment 21

Site Confirmation

Site Number: 001
Subject Number: 5001-0001 (ABC)

I have entered, cross-checked, and hereby confirm the preceding data.

Signature of: abc

Clear Box

FIG. 147G

Assignment 22

Site Confirmation

Site Number: 001
Subject Number: 5001-0001 (ABC)

I have entered, cross-checked, and hereby confirm the preceding data.

Signature of: abc

ABC

Clear Box

Assignment 23

Send Information

Phone# 18776571747
☐ Dial prefix
9_____ Help

Connect the LogPad to the TeleCradle Wireless pak, or other modem Tap Send Now when ready.

Send Now

Assignment 24

Sending...

LogPad Assigned

Thank you! You have successfully assigned this LogPad.

Assignment 25

Subject Phone Setup
Phone# 18776571747
☐ Dial prefix
9 ............................ [Help]

LogPad Main Gateway / Subject Gateway Access / SEMS 1 Code (IF SEMS selected)

AZ-7208
PHT LogPad B0.OIT [Site Use]
07-Aug-2008          05:54AM
Site Number:      001
Subject Initials:  ABC
Subject Numbers: 5001-0001
[ SEMS ]
last Info sent 07-Aug-2008
09:52 AM Enter Access Code
1 2 3    * #
4 5 6    . .
7 8 9
CE 0 C SEMS
For the following question. please select one number to rate your pelvic pain (unrelated to your menstrual period) in the past 24 hours.
How would you rate your pelvic pain in the past 24 hours? Pelvic pain is defined as localized pain in the lower abdomen unrelated to the menstrual cycle.
NO PAIN            PAIN AS BAD AS YOU CAN IMAGINE
0 1 2 3 4 5 6 7 8 9 10

LogPad Main Gateway / Site Gateway Access / End LogPad Use Code (If Site Use selected)

AZ-7208
PHT LogPad B0.OIT [Site Use]
07-Aug-2008          09:54 AM
Site Number:      001
Subject ID:       ABC
Subject Initials: 5001-0001
[ SEMS ]
Last info sent: 07-Aug-2008
09:52 AM Enter Site Access Code
1 2 3    * #
4 5 6    . .
7 8 9
CE 0 C Site Use Gateway

[ End LogPad Use ]

FIG. 147I

Subject Gateway 1

Enter Access Code

[keypad: 1 2 3 * #
4 5 6 . .
7 8 9
CE 0 C
←]

SEMS 2

SEMS

For the following question, please place a vertical mark on the line to show how you would rate your pelvic pain (unrelated to your menstrual period) in the past 24 hours.

|————————————|
No Pain          Pain as Bad as
                 You Can
                 Imagine

←

SEMS 1

SEMS

For the following question, please select one number to rate your pelvic pain (unrelated to your menstrual period) in the past 24 hours.

How would you rate your pelvic pain in the past 24 hours? Pelvic pain is defined as localized pain in the lower abdomen unrelated to the menstrual cycle.

NO PAIN                PAIN AS BAD AS YOU CAN IMAGINE 0 1 2 3 4 5 6 7 8 9 10

←

SEMS 3

SEMS

In the past 24 hours, did you menstruate?

☐ Yes
☐ No

SEMS 4

How would you describe the amount of bleeding in the past 24 hours compared to a normal menstrual period?
☐ Spotting
☐ Light
☐ Moderate
☐ Heavy

SEMS 5

For the following question, please select one number to rate your pelvic pain related to menstruation in the past 24 hours.
How would you rate your pelvic pain due to menstruation in the past 24 hours?

Pain as Bad as
　No　　　　You Can
Pain　　　　Imagine
|0|1|2|3|4|5|6|7|8|9|10|

SEMS 6

For the following question, please place a vertical mark on the line to show how you could rate your pelvic pain related to the menses in the past 24 hours.

No pain　　　Pain as Bad as
　　　　　　You Can
　　　　　　Imagine

SEMS 7

In the past 24 hours, did you have or attempt to have vaginal sexual intercourse?
☐ Yes
☐ No

FIG. 147K

FIG. 147L

Profile of Mood States (POMS)™ Brief Form

Below is a list of words that describe feelings people have. Please read each word carefully. Then mark with an X the word that best describes how you have been feeling during the PAST WEEK, INCLUDING TODAY.

|  | Not at all | A little | Moderately | Quite a bit | Extremely |
|---|---|---|---|---|---|
| 1. Tense | ☐ | ☐ | ☐ | ☐ | ☐ |
| 2. Angry | ☐ | ☐ | ☐ | ☐ | ☐ |
| 3. Worn out | ☐ | ☐ | ☐ | ☐ | ☐ |
| 4. Lively | ☐ | ☐ | ☐ | ☐ | ☐ |
| 5. Contused | ☐ | ☐ | ☐ | ☐ | ☐ |
| 6. Shaky | ☐ | ☐ | ☐ | ☐ | ☐ |
| 7. Sad | ☐ | ☐ | ☐ | ☐ | ☐ |
| 8. Active | ☐ | ☐ | ☐ | ☐ | ☐ |
| 9. Grouchy | ☐ | ☐ | ☐ | ☐ | ☐ |
| 10. Energetic | ☐ | ☐ | ☐ | ☐ | ☐ |
| 11. Unworthy | ☐ | ☐ | ☐ | ☐ | ☐ |
| 12. Uneasy | ☐ | ☐ | ☐ | ☐ | ☐ |
| 13. Fatigued | ☐ | ☐ | ☐ | ☐ | ☐ |

FIG. 148A

Profile of Mood States (POMS)™ Brief Form

Below is a list of words that describe feelings people have. Please read each word carefully. Then mark with an X the word that best describes how you have been feeling during the PAST WEEK, INCLUDING TODAY.

|  | Not at all | A little | Moderately | Quite a bit | Extremely |
|---|---|---|---|---|---|
| 14. Annoyed | ☐ | ☐ | ☐ | ☐ | ☐ |
| 15. Discouraged | ☐ | ☐ | ☐ | ☐ | ☐ |
| 16. Nervous | ☐ | ☐ | ☐ | ☐ | ☐ |
| 17. Lonely | ☐ | ☐ | ☐ | ☐ | ☐ |
| 18. Muddled | ☐ | ☐ | ☐ | ☐ | ☐ |
| 19. Extrausted | ☐ | ☐ | ☐ | ☐ | ☐ |
| 20. Anxious | ☐ | ☐ | ☐ | ☐ | ☐ |
| 21. Gloomy | ☐ | ☐ | ☐ | ☐ | ☐ |
| 22. Sluggish | ☐ | ☐ | ☐ | ☐ | ☐ |
| 23. Weary | ☐ | ☐ | ☐ | ☐ | ☐ |
| 24. Bewildered | ☐ | ☐ | ☐ | ☐ | ☐ |
| 25. Furious | ☐ | ☐ | ☐ | ☐ | ☐ |
| 26. Efficient | ☐ | ☐ | ☐ | ☐ | ☐ |

FIG. 148B

Profile of Mood States (POMS)™ Brief Form

Below is a list of words that describe feelings people have. Please read each word carefully. Then mark with an X the word that best describes how you have been feeling during the PAST WEEK. INCLUDING TODAY.

|  | Not at all | A little | Moderately | Quite a bit | Extremely |
|---|---|---|---|---|---|
| 27. Full of pep | ☐ | ☐ | ☐ | ☐ | ☐ |
| 28. Bad-tempered | ☐ | ☐ | ☐ | ☐ | ☐ |
| 29. Forgetful | ☐ | ☐ | ☐ | ☐ | ☐ |
| 30. Vigorous | ☐ | ☐ | ☐ | ☐ | ☐ |

FIG. 148C

Baseline Clinical Questionnaire

Please respond to the following questions based on the patient's records and a clinical assessment of their disease state.

| General | |
|---|---|
| 1. Height (in inches): | ☐☐ inches |
| 2. Weight (in pounds): | ☐☐☐ pounds (lbs) |
| 3. Parity (#times subject has given birth): | ☐☐ times |

| Endometriosis | |
|---|---|
| 4. Date of Endometriosis Diagnosis | ☐☐ mm  ☐☐ dd  ☐☐☐☐ yyyy |
| 5. Endometriosis Stage [Based on revised American Fertility Society Classification of Endometriosis] (Please mark with an X the corresponding box for the stage that applies to this patient): <br> ☐ Stage I <br> ☐ Stage II <br> ☐ Stage III <br> ☐ Stage IV <br> ☐ Stage Unknown | |
| 6. Date of Endometriosis is Staging | ☐☐ mm  ☐☐ dd  ☐☐☐☐ yyyy |
| 7. Previous Surgical Reduction for Endometriosis | ☐ Yes <br> ☐ No <br> ☐ Unknown |

FIG. 149A

Baseline Clinical Questionnaire

| Co-Morbidities |
|---|
| 8. Mark with an X the corresponding box for any co-morbidities that apply to this patient. |
| ☐ None  ☐ Congestive heart failure  ☐ Acute myocardial infarction  ☐ Stroke  ☐ Epilepsy  ☐ Parkinson's disease<br><br>☐ Hypertension  ☐ Arthritis  ☐ Anxiety disorder  ☐ Asthma  ☐ Migraines<br><br>☐ Other co-morbidity: _____<br>☐ Other co-morbidity: _____ |

| Analgesic Medications Used to Treat Endometriosis Pain |
|---|
| 9. Mark with an X any analgesic medications that the patient has taken within the past 3 months |
| ☐ None  ☐ Mild analgesics[1]  ☐ Moderate analgesics[2]  ☐ Strong analgesics[3]<br><br>☐ Other (specify): _____<br>☐ Other (specify): _____ |

[1] Mild analgesics = none to occasional use of non-narcotic analgesics or antiprostaglandin drugs
[2] Moderate analgesics = regular use of non-narcotic analgesics or antiprostaglandin drugs
[3] Strong analgesics = requires narcotic analgesics

FIG. 149B

Baseline Clinical Questionnaire

| Menstrual Cycle | |
|---|---|
| 10. Please indicate when the patient most recently started menstruating: | ☐☐ mm  ☐☐ dd  [2][0]☐☐ yyyy |

| Outpatient Visits | |
|---|---|
| 11. Please indicate the number of outpatient visits for endometriosis in the past 6 months: | ☐☐ visits |

| Sexual Activity | | |
|---|---|---|
| 12. Is the patient sexually active (currently having vaginal sexual intercourse)? | ☐ Yes (stop here with question 12) | ☐ No (proceed to question 12a) |
| 12a. Please mark with an X all the reasons that the participant is <u>not sexually active (currently)</u> | ☐ Does not have a partner at the moment<br>☐ Is abstaining for personal reasons.<br>☐ Endometriosis-related pain makes sexual relations uncomfortable.<br>☐ Has a physical problem not related to endometriosis that makes sexual relations uncomfortable.<br>☐ Other (specify): _____ | |

FIG. 149C

Final Clinical Questionnaire

Instructions: Please respond to the following questions based on the patient's records and a clinical assessment of their disease state.

| Analgesic Medications Used to Treat Endometriosis Pain |
|---|
| 1. Mark with an X any analgesic medications that the patient has taken within the past 3 months |
| ☐ None  ☐ Mild analgesics[1]  ☐ Moderate analgesics[2]  ☐ Strong analgesics[3] <br><br> ☐ Other (specify): _____ <br> ☐ Other (specify): _____ |

[1] Mild analgesics = none to occasional use of non-narcotic analgesics or antiprostaglandin drugs
[2] Moderate analgesics = regular use of non-narcotic analgesics or antiprostaglandin drugs
[3] Strong analgesics = requires narcotic analgesics

| Outpatient Visits | |
|---|---|
| 2. Please indicate the number of outpatient visits for endometriosis in the past 6 months: | ☐☐ visits |

FIG. 150A

Final Clinical Questionnaire

| Sexual Activity | | |
|---|---|---|
| 3. Is the patient sexually active (currently having vaginal sexual intercourse)? | ☐ Yes (stop here with question 3) | ☐ No (proceed to question 3a) |
| 3a. Please mark with an X all the reasons that the participant is <u>not sexually active (currently)</u>. | ☐ Does not have a partner at the moment. <br> ☐ Is abstaining for personal reasons. <br> ☐ Endometriosis-related pain makes sexual relations uncomfortable. <br> ☐ Has a physical problem not related to endometriosis that makes sexual relations uncomfortable. <br> ☐ Other (specify): _____ | |

FIG. 150B

 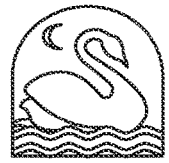

University of Oxford   National Endometriosis Society

The Endometriosis Health Profile Questionnaire (EHP 30)

©Nuffield Department of Obstetrics & Gynaecology
& Health Services Research Unit
University of Oxford In collaboration with The National Endometriosis Society

- This Questionnaire has been developed to measure the effect Endometriosis has upon a woman's quality of life.
- Please answer all the questions.
- We are aware that you may have had endometriosis for a long time. We also understand that how you feel now may be different to how you have felt in the past. However, please would you answer the questions only in relation to the effect that endometriosis has had on your life during the last 4 weeks.
- There are no right or wrong answers, so please tick the answers which best represent your feelings and experiences.
- Due to the personal nature of some of the questions please understand that you do not have to answer any questions if you would prefer not to.
- The information and answers you give will be treated with the utmost confidentiality.
- If you have any problems or would like any help or assistance with the completion of this questionnaire please contact xxxxxx who will be happy to help you.
- Once you have completed the questionnaire please could you return it in the pre-paid envelope provided.
- We would like to thank you very much in anticipation for taking the time to help us with this important research and we look forward to receiving your answers.
- This research is being funded with an educational grant from Pharmacia, USA.

FIG. 151A

PART 1: CORE QUESTIONNAIRE

DURING THE LAST 4 WEEKS, HOW OFTEN
BECAUSE OF YOUR ENDOMETRIOSIS HAVE YOU.....

|  | Never | Rarely | Sometimes | Often | Always |
|---|---|---|---|---|---|
| 1. Been unable to go to social events because of the pain? | ☐ | ☐ | ☐ | ☐ | ☐ |
| 2. Been unable to do jobs around the home because of the pain? | ☐ | ☐ | ☐ | ☐ | ☐ |
| 3. Found it difficult to stand because of the pain? | ☐ | ☐ | ☐ | ☐ | ☐ |
| 4. Found it difficult to sit because of the pain? | ☐ | ☐ | ☐ | ☐ | ☐ |
| 5. Found it difficult to walk because of the pain? | ☐ | ☐ | ☐ | ☐ | ☐ |
| 6. Found it difficult to exercise or do the leisure activities you would like to do because of the pain? | ☐ | ☐ | ☐ | ☐ | ☐ |
| 7. Lost your appetite and/or been unable to eat because of the pain? | ☐ | ☐ | ☐ | ☐ | ☐ |

Please check that you have ticked one box for each question before moving onto the next page

FIG. 151B

DURING THE LAST 4 WEEKS, HOW OFTEN
BECAUSE OF YOUR ENDOMETRIOSIS HAVE YOU.....

| | Never | Rarely | Sometimes | Often | Always |
|---|---|---|---|---|---|
| 8. Been unable to sleep properly because of the pain? | ☐ | ☐ | ☐ | ☐ | ☐ |
| 9. Had to go to bed/lie down because of the pain? | ☐ | ☐ | ☐ | ☐ | ☐ |
| 10. Been unable to do the things you want to do because of the pain? | ☐ | ☐ | ☐ | ☐ | ☐ |
| 11. Felt unable to cope with the pain? | ☐ | ☐ | ☐ | ☐ | ☐ |
| 12. Generally felt unwell? | ☐ | ☐ | ☐ | ☐ | ☐ |
| 13. Felt frustrated because your symptoms are not getting better? | ☐ | ☐ | ☐ | ☐ | ☐ |
| 14. Felt frustrated because you are not able to control your symptoms? | ☐ | ☐ | ☐ | ☐ | ☐ |

Please check that you have ticked one box for each question before moving onto the next page

FIG. 151C

DURING THE LAST 4 WEEKS, HOW OFTEN
BECAUSE OF YOUR ENDOMETRIOSIS HAVE YOU.....

| | Never | Rarely | Sometimes | Often | Always |
|---|---|---|---|---|---|
| 15. Felt unable to forget your symptoms? | ☐ | ☐ | ☐ | ☐ | ☐ |
| 16. Felt as though your symptoms are ruling your life? | ☐ | ☐ | ☐ | ☐ | ☐ |
| 17. Felt your symptoms are taking away your life? | ☐ | ☐ | ☐ | ☐ | ☐ |
| 18. Felt depressed? | ☐ | ☐ | ☐ | ☐ | ☐ |
| 19. Felt weepy/tearful? | ☐ | ☐ | ☐ | ☐ | ☐ |
| 20. Felt miserable? | ☐ | ☐ | ☐ | ☐ | ☐ |
| 21. Had mood swings? | ☐ | ☐ | ☐ | ☐ | ☐ |
| 22. Felt bad tempered or short tempered? | ☐ | ☐ | ☐ | ☐ | ☐ |

Please check that you have ticked one box for each question before moving onto the next page

FIG. 151D

DURING THE LAST 4 WEEKS, HOW OFTEN
BECAUSE OF YOUR ENDOMETRIOSIS HAVE YOU.....

| | Never | Rarely | Sometimes | Often | Always |
|---|---|---|---|---|---|
| 23. Felt violent or aggressive? | ☐ | ☐ | ☐ | ☐ | ☐ |
| 24. Felt unable to tell people how you feel? | ☐ | ☐ | ☐ | ☐ | ☐ |
| 25. Felt others do not understand what you are going through? | ☐ | ☐ | ☐ | ☐ | ☐ |
| 26. Felt as though others think you are moaning? | ☐ | ☐ | ☐ | ☐ | ☐ |
| 27. Felt alone? | ☐ | ☐ | ☐ | ☐ | ☐ |
| 28. Felt frustrated as you cannot always wear the clothes you would choose? | ☐ | ☐ | ☐ | ☐ | ☐ |
| 29. Felt your appearance has been affected? | ☐ | ☐ | ☐ | ☐ | ☐ |
| 30. Lacked confidence? | ☐ | ☐ | ☐ | ☐ | ☐ |

Please check that you have ticked one box for each question

FIG. 151E

| Mean (SD) VAS Score (mm): Overall Pelvic Pain | | | | |
|---|---|---|---|---|
| | N | Baseline | N | Week 24 |
| Placebo | 97 | 15.6 (14.3) | 71 | 10.4 (12.4) |
| Relugolix 10 mg | 103 | 14.6 (12.0) | 80 | 6.9 (9.2) |
| Relugolix 20 mg | 100 | 15.6 (15.1) | 77 | 5.5 (9.2) |
| Relugolix 40 mg | 103 | 15.3 (12.0) | 88 | 3.0 (6.2) |
| Leuprorelin | 81 | 15.2 (15.1) | 63 | 2.2 (5.2) |

| Mean (SD) VAS Score(mm) : Dysmenorrhea | | | | |
|---|---|---|---|---|
| | N | Baseline | N | Week 24 |
| Placebo | 97 | 28.4 (16.6) | 71 | 18.8 (14.9) |
| Relugolix 10 mg | 103 | 28.2 (17.6) | 80 | 11.8 (15.4) |
| Relugolix 20 mg | 100 | 27.7 (18.9) | 77 | 6.1 (13.2) |
| Relugolix 40 mg | 103 | 30.4 (17.0) | 88 | 0.4 (2.3) |
| Leuprorelin | 81 | 27.1 (19.8) | 63 | 0.0 (0.0) |

| Mean (SD) VAS Score (mm): Non-Menstrual Pelvic Pain | | | | |
|---|---|---|---|---|
| | N | Baseline | N | Week 24 |
| Placebo | 97 | 11.9 (14.7) | 71 | 7.6 (12.5) |
| Relugolix 10 mg | 103 | 10.5 (11.9) | 80 | 5.2 (8.6) |
| Relugolix 20 mg | 100 | 11.8 (14.7) | 77 | 4.6 (8.2) |
| Relugolix 40 mg | 103 | 10.6 (11.8) | 88 | 3.0 (6.3) |
| Leuprorelin | 81 | 11.8 (15.6) | 63 | 2.2 (5.2) |

| Mean (SD) VAS Score (mm): Dyspareunia | | | | |
|---|---|---|---|---|
| | N | Baseline | N | Week 24 |
| Placebo | 41 | 11.0 (14.2) | 20 | 9.2 (12.7) |
| Relugolix 10 mg | 46 | 8.8 (14.2) | 36 | 5.6 (11.1) |
| Relugolix 20 mg | 47 | 12.5 (16.5) | 29 | 3.8 (9.0) |
| Relugolix 40 mg | 44 | 9.4 (15.4) | 31 | 3.5 (9.6) |
| Leuprorelin | 26 | 9.5 (10.7) | 18 | 5.6 (12.6) |

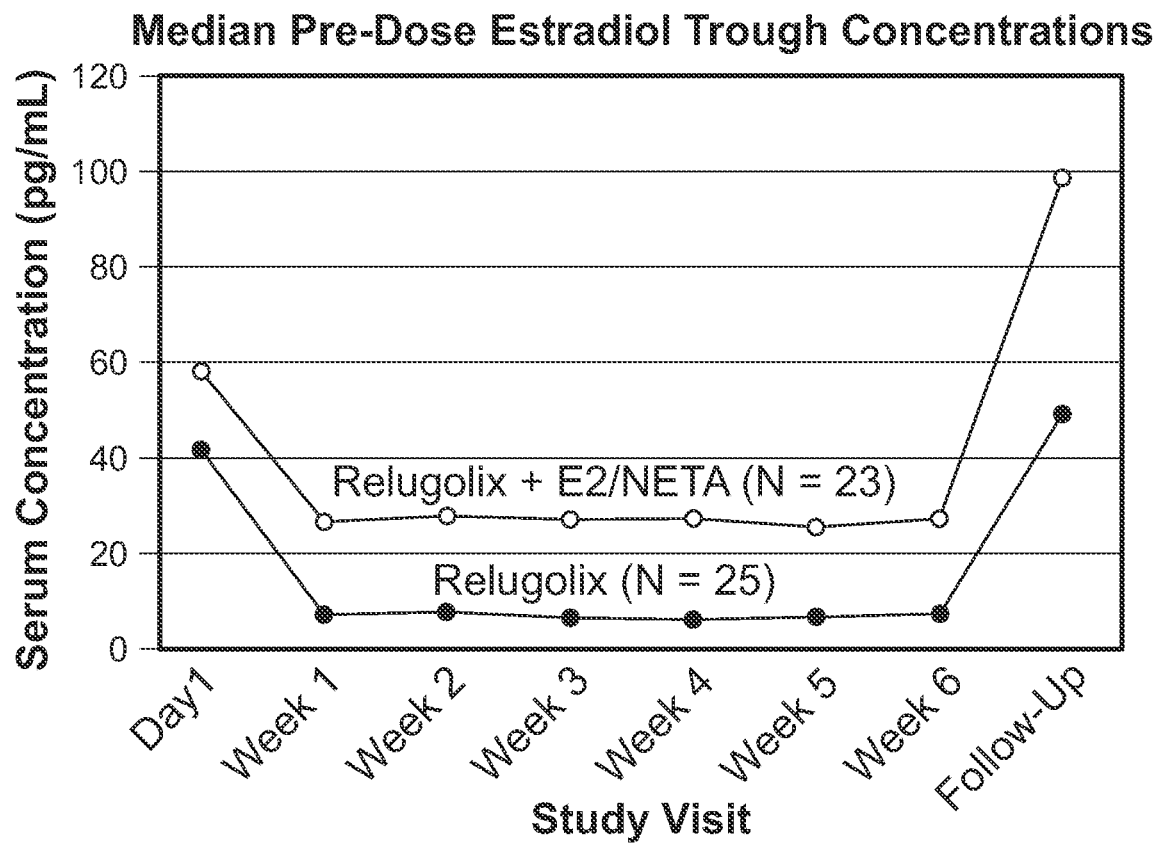
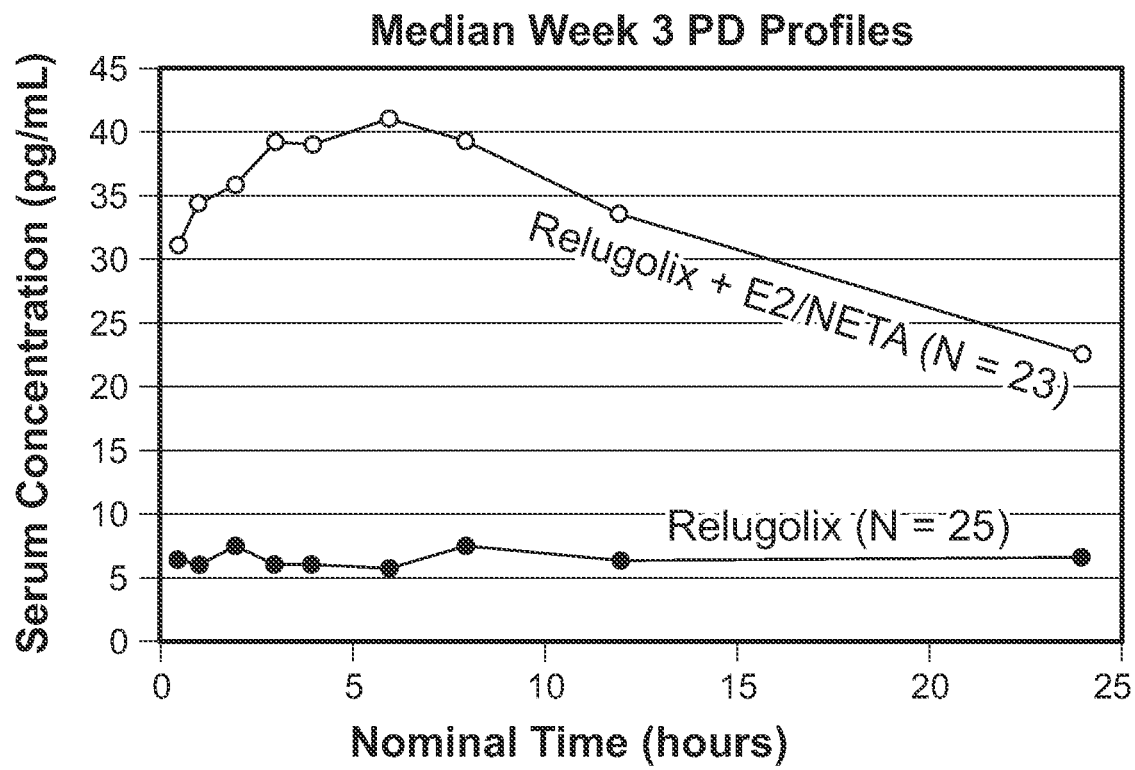
FIG. 163

Mean (SD) Serum Estradiol on Last Day of Treatment (Week 6) – top line Compound 1 plus add-back and bottom line Compound 1 without add-back.

Mean (SD) C-Telopeptide and N-Telopeptide (Compound 1 (relugolix) left side; Compound 1 plus add-back right side) of each weekly result.

|  | Relugolix[1] | Elagolix[2] |
|---|---|---|
| Observed Half-life | 37 - 42 hours | 2 - 6 hours |
| Observed Potency[3] | $IC_{50} = 0.12$ nM | $IC_{50} = 1.5$ nM |
| Phase 3 Dose Frequency | Uterine Fibroids[4]: Once daily (planned)<br>Endometriosis[5]: Once daily (planned) | Uterine Fibroids[4]: Twice daily<br>Endometriosis[5]: Once or twice daily |
| Phase 3 Dose by Indication | Uterine Fibroids[4]: 40 mg once daily (planned)<br>Endometriosis[5]: 40 mg once daily (planned) | Uterine Fibroids[4]: 300 mg twice daily<br>Endometriosis[5]: 150 mg once daily, or 200 mg twice daily |
| Dose at Which Maximum Estrogen Suppression Observed | 40 mg once daily | 200 mg - 300 mg twice daily |
| Use of Add-back Therapy in Phase 3 | Uterine Fibroids[4]: Phase 3 clinical trials planned to start first quarter of 2017 with add-back therapy<br>Endometriosis[5]: Phase 3 clinical trials planned to start first half of 2017 with add-back therapy | Uterine Fibroids[4]: Phase 3 clinical trials with and without add-back therapy started in 2016<br>Endometriosis[5]: Not in initial Phase 3 trials; Phase 3b with add-back therapy expected to start in 2016 |
| Food Effect | Yes: Dosed on empty stomach once daily | Yes: Dosed on empty stomach up to twice daily |
| Clinical Trials Ongoing in Prostate Cancer | Yes: Phase 2 clinical trials ongoing; Phase 3 clinical trial planned to start in first quarter of 2017 | No |

1 Based on the results of clinical trials to date and our Phase 3 development plan for relugolix
2 Based on publicly available nonclinical and clinical data to date and Phase 3 development plan for elagolix
3 $IC_{50}$ is a quantitative measure of the drug concentration needed to inhibit a given biological process by half; a lower $IC_{50}$ indicates a more potent drug
4 Target indication of heavy menstrual bleeding associated with uterine fibroids
5 Target indication of endometriosis-associated pain

FIG. 167

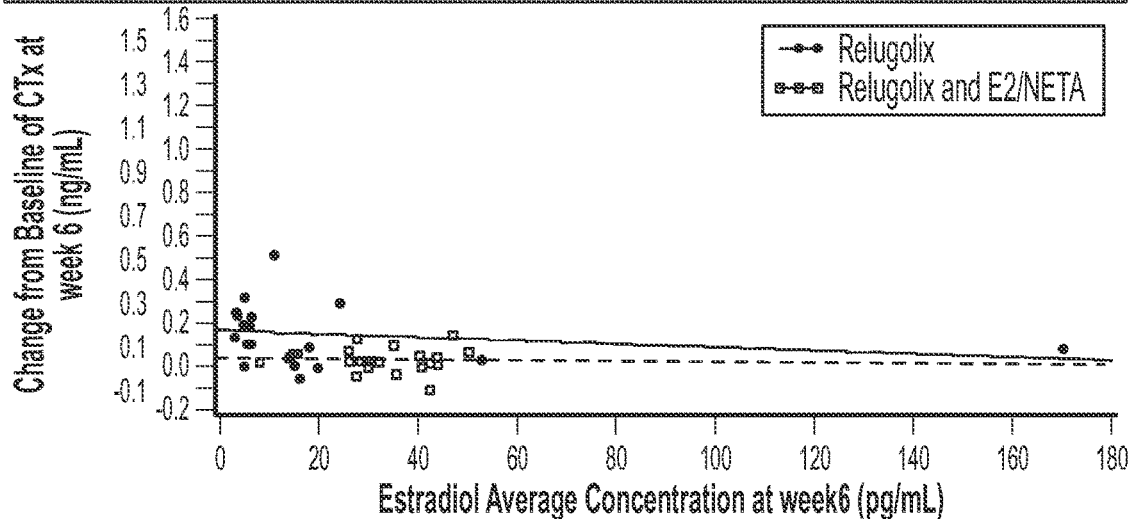

CTX: C-telopeptide
Regression equation for Relugolix=0.169-0.000778 x Cavg (pg/mL); n=24; r=0.213; p-value=0.382
Regression equation for Relugolix and E2/NETA=0.037-0.000136 x Cavg (pg/mL); n=22; r=0.027; p-value=0.905

FIG. 170

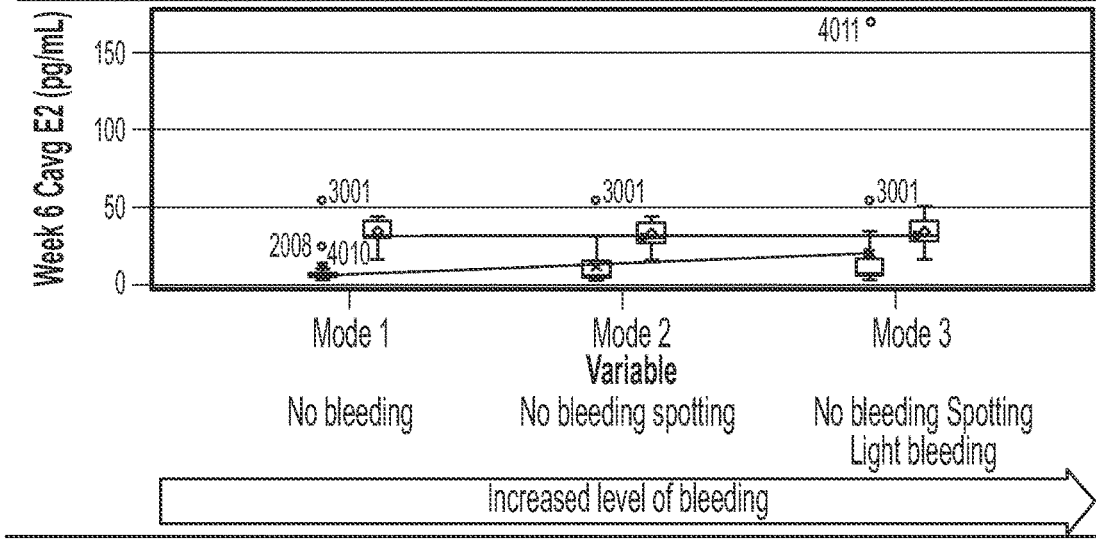

*: Mean Relugolix; ◇: Mean Relugolix and E2/NETA; Solid Line: Median;
Box: 25% and 75% quartiles (IQR); Whiskers: Lowest/highest values within 1.5*IQR of the lower/upper quartiles
Circles: Observations beyond Whiskers
Model 1: No Bleeding; Mode 2: No light/normal/heavy Bleeding; Mode 3: No normal/heavy Bleeding

FIG. 171

Regression equation for Compound 1 (relugolix)=12.178+4.63203 x BMI (kg/m$^2$); n=25; r=0.294; p-value=0.154
Regression equation for Compound 1 and E$_2$/NETA=388.202-9.919759 x BMI (kg/m$^2$); n=23; r=0.346; p-value=0.106

Add New Pain Medication

Select the medication and tap 'Next' to continue.

🔍 Search listed medications

☐ Medication not listed

< Back | Next >

Add New Pain Medication

Do you know the medication name?

If you have taken a medication, which name you are not sure, you may select 'Name not known'.

○ Name known
○ Name not known

< Back | Next >

FIG. 180C (Cont.)

Add New Pain Medication

On the next few pages, you are going to be asked to fill in the details of a new medication:

1. Name or description
2. Strength and unit
3. Route

Tap 'Next' to continue

< Back | Next >

FIG. 180D

Add New Pain Medication

Enter a description of the medication as you know it.

Tap to type:

(Medication description)

The description may be for example "Early morning pain pill", "Large pink heart tablet" or any other text you may use for identifying your medications.

[ ⌄ Back ] [ Next ⌃ ]

Add New Pain Medication

Type the medication strength and select the unit of measure for it.

0 . 00

Tap to select: ▸

If you do not know the strength or the unit, check below.

☐ Strength or unit not known

[ ⌄ Back ] [ Next ⌃ ]

Add New Pain Medication

Please confirm the medication details by tapping 'Save'.

Back | Save

Medication saved

Your new medication has been added to your listed medications.

If you took the added medication pain medicine [Strength or unit not known], Oral, report the intake time and the amount taken by tapping 'Continue'.

If you did not take the added medication, please tap 'Exit' to go back to the reported medications.

Continue

Exit

FIG. 180E (Cont.)

| Concept(s) | Assessment | Item | Subject-reported symptoms and impacts (N=15)* |
|---|---|---|---|
| *Co-primary endpoints* | | | |
| Dysmenorrhea and NMPP | Numerical Rating Scal for Pelvic Pain item of the Symptoms of Endometriosis Scale [Screen 4] | How would you rate your worst pelvic pain in the past 24 hours? [0 = No pain, 10 = Pain as bad as you can imagine] | Pelvic pain 15 (100.0%) S=15 (100.0%), P=0 (0.0%) |
| *Secondary endpoints* | | | |
| Dysmenorrhea | Patient Global Impression of Change (Dysmenorrhea) | Compared to when you started the treatment in this study, painful periods are: Much better Better A little better The same A little worse Worse Much worse Pelvic pain is defined as localized pain in the lower part of the stomach, below the belly button. | |
| NMPP | Patient Global Impression of Change (NMPP) | Compared to when you started the treatment in this study, your pelvic pain when you are not having a period (i.e. not on your period) overall is: Much Better | Pelvic pain 15 (100.0%) S=15 (100.0%), P=0 (0.0%) |

FIG. 183A

| Concept(s) | Assessment | Item | Subject-reported symptoms and impacts (N=15)* |
|---|---|---|---|
| | Subject Biberoglu and Behrman pain Garding Scale (sB&B), Screen 14 | Better<br>A little better<br>The same<br>A little worse<br>Worse<br>Much worse<br>Pelvic pain is defined as localized pain in the lower part of the stomach, below the belly button. | |
| | | Pelvic Pain<br>Severe. Requires strong analgesics.<br>Moderate. Noticeable pelvic pain.<br>Mild. Occasional pelvic pain.<br>No pain. No pelvic pain during past 24 hours. | |
| | Numerical Rating Scale for Dyspareunia item of the symptoms of Endometriosis Scale [SEMS item 3] | How would you rate your worst pelvic pain during vaginal sexual intercourse in the past 24 hours? [0=No pain, 10=Pain as bad as you can imagine]<br>Pelvic pain is defined as localized pain in the lower part of stomach, below the belly button. | Pain during sex<br>9 (60.0%)<br>S=8 (53.3%),<br>P=1 (6.7%) |
| Dyspareunia | Avoidance of sexual intercourse due to pain item in the symptoms of Endometriosis Scale [SEMS item 6] | In the past 24 hours, have you avoided vaginal sexual intercourse because you expected it to be painful? | |
| | Patient Global Impression of Change (Dyspareunia) | Compared to when you started the treatment in this study, your pelvic pain when you have vaginal sexual intercourse is:<br>Much better | |

FIG. 183B

| Concept(s) | Assessment | Item | Subject-reported symptoms and impacts (N=15)* |
|---|---|---|---|
| Global impression of severity of symptoms (pain) | Subject Biberoglu and Behrman pain Garding Scale (sB&B), Screen 15 | Better<br>A little better<br>The same<br>A little worse<br>Worse<br>Much worse<br>Not applicable: I have not had vaginal sexual intercourse since starting the study treatment<br>For this study, we defined vaginal sexual intercourse as penetration of any duration.<br><br>Deep dyspareunia (pain during intercourse)<br>Severe. Avoids intercourse because of pain<br>Moderate. Intercourse painful to the point of causing interruption<br>Mild. Tolerated pain<br>No pain. No pain during intercourse<br>No intercourse. No intercourse for other reasons | |
| | Patient Global Assessment (for pain) | How would you rate your pelvic pain right now?<br>Absent<br>Mild<br>Moderate<br>Severe<br>Very Severe<br>Pelvic pain is defined as localized pain in the lower part of the stomach, below the belly button | Pelvic pain<br>15 (100.0%)<br>S=15 (100.0%),<br>P=0 (0.0%) |

FIG. 183C

METHODS OF TREATING ENDOMETRIOSIS

CROSS-REFERENCE TO RELATED APPLICATIONS

This application is a divisional of U.S. patent application Ser. No. 16/370,299, filed Mar. 29, 2019, now issued as U.S. Pat. No. 11,033,551, which is a continuation application of International Application No. PCT/EP2017/074907, filed Sep. 29, 2017, which claims priority to U.S. Provisional Application No. 62/402,034, filed Sep. 30, 2016; U.S. Provisional Application No. 62/402,055, filed Sep. 30, 2016; U.S. Provisional Application No. 62/402,150, filed Sep. 30, 2016; U.S. Provisional Application No. 62/492,839, filed May 1, 2017; and U.S. Provisional Application No. 62/528,409, filed Jul. 3, 2017; the disclosures of which are incorporated herein by reference in their entireties.

FIELD

The present disclosure generally relates to methods of treating estrogen-sensitive conditions, and more specifically relates to methods of treating uterine fibroids, endometriosis, adenomyosis, heavy menstrual bleeding, or pain associated with uterine fibroids, endometriosis, or adenomyosis in a subject in need thereof. The present disclosure also relates to methods of treating one or more side effects of gonadotropin-releasing hormone (GnRH) antagonist administration.

BACKGROUND

Hormone-sensitive diseases of the reproductive system, such as uterine fibroids, endometriosis, and adenomyosis, can have a significant effect on the quality of life for many women. In these conditions, hormones such as estrogens and progesterone can have an impact on the severity and/or frequency of symptoms.

For example, uterine fibroids are benign, estrogen-sensitive tumors (myomas) that grow in the muscular wall of the uterus in approximately 25% of women of reproductive age. Most uterine fibroids are asymptomatic, but approximately 25% of women with uterine fibroids develop symptoms requiring treatment. In addition to an individual's genetic predisposition, estrogens, progesterone and human growth hormone may all play important roles in the regulation of fibroid growth. Although uterine fibroids are benign tumors that are often asymptomatic, they can cause debilitating symptoms such as abnormal uterine bleeding, heavy or painful periods, anemia, abdominal pain, backache, increased abdominal girth and bloating, urinary frequency or retention, constipation or painful defecation, pregnancy loss, painful intercourse and, in some cases, infertility. Endometriosis is a gynecological medical condition in which cells from the lining of the uterus grow outside the uterine cavity, most commonly on the ovaries. Endometriosis is a chronic and usually progressive disease that occurs almost exclusively in women of reproductive age and can cause nonmenstrual pelvic pain, dysmenorrhea, dyspareunia, and infertility. It has an estimated prevalence of 10% among fertile women and from 20% to 40% among infertile women. Endometriosis lesions outside the uterus exhibit a pattern of hormonal responsiveness similar to that of the lining of the uterus. During the menstrual cycle, the lesions grow, differentiate and shed into the abdomen, thereby inducing a cascade of inflammatory events that may lead to nonmenstrual pelvic pain, pain during menstruation, painful intercourse and, in some cases, infertility. Adenomyosis is a condition distinct from endometriosis where endometrial tissue is found within the myometrium (muscular layer of the uterus). Patients with adenomyosis may experience heavy menstrual bleeding (HMB) and chronic pain, among other symptoms.

Non-surgical therapies for these conditions may include non-steroidal anti-inflammatory drugs, oral contraceptives, and GnRH agonists. Surgical interventions may include hysterectomy and myomectomy and may be used when the non-surgical therapies are unsuccessful in treating symptoms or cease to be effective.

As these conditions are hormone-sensitive, there is an interest in methods of treatment that include regulating one or more hormones, such as estrogen or progesterone, for example using a GnRH agonist (GnRH receptor agonist) or GnRH antagonist (GnRH receptor antagonist). Achieving a balance of estrogen and progesterone that alleviates one or more symptoms while also avoiding serious side effects of hormone suppression is challenging. For example, bone mineral density (BMD) loss may occur if estradiol levels drop below a certain threshold. Bone mineral density loss over time can lead to serious negative effects such as increased bone fracture or osteoporosis. Suppressing progesterone without concurrent estrogen suppression can lead to endometrial hyperplasia, which is a risk factor for endometrial cancer. Conversely, estrogen or progesterone sensitive symptoms and disorders may be aggravated if the estrogen or progesterone levels are above an upper therapeutic limit. The balancing of these hormone interactions is further complicated by the sensitivities of the conditions themselves, as hormone-responsive gynecological conditions are not all responsive to the same levels of estrogen or progesterone. For example, certain conditions exhibit a hierarchy of responsivity to estrogen—myomas (e.g., uterine fibroids) are generally more responsive to estrogen than endometriosis. (See R. L. Barbieri, Am. J. Obstet. Gynecol (1992), 166(2): 740-745). In addition, certain symptoms of one condition may be reduced more readily by suppressing progesterone, while other symptoms of the same condition may respond more readily to estrogen suppression. Thus, the development of a therapy that may be used to treat more than one condition, or more than one symptom, or combinations thereof, is challenging.

GnRH peptide agonists, such as leuprolide acetate (sold by AbbVie Endocrine Inc. under the trademarks LUPRON and LUPANETA), are commonly used for the treatment of benign sex hormone-dependent gynecological diseases, such as endometriosis and uterine fibroids. However, the suppressive effects of GnRH agonists on sex hormone secretion are generally preceded by a transient increase in the secretion of gonadotropins. That is followed by a decrease in responsiveness (desensitization) in the pituitary gland and a decrease in secretion of the pituitary sex hormones luteinizing hormone (LH) and follicle-stimulating hormone (FSH). The initial increase in hormones caused by GnRH agonists can lead to a temporary worsening of symptoms known as clinical flare. This initial stimulatory (or flare) phase, in which LH and FSH are secreted in supraphysiological amounts, may be disadvantageous in sex-steroid-dependent diseases. The temporary worsening of symptoms can include a worsening of HMB. The effectiveness of GnRH agonist therapy does not begin to appear until about 3 to 4 weeks after the initial dose. Further, the complete estrogen withdrawal that results from treatment with GnRH agonists can result in unacceptable side-effects, in particular, accelerated bone mineral density loss. GnRH agonists also cannot be orally administered because they are peptides. In addition, these agonists are only available as depot formulations and it can take months for effects to subside.

In contrast, instead of down regulation and desensitization, GnRH antagonists exhibit a classical competitive blockade of the GnRH receptors on the cell membrane of the gonadotropic cells. Inhibition of GnRH receptors decreases the release of gonadotropins, thereby decreasing the downstream production of estrogen and progesterone in women. Therefore, GnRH antagonists can have a rapid onset of action and achieve hormone suppression more quickly than GnRH agonists. Without any intrinsic agonist activity, the clinical flare associated with GnRH agonists may be completely avoided. Further, the effects of GnRH antagonists may be reversible, and lead to a rapid recovery of gonadal functioning following discontinuation thereof. Therefore, GnRH antagonists may provide more control for patients and their physicians to eliminate any unwanted side-effects of hormone suppression.

On an individual patient basis, the GnRH antagonist treatment strategy has been to "thread the needle" with either a lower dose of antagonist, e.g., elagolix lower dose, or higher dose with add-back, but still not a maximally suppressive dose, or the approach taken with Obseva (which is individual patient titration). Many woman do not respond sufficiently to these treatments. Thus, current GnRH antagonist treatments result in significant variability in women's responses, caused by incomplete suppression by the GnRH antagonist. Across women, likely the present methods and uses may avoid the causes of the variability caused by incomplete suppression by a GnRH antagonist, which would otherwise be added variability on top of the variability caused by dosing the hormones administered in combination. With very suppressive doses, the variability caused by incomplete suppression may be minimized or eliminated, and variability may be due only to hormone dosing.

There have been attempts to combine a hormone replacement medicament with an active ingredient that suppresses sex hormone levels to mitigate the effect that the active ingredient has on bone mineral density loss. However, existing GnRH agonists are generally provided in a dosage form that is separate from the hormone replacement medicament, e.g., an injection followed by either a capsule or tablet. This creates compliance issues for subjects who must remember to take not only the active product ingredient, but also the hormone replacement medicament in the separate dosage form. This presents significant safety concerns for chronic dosing of a GnRH agonist or antagonist, since any adverse effects, e.g., bone mineral density loss, due to lack of compliance will be experienced over an extended period of time. For these and additional reasons, the U.S. Food and Drug Administration has not permitted chronic dosing regimens for GnRH agonists or antagonists to date. As described above, GnRH agonist treatment typically has an initial "flare" period. Administering a hormone replacement medicament starting at the beginning of GnRH agonist treatment can further exacerbate hormonal flare symptoms. Waiting to administer a hormone replacement medicament until hormonal levels are suppressed following the flare can still lead to vasomotor and other symptoms. Selective progesterone receptor modulators (SPRMs) are yet another class of compounds that might be used to modulate the effects of hormones. SPRMs are agents that can have mixed antagonistic and agonistic effects on progesterone receptors in a tissue-specific manner.

Achieving a balance of hormones, symptoms, and side effects in treating a hormone-responsive condition such as uterine fibroids, endometriosis, or adenomyosis can be difficult, as discussed above. Merely combining any GnRH antagonist, GnRH agonist, or SPRM with a hormone replacement medicament may not result in sufficient hormone suppression to adequately treat one or more symptoms, or may not maintain hormone levels high enough to avoid one or more deleterious side effects. In some cases, the blood plasma concentration of one or more hormones in a subject can vary over the course of each day such that neither adequate treatment nor the avoidance of certain side effects is achieved. In other cases, variation or imbalance over a longer period of time, such as over a few months, may prevent a therapy from being used long term, such as for more than 3, 6, or 12 months. For example, certain therapies are prescribed only for intermittent use, requiring the subject to stop treatment for a period of time to reduce the risk of deleterious side effects such as endometrial hyperplasia or bone mineral density loss. Treatment with these therapies may also require additional monitoring of unwanted side effects, such as ultrasound, endometrial biopsy, and/or bone densitometry.

Thus, what is needed is a method for treating hormone-sensitive gynecological conditions, such as uterine fibroids, endometriosis, or adenomyosis, or symptoms associated with such conditions, which effectively treats the condition or symptom while minimizing or avoiding one or more side-effects normally associated with a GnRH antagonist, and helps assure proper dosing so that the GnRH antagonist can be used safely for long-term therapy, and as an alternative to invasive surgical procedures. Further, what is needed is a non-peptide preparation that can be administered orally, preferably once-daily.

SUMMARY

Rather than attempting to achieve a target range of hormones by administration of certain doses of GnRH antagonist to decrease hormone levels, the present methods and uses can employ a very suppressive dose which, when combined with the hormone medicaments described herein, may consistently provide hormone levels in a range that is both efficacious for treating symptoms of e.g., endometriosis, uterine fibroids, adenomyosis, etc. as described herein, while at the same time minimizing side-effects effects normally associated with a GnRH antagonist treatment. Thus, employed as in the methods and uses described herein, the very suppressive doses, when combined with administration of hormones, may lead to a tighter distribution of estradiol levels for many women that are both efficacious with respect to symptoms of the conditions described herein, but while minimizing one or more side-effects of GnRH antagonist treatments.

In one aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in the treatment of one or more of uterine fibroids, endometriosis, adenomyosis, heavy menstrual bleeding, or pain associated with uterine fibroids, endometriosis, or adenomyosis in a pre-menopausal woman.

In some variations, the treatment comprises orally administering the combined preparation to the pre-menopausal woman once-daily for at least 24 consecutive weeks. In certain variations, the progestin is norethindrone or a salt thereof in an amount of about 0.1 mg to about 0.5 mg. In still other variations, the combined preparation comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In other variations, the combined preparation comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations, the combined preparation comprises about 1 mg of estradiol or a corresponding amount of estradiol equivalent. In other variations, the progestin is norethindrone acetate (NETA) and the combined preparation comprises about 0.5 mg NETA.

In other variations, the combined preparation comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In certain variations, the combined preparation is a single dosage form. In other variations, the combined preparation comprises separate dosage forms that are co-administered.

In still other variations, prior to administration of the combined preparation, the treatment further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

In some variations, the combined preparation is for use in the treatment of endometriosis. In other variations, the combined preparation is for use in the treatment of adenomyosis. In still other variations, the combined preparation is for use in the treatment of uterine fibroids.

In some variations, the combined preparation is for use in the treatment of heavy menstrual bleeding. In certain variations, the heavy menstrual bleeding is associated with a non-malignant etiology. In some variations, the heavy menstrual bleeding is associated with one or more of uterine fibroids, endometriosis, or adenomyosis.

In some variations, the combined preparation is for use in the treatment of pain associated with uterine fibroids, endometriosis, or adenomyosis. In certain variations, the pain is associated with endometriosis. In some variations, the pain is chronic pain, dyspareunia, pain associated with defecation, or pain associated with urination.

In another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent, and about 0.01 mg to about 5 mg of a progestin; for simultaneous or sequential use in a method of maintaining bone mineral density in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In some variations, the method comprises orally administering the combined preparation to the pre-menopausal woman once-daily for at least 24 consecutive weeks.

In still another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in the treatment of one or more of hot flashes, night sweats and other vasomotor symptoms in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In some variations, the treatment comprises orally administering the combined preparation to the pre-menopausal woman once-daily for at least 24 consecutive weeks.

In another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in a method for maintaining one or both of lipid profile or blood glucose range in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations, the method comprises orally administering the combined preparation to the pre-menopausal woman once-daily for at least 24 consecutive weeks.

In other variations, or more of the pre-menopausal woman's lipid profile or blood glucose range does not change in a clinically meaningful way after or during treatment as compared to the lipid profile or blood glucose range prior to treatment.

In a further aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in a method for treating one or both of vulvovaginal atrophy or vaginal dryness in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In some variations, the method comprises orally administering the combined preparation to the pre-menopausal woman once-daily for at least 24 consecutive weeks.

In still another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in the treatment of headache in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations, the treatment comprises orally administering the combined preparation to the pre-menopausal woman once-daily for at least 24 consecutive weeks.

In certain variations, the headache is a migraine associated with the menstrual cycle.

In another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in a method of contraception in a pre-menopausal woman in need thereof.

In some variations, the method comprises orally administering the combined preparation to the pre-menopausal woman once-daily for at least 24 consecutive weeks.

In some variations, of any of the above aspects, the progestin is norethindrone or a salt thereof in an amount of about 0.1 mg to about 0.5 mg. In certain variations, the combined preparation comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In still further variations, the combined preparation comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations, the combined preparation is a single dosage form. In other variations, the combined preparation comprises separate dosage forms that are co-administered.

In some variations, the combined preparation comprises about 1 mg of estradiol or a corresponding amount of estradiol equivalent. In other variations, the progestin is norethindrone acetate (NETA) and the combination comprises about 0.5 mg NETA.

In certain variations, the combined preparation comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations, prior to administration of the combined preparation, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

In another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in a method of achieving amenorrhea in a pre-menopausal woman for at least 12 or at least 24 weeks. In some variations, the method comprises orally administering the combined preparation to the pre-menopausal woman once-daily for at least 12 or at least 24 consecutive weeks.

In another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in a method of improving fertility or preventing miscarriages in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In some variations, the method comprises orally administering the combined preparation to the pre-menopausal woman once-daily for at least 12 or at least 24 consecutive weeks, and discontinuing the treatment for at least 4 weeks while the woman attempts or re-attempts conception.

In still another aspect, provided herein is a combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; for simultaneous or sequential use in the treatment of anemia in a pre-menopausal woman. In one variation, the method comprises orally administering the combined preparation to the pre-menopausal woman once-daily for at least 12 or at least 24 consecutive weeks.

In some variations, the pre-menopausal woman is experiencing heavy menstrual bleeding. In certain variations, the heavy menstrual bleeding is associated with a non-malignant etiology.

In still other variations, the pre-menopausal woman has one or more of uterine fibroids, endometriosis, adenomyosis, heavy menstrual bleeding, or symptoms related to one or more of uterine fibroids, endometriosis, or adenomyosis.

In some variations of any of the above aspects, administration of the combined preparation is once-daily for at least 48 consecutive weeks, at least 72 consecutive weeks, or at least 96 consecutive weeks.

In certain variations, administration of the combined preparation is suspended for conception and pregnancy. In some variations, administration is resumed after delivery.

In other variations, the combined preparation is administered pre-prandial. In some variations, the administering is at least 30 minutes before eating or while subject is fasting. In certain variations, the combined preparation is administered at least 1 hour before eating or at least 2 hours after eating.

In some variations, the combined preparation is administered as one or more immediate release dosage forms.

In still another aspect, provided herein is a combined preparation of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 1.5 mg to about 5.0 mg of estradiol or a corresponding amount of estradiol equivalent; and about 0.5 mg to about 2.0 mg norethindrone acetate or other progestin; for simultaneous or sequential use in the treatment of symptomatic uterine fibroids or endometriosis in a pre-menopausal woman.

In some variations, the treatment comprises administering the combined preparation to said woman once-daily. In certain variations, administration of the combined preparation suppresses the endometrium. In some variations, the combined preparation is in a single dosage form.

In another aspect, provided herein is a combined preparation of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a pharmaceutically acceptable salt thereof; about 1.5 mg to about 5 mg estradiol or a corresponding amount of estradiol equivalent; and about 0.5 mg to about 2.0 mg norethindrone acetate or other progestin; for simultaneous or sequential use in the treatment of one or more of hot flashes and other vasomotor symptoms and bone mineral density loss in a pre-menopausal woman who continues to have one or more of hot flashes and other vasomotor symptoms and bone mineral density loss when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, wherein the treatment comprises administering the combined preparation to said pre-menopausal woman. In one variation, administration of the combined preparation suppresses endometrial tissue.

In one aspect, provided is a method for treating one or more of uterine fibroids, endometriosis or adenomyosis in a pre-menopausal woman in need thereof, the method comprising orally administering to the pre-menopausal woman once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (Compound 1), or a corresponding amount of a pharmaceutically acceptable salt thereof, about 0.5 mg to about 2 mg of estradiol or a corresponding amount of estradiol equivalent; and about 0.01 mg to about 5 mg of a progestin. In some variations, the progestin is norethindrone or a salt thereof in an amount of about 0.1 mg to about 0.5 mg.

In some variations, the pre-menopausal woman is treated for endometriosis. In other variations, the pre-menopausal woman is treated for adenomyosis. In still further variations, the pre-menopausal woman is treated for uterine fibroids.

In another aspect, provided is a method for treating heavy menstrual bleeding in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

In some variations, the heavy menstrual bleeding is associated with a non-malignant etiology. In certain variations, the heavy menstrual bleeding is associated with one or more of uterine fibroids, endometriosis, or adenomyosis.

In still another aspect, provided herein is a method for treating pain associated with uterine fibroids, endometriosis, or adenomyosis in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

In some variations, the pain is associated with endometriosis. In some variations, the pain is chronic pain, dyspareunia, pain associated with defecation, or pain associated with urination.

In certain variations of the preceding methods, after treatment is discontinued, said pre-menopausal woman conceives or gives birth. In some variations, prior to treatment the pre-menopausal women experienced one or more miscarriages or an inability to conceive or a combination thereof.

In one aspect, provided is a method for maintaining bone mineral density in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent, and about 0.01 mg to about 5 mg of a progestin.

In another aspect, provided is a method for treating one or more of hot flashes, night sweats, or vasomotor symptoms other than hot flashes or night sweats in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

In yet another aspect, provided is a method for maintaining one or both of lipid profile or blood glucose range in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; wherein one or more of the pre-menopausal woman's lipid profile or blood glucose range does not change in a clinically meaningful way after or during treatment as compared to the lipid profile or blood glucose range prior to treatment.

In another aspect, provided is a method for treating one or both of vulvovaginal atrophy or vaginal dryness in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

In still another aspect, provided is also a method for treating headache in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin. In some variations, the headache is a migraine associated with the menstrual cycle.

In one aspect, provided is a method of contraception in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

In certain variations of any of the methods above, the progestin is norethindrone or a salt thereof in an amount of about 0.1 mg to about 0.5 mg. In other variations, the combination comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. In certain variations, the combination comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations of any of the methods provided above, the combination is a single dosage form. In other variations of the methods provided above, the combination comprises separate dosage forms that are co-administered.

In other variations of any of the methods above, the combination comprises about 1 mg of estradiol or a corresponding amount of estradiol equivalent.

In still other variations of any of the methods above, the progestin is norethindrone acetate (NETA) and the combination comprises about 0.5 mg NETA.

In certain variations of any of the methods above, the combination comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2, 4-dioxo-1,2,3,4-tetrahydrothieno[2,3-d]pyrimidin-6-yl)phenyl)-N'-methoxyurea, or a corresponding amount of a pharmaceutically acceptable salt thereof.

In some variations of any of the methods above, the treatment results in one or both of contraception and amenorrhea during treatment.

In other variations of any of the methods above, after at least 4 consecutive weeks of administration of the combination, the pre-menopausal woman's ovarian estrogen production is suppressed.

In yet other variations of any of the methods above, after at least 4 consecutive weeks of administration of the combination, the pre-menopausal woman's serum estradiol concentration is between 20 pg/ml and 50 pg/ml between daily doses of the combination.

In certain variations of any of the methods above, after at least 4 consecutive weeks of administration of the combination, the pre-menopausal woman's ovarian progesterone production is suppressed.

In still other variations of any of the methods above, after at least 4 consecutive weeks of administration of the combination, the pre-menopausal woman's serum progesterone concentration is less than about 5 ng/ml between daily doses of the combination.

In some variations of any of the methods above, for a pre-menopausal woman with uterine fibroids, one or both of the number and size of the uterine fibroids are reduced during and/or after treatment compared to one or both of the number and size of the uterine fibroids prior to treatment.

In certain variations of any of the methods above, prior to administration of the combination, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

In some variations of any of the methods above, during and/or after treatment, the pre-menopausal woman experiences an improvement in one or more of the following symptoms, which are selected from the group consisting of anemia, irregular periods, spotting, inflammation, pain, fatigue, urinary obstruction, urinary frequency, incontinence, constipation, anxiety, sleep disturbance, quality of life, activities of daily living, female sexual dysfunction, and depression. In some variations, the pain is chronic pain. In other variations, the pain is dyspareunia. In still further variations, the pain is pain with defecation or pain with urination.

In one aspect, provided is a method of achieving amenorrhea in a pre-menopausal woman in need thereof for at least 12 or at least 24 weeks, the method comprising orally administering to the pre-menopausal woman in need thereof once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

In another aspect, provided is a method for preventing miscarriages in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; and discontinuing the treatment for at least 4 weeks while the woman re-attempts conception.

In still another aspect, provided is a method for improving fertility in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; and discontinuing the treatment for a time period of at least 4 weeks while the pre-menopausal woman attempts conception. In some variations, after treatment is discontinued, said pre-menopausal woman conceives or gives birth. In certain variations, prior to treatment the pre-menopausal women experienced one or more miscarriages, an inability to conceive, or a combination thereof.

In one aspect, provided is a method of treating anemia in a pre-menopausal woman in need thereof, the method comprising orally administering to the pre-menopausal woman once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

In certain variations, the pre-menopausal woman is experiencing heavy menstrual bleeding. In some variations, the heavy menstrual bleeding is associated with a non-malignant etiology.

In some variations of the method above, the pre-menopausal woman has one or more of uterine fibroids, endometriosis, adenomyosis, heavy menstrual bleeding, or symptoms related to one or more of uterine fibroids, endometriosis, or adenomyosis.

In certain variations of any of the methods above, administration of the combination is once-daily for at least 48 consecutive weeks, at least 72 consecutive weeks, or at least 96 consecutive weeks.

In other variations of any of the methods above, administration of the combination is suspended for conception and pregnancy. In some variations, administration is resumed after delivery.

In some variations of any of the methods above, the combination is administered pre-prandial. In other variations of any of the methods above, the administering is at least 30 minutes before eating, or while subject is fasting. In some variations of any of the methods above, the combination is administered at least 1 hour before eating or at least 2 hours after eating.

In certain variations of any of the methods above, the combination is administered as one or more immediate release dosage forms.

In other variations of any of the methods above, the pre-menopausal woman's bone mineral density during and/or after treatment is within ±2% of the pre-menopausal woman's bone mineral density prior to treatment.

In another aspect, provided herein is also a method of treating a pre-menopausal woman with symptomatic uterine fibroids or endometriosis, the method comprising administering to said woman once-daily a combination of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.5 mg to about 5.0 mg of estradiol or a corresponding amount of estradiol equivalent; and about 0.5 mg to about 2.0 mg norethindrone acetate or other progestin, and wherein administration of the combination suppresses the endometrium. In some variations, the combination is effective in treating the symptoms of the uterine fibroids or endometriosis and reducing one or more side effects including one or more of hot flashes, night sweats, bone mineral density loss, or vasomotor symptoms other than hot flashes or night sweats. In certain variations, the combination is in a single dosage form.

In still another aspect, provided herein is a method of treating a pre-menopausal woman who continues to have one or more of hot flashes, night sweats, vasomotor symptoms other than hot flashes or night sweats, or bone mineral density loss when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, the method comprising administering to said pre-menopausal woman a combination of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a pharmaceutically acceptable salt thereof; about 1.5 mg to about 5 mg estradiol or a corresponding amount of estradiol equivalent; and about 0.5 mg to about 2.0 mg norethindrone acetate or other progestin, and where administration of the combination suppresses endometrial tissue.

In one aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or more of uterine fibroids, endometriosis or adenomyosis in a pre-menopausal woman.

In another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of heavy menstrual bleeding in a pre-menopausal woman.

In yet another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and a progestin for the manufacture of a medicament for the treatment of pain associated with uterine fibroids, endometriosis, or adenomyosis in a pre-menopausal woman. In some variations, the pain is chronic pain, dyspareunia, pain associated with defecation, or pain associated with urination.

In still another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for maintaining bone mineral density in a pre-menopausal woman.

In another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or more of hot flashes, night sweats and other vasomotor symptoms in a pre-menopausal woman.

In one aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for maintaining one or both of lipid profile or blood glucose range in a pre-menopausal woman.

In another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or both of vulvovaginal atrophy or vaginal dryness in a pre-menopausal woman.

In still a further aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of headache in a pre-menopausal woman.

In one aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for contraception in a pre-menopausal woman.

In some variations, the pre-menopausal woman has been treated with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea for one or more of uterine fibroids, endometriosis, adenomyosis or heavy menstrual bleeding.

In another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for achieving amenorrhea in a pre-menopausal woman.

In one aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for preventing miscarriages in a pre-menopausal woman.

In still another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for improving fertility in a pre-menopausal woman.

In another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of anemia in a pre-menopausal woman.

In some variations of any of the uses above, the medicament contains about 10 mg to about 60 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof, about 0.5 mg to about 2 mg of the estradiol or a corresponding amount of the estradiol equivalent; and about 0.01 mg to about 5 mg of the progestin.

In one aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and norethindrone acetate or other progestin for the manufacture of a medicament for treating symptomatic uterine fibroids or endometriosis in a pre-menopausal woman. In some variations, the medicament contains about 65 mg to about 140 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof, about 1.5 mg to about 5.0 mg of the estradiol or a corresponding amount of the estradiol equivalent; and about 0.5 mg to about 2.0 mg of the norethindrone acetate or other progestin.

In still another aspect, provided herein is use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and norethindrone acetate or other progestin for the manufacture of a medicament for treating a pre-menopausal woman who continues to have one or more of hot flashes and other vasomotor symptoms and bone mineral density loss when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, wherein the medicament contains about 65 mg to about 140 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof, about 1.5 mg to about 5.0 mg of the estradiol or a corresponding amount of the estradiol equivalent; and about 0.5 mg to about 2.0 mg of the norethindrone acetate or other progestin.

Other objects and advantages of the present disclosure will become apparent from the detailed description that follows.

BRIEF DESCRIPTION OF THE DRAWINGS

Embodiments of the present disclosure are described more fully hereinafter with reference to the accompanying drawings, in which some, but not all, embodiments of the disclosure are shown. Like numbers refer to like elements throughout.

FIG. 1 is an illustrative Pictorial Blood Loss Assessment Chart score sheet for evaluating menstrual blood loss volume.

FIG. 2 is an illustrative Numerical Rating Scale (NRS) score sheet for measuring uterine fibroid pain.

FIGS. 3A-C show questions from an illustrative Uterine Fibroid Symptom and Health-Related Quality of Life (UFS-QOL) questionnaire used for quality of life analyses.

FIG. 4 is a table of the dose escalation scheme for Cohorts 1-10 in accordance with Example 4.

FIGS. 5A-C are tables of plasma pharmacokinetic (PK) parameters for Cohorts 1 to 6 in accordance with Example 4.

FIGS. 6A-C are tables of plasma PK parameters for Cohort 7 in accordance with Example 4.

FIGS. 7A-F are tables of plasma PK parameters for Cohorts 8 to 10 in accordance with Example 4.

FIG. 8 is a table of plasma and urine PK parameters for Cohorts 1 to 6 in accordance with Example 4.

FIG. 9 is table of plasma and urine PK parameters for Cohort 7 in accordance with Example 4.

FIG. 10 is a table of urine PK parameters for Cohort 7 in accordance with Example 4.

FIG. 11 is a table of plasma and urine PK parameters for Cohorts 8 to 10 on Days 1 and 14 of the treatment period in accordance with Example 4.

FIG. 12 is a table of urine PK parameters for Cohorts 8 to 10 on Day 1 of the treatment period in accordance with Example 4.

FIG. 13 is a table of urine PK parameters for Cohorts 8 to 10 on Day 14 of the treatment period in accordance with Example 4.

FIG. 14 shows a statistical analysis of plasma PK parameters in the fed and fasted states in accordance with Example 4.

FIG. 16 shows a steady-state assessment of plasma concentrations of Compound 1 for Cohorts 8 to 10 in accordance with Example 4.

FIGS. 30A-H are tables of demographic and baseline characteristics in accordance with Example 5A.

FIG. 31 is a table of total Pictorial Blood Loss Assessment Chart (PBAC) scores from Weeks 6 to 12 for a treatment period of 12 weeks in accordance with Example 5A.

FIG. 32 is a table of total Pictorial Blood Loss Assessment Chart (PBAC) scores from Weeks 6 to 12 showing change from baseline for a treatment period of 12 weeks in accordance with Example 5A.

FIG. 33 is a table of proportion of subjects with a total Pictorial Blood Loss Assessment Chart (PBAC) score of less than 10 from Weeks 6 to 12, compared with uterine volume at baseline for a treatment period of 12 weeks in accordance with Example 5A.

FIG. 34 is a table of myoma volumes for a treatment period of 12 weeks in accordance with Example 5A.

FIG. 35 is a table of uterine volumes for a treatment period of 12 weeks in accordance with Example 5A.

FIG. 37 is a table of plasma concentrations of unchanged Compound 1 depicted in FIG. 36.

FIG. 39 is a table of plasma concentrations of unchanged Compound 1 depicted in FIG. 38.

FIG. 40 is a table of plasma concentrations of unchanged Compound 1 for a treatment period of 12 weeks in which Compound 1 was not administered 30 minutes before a meal.

FIG. 41 is a table of NRS scores measuring pain symptoms for a treatment period of 12 weeks in accordance with Example 5A.

FIG. 42 is a table of UFS-QOL scores measuring symptom severity for a treatment period of 12 weeks in accordance with Example 5A.

FIG. 43 is a table of UFS-QOL scores (Health Related Quality of Life (HRQL) Total) for a treatment period of 12 weeks in accordance with Example 5A.

FIG. 44 is a table of UFS-QOL scores measuring the effect of uterine fibroids on a subject's level of concern for a treatment period of 12 weeks in accordance with Example 5A.

FIG. 45 is a table of UFS-QOL scores measuring a subject's activities for a treatment period of 12 weeks in accordance with Example 5A.

FIG. 46 is a table of UFS-QOL scores measuring a subject's energy/mood for a treatment period of 12 weeks in accordance with Example 5A.

FIG. 47 is a table of UFS-QOL scores measuring a subject's level of control for a treatment period of 12 weeks in accordance with Example 5A.

FIG. 48 is a table of UFS-QOL scores measuring a subject's self-consciousness for a treatment period of 12 weeks in accordance with Example 5A.

FIG. 49 is a table of UFS-QOL scores measuring a subject's sexual function for a treatment period of 12 weeks in accordance with Example 5A.

FIG. 50 is a table of hemoglobin concentrations for a treatment period of 12 weeks in accordance with Example 5A.

FIG. 51 is a table of hemoglobin concentrations in subjects taking iron drug concomitant medications for a treatment period of 12 weeks in accordance with Example 5A.

FIG. 52 is a table of hemoglobin concentrations in subjects not taking iron drug concomitant medications for a treatment period of 12 weeks in accordance with Example 5A.

FIG. 53 is a table of hematocrit percentage for a treatment period of 12 weeks in accordance with Example 5A.

FIG. 54 is a table of serum iron concentrations for a treatment period of 12 weeks in accordance with Example 5A.

FIG. 55 is a table of ferritin concentrations for a treatment period of 12 weeks in accordance with Example 5A.

FIG. 57 is a table of serum LH concentrations depicted in FIGS. 56A-D.

FIG. 59 is a table of serum FSH concentrations depicted in FIGS. 58A-D.

FIG. 61 is a table of serum estradiol ($E_2$) concentrations depicted in FIGS. 60A-D.

FIG. 63 is a table of serum progesterone concentrations depicted in FIGS. 62A-D.

FIG. 64 is a table showing the return of menstrual cycles following administering placebo or one of the three Compound 1 formulations (10 mg, 20 mg and 40 mg) for a treatment period of 12 weeks in accordance with Example 5A.

FIGS. 65A-C are a portion of questions included in the patient diary in accordance with Example 6.

FIGS. 66A-B are questions from an illustrative Work Product and Activity Impairment Questionnaire (General Health) used for quality of life analyses.

FIG. 67 is an illustrative Patient Global Impression of Change Questionnaire for determining change in uterine fibroid symptoms since starting treatment.

FIG. 71 is a table of plasma concentrations of unchanged Compound 1 depicted in FIG. 70.

FIG. 73 is a table of plasma concentrations of unchanged Compound 1 depicted in FIG. 72.

FIG. 75 is a table of plasma concentrations of unchanged Compound 1 depicted in FIG. 74.

FIGS. 76A-C is a table of demographic and baseline characteristics in accordance with Example 8.

FIGS. 78A-B is a table of serum LH concentrations depicted in FIG. 77.

FIGS. 80A-B is a table of serum FSH concentrations depicted in FIG. 79.

FIGS. 82A-B is a table of serum estradiol ($E_2$) concentrations depicted in FIG. 81.

FIGS. 84A-B is a table of serum progesterone concentrations depicted in FIG. 83.

FIG. 85 is a table of biochemical endometriosis marker (CA125) concentrations for a treatment period of 24 weeks in accordance with Example 8.

FIG. 86 is a table of percent changes from baseline in biochemical endometriosis marker (CA125) concentrations for a treatment period of 24 weeks in accordance with Example 8.

FIG. 88 is a table of the mean of VAS scores by visit for pelvic pain depicted in FIG. 87.

FIG. 90 is a table of changes from baseline in mean of VAS scores by visit depicted in FIG. 89.

FIG. 91 is a table of changes from baseline in mean of VAS scores by visit (comparison with leuprolide acetate) for pelvic pain for a treatment period of 168 days in accordance with Example 8.

FIG. 93 is a table of the mean of VAS scores by visit for dyspareunia depicted in FIG. 92.

FIG. 95 is a table of changes from baseline in mean of VAS scores by visit for dyspareunia depicted in FIG. 94.

FIG. 96 is a table of changes from baseline in mean of VAS scores by visit (comparison with leuprolide acetate) for dyspareunia for a treatment period of 168 days in accordance with Example 8.

FIG. 98 is a table of the mean of VAS scores by visit for dysmenorrhea depicted in FIG. 97.

FIG. 100 is a table of changes from baseline in mean of VAS scores by visit for dysmenorrhea depicted in FIG. 99.

FIG. 101 is a table of changes from baseline in mean of VAS scores by visit (comparison with leuprolide acetate) for dysmenorrhea for a treatment period of 168 days in accordance with Example 8.

FIG. 102 is a table of the mean of modified Biberoglu & Behrman (M-B&B) scores for pelvic pain for a treatment period of 168 days in accordance with Example 8.

FIG. 103 is a table of the mean of M-B&B scores for dysmenorrhea for a treatment period of 168 days in accordance with Example 8.

FIG. 104 is a table of the mean of M-B&B scores for deep dyspareunia for a treatment period of 168 days in accordance with Example 8.

FIG. 105 is a table of changes from baseline in the mean of M-B&B scores for pelvic pain for a treatment period of 168 days in accordance with Example 8.

FIG. 106 is a table of changes from baseline in the mean of M-B&B scores for dysmenorrhea for a treatment period of 168 days in accordance with Example 8.

FIG. 107 is a table of changes from baseline in the mean of M-B&B scores for deep dyspareunia for a treatment period of 168 days in accordance with Example 8.

FIG. 108 is a table of changes from baseline in the mean of M-B&B scores (comparison with leuprolide acetate) for pelvic pain for a treatment period of 168 days in accordance with Example 8.

FIG. 109 is a table of changes from baseline in the mean of M-B&B scores (comparison with leuprolide acetate) for dysmenorrhea for a treatment period of 168 days in accordance with Example 8.

FIG. 110 is a table of changes from baseline in the mean of M-B&B scores (comparison with leuprolide acetate) for deep dyspareunia for a treatment period of 168 days in accordance with Example 8.

FIG. 111 is a table of the mean of Biberoglu & Behrman (B&B) scores by visit for dysmenorrhea for a treatment period of 24 weeks in accordance with Example 8.

FIG. 112 is a table of the mean of B&B scores by visit for dyspareunia for a treatment period of 24 weeks in accordance with Example 8.

FIG. 113 is a table of the mean of B&B scores by visit for pelvic pain for a treatment period of 24 weeks in accordance with Example 8.

FIG. 114 is a table of the mean of B&B scores by visit for pelvic tenderness for a treatment period of 24 weeks in accordance with Example 8.

FIG. 115 is a table of the mean of B&B scores by visit for induration for a treatment period of 24 weeks in accordance with Example 8.

FIG. 116 is a table of changes from baseline in the mean of B&B scores by visit for dysmenorrhea for a treatment period of 24 weeks in accordance with Example 8.

FIG. 117 is a table of changes from baseline in the mean of B&B scores by visit for dyspareunia for a treatment period of 24 weeks in accordance with Example 8.

FIG. 118 is a table of changes from baseline in the mean of B&B scores by visit for pelvic pain for a treatment period of 24 weeks in accordance with Example 8.

FIG. 119 is a table of changes from baseline in the mean of B&B scores by visit for pelvic tenderness for a treatment period of 24 weeks in accordance with Example 8.

FIG. 120 is a table of changes from baseline in the mean of B&B scores by visit for induration for a treatment period of 24 weeks in accordance with Example 8.

FIG. 121 is a table of proportion of days with usage of a pain killer for a treatment period of 168 days in accordance with Example 8.

FIG. 122 is a table of changes from baseline in proportion of days with usage of a pain killer for a treatment period of 168 days in accordance with Example 8.

FIG. 123 is a table of changes from baseline in proportion of days with usage of a pain killer (comparison with leuprolide acetate) for a treatment period of 168 days in accordance with Example 8.

FIG. 124 is a table of mean of amount of bleeding for a treatment period of 168 days in accordance with Example 8.

FIG. 125 is a table of changes from baseline in mean of amount of bleeding for a treatment period of 168 days in accordance with Example 8.

FIG. 126 is a table of changes from baseline in mean of amount of bleeding (comparison with leuprolide acetate) for a treatment period of 168 days in accordance with Example 8.

Figure 15A:
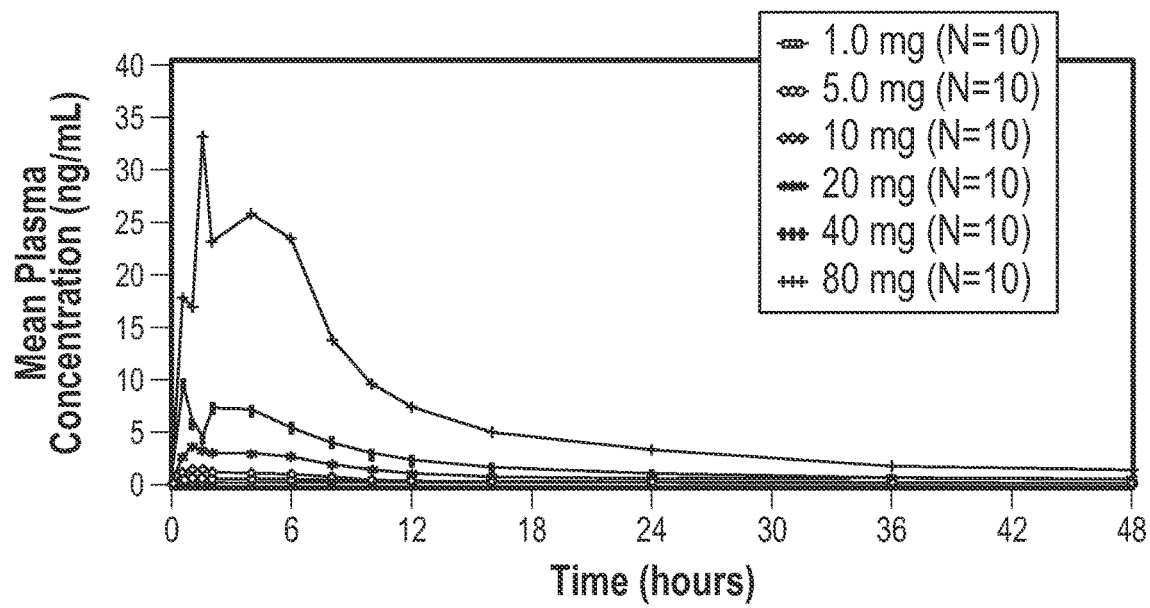
FIGS. 15A and 15B graphically depict mean plasma concentrations versus time profiles following single doses of Compound 1 in accordance with Example 4.

FIGS. 127A-B is a table of the number of subjects who achieved amenorrhea for a treatment period of 168 days in accordance with Example 8.

FIG. 128 is a table of the proportion of subjects who achieved amenorrhea (comparison with leuprolide acetate) for a treatment period of 168 days in accordance with Example 8.

FIG. 129 is a table of statistics for quality of life (QOL) by the Endometriosis Health Profile-30 (EHP-30) with respect to pain for a treatment period of 24 weeks in accordance with Example 8.

FIG. 130 is a table of statistics for QOL (EHP-30) with respect to control & powerlessness for a treatment period of 24 weeks in accordance with Example 8.

FIG. 131 is a table of statistics for QOL (EHP-30) with respect to emotional well-being for a treatment period of 24 weeks in accordance with Example 8.

FIG. 132 is a table of statistics for QOL (EHP-30) with respect to social support for a treatment period of 24 weeks in accordance with Example 8.

FIG. 133 is a table of statistics for QOL (EHP-30) with respect to self image for a treatment period of 24 weeks in accordance with Example 8.

FIG. 134 is a table of statistics for change from baseline in QOL (EHP-30) with respect to pain for a treatment period of 24 weeks in accordance with Example 8.

FIG. 135 is a table of statistics for change from baseline in QOL (EHP-30) with respect to control and powerlessness for a treatment period of 24 weeks in accordance with Example 8.

FIG. 136 is a table of statistics for change from baseline in QOL (EHP-30) with respect to emotional well-being for a treatment period of 24 weeks in accordance with Example 8.

FIG. 137 is a table of statistics for change from baseline in QOL (EHP-30) with respect to social support for a treatment period of 24 weeks in accordance with Example 8.

FIG. 138 is a table of statistics for change from baseline in QOL (EHP-30) with respect to self-image for a treatment period of 24 weeks in accordance with Example 8.

FIG. 139 is a table of statistics for change from baseline in QOL (EHP-30) (comparison with leuprolide acetate) with respect to pain for a treatment period of 24 weeks in accordance with Example 8.

FIG. 140 is a table of statistics for change from baseline in QOL (EHP-30) (comparison with leuprolide acetate) with respect to control and powerlessness for a treatment period of 24 weeks in accordance with Example 8.

FIG. 141 is a table of statistics for change from baseline in QOL (EHP-30) (comparison with leuprolide acetate) with respect to emotional well-being for a treatment period of 24 weeks in accordance with Example 8.

FIG. 142 is a table of statistics for change from baseline in QOL (EHP-30) (comparison with leuprolide acetate) with respect to social support for a treatment period of 24 weeks in accordance with Example 8.

FIG. 143 is a table of statistics for change from baseline in QOL (EHP-30) (comparison with leuprolide acetate) with respect to self-image for a treatment period of 24 weeks in accordance with Example 8.

FIG. 144 is an illustrative endometriosis pain questionnaire used for psychometric analyses.

FIG. 145 is an illustrative M-B&B grading scale used for dysmenorrhea, pelvic pain, and deep dyspareunia.

FIGS. 146A-C is an illustrative Symptoms of Endometriosis Scale (SEMS) used for psychometric analyses.

Figure 147D:
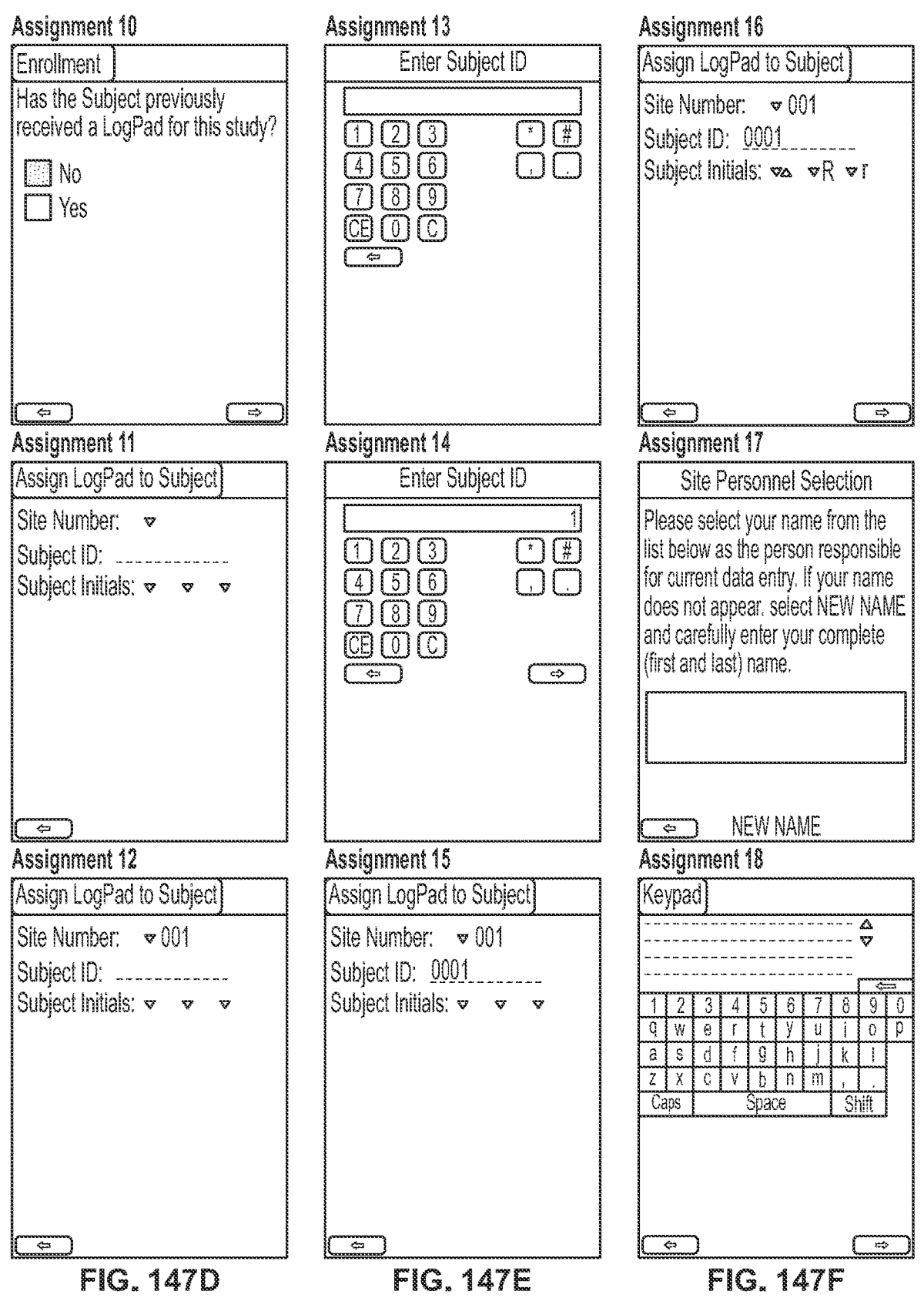

FIGS. 147A-M is an illustrative electronic Symptoms of Endometriosis Scale (SEMS) used for psychometric analyses.

FIGS. 148A-C is an illustrative mood states form used for psychometric analyses.

FIGS. 149A-C is an illustrative baseline clinical questionnaire used for psychometric analyses.

FIGS. 150A-B is an illustrative final clinical questionnaire used for psychometric analyses.

FIGS. 151A-E is an illustrative Endometriosis Health Profile (EHP-30) questionnaire used for quality of life analyses.

Figures 152A, 152B:
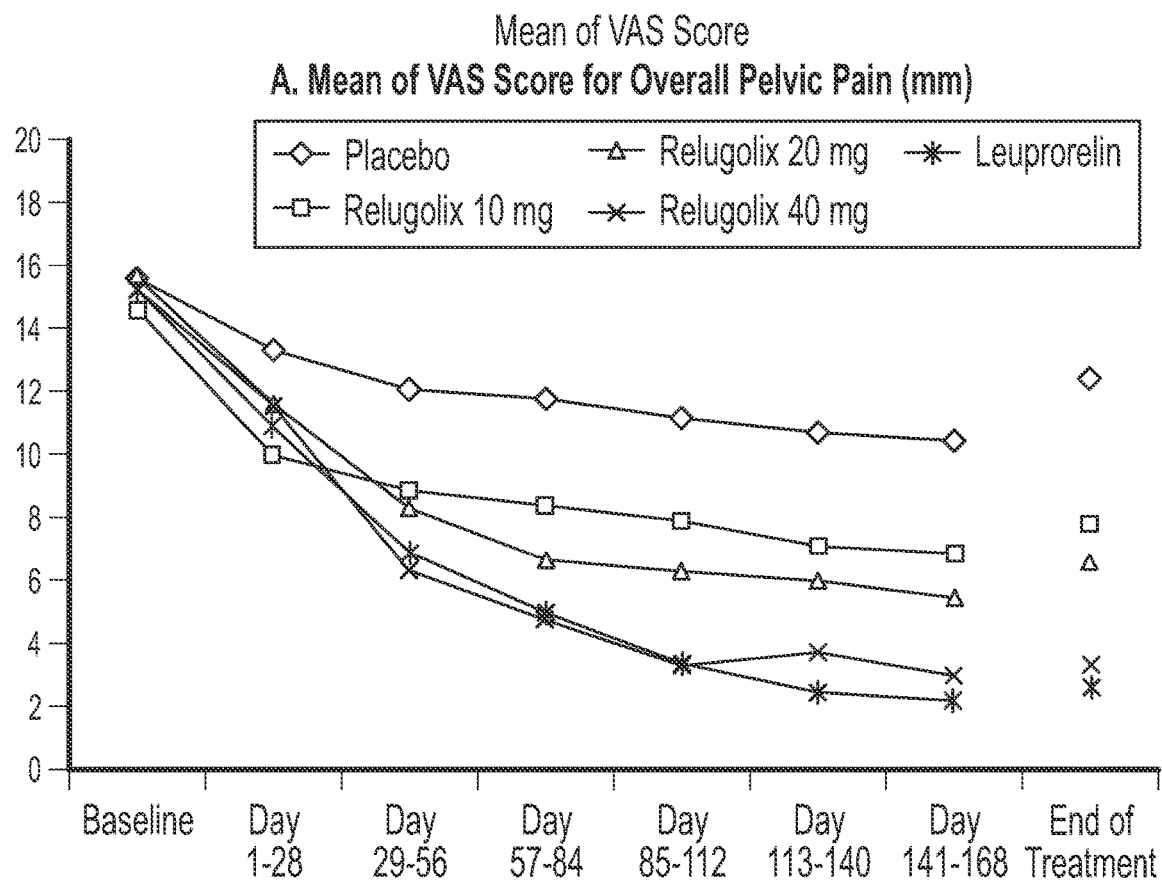

FIG. 152A (graph) and FIG. 152B (table) report the mean VAS score for overall pelvic pain (mm) according to Example 8A.

Figures 153A, 153B:
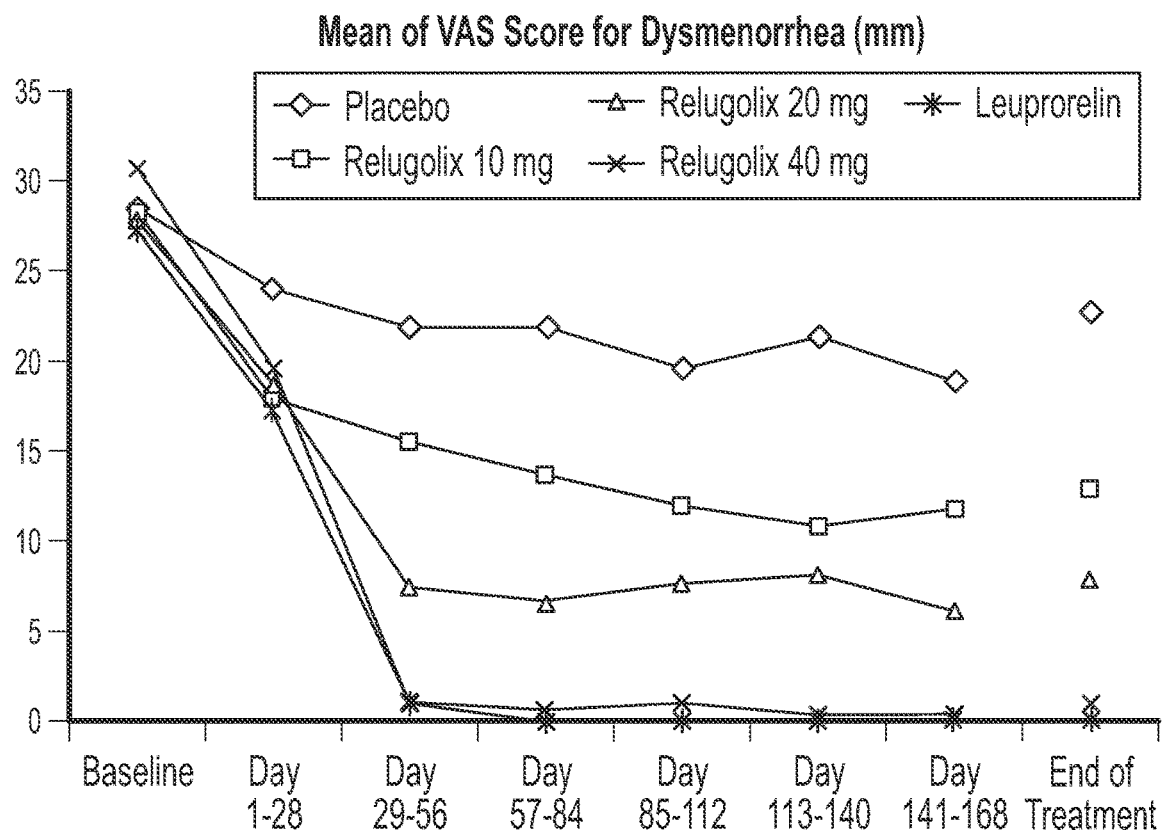

FIG. 153A and FIG. 153B (table) report the mean VAS score for dysmenorrhea (mm) according to Example 8A.

Figures 154A, 154B:
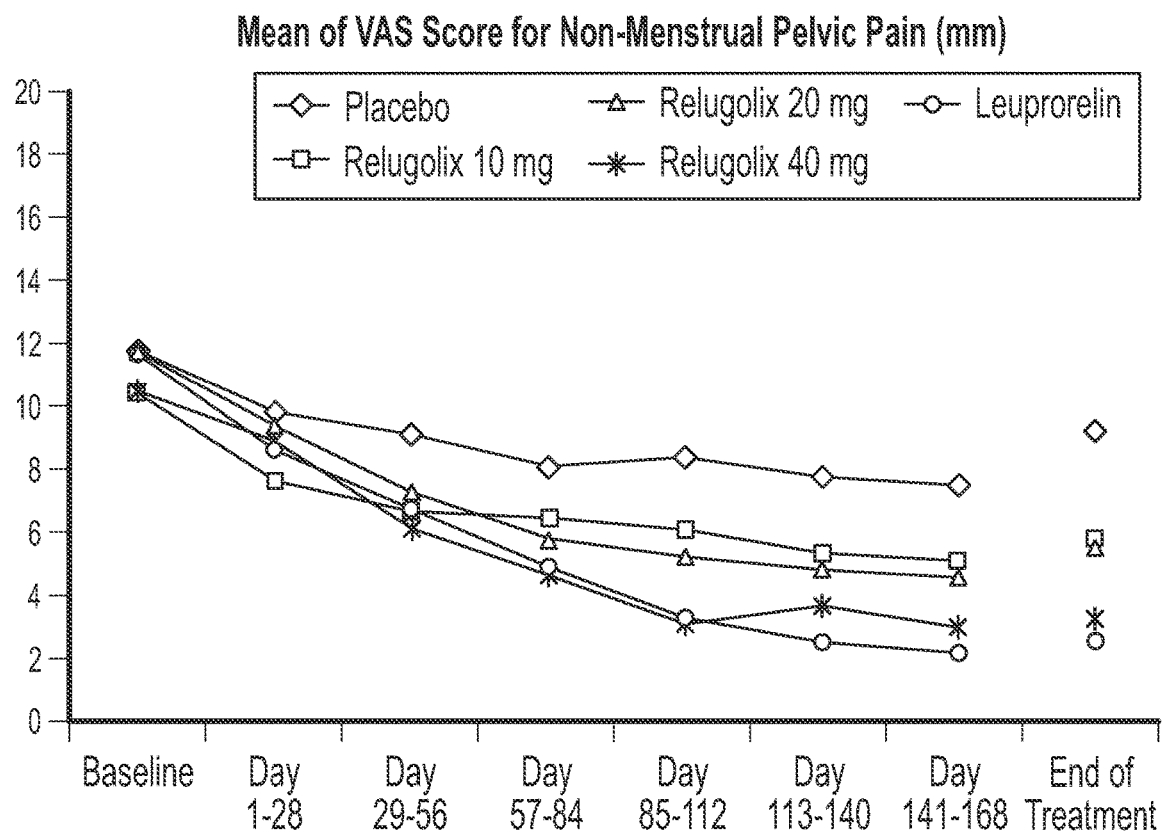

FIG. 154A and FIG. 154B (table) report the mean VAS score for nonmenstrual pelvic pain (mm) according to Example 8A.

Figures 155A, 155B:
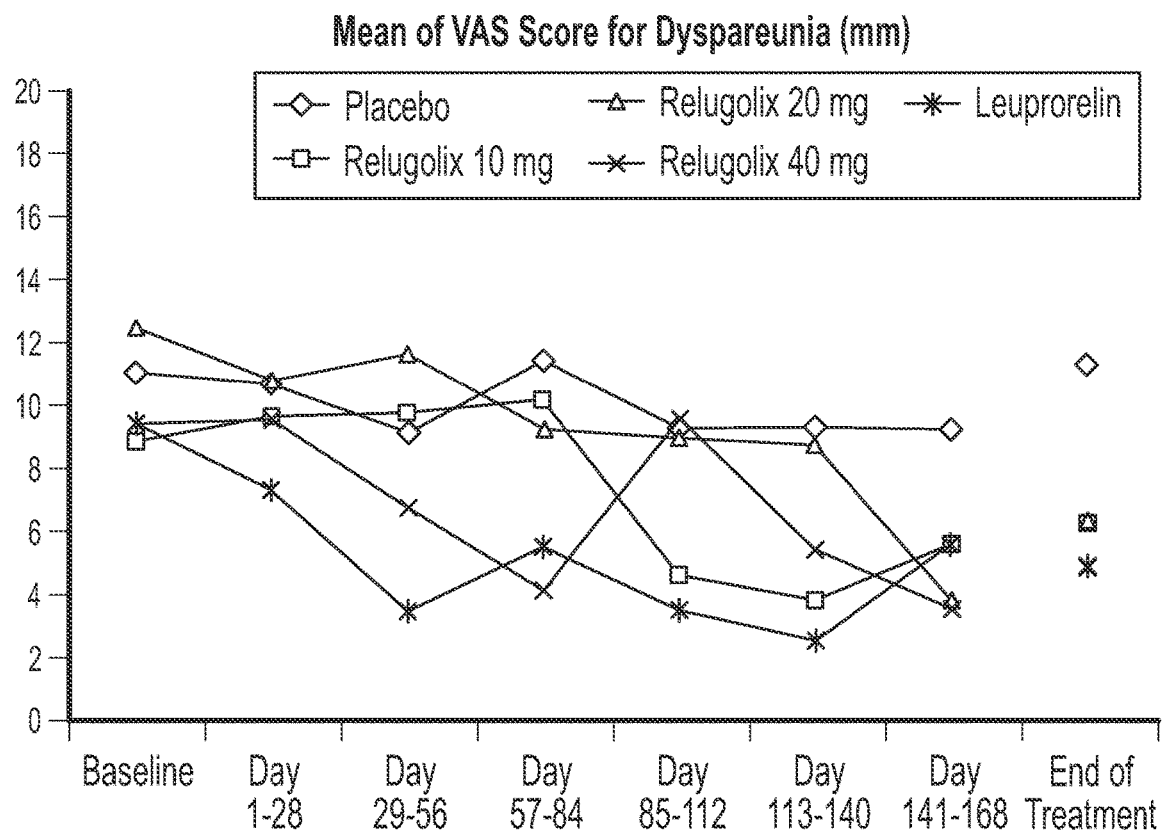

FIG. 155A and FIG. 155B (table) report the mean VAS score for dyspareunia (mm) according to Example 8A.

Figure 156A:
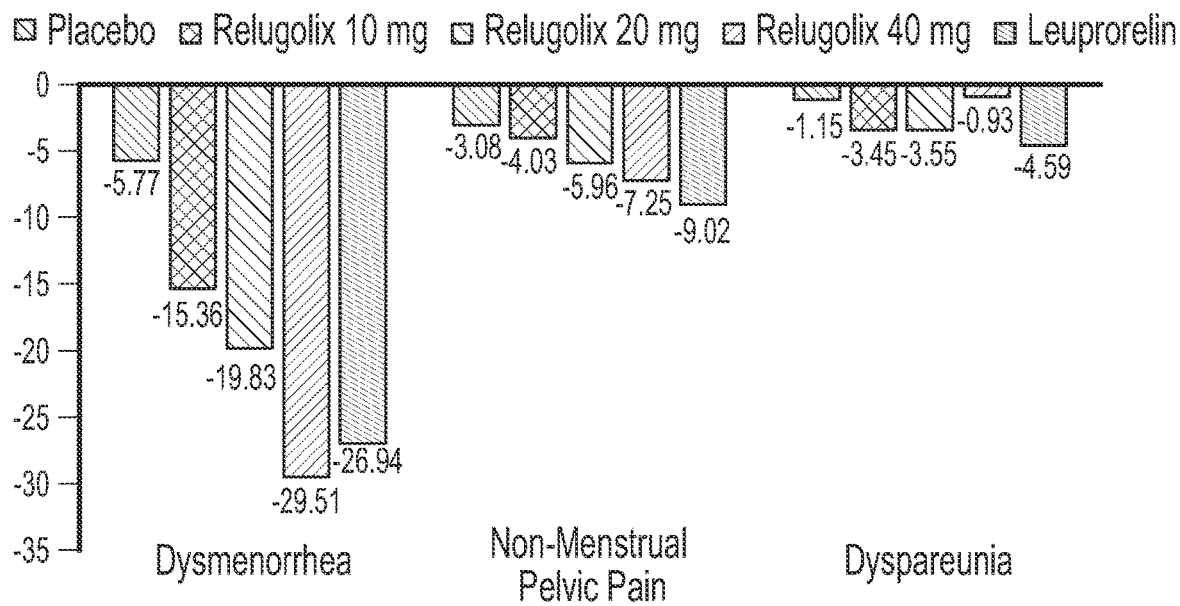
Figure 156B:
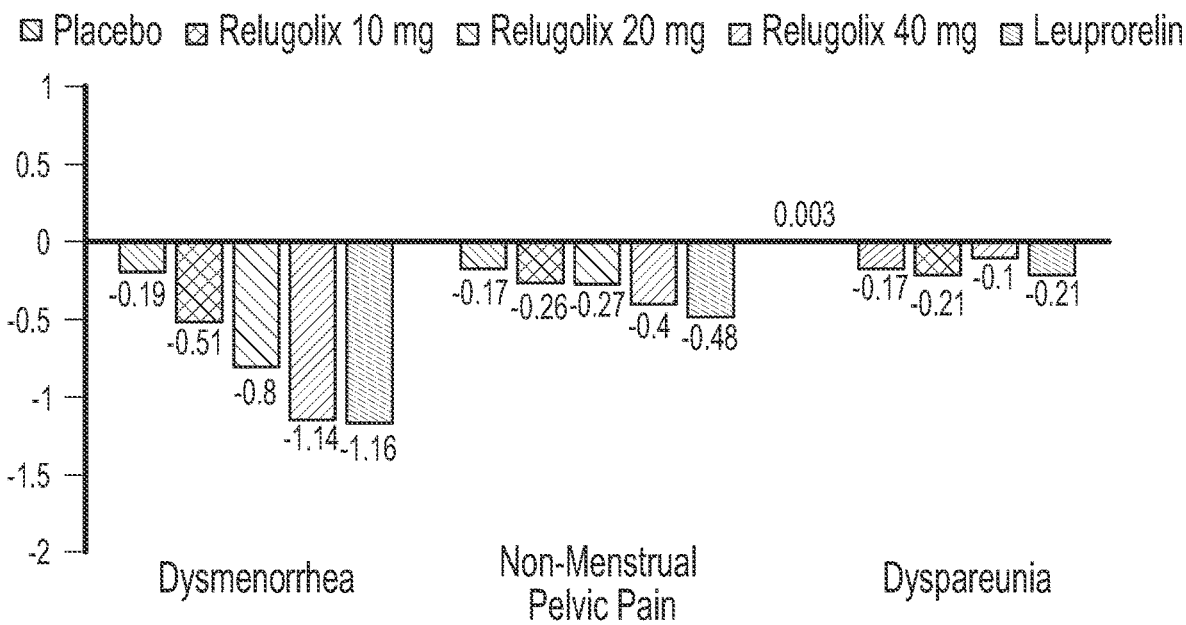

FIGS. 156A-B reports the change from bassline in mean VAS score at the end of the treatment period (mm) according to Example 8A (Mean of VAS Score and Modified (Patient) B&B). From left to right in each group, the bars are: placebo, Compound 1 (relugolix) 10 mg, Compound 1 20 mg, Compound 1 40 mg, leuprorelin.

Figure 157:
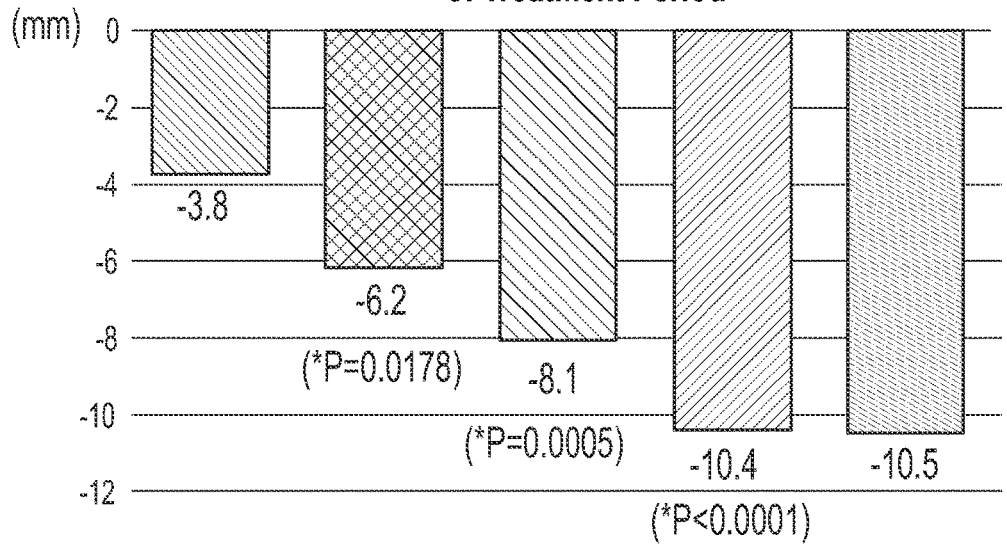

FIG. 157 reports treatment with Compound 1 for 12 weeks resulted in a significant dose-dependent decrease in overall pelvic pain according to Example 7. From left to right in each group, the bars are: placebo, Compound 1 (relugolix) 10 mg, Compound 1 20 mg, Compound 1 40 mg, leuprorelin.

Figure 158:
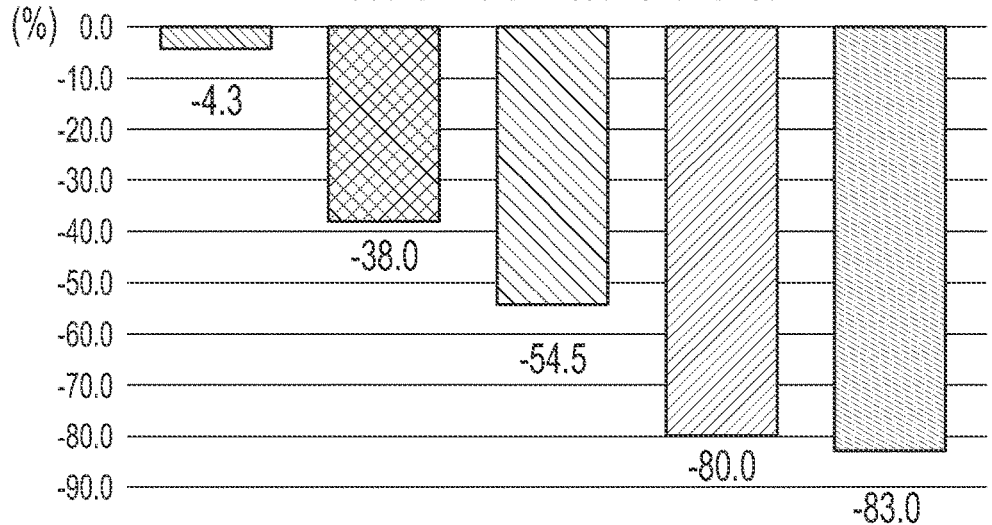

FIG. 158 reports mean percent change from baseline of VAS for overall pelvic pain at the end of treatment period according to Example 7. From left to right in each group, the bars are: placebo, Compound 1 (relugolix) 10 mg, Compound 1 20 mg, Compound 1 40 mg, leuprorelin.

Figure 159:
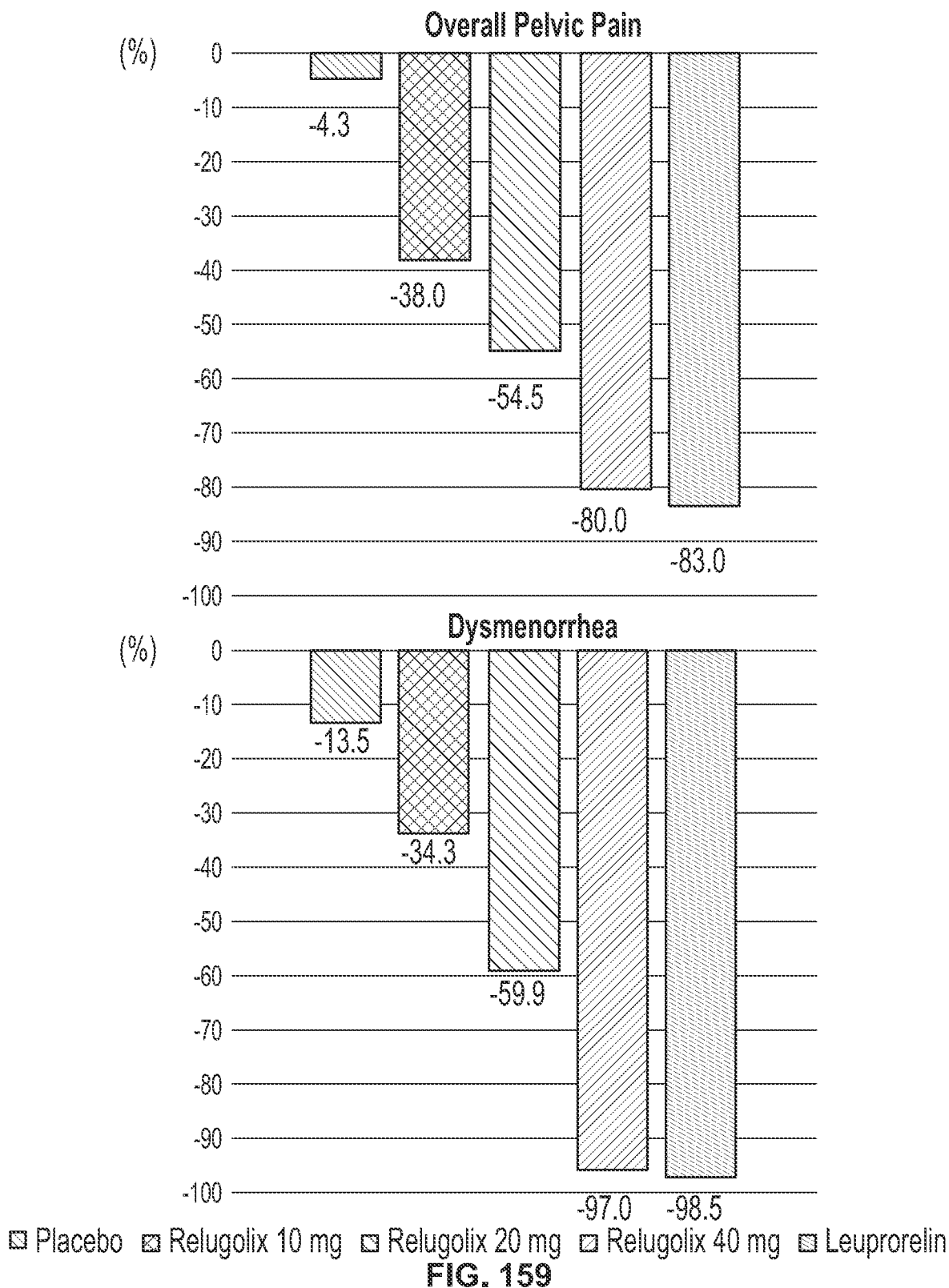

FIG. 159 reports mean percent change from baseline of VAS for overall pelvic pain and dysmenorrhea at the end of treatment period according to Example 7. From left to right in each group, the bars are: placebo, Compound 1 (relugolix) 10 mg, Compound 1 20 mg, Compound 1 40 mg, Leuprorelin.

Figure 160:
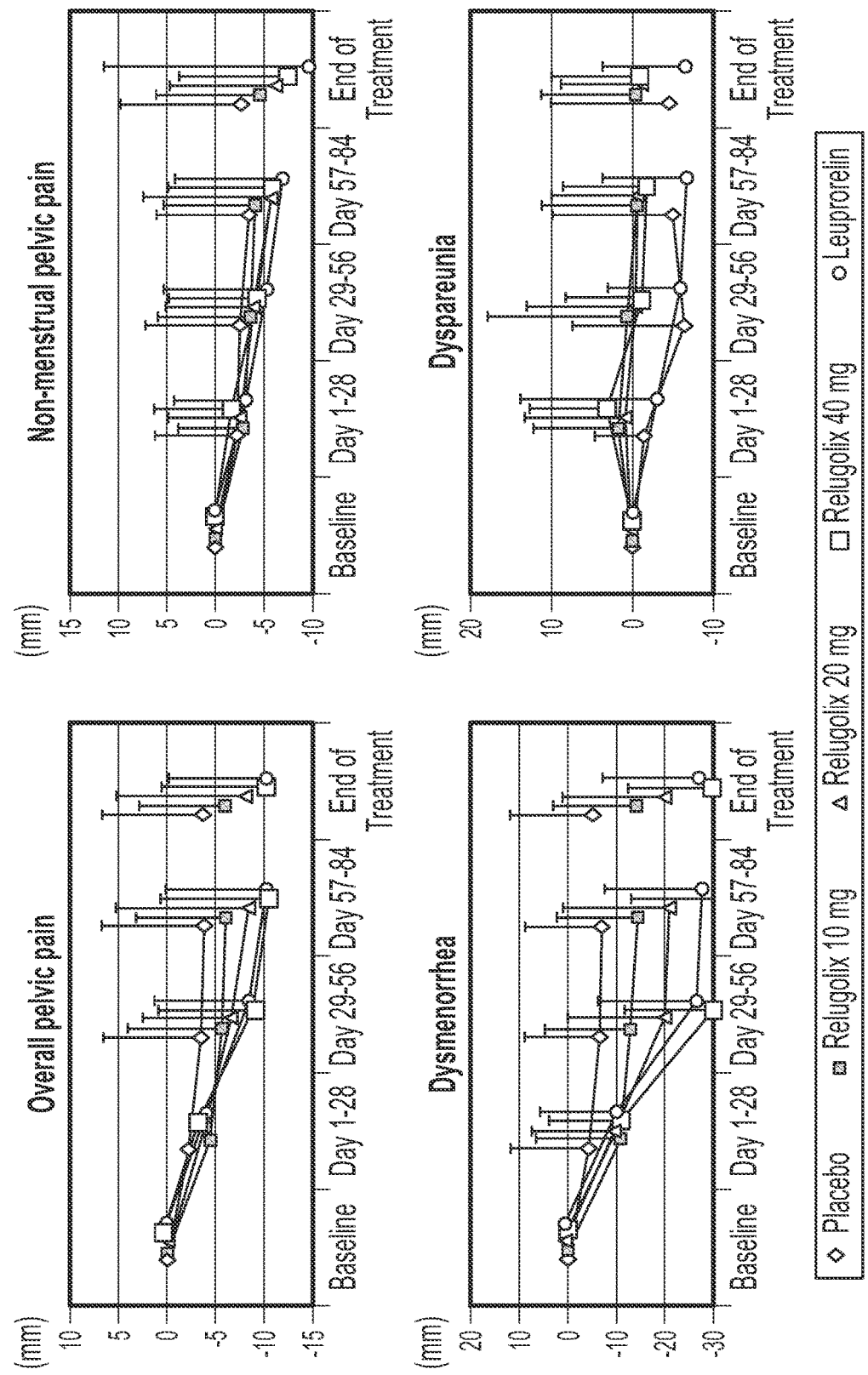

FIG. 160 reports change from baseline in mean VAS score for overall pelvic pain, non-menstrual pelvic pain, dysmenorrhea, and dyspareunia by visit according to Example 7. The diamond marker indicates placebo; the lighter square marker indicates Compound 1 10 mg; the triangle marker indicates Compound 1 20 mg; the darker square marker indicates Compound 1 40 mg; and the circle marker indicates leuprorelin.

Figure 161:
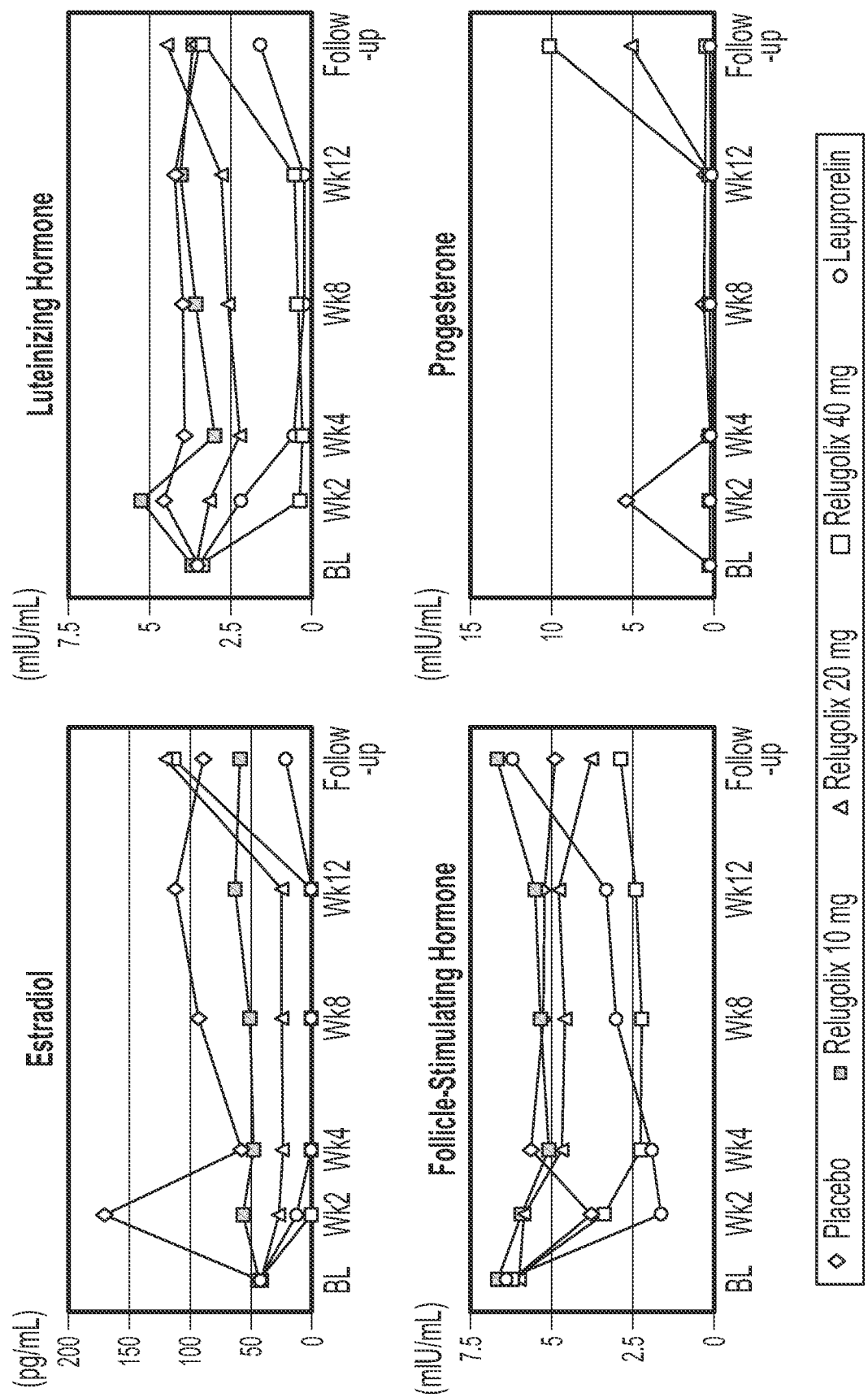

FIG. 161 shows serum concentration (median) of pharmacodynamic markers as determined in Example 7. The diamond marker indicates placebo; the lighter square marker indicates Compound 1 10 mg; the triangle marker indicates Compound 1 20 mg; the darker square marker indicates Compound 1 40 mg; and the circle marker indicates leuprorelin.

Figure 162:
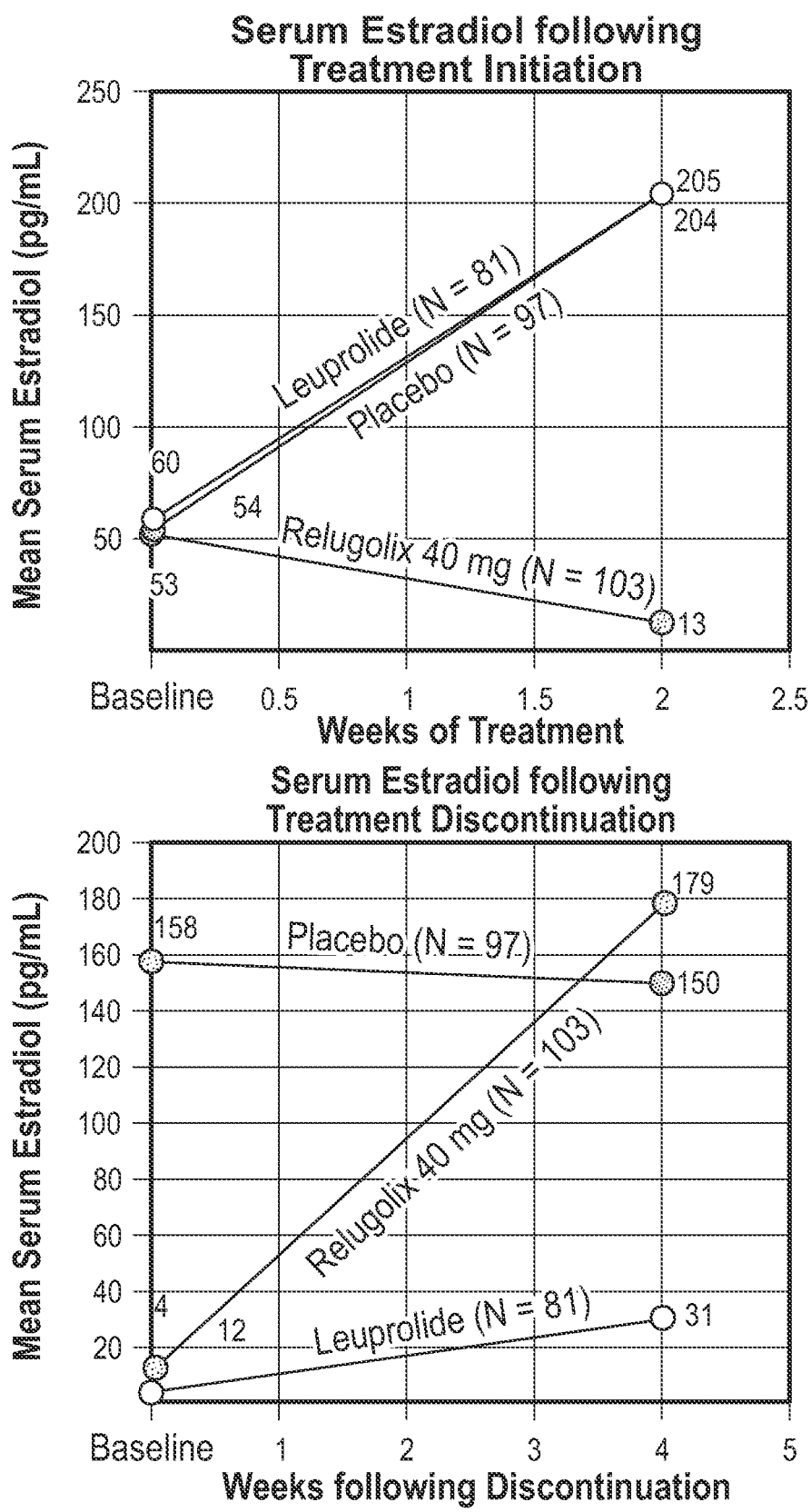

FIG. 162 is a graph depicting the onset/offset of endocrine effects after administration of Compound 1 as described in the study in Example 7.

FIG. 163 Estradiol levels in healthy volunteer women treated in phase 1 study with Compound 1, with and without hormonal add-back therapy.

Figure 164:
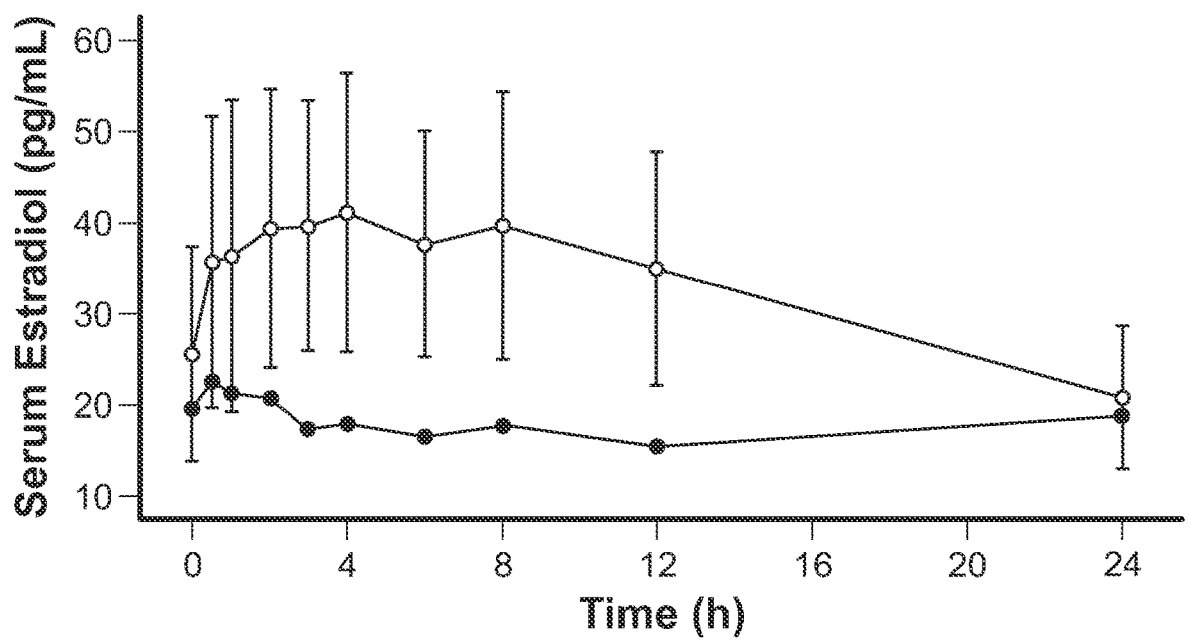

FIG. 164 is a graph depicting the mean and standard deviation (SD) serum estradiol on last day of treatment (Week 6)—top line is Compound 1 plus add-back and bottom line Compound 1 without add-back.

Figure 165:
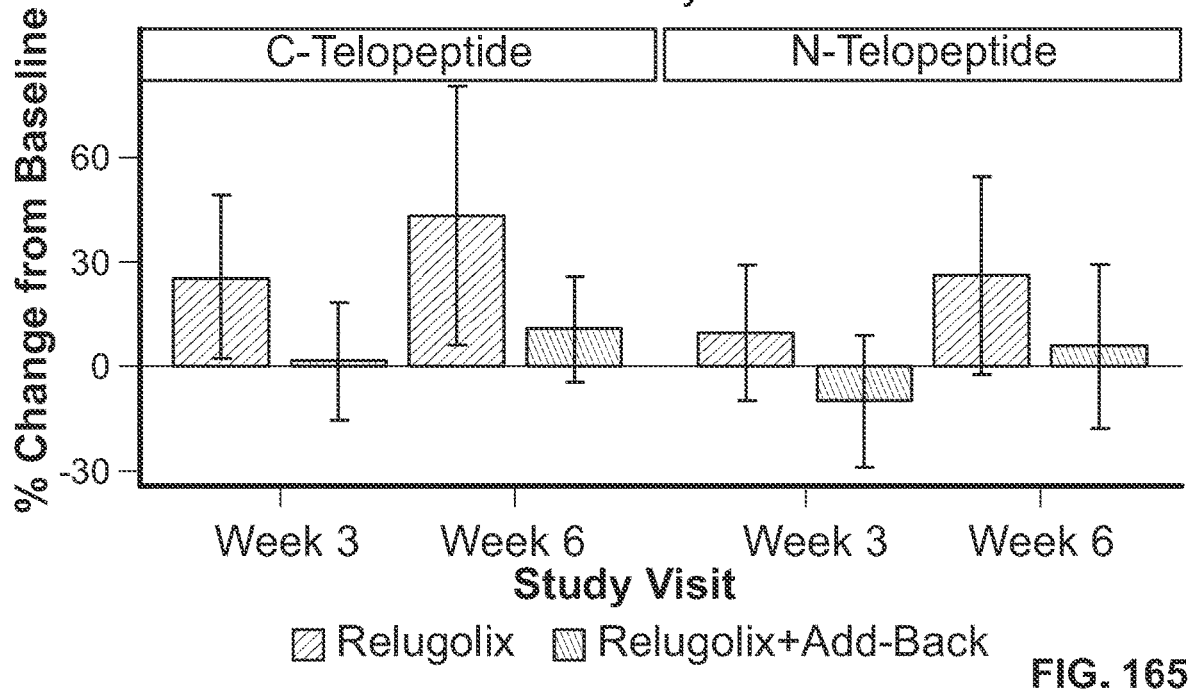

FIG. 165 is a graph depicting the mean and standard deviation (SD) C-telopeptide and N-telopeptide (Compound 1 left side; Compound 1 plus add-back right side) of each weekly result.

Figure 166:
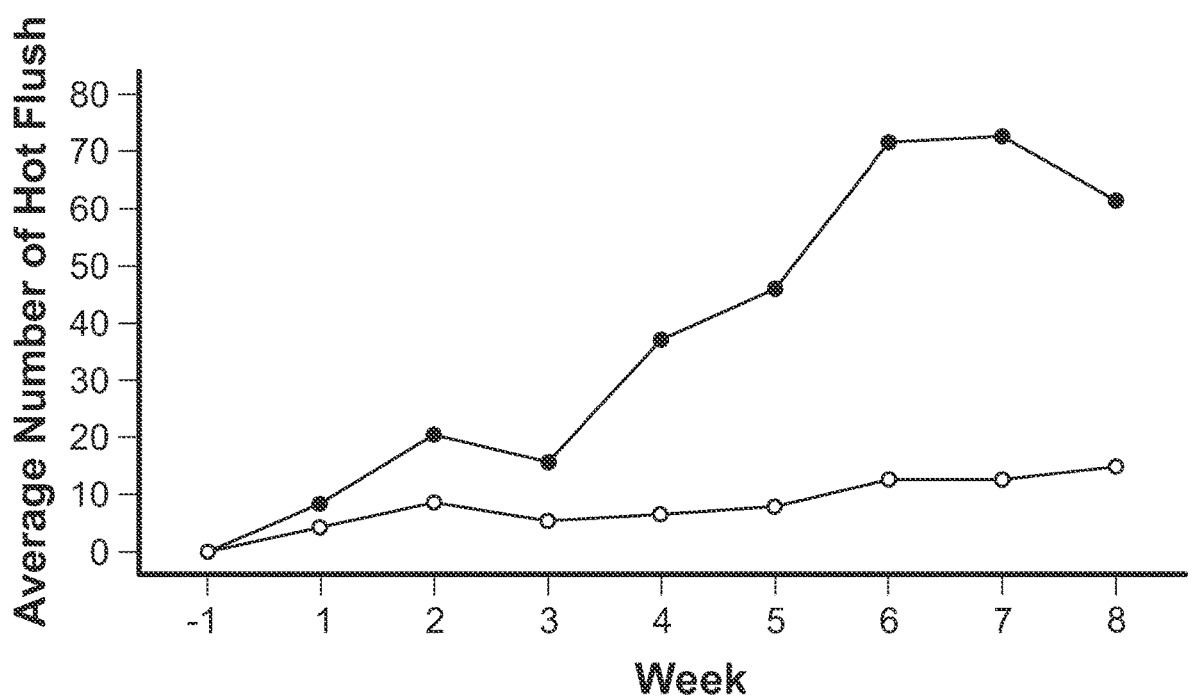

FIG. 166 is a graph depicting the average number of hot flash (any severity)—top line with Compound 1; bottom line Compound 1 plus add-back.

FIG. 167 is a table summarizing some differences between Compound 1 (relugolix) and the GnRH antagonist elagolix.

Figure 168:
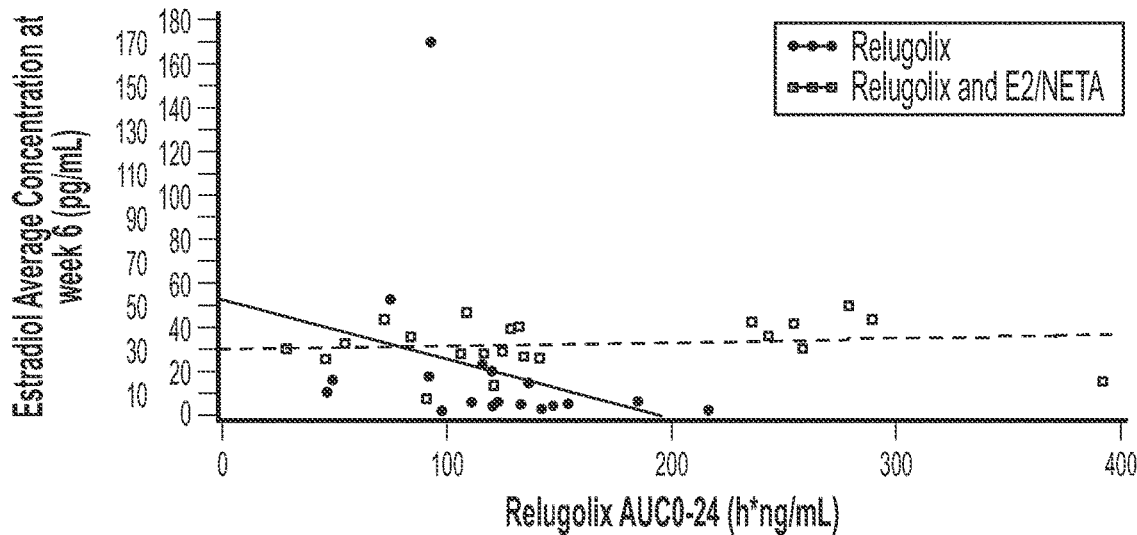

FIG. 168 depicts a scatter plot of Compound 1 (relugolix) $AUC_{024}$ compared to $C_{avg}$ estradiol ($E_2$) concentration at Week 6 in the study described in Example 9.

Figure 169:
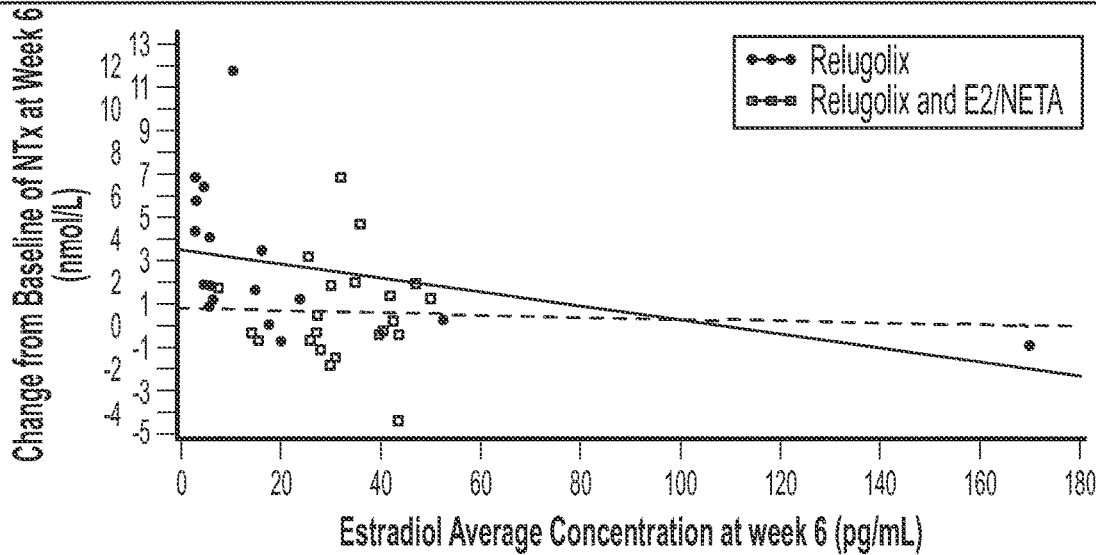

FIG. 169 depicts a scatter plot of $C_{avg}$ estradiol ($E_2$) compared to change from baseline of N-telopeptide (NTx) at Week 6 of the study described in Example 9.

FIG. 170 depicts a scatter plot of $C_{avg}$ estradiol ($E_2$) compared to change from baseline of C-telopeptide (CTx) at Week 6 of the study described in Example 9.

FIG. 171 depicts a box plot graph of degree of subject-reported menstrual bleeding vs. $C_{avg}$ estradiol ($E_2$) at Week 6 of the study described in Example 9.

Figure 172:
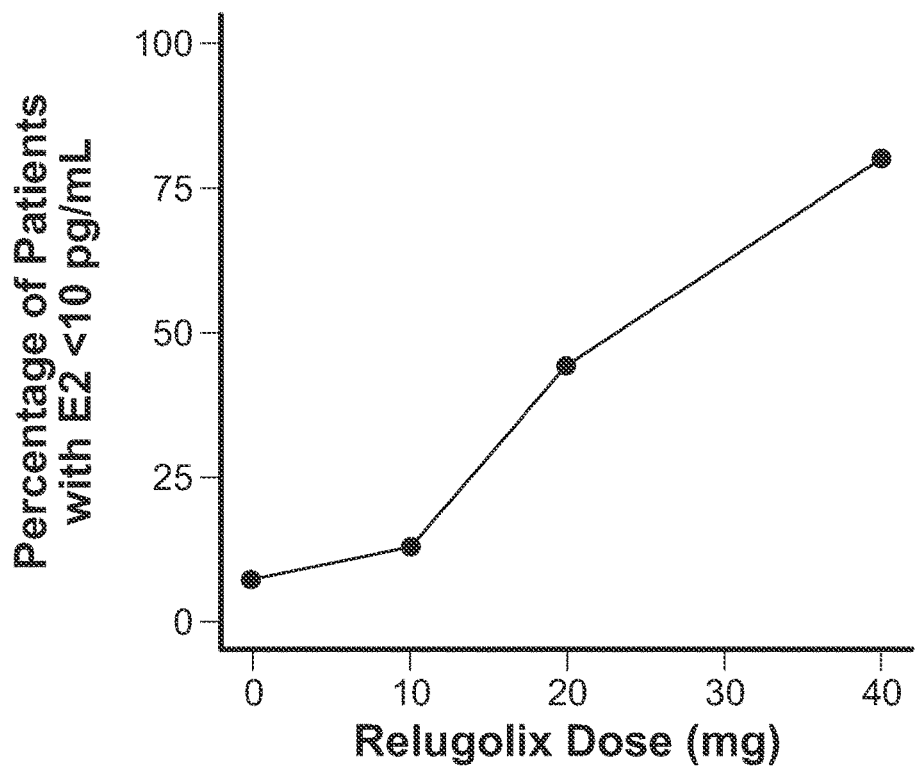

FIG. 172 is a graph depicting the percentage of subjects with a serum estradiol ($E_2$) level of less than 10 pg/mL vs. dose of Compound 1 (relugolix), in the study described in Example 5A.

Figure 173:
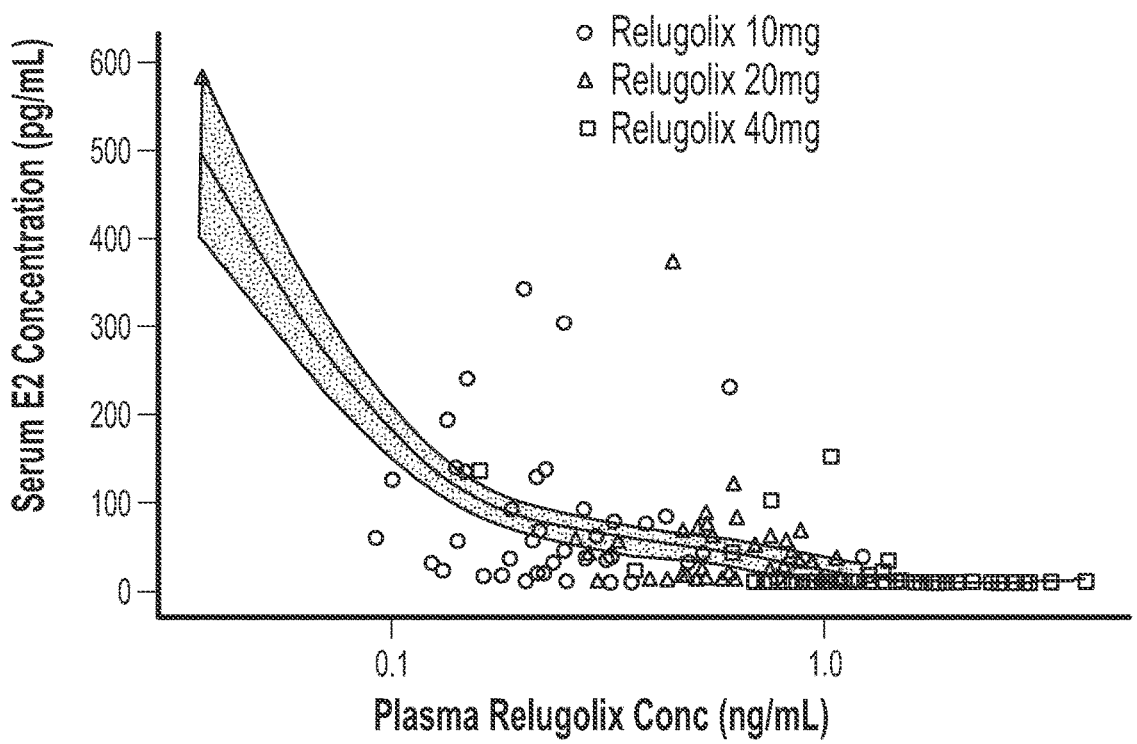

FIG. 173 is a graph depicting the serum estradiol ($E_2$) level of individual subjects vs. plasma Compound 1 concentration, in the study described in Example 5A.

Figure 174:
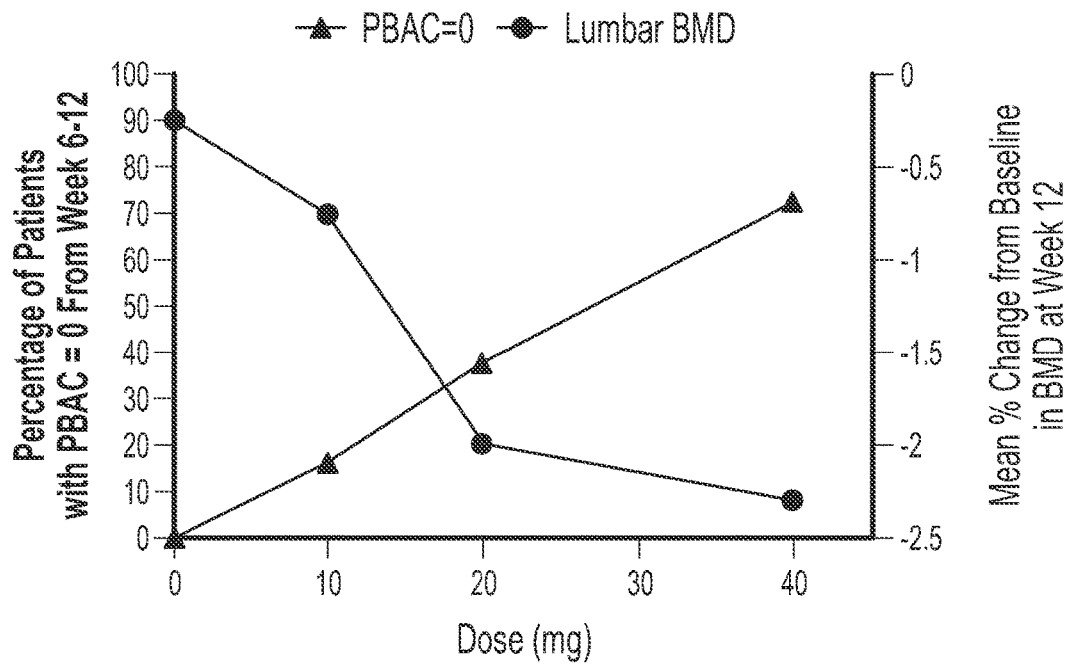

FIG. 174 is a graph depicting the percentage of subjects with Pictorial Blood Loss Assessment Chart (PBAC) scores of 0 from weeks 6–12, and the mean change from baseline in bone mineral density at week 12, vs. dose of Compound 1 in the study described in Example 5A.

Figure 175:
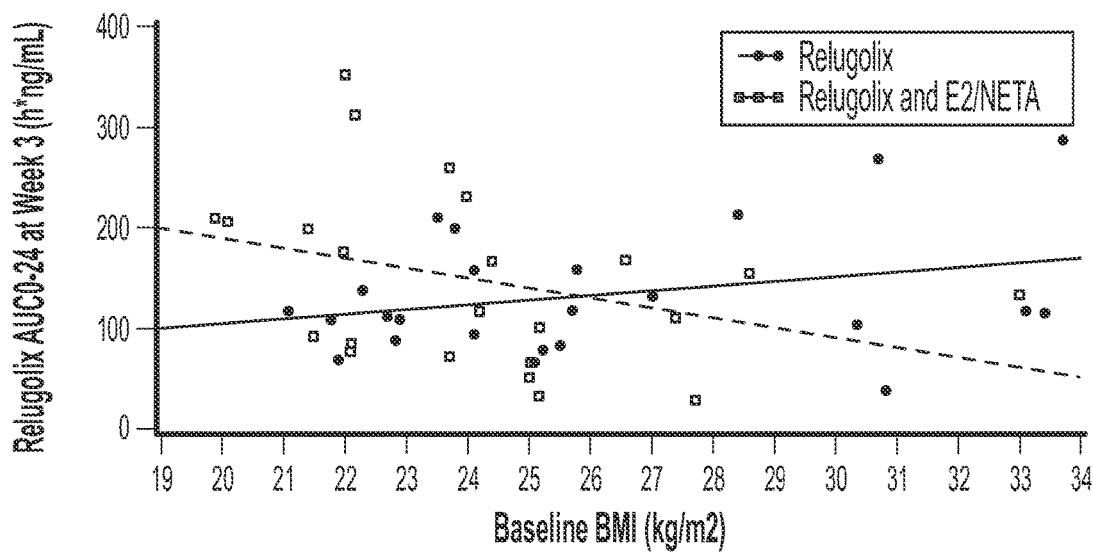

FIG. 175 is a graph depicting Compound 1 (relugolix) $AUC_{0-24}$ at week 3 compared with baseline body mass index in the study described in Example 9.

Figure 176:
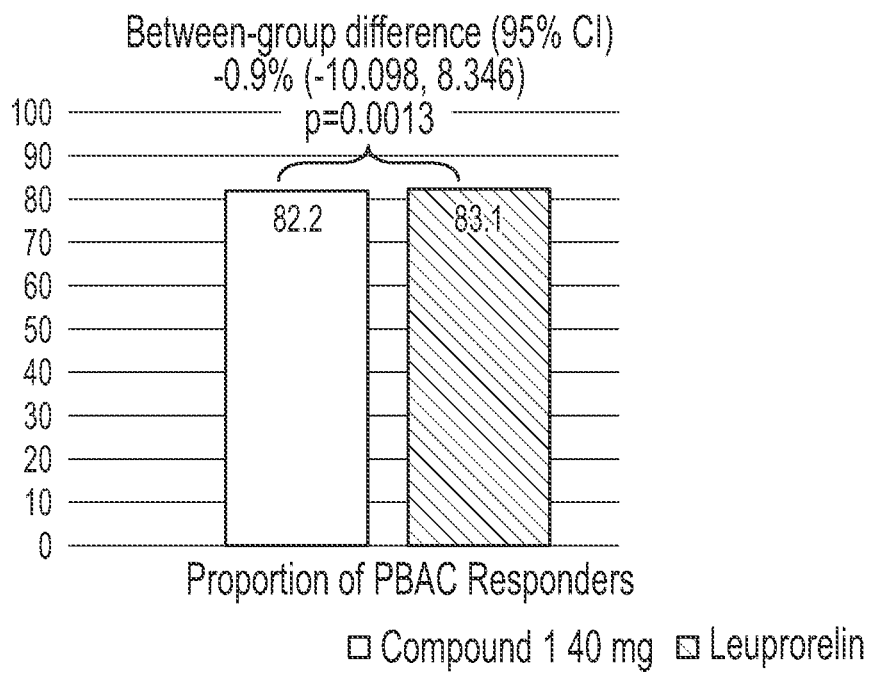

FIG. 176 is a graph of the proportion of PBAC responders with primary endpoint results in the study described in Example 10.

Figure 177:
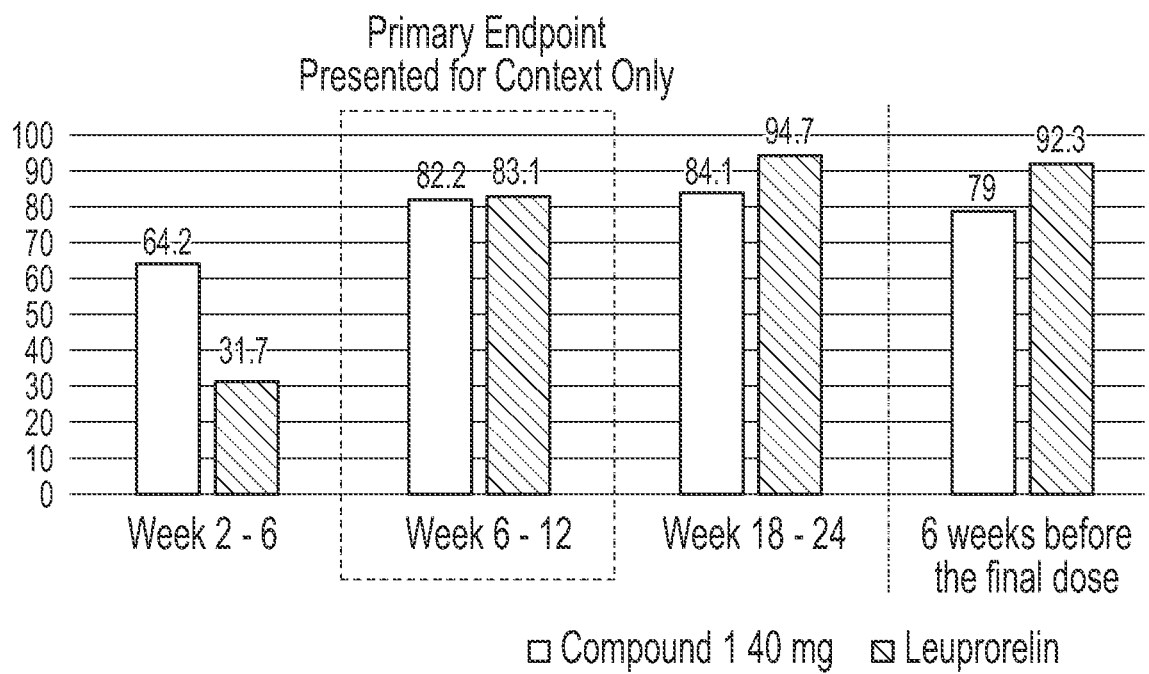

FIG. 177 is a graph depicting the proportion of responders with secondary endpoint results in the study described in Example 10. The primary endpoint results are also included for context.

Figure 178A:
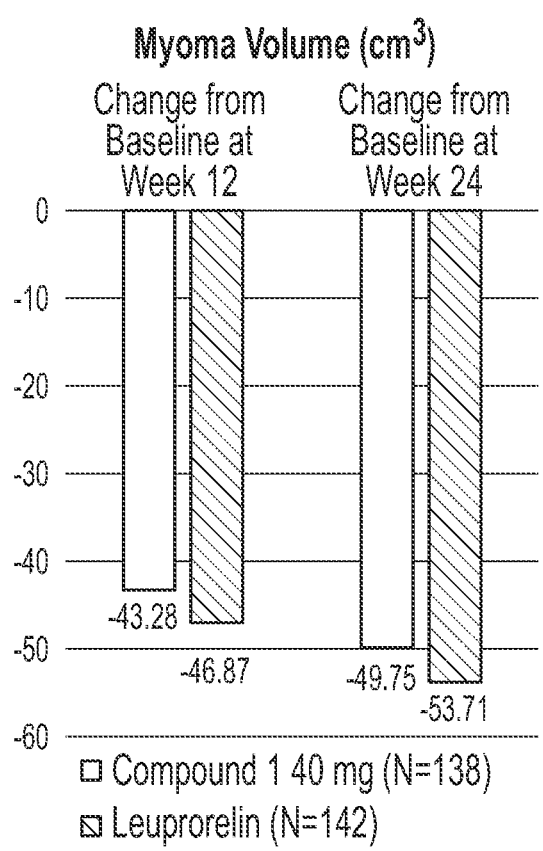
Figure 178B:
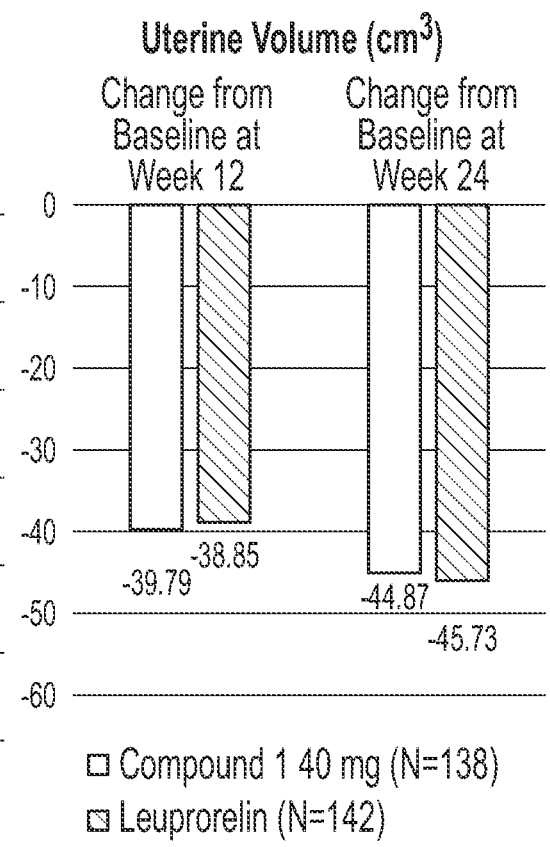
Figure 178C:
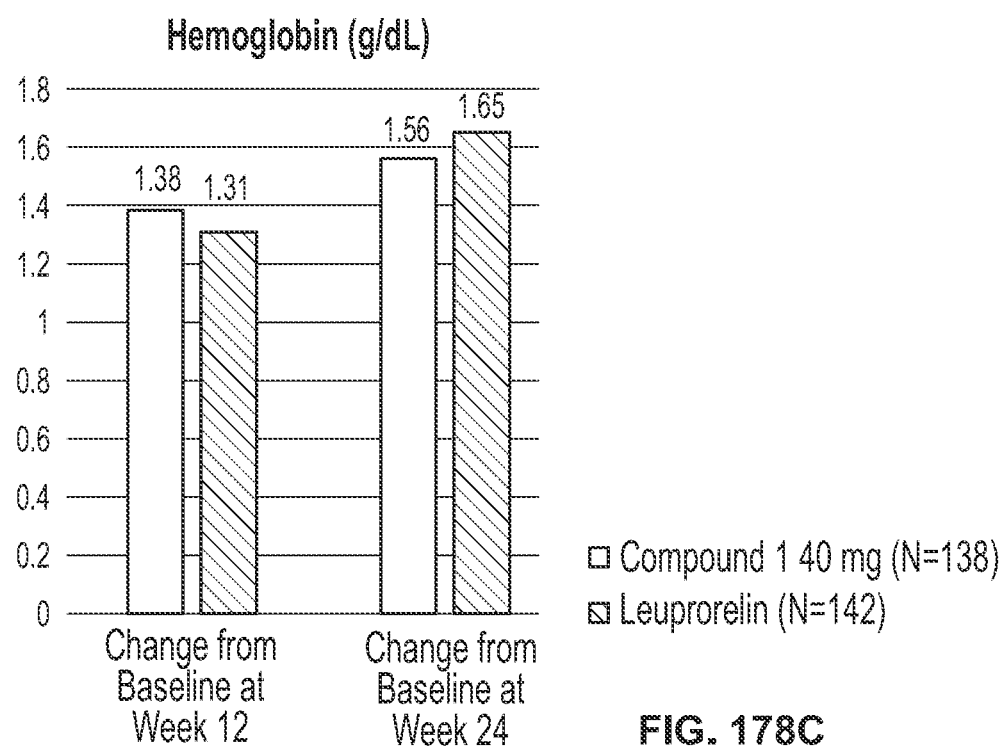

FIGS. 178A-C depict graphs of secondary endpoint myoma volume, secondary endpoint uterine volume, and secondary hemoglobin for subjects in the study described in Example 10

Figure 179:
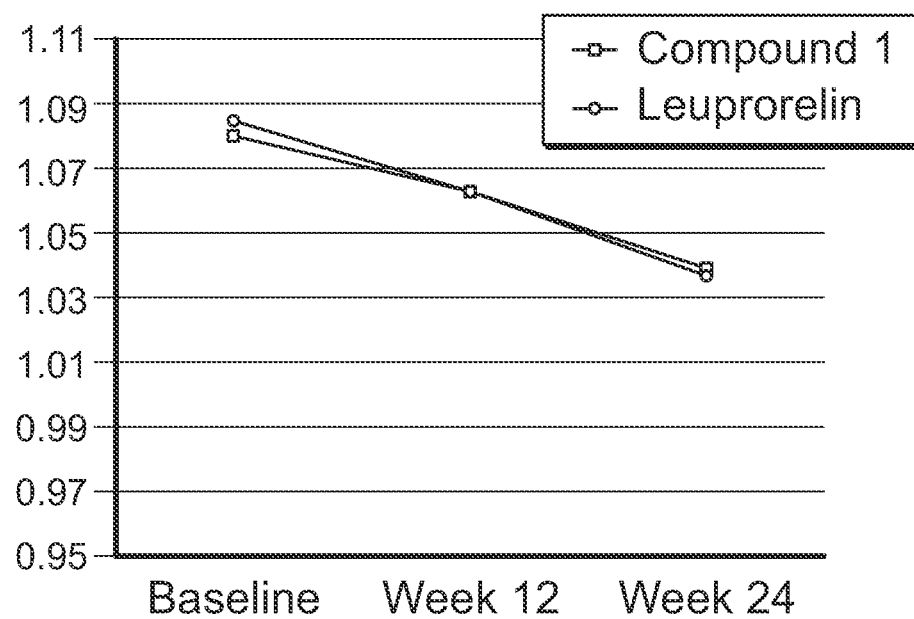

FIG. 179 depicts a graph of bone mineral density over time in the two different treatment groups in the study described in Example 10.

Figure 180A:
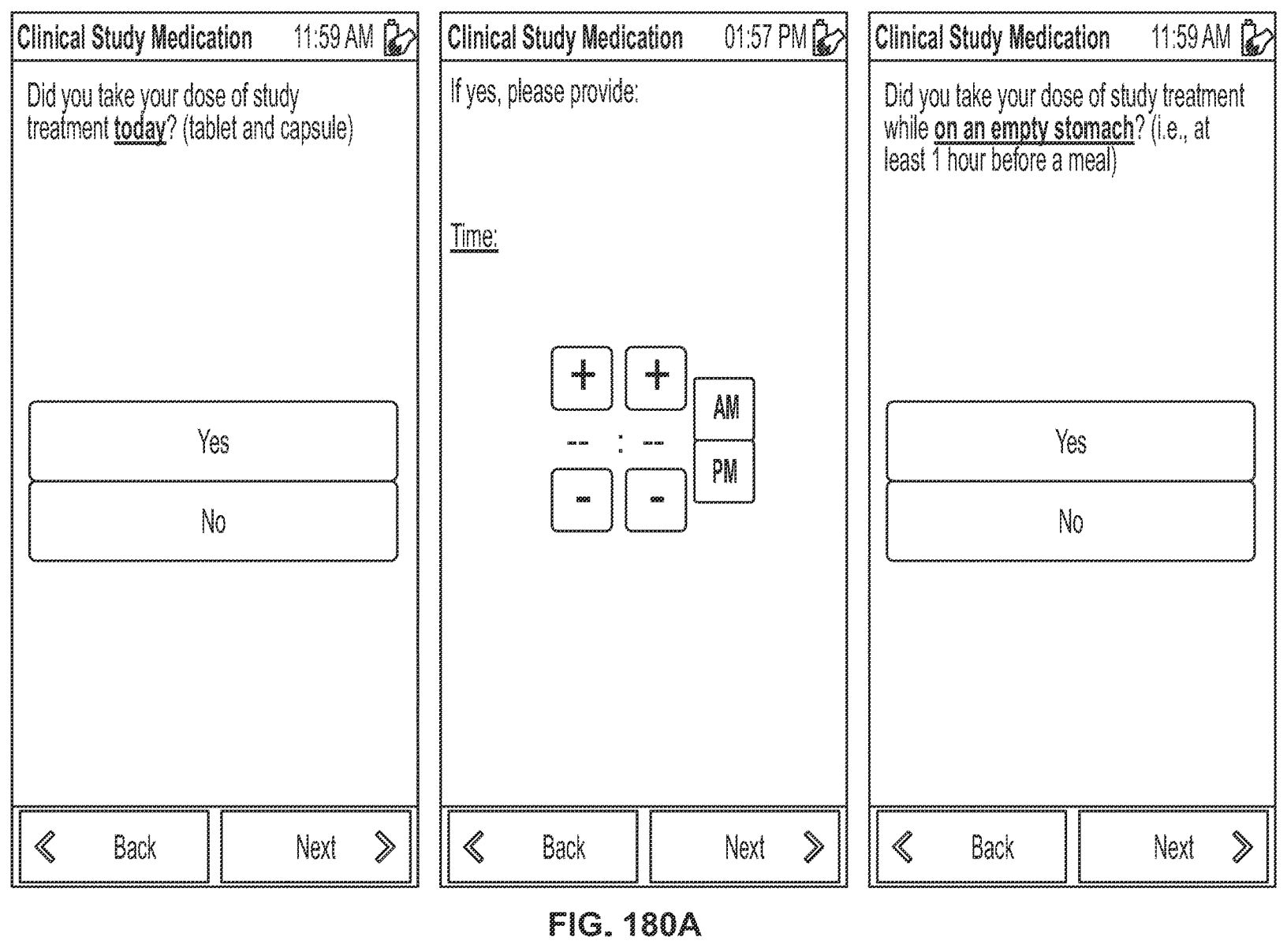
Figure 180A:
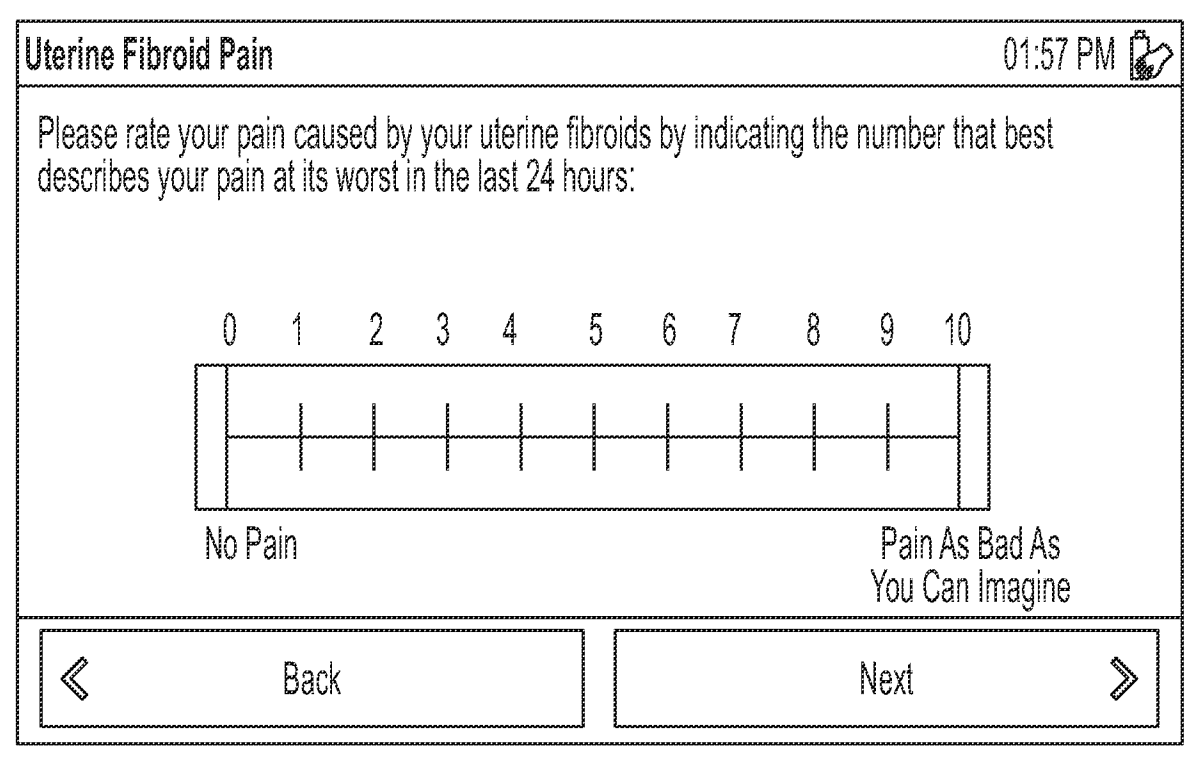
Figure 180B:
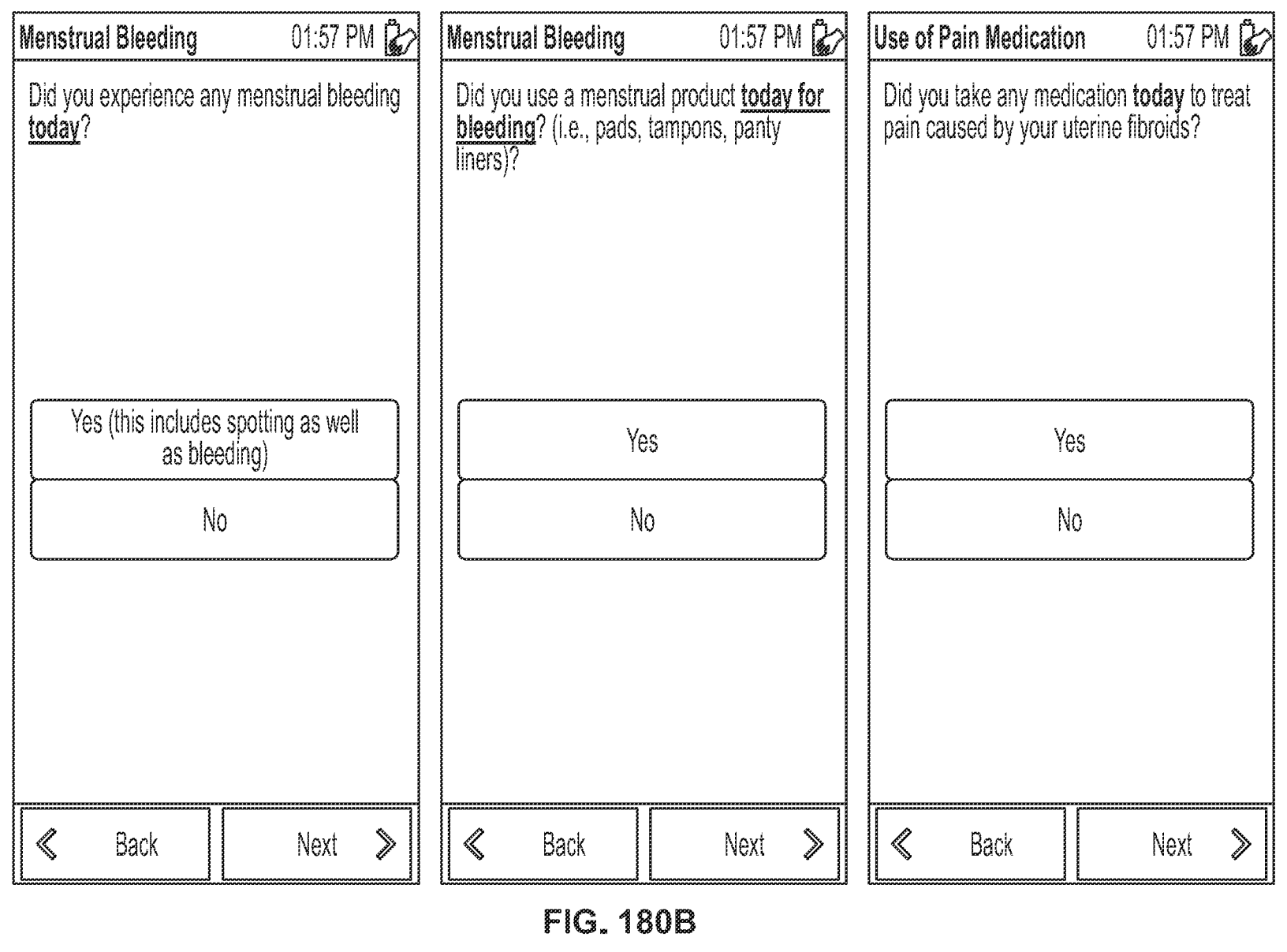
Figure 180B:
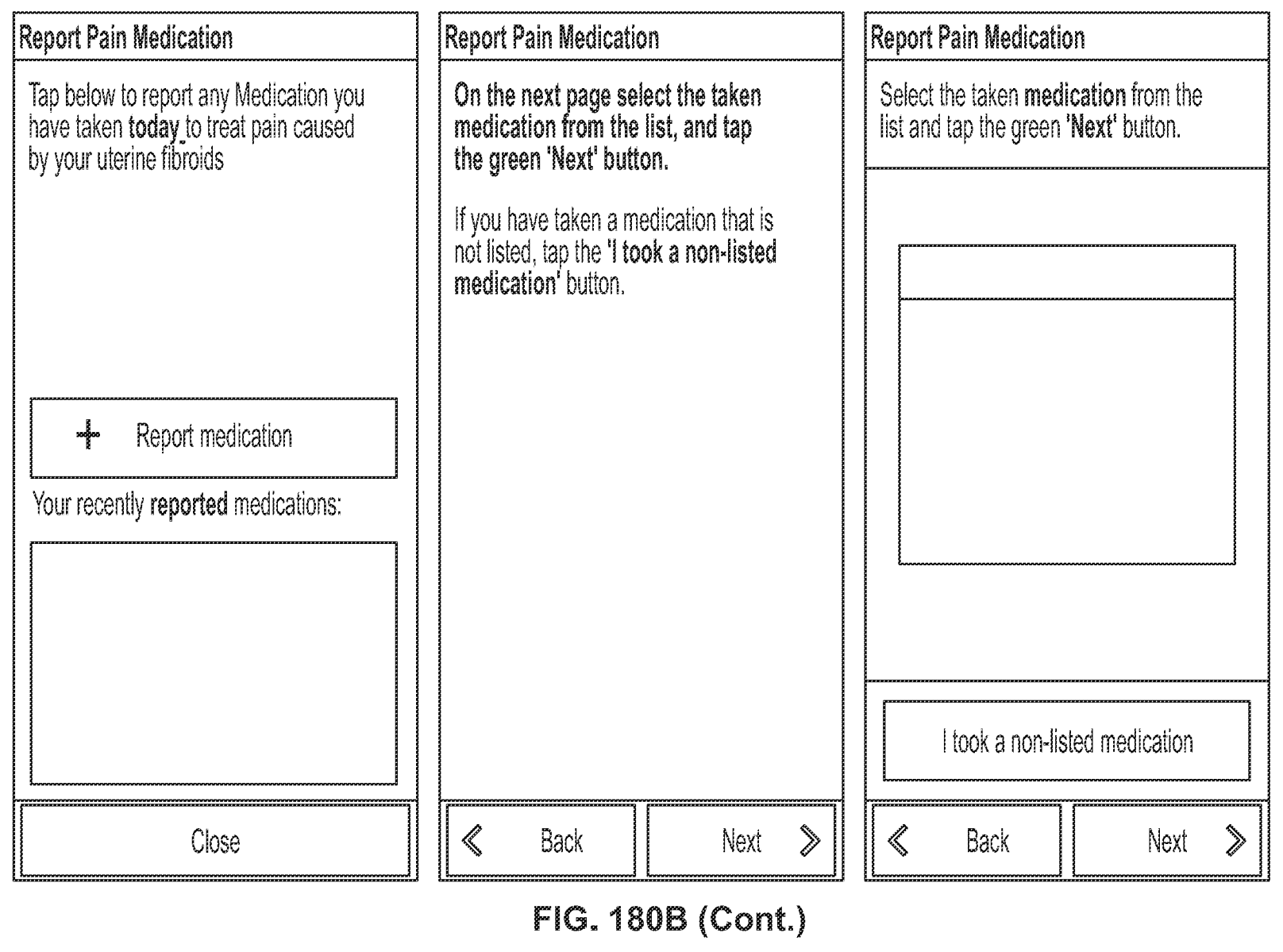
Figure 180C:
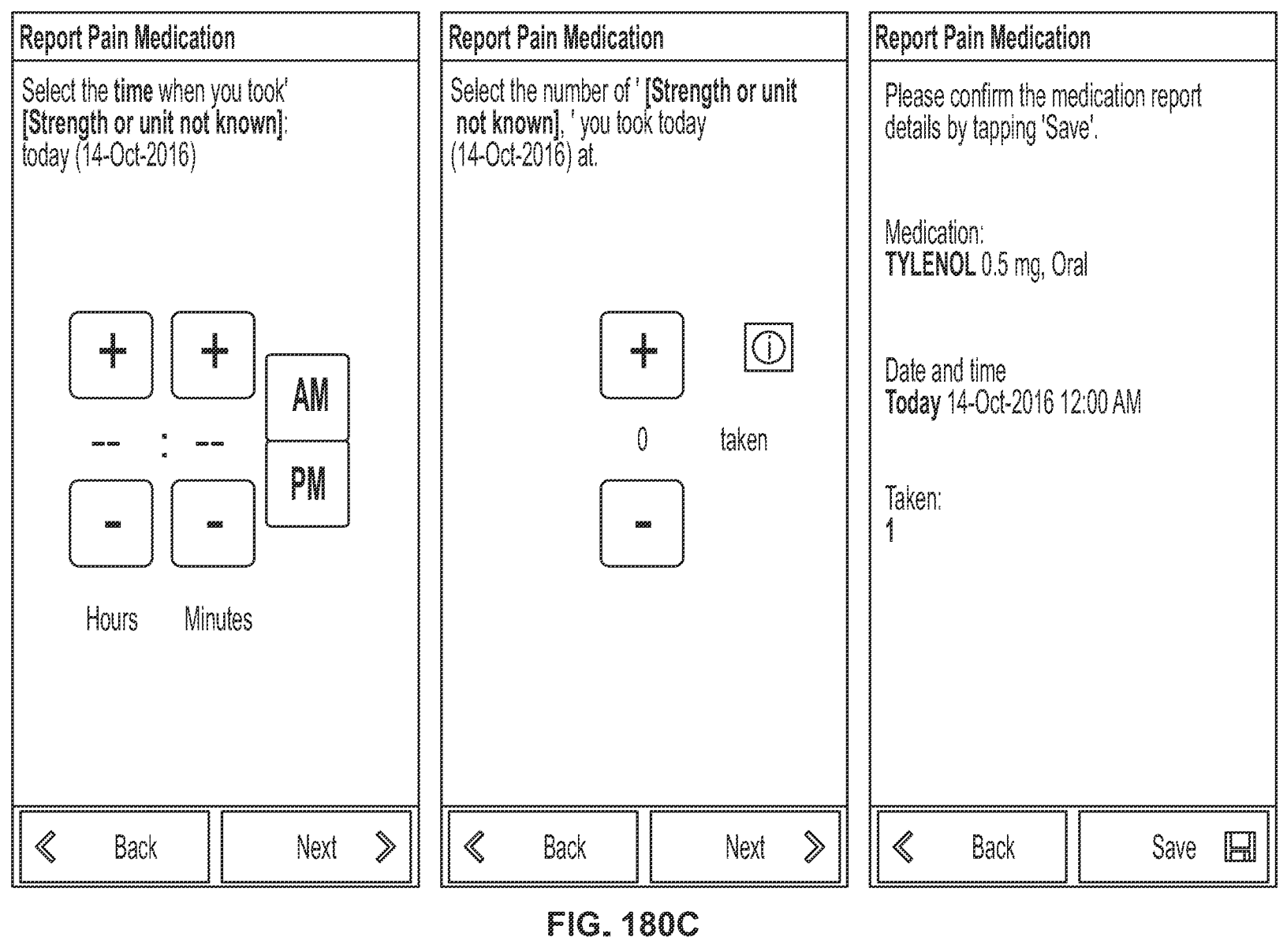
Figure 180D:
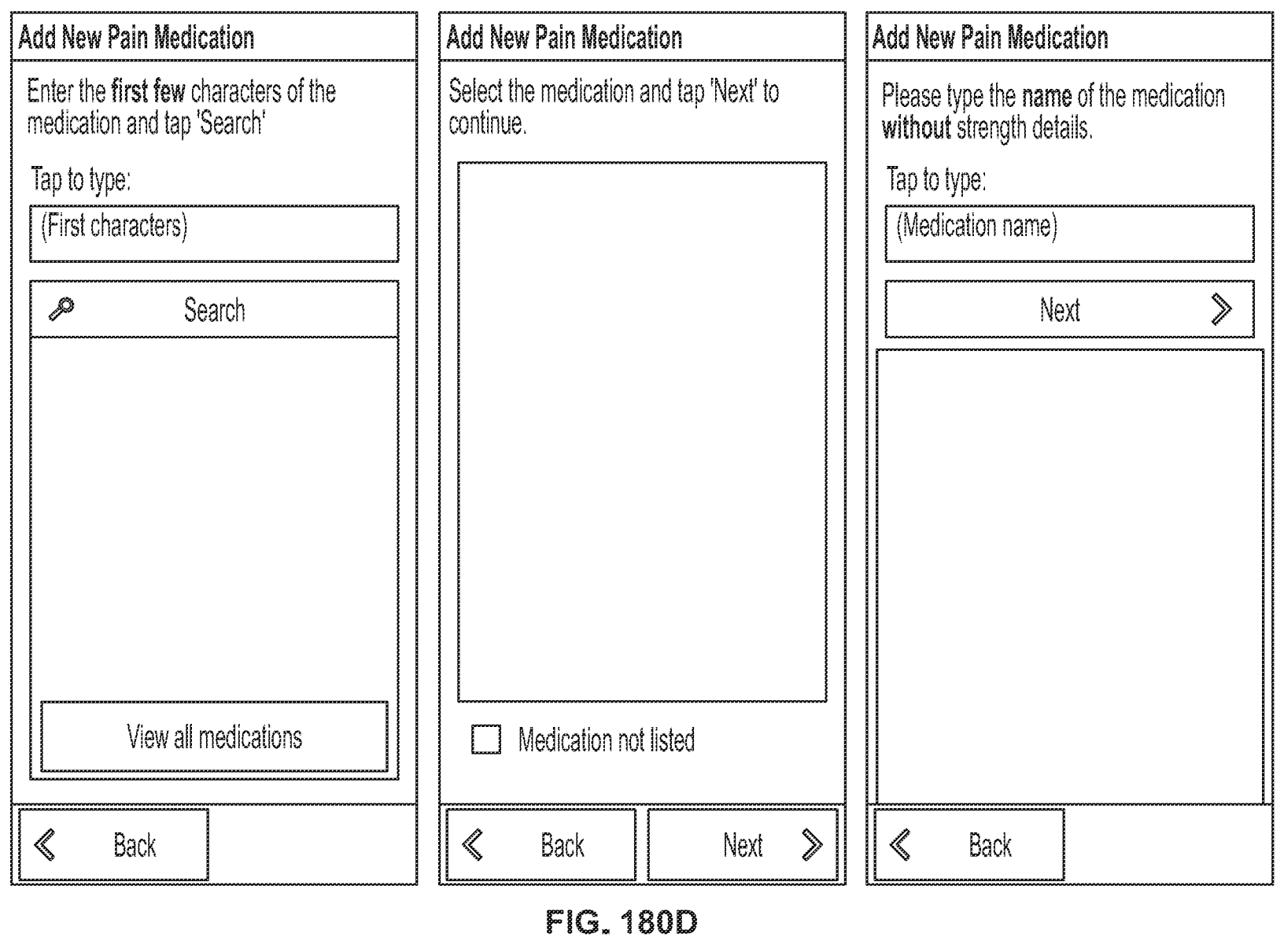
Figure 180E:
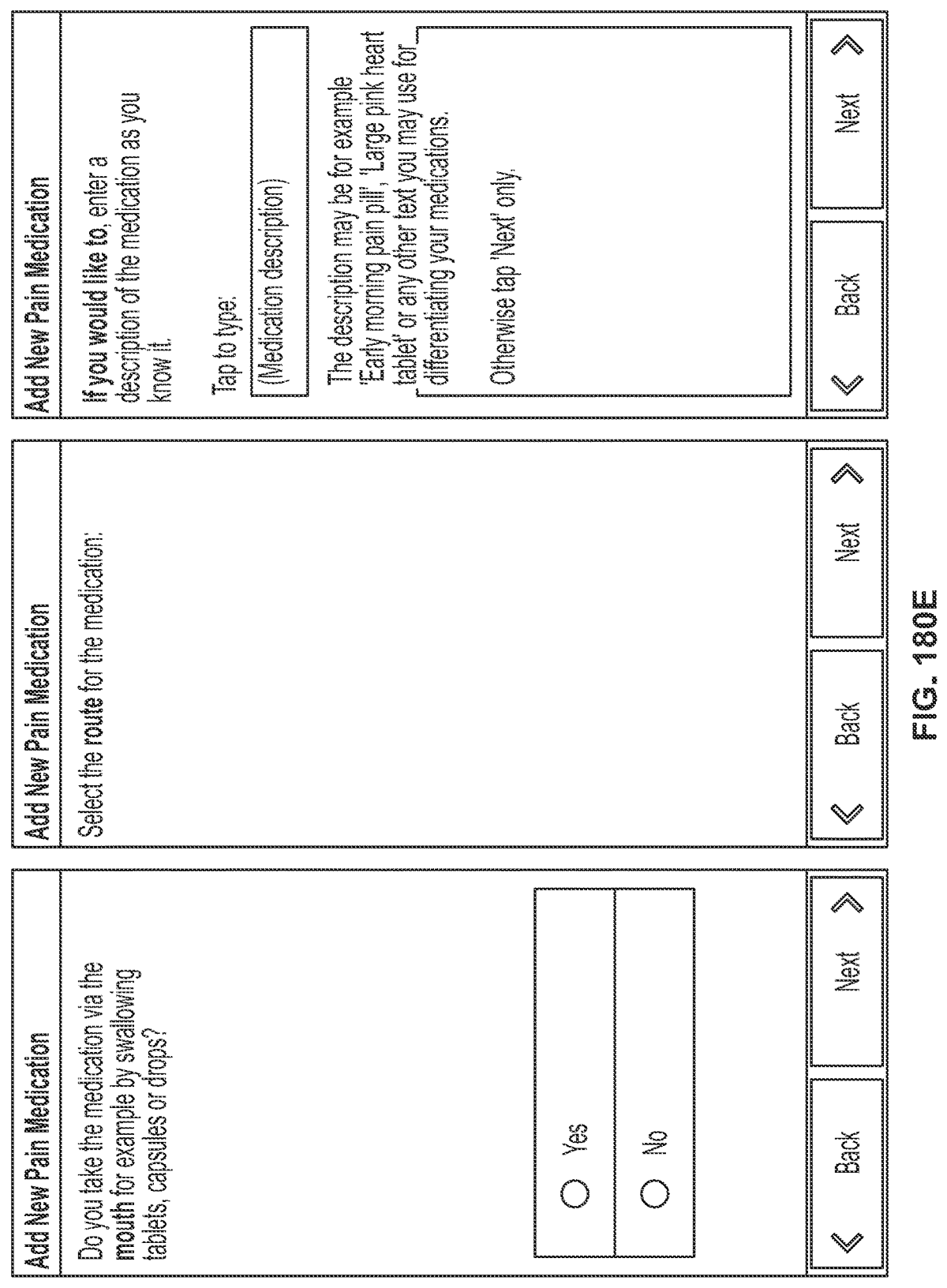

FIGS. 180A-E depict eDiary entries for the studies described in Examples 13 and 14.

Figure 181:
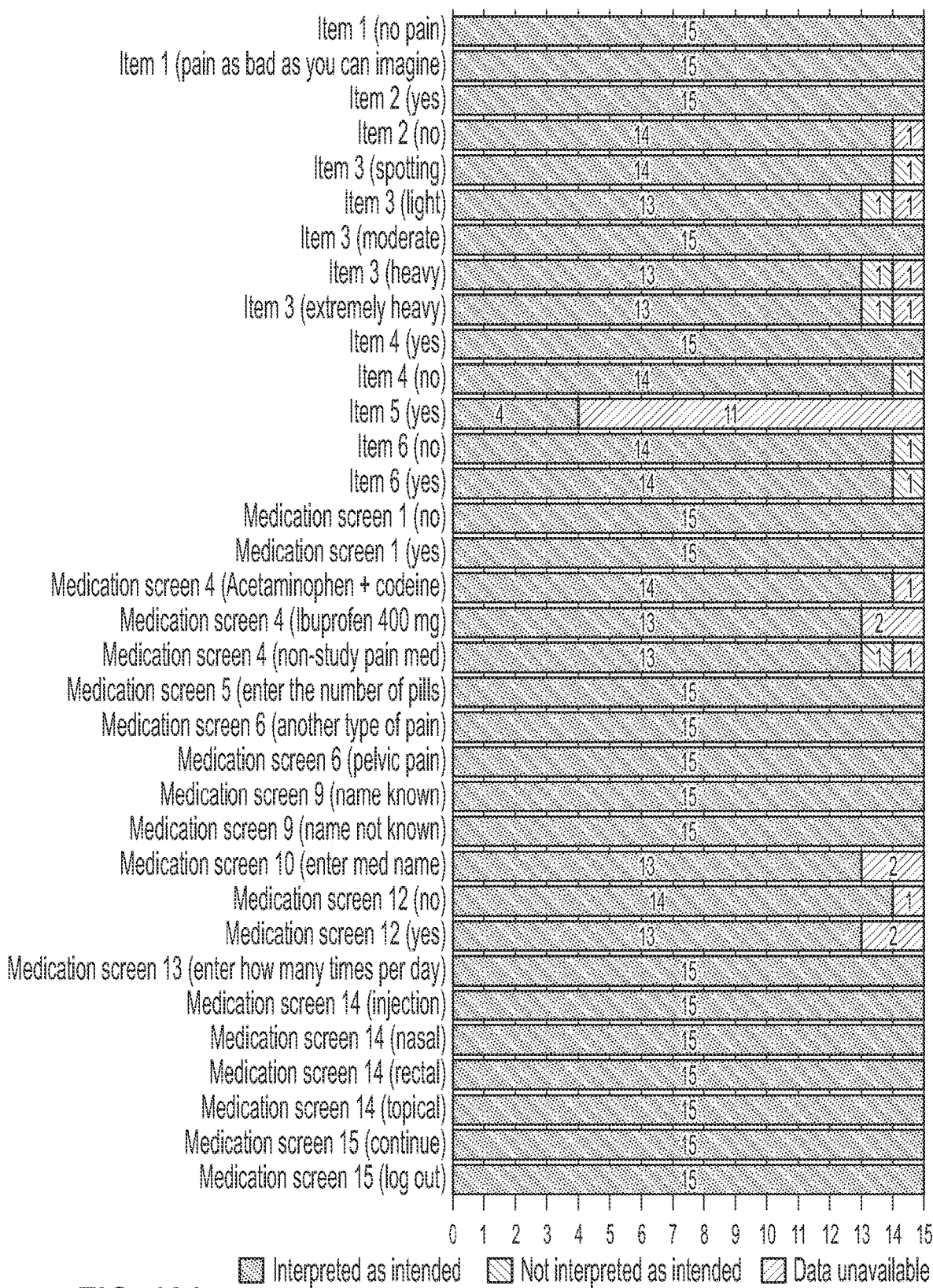

FIG. 181 presents a summary of the cognitive debriefing findings in the study described in Example 18.

Figure 182:
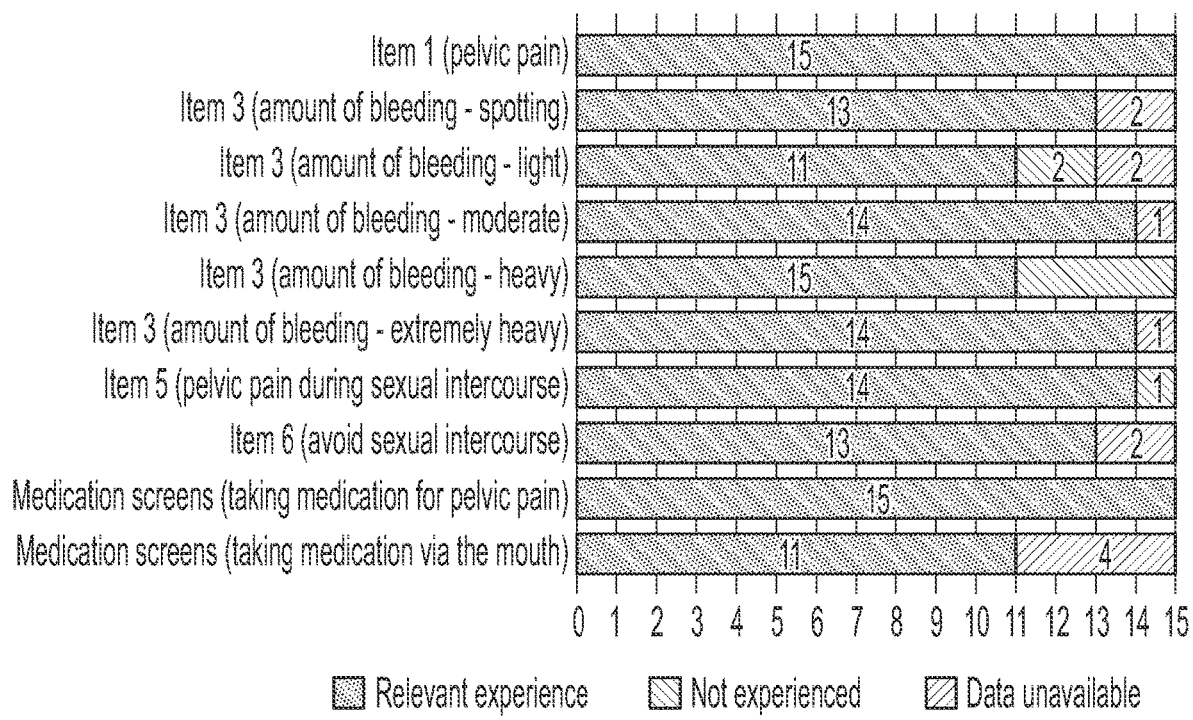

FIG. 182 presents a summary of each of the concepts measured by the SEMS evaluated in Example 18, along with the number of subjects that reported relevance of that concept.

FIGS. 183A-C present a comparison of subject-reported symptoms with patient-reported outcomes (PRO) in the study described in Example 18.

DETAILED DESCRIPTION

As discussed above, achieving a balance of hormones that alleviates one or more symptoms of conditions such as uterine fibroids, endometriosis, and/or adenomoysis while also avoiding certain side effects of hormone suppression is challenging. It has been surprisingly found that in some embodiments, the methods provided herein may treat uterine fibroids, endometriosis, or adenomyosis, or one or more symptoms associated with these conditions. It has also been surprisingly found that in some embodiments, these methods may further include preventing or ameliorating one or more side effects of GnRH antagonist administration, such as bone mineral density loss or vasomotor symptoms. For example, rather than using a dose that merely decreases hormone levels, suppressing the hormones completely or nearly completely and then adding back a particular amount of hormones as described herein, may lead to a tighter distribution of estradiol levels for a large number of women and may simultaneously be efficacious with regard to the symptoms described herein, while also controlling side-effects normally associated with GnRH antagonist treatment. In other words, compared to the "thread the needle" approach described above, the present methods and uses may surprisingly lead to successful treatment of more women. Thus, for example, the uses and methods described herein may result in less bone mineral density loss for a given level of efficacy (with respect to symptom control), or, alternatively, greater efficacy of symptom control for a given amount of bone mineral density change.

Disclosed herein are methods of using the orally active GnRH antagonist (N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea) (Compound 1), or a pharmaceutically acceptable salt thereof, for the treatment of uterine fibroids, endometriosis, adenomyosis, or heavy menstrual bleeding; infertility; pain associated with uterine fibroids, endometriosis, or adenomyosis; anemia; or one or more symptoms of uterine fibroids, endometriosis, or adenomyosis; or for preventing miscarriage. Also disclosed are methods of contraception; maintaining bone density, a normal lipid profile, or normal blood glucose range; or treating one or more of hot flashes, night sweats, other vasomotor symptoms, vulvovaginal atrophy, vaginal dryness, fatigue, malaise, and headache in a pre-menopausal woman being treated for one or more of uterine fibroids, endometriosis, adenomyosis, or heavy menstrual bleeding with Compound 1 or a pharmaceutically acceptable salt thereof. Once-daily, oral administration of Compound 1 or a pharmaceutically acceptable salt to a subject may result in rapid suppression of estrogen and progesterone levels, without an initial rise in hormones that lead to an aggravation of symptoms, also known as a clinical or hormonal flare.

A pre-menopausal woman may, for example, include a woman who has started having menstrual periods but who has not yet reached menopause. A pre-menopausal woman may include a woman who is experiencing peri-menopause. Whether a woman is pre-menopausal may be determined by evaluating a woman's medical history, for example by asking questions to the woman. In a woman who has not had a period for a year or longer, FSH levels in serum greater than or equal to 30 mIU/mL may also indicate the woman has reached menopause.

The methods provided herein include co-administration of a hormone replacement medicament (e.g., a combination of an estradiol or estradiol equivalent and a progestin). As discussed above, suppression of estrogen and/or progesterone, for example by administration of a GnRH agonist or GnRH antagonist, or altering the action of progesterone, for example by administration of a SPRM, can lead to unwanted and side effects.

Suppression of estrogen can cause bone mineral density loss and vasomotor side effects, such as hot flashes or night sweats. Bone mineral density loss can be a side effect of particular note, as a subject may be unaware that bone mineral density is being lost in the short term (e.g., over weeks or months), but over time it can lead to significant health problems such as an increased chance of bone fracture and/or osteoporosis. This loss of bone mineral density may occur when estrogen levels drop below a certain threshold and can happen over short periods of time, for example, for just a few hours each day if estrogen drops below the threshold. Thus, if estrogen levels are not maintained consistently over the course of each day during treatment, a subject may be losing bone mineral density during a portion of the day, which can result in cumulative negative long-term health consequences.

Similarly, suppression of progesterone without concurrent suppression of estrogen can also lead to deleterious side effects. Unopposed estrogen in women can cause endometrial hyperplasia, which is a risk factor for endometrial cancer. Therapies that suppress progesterone without concurrent estrogen suppression may lead to negative effects administered long term, for example three months or more. Patients may be prescribed cycles of therapy with breaks in between to reduce the risk of serious adverse side effects, such as endometrial hyperplasia. This type of intermittent scheduling may be required for therapies using SPRMs, which selectively modulate progesterone receptors.

Administering a combination of a hormone replacement medicament with Compound 1, or a pharmaceutically acceptable salt thereof, as described herein, may help maintain bone mineral density or treat one or more vasomotor symptoms (e.g., hot flashes or night sweats) or other side effects of administration of Compound 1 or a pharmaceutically acceptable salt thereof. These other side effects may include, for example, vulvovaginal atrophy, vaginal dryness, fatigue, malaise, and headache. Administering a hormone replacement medicament may also, in some embodiments, prevent or reduce one or more symptoms of unopposed estrogen. The ability to mitigate the side effects of treatment with a GnRH antagonist, while maintaining efficacy (e.g., the reduction of heavy menstrual bleeding associated with uterine fibroids or adenomyosis, or pain associated with uterine fibroids, endometriosis, or adenomyosis, etc.) could allow for long-term use of Compound 1 or a pharmaceutically acceptable salt thereof. In addition, such safe and efficacious long-term treatment may provide an alternative to surgical (e.g., hysterectomy or myoectomy) or other invasive procedures (e.g., laparoscopy) typically prescribed for certain of the conditions described herein, such as uterine fibroids and endometriosis. Thus, women with these conditions may in some embodiments effectively manage the symptoms of their disease long-term, without sacrificing their reproductive potential.

There may exist an upper estrogen limit and an upper progesterone limit for certain conditions as well. The disorders described herein and their symptoms are estrogen sensitive, such as endometriosis and uterine fibroids. These disorders may be aggravated by hormones such as estrogen rising above the upper limit, even if the level is above the limit only for a short period of time, for example a few hours daily. In some cases, this aggravation of the disorder may not be known to the subject in the short term, but can over time lead to a flare of symptoms. Similarly, certain symptoms of uterine fibroids are believed to have a greater response to progesterone than to estrogen, for example fibroid tumor growth.

The dose of the hormone replacement medicament and Compound 1 or a pharmaceutically acceptable salt thereof, and their consistent administration in combination, may be important to maintaining the concentration of Compound 1 and estrogen within a treatment window, wherein the level of Compound 1 is sufficient to suppress endogenous estrogen production, thereby treating the symptoms and/or conditions, while the level of estrogen provided by the hormone replacement medicament (e.g., a combination of an estradiol or estradiol equivalent and a progestin) is sufficient to prevent one or more symptoms of a hypoestrogenic state (e.g., bone mineral density loss, vasomotor symptoms, vulvovaginal atrophy, vaginal dryness, fatigue, malaise, or headache). As described above, falling outside of this treatment window over the course of the day may lead to one or more negative side effects, such as bone mineral density loss, vasomotor symptoms, or exacerbation of the symptom or condition being treated.

Merely combining any GnRH antagonist or GnRH agonist with a hormone replacement medicament may not result in sufficient hormone suppression to adequately treat one or more symptoms, or may not maintain hormone levels high enough to avoid one or more deleterious side effects. In some cases, for other therapies, the blood plasma concentration of one or more hormones in a subject can vary over the course of each day such that neither adequate treatment nor the avoidance of certain side effects is achieved. In other cases, in other therapies, variation or imbalance over a longer period of time, such as over a few months, may prevent a therapy from being used long term, such as for more than 3, 6, or 12 months. Surprisingly, it has been found that once-daily administration of Compound 1, or a pharmaceutically acceptable salt thereof, and a hormone replacement medicament may result in greater stability of the blood plasma concentration of estrogen than administration of other GnRH antagonists or GnRH agonists.

FIG. 163 depicts two graphs demonstrating the effect on serum estradiol levels of once-daily oral administration of Compound 1, or a combination of Compound 1 and a hormonal replacement medicament comprising estradiol and the progestin norethindrone acetate ($E_2$/NETA), according to Example 9. The graph on the left depicts the median serum estradiol trough concentration as measured in a blood sample taken at the study visit prior to that day's administration. As is shown in this graph, administration of Compound 1 once-daily results in a serum estradiol concentration that is consistently below 10 pg/mL over multiple weeks. Subjects that were administered estradiol and NETA ($E_2$/NETA) add-back also had a consistent trough serum estradiol concentration as measured at each study visit, but above the 20 pg/mL threshold. As shown in the right graph, the median estradiol concentration during the study visit of week 3 stayed between 20 pg/mL to 50 pg/mL during the 24 hours following administration Compound 1 and estradiol and NETA ($E_2$/NETA). Administration of Compound 1 without a hormone replacement medicament resulted in serum estradiol levels of below 10 pg/mL over the subsequent 24 hours. Maintaining serum estradiol levels within this 20 pg/mL to 50 pg/mL range by administration of Compound 1 and a hormone replacement medicament, such as estradiol or an estradiol equivalent and progestin, may provide relief from one or more symptoms of an estrogen-sensitive condition (such as uterine fibroids, endometriosis, or adenomyosis) or heavy menstrual bleeding, while also reducing one or more GnRH antagonist side effects, such as bone mineral density loss or vasomotor symptoms.

In contrast, other GnRH antagonists, such as elagolix, are less effective or not effective at suppressing estrogen levels with once-daily administration. FIG. 167 summarizes some aspects of administration of elagolix compared with Compound 1 (relugolix). In some studies, maximum suppression of estrogen was achieved with 200 or greater mg of elagolix administered twice daily, while other studies disclose that 200 mg of elagolix administered once-daily is less effective at suppressing $E_2$ (estradiol) than 200 mg split over 7 administrations throughout the day. (See J. W. Ng, et al., "Dose-Dependent Suppression of Gonadotropins and Ovarian Hormones by Elagolix in Healthy Premenopausal Females" (poster, 2016); J. Grundy, et al., Nature (2008), Vol 83: Supplement 1, S9) The IC50 of elagolix is 1.5 nM, and the half-life of elagolix is 2.4–6.3 h. (See Chen et al., J. Med. Chem. 2008, 51:7478–7485, compound 10b; Struthers et al., J. Clin. Endocrinol. Metab., February 2009, 94(2):545–551) In contrast, Compound 1 can suppress $E_2$ to below 10 pg/mL in the majority of subjects with administration of 40 mg per day, has an IC50 of 0.12 nM, and has a half-life of 37–42 hours.

It is further surprising that uterine fibroids and endometriosis, which are both estrogen-responsive diseases, may in some embodiments be treated using the same dosage of Compound 1, or a pharmaceutically acceptable salt thereof. Estrogen-dependent diseases do not have the same sensitivity to estrogen. These diseases are not all responsive to the same levels of estrogen, but rather exhibit a hierarchy of responsivity. Myomas (e.g., uterine fibroids) are generally more responsive to estrogen than endometriosis, and thus the ability to treat endometriosis using the same dosage of Compound 1, or a pharmaceutically acceptable salt thereof, as can be effective for uterine fibroids is surprising. A discussion of estrogen sensitivity may be found in R. L. Barbieri, Am. J. Obstet. Gynecol (1992), 166(2): 740–745.

It is also surprising that in some embodiments, the methods herein may treat symptoms or conditions that are sensitive to progesterone, and symptoms or conditions that are sensitive to estrogen. For certain conditions and/or symptoms, the suppression of progesterone may lead to better amelioration. For example, it is thought that fibroid tissue responds to progesterone, and thus the consistent suppression of progesterone may reduce the size and/or number of fibroids in a subject with uterine fibroids. (See S. E. Bulun, Uterine Fibroids, N. Engl. J. Med. (2013), 369: 1344–1355) Compound 1, or a pharmaceutically acceptable salt thereof, may also suppress endogenous progesterone production. The dose of Compound 1, or a pharmaceutically acceptable salt thereof, administered as described herein may be sufficient to suppress endogenous progesterone production, wherein this progesterone suppression can treat the symptoms and/or conditions, while the level of estrogen and progestin provided by the hormone replacement medicament (e.g., a combination of an estradiol or estradiol equivalent and a progestin) may be sufficient to prevent one or more symptoms of a hypoestrogenic state (e.g., bone mineral density loss, vasomotor symptoms, vulvovaginal atrophy, vaginal dryness, fatigue, malaise, or headache), and/or prevent symptoms associated with unopposed estrogen. Further, it may be desirable to suppress both progesterone and estrogen to treat, for example, multiple symptoms of one condition. For example, it is thought that heavy menstrual bleeding associated with uterine fibroids may be associated with estrogen levels, and thus the suppression of both estrogen and progesterone lead to greater symptom relief in certain women with uterine fibroids.

As was mentioned previously, the combination of just any GnRH agonist or GnRH antagonist with a hormone replacement medicament cannot always achieve effective treatment of a hormone-sensitive condition, and/or ameliorate side effects of hormone suppression. GnRH agonists, which also lead to the suppression of estrogen after an initial clinical flare period, can be co-administered with add-back hormonal therapy. However, combining GnRH agonists to suppress estrogen with add-back hormonal therapy has had mixed results. A review of the data from a dozen clinical trials evaluating uterine fibroid treatment using GnRH agonists with add-back hormonal therapy found the treatment outcome and effect on bone mass, vasomotor symptoms, and quality of life varied widely, with some data inconclusive. (See R. M. Moroni, et al., Cochrane Database of Systemic Reviews (2015), Issue 3, Article No: CD010854) Leuprolelin, a GnRH agonist, can be combined with hormonal add-back therapy for up to 6 months. The FDA did not approve extending the treatment period to up to 12 months. Data associated with the request to extend treatment up to 12 months showed that 10 of 157 women had a decrease of more than 5.0% in one or more post baseline bone mineral density measurements, and all but one of these decreases was after the 24 week visit. In addition, the request did not include data showing treatment for up to 1 year resulted in better suppression of endometriosis symptoms or prolongation of therapeutic benefit after completion of therapy. (See Medical Review(s) Part 1, Part 2, and Part 3 at www.accessdata.fda.gov/drugsatfda_docs/nda/2001/20-708S011_Lupron.cfm, accessed Sep. 18, 2017)

It is surprising that administering a combination of Compound 1, or a pharmaceutically acceptable salt thereof, and a hormone replacement medicament (e.g., a combination of an estradiol or estradiol equivalent and a progestin) may result in effective treatment of uterine fibroids and/or the reduction, prevention, or amelioration, of one or more symptoms associated with a hypoestrogenic state (e.g., bone mineral density loss, vasomotor symptoms such as hot flashes or night sweats, vulvovaginal atrophy, vaginal dryness, fatigue, malaise, or headache) in view of the inconsistent results achieved by administration of GnRH agonists. For example, FIG. 165 depicts graphs showing the change compared to baseline of C-telopeptide and N-telopeptide at two time points during administration of Compound 1 (relugolix) alone, or with estradiol/norethindrone add-back. C-telopeptide and N-telopeptide are biomarkers related to bone turnover. As shown in FIG. 165, the use of estradiol/norethindrone add-back in combination with Compound 1 resulted in a significant decrease in the change from baseline of both C-telopeptide and N-telopeptide resulting from treatment with Compound 1 alone. This indicates administration of the combination of Compound 1 and a hormone replacement medicament resulted in less bone resorption than Compound 1 alone.

Compound 1, or a pharmaceutically acceptable salt thereof, has a faster onset of action than currently available GnRH agonists, and unlike available peptide GnRH agonists that are given either subcutaneously or intranasally, Compound 1 is a non-peptide preparation that can be administered orally and once-daily. When compared to GnRH agonists, such as leuprolide acetate, which is typically administered as a depot formulation, Compound 1 or a pharmaceutically acceptable salt thereof offers several advantages. Such advantages include, but are not limited to, oral administration, rapid onset of estrogen suppression, absence of clinical flare, and rapid return to baseline estrogen levels after treatment is suspended. In contrast to a treatment which uses depot injections, treatment with an oral formulation comprising Compound 1 or a pharmaceutically acceptable salt thereof administered once-daily may allow for a short term holiday in which a subject may stop treatment for a period of time and later restart treatment with no or very minimal adverse effects. For example, a more rapid return of hormone levels to baseline may be advantageous in the management of a concurrent illness, or in the restoration of fertility in women desiring to attempt conception and pregnancy. This contrast is illustrated in FIG. 162, which depicts the serum estradiol concentration in subjects following discontinuation of Compound 1 (relugolix) or leuprolide (right graph) in the study described in Example 7. As seen in the graph, four weeks after discontinuation of Compound 1, the mean estradiol serum concentration has returned to levels similar to control (placebo), while the mean estradiol serum concentration in subjects discontinuing leuprolide is only about one-fifth of the control. Thus, the treatment methods of this disclosure may provide a desirable quick on/off option for pre-menopausal women, permitting intermittent treatment as needed or desired.

Thus, provided herein are methods of treating uterine fibroids, endometriosis, or adenomyosis in a pre-menopausal woman, comprising administering once-daily an oral dosage form of gonadotropin-releasing hormone (GnRH) antagonist Compound 1, or a pharmaceutically acceptable salt thereof, in combination with an estradiol or estradiol equivalent and a progestin to the pre-menopausal woman. Also provided herein are pharmaceutical compositions comprising Compound 1 and an estradiol or estradiol equivalent and a progestin medicament for use in treating uterine fibroids, endometriosis, or adenomyosis. As discussed below, in some embodiments the methods comprise administering to a pre-menopausal woman a combination of between about 10 mg to about 60 mg of Compound 1, or an equivalent amount of a pharmaceutically acceptable salt thereof, and a hormone replacement medicament In certain embodiments, it may be desirable to first administer Compound 1, or a pharmaceutically acceptable salt thereof, without add-back therapy for a period of time prior to transitioning to administration of the combination. The combination may be administered, for example, as either a fixed dose or in two or more separate dosage forms that are co-administered. This may be desirable, for example, in a woman with severe symptoms, or a plurality of symptoms, or with a desire to more quickly alleviate one or more symptoms. Administration of Compound 1, or a pharmaceutically acceptable salt thereof, without a hormone replacement medicament may result in lower serum estradiol and/or serum progesterone levels more rapidly than administration of the combination, and therefore may more quickly alleviate one or more symptoms of an estrogen- or progesterone-sensitive condition.

Further provided herein are methods of treating, and pharmaceutical compositions for use in treating, one or more symptoms or conditions selected from the group consisting of heavy menstrual bleeding, infertility, female sexual dysfunction (for example, decreased libido, decreased arousal, or decreased sexual activity), gender transition, spotting, sex-hormone driven cancers, analgesic compound use (for example reducing analgesic compound use) amenorrhea, fertility (for example maintaining fertility), anemia (associated with heavy menstrual bleeding or independent of heavy menstrual bleeding), pain (for example dyspareunia, chronic pain, pain with defecation, or pain with urination), inflammation, irregular menstruation, symptoms related to fibroid size and/or bulk, pregnancy loss, depression, chronic fatigue, anxiety, and sleep disturbance. In some embodiments, one or more of these symptoms or conditions are associated with uterine fibroids, endometriosis, or adenomyosis. In other embodiments, one or more of these symptoms or conditions are not related to uterine fibroids, endometriosis, or adenomyosis. In certain embodiments, one or more of these symptoms or conditions is in a pre-menopausal woman that has not been diagnosed with uterine fibroids, has not been diagnosed with endometriosis, or has not been diagnosed with adenomyosis, or any combination of the foregoing.

The methods provided herein may allow, after treatment is discontinued, the pre-menopausal woman to conceive, be pregnant, or to give birth. The ability to conceive, be pregnant, or give birth after discontinuing the treatment as described herein may be an advantage over other methods. As discussed above, many methods of treating uterine fibroids, endometriosis, or adenomyosis, or symptoms related to these conditions (e.g., heavy menstrual bleeding or pain associated with one or more of these conditions) in both the short or long term involve surgical intervention (e.g., hysterectomy) that preclude pregnancy. In contrast, the methods described herein, such as methods of treating endometriosis, uterine fibroids, adenomyosis; heavy menstrual bleeding; or pain associated with uterine fibroids, endometriosis, or adenomyosis, over a long period of time such as at least 24 consecutive weeks, may allow the condition or symptom to be controlled enough to avoid surgical intervention, and allow the pre-menopausal women to conceive, be pregnant, or give birth after discontinuing treatment. In certain variations, the pre-menopausal woman has experienced one or more miscarriages, or an inability to conceive, or a combination thereof prior to treatment as described herein.

Further provided herein are methods for reducing one or more side effects associated with the administration of a GnRH antagonist, such as Compound 1, wherein the side effect is selected from the group consisting of bone mineral density loss, hot flashes, night sweats, vasomotor symptoms other than hot flashes or night sweats, vulvovaginal atrophy, vaginal dryness, fatigue, malaise, and headache. In addition, provided herein are methods for maintaining the lipid profile, or for maintaining normal glucose range, in a subject that has been administered a GnRH antagonist, such as Compound 1 or a pharmaceutically acceptable salt thereof. Such methods may include administration of Compound 1 or a pharmaceutically acceptable salt thereof and a hormone replacement medicament to a pre-menopausal woman. In some embodiments, the subject has been diagnosed with uterine fibroids, endometriosis, or adenomyosis. In other embodiments, the pre-menopausal woman has not been diagnosed with uterine fibroids, endometriosis or adenomyosis.

As noted above, the methods and uses described herein may for a number of women increase response rates with respect to symptoms of the conditions described herein and tighten distribution (narrow the range of) of estradiol levels experienced, while still protecting bone health.

Throughout the present disclosure, amounts of Compound 1 disclosed refer to the amount of Compound 1 free form present in the formulation. The term "corresponding amount" as used herein refers to the amount of a pharmaceutically acceptable salt of Compound 1 required to obtain the amount of Compound 1 free form recited in the formulation or method. It would be clear to one of skill in the art how to calculate the "corresponding amount" of the salt of a compound, such as the corresponding amount of the pharmaceutically acceptable salt of Compound 1, taking into account the difference in molecular weight between the free form of a compound and a salt form. For example, about 40 mg of Compound 1 would correspond to about 42.3 mg of the hydrochloride salt of Compound 1.

Physiologically acceptable, pharmaceutically acceptable, or pharmacologically acceptable compounds and compositions may include materials which are not biologically, or otherwise, undesirable. For example, the material may be administered to an individual without causing any substantially undesirable biological effects or interacting in a deleterious manner with any of the components of the composition in which it is contained.

As used herein, treating or treatment of a condition, such as a specified disease or disorder, may include treating one or more symptoms of the condition and/or preventing the occurrence of the condition. Treatment may include ameliorating one or more symptoms (e.g., pain) or preventing one or more symptoms, such as preventing new fibroids or making existing fibroids shrink, preventing new endometriomas or endometriosis lesions, or decreasing the number or inflammation associated with existing lesions. Ameliorating pain may include, for example, reducing pelvic pain (including dysmenorrhea), non-menstrual pelvic pain, or dyspareunia.

Provided are also combined preparations for use in any of the methods described herein. In some embodiments, the combined preparation is for simultaneous or sequential use. In certain embodiments, the combined preparation comprises Compound 1 or a pharmaceutically acceptable salt thereof, and a hormone replacement medicament. In some embodiments, the hormone replacement medicament comprises estradiol or estradiol equivalent, and progestin. Further provided is the use of Compound 1 or a pharmaceutically acceptable salt thereof, for the manufacture of a medicament for treatment according to any of methods described herein. Provided is also the use of Compound 1 or a pharmaceutically acceptable salt thereof, and a hormone replacement medicament for the manufacture of a medicament for treatment according to any of methods described herein. In some embodiments, the hormone replacement medicament comprises estradiol or estradiol equivalent and progestin.

I. Compound 1

Compound 1 is N-(4-(1-(2,6-difluorobenzyl)-5-((dimethylamino)methyl)-3-(6-methoxy-3-pyridazinyl)-2,4-dioxo-1, 2,3,4-tetrahydrothieno[2,3-d]pyrimidin-6-yl)phenyl)-N'-methoxyurea. Compound 1 is represented by the chemical structure below:

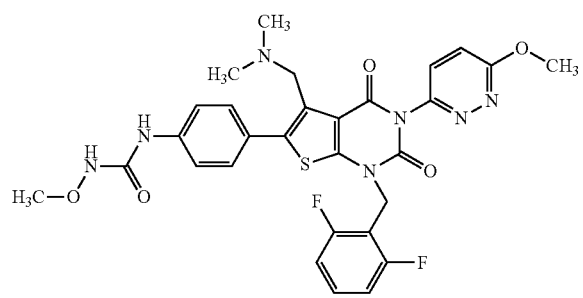

Compound 1 and pharmaceutical compositions including Compound 1 can be produced by methods described in U.S. Pat. Nos. 7,300,935, 8,058,280, 9,346,822, 9,758,528, PCT Publication No. WO 2016/136,849, and U.S. Pat. No. 8,735,401, the disclosures of which are incorporated herein by reference in their entireties. Compound 1 may also be referred to herein as "relugolix".

As used herein, salts of Compound 1 are preferably physiologically acceptable acid addition salts. Such salts include, for example, salts with inorganic acids (e.g., hydrochloric acid, hydrobromic acid, nitric acid, sulfuric acid, phosphoric acid, and the like), and salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like).

Compound 1 is an orally active, non-peptide compound. It is thought that Compound 1 antagonizes GnRH through the GnRH receptors that are present in the pituitary anterior lobe basophiles (secretory cells), and inhibits the GnRH-stimulated secretion of luteinizing hormone and follicle stimulating hormone from these cells. As a result, the drug decreases blood concentrations of hormones, including estradiol and progesterone. As Compound 1 is a GnRH antagonist, it is thought that it does not cause clinical flare and has a faster onset of action than GnRH agonists. Unlike known GnRH agonists, Compound 1 is not a peptide preparation. While GnRH agonists are given either intramuscularly, subcutaneously, or intranasally, Compound 1 can be administered orally, which may make possible daily administration and maintenance of a steady state plasma level of the GnRH antagonist. Additionally, Compound 1 has been shown to have a higher affinity for human GnRH receptors than leuprolide acetate (a peptide agonist) and cetrorelix (a peptide antagonist).

Unlike GnRH agonists such as leuprolide acetate, Compound 1 is not a depot, or a slow-release formulation and hormone levels return to baseline more rapidly after treatment with Compound 1 is discontinued, which may provide more control for patients and their physicians. Thus, in contrast to a treatment which uses depot injections, the treatment methods of this disclosure may allow for short term holidays in which subjects can stop treatment for a period of time and later restart treatment with no adverse effects. For example, a more rapid return of hormone levels to baseline may be advantageous in the management of a concurrent illness, and the restoration of fertility in women desiring to attempt pregnancy. Further, as a GnRH antagonist, Compound 1 has a rapid onset of action. Thus, the treatment methods of this disclosure may provide a desirable quick on/off option for subjects, permitting intermittent treatment as needed or desired.

In some embodiments, an immediate release version of Compound 1 has an elimination half-life ($T_{1/2}$), sometimes called a mean plasma half-life, of between about 37 hours and about 42 hours. In fact, $T_{1/2}$ of an immediate release version of Compound 1 has been found to reach about 61 hours.

In some embodiments, the methods provided herein do not include administering Compound 1 or a pharmaceutically acceptable salt thereof within 6 hours of administering a P-glycoprotein (P-gp) inhibitor, CYP3A inducer, or a P-gp inducer, or any combinations thereof. P-gp mediates the export of drugs from certain cells, such as those located in the small intestine, blood-brain barrier, hepatocytes, and kidney proximal tube. P-gp may be affected by P-gp inducers or inhibitors, which impair P-gp mediated uptake or efflux, or enhance P-gp activity, respectively. CYP3A is a subfamily of monooxygenases which may be involved in drug metabolism. P-gp or CYP3A inducers may include carbamazepine, rifampin, St. John's wort, bosentan, efavirenz, mitotane, modafinil, or nafcillin. P-gp inhibitors may include amiodarone, azithromycin, captopril, carvedilol, clarithromycin, conivaptan, cyclosporine, diltiazem, dronedarone, eliglustat, erythromycin, felodipine, itraconazole, ketoconazole, lapatinib, lopinavir/ritonavir, propafenone, quercetin, quinidine, reserpine, ranolazine, saquinavir, telaprevir, tipranavir, ticagrelor, tacrolimus, and verapamil. A discussion of the P-gp transport system may be found in J. D. Wesslery, et al. JACC (2013) 61(25): 2495–502. In some embodiments, Compound 1 or a pharmaceutically acceptable salt thereof is administered no less than 6 hours, no less than 8 hours, no less than 10 hours, or no less than 12 hours before a P-gp inhibitor, CYP3A inducer, or a P-gp inducer, or any combinations thereof is administered. In some embodiments, Compound 1 or a pharmaceutically acceptable salt thereof is administered no less than 6 hours, no less than 8 hours, no less than 10 hours, or no less than 12 hours after a P-gp inhibitor, CYP3A inducer, or a P-gp inducer, or any combinations thereof is administered. In certain embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours before a P-gp inhibitor, CYP3A inducer, or a P-gp inducer, or any combinations thereof is administered. In other embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours after a P-gp inhibitor, CYP3A inducer, or a P-gp inducer, or any combinations thereof is administered.

II. Hormone Replacement Medicament

As described above, provided herein are methods of treating or preventing a condition or symptom as described herein, comprising administering to a pre-menopausal woman in need thereof a combination of Compound 1, or a pharmaceutically acceptable salt thereof, and a hormone replacement medicament. In some embodiments, the hormone replacement medicament comprises estradiol or an estradiol equivalent, or a progestin, or a combination thereof.

In some embodiments, Compound 1 or a pharmaceutically acceptable salt thereof is administered at a dose that suppresses estrogen production, such as a dose that results in sustained estrogen suppression throughout a 24-hour period. In some embodiments, the dose suppresses estradiol production to a blood serum level of less than 20 pg/mL or less than 10 pg/mL. In some embodiments, the co-administration of a hormone replacement medicament with Compound 1, or a pharmaceutically acceptable salt thereof, can prevent, decrease, or otherwise ameliorate symptoms associated with a hypoestrogenic state, such as bone mineral density loss, one or more vasomotor symptoms, vulvovaginal atrophy, vaginal dryness, fatigue, malaise, or headache. In some embodiments, the one or more vasomotor symptoms is selected from hot flashes and night sweats.

The hormone replacement medicament may comprise progestin. A progestin may, for example, refer to a compound that has a similar biological activity as progesterone. Examples of progestins that may be used in the methods and compositions provided herein include norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogestrone acetate, promegestone, and dienogest. In some embodiments, the progestin is norethindrone acetate.

The hormone replacement medicament may comprise estradiol or an estradiol equivalent. The estradiol equivalent may, for example, be a compound that has biological activity similar to estradiol (17-β-estradiol). Examples of estradiol equivalents include equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, and stilbestrol.

III. Uterine Fibroids

Uterine fibroids are benign, estrogen-sensitive tumors (myomas) that grow in the muscular wall of the uterus in approximately 25% of women of reproductive age. The most common symptom of uterine fibroids is HMB, with a menstrual period of increased duration (10 to 14 days, rather than the usual 5 to 7 days) and increased volume (300 to 500 mL per menstrual cycle, compared to less than 80 mL for a normal menstrual cycle). In particular, HMB is thought to be caused by the combination of an increase in surface area of the uterine cavity, poor uterine contraction due to the myoma, and increased circulation, congestion, or impaired hemostasis due to hypertrophy of the endometrium in the vicinity of the myoma. Persistent HMB can induce iron-deficiency anemia and associated fatigue and loss of energy. Therefore, HMB is a primary factor that deteriorates the quality of life of patients with uterine fibroids. Other symptoms that can occur in addition to or independent of HMB include compression or pain in the abdomen and pelvis due to large myoma, low back pain, urinary frequency or urinary tract obstruction, constipation and pregnancy loss.

Provided herein is a method for treating uterine fibroids in a pre-menopausal woman in need thereof, comprising orally administering to the pre-menopausal woman once-daily a combination of Compound 1, or a pharmaceutically acceptable salt thereof, and a hormone replacement medicament (e.g., a combination of an estradiol or estradiol equivalent and a progestin). Provided is also method for treating heavy menstrual bleeding associated with uterine fibroids in a pre-menopausal woman, comprising administering to the pre-menopausal woman once-daily a combination of Compound 1, or a pharmaceutically acceptable salt thereof, and a hormone replacement medicament. Additionally provided is a method for treating pain associated with uterine fibroids in a pre-menopausal woman in need thereof, comprising administering to the pre-menopausal woman once-daily a combination of Compound 1, or a pharmaceutically acceptable salt thereof, and a hormone replacement medicament. Further provided is a method for treating a pre-menopausal woman with symptomatic uterine fibroids, comprising administering to the pre-menopausal woman once-daily a combination of Compound 1, or a pharmaceutically acceptable salt thereof, and a hormone replacement medicament. The combination may be administered, for example, as either as a fixed dose or in two or more separate dosage forms that are co-administered. Further provided are combined preparations for use in any of these methods. In some embodiments, the combined preparation is for simultaneous or sequential use. In certain embodiments, the combined preparation comprises Compound 1, or a pharmaceutically acceptable salt thereof, and a hormone replacement medicament. In certain embodiments, the hormone replacement medicament comprises estradiol or estradiol equivalent, and progestin. Further provided is the use of Compound 1, or a pharmaceutically acceptable salt thereof, and a hormone replacement medicament for the manufacture of a medicament for treatment according to any of these methods. In some embodiments, the hormone replacement medicament comprises estradiol or estradiol equivalent, and progestin.

In some embodiments of the methods of treating uterine fibroids, heavy menstrual bleeding associated with uterine fibroids, pain associated with uterine fibroids, or a woman with symptomatic uterine fibroids provided herein, the pre-menopausal woman experiences an improvement of one or more symptoms during the treatment, or after the treatment. The one or more symptoms may be selected from the group consisting of anemia, heavy menstrual bleeding, irregular periods, spotting, inflammation, pain, fatigue, urinary obstruction, urinary frequency, incontinence, constipation, anxiety, sleep disturbance, quality of life, activities of daily living, female sexual dysfunction and depression. Pain may be, for example, back pain, pelvic pain, uterine pain, chronic pain, pain with defecation, pain with urination, or dyspareunia, or any combinations thereof. Thus, provided herein are methods of treating one or more symptoms associated with uterine fibroids in a pre-menopausal woman in need thereof, comprising administering to the pre-menopausal woman once-daily a combination of Compound 1, or a pharmaceutically acceptable salt thereof, and a hormone replacement medicament.

Activities of daily living may, for example, include one or more activities that people tend to do every day without requiring assistance. These activities may be: eating, bathing, dressing, toileting, transferring (walking), and continence.

Anemia may, for example, include a medical condition in which the red blood cell count or hemoglobin is lower than normal. For men, anemia is typically defined as a blood hemoglobin level of less than 13.5 gram/100 mL, and in women as blood hemoglobin of less than 12.0 gram/100 mL.

Anxiety may, for example, include feeling worry, nervousness, or unease, and may be associated with an imminent event or an event with an uncertain outcome.

Chronic pain may, for example, include ongoing or recurrent pain lasting beyond the usual course of an acute illness or injury, or more than 3 to 6 months. Chronic pain may adversely affect the well-being of a subject.

Constipation may, for example, include the occurrence of three or fewer bowel movements per week, and may include when a bowel movement is associated with hard, dry stools, a perception of incomplete evacuation, or the need for straining to pass a bowel movement, or any combinations thereof.

Depression may, for example, include major depressive disorder or clinical depression, and be a serious mood disorder. It may have symptoms that affect how a subject feels, thinks, and handles daily activities such as sleeping, eating, or working. In some embodiments, to be diagnosed with depression, the symptoms must be present for at least two weeks. An individual experiencing one or more of the following signs and symptoms most of the day, nearly every day, for at least two weeks, may be suffering from depression: persistent sad, anxious, or "empty" mood; feelings of hopelessness, or pessimism; irritability; feelings of guilt, worthlessness, or helplessness; loss of interest or pleasure in hobbies and activities; decreased energy or fatigue; moving or talking more slowly; feeling restless or having trouble sitting still; difficulty concentrating, remembering, or making decisions; difficulty sleeping, early-morning awakening, or oversleeping; appetite and/or weight changes; thoughts of death or suicide, or suicide attempts; aches or pains, headaches, cramps, or digestive problems without a clear physical cause and/or that do not ease even with treatment. Not everyone who is depressed may experience every symptom. Some people experience only a few symptoms while others may experience many. Several persistent symptoms in addition to low mood may be required for a diagnosis of major depression, but people with only a few—but distressing—symptoms may benefit from treatment of their "subsyndromal" depression. The severity and frequency of symptoms and how long they last will vary depending on the individual and his or her particular illness. Symptoms may also vary depending on the stage of the illness.

Fatigue may, for example, include feelings of tiredness distinct from weakness, and which has a gradual onset.

Female sexual dysfunction may, for example, include persistent, recurrent problems with sexual response, desire, orgasm, or pain associated with sexual activity, which distress the woman and/or strain her relationship with her partner. Female sexual dysfunction may be measured using one or more questionnaires which assess parameters of sexual function, such as desire, libido, and arousal.

Dyspareunia may, for example, include painful sexual intercourse due to medical or psychological causes. The pain can primarily be on the external surface of the genitalia, or deeper in the pelvis upon deep pressure against the cervix. It can affect a small portion of the vulva or vagina or be felt all over the surface.

Heavy menstrual bleeding (HMB) may, for example, include any of the following: bleeding that lasts more than 7 days; bleeding that soaks through one or more tampons or pads every hour for several hours in a row; needing to wear more than one pad at a time to control menstrual flow; needing to change pads or tampons during the night; or menstrual flow with blood clots that are as big as a quarter or larger. Heavy menstrual bleeding may refer to a menstrual period of increased duration (10 to 14 days, rather than the usual 5 to 7 days) and increased volume (300 to 500 mL per menstrual cycle, compared to less than 80 mL for a normal menstrual cycle). Heavy menstrual bleeding may disrupt activities of daily living. Using the alkaline hematin method, the amount of blood collected in feminine products can be quantified. Heavy menstrual bleeding may include the loss of >80 mL of blood in a given period, as assessed by the alkaline hematin method. Heavy menstrual bleeding may also include a score of at least 100 using the Pictorial Blood Loss Assessment Chart.

Hot flashes may also be referred to as hot flushes.

Incontinence may, for example, include the involuntary leakage of urine.

Inflammation may, for example, include a biological process by which the white blood cells in the body and substances the cells produce are involved in a protective response against one or more foreign organisms, such as bacteria and/or viruses. Inflammatory response may be triggered by disease conditions in the absence of an infection, or by harmful stimuli such as damaged cells or an irritant. Sometimes inflammation may cause damage to the body while trying to protect it.

Irregular periods may, for example, include menstrual periods that occur more frequently than every 21 days; menstrual periods which occur less frequently than every 35 days; or a menstrual period that lasts longer than 8 days. Missed, early, or late periods may also be signs of an irregular cycle, in particular if the one or more signs occur frequently and the time between periods and the duration vary significantly from month to month.

Pain may, for example, include physical suffering or discomfort as a result of illness or injury.

Quality of life (QOL) may, for example, include the general well-being of a subject related to their health and happiness. The QOL of subject may be measured through one or more tools that capture the individual's perception of how one or more diseases, syndromes, or symptoms affect different areas of their life, such as the ability to perform activities of daily living.

Sleep disturbance may, for example, include one or more conditions that affect a subject's sleep. These may include insomnia, the inability to fall asleep and/or stay asleep; hypersomnia, being excessively sleepy; or sleep disorders, which involve difficulty breathing during sleep. Certain conditions, syndromes, or symptoms disclosed herein may cause sleep disturbance, such as uterine fibroids, endometriosis, adenomyosis, heavy menstrual bleeding, or pain.

Spotting may, for example, include light bleeding from the vagina. The bleeding may just be a few spots, or it may be a very light flow. Spotting may occur in between periods, just before or just after the normal period. While spotting may be similar to a menstrual period, spotting is much lighter and is often short-lived. In most cases, the bleeding stops in just a few hours or days.

Urinary obstruction may, for example, include a partial or complete blockage of the flow of urine out of the body.

Urinary frequency may, for example, include the need to urinate many times during the day, at night (nocturia), or both. Urination may occur in normal or less-than-normal volumes.

In some embodiments, the methods of treating uterine fibroids, heavy menstrual bleeding associated with uterine fibroids, pain associated with uterine fibroids, or a woman with symptomatic uterine fibroids provided herein result in the reduction of the number of uterine fibroids, the reduction of the size of one or more uterine fibroids, or the prevention of uterine fibroid growth, or any combination thereof, during and/or after treatment. The size and/or number of uterine fibroids may be assessed by, for example, transvaginal ultrasound, abdominal ultrasound, magnetic resonance imaging, computed tomography, or laparoscopy. In some embodiments, the methods of treating a pre-menopausal woman with symptomatic uterine fibroids provided herein suppresses the endometrium in the woman. Suppression of the endometrium may include, for example, endometrial thickness in a transvaginal ultrasound that is less than or equal to 4 mm; or an endometrial biopsy showing endometrial atrophy or weak secretory features; or a scarce sample that is consistent with atrophy.

In some embodiments, the method of treating uterine fibroids, heavy menstrual bleeding associated with uterine fibroids, pain associated with uterine fibroids, or a woman with symptomatic uterine fibroids results in one or both of contraception and amenorrhea during treatment. Amenorrhea may, for example, refer to the absence of menstruation, such as one or more missed menstrual periods. A woman who has missed at least three menstrual periods in a row may have amenorrhea, as may a girl who has not begun menstruation by age 15. Contraception may, for example, refer to one or more methods used to prevent pregnancy. These may include barrier methods prevent sperm from reaching the egg by physically blocking preventing contact, for example condoms, diaphragm, or spermicide. Hormonal methods of contraception may include progestin-only contraceptives or combined hormonal contraceptives comprising a progestin and an estrogen. Hormonal methods of contraception act by inhibiting secretion of gonadotropins, preventing ovulation, and changing the consistency of the mucus located in the cervix making it more difficult for the sperm to pass. Contraception may further include intrauterine devices, which are implants that are placed inside the uterus and work as a barrier method making the pass of sperm more difficult and also affect the endometrium impairing implantation of a fertilized egg. Certain intrauterine devices may further comprise hormones.

Administration of the combination as in the method of treating uterine fibroids, heavy menstrual bleeding associated with uterine fibroids, pain associated with uterine fibroids, or a woman with symptomatic uterine fibroids may result in suppression of the pre-menopausal woman's ovarian estrogen production. For example, in some embodiments, after at least 4 consecutive weeks, at least 8 consecutive weeks, at least 12 consecutive weeks, or at least 16 consecutive weeks of administration of the combination, the pre-menopausal woman's ovarian estrogen production is suppressed. In some embodiments, after at least 4 consecutive weeks of administration of the combination, the pre-menopausal woman's ovarian estrogen production is suppressed. Suppression of ovarian estrogen production may be demonstrated by estrogen blood levels that are in the post-menopausal range, such as estradiol levels of <20 pg/mL, in a subject that is administered Compound 1 or a pharmaceutically acceptable salt thereof without co-administration of a hormone replacement medicament. Suppression of ovarian estrogen production in a subject that is co-administered Compound 1 or a pharmaceutically acceptable salt thereof and a hormone replacement medicament comprising estradiol or an estradiol equivalent may be demonstrated by estradiol blood levels of between 20 pg/mL and 50 pg/mL. In some embodiments, for example in women who are administered a higher dose of hormone replacement medicament (comprising, for example, up to 5 mg estradiol or estradiol equivalent), suppression of ovarian estrogen production in a woman co-administered Compound 1 or a pharmaceutically acceptable salt thereof and a hormone replacement medicament may be demonstrated by estradiol blood levels of between 55 pg/mL and 150 pg/mL. Suppression of ovarian estrogen production may also be demonstrated by ultrasound showing no growing ovarian follicles, and/or by the presence of amenorrhea.

As described above, the method of treating uterine fibroids, heavy menstrual bleeding associated with uterine fibroids, pain associated with uterine fibroids, or a woman with symptomatic uterine fibroids, may result in the pre-menopausal woman's serum estradiol concentration to be within a certain range. In some embodiments, administration of the combination results in the pre-menopausal woman's serum estradiol concentration to be within about 20 pg/mL and about 50 pg/mL, between daily doses of the combination. In certain embodiments, the pre-menopausal woman's serum estradiol concentration is between about 20 pg/mL and about 50 pg/mL between daily doses of the combination after at least 4 consecutive weeks, at least 8 consecutive weeks, or at least 12 consecutive weeks of administration of the combination. In one embodiment, the pre-menopausal woman's serum estradiol concentration is between about 20 pg/mL and about 50 pg/mL between daily doses of the combination after at least 4 consecutive weeks of administration of the combination.

Administration of the combinations described herein in the method of treating uterine fibroids, heavy menstrual bleeding associated with uterine fibroids, pain associated with uterine fibroids, or a woman with symptomatic uterine fibroids, may result in suppression of the pre-menopausal woman's ovarian progesterone production. For example, in some embodiments, after at least 4 consecutive weeks, at least 8 consecutive weeks, at least 12 consecutive weeks, or at least 16 consecutive weeks of administration of the combination, the pre-menopausal woman's ovarian progesterone production is suppressed. In some embodiments, after at least 4 consecutive weeks of administration of the combination, the pre-menopausal woman's ovarian progesterone production is suppressed. Suppression of ovarian progesterone production may be demonstrated, for example, by progesterone blood levels that are in the postmenopausal range, e.g., progesterone levels of <2 ng/mL, in a woman who has not been administered progesterone. Suppression of ovarian progesterone production may also be demonstrated by ultrasound showing no growing ovarian follicles, and/or by the presence of amenorrhea.

As described above, the method for treating uterine fibroids, heavy menstrual bleeding associated with uterine fibroids, pain associated with uterine fibroids, or a woman with symptomatic uterine fibroids, may result in the pre-menopausal woman's serum progesterone concentration to be within a certain range. In some embodiments, administration of the combination results in the pre-menopausal woman's serum progesterone concentration to be less than about 5 ng/mL, less than about 4 ng/mL, less than about 3 ng/mL, less than about 2 ng/mL, or less than about 1 ng/mL between daily doses of the combination. In certain embodiments, the pre-menopausal woman's serum progesterone concentration is less than about 5 ng/mL between daily doses of the combination after at least 4 consecutive weeks, at least 8 consecutive weeks, or at least 12 consecutive weeks of administration of the combination. In one embodiment, the pre-menopausal woman's serum progesterone concentration is less than about 5 ng/mL between daily doses of the combination after at least 4 consecutive weeks of administration of the combination.

In some embodiments of any of the above methods, administration of the combination results in any combination of suppression of the pre-menopausal woman's ovarian estrogen production, suppression of the pre-menopausal woman's ovarian progesterone production, or in the pre-menopausal woman's serum progesterone concentration being less than about 5 ng/mL between daily doses of the combination, as described above.

In some embodiments, the combination of Compound 1, or a pharmaceutically acceptable salt thereof, and the hormone replacement medicament is orally administered for at least 24 consecutive weeks. In certain embodiments, the combination comprises about 10 mg to about 60 mg of Compound 1, or a corresponding amount of a pharmaceutically acceptable salt thereof. In some embodiments, the combination comprises about 20 mg to about 50 mg, about 30 mg to about 50 mg, or about 40 mg, of Compound 1, or a corresponding amount of a pharmaceutically acceptable salt thereof.

The hormone replacement medicament may comprise estradiol or an estradiol equivalent, a progestin, or any combination thereof. In certain embodiments, the hormone replacement medicament comprises estradiol, or an estradiol equivalent. In other embodiments, the hormone replacement medicament comprises a progestin. The progestin may be, for example, norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogesterone acetate, promegestone, or dienogest. The estradiol equivalent may be, for example, equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, or stilbestrol. In certain embodiments, the hormone replacement medicament comprises both an estradiol or an estradiol equivalent, and a progestin. The progestin may be, for example, norethindrone or a salt thereof.

In some embodiments of any of the methods described above, the hormone replacement medicament comprises about 0.01 mg to about 5 mg of a progestin. For example, in some embodiments, the hormone replacement medicament comprises about 0.01 mg, about 0.05 mg, about 0.1 mg, about 0.5 mg, about 0.75 mg, about 1 mg, about 1.25 mg, about 1.5 mg, about 2 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg progestin. In some embodiments, the hormone replacement medicament comprises about 0.1 mg to about 0.5 mg of a progestin, for example about 0.1 mg, about 0.2 mg, about 0.3 mg, about 0.4 mg, or about 0.5 mg of progestin. In some embodiments, the progestin is a norethindrone salt, for example norethindrone acetate. In certain embodiments, the hormone replacement medicament comprises about 0.5 mg of norethindrone acetate. In other embodiments, the combination comprises between about 0.625 mg to about 5 mg nomegestrol acetate, or about 0.05 mg to about 0.5 mg levonorgestrel, or about 0.5 to about 5 mg dienogest.

In some embodiments, the hormone replacement medicament comprises from about 0.5 to about 2 mg of estradiol, or a corresponding amount of estradiol equivalent. For example, in some embodiments, the hormone replacement medicament comprises from about 0.5 mg to about 1 mg, from about 0.5 mg to about 1.5 mg, from about 1 mg to about 1.5 mg, from about 1 mg to about 2 mg, from about 1.5 mg to about 2 mg, about 0.5 mg, about 0.75 mg, about 1 mg, about 1.25 mg, about 1.5 mg, or about 2 mg estradiol, or a corresponding amount of an estradiol equivalent.

In one embodiment, the hormone replacement medicament comprises about 0.5 mg to about 2 mg of estradiol or a corresponding amount of estradiol equivalent, and about 0.01 mg to about 5 mg of a progestin. In some embodiments, the hormone replacement medicament comprises about 1 mg of estradiol, or a corresponding amount of estradiol equivalent. In certain embodiment, the progestin is norethindrone or a salt thereof in an amount of about 0.1 mg to about 0.5 mg. In one embodiment, the progestin is norethindrone acetate (NETA). In certain embodiments, the combination comprises about 0.5 mg of NETA.

In one embodiment, the combination comprises about 0.5 mg NETA, about 1 mg estradiol, and about 40 mg of Compound 1, or a corresponding amount of a pharmaceutically acceptable salt thereof.

In some embodiments, there exists a population of pre-menopausal women for whom about 10 mg to about 60 mg, about 20 mg to about 50 mg, about 30 mg to about 50 mg, or about 40 mg of Compound 1, or a corresponding amount of a pharmaceutically acceptable salt thereof does not adequately treat their symptom and/or condition (e.g., uterine fibroids, heavy menstrual bleeding associated with uterine fibroids, pain associated with uterine fibroids, or one or more symptoms associated with uterine fibroids). Thus, in some embodiments, the combination orally administered daily to a pre-menopausal woman comprises about 65 mg to about 140 mg of Compound 1, or a corresponding amount of a pharmaceutically acceptable salt thereof. In some embodiments, the combination orally administered daily to a pre-menopausal woman comprises about 65 mg to about 120 mg of Compound 1, or a corresponding amount of a pharmaceutically acceptable salt thereof. For example, in some embodiments the combination comprises about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof.

In some embodiments, there exists a population of pre-menopausal women for whom about 0.5 mg to about 2 mg, about 0.5 to about 1.5 mg, about 0.5 to about 1 mg, or about 1 mg to about 2 mg, of estradiol or a corresponding amount of estradiol equivalent does not adequately treat one or more side effects of hypoestrogenic state (e.g., bone mineral density loss, one or more vasomotor symptoms, vulvovaginal atrophy, vaginal dryness, fatigue, malaise, or headache). There may also exist a population of pre-menopausal women who experience one or more side effects of GnRH antagonist administration (e.g., bone mineral density loss, one or more vasomotor symptoms, vulvovaginal atrophy, vaginal dryness, fatigue, malaise, or headache) when their serum estradiol level is between 20 pg/mL and 50 pg/mL, and for whom this experience more negatively impacts their QOL than if their symptom and/or condition (e.g., uterine fibroids, heavy menstrual bleeding associated with uterine fibroids, pain associated with uterine fibroids, or one or more symptoms associated with uterine fibroids) was not as well treated (for example, if their serum estradiol level were greater than 50 pg/mL). Thus, certain women may prefer administration of a higher dosage of hormone replacement medicament, such that their average daily circulating serum estradiol level is about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. Administration of a higher dosage of hormone replacement medicament may achieve such average daily circulating serum estradiol levels and may further reduce one or side effects of GnRH antagonist administration, and still provide some treatment of the symptom and/or condition. Thus, in some embodiments, the combination orally administered daily to a pre-menopausal woman comprises between 1.5 mg to 5.0 mg, between about 2 mg to about 5 mg, between about 3 mg to about 5, between about 4 mg to about 5 mg, between about 1.5 mg to about 4 mg, between about 2 mg to about 4 mg, between about 3 mg to about 4 mg, between about 1.5 mg to about 3 mg, or between about 2 mg to about 3 mg of estradiol, or an estradiol equivalent. For example, in some embodiments, the combination comprises about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg estradiol or an estradiol equivalent.

As discussed above, in some embodiments administration of Compound 1 or a pharmaceutically acceptable salt thereof without the co-administration of a hormone replacement medicament may more rapidly treat one or more symptoms associated with uterine fibroids, or heavy menstrual bleeding associated with uterine fibroids, or pain associated with uterine fibroids, as progesterone and estrogen levels may be suppressed without supplementation by estradiol, an estradiol equivalent, and/or a progestin. However, also as discussed above, one or more negative side effects (e.g., bone mineral density loss) may result from longer-term treatment without the use of a hormone replacement medicament. Thus, in some embodiments of the methods provided herein for treating uterine fibroids, heavy menstrual bleeding associated with uterine fibroids, pain associated with uterine fibroids, or a woman with symptomatic uterine fibroids, prior to administration of the combination of Compound 1 or a pharmaceutically acceptable salt thereof and a hormone replacement medicament, the pre-menopausal woman is orally administered Compound 1 or a pharmaceutically acceptable salt thereof once-daily. In certain embodiments, the pre-menopausal woman is orally administered about 10 mg to about 60 mg, or about 20 mg to about 50 mg, or about 30 mg to about 50 mg, for example about 10 mg, about 20 mg, about 30 mg, about 40 mg, about 50 mg, or about 60 mg, of Compound 1, or a corresponding amount of a pharmaceutically acceptable salt thereof, once-daily before administration of any of the combinations described herein. In other embodiments, the pre-menopausal woman is orally administered about 65 mg to about 140 mg of Compound 1, or about 65 mg to about 120 mg of Compound 1, or a corresponding amount of a pharmaceutically acceptable salt thereof, for example about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof, once-daily before administration of any of the combinations described herein. Further provided is the use of Compound 1 or a pharmaceutically acceptable salt thereof for the manufacture of a medicament for treatment according to any of these methods.

In some embodiments, the pre-menopausal woman is orally administered Compound 1, or a pharmaceutically acceptable salt thereof, once-daily for at least 4 consecutive weeks, at least 8 consecutive weeks, at least 12 consecutive weeks, at least 16 consecutive weeks, at least 20 consecutive weeks, or up to 24 consecutive weeks, before being administered any of the combinations described herein. In one embodiment, the pre-menopausal woman is orally administered between about 10 mg to about 60 mg, about 20 mg to about 50 mg, about 30 mg to about 50 mg, or about 40 mg of Compound 1, or a corresponding amount of a pharmaceutically acceptable salt thereof, once-daily for at least 4 consecutive weeks and up to 24 consecutive weeks, prior to administration of a combination of Compound 1 or a pharmaceutically acceptable salt thereof and a hormone replacement medicament. Administration of Compound 1, or a pharmaceutically acceptable salt thereof, without the co-administration of a hormone replacement medicament for a period of time prior to co-administration of the combination may treat one or more symptoms of uterine fibroids, or heavy menstrual bleeding associated with uterine fibroids, or pain associated with uterine fibroids, more aggressively at the beginning, prior to transitioning to a longer term treatment. This may be desirable, for example, in a woman with severe symptoms, or a plurality of symptoms, or with a desire to more quickly alleviate one or more symptoms.

The combination of Compound 1, or a pharmaceutically acceptable salt thereof, and a hormone replacement medicament may be orally administered to the pre-menopausal woman once-daily for at least 24 consecutive weeks, at least 36 consecutive weeks, at least 48 consecutive weeks, at least 72 consecutive weeks, or at least 96 consecutive weeks, in the method of treating uterine fibroids, heavy menstrual bleeding associated with uterine fibroids, pain associated with uterine fibroids, or a woman with symptomatic uterine fibroids as described above. In some embodiments, administration of the combination is suspended for conception and/or pregnancy. Administration of the combination may resume after delivery. In certain embodiments, the pre-menopausal woman's bone mineral density during treatment according to one of the above methods is within + or −3%, or + or −2%, of the bone mineral density prior to starting treatment. Bone mineral density may be assessed, for example, by x-ray or by dual-energy x-ray absorptiometry.

As discussed above, bone mineral density loss may be a concern in subjects being administered GnRH agonists or antagonists. In some embodiments, long-term treatment with Compound 1 is done in combination with a hormone replacement medicament, either as a fixed dose or in two or more separate dosage forms that are co-administered. This forced compliance with a hormone replacement medicament regimen may provide protection to women against certain adverse effects caused by Compound 1, for example by preventing and/or minimizing bone mineral density loss due to lowered estrogen levels. This protection against bone loss, by virtue of the oral fixed combination dosage, creates a long term dosing regimen that may be safe for a majority of women.

Furthermore, administering a once-daily dose of Compound 1, or a pharmaceutically acceptable salt thereof, may allow women to start from a stable, consistent baseline of very low estrogen. A hormone replacement medicament that is also administered with Compound 1 may replace, in a controlled fashion, the dose of estradiol thought to prevent bone mineral density loss in the majority of women, and may mitigate other tolerability adverse effects, such as vasomotor symptoms. In particular, at estradiol concentrations between 30–50 pg/mL, it is believed that the majority of symptomatic benefits associated with estrogen suppression may be achieved, while side-effects, including bone mineral density loss, are minimized. An estradiol concentration between 20 pg/mL to 50 pg/mL may also provide symptomatic benefits associated with estrogen suppression may be achieved, while side-effects, including bone mineral density loss, are minimized. Co-administration of Compound 1 and the hormone replacement medicament, as described herein, may achieve this estradiol target in a majority of women. Compound 1 and the hormone replacement medicament may be administered as a fixed dose combination, or may be two or more separate dosages that are co-administered.

In accordance with this disclosure, a method is provided for reducing menstrual blood loss or achieving amenorrhea in a subject having heavy menstrual bleeding due to uterine fibroids. The method includes: administering to the subject, in a first oral dose or dosage form, from 10 mg to 60 mg per day of Compound 1 or a pharmaceutically acceptable salt thereof, and co-administering to the subject, in a second oral dose or dosage form, from 0.05 mg to 5 mg per day of at least one of an estrogen and a progestogen. In some embodiments, a corresponding amount of a pharmaceutically acceptable salt of Compound 1 is administered.

Also, in accordance with this disclosure, another method is provided for reducing blood loss or achieving amenorrhea in a subject having heavy menstrual bleeding due to uterine fibroids. The method includes administering to the subject, from 10 mg to 60 mg per day of the Compound 1, and from 0.05 mg to 5 mg per day of at least one of an estrogen and a progestogen. In some embodiments, a corresponding amount of a pharmaceutically acceptable salt of Compound 1 is administered.

Yet another method in accordance with this disclosure is provided for reducing menstrual blood loss or achieving amenorrhea in a subject having heavy menstrual bleeding due to uterine fibroids. The method includes administering to the subject, from 10 mg to 60 mg per day of the Compound 1, and from 0.01 mg to 5 mg of NETA as the sole hormone replacement medicament. In some embodiments, a corresponding amount of a pharmaceutically acceptable salt of Compound 1 is administered.

Further, in accordance with this disclosure, a method is provided for suppressing sex hormones in a subject having uterine fibroids. The method includes administering to the subject, from 10 mg to 60 mg per day of Compound 1. The sex hormones suppressed include estradiol, LH and FSH. Still further, in some embodiments, a post-ovulatory rise in progesterone is suppressed in the subject. In some embodiments, a corresponding amount of a pharmaceutically acceptable salt of Compound 1 is administered.

In an embodiment for treating uterine fibroids in a premenopausal woman, an oral fixed dosage form is administered to the subject. The oral fixed combination dosage is from 10 mg to 60 mg, preferably 40 mg, per day of Compound 1 or an equivalent amount of a pharmaceutically acceptable salt thereof and from 0.01 mg to 5 mg per day of an estrogen and/or a progestogen. The single oral dosage form can be administered once-daily. The single oral dosage form may be administered daily for long term therapy, or for a shorter treatment period. A shorter treatment period may include administering daily for at least 7 consecutive days, 14 consecutive days, 28 consecutive days, 56 consecutive days, 84 consecutive days or 168 consecutive days. Preferably, the treatment period is long term therapy, which may include daily administration of consecutive day periods of at least 48 weeks, which can be consecutive day periods of at least two separate 24 week periods. Further, the preferred longer periods of administration may include: consecutive day periods of 52 weeks or greater, consecutive day periods of 76 weeks or greater, consecutive day periods of 104 weeks or greater, or consecutive day periods of 128 weeks or greater.

In accordance with this disclosure, oral therapy that can be used longer-term has the potential to enable women to avoid surgical intervention that can result in postoperative complications or complications with future pregnancy or even preclude the potential for future pregnancy. In particular, a fixed combination, oral dosage form, which is a once-daily, single pill having both Compound 1 or a pharmaceutically acceptable salt thereof and low-dose estrogen and progesterone, may be used longer-term, unlike other currently approved GnRH agonist therapies. This low dose may minimize bone mineral density loss in a hypoestrogenic state, and also other hypoestrogenic symptoms such as hot flashes, commonly associated with GnRH agonists and antagonists.

While Compound 1 can be administered in an amount of 10 mg, 20 mg, 40 mg or 60 mg per day, it is preferably administered at 40 mg. Further, the excipient base may optimize stability in the composition, and the 40 mg amount of Compound 1 may maintain an efficacious dose for treatment of the symptoms of uterine fibroids. In some embodiments, a corresponding amount of a pharmaceutically acceptable salt of Compound 1 is administered.

In another embodiment for treating uterine fibroids in a premenopausal woman, a first oral dose or dosage form and a second oral dose or dosage form are administered to the subject. In one embodiment, the first oral dosage is from 10 mg to 60 mg per day of Compound 1 or a corresponding amount of a pharmaceutically acceptable salt thereof, and the second oral dosage is from 0.01 mg to 5 mg per day of an estrogen and/or a progestogen. The first and second oral dosage forms can be administered once or twice per day. For example, the first and second oral dosage forms can be administered daily for a shorter treatment period. In some embodiments, treatment period is daily administration of consecutive day periods of at least 48 weeks which can be consecutive day periods of at least two separate 24 week periods. Further, in some embodiments, the preferred periods of long term administration are: consecutive day periods of 48 weeks or greater, consecutive day periods of 52 weeks or greater, consecutive day periods of 76 weeks or greater, consecutive day periods of 104 weeks or greater, or consecutive day periods of 128 weeks or greater.

In some embodiments the first oral dosage form is a tablet or capsule, and the second oral dosage form is a tablet or capsule. Both oral dosage forms preferably have an immediate release profile in certain embodiments.

In some embodiments, the hormone replacement medicament, such as estradiol, is administered in an amount per day of 0.5 mg, 1.0 mg, 1.5 mg or 2.0 mg, and the norethindrone acetate is administered in an amount per day of 0.1 mg or 0.5 mg. The estradiol and NETA can be administered once per day for the same period as Compound 1. As with Compound 1, in some embodiments it is preferred that the hormone replacement medicament, such as estradiol and norethindrone acetate, is used for administration for the entire treatment period, for example, consecutive day periods of 48 weeks or greater, including consecutive day periods of 52 weeks or greater, consecutive day periods of 76 weeks or greater, consecutive day periods of 104 weeks or greater, or consecutive day periods of 128 weeks or greater.

The main symptoms of uterine fibroids are heavy menstrual bleeding, anemia, and compression and pain in the bladder or pelvis (e.g., lower abdominal pain and low back pain). These symptoms may significantly reduce the QOL of patients with uterine fibroids.

In accordance with this disclosure, another method for treating heavy menstrual bleeding includes administering to the subject from 10 mg to 60 mg per day of Compound 1 or a pharmaceutically acceptable salt thereof, and preferably from 0.01 mg to 5 mg per day of an estrogen and/or a progestogen. In some embodiments, a corresponding amount of a pharmaceutically acceptable salt of Compound 1 is administered.

Further, in accordance with this disclosure, still another method for treating heavy menstrual bleeding includes: administering to the subject, in a first oral dosage form, from 10 mg to 60 mg per day of Compound 1 or a pharmaceutically acceptable salt thereof, and co-administering to the subject, in a second oral dosage form, from 0.01 mg to 5 mg per day of at least one of an estrogen and a progestogen. In some embodiments, a corresponding amount of a pharmaceutically acceptable salt of Compound 1 is administered.

Further, in accordance with this disclosure, still another method for treating heavy menstrual bleeding includes: administering to the subject, in a first oral dosage form, from 10 mg to 60 mg per day of Compound 1 or a pharmaceutically acceptable salt thereof, and co-administering to the subject, in a second oral dosage form, from 0.01 mg to 5 mg per day of at least one of an estrogen and a progestogen. In some embodiments, a corresponding amount of a pharmaceutically acceptable salt of Compound 1 is administered.

Several benefits may result from treating heavy menstrual bleeding associated with uterine fibroids by administering Compound 1, or a pharmaceutically acceptable salt thereof. In particular, these benefits include a reduction in menstrual blood loss, an improvement in QOL measurements, as well as a reduction in myoma and uterine volumes, as further described herein.

Typical methods used to evaluate menstrual blood loss volume associated with uterine fibroids include the Pictorial Blood Loss Assessment Chart (PBAC) score and the alkaline hematin method. FIG. 1 shows an illustrative PBAC score sheet that includes two items (tampon and towel) across three pictographic ranges (1: lightly stained; 5: moderately stained; 10: saturated). These items represent the level of stained sanitary materials over the course of a menstrual cycle, with a total score ranging from 0 (none) to infinity. Higher scores indicate heavier blood loss. The PBAC score sheet also allows subjects to indicate: whether they experienced bleeding between periods that required sanitary protection; whether they passed clots, and if so, approximate size of the clots; whether they experienced episodes of flooding; and whether they required double protection (used both a pad and tampon simultaneously). Flooding may include, for example, bleeding so heavy that feminine hygiene products are rapidly soaked and/or saturated. Flooding may also include menstrual bleeding that requires more than 14 feminine hygiene products.

In some embodiments, the change from baseline in mean PBAC score can result in a 3.0 to 5.0 fold (300% to 500%), particularly a 3.5 to 4.5 fold (350% to 450%), and more particularly a 4.0 to 4.2 fold (400% to 420%), reduction in PBAC score from weeks 6 to 12 of the treatment period.

In some embodiments, the percent change from baseline in mean myoma volume can result in a 3.5 to 6.5 fold (350% to 650%), particularly a 4.0 to 5.5 fold (400% to 550%), and more particularly a 4.5 to 5.1 fold (450% to 510%), reduction in myoma volume at the end of a 12 week consecutive week treatment period.

In some embodiments, the percent change from baseline in mean uterine volume can result in a 4.0 to 7.0 fold (400% to 700%), particularly a 4.5 to 6.5 fold (450% to 650%), and more particularly a 4.8 to 5.5 fold (480% to 550%), reduction in uterine volume at the end of a 12 week consecutive treatment period.

Pain associated with uterine fibroids may be assessed using a numerical self-reporting instrument. For example, the Numerical Rating Scale (NRS) is an 11-item self-reported instrument for assessing pain. As shown in FIG. 2, it includes 11 items ranging from 0 (No Pain) to 10 (Worst Pain Possible). Higher NRS scores reflect greater levels of pain.

Quality of life (QOL) may be assessed using a self-reported instrument. For example, the Uterine Fibroid Symptom Quality of Life (UFS-QOL) questionnaire is a 37-item self-reported instrument assessing differences in symptom severity and health-related quality of life. It includes eight symptom-related questions and 29 health-related quality of life questions across eight subscales (symptom severity, concern, activities, energy/mood, control, self-consciousness, sexual function, and health-related quality of life total score), with subscale and total score ranging from 37 (not at all/none of the time) to 116 (a very great deal/all of the time). An exemplary UFS-QOL questionnaire is shown in FIGS. 3A-C. Higher UFS-QOL scores reflect greater symptom severity and symptom impact on health-related quality of life.

In some embodiments, the change from baseline in mean UFS-QOL symptom severity score can result in a 1.0 to 6.0 fold (100% to 600%), particularly a 2.0 to 5.0 fold (200% to 500%), and more particularly a 2.5 to 4.5 fold (250% to 450%), reduction in symptom severity.

In some embodiments, the change from baseline in mean UFS-QOL Score (HRQL total) can result in a 0.01 to 4.0 fold (1% to 400%), particularly a 0.05 to 2.0 fold (5% to 200%), and more particularly a 0.10 to 1.0 fold (10% to 100%), reduction in UFS-QOL HRQL total score.

In some embodiments, the change from baseline in mean blood concentration of hemoglobin can result in a 3.0 to 6.0 fold (300% to 600%), particularly a 3.5 to 5.5 fold (350% to 550%), and more particularly a 3.8 to 5.2 fold (380% to 520%), increase in blood concentration of hemoglobin.

In some embodiments, the change from baseline in mean hematocrit value can result in a 3.0 to 7.0 fold (300% to 700%), particularly a 3.5 to 6.5 fold (350% to 650%), and more particularly a 4.2 to 5.4 fold (420% to 540%), increase in hematocrit value.

In some embodiments, the change from baseline in mean iron value can result in a 6.0 to 16.0 fold (600% to 1600%), particularly a 8.0 to 14.0 fold (800% to 1400%), and more particularly a 9.0 to 13.0 fold (900% to 1300%), increase in iron value.

In some embodiments, the change from baseline in mean ferritin concentration can result in a 2.0 to 6.0 fold (200% to 600%), particularly a 2.5 to 5.5 fold (250% to 550%), and more particularly a 3.0 to 4.5 fold (300% to 450%), increase in ferritin concentrations.

In some embodiments, the change from baseline in median LH concentrations can result in a 3.0 to 9.0 fold (300% to 900%), particularly a 4.0 to 8.0 fold (400% to 800%), and more particularly a 4.7 to 6.7 fold (470% to 670%), reduction in LH concentrations.

In some embodiments, the change from baseline in median FSH concentrations can result in a 1.0 to 5.0 fold (100% to 500%), particularly a 1.5 to 4.5 fold (150% to 450%), and more particularly a 2.1 to 4.1 fold (210% to 410%), reduction in FSH concentrations.

In some embodiments, the change from baseline in median estradiol concentrations can result in a 0.2 to 3.2 fold (20% to 320%), particularly a 0.8 to 2.6 fold (80% to 260%), and more particularly a 1.0 to 2.4 fold (100% to 240%), reduction in estradiol concentrations.

In some embodiments, the change from baseline in median progesterone concentrations can result in a 0.5 to 4.0 fold (50% to 400%), particularly a 0.8 to 3.7 fold (80% to 370%), and more particularly a 1.2 to 3.2 fold (120% to 320%), reduction in progesterone concentrations.

It should be understood that a combination of two, three, four, five, or more of the above embodiments may occur as a result of the methods described. For example, in some embodiments, the methods provided herein result in change from baseline in median LH concentration, median FSH concentration, median estradiol concentration, and median progesterone concentration as described above. In certain embodiments of any of the embodiments above, about 40 mg Compound 1, or an equivalent amount of a pharmaceutically acceptable salt thereof, is administered per day.

In certain embodiments, for any of the methods of treating uterine fibroids, treating heavy menstrual bleeding associated with uterine fibroids, treating pain associated with uterine fibroids, or treating a pre-menopausal woman with symptomatic uterine fibroids described above, the pre-menopausal woman achieves a menstrual blood loss volume of <80 mL during treatment; or achieves at least a 50% reduction from baseline in menstrual blood loss volume during treatment, as compared to before beginning treatment; or has a PBAC score of less than 10; or any combinations thereof. In some embodiments, the pre-menopausal woman achieves a menstrual blood loss volume of <80 mL, at least a 50% reduction from baseline in menstrual blood loss volume, or a PBAC score of less than 10, or any combinations thereof, within at least 30 weeks, within at least 24 weeks, or within at least 12 weeks of beginning treatment. In certain embodiments, menstrual blood loss volume is measured by the alkaline hematin method.

In certain embodiments, for any of the methods of treating uterine fibroids, treating heavy menstrual bleeding associated with uterine fibroids, treating pain associated with uterine fibroids, or treating a pre-menopausal woman with symptomatic uterine fibroids described above, the pre-menopausal woman has a maximum NRS score of 1 or less for uterine fibroid pain 6 weeks, 8 weeks, or 10 weeks, after beginning treatment; or has an increase in the number of days with an NRS score of 0 within 6 weeks, 8 weeks, or 10 weeks, after beginning treatment, compared to the 6 weeks, 8 weeks, or 10 weeks immediately before beginning treatment. In some embodiments, the mean NRS score over 35 days during treatment is reduced by at least 30% within 6 weeks, 8 weeks, or 10 weeks after beginning treatment. In certain of these embodiments, the pre-menopausal woman has a maximum NRS score for uterine fibroid associated pain of ≥4 6 weeks, 8 weeks, or 10 weeks immediately before beginning treatment.

In other embodiments, for any of the methods of treating uterine fibroids, treating heavy menstrual bleeding associated with uterine fibroids, treating pain associated with uterine fibroids, or treating a pre-menopausal woman with symptomatic uterine fibroids described above, the pre-menopausal woman has a hemoglobin increase of ≥1 g/dL during treatment, compared to before beginning treatment. In certain embodiments, the pre-menopausal woman had a hemoglobin level of <12 g/dL before beginning treatment. In some embodiments, this increase is within 20 weeks, 24 weeks, or 28 weeks of beginning treatment.

In still further embodiments, for any of the methods of treating uterine fibroids, treating heavy menstrual bleeding associated with uterine fibroids, treating pain associated with uterine fibroids, or treating a pre-menopausal woman with symptomatic uterine fibroids described above, the pre-menopausal woman has a decrease in impact of uterine fibroids as measured by the UFS-QOL; a decrease in in the interference of uterine fibroids with physical activities as measured by the UFS-QOL activities domain; a decrease in the interference of uterine fibroids with social activities as measured by the UFS-QOL; a decrease in embarrassment caused by uterine fibroids as measured by the UFS-QOL; a decrease in uterine fibroid-related symptoms as measured by UFS-QOL Symptom Severity; a decrease in uterine fibroid-related quality of life problems as measured by UFS-QOL Health-related Quality of Life; a change from baseline in uterine fibroid related function based on the Patient Global Assessment (PGA); a decrease in uterine fibroid symptoms based on the PGA; a change from baseline for physical activities as measured by the Menorrhagia Impact Questionnaire Score; a change from baseline for social and leisure activities as measured by the Menorrhagia Impact Questionnaire Score; a reduction in uterine volume; or a reduction in uterine fibroid volume. In some embodiments of any of these metrics, the decrease or change is at least 10%, at least 20%, at least 30%, at least 40%, at least 50%, at least 60%, at least 70%, at least 80%, at least 90%, at least 100%, or more. In certain embodiments, the decrease or change occurs within 6 weeks, within 12 weeks, within 18 weeks, within 24 weeks, or within 30 weeks of beginning treatment.

For all methods of the present disclosure, subjects may receive bone mineral density monitoring. However, as noted above, in the fixed combination oral dosage form of the present disclosure, bone mineral density loss may be minimized since the hormone replacement medicament and Compound 1 are integrated into a single dosage form. Thus, in at least one embodiment, treatment with Compound 1, or a pharmaceutically acceptable salt thereof, will occur without bone mineral density monitoring.

IV. Endometriosis

Endometriosis is a sex hormone-dependent benign disease where tissue morphologically and functionally similar to the endometrium develops outside the uterine cavity. Main clinical symptoms of endometriosis are pain during menstruation or dysmenorrhea and infertility. Patients with endometriosis also frequently experience non-menstrual pelvic pain, such as lower abdominal pain and low back pain, as well as dyspareunia, painful defecation, and painful urination. These symptoms can significantly reduce quality of life (QOL).

Provided herein is a method for treating endometriosis in a pre-menopausal woman in need thereof, comprising orally administering to the pre-menopausal woman once-daily a combination of Compound 1, or a pharmaceutically acceptable salt thereof, and a hormone replacement medicament (e.g., a combination of an estradiol or estradiol equivalent and a progestin). Additionally provided is a method for treating pain associated with endometriosis in a pre-menopausal woman in need thereof, comprising administering to the pre-menopausal woman once-daily a combination of Compound 1, or a pharmaceutically acceptable salt thereof, and a hormone replacement medicament. Also provided is a method for treating heavy menstrual bleeding associated with endometriosis in a pre-menopausal woman, comprising administering to the pre-menopausal woman once-daily a combination of Compound 1, or a pharmaceutically acceptable salt thereof, and a hormone replacement medicament. Further provided is a method for treating a pre-menopausal woman with symptomatic endometriosis, comprising administering to the pre-menopausal woman once-daily a combination of Compound 1, or a pharmaceutically acceptable salt thereof, and a hormone replacement medicament. The combination may be administered, for example, as either as a fixed dose or in two or more separate dosage forms that are co-administered. Further provided are combined preparations for use in any of these methods. In some embodiments, the combined preparation is for simultaneous or sequential use. In certain embodiments, the combined preparation comprises Compound 1, or a pharmaceutically acceptable salt thereof, and a hormone replacement medicament. In certain embodiments, the hormone replacement medicament comprises estradiol or estradiol equivalent, and progestin. Further provided is the use of Compound 1, or a pharmaceutically acceptable salt thereof, and a hormone replacement medicament for the manufacture of a medicament for treatment according to any of these methods. In some embodiments, the hormone replacement medicament comprises estradiol or estradiol equivalent, and progestin.

In some embodiments of the methods of treating endometriosis, pain associated with endometriosis, heavy menstrual bleeding associated with endometriosis, or a pre-menopausal woman with symptomatic endometriosis, the pre-menopausal woman experiences an improvement of one or more symptoms during the treatment, or after the treatment. The one or more symptoms may be selected from the group consisting of anemia, heavy menstrual bleeding, irregular periods, spotting, inflammation, pain, fatigue, urinary obstruction, urinary frequency, incontinence, constipation, anxiety, sleep disturbance, quality of life, activities of daily living, female sexual dysfunction and depression. Pain may be, for example, back pain, pelvic pain, chronic pain, dyspareunia, uterine pain, pain with defecation, pain with urination, or any combinations thereof. In some embodiments, the method of treating a pre-menopausal woman with symptomatic endometriosis suppresses the endometrium in the woman. Suppression of endometrium may include, for example, endometrial thickness on a transvaginal ultrasound of less than or equal to 4 mm; or an endometrial biopsy showing endometrial atrophy or weak secretory features; or a scarce sample that is consistent with atrophy. In some embodiments, the method of treating a pre-menopausal woman with symptomatic endometriosis decreases the number and size, or prevents the growth of, endometriomas or endometriotic lesions. Suppressing or preventing the growth of endometriotic lesions and endometriomas may improve pain symptoms, such as chronic pain, dyspareunia, pain with defecation, or pain with urination. Thus, provided herein is a method of treating one or more symptoms associated with endometriosis in a pre-menopausal woman in need thereof, comprising administering to the pre-menopausal woman once-daily a combination of Compound 1, or a pharmaceutically acceptable salt thereof, and a hormone replacement medicament.

In some embodiments, the methods of treating endometriosis, pain associated with endometriosis (such as dyspareunia, chronic pain, pain with defecation, or pain with urination), heavy menstrual bleeding associated with endometriosis, or a pre-menopausal woman with symptomatic endometriosis provided herein results in one or both of contraception and amenorrhea during treatment.

Administration of the combination as provided herein in the method of treating endometriosis, pain associated with endometriosis (such as dyspareunia, chronic pain, pain with defecation, or pain with urination), heavy menstrual bleeding associated with endometriosis, or a pre-menopausal woman with symptomatic endometriosis may result in suppression of the pre-menopausal woman's ovarian estrogen production. For example, in some embodiments, after at least 4 consecutive weeks, at least 8 consecutive weeks, at least 12 consecutive weeks, or at least 16 consecutive weeks of administration of the combination, the pre-menopausal woman's ovarian estrogen production is suppressed. In some embodiments, after at least 4 consecutive weeks of administration of the combination, the pre-menopausal woman's ovarian estrogen production is suppressed. Suppression of ovarian estrogen production may be demonstrated by estrogen blood levels that are in the postmenopausal range, such as estradiol levels of <20 pg/mL, in a subject that is administered Compound 1 or a pharmaceutically acceptable salt thereof without co-administration of a hormone replacement medicament. Suppression of ovarian estrogen production in a subject that is co-administered Compound 1 or a pharmaceutically acceptable salt thereof and a hormone replacement medicament comprising estradiol or an estradiol equivalent may be demonstrated by estradiol blood levels of between 20 and 50 pg/mL. In some embodiments, for example in women who are administered a higher dose of hormone replacement medicament (comprising, for example, up to 5 mg estradiol or estradiol equivalent), suppression of ovarian estrogen production in a woman co-administered Compound 1 or a pharmaceutically acceptable salt thereof and a hormone replacement medicament may be demonstrated by estradiol blood levels of between 55 pg/mL and 150 pg/mL. Suppression of ovarian estrogen production may also be demonstrated by ultrasound showing no growing ovarian follicles, and/or by the presence of amenorrhea.

As described above, the methods of treating endometriosis, pain associated with endometriosis (such as dyspareunia, chronic pain, pain with defecation, or pain with urination), heavy menstrual bleeding associated with endometriosis, or a pre-menopausal woman with symptomatic endometriosis provided herein may result in the pre-menopausal woman's serum estradiol concentration to be within a certain range. In some embodiments, administration of the combination results in the pre-menopausal woman's serum estradiol concentration to be within about 20 pg/mL and about 50 pg/mL, between daily doses of the combination. In certain embodiments, the pre-menopausal woman's serum estradiol concentration is between about 20 pg/mL and about 50 pg/mL between daily doses of the combination after at least 4 consecutive weeks, at least 8 consecutive weeks, or at least 12 consecutive weeks of administration of the combination. In one embodiment, the pre-menopausal woman's serum estradiol concentration is between about 20 pg/mL and about 50 pg/mL between daily doses of the combination after at least 4 consecutive weeks of administration of the combination.

Administration of the combinations provided herein in the method of treating endometriosis, pain associated with endometriosis (such as dyspareunia, chronic pain, pain with defecation, or pain with urination), heavy menstrual bleeding associated with endometriosis, or a pre-menopausal woman with symptomatic endometriosis may result in suppression of the pre-menopausal woman's ovarian progesterone production. For example, in some embodiments, after at least 4 consecutive weeks, at least 8 consecutive weeks, at least 12 consecutive weeks, or at least 16 consecutive weeks of administration of the combination, the pre-menopausal woman's ovarian progesterone production is suppressed. In some embodiments, after at least 4 consecutive weeks of administration of the combination, the pre-menopausal woman's ovarian progesterone production is suppressed. Suppression of ovarian progesterone production may be demonstrated, for example, by progesterone blood levels that are in the postmenopausal range, e.g., progesterone levels of <2 ng/mL, in a woman who has not been administered progesterone. Suppression of ovarian progesterone production may also be demonstrated by ultrasound showing no growing ovarian follicles, and/or by the presence of amenorrhea.

As described above, the methods for treating endometriosis, pain associated with endometriosis (such as dyspareunia, chronic pain, pain with defecation, or pain with urination), heavy menstrual bleeding associated with endometriosis, or a pre-menopausal woman with symptomatic endometriosis may result in the pre-menopausal woman's serum progesterone concentration to be within a certain range. In some embodiments, administration of the combination results in the pre-menopausal woman's serum progesterone concentration to be less than about 5 ng/mL, less than about 4 ng/mL, less than about 3 ng/mL, less than about 2 ng/mL, or less than about 1 ng/mL between daily doses of the combination. In certain embodiments, the pre-menopausal woman's serum progesterone concentration is less than about 5 ng/mL between daily doses of the combination after at least 4 consecutive weeks, at least 8 consecutive weeks, or at least 12 consecutive weeks of administration of the combination. In one embodiment, the pre-menopausal woman's serum progesterone concentration is less than about 5 ng/mL between daily doses of the combination after at least 4 consecutive weeks of administration of the combination.

In some embodiments of any of the above methods, administration of the combination results in any combination of suppression of the pre-menopausal woman's ovarian estrogen production, suppression of the pre-menopausal woman's ovarian progesterone production, or in the pre-menopausal woman's serum progesterone concentration being less than about 5 ng/mL between daily doses of the combination, as described above.

In some embodiments, the combination of Compound 1, or a pharmaceutically acceptable salt thereof, and the hormone replacement medicament is orally administered for at least 24 consecutive weeks. In certain embodiments, the combination comprises about 10 mg to about 60 mg of Compound 1, or a corresponding amount of a pharmaceutically acceptable salt thereof. In some embodiments, the combination comprises about 20 mg to about 50 mg, or about 30 mg to about 50 mg, or about 40 mg of Compound 1, or a corresponding amount of a pharmaceutically acceptable salt thereof. Compound 1 or a pharmaceutically acceptable salt thereof and the hormone replacement medicament may be administered as a fixed dose combination dosage, or may be two or more separate dosages that are co-administered.

The hormone replacement medicament may comprise estradiol or an estradiol equivalent, a progestin, or any combination thereof. In certain embodiments, the hormone replacement medicament comprises estradiol, or an estradiol equivalent. In other embodiments, the hormone replacement medicament comprises a progestin. The progestin may be, for example, norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogestrone acetate, promegestone, or dienogest. The estradiol equivalent may be, for example, equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, or stilbestrol. In certain embodiments, the hormone replacement medicament comprises both an estradiol or an estradiol equivalent, and a progestin. The progestin may be, for example, norethindrone or a salt thereof.

In some embodiments of any of the methods described herein, the hormone replacement medicament comprises about 0.01 mg to about 5 mg of a progestin. For example, in some embodiments, the hormone replacement medicament comprises about 0.01 mg, about 0.05 mg, about 0.1 mg, about 0.5 mg, about 0.75 mg, about 1 mg, about 1.25 mg, about 1.5 mg, about 2 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg progestin. In some embodiments, the hormone replacement medicament comprises about 0.1 mg to about 0.5 mg of a progestin, for example about 0.1 mg, about 0.2 mg, about 0.3 mg, about 0.4 mg, or about 0.5 mg of progestin. In some embodiments, the progestin is a norethindrone salt, for example norethindrone acetate. In certain embodiments, the hormone replacement medicament comprises about 0.5 mg of norethindrone acetate. In other embodiments, the combination comprises between about 0.625 mg to about 5 mg nomegestrol acetate, or about 0.05 mg to about 0.5 mg levonorgestrel, or about 0.5 to about 5 mg dienogest.

In some embodiments, the hormone replacement medicament comprises from about 0.5 to about 2 mg of estradiol, or a corresponding amount of estradiol equivalent. For example, in some embodiments, the hormone replacement medicament comprises from about 0.5 mg to about 1 mg, from about 0.5 mg to about 1.5 mg, from about 1 mg to about 1.5 mg, from about 1 mg to about 2 mg, from about 1.5 mg to about 2 mg, about 0.5 mg, about 0.75 mg, about 1 mg, about 1.25 mg, about 1.5 mg, or about 2 mg estradiol, or a corresponding amount of an estradiol equivalent.

In one embodiment, the hormone replacement medicament comprises about 0.5 mg to about 2 mg of estradiol or a corresponding amount of estradiol equivalent, and about 0.01 mg to about 5 mg of a progestin. In certain embodiment, the progestin is norethindrone or a salt thereof in an amount of about 0.1 mg to about 0.5 mg. In one embodiment, the progestin is norethindrone acetate (NETA). In certain embodiments, the combination comprises about 0.5 mg of NETA.

In one embodiment, the combination comprises about 0.5 mg NETA, about 1 mg estradiol, and about 40 mg of Compound 1, or a corresponding amount of a pharmaceutically acceptable salt thereof.

In some embodiments, there exists a population of pre-menopausal women for whom about 10 mg to about 60 mg, about 20 mg to about 50 mg, about 30 mg to about 50 mg, or about 40 mg of Compound 1, or a corresponding amount of a pharmaceutically acceptable salt thereof does not adequately treat their symptom and/or condition (e.g., endometriosis, pain associated with endometriosis, heavy menstrual bleeding associated with endometriosis, or one or more other symptoms associated with endometriosis). Thus, in some embodiments, the combination orally administered daily to a pre-menopausal woman comprises about 65 mg to about 140 mg of Compound 1, or a corresponding amount of a pharmaceutically acceptable salt thereof. In some embodiments, the combination orally administered daily to a pre-menopausal woman comprises about 65 mg to about 120 mg of Compound 1, or a corresponding amount of a pharmaceutically acceptable salt thereof. For example, in some embodiments the combination comprises about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof.

In some embodiments, there exists a population of pre-menopausal women for whom about 0.5 mg to about 2 mg, about 0.5 to about 1.5 mg, about 0.5 to about 1 mg, or about 1 mg to about 2 mg, of estradiol or a corresponding amount of estradiol equivalent does not adequately treat one or more side effects of hypoestrogenic state (e.g., bone mineral density loss, one or more vasomotor symptoms, vulvovaginal atrophy, vaginal dryness, fatigue, malaise, or headache). There may also exist a population of pre-menopausal women who experience one or more side effects of GnRH antagonist administration (e.g., bone mineral density loss, one or more vasomotor symptoms, vulvovaginal atrophy, vaginal dryness, fatigue, malaise, or headache) when their serum estradiol level is between 20 pg/mL and 50 pg/mL, and for whom this experience more negatively impacts their QOL than if their symptom and/or condition (e.g., endometriosis, pain associated with endometriosis, heavy menstrual bleeding associated with endometriosis, or one or more other symptoms associated with endometriosis) was not as well treated (for example, if their serum estradiol level were greater than 50 pg/mL). Thus, certain women may prefer administration of a higher dosage of hormone replacement medicament, such that their average daily circulating serum estradiol level is about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. Administration of a higher dosage of hormone replacement medicament may achieve such average daily circulating serum estradiol levels and may further reduce one or side effects of GnRH antagonist administration, and still provide some treatment of the symptom and/or condition. Thus, in some embodiments, the combination orally administered daily to a pre-menopausal woman comprises between 1.5 mg to 5.0 mg, between about 2 mg to about 5 mg, between about 3 mg to about 5, between about 4 mg to about 5 mg, between about 1.5 mg to about 4 mg, between about 2 mg to about 4 mg, between about 3 mg to about 4 mg, between about 1.5 mg to about 3 mg, or between about 2 mg to about 3 mg of estradiol, or an estradiol equivalent. For example, in some embodiments, the combination comprises about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg estradiol or an estradiol equivalent.

As discussed above, administration of Compound 1 or a pharmaceutically acceptable salt thereof without the co-administration of a hormone replacement medicament may more rapidly treat one or more symptoms associated with endometriosis, or pain associated with endometriosis, or heavy menstrual bleeding associated with endometriosis, as progesterone and estrogen levels may be suppressed without supplementation by estradiol, an estradiol equivalent, and/or a progestin. However, also as discussed above, one or more negative side effects (e.g., bone mineral density loss) may result from longer-term treatment without the use of a hormone replacement medicament. Thus, in some embodiments of the methods provided herein for treating uterine endometriosis, pain associated with endometriosis, heavy menstrual bleeding associated with endometriosis, or a woman with symptomatic endometriosis, prior to administration of the combination of Compound 1 or a pharmaceutically acceptable salt thereof and a hormone replacement medicament, the pre-menopausal woman is orally administered Compound 1 or a pharmaceutically acceptable salt thereof once-daily. In certain embodiments, the pre-menopausal woman is orally administered about 10 mg to about 60 mg, or about 20 mg to about 50 mg, or about 30 mg to about 50 mg, for example about 10 mg, about 20 mg, about 30 mg, about 40 mg, about 50 mg, or about 60 mg, of Compound 1, or a corresponding amount of a pharmaceutically acceptable salt thereof, once-daily before administration of any of the combinations described herein. In other embodiments, the pre-menopausal woman is orally administered about 65 mg to about 140 mg of Compound 1, or about 65 mg to about 120 mg of Compound 1, or a corresponding amount of a pharmaceutically acceptable salt thereof, for example about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof, once-daily before administration of any of the combinations described herein. Further provided is the use of Compound 1 or a pharmaceutically acceptable salt thereof for the manufacture of a medicament for treatment according to any of these methods.

In some embodiments, the pre-menopausal woman is orally administered Compound 1, or a pharmaceutically acceptable salt thereof, once-daily for at least 4 consecutive weeks, at least 8 consecutive weeks, at least 12 consecutive weeks, at least 16 consecutive weeks, at least 20 consecutive weeks, or up to 24 consecutive weeks, before being administered any of the combinations described herein. In one embodiment, the subject is orally administered between about 10 mg to about 60 mg, about 20 mg to about 50 mg, about 30 mg to about 50 mg, or about 40 mg of Compound 1, or a corresponding amount of a pharmaceutically acceptable salt thereof, once-daily for at least 4 consecutive weeks and up to 24 consecutive weeks, prior to administration of a combination of Compound 1 or a pharmaceutically acceptable salt thereof and a hormone replacement medicament. Administration of Compound 1, or a pharmaceutically acceptable salt thereof, without the co-administration of a hormone replacement medicament for a period of time prior to co-administration of the combination may treat one or more symptoms of endometriosis, or heavy menstrual bleeding associated with endometriosis, or pain associated with endometriosis, more aggressively at the beginning, prior to transitioning to a longer term treatment. This may be desirable, for example, in a woman with severe symptoms, or a plurality of symptoms, or with a desire to more quickly alleviate one or more symptoms.

The combination of Compound 1, or a pharmaceutically acceptable salt thereof, and a hormone replacement medicament may be orally administered to the pre-menopausal woman once-daily for at least 24 consecutive weeks, at least 36 consecutive weeks, at least 48 consecutive weeks, at least 72 consecutive weeks, or at least 96 consecutive weeks in the method of treating endometriosis, heavy menstrual bleeding associated with endometriosis, pain associated with endometriosis, or one or more other symptoms associated with endometriosis, as described above. In some embodiments, administration of the combination is suspended for conception and/or pregnancy. Administration of the combination may resume after delivery. In certain embodiments, the pre-menopausal woman's bone mineral density during treatment according to one of the above methods is within + or −3%, or + or −2%, of the bone mineral density prior to starting treatment.

As discussed above, bone mineral density loss may be a concern in subjects being administered GnRH agonists or antagonists. In some embodiments, long-term treatment with Compound 1 is done in combination with a hormone replacement medicament, either as a fixed dose or in two or more separate dosage forms that are co-administered. This forced compliance with a hormone replacement medicament regimen may provide protection to women against certain adverse effects caused by Compound 1, for example by preventing and/or minimizing bone mineral density loss due to lowered estrogen levels. This protection against bone loss, by virtue of the oral fixed combination dosage, creates a long term dosing regimen that may be safe for a majority of women.

In some embodiments, by administering a once-daily dose of Compound 1, or a pharmaceutically acceptable salt thereof, may allow women to start from a stable baseline of very low estrogen. A hormone replacement medicament that is also administered with Compound 1 may replace, in a controlled fashion, the dose of estradiol thought to prevent bone mineral density loss in the majority of women, and may mitigate other tolerability adverse effects, such as vasomotor symptoms. In particular, at estradiol concentrations between 30–50 pg/mL, it is believed that the majority of symptomatic benefits associated with estrogen suppression are achieved, while side effects, including bone mineral density loss, are minimized. An estradiol concentration between 20 pg/mL to 50 pg/mL may also provide symptomatic benefits associated with estrogen suppression may be achieved, while side-effects, including bone mineral density loss, are minimized. Co-administration of Compound 1 and the hormone replacement medicament, as described herein, may achieve this estradiol target in a majority of women. Compound 1 and the hormone replacement medicament may be administered as a fixed dose combination, or may be two or more separate dosages that are co-administered.

In accordance with this disclosure, a method is provided for reducing menstrual blood loss or achieving amenorrhea in a subject having heavy menstrual bleeding due to endometriosis. The method includes: administering to the subject, in a first oral dose or dosage form, from 10 mg to 60 mg per day of Compound 1; and co-administering to the subject, in a second oral dose or dosage form, from 0.01 mg to 5 mg per day of at least one of an estrogen and a progestin. In some embodiments, a corresponding amount of a pharmaceutically acceptable salt of Compound 1 is administered.

Also, in accordance with this disclosure, another method is provided for reducing blood loss or achieving amenorrhea in a subject having heavy menstrual bleeding due to endometriosis. The method includes administering to the subject, from 10 mg to 60 mg per day of Compound 1, and from 0.01 mg to 5 mg per day of at least one of an estrogen and a progestin. In some embodiments, a corresponding amount of a pharmaceutically acceptable salt of Compound 1 is administered.

Yet another method in accordance with this disclosure is provided for reducing menstrual blood loss or achieving amenorrhea in a subject having heavy menstrual bleeding due to endometriosis. The method includes administering to the subject, from 10 mg to 60 mg per day of Compound 1, and from 0.01 mg to 5 mg of NETA as the sole hormone replacement medicament. In some embodiments, a corresponding amount of a pharmaceutically acceptable salt of Compound 1 is administered.

For treatment of endometriosis, Compound 1, or a pharmaceutically acceptable salt thereof, is preferably administered orally, as formulated with pharmaceutically acceptable excipients. The oral dose may be in the form of a solid preparation. Further, the oral dosage form may have an immediate release profile. However, the oral dosage form can have other release profiles including, for example, sustained release, controlled release, delayed release, extended release, and the like.

Main symptoms of endometriosis include pain and infertility. In particular, pain symptoms including not only menstrual cramps, but also frequent pelvic pain (e.g., lower abdominal pain and low back pain) and dyspareunia outside the menstruation period may significantly reduce the QOL of patients with endometriosis. As stated above, Compound 1 is a GnRH antagonist. Thus, it may induce atrophy of the endometrium by decreasing blood $E_2$ levels. In patients with endometriosis, it may suppress growth of endometriotic lesions and, therefore, may improve pain symptoms.

Several benefits may result from treating pelvic pain associated with endometriosis by administering Compound 1, or a pharmaceutically acceptable salt thereof. In particular, a reduction in pelvic pain may result from such an administration as described herein. The pelvic pain can be at least one of dysmenorrhea, nonmenstrual pelvic pain, and dyspareunia.

Typical methods used to evaluate responses to pain associated with endometriosis include, for example, a visual analogue scale (VAS) score, a modified Biberoglu & Behrman (M-B&B) score, and a Biberoglu & Behrman (B&B) score. Methods of evaluating responses to pain associated with endometriosis also include the Numerical Rating Scale (NRS) and the Symptoms of Endometriosis Scale (SEMS).

A typical method used to evaluate quality of life (QOL) associated with endometriosis includes an Endometriosis Health Profile (EHP-30) score. An exemplary EHP-30 questionnaire is provided in FIGS. 151A-E, comprising 30 questions each with 5 answer choices.

Illustrative scales, electronic diary formats, questionnaires, forms, and the like used in the generation of M-B&B scores may include, for example: endometriosis pain questionnaire (see FIG. 144); M-B&B grading scale (see FIG. 145); SEMS as tested in subjects (see FIGS. 146A-C); electronic SEMS as tested in subjects (see FIGS. 147A-M); mood states form (see FIGS. 148A-C); baseline clinical questionnaire (see FIGS. 149A-C); and final clinical questionnaire (see FIGS. 150A-B).

An exemplary VAS score may be evaluated using a 100 mm scale. For pain intensity, the scale may be anchored by "no pain" (score of 0) and "pain as bad as you can imagine" (score of 100). Other questions may evaluate: presence or absence of menstruation, amount of bleeding (if menstruating); whether the subject had sexual intercourse; VAS assessment of dyspareunia (if the subject had sexual intercourse); study drug compliance; and the use of analgesics.

The above items may be evaluated using a patient diary that is distributed by the sponsor. Subjects may fill out the patient diary every day during the treatment period or until early termination. If taking prohibited analgesics, subjects may record this fact in the patient diary along with the accompanying pain symptoms before use of analgesics.

In some embodiments of the methods provided herein, the change from baseline in the VAS score can result in a 1.5 to 4.5 fold (150 to 450%), particularly a 2.0 to 4.0 fold (200 to 400%), and more particularly a 2.25 to 3.75 fold (225 to 375%), increase in proportion of days without pelvic pain.

In some embodiments of the methods provided herein, the change from baseline in the VAS score can result in a 1.5 to 4.5 fold (150 to 450%), particularly a 2.0 to 4.0 fold (200 to 400%), and more particularly a 2.25 to 3.75 fold (225 to 375%), reduction in pelvic pain.

In some embodiments of the methods provided herein, the change from baseline in the M-B&B score can result in a 1.25 to 4.0 fold (125 to 400%), particularly a 1.5 to 3.5 fold (150 to 350%), and more particularly a 1.75 to 3.25 fold (175 to 325%), reduction in pelvic pain.

In some embodiments of the methods provided herein, the change from baseline in the M-B&B score can result in a 1.25 to 4.5 fold (125 to 450%), particularly a 1.5 to 4.0 fold (150 to 400%), and more particularly a 1.75 to 3.75 fold (175 to 375%), increase in proportion of days without pelvic pain.

In some embodiments of the methods provided herein, the change from baseline in the VAS score can result in a 1.25 to 5.0 fold (125 to 500%), particularly a 1.5 to 4.5 fold (150 to 450%), and more particularly a 1.6 to 4.0 fold (160 to 400%), reduction in dysmenorrhea.

In some embodiments of the methods provided herein, the change from baseline in the VAS score can result in a 2.0 to 10.0 fold (200 to 1000%), particularly a 4.0 to 8.0 fold (400 to 800%), and more particularly a 4.5 to 7.5 fold (450 to 750%), increase in proportion of days without dysmenorrhea.

In some embodiments of the methods provided herein, the change from baseline in the M-B&B score can result in a 3.0 to 11.0 fold (300 to 1100%), particularly a 4.0 to 9.0 fold (400 to 900%), and more particularly a 5.0 to 8.0 fold (500 to 800%), reduction in dysmenorrhea.

In some embodiments of the methods provided herein, the change from baseline in the M-B&B score can result in a 2.0 to 9.0 fold (200 to 900%), particularly a 3.5 to 7.5 fold (350 to 750%), and more particularly a 4.0 to 7.0 fold (400 to 700%), increase in proportion of days without dysmenorrhea.

In some embodiments of the methods provided herein, the change from baseline in the M-B&B score can result in a 25 to 100 fold (2500 to 10000%), particularly a 50 to 75 fold (5000 to 7500%), and more particularly a 55 to 70 fold (5500 to 7000%), increase in subjects without dysmenorrhea.

In some embodiments of the methods provided herein, the change from baseline in the M-B&B score can result in a 1.05 to 2.5 fold (105 to 250%), particularly a 1.1 to 1.5 fold (110 to 150%), and more particularly a 1.2 to 1.4 fold (120 to 140%), increase in subjects without dyspareunia.

In some embodiments of the methods provided herein, the change from baseline in the M-B&B score can result in a 2.0 to 10 fold (200 to 1000%), particularly a 3.0 to 9.0 fold (300 to 900%), and more particularly a 3.5 to 8.5 fold (350 to 850%), increase in proportion of days without deep dyspareunia.

In some embodiments of the methods provided herein, the change from baseline in the M-B&B score can result in a 10 to 50 fold (1000 to 5000%), particularly a 20 to 40 fold (2000 to 4000%), and more particularly a 25 to 35 fold (2500 to 3500%), reduction in deep dyspareunia.

In some embodiments of the methods provided herein, the change from baseline in the VAS score can result in a 1.1 to 5.0 fold (110 to 500%), particularly a 1.5 to 4.0 fold (150 to 400%), and more particularly a 1.75 to 3.75 fold (175 to 375%), reduction in pelvic pain, dysmenorrhea and dyspareunia.

In some embodiments of the methods provided herein, the change from baseline in the EHP-30 score can result in a 1.5 to 7.5 fold (150 to 750%), particularly a 2.5 to 6.5 fold (250 to 650%), and more particularly a 3.0 to 6.0 fold (300 to 600%), increase in quality of life (QOL).

It should be understood that a combination of two, three, four, five, or more of the above embodiments may occur as a result of the methods described. For example, in some embodiments, the methods provided herein result in a change from baseline in the VAS score of pelvic pain, and a change from baseline in the M-B&B score for deep dyspareunia as described above. In certain embodiments of any of the embodiments above, about 40 mg Compound 1, or an equivalent amount of a pharmaceutically acceptable salt thereof, is administered per day.

In certain embodiments, for any of the methods of treating endometriosis, treating pain associated with endometriosis, treating heavy menstrual bleeding associated with endometriosis, or treating a pre-menopausal woman with symptomatic endometriosis described above, the pre-menopausal woman has a decrease of dysmenorrhea as measured by a change from baseline in dysmenorrhea NRS score; a decrease of pain as measured by a change from baseline in NMPP NRS score; a decrease of dyspareunia as measured by a change from baseline in dyspareunia NRS score; a decrease of dyspareunia functional impairment as measured by a change from baseline on the sB&B scale; a decrease of pain as measured by a change from baseline in severity score on the PGA for pain; a decrease of function impairment as measured by a change from baseline on the PGA for function; has an improvement as measured by a change from baseline in each of the non-pain EHP-30 domains (Control and Powerlessness, Social Support, Emotional Well-Being, and Self-Image); a decrease of dysmenorrhea functional impairment as measured by a change from baseline on the sB&B scale; a decrease of NMPP functional impairment as measured by a change from baseline on the sB&B scale; or a decrease of pain as measured by a change from baseline in EHP-30 Pain Domain score. In some embodiments, the baseline for any of these metrics is from evaluation within the 6 weeks, 8 weeks, or 10 weeks immediately before beginning treatment. In certain embodiments, for any of the methods of treating endometriosis, treating pain associated with endometriosis, treating heavy menstrual bleeding associated with endometriosis, or treating a pre-menopausal woman with symptomatic endometriosis described above, the pre-menopausal woman is better or much better on the PGIC for dysmenorrhea; is better or much better on the PGIC for NMPP; is better or much better on the PGIC for dyspareunia, as compared to the 6 weeks, 8 weeks, or 10 weeks, immediately before beginning treatment. In some embodiments of any of these metrics, the decrease or change is at least 10%, at least 20%, at least 30%, at least 40%, at least 50%, at least 60%, at least 70%, at least 80%, at least 90%, at least 100%, or more. In certain embodiments, the decrease or change occurs within 6 weeks, within 12 weeks, within 18 weeks, within 24 weeks, or within 30 weeks of beginning treatment.

For all methods of the present disclosure, subjects may receive bone mineral density monitoring to ensure their safety. However, as noted above, in the fixed combination oral dosage form of the present disclosure, bone mineral density loss may be minimized since the hormone replacement medicament and Compound 1 are integrated into a single dosage form. Thus, in at least one embodiment, treatment with Compound 1, or a pharmaceutically acceptable salt thereof, will occur without bone mineral density monitoring.

V. Adenomyosis

Adenomyosis can refer to a condition in which the inner lining of the uterus (the endometrium) breaks into the muscle wall of the uterus (the myometrium). Adenomyosis can cause dysmenorrhea, dyspareunia, lower abdominal pressure, and bloating before menstrual periods and can result in heavy menstrual bleeding. The condition may be located throughout the entire uterus or localized in one spot. Using magnetic resonance imaging (MRI) or transvaginal ultrasound, doctors can see characteristics of the disease in the uterus. Because the symptoms are so similar, adenomyosis is often misdiagnosed as uterine fibroids. However, the two conditions are not the same. While fibroids are benign tumors growing in or on the uterine wall, adenomyosis is less of a defined mass of cells within the uterine wall.

Provided herein is a method for treating adenomyosis in a pre-menopausal woman in need thereof, comprising orally administering to the pre-menopausal woman once-daily a combination of Compound 1, or a pharmaceutically acceptable salt thereof, and a hormone replacement medicament (e.g., a combination of an estradiol or estradiol equivalent and a progestin). Also provided herein is a method for treating heavy menstrual bleeding associated with adenomyosis in a pre-menopausal woman in need thereof, comprising orally administering to the pre-menopausal woman once-daily a combination of Compound 1, or a pharmaceutically acceptable salt thereof, and a hormone replacement medicament. Provided is also a method for treating a pre-menopausal woman with symptomatic adenomyosis, comprising administering to the pre-menopausal woman once-daily a combination of Compound 1, or a pharmaceutically acceptable salt thereof, and a hormone replacement medicament. Further provided are combined preparations for use in any of these methods. In some embodiments, the combined preparation is for simultaneous or sequential use. In certain embodiments, the combined preparation comprises Compound 1, or a pharmaceutically acceptable salt thereof, and a hormone replacement medicament. In certain embodiments, the hormone replacement medicament comprises estradiol or estradiol equivalent, and progestin. Further provided is the use of Compound 1, or a pharmaceutically acceptable salt thereof, and a hormone replacement medicament for the manufacture of a medicament for treatment according to any of these methods. In some embodiments, the hormone replacement medicament comprises estradiol or estradiol equivalent, and progestin.

In some embodiments of the methods of treating adenomyosis, heavy menstrual bleeding associated with adenomyosis, pain associated with adenomyosis, or a pre-menopausal woman with symptomatic adenomyosis, the pre-menopausal woman experiences an improvement of one or more symptoms during the treatment, or after the treatment. The one or more symptoms may be selected from the group consisting of anemia, heavy menstrual bleeding, irregular periods, spotting, inflammation, pain, fatigue, urinary obstruction, urinary frequency, incontinence, constipation, anxiety, sleep disturbance, quality of life, activities of daily living, female sexual dysfunction and depression. Pain may be, for example, back pain, pelvic pain, uterine pain, chronic pain, pain with defecation, pain with urination, or dyspareunia, or any combinations thereof. Thus, provided herein is a method of treating one or more symptoms associated with adenomyosis in a pre-menopausal woman in need thereof, comprising orally administering to the pre-menopausal woman once-daily a combination of Compound 1, or a pharmaceutically acceptable salt thereof, and a hormone replacement medicament.

In some embodiments, the methods of treating adenomyosis, heavy menstrual bleeding associated with adenomyosis, pain associated with adenomyosis, or a pre-menopausal woman with symptomatic adenomyosis provided herein results in one or both of contraception and amenorrhea during treatment.

Administration of the combinations as provided herein in the methods of treating adenomyosis, heavy menstrual bleeding associated with adenomyosis, pain associated with adenomyosis, or a pre-menopausal woman with symptomatic adenomyosis may result in suppression of the pre-menopausal woman's ovarian estrogen production. For example, in some embodiments, after at least 4 consecutive weeks, at least 8 consecutive weeks, at least 12 consecutive weeks, or at least 16 consecutive weeks of administration of the combination, the pre-menopausal woman's ovarian estrogen production is suppressed. In some embodiments, after at least 4 consecutive weeks of administration of the combination, the pre-menopausal woman's ovarian estrogen production is suppressed. Suppression of ovarian estrogen production may be demonstrated by estrogen blood levels that are in the postmenopausal range, such as estradiol levels of <20 pg/mL, in a subject that is administered Compound 1 or a pharmaceutically acceptable salt thereof without co-administration of a hormone replacement medicament. Suppression of ovarian estrogen production in a subject that is co-administered Compound 1 or a pharmaceutically acceptable salt thereof and a hormone replacement medicament comprising estradiol or an estradiol equivalent may be demonstrated by estradiol blood levels of between 20 and 50 pg/mL. In some embodiments, for example in women who are administered a higher dose of hormone replacement medicament (comprising, for example, up to 5 mg estradiol or estradiol equivalent), suppression of ovarian estrogen production in a woman co-administered Compound 1 or a pharmaceutically acceptable salt thereof and a hormone replacement medicament may be demonstrated by estradiol blood levels of between 55 pg/mL and 150 pg/mL. Suppression of ovarian estrogen production may also be demonstrated by ultrasound showing no growing ovarian follicles, and/or by the presence of amenorrhea.

As described above, the methods of treating adenomyosis, heavy menstrual bleeding associated with adenomyosis, pain associated with adenomyosis, or a pre-menopausal woman with symptomatic adenomyosis may result in the pre-menopausal woman's serum estradiol concentration to be within a certain range. In some embodiments, administration of the combination results in the pre-menopausal woman's serum estradiol concentration to be within about 20 pg/mL and about 50 pg/mL, between daily doses of the combination. In certain embodiments, the pre-menopausal woman's serum estradiol concentration is between about 20 pg/mL and about 50 pg/mL between daily doses of the combination after at least 4 consecutive weeks, at least 8 consecutive weeks, or at least 12 consecutive weeks of administration of the combination. In one embodiment, the pre-menopausal woman's serum estradiol concentration is between about 20 pg/mL and about 50 pg/mL between daily doses of the combination after at least 4 consecutive weeks of administration of the combination.

Administration of the combinations as provided herein in the methods of treating adenomyosis, heavy menstrual bleeding associated with adenomyosis, pain associated with adenomyosis, or a pre-menopausal woman with symptomatic adenomyosis may result in suppression of the pre-menopausal woman's ovarian progesterone production. For example, in some embodiments, after at least 4 consecutive weeks, at least 8 consecutive weeks, at least 12 consecutive weeks, or at least 16 consecutive weeks of administration of the combination, the pre-menopausal woman's ovarian progesterone production is suppressed. In some embodiments, after at least 4 consecutive weeks of administration of the combination, the pre-menopausal woman's ovarian progesterone production is suppressed. Suppression of ovarian progesterone production may be demonstrated, for example, by progesterone blood levels that are in the postmenopausal range, e.g., progesterone levels of <2 ng/mL, in a woman who has not been administered progesterone. Suppression of ovarian progesterone production may also be demonstrated by ultrasound showing no growing ovarian follicles, and/or by the presence of amenorrhea.

As described above, the methods for treating adenomyosis, heavy menstrual bleeding associated with adenomyosis, pain associated with adenomyosis may result in the pre-menopausal woman's serum progesterone concentration to be within a certain range. In some embodiments, administration of the combination results in the pre-menopausal woman's serum progesterone concentration being less than about 5 ng/mL, less than about 4 ng/mL, less than about 3 ng/mL, less than about 2 ng/mL, or less than about 1 ng/mL between daily doses of the combination. In certain embodiments, the pre-menopausal woman's serum progesterone concentration is less than about 5 ng/mL between daily doses of the combination after at least 4 consecutive weeks, at least 8 consecutive weeks, or at least 12 consecutive weeks of administration of the combination. In one embodiment, the pre-menopausal woman's serum progesterone concentration is less than about 5 ng/mL between daily doses of the combination after at least 4 consecutive weeks of administration of the combination.

In some embodiments of any of the above methods, administration of the combination results in any combination of suppression of the pre-menopausal woman's ovarian estrogen production, suppression of the pre-menopausal woman's ovarian progesterone production, or in the pre-menopausal woman's serum progesterone concentration being less than about 5 ng/mL between daily doses of the combination, as described above.

In some embodiments, the combination of Compound 1, or a pharmaceutically acceptable salt thereof, and the hormone replacement medicament is orally administered for at least 24 consecutive weeks. In certain embodiments, the combination comprises about 10 mg to about 60 mg of Compound 1, or a corresponding amount of a pharmaceutically acceptable salt thereof. In some embodiments, the combination comprises about 20 mg to about 50 mg, 30 mg to about 50 mg, or about 40 mg, of Compound 1, or a corresponding amount of a pharmaceutically acceptable salt thereof.

The hormone replacement medicament may comprise estradiol or an estradiol equivalent, a progestin, or any combination thereof. In certain embodiments, the hormone replacement medicament comprises estradiol, or an estradiol equivalent. In other embodiments, the hormone replacement medicament comprises a progestin. The progestin may be, for example, norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogestrone acetate, promegestone, or dienogest. The estradiol equivalent may be, for example, equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, or stilbestrol. In certain embodiments, the hormone replacement medicament comprises both an estradiol or an estradiol equivalent, and a progestin. The progestin may be, for example, norethindrone or a salt thereof.

In some embodiments of any of the methods described herein, the hormone replacement medicament comprises about 0.01 mg to about 5 mg of a progestin. For example, in some embodiments, the hormone replacement medicament comprises about 0.01 mg, about 0.05 mg, about 0.1 mg, about 0.5 mg, about 0.75 mg, about 1 mg, about 1.25 mg, about 1.5 mg, about 2 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg progestin. In some embodiments, the hormone replacement medicament comprises about 0.1 mg to about 0.5 mg of a progestin, for example about 0.1 mg, about 0.2 mg, about 0.3 mg, about 0.4 mg, or about 0.5 mg of progestin. In some embodiments, the progestin is a norethindrone salt, for example norethindrone acetate. In certain embodiments, the hormone replacement medicament comprises about 0.5 mg of norethindrone acetate. In other embodiments, the combination comprises between about 0.625 mg to about 5 mg nomegestrol acetate, or about 0.05 mg to about 0.5 mg levonorgestrel, or about 0.5 to about 5 mg dienogest.

In some embodiments, the hormone replacement medicament comprises from about 0.5 to about 2 mg of estradiol, or a corresponding amount of estradiol equivalent. For example, in some embodiments, the hormone replacement medicament comprises from about 0.5 mg to about 1 mg, from about 0.5 mg to about 1.5 mg, from about 1 mg to about 1.5 mg, from about 1 mg to about 2 mg, from about 1.5 mg to about 2 mg, about 0.5 mg, about 0.75 mg, about 1 mg, about 1.25 mg, about 1.5 mg, or about 2 mg estradiol, or a corresponding amount of an estradiol equivalent.

In one embodiment, the hormone replacement medicament comprises about 0.5 mg to about 2 mg of estradiol or a corresponding amount of estradiol equivalent, and about 0.01 mg to about 5 mg of a progestin. In certain embodiment, the progestin is norethindrone or a salt thereof in an amount of about 0.1 mg to about 0.5 mg. In one embodiment, the progestin is norethindrone acetate (NETA). In certain embodiments, the combination comprises about 0.5 mg of NETA.

In one embodiment, the combination comprises about 0.5 mg NETA, about 1 mg estradiol, and about 40 mg of Compound 1, or a corresponding amount of a pharmaceutically acceptable salt thereof.

In some embodiments, there exists a population of pre-menopausal women for whom about 10 mg to about 60 mg, about 20 mg to about 50 mg, about 30 mg to about 50 mg, or about 40 mg of Compound 1, or a corresponding amount of a pharmaceutically acceptable salt thereof does not adequately treat their symptom and/or condition (e.g., adenomyosis, heavy menstrual bleeding associated with adenomyosis, pain associated with adenomyosis, or one or more symptoms associated with adenomyosis). Thus, in some embodiments, the combination orally administered daily to a pre-menopausal woman comprises about 65 mg to about 140 mg of Compound 1, or a corresponding amount of a pharmaceutically acceptable salt thereof. In some embodiments, the combination orally administered daily to a pre-menopausal woman comprises about 65 mg to about 120 mg of Compound 1, or a corresponding amount of a pharmaceutically acceptable salt thereof. For example, in some embodiments the combination comprises about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof.

In some embodiments, there exists a population of pre-menopausal women for whom about 0.5 mg to about 2 mg, about 0.5 to about 1.5 mg, about 0.5 to about 1 mg, or about 1 mg to about 2 mg, of estradiol or a corresponding amount of estradiol equivalent does not adequately treat one or more side effects of hypoestrogenic state (e.g., bone mineral density loss, one or more vasomotor symptoms, vulvovaginal atrophy, vaginal dryness, fatigue, malaise, or headache). There may also exist a population of pre-menopausal women who experience one or more side effects of GnRH antagonist administration (e.g., bone mineral density loss, one or more vasomotor symptoms, vulvovaginal atrophy, vaginal dryness, fatigue, malaise, or headache) when their serum estradiol level is between 20 pg/mL and 50 pg/mL, and for whom this experience more negatively impacts their QOL than if their symptom and/or condition (e.g., adenomyosis, heavy menstrual bleeding associated with adenomyosis, pain associated with adenomyosis, or one or more symptoms associated with adenomyosis) was not as well treated (for example, if their serum estradiol level were greater than 50 pg/mL). Thus, certain women may prefer administration of a higher dosage of hormone replacement medicament, such that their average daily circulating serum estradiol level is about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. Administration of a higher dosage of hormone replacement medicament may achieve such average daily circulating serum estradiol levels and may further reduce one or side effects of GnRH antagonist administration, and still provide some treatment of the symptom and/or condition. Thus, in some embodiments, the combination orally administered daily to a pre-menopausal woman comprises between 1.5 mg to 5.0 mg, between about 2 mg to about 5 mg, between about 3 mg to about 5, between about 4 mg to about 5 mg, between about 1.5 mg to about 4 mg, between about 2 mg to about 4 mg, between about 3 mg to about 4 mg, between about 1.5 mg to about 3 mg, or between about 2 mg to about 3 mg of estradiol, or an estradiol equivalent. For example, in some embodiments, the combination comprises about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg estradiol or an estradiol equivalent.

Administration of Compound 1 or a pharmaceutically acceptable salt thereof without the co-administration of a hormone replacement medicament may more rapidly treat one or more symptoms associated with adenomyosis, or heavy menstrual bleeding associated with adenomyosis, or pain associated with adenomyosis, as progesterone and estrogen levels may be suppressed without supplementation by estradiol, an estradiol equivalent, and/or a progestin. However, as discussed above, one or more negative side effects (e.g., bone mineral density loss) may result from longer-term treatment without the use of a hormone replacement medicament. Thus, in some embodiments of the methods provided herein for treating adenomyosis, heavy menstrual bleeding associated with adenomyosis, pain associated with adenomyosis, or a woman with symptomatic adenomyosis, prior to administration of the combination of Compound 1 or a pharmaceutically acceptable salt thereof and a hormone replacement medicament, the pre-menopausal woman is orally administered Compound 1 or a pharmaceutically acceptable salt thereof once-daily. In certain embodiments, the pre-menopausal woman is orally administered about 10 mg to about 60 mg, or about 20 mg to about 50 mg, or about 30 mg to about 50 mg, for example about 10 mg, about 20 mg, about 30 mg, about 40 mg, about 50 mg, or about 60 mg, of Compound 1, or a corresponding amount of a pharmaceutically acceptable salt thereof, once-daily before administration of any of the combinations described herein. In other embodiments, the pre-menopausal woman is orally administered about 65 mg to about 140 mg of Compound 1, or about 65 mg to about 120 mg of Compound 1, or a corresponding amount of a pharmaceutically acceptable salt thereof, for example about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof, once-daily before administration of any of the combinations described herein. Further provided is the use of Compound 1 or a pharmaceutically acceptable salt thereof for the manufacture of a medicament for treatment according to any of these methods.

In some embodiments, the pre-menopausal woman is orally administered Compound 1, or a pharmaceutically acceptable salt thereof, once-daily for at least 4 consecutive weeks, at least 8 consecutive weeks, at least 12 consecutive weeks, at least 16 consecutive weeks, at least 20 consecutive weeks, or up to 24 consecutive weeks, before being administered any of the combinations described herein. In one embodiment, the subject is orally administered between about 10 mg to about 60 mg of Compound 1, or a corresponding amount of a pharmaceutically acceptable salt thereof, once-daily for at least 4 consecutive weeks and up to 24 consecutive weeks, prior to administration of a combination of Compound 1 or a pharmaceutically acceptable salt thereof and a hormone replacement medicament. Administration of Compound 1, or a pharmaceutically acceptable salt thereof, without the co-administration of a hormone replacement medicament for a period of time prior to co-administration of the combination may treat one or more symptoms of adenomyosis, or heavy menstrual bleeding associated with adenomyosis, or pain associated with adenomyosis, more aggressively at the beginning, prior to transitioning to a longer term treatment. This may be desirable, for example, in a woman with severe symptoms, or a plurality of symptoms, or with a desire to more quickly alleviate one or more symptoms.

The combination of Compound 1, or a pharmaceutically acceptable salt thereof, and a hormone replacement medicament may be orally administered to the pre-menopausal woman once-daily for at least 24 consecutive weeks, at least 36 consecutive weeks, at least 48 consecutive weeks, at least 72 consecutive weeks, or at least 96 consecutive weeks, in the method of treating adenomyosis, heavy menstrual bleeding associated with adenomyosis, pain associated with adenomyosis, or a pre-menopausal woman with symptomatic adenomyosis, or one or more other symptoms associated with adenomyosis, as described above. In some embodiments, administration of the combination is suspended for conception and/or pregnancy. Administration of the combination may resume after delivery. In certain embodiments, the pre-menopausal woman's bone mineral density during treatment according to one of the above methods is within + or −3%, or + or −2%, of the bone mineral density prior to starting treatment.

VI. Other Symptoms and Conditions

Further provided herein are methods of treating, and pharmaceutical compositions for use in such methods, one or more symptoms or conditions selected from the group consisting of heavy menstrual bleeding, infertility, female sexual dysfunction (for example, decreased libido, decreased arousal, or decreased sexual activity), gender transition, spotting, sex-hormone driven cancers, reduction of analgesic compound use, amenorrhea, and the preservation of fertility, anemia (associated with heavy menstrual bleeding or independent of heavy menstrual bleeding), pain (such as dyspareunia, chronic pain, pain with defecation, or pain with urination), inflammation, irregular menstruation, symptoms related to fibroid size and/or bulk, pregnancy loss, depression, chronic fatigue, anxiety, and sleep disturbance in a pre-menopausal woman in need thereof. Also provided is a method of contraception in a pre-menopausal woman in need thereof. One or more of the symptoms or conditions may be associated with endometriosis, uterine fibroids, or adenomyosis, or may be not be associated with endometriosis, uterine fibroids, or adenomyosis. For example, in some embodiments, the pre-menopausal woman has been diagnosed with one or more of endometriosis, uterine fibroids, or adenomyosis. In other embodiments, the pre-menopausal woman has not been diagnosed with one or more of endometriosis, uterine fibroids, or adenomyosis. Further provided are combined preparations for use in any of these methods. In some embodiments, the combined preparation is for simultaneous or sequential use. In certain embodiments, the combined preparation comprises Compound 1, or a pharmaceutically acceptable salt thereof, and a hormone replacement medicament. In certain embodiments, the hormone replacement medicament comprises estradiol or estradiol equivalent, and progestin. Further provided is the use of Compound 1, or a pharmaceutically acceptable salt thereof, and a hormone replacement medicament for the manufacture of a medicament for treatment according to any of these methods. In some embodiments, the hormone replacement medicament comprises estradiol or estradiol equivalent, and progestin.

These methods may comprise administering to a pre-menopausal woman in need thereof a combination of Compound 1, or a pharmaceutically acceptable salt thereof, and a hormone replacement medicament (e.g., a combination of an estradiol or estradiol equivalent and a progestin). In some embodiments, the hormone replacement medicament comprises estradiol or an estradiol equivalent, or a progestin, or a combination thereof. The combination may be administered, for example, as either as a fixed dose or in two or more separate dosage forms that are co-administered.

Provided herein are methods of treating heavy menstrual bleeding in a pre-menopausal woman in need thereof, comprising orally administering to the pre-menopausal woman once-daily a combination comprising Compound 1, or a pharmaceutically acceptable salt thereof, and a hormone replacement medicament. The heavy menstrual bleeding may be, for example, heavy menstrual bleeding associated with a non-malignant etiology such as, for example, uterine fibroids, endometriosis, adenomyosis, etc. Methods of treating heavy menstrual bleeding described herein should not be used for the treatment of heavy menstrual bleeding related to malignant etiologies, for example endometrial cancer. Treating heavy menstrual bleeding may include a greater than 50% reduction in menstrual blood loss compared to baseline prior to treatment. Treating heavy menstrual bleeding may include having menstrual blood loss of less than 80 mL.

In some embodiments, the heavy menstrual bleeding is associated with one or more uterine fibroids, endometriosis, or adenomyosis. Methods of treating heavy menstrual bleeding in a pre-menopausal woman with uterine fibroids, as provided herein, may reduce the number of uterine fibroids, the size of one or more uterine fibroids, or a combination thereof, during and/or after treatment, as compared to the number or size of uterine fibroids prior to treatment.

Provided herein are methods of treating pain associated with uterine fibroids, endometriosis, or adenomyosis in a pre-menopausal woman in need thereof, comprising orally administering to the pre-menopausal woman once-daily a combination comprising Compound 1, or a pharmaceutically acceptable salt thereof, and a hormone replacement medicament (e.g., a combination of an estradiol or estradiol equivalent and a progestin). The pain may be, for example, pelvic pain, back pain, uterine pain, chronic pain, pain with defecation, pain with urination, or dyspareunia, or any combinations thereof. In some embodiments, the pain is associated with endometriosis. In other embodiments, the pain is associated with adenomyosis.

Further provided herein are methods of treating anemia in a pre-menopausal woman in need thereof, comprising orally administering to the pre-menopausal woman once-daily a combination comprising Compound 1, or a pharmaceutically acceptable salt thereof, and a hormone replacement medicament (e.g., a combination of an estradiol or estradiol equivalent and a progestin). In some embodiments, the pre-menopausal woman is experiencing heavy menstrual bleeding. The heavy menstrual bleeding may be associated with a non-malignant etiology, such as endometriosis or uterine fibroids. In some embodiments, the pre-menopausal woman has one or more of uterine fibroids, endometriosis, heavy menstrual bleeding, or symptoms related to one or more of uterine fibroids, endometriosis, or adenomyosis.

Provided herein are methods of improving fertility in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering to the pre-menopausal woman once-daily a combination comprising Compound 1, or a pharmaceutically acceptable salt thereof, and a hormone replacement medicament (e.g., a combination of an estradiol or estradiol equivalent and a progestin), for at least 12 consecutive weeks; and then discontinuing the treatment for at least 4 weeks while the pre-menopausal woman attempts conception. Provided herein are also methods of preventing miscarriage in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering to the pre-menopausal woman once-daily a combination comprising Compound 1, or a pharmaceutically acceptable salt thereof, and a hormone replacement medicament, for at least 12 consecutive weeks; and then discontinuing the treatment for at least 4 weeks while the pre-menopausal woman attempts conception. In certain embodiments, the combination is orally administered to the pre-menopausal woman once-daily for at least 16 weeks, at least 20 weeks, at least 24 weeks, at 36 weeks, at least 48 weeks, at least 72 weeks, or more, before discontinuing treatment. In certain embodiments, the treatment is discontinued for at least 4 weeks, at least 8 weeks, at least 12 weeks, at least 16 weeks, at least 20 weeks, at least 24 weeks, at least 28 weeks, between 4 to 28 weeks, between 4 to 24 weeks, between 4 to 20 weeks, between 4 to 16 weeks, between 4 to 12 weeks, or between 4 to 8 weeks while the pre-menopausal women attempts conception. In some embodiments, the pre-menopausal woman conceives, becomes pregnant, or gives birth. In certain embodiments, the pre-menopausal woman experienced one or more miscarriages, or an inability to conceive, or a combination thereof prior to treatment.

Also provided is a method of contraception in a pre-menopausal woman in need thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg of Compound 1, or a corresponding amount of a pharmaceutically acceptable salt thereof, about 0.5 mg to about 2 mg estradiol or a corresponding amount of estradiol equivalent; and about 0.01 mg to about 5 mg of a progestin. The combination comprising Compound 1 or a pharmaceutically acceptable salt thereof and the hormone replacement medicament may be administered as a fixed dose combination dosage, or may be two or more separate dosages that are co-administered. Contraception may be demonstrated, for example, by ovarian suppression of estrogen and/or progesterone production as discussed above, or by lower rate of pregnancy occurring over 10 menstrual cycles with unprotected intercourse, or by suppression of ovulation.

In some embodiments, the methods provided herein, such as for treating heavy menstrual bleeding, anemia, or pain; or for contraception; or for improving fertility, result in one or both of contraception and amenorrhea during treatment. After discontinuation of the methods provided herein, the pre-menopausal woman may, in some embodiments, conceive, be pregnant, or give birth.

In other embodiments of any of the foregoing methods, the pre-menopausal woman experiences an improvement in one or more symptoms selected from the group consisting of anemia, irregular periods, spotting, inflammation, pain, fatigue, urinary obstruction, urinary frequency, incontinence, constipation, anxiety, sleep disturbance, quality of life, activities of daily living, female sexual dysfunction and depression, during and/or after the methods described above, such as for treating heavy menstrual bleeding, anemia, or pain; or for contraception; or for improving fertility. In some variations, the pain is dyspareunia. In other variations, the pain is chronic pain. In still further variations, the pain is pain with defecation or pain with urination.

In a pre-menopausal woman with uterine fibroids, the methods discussed above, such as for treating heavy menstrual bleeding, anemia, or pain; or for contraception; or for improving fertility, may result in the reduction of the number of uterine fibroids, the reduction of the size of one or more uterine fibroids, or prevention of uterine fibroid growth, or any combination thereof, during and/or after treatment. The size and/or number of uterine fibroids may be assessed by, for example, transvaginal ultrasound, abdominal ultrasound, magnetic resonance imaging, computed tomography, or laparoscopy. In some embodiments, in a pre-menopausal woman with symptomatic uterine fibroids or symptomatic endometriosis, treatment according to the methods discussed above, such as for heavy menstrual bleeding, anemia, or pain; or for contraception; or for improving fertility, suppresses the endometrium in the woman.

In some embodiments of the methods provided herein, for example of treating heavy menstrual bleeding, anemia, or pain; or for contraception; or for improving fertility, Compound 1 or a pharmaceutically acceptable salt thereof is administered at an estrogen suppressing dose, such as a dose that results in sustained estrogen suppression throughout a 24-hour period. In some embodiments, the dose suppresses estradiol production to a blood serum level of less than 20 pg/mL or less than 10 pg/mL. In some embodiments, the co-administration of a hormone replacement medicament (e.g., a combination of an estradiol or estradiol equivalent and a progestin) with Compound 1, or a pharmaceutically acceptable salt thereof, can prevent, decrease, or otherwise ameliorate symptoms associated with a hypoestrogenic state, such as bone mineral density loss, one or more vasomotor symptoms, vulvovaginal atrophy, vaginal dryness, fatigue, malaise, or headache. In some embodiments, the one or more vasomotor symptoms is selected from hot flashes and night sweats.

Administration of the combination as provided herein in the methods discussed above, such as for treating heavy menstrual bleeding, anemia, or pain; or for contraception; or for improving fertility, may result in suppression of the pre-menopausal woman's ovarian estrogen production. For example, in some embodiments, after at least 4 consecutive weeks, at least 8 consecutive weeks, at least 12 consecutive weeks, or at least 16 consecutive weeks of administration of the combination, the pre-menopausal woman's ovarian estrogen production is suppressed. In some embodiments, after at least 4 consecutive weeks of administration of the combination, the pre-menopausal woman's ovarian estrogen production is suppressed. Suppression of ovarian estrogen production may be demonstrated by estrogen blood levels that are in the postmenopausal range, such as estradiol levels of <20 pg/mL, in a subject that is administered Compound 1 or a pharmaceutically acceptable salt thereof without co-administration of a hormone replacement medicament. Suppression of ovarian estrogen production in a subject that is co-administered Compound 1 or a pharmaceutically acceptable salt thereof and a hormone replacement medicament comprising estradiol or an estradiol equivalent may be demonstrated by estradiol blood levels of between 20 and 50 pg/mL. In some embodiments, for example in women who are administered a higher dose of hormone replacement medicament (comprising, for example, up to 5 mg estradiol or estradiol equivalent), suppression of ovarian estrogen production in a woman co-administered Compound 1 or a pharmaceutically acceptable salt thereof and a hormone replacement medicament may be demonstrated by estradiol blood levels of between 55 pg/mL and 150 pg/mL. Suppression of ovarian estrogen production may also be demonstrated by ultrasound showing no growing ovarian follicles, and/or by the presence of amenorrhea.

The methods discussed above, such as for treating heavy menstrual bleeding, anemia, or pain; or for contraception; or for improving fertility, may result in the pre-menopausal woman's serum estradiol concentration to be within a certain range. In some embodiments, administration of the composition results in the pre-menopausal woman's serum estradiol concentration to be within about 20 pg/mL and about 50 pg/mL, between daily doses of the combination. In certain embodiments, the pre-menopausal woman's serum estradiol concentration is between about 20 pg/mL and about 50 pg/mL between daily doses of the combination after at least 4 consecutive weeks, at least 8 consecutive weeks, or at least 12 consecutive weeks of administration of the composition. In one embodiment, the pre-menopausal woman's serum estradiol concentration is between about 20 pg/mL and about 50 pg/mL between daily doses of the combination after at least 4 consecutive weeks of administration of the combination. The combination comprising Compound 1 or a pharmaceutically acceptable salt thereof and the hormone replacement medicament may be administered as a fixed dose combination dosage, or may be two or more separate dosages that are co-administered.

Administration of the combination as provided herein in the methods discussed above, such as for treating heavy menstrual bleeding, anemia, or pain; or for contraception; or for improving fertility, may result in suppression of the pre-menopausal woman's ovarian progesterone production. For example, in some embodiments, after at least 4 consecutive weeks, at least 8 consecutive weeks, at least 12 consecutive weeks, or at least 16 consecutive weeks of administration of the combination, the pre-menopausal woman's ovarian progesterone production is suppressed. In some embodiments, after at least 4 consecutive weeks of administration of the combination, the pre-menopausal woman's ovarian progesterone production is suppressed. Suppression of ovarian progesterone production may be demonstrated, for example, by progesterone blood levels that are in the postmenopausal range, e.g., progesterone levels of <2 ng/mL, in a woman who has not been administered progesterone. Suppression of ovarian progesterone production may also be demonstrated by ultrasound showing no growing ovarian follicles, and/or by the presence of amenorrhea.

The methods discussed above, such as for treating heavy menstrual bleeding, anemia, or pain; or for contraception; or for improving fertility, may result in the pre-menopausal woman's serum progesterone concentration to be within a certain range. In some embodiments, administration of the combination results in the pre-menopausal woman's serum progesterone concentration to be less than about 5 ng/mL, less than about 4 ng/mL, less than about 3 ng/mL, less than about 2 ng/mL, or less than about 1 ng/mL between daily doses of the combination. In certain embodiments, the pre-menopausal woman's serum progesterone concentration is less than about 5 ng/mL between daily doses of the combination after at least 4 consecutive weeks, at least 8 consecutive weeks, or at least 12 consecutive weeks of administration of the combination. In one embodiment, the pre-menopausal woman's serum progesterone concentration is less than about 5 ng/mL between daily doses of the combination after at least 4 consecutive weeks of administration of the combination.

In some embodiments of any of the above methods, administration of the combination results in any combination of suppression of the pre-menopausal woman's ovarian estrogen production, suppression of the pre-menopausal woman's ovarian progesterone production, or in the pre-menopausal woman's serum progesterone concentration being less than about 5 ng/mL between daily doses of the combination, as described above.

Any of the combinations described herein may be suitable for treating the symptoms and/or conditions described above, such as heavy menstrual bleeding, anemia, or pain; or for improving fertility; or for contraception. In certain embodiments, the combination comprises about 10 mg to about 60 mg about 20 mg to about 50 mg, or about 30 mg to about 50 mg of Compound 1, for example about 10 mg, about 20 mg, about 30 mg, about 40 mg, about 50 mg, or about 60 mg, or a corresponding amount of a pharmaceutically acceptable salt thereof. The hormone replacement medicament may comprise, for example, estradiol or an estradiol equivalent; or progestin; or a combination thereof as described herein. In certain variations, the combination comprises about 0.5 mg to about 2 mg estradiol, such as about 0.5 mg, about 0.75 mg, about 1 mg, about 1.25 mg, about 1.5 mg, about 1.75 mg, or about 2 mg of estradiol, or a corresponding amount of estradiol equivalent; and about 0.01 mg to about 5 mg, such as about 1 mg, about 2 mg, about 3 mg, about 4 mg, or about 5 mg, or progestin. In some embodiments, the combination is administered once-daily for at least 24 consecutive weeks.

The hormone replacement medicament may comprise estradiol or an estradiol equivalent, a progestin, or any combination thereof. In certain embodiments, the hormone replacement medicament comprises estradiol, or an estradiol equivalent. In other embodiments, the hormone replacement medicament comprises a progestin. The progestin may be, for example, norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogestrone acetate, promegestone, or dienogest. The estradiol equivalent may be, for example, equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, or stilbestrol. In certain embodiments, the hormone replacement medicament comprises both an estradiol or an estradiol equivalent, and a progestin. The progestin may be, for example, norethindrone or a salt thereof.

In some embodiments of any of the methods described herein, the hormone replacement medicament comprises about 0.01 mg to about 5 mg of a progestin. For example, in some embodiments, the hormone replacement medicament comprises about 0.01 mg, about 0.05 mg, about 0.1 mg, about 0.5 mg, about 0.75 mg, about 1 mg, about 1.25 mg, about 1.5 mg, about 2 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg progestin. In some embodiments, the hormone replacement medicament comprises about 0.1 mg to about 0.5 mg of a progestin, for example about 0.1 mg, about 0.2 mg, about 0.3 mg, about 0.4 mg, or about 0.5 mg of progestin. In some embodiments, the progestin is a norethindrone salt, for example norethindrone acetate. In certain embodiments, the hormone replacement medicament comprises about 0.5 mg of norethindrone acetate. In other embodiments, the combination comprises between about 0.625 mg to about 5 mg nomegestrol acetate, or about 0.05 mg to about 0.5 mg levonorgestrel, or about 0.5 to about 5 mg dienogest.

In some embodiments, the hormone replacement medicament comprises from about 0.5 to about 2 mg of estradiol, or a corresponding amount of estradiol equivalent. For example, in some embodiments, the hormone replacement medicament comprises from about 0.5 mg to about 1 mg, from about 0.5 mg to about 1.5 mg, from about 1 mg to about 1.5 mg, from about 1 mg to about 2 mg, from about 1.5 mg to about 2 mg, about 0.5 mg, about 0.75 mg, about 1 mg, about 1.25 mg, about 1.5 mg, or about 2 mg estradiol, or a corresponding amount of an estradiol equivalent.

In one embodiment, the hormone replacement medicament comprises about 0.5 mg to about 2 mg of estradiol or a corresponding amount of estradiol equivalent, and about 0.01 mg to about 5 mg of a progestin. In certain embodiments, the progestin is norethindrone or a salt thereof in an amount of about 0.1 mg to about 0.5 mg. In one embodiment, the progestin is norethindrone acetate (NETA). In certain embodiments, the combination comprises about 0.5 mg of NETA.

In one embodiment, the combination comprises about 0.5 mg NETA, about 1 mg estradiol, and about 40 mg of Compound 1, or a corresponding amount of a pharmaceutically acceptable salt thereof.

The combination comprising Compound 1 or a pharmaceutically acceptable salt thereof and the hormone replacement medicament may be administered as a fixed dose combination dosage, or may be two or more separate dosages that are co-administered.

In some embodiments, there exists a population of pre-menopausal women for whom about 10 mg to about 60 mg, about 20 mg to about 50 mg, about 30 mg to about 50 mg, or about 40 mg of Compound 1, or a corresponding amount of a pharmaceutically acceptable salt thereof does not adequately treat their symptom and/or condition (e.g., heavy menstrual bleeding, anemia, pain, or infertility). Thus, in some embodiments, the combination orally administered daily to a pre-menopausal woman comprises about 65 mg to about 140 mg of Compound 1, or a corresponding amount of a pharmaceutically acceptable salt thereof. In some embodiments, the combination orally administered daily to a pre-menopausal woman comprises about 65 mg to about 120 mg of Compound 1, or a corresponding amount of a pharmaceutically acceptable salt thereof. For example, in some embodiments the combination comprises about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof.

In some embodiments, there exists a population of pre-menopausal women for whom about 0.5 mg to about 2 mg, about 0.5 to about 1.5 mg, about 0.5 to about 1 mg, or about 1 mg to about 2 mg, of estradiol or a corresponding amount of estradiol equivalent does not adequately treat one or more side effects of hypoestrogenic state (e.g., bone mineral density loss, one or more vasomotor symptoms, vulvovaginal atrophy, vaginal dryness, fatigue, malaise, or headache). There may also exist a population of pre-menopausal women who experience one or more side effects of GnRH antagonist administration (e.g., bone mineral density loss, one or more vasomotor symptoms, vulvovaginal atrophy, vaginal dryness, fatigue, malaise, or headache) when their serum estradiol level is between 20 pg/mL and 50 pg/mL, and for whom this experience more negatively impacts their QOL than if their symptom and/or condition (e.g., heavy menstrual bleeding, anemia, pain, or infertility) was not as well treated (for example, if their serum estradiol level were greater than 50 pg/mL). Thus, certain women may prefer administration of a higher dosage of hormone replacement medicament, such that their average daily circulating serum estradiol level is about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. Administration of a higher dosage of hormone replacement medicament may achieve such average daily circulating serum estradiol levels and may further reduce one or side effects of GnRH antagonist administration, and still provide some treatment of the symptom and/or condition. Thus, in some embodiments, the combination orally administered daily to a pre-menopausal woman comprises between 1.5 mg to 5.0 mg, between about 2 mg to about 5 mg, between about 3 mg to about 5, between about 4 mg to about 5 mg, between about 1.5 mg to about 4 mg, between about 2 mg to about 4 mg, between about 3 mg to about 4 mg, between about 1.5 mg to about 3 mg, or between about 2 mg to about 3 mg of estradiol, or an estradiol equivalent. For example, in some embodiments, the combination comprises about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg estradiol or an estradiol equivalent.

Administration of Compound 1 or a pharmaceutically acceptable salt thereof without the co-administration of a hormone replacement medicament may more rapidly treat one or more symptoms or conditions discussed above, for example heavy menstrual bleeding, anemia, or pain, as progesterone and estrogen levels may be suppressed without supplementation by estradiol, an estradiol equivalent, and/or a progestin. However, as discussed above, one or more negative side effects (e.g., bone mineral density loss) may result from longer-term treatment without the use of a hormone replacement medicament. Thus, in some embodiments of the methods provided herein for treating one or more symptoms or conditions discussed herein, such as heavy menstrual bleeding, anemia pain; or for contraception; prior to administration of the combination of Compound 1 or a pharmaceutically acceptable salt thereof and a hormone replacement medicament, the pre-menopausal woman is orally administered Compound 1 or a pharmaceutically acceptable salt thereof once-daily. In certain embodiments, the pre-menopausal woman is orally administered about 10 mg to about 60 mg, or about 20 mg to about 50 mg, or about 30 mg to about 50 mg, for example about 10 mg, about 20 mg, about 30 mg, about 40 mg, about 50 mg, or about 60 mg, of Compound 1, or a corresponding amount of a pharmaceutically acceptable salt thereof, once-daily before administration of any of the combinations described herein. In other embodiments, the pre-menopausal woman is orally administered about 65 mg to about 140 mg of Compound 1, or about 65 mg to about 120 mg of Compound 1, or a corresponding amount of a pharmaceutically acceptable salt thereof, for example about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof, once-daily before administration of any of the combinations described herein. Further provided is the use of Compound 1 or a pharmaceutically acceptable salt thereof for the manufacture of a medicament for treatment according to any of these methods.

In some embodiments, the pre-menopausal woman is orally administered Compound 1, or a pharmaceutically acceptable salt thereof, once-daily for at least 4 consecutive weeks, at least 8 consecutive weeks, at least 12 consecutive weeks, at least 16 consecutive weeks, at least 20 consecutive weeks, or up to 24 consecutive weeks, before being administered any of the combinations described herein. In one embodiment, the subject is orally administered between about 10 mg to about 60 mg, about 20 mg to about 50 mg, about 30 mg to about 50 mg, or about 40 mg of Compound 1, or a corresponding amount of a pharmaceutically acceptable salt thereof, once-daily for at least 4 consecutive weeks and up to 24 consecutive weeks, prior to administration of a combination of Compound 1 or a pharmaceutically acceptable salt thereof and a hormone replacement medicament. Administration of Compound 1, or a pharmaceutically acceptable salt thereof, without the co-administration of a hormone replacement medicament for a period of time prior to co-administration of the combination may treat one or more symptoms of more aggressively at the beginning, prior to transitioning to a longer term treatment. This may be desirable, for example, in a woman with severe symptoms, or a plurality of symptoms, or with a desire to more quickly alleviate one or more symptoms.

The combination of Compound 1, or a pharmaceutically acceptable salt thereof, and a hormone replacement medicament may be orally administered to the pre-menopausal woman once-daily for at least 24 consecutive weeks, at least 36 consecutive weeks, at least 48 consecutive weeks, at least 72 consecutive weeks, or at least 96 consecutive weeks, in the method of treating heavy menstrual bleeding, anemia, or pain; or for contraception; or for improving fertility, as described above. In some embodiments, administration of the combination is suspended for conception and/or pregnancy. Administration of the combination may resume after delivery. In certain embodiments, the pre-menopausal woman's bone mineral density during treatment according to one of the above methods is within + or −3%, or + or −2%, of the bone mineral density prior to starting treatment.

In an embodiment, heart benefits may be provided by the treatment methods of this disclosure. Also, the treatment methods of this disclosure may be useful in sexual reassignment/cross gender transition protocols. Further, the treatment methods of this disclosure may be useful in preserving fertility during chemotherapy.

VI. GnRH Antagonist Side-Effects

Further provided herein are methods for reducing one or more side effects associated with the administration of a GnRH antagonist, such as Compound 1 or a pharmaceutically acceptable salt thereof. The one or more side effects may be selected from the group consisting of bone mineral density loss, vasomotor symptoms (such as night sweats or hot flashes), vulvovaginal atrophy, vaginal dryness, fatigue, malaise, and headache. In addition, provided herein are methods for maintain the lipid profile, or for maintaining normal glucose range, in a subject that has been administered a GnRH antagonist, such as Compound 1 or a pharmaceutically acceptable salt thereof. Such methods comprise orally administering once-daily a combination of Compound 1, or a pharmaceutically acceptable salt thereof, and a hormone replacement medicament (e.g., a combination of an estradiol or estradiol equivalent and a progestin) to a pre-menopausal woman in need thereof. In some embodiments, the subject has been diagnosed with uterine fibroids, endometriosis, adenomyosis, heavy menstrual bleeding, or pain associated with uterine fibroids, endometriosis, or adenomyosis. In other embodiments, the subject has not been diagnosed with uterine fibroids, endometriosis, adenomyosis, heavy menstrual bleeding, or pain associated with uterine fibroids, endometriosis, or adenomyosis. The combination may be administered, for example, as either as a fixed dose or in two or more separate dosage forms that are co-administered. Further provided are combined preparations for use in any of these methods. In some embodiments, the combined preparation is for simultaneous or sequential use. In certain embodiments, the combined preparation comprises Compound 1, or a pharmaceutically acceptable salt thereof, and a hormone replacement medicament. In certain embodiments, the hormone replacement medicament comprises estradiol or estradiol equivalent, and progestin. Further provided is the use of Compound 1, or a pharmaceutically acceptable salt thereof, and a hormone replacement medicament for the manufacture of a medicament for treatment according to any of these methods. In some embodiments, the hormone replacement medicament comprises estradiol or estradiol equivalent, and progestin.

Provided herein is a method for maintaining bone density in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof, about 0.5 mg to about 2 mg estradiol or a corresponding amount of estradiol equivalent; and about 0.01 mg to about 5 mg, or about 0.1 mg to about 0.5 mg of a progestin. Maintaining bone mineral density may include that bone mineral density during treatment is within + or −3% when compared to bone mineral density prior to initiation of the treatment. In some embodiments, maintaining bone density comprises bone mineral density during treatment is within + or −2% when compared to bone mineral density prior to initiation of the treatment.

Provided herein is a method for treating one or both of vulvovaginal atrophy or vaginal dryness in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof; about 0.5 mg to about 2 mg estradiol or a corresponding amount of estradiol equivalent; and about 0.01 mg to about 5 mg, or about 0.1 mg to about 0.5 mg of a progestin. Treatment of vulvovaginal atrophy or vaginal dryness may include increasing the percentage of superficial cells and decreasing the percentage of parabasal cells in the vaginal epithelium, a decrease in vaginal pH from greater than 5.0 to less than 5.0; and/or improvement in one or more symptoms selected from dryness, dyspareunia, and bleeding as reported by the subject.

Provided herein is a method for treating headache in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof, about 0.5 mg to about 2 mg estradiol or a corresponding amount of estradiol equivalent; and about 0.01 mg to about 5 mg, or about 0.1 mg to about 0.5 mg of a progestin.

Provided herein is a method for treating fatigue or malaise in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g. a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof, about 0.5 mg to about 2 mg estradiol or a corresponding amount of estradiol equivalent; and about 0.01 mg to about 5 mg, or about 0.1 mg to about 0.5 mg of a progestin.

In any of the preceding methods, the combination comprising Compound 1 or a pharmaceutically acceptable salt thereof and the hormone replacement medicament may be administered as a fixed dose combination dosage, or may be two or more separate dosages that are co-administered.

In some variations, the headache is a migraine associated with the menstrual cycle. Treatment of headache may include decreasing the frequency and/or severity of headache, as reported by the subject. Migraines may, for example, include a primary headache disorder characterized by recurrent headaches that are moderate to severe. The headaches may affect one half of the head, be pulsating in nature, and last from two to 72 hours. Associated symptoms may include nausea, vomiting, and sensitivity to light, sound, or smell. The pain is generally made worse by physical activity. A migraine may be accompanied by an aura: typically a short period of visual disturbance which signals that the headache will soon occur. Occasionally, an aura can occur with little or no headache following it.

Further provided herein is a method for maintaining one or both of a normal lipid profile or normal blood glucose range in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof, about 0.5 mg to about 2 mg estradiol or a corresponding amount of estradiol equivalent; and about 0.01 mg to about 5 mg, or about 0.1 mg to about 0.5 mg of a progestin. In some embodiments, maintaining one or both of a normal lipid profile or normal blood glucose range includes that no clinically meaningful changes in the lipid profile and/or blood glucose range occur during treatment, as compared to before treatment commences.

Provided herein is also a method of treating one or more of night sweats, hot flashes, or other vasomotor symptoms in a pre-menopausal woman in need thereof, who is being treated for one or more of uterine fibroids, endometriosis, adenomyosis, heavy menstrual bleeding, one or more symptoms associated with uterine fibroids, one or more symptoms associated with endometriosis (e.g., pain), or one or more symptoms associated with adenomyosis (e.g., pain) with Compound 1 or a pharmaceutically acceptable salt thereof, comprising orally administering once-daily to the pre-menopausal woman a combination of Compound 1 or a pharmaceutically acceptable salt thereof and a hormone replacement medicament (e.g., a combination of an estradiol or estradiol equivalent and a progestin). In some embodiments, the combination is administered once-daily for at least 24 consecutive weeks, at least 28 consecutive weeks, at least 32 consecutive weeks, at least 36 consecutive weeks, or at least 40 consecutive weeks. In some embodiments, the combination comprises about 10 mg to about 60 mg, about 20 mg to about 50 mg, about 30 mg to about 50 mg, or about 40 mg of Compound 1, or a corresponding amount of a pharmaceutically acceptable salt thereof; about 0.5 mg to about 2 mg estradiol or a corresponding amount of estradiol equivalent; and about 0.01 mg to about 5 mg, or about 0.1 mg to about 0.5 mg of a progestin. Treatment of night sweats, hot flashes, or other vasomotor symptoms may include decreasing the frequency and/or severity of night sweats, hot flashes, or other vasomotor symptoms, as reported by the subject.

In some embodiments, the methods described above, such as for treating one or more side effects associated with the administration of a GnRH antagonist (such as bone mineral density loss, vasomotor symptoms (such as night sweats or hot flashes), vulvovaginal atrophy, vaginal dryness, or headache), or for maintaining the lipid profile, or for maintaining normal glucose range, in a pre-menopausal woman result in one or both of contraception and amenorrhea during treatment. After discontinuation of the methods provided herein, the pre-menopausal woman may, in some embodiments, conceive, be pregnant, or give birth.

In other embodiments, the pre-menopausal woman experiences an improvement in one or more symptoms selected from the group consisting of anemia, irregular periods, spotting, inflammation, pain, fatigue, urinary obstruction, urinary frequency, incontinence, constipation, anxiety, sleep disturbance, quality of life, activities of daily living, female sexual dysfunction and depression, during and/or after the methods described above, such as for treating one or more side effects associated with the administration of a GnRH antagonist (such as bone mineral density loss, vasomotor symptoms (such as night sweats or hot flashes), vulvovaginal atrophy, vaginal dryness, or headache), or for maintaining the lipid profile, or for maintaining normal glucose range. In some variations, the pain is dyspareunia. In other variations, the pain is chronic pain. In still further variations, the pain is pain with defecation or pain with urination.

In a pre-menopausal woman with uterine fibroids, the methods discussed above, such as for treating one or more side effects associated with the administration of a GnRH antagonist (such as bone mineral density loss, vasomotor symptoms (such as night sweats or hot flashes), vulvovaginal atrophy, vaginal dryness, or headache), or for maintaining the lipid profile, or for maintaining normal glucose range, may result in the reduction of the number of uterine fibroids, the reduction of the size of one or more uterine fibroids, or prevention of uterine fibroid growth, or any combination thereof, during and/or after treatment. In some embodiments, the size of one or more uterine fibroids is reduced to be undetectable, and/or the number of uterine fibroids is reduced to zero. The size and/or number of uterine fibroids may be assessed by, for example, transvaginal ultrasound, abdominal ultrasound, magnetic resonance imaging, computed tomography, or laparoscopy. In some embodiments, in a pre-menopausal woman with symptomatic uterine fibroids or symptomatic endometriosis, the endometrium in the woman is suppressed as a result of treatment according to the methods discussed above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range.

Administration of the combination as provided herein in the methods discussed above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range, may result in suppression of the pre-menopausal woman's ovarian estrogen production. For example, in some embodiments, after at least 4 consecutive weeks, at least 8 consecutive weeks, at least 12 consecutive weeks, or at least 16 consecutive weeks of administration of the combination, the pre-menopausal woman's ovarian estrogen production is suppressed. In some embodiments, after at least 4 consecutive weeks of administration of the combination, the pre-menopausal woman's ovarian estrogen production is suppressed. Suppression of ovarian estrogen production may be demonstrated by estrogen blood levels that are in the postmenopausal range, such as estradiol levels of <20 pg/mL, in a subject that is administered Compound 1 or a pharmaceutically acceptable salt thereof without co-administration of a hormone replacement medicament. Suppression of ovarian estrogen production in a subject that is co-administered Compound 1 or a pharmaceutically acceptable salt thereof and a hormone replacement medicament comprising estradiol or an estradiol equivalent may be demonstrated by estradiol blood levels of between 20 and 50 pg/mL. In some embodiments, for example in women who are administered a higher dose of hormone replacement medicament (comprising, for example, up to 5 mg estradiol or estradiol equivalent), suppression of ovarian estrogen production in a woman co-administered Compound 1 or a pharmaceutically acceptable salt thereof and a hormone replacement medicament may be demonstrated by estradiol blood levels of between 55 pg/mL and 150 pg/mL. Suppression of ovarian estrogen production may also be demonstrated by ultrasound showing no growing ovarian follicles, and/or by the presence of amenorrhea.

The methods discussed above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range, may result in the pre-menopausal woman's serum estradiol concentration to be within a certain range. In some embodiments, administration of the combination results in the pre-menopausal woman's serum estradiol concentration to be within about 20 pg/mL and about 50 pg/mL, between daily doses of the combination. In certain embodiments, the pre-menopausal woman's serum estradiol concentration is between about 20 pg/mL and about 50 pg/mL between daily doses of the combination after at least 4 consecutive weeks, at least 8 consecutive weeks, or at least 12 consecutive weeks of administration of the combination. In one embodiment, the pre-menopausal woman's serum estradiol concentration is between about 20 pg/mL and about 50 pg/mL between daily doses of the combination after at least 4 consecutive weeks of administration of the combination.

Administration of the combination as provided herein in the methods discussed above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range, may result in suppression of the pre-menopausal woman's ovarian progesterone production. For example, in some embodiments, after at least 4 consecutive weeks, at least 8 consecutive weeks, at least 12 consecutive weeks, or at least 16 consecutive weeks of administration of the combination, the pre-menopausal woman's ovarian progesterone production is suppressed. In some embodiments, after at least 4 consecutive weeks of administration of the combination, the pre-menopausal woman's ovarian progesterone production is suppressed. Suppression of ovarian progesterone production may be demonstrated, for example, by progesterone blood levels that are in the postmenopausal range, e.g., progesterone levels of <2 ng/mL, in a woman who has not been administered progesterone. Suppression of ovarian progesterone production may also be demonstrated by ultrasound showing no growing ovarian follicles, and/or by the presence of amenorrhea.

The methods discussed above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range, may result in the pre-menopausal woman's serum progesterone concentration to be within a certain range. In some embodiments, administration of the combination results in the pre-menopausal woman's serum progesterone concentration to be less than about 5 ng/mL, less than about 4 ng/mL, less than about 3 ng/mL, less than about 2 ng/mL, or less than about 1 ng/mL between daily doses of the combination. In certain embodiments, the pre-menopausal woman's serum progesterone concentration is less than about 5 ng/mL between daily doses of the combination after at least 4 consecutive weeks, at least 8 consecutive weeks, or at least 12 consecutive weeks of administration of the combination. In one embodiment, the pre-menopausal woman's serum progesterone concentration is less than about 5 ng/mL between daily doses of the combination after at least 4 consecutive weeks of administration of the combination.

In some embodiments of any of the above methods, administration of the combination results in any combination of suppression of the pre-menopausal woman's ovarian estrogen production, suppression of the pre-menopausal woman's ovarian progesterone production, or in the pre-menopausal woman's serum progesterone concentration being less than about 5 ng/mL between daily doses of the combination, as described above.

Any of the combinations described herein may be suitable for treating the symptoms and/or conditions described above, such as for treating one or more side effects associated with the administration of a GnRH antagonist (such as bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range. In certain embodiments, the combination comprises about 10 mg to about 60 mg, about 20 mg to about 50 mg, or about 30 mg to about 50 mg of Compound 1, for example about 10 mg, about 20 mg, about 30 mg, about 40 mg, about 50 mg, or about 60 mg, or a corresponding amount of a pharmaceutically acceptable salt thereof. The hormone replacement medicament may comprise, for example, estradiol or an estradiol equivalent; or progestin; or a combination thereof as described herein. In certain variations, the combination comprises about 0.5 mg to about 2 mg estradiol, such as about 0.5 mg, about 0.75 mg, about 1 mg, about 1.25 mg, about 1.5 mg, about 1.75 mg, or about 2 mg of estradiol, or a corresponding amount of estradiol equivalent; and about 0.01 mg to about 5 mg, such as about 1 mg, about 2 mg, about 3 mg, about 4 mg, or about 5 mg, or progestin. In some embodiments, the combination is administered once-daily for at least 24 consecutive weeks. The combination comprising Compound 1 or a pharmaceutically acceptable salt thereof and the hormone replacement medicament may be administered as a fixed dose combination dosage, or may be two or more separate dosages that are co-administered.

The hormone replacement medicament may comprise estradiol or an estradiol equivalent, a progestin, or any combination thereof. In certain embodiments, the hormone replacement medicament comprises estradiol, or an estradiol equivalent. In other embodiments, the hormone replacement medicament comprises a progestin. The progestin may be, for example, norethindrone, norethindrone acetate, norgestimate, norgestrel, levonorgestrel, drospirenone, medroxyprogesterone, progesterone, cyproterone, desogestrel, etonogestrel, nomegestrol acetate, medroxyprogestrone acetate, promegestone, or dienogest. The estradiol equivalent may be, for example, equine conjugated estrogens, synthetic conjugated estrogens, esterified estrogens (e.g., cypionate, estradiol valerate, estradiol acetate, estradiol benzoate), estropipate, ethinylestradiol, estrone, estriol, sterol, mestranol, moxestrol, quinestrol, methylstradiol, tibolone, or stilbestrol. In certain embodiments, the hormone replacement medicament comprises both an estradiol or an estradiol equivalent, and a progestin. The progestin may be, for example, norethindrone or a salt thereof.

In some embodiments of any of the methods described herein, the hormone replacement medicament comprises about 0.01 mg to about 5 mg of a progestin. For example, in some embodiments, the hormone replacement medicament comprises about 0.01 mg, about 0.05 mg, about 0.1 mg, about 0.5 mg, about 0.75 mg, about 1 mg, about 1.25 mg, about 1.5 mg, about 2 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg progestin. In some embodiments, the hormone replacement medicament comprises about 0.1 mg to about 0.5 mg of a progestin, for example about 0.1 mg, about 0.2 mg, about 0.3 mg, about 0.4 mg, or about 0.5 mg of progestin. In some embodiments, the progestin is a norethindrone salt, for example norethindrone acetate. In certain embodiments, the hormone replacement medicament comprises about 0.5 mg of norethindrone acetate. In other embodiments, the combination comprises between about 0.625 mg to about 5 mg nomegestrol acetate, or about 0.05 mg to about 0.5 mg levonorgestrel, or about 0.5 to about 5 mg dienogest.

In some embodiments, the hormone replacement medicament comprises from about 0.5 to about 2 mg of estradiol, or a corresponding amount of estradiol equivalent. For example, in some embodiments, the hormone replacement medicament comprises from about 0.5 mg to about 1 mg, from about 0.5 mg to about 1.5 mg, from about 1 mg to about 1.5 mg, from about 1 mg to about 2 mg, from about 1.5 mg to about 2 mg, about 0.5 mg, about 0.75 mg, about 1 mg, about 1.25 mg, about 1.5 mg, or about 2 mg estradiol, or a corresponding amount of an estradiol equivalent.

In one embodiment, the hormone replacement medicament comprises about 0.5 mg to about 2 mg of estradiol or a corresponding amount of estradiol equivalent, and about 0.01 mg to about 5 mg of a progestin. In certain embodiment, the progestin is norethindrone or a salt thereof in an amount of about 0.1 mg to about 0.5 mg. In one embodiment, the progestin is norethindrone acetate (NETA). In certain embodiments, the combination comprises about 0.5 mg of NETA.

In one embodiment, the combination comprises about 0.5 mg NETA, about 1 mg estradiol, and about 40 mg of Compound 1, or a corresponding amount of a pharmaceutically acceptable salt thereof.

In some embodiments, there exists a population of pre-menopausal women for whom about 0.5 mg to about 2 mg, about 0.5 to about 1.5 mg, about 0.5 to about 1 mg, or about 1 mg to about 2 mg, of estradiol or a corresponding amount of estradiol equivalent does not adequately treat one or more side effects of hypoestrogenic state (e.g., bone mineral density loss, one or more vasomotor symptoms, vulvovaginal atrophy, vaginal dryness, fatigue, malaise, or headache). There may also exist a population of pre-menopausal women who experience one or more side effects of GnRH antagonist administration (e.g., bone mineral density loss, one or more vasomotor symptoms, vulvovaginal atrophy, vaginal dryness, fatigue, malaise, or headache) when their serum estradiol level is between 20 pg/mL and 50 pg/mL, and for whom this experience more negatively impacts their QOL than for other women. Thus, certain women may prefer administration of a higher dosage of hormone replacement medicament, such that their average daily circulating serum estradiol level is about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. Administration of a higher dosage of hormone replacement medicament may achieve such average daily circulating serum estradiol levels and may further reduce one or side effects of GnRH antagonist administration than administration of a lower dosage of hormone replacement medicament. Thus, in some embodiments, the combination orally administered daily to a pre-menopausal woman comprises between 1.5 mg to 5.0 mg, between about 2 mg to about 5 mg, between about 3 mg to about 5, between about 4 mg to about 5 mg, between about 1.5 mg to about 4 mg, between about 2 mg to about 4 mg, between about 3 mg to about 4 mg, between about 1.5 mg to about 3 mg, or between about 2 mg to about 3 mg of estradiol, or an estradiol equivalent. For example, in some embodiments, the combination comprises about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5 mg estradiol or an estradiol equivalent.

The combination of Compound 1, or a pharmaceutically acceptable salt thereof, and a hormone replacement medicament may be orally administered to the pre-menopausal woman once-daily for at least 24 consecutive weeks, at least 36 consecutive weeks, at least 48 consecutive weeks, at least 72 consecutive weeks, or at least 96 consecutive weeks, in the method of treating the symptoms and/or conditions described above, such as for treating one or more side effects associated with the administration of a GnRH antagonist (such bone mineral density loss, vasomotor symptoms (such as night sweats or hot flashes), vulvovaginal atrophy, vaginal dryness, fatigue, malaise, or headache), or for maintaining the lipid profile, or for maintaining normal glucose range. In some embodiments, administration of the combination is suspended for conception and/or pregnancy. Administration of the combination may resume after delivery. In certain embodiments, the pre-menopausal woman's bone mineral density during treatment according to one of the above methods is within + or −3%, or + or −2%, of the bone mineral density prior to starting treatment.

In some embodiments, following administering doses of 40 mg per day for 28 consecutive days of Compound 1, and 0.01 mg to 5 mg per day of at least one of an estrogen and a progestogen, bone mineral density loss is minimized. In some embodiments, a corresponding amount of a pharmaceutically acceptable salt of Compound 1 is administered.

Provided herein are methods of treating one or more side-effects associated with administration of GnRH antagonists. Additional side-effects associated with administration of a GnRH antagonist include vasomotor symptoms, hot flashes, vaginal dryness, and decreased libido.

In an embodiment, Compound 1, is co-administered with a medicament to counteract any decrease in libido caused by the GnRH antagonist, possibly as separate oral dosage forms, and preferably in a fixed combination oral dosage form. Such medicaments for increasing female libido allow the subject to maintain sexual activity during the treatment period. These medicaments include $5-HT_{1a}$ receptor agonists such as flibanserin. Similar to Compound 1, flibanserin is once-daily orally administered. In another embodiment, a $5-HT_{1a}$ receptor agonist, such as flibanserin, is co-administered with the hormone replacement medicament and Compound 1, possibly as separate oral dosage forms, and preferably in a fixed combination oral dosage form. In some embodiments, a pharmaceutically acceptable salt of Compound 1 is co-administered with the medicament.

In an embodiment, Compound 1, is co-administered with at least one compound to reduce the incidence of hot flashes in subjects, possibly as separate oral dosage forms, and preferably in a fixed combination oral dosage form. In one embodiment, the at least one compound for reducing hot flashes is selected from the group consisting of gabapentin, pregabalin, venlafaxine, fluoxetine, paroxetine, aspirin (including enteric and non-enteric coated aspirin), and NK3 receptor antagonists. In another embodiment, the at least one compound for reducing hot flashes is co-administered with Compound 1, and the hormone replacement medicament, possibly as separate oral dosage forms, and preferably in a fixed combination oral dosage form. In some embodiments, a pharmaceutically acceptable salt of Compound 1 is co-administered with the compound.

In an embodiment, heart benefits may be provided by the treatment methods of this disclosure. Also, the treatment methods of this disclosure may be useful in sexual reassignment/cross gender transition protocols. Further, the treatment methods of this disclosure may be useful in preserving fertility during chemotherapy.

Additional side effects associated with administration of a GnRH antagonist may include vasomotor symptoms, hot flashes, vaginal dryness, and decreased libido.

VIII. Pharmaceutical Compositions

Some of the methods provided herein comprise administering to a pre-menopausal woman a combination of Compound 1, or a pharmaceutically acceptable salt thereof, and a hormone replacement medicament. These methods may include treating one or more of uterine fibroids, endometriosis, adenomyosis; heavy menstrual bleeding; pain associated with uterine fibroids, endometriosis, or adenomyosis; or a pre-menopausal woman with symptomatic uterine fibroids or endometriosis. The methods may also include maintaining bone mineral density; treating hot flashes, night sweats, or other vasomotor symptoms; maintaining one or both of lipid profile or blood glucose range; treating one or both of vulvovaginal atrophy or vaginal dryness; treating fatigue or malaise; treating headache; or a method of contraception in a pre-menopausal woman being treated for one or more of uterine fibroids, endometriosis, adenomyosis, or heavy menstrual bleeding. The methods may further include achieving amenorrhea, preventing miscarriage, improving fertility, or treating anemia.

The combination administered in any of the methods described herein may be a single dosage form, or comprise separate dosage forms that are co-administered. Separate dosage forms may be separate physical forms, for example two, three, four, five, or more separate tablets. For example, in some embodiments, the combination comprises one tablet comprising Compound 1 or a pharmaceutically acceptable salt thereof; and a second tablet comprising the hormone replacement medicament (e.g., estradiol and NETA); or a second and third tablet comprising the hormone replacement medicament (e.g., a second tablet comprising estradiol and a third tablet comprising NETA).

Co-administration of separate dosage forms may include administration at the same time, or close in time, for example administration of separate dosage forms within 30 min or less of each other, within 20 min or less of each other, within 15 min or less of each other, within 10 min or less of each other, or within 5 min or less of each other.

In accordance with this disclosure, several methods are provided that include treating uterine fibroids in a subject, reducing menstrual blood loss associated with uterine fibroids or achieving amenorrhea in a subject, suppressing sex hormones in a subject, or reducing bone mineral density loss in a subject caused by administration of a GnRH antagonist, reducing vasomotor symptoms or hot flashes in a subject, and reducing symptoms of decreased libido in a subject. All such methods may, in some embodiments, be of a long duration, for example consecutive day periods of 48 weeks or greater, for example, consecutive day periods of 52 weeks or greater, consecutive day periods of 76 weeks or greater, consecutive day periods of 104 weeks or greater, or consecutive day periods of 128 weeks or greater.

The hormone replacement medicament is sometimes referred to as an add-back or add-back hormone replacement therapy. Co-administration of the hormone replacement medicament may mitigate or avoid one or more side-effects or symptoms normally associated with a GnRH antagonist, such as bone mineral density loss and vasomotor symptoms or hot flashes. The hormone replacement medicament is co-administered with Compound 1, possibly as a separate oral dosage form, or in a fixed combination oral dosage form.

In particular, the fixed dose combination, oral dosage therapy, as compared to separate dosage forms that are co-administered, may help to ensure correct administration of both Compound 1, or a pharmaceutically acceptable salt thereof, and the hormone replacement medicament(s) and in the correct ratios. In particular, the fixed combination, oral dosage form therapy may enhance patient compliance. In addition, the fixed combination, oral dosage form may improve patient outcomes by helping to ensure that the add-back therapy is always taken to address known side-effects, such as bone mineral density loss and hot flashes. Additionally, the fixed combination, oral dosage form may offer an advantage over therapies that cannot be administered as one combination dosage form or pill, once-daily. Still further, this optimal therapy may allow for a quick on and off during intermittent treatment, may help maintain the sexual activity of the woman, and may help preserve future fertility. Yet further, the estradiol levels of the woman may be controlled during such treatment.

In some embodiments, it may be important for the therapy (e.g., treatment of uterine fibroids, endometriosis, adenomyosis, heavy menstrual bleeding or pelvic pain) that Compound 1, or a pharmaceutically acceptable salt thereof, and a hormone replacement medicament be combined upon every administration. The treatment effectiveness of the GnRH antagonist without the adverse effects of a hypoestrogenic state may require the consistent and correct intake by the patient of both Compound 1, or a pharmaceutically acceptable salt thereof, and the hormone replacement medicament, without inadvertently taking either alone or in an incorrect ratio. Thus, to help ensure such treatment, an administration mode of a single formulation of Compound 1, or a pharmaceutically acceptable salt thereof, and the hormone replacement medicament may be highly beneficial. Thus, Compound 1, or a pharmaceutically acceptable salt thereof, and the hormone replacement medicament may be administered as a single dosage form. Alternatively, Compound 1, or a pharmaceutically acceptable salt thereof, and the hormone replacement medicament may be administered as a combination of separate dosage forms, for example within 15 minutes of each other. The separate dosage forms may comprise separate physical forms, for example 2 separate tablets wherein one tablet comprises Compound 1 or a pharmaceutically acceptable salt thereof, and the other tablet comprises the hormone replacement medicament.

In accordance with this disclosure, several methods are provided that include: a method for treating endometriosis in a subject; a method for reducing pain associated with endometriosis in a subject including nonmenstrual pelvic pain, dysmenorrhea and dyspareunia; a method for reducing menstrual bleeding associated with endometriosis or achieving amenorrhea in a subject; a method for suppressing sex hormone in a subject; a method for reducing bone mineral density loss in a subject caused by administering a GnRH antagonist to the subject; methods for reducing vasomotor symptoms or hot flashes in a subject; and a method for reducing symptoms of decreased libido in a subject. The methods include administering to the subject, 10 mg to 60 mg per day of Compound 1. In some embodiments, a corresponding amount of a pharmaceutically acceptable salt of Compound 1 is administered. With respect to the method for suppressing sex hormone in a subject, the sex hormone is preferably estradiol. Further, luteinizing hormone (LH) and follicle stimulating hormone (FSH) may be suppressed in the subject in addition to estradiol. Still further, a post ovulatory rise in progesterone may be suppressed in the subject.

Accordingly, the fixed combination, oral dosage form or product, as compared to separate dosage forms that are co-administered, may ensure correct administration of both Compound 1 and the hormone replacement medicament.

Moreover, the oral dosage forms of the present disclosure having Compound 1, at the desired dosing amount of 40 mg, and the hormone replacement medicament in an amount no greater than 5 mg, may be one solution for the long term treatment of uterine fibroids or endometriosis. In other embodiments, a corresponding amount of a pharmaceutically acceptable salt of Compound 1 is co-administered with a hormone replacement medicament.

In some embodiments, as used herein, the oral dosage forms are solid (including semi-solid) preparations, including but not limited to, tablets, capsules, caplets, pills, granules, oral dissolving films, lozenges, gums, and powders. Preferably, the oral dosage form is a tablet or a capsule.

A. Hormone Replacement Medicament

The hormone replacement medicament in the fixed combination, oral dosage form can be one component, namely a progestogen. Progestogens include, but are not limited to, progesterone and synthetic progestins such as norethindrone acetate (also known as norethisterone acetate or NETA), norgestimate, norgestrel, levonorgestrel, drospirenone, medroxyprogesterone, cyproterone, desogestrel and etonogestrel. In one embodiment, the hormone replacement medicament is NETA.

The hormone replacement medicament can also have an estrogen. An estrogen includes, but is not limited to, steroidal estrogens such as estradiol, estrone, estriol, estetrol, estradiol esters such as cypionate, estradiol valerate, estradiol acetate and estradiol benzoate, ethinyl estradiol and derivatives such as mestranol, moxestrol and quinestrol, and other estrogens such as methylestradiol. The estrogen in the hormone replacement medicament can also be a non-steroidal estrogen including, but not limited to, stilbestrol estrogens. In the oral dosage form or product having 40 mg of Compound 1, the estrogen can be present at 0.1 to 2 mg.

The preferred hormone replacement medicament is an estrogen, a progestogen, or a combination thereof. In one embodiment, the estrogen is estradiol. In another preferred embodiment, the estrogen is estradiol and the progesterone is NETA. In other embodiments, the estrogen is an estradiol equivalent.

The specific dose of the hormone replacement medicament may be dependent on the particular estrogen and/or progestogen used. When the hormone replacement medicament in the fixed dosage form is only a progestin, the amount of the hormone replacement medicament may be no greater than 5 mg, for example from 0.01 mg to 5 mg. In one embodiment, the hormone replacement medicament is 0.05 mg to 2.5 mg. In an embodiment of the present disclosure in which the fixed dose combination product is recommended for use in treating uterine fibroids and the hormone replacement medicament is only NETA, NETA can be present in an amount up to 5 mg.

When the hormone replacement medicament in the fixed dosage form is a combination of an estrogen and a progestogen, in one embodiment, the fixed dose 40 mg of Compound 1 is co-administered with a combination of 0.1 to 2 mg of estradiol and 0.1 to 0.5 mg of NETA. In another embodiment, the 40 mg of Compound 1 is co-administered with a combination of 2 mg of estradiol and 0.5 mg of NETA. In yet another embodiment, the 40 mg of Compound 1 is co-administered with a combination of 1.5 mg of estradiol and 0.5 mg of NETA. In a preferred embodiment, the 40 mg of Compound 1 is co-administered with a combination of 1 mg of estradiol and 0.5 mg of NETA. In another embodiment, the hormone replacement medicament is a combination of 0.5 mg of estradiol and 0.1 mg of NETA. In some embodiments, a corresponding amount of a pharmaceutically acceptable salt of Compound 1 is co-administered with the hormone replacement medicament.

In some embodiments, the estradiol and NETA can be administered once per day, and for the same period as Compound 1. As with Compound 1, the estradiol and NETA can be used for long term administration, for example, consecutive day periods of 48 weeks or greater, consecutive day periods of 76 weeks or greater, consecutive day periods of 104 weeks or greater, or consecutive day periods of 128 weeks or greater.

It is envisioned that in addition to the above named hormone replacement medicaments, other ingredients can be used to mitigate or avoid side-effects normally associated with a GnRH antagonist. For example, calcium supplementation, calcitonin, Vitamin D supplementation, strontium, or therapies such as bisphosphonates, can be co-administered with the oral dosage form to minimize bone mineral density loss that may occur from use of the GnRH antagonist.

In embodiments for the treatment of uterine fibroids, such possible other ingredients may include: a selective estrogen receptor modulator (SERM), selective progesterone receptor modulator (SPRM), a dopamine promoter, and silibins. In some embodiments, to provide examples but not to be limiting, the SERM can be raloxifene, the SPRM can be vilaprisan, asoprisnil or ulipristal acetate and the dopamine promoter can be bromocriptine.

A dosage of 1 mg of estrogen may be sufficient to protect against bone mineral density loss. However, due to the cardioprotective effects provided by estrogen, young patients receiving a low dose of estrogen, namely a 1 mg dose of estrogen, may face an increased cardiovascular risk, especially for long term administration of the hormone replacement medicament. Further, women in their 20s and 30s who receive doses of 1 mg of estrogen over a long period of time may risk premature ovarian failure due to the low estrogen levels. For these reasons, young women may require a dosage above 1 mg of estrogen, and possibly up to 2 mg of estrogen, to protect against these adverse effects. For such patients, physicians can start dosage of estrogen at 1 mg and increase such dosage, possibly up to 2 mg of estrogen, so long as the subject's symptoms (e.g., pain associated with endometriosis including nonmenstrual pelvic pain, dysmenorrhea and dyspareunia; HMB; pain associated with uterine fibroids or adenomyosis) do not resume. For young women, the higher the tolerable dose of hormone replacement medicament, the better the expected impact on bone and cardiovascular health. Hypoestrogenic symptoms may bone mineral density loss, vasomotor symptoms, fatigue, malaise, and headache. There may exist some patients for whom a hormone replacement medicament comprising up to 2 mg of estradiol or estradiol equivalent more adequately treats one or more hypoestrogenic symptoms than a hormone replacement medicament comprising 1 mg or less of estradiol or estradiol equivalent.

B. Compound 1 or a Pharmaceutically Acceptable Salt Thereof

In some embodiments of any of the methods described herein, the combination comprises about 10 mg to about 60 mg, about 20 mg to about 50 mg, about 30 mg to about 50 mg, or about 40 mg of Compound 1, or a corresponding amount of a pharmaceutically acceptable salt thereof. For example, the combination may comprise about 10 mg, about 20 mg, about 25 mg, about 30 mg, about 35 mg, about 40 mg, about 45 mg, about 50 mg, about 55 mg, or about 60 mg of Compound 1, or a corresponding amount of a pharmaceutically acceptable salt thereof. In one embodiment, the combination comprises about 40 mg of Compound 1, or a pharmaceutically acceptable salt thereof. These methods may include treating one or more of uterine fibroids, endometriosis, adenomyosis; heavy menstrual bleeding; or pain associated with uterine fibroids, endometriosis, or adenomyosis in a pre-menopausal woman. The methods may also include maintaining bone mineral density; treating hot flashes, night sweats, or other vasomotor symptoms; maintaining one or both of lipid profile or blood glucose range; treating one or both of vulvovaginal atrophy or vaginal dryness; treating fatigue or malaise; treating headache; or a method of contraception in a pre-menopausal woman being treated for one or more of uterine fibroids, endometriosis, adenomyosis, or heavy menstrual bleeding. The methods may further include achieving amenorrhea, preventing miscarriage, improving fertility, or treating anemia.

In some embodiments, there exists a population of pre-menopausal women for whom 10 mg to 60 mg of Compound 1, or a corresponding amount of a pharmaceutically acceptable salt thereof does not adequately treat their symptom and/or condition (e.g., endometriosis; uterine fibroids; adenomyosis; heavy menstrual bleeding; pain associated with uterine fibroids, endometriosis, or adenomyosis; or one or more other symptoms associated with endometriosis, uterine fibroids, adenomyosis; or one or more side effects of GnRH antagonist administration). Thus, in some embodiments, the combination orally administered daily to a pre-menopausal woman comprises about 65 mg to about 140 mg of Compound 1, or a corresponding amount of a pharmaceutically acceptable salt thereof. In some embodiments, the combination orally administered daily to a pre-menopausal woman comprises about 65 mg to about 120 mg of Compound 1, or a corresponding amount of a pharmaceutically acceptable salt thereof. For example, in some embodiments the combination comprises about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, or about 140 mg, of Compound 1, or a corresponding amount of a pharmaceutically acceptable salt thereof.

In some embodiments, it should be noted that 40 mg, instead of 10 mg or 20 mg, of Compound 1 is preferred since it may be efficacious enough to address the needs of the majority of patients that will possibly need treatment. In other words, if 10 mg or 20 mg of Compound 1 is used, such doses may provide satisfactory treatment for only a minority of patients in treating uterine fibroids or endometriosis, or other of the symptoms and conditions described above. A complete response rate at such doses has been shown to be 21–44% for uterine fibroids, and thus, may not constitute efficacious treatment for the majority of patients. A complete response rate at such doses may not constitute efficacious treatment for the majority of patients with endometriosis. In some embodiments, a corresponding amount of a pharmaceutical salt of Compound 1 is administered.

In another embodiment, Compound 1 can be administered in the form of an oral thin dissolving film that: 1) adheres to the inside of a patient's cheek; 2) dissolves on the patient's tongue; or 3) is sublingual, i.e., placed under the patient's tongue.

In some embodiments, the weight ratio of Compound 1 to the hormone replacement medicament for may be from 10:01 to 10:5, or from 60:0.01 to 60:5. In certain embodiments, the weight ratio of the dose may be from 40:0.01 to 40:5. In some embodiments, a corresponding amount of a pharmaceutical salt of Compound 1 is administered.

In some embodiments, for the treatment of uterine fibroids or endometriosis, it may be desirable to provide chronic treatment or long-term therapy, perhaps at lower doses of Compound 1, such as 20 mg per day or 10 mg per day. The level of the single or dual hormones in the dosage product with 20 mg of Compound 1 that is needed to reduce bone mineral density loss may be the same or less than that needed for the combination product with 40 mg of Compound 1. The selected hormone replacement medicament can comprise one of several previously enumerated progestogens and can also include one of several previously enumerated estrogens. For example, an oral dosage product having 20 mg of Compound 1 can have 0.25 mg to 5 mg of NETA alone or 0.05 to 2 mg of estradiol and 0.05 mg to 0.5 mg of NETA. In some embodiments, a corresponding amount of a pharmaceutical salt of Compound 1 is administered. In some embodiments, the chronic or long-term therapy is for the treatment of adenomyosis or heavy menstrual bleeding.

Depending on one or more of the following: symptom severity, subject age, weight and sensitivity, the duration and intervals of administration can be altered. However, for use in the treatment of uterine fibroids or endometriosis, the daily dose may be a fixed amount normally from 10 mg to 60 mg of Compound 1, preferably from 20 mg to 50 mg, and most preferably 40 mg, administered preferably once per day. For use in the treatment of adenomyosis or heavy menstrual bleeding, the daily dose may be a fixed amount normally from 10 mg to 60 mg of Compound 1, preferably from 20 mg to 50 mg, and most preferably 40 mg, administered preferably once per day.

C. Excipients

The oral dosage forms may be solid (including semi-solid) preparations, including but not limited to, tablets, capsules, caplets, pills, lozenges, gums, granules and powders. Preferably, the oral dosage form is a tablet or a capsule. The oral dosage form may comprise Compound 1 and a pharmaceutically acceptable excipient. In some embodiments, the oral dosage form comprises a pharmaceutically acceptable salt of Compound 1 and a pharmaceutically acceptable excipient.

The essential excipients may be a blend of excipients, and amounts, that optimize the efficacy of the formulation. The following are core excipients and include various organic or inorganic excipients or carrier substances, including, but not limited to, one or more fillers or diluents, lubricants, binders, surfactants, pH adjusters, sweeteners, flavors, and disintegrants. There can be a film coat with pharmaceutical additives, including, but not limited to, one or more film formers, coating bases, coating additives, plasticizers, organic acids, pigments or antioxidants, light shielding agents, flow-aids or polishing agents, and colorants.

Diluents for use in the present disclosure include organic materials and inorganic materials including, but not limited to, dextrose, lactose, mannitol, D-mannitol (e.g., PEARLITOL 50C, PEARLITOL 100SD, PEARLITOL 200SD, PEARLITOL 300 DC, and PEARLITOL 400DC), sodium starch, sucrose, calcium phosphate, anhydrous calcium phosphate, precipitated calcium carbonate, calcium sulphate, calcium carbonate, calcium silicate, sorbitol, corn starch, potato starch, wheat starch, rice starch, partly pregelatinized starch, pregelatinized starch, porous starch, and calcium carbonate starch. In some embodiments, the diluent is mannitol.

Diluents or fillers for use in the present disclosure may include organic materials and inorganic materials, including but not limited to hydroxypropyl cellulose, crystalline cellulose (e.g., CEOLUS KG-802 (grade: KG-802) and CEOLUS PH-302 (grade: PH-302)), crystalline cellulose (particles), crystalline cellulose (fine particles), microcrystalline cellulose, hydroxypropyl methylcellulose (e.g., hypromellose 2910), starch, gelatin, sucrose, dextrin, lactose, povidone (polyvinylpyrrolidone), copolyvidone, acacia, sodium alginate, and carboxymethylcellulose. In some embodiments, the diluent is D-mannitol. In some embodiments, the diluent is microcrystalline cellulose. In some embodiments, the diluent is lactose.

Binders for use in the present disclosure include, but are not limited to, hydroxypropyl cellulose, crystalline cellulose (e.g., CEOLUS KG-802 (grade: KG-802) and CEOLUS PH-302 (grade: PH-302)), crystalline cellulose (particles), crystalline cellulose (fine particles), microcrystalline cellulose, hydroxypropyl methylcellulose (e.g., hypromellose 2910), starch, gelatin, sucrose, dextrin, lactose, povidone (polyvinylpyrrolidone), and copolyvidone. Natural and synthetic gums that can be used as binders include, but are not limited to, acacia, sodium alginate, and carboxymethylcellulose. In some embodiments, the binder is hydroxypropyl methylcellulose. In some embodiments, the binder is hydroxypropyl cellulose.

Disintegrants for use in the present disclosure include, but are not limited to, crosslinked polymers, such as crosslinked polyvinylpyrrolidone (crospovidone), crosslinked sodium carboxylmethyl cellulose (croscarmellose sodium), crosslinked carmellose sodium, microcrystalline cellulose, carboxymethyl cellulose, carboxylmethyl cellulose calcium, carboxylmethyl starch sodium and sodium starch glycolate. Additional disintegrants for use in the present disclosure include, but are not limited to, corn starch, sodium carboxymethyl starch, low-substituted hydroxypropylcellulose (L-HPC), hydroxypropyl starch, and magnesium alumino metasilicate. In some embodiments, the disintegrant is sodium starch glycolate. In some embodiments, the disintegrant is crosslinked sodium carboxylmethyl cellulose.

Lubricants for use in the present disclosure include, but are not limited to, magnesium stearate; stearic acid; sodium stearyl fumarate; triethyl citrate; inorganic lubricants, namely talc, colloidal silica and fumed silicon dioxide; polymeric lubricants, such as polyethylene glycol, PEG 4000, and PEG 6000; mineral oils; and hydrogenated vegetable oils. However, other compounds, such as fatty acids and metallic salts thereof, fatty acid esters and salts thereof, organic waxes, polymers and inorganic substances, can be employed. Useful fatty acids include, but are not limited to, lauric acid, palmitic acid and stearic acid. Useful metallic salts include, but are not limited to, those of calcium, magnesium and zinc. Useful fatty acid esters include, but are not limited to, glyceride esters, such as glyceryl monostearate, glyceryl tribehenate, glyceryl palmitostearate and glyceryl dibehenate. Useful sugar esters include, but are not limited to sucrose esters of fatty acids, sorbitan monostearate, and sucrose monopalmitate. Useful salts thereof include, but are not limited to, sodium oleate, sodium benzoate, sodium acetate, magnesium lauryl sulfate, and sodium lauryl sulfate. In some embodiments, lubricants include magnesium stearate, calcium stearate, talc and colloidal silica. In some embodiments, the lubricant is magnesium stearate. As used herein, polyethylene glycol is a generic term of compounds represented by the formula $H(OCH_2CH_2)_nOH$ wherein n is a natural number (compound wherein n is not less than 2000 is sometimes referred to as polyethylene oxide).

Examples of colorants used in the formulations of the disclosure include, but are not limited to, food colors such as Food Color Yellow No. 5, Food Color Red No. 2, Food Color Blue No. 2 and the like, food lake colors, red ferric oxide, and yellow ferric oxide.

Examples of pH adjusters used in the formulations of the disclosure include, but are not limited to, citric acid or a salt thereof, phosphoric acid or a salt thereof, carbonic acid or a salt thereof, tartaric acid or a salt thereof, fumaric acid or a salt thereof, acetic acid or a salt thereof, and amino acid or a salt thereof.

Examples of surfactants used in the formulations of the disclosure include, but are not limited to, sodium lauryl sulfate, polysorbate 80, polyoxyethylene(160), and polyoxypropylene(30)glycol.

Examples of sweeteners used in the formulations of the disclosure include aspartame (trade name), acesulfame potassium, sucralose, thaumatin, saccharin sodium, and dipotassium glycyrrhizinate.

Examples of the flavors used in the formulations of the disclosure include menthol, peppermint oil, lemon oil, and vanillin.

In some embodiments, the pigments for use herein include, but are not limited to, titanium dioxide.

In some embodiments, the film former/film coating base is a sugar coating base. Sugar coating bases for use herein include, but are not limited to, sucrose in combination with one or more of talc, precipitated calcium carbonate, gelatin, gum arabic, pullulan, or carnauba wax.

In some embodiments, the film former/film coating base is a water-soluble film coating base. Water-soluble film coating bases for use herein include, but are not limited to, cellulose polymers such as hydroxypropylcellulose, hydroxypropyl methylcellulose (e.g., hypromellose 2910, TC-5), hydroxyethylcellulose, methylhydroxyethylcellulose and the like; synthetic polymers such as polyvinyl acetaldiethylaminoacetate, aminoalkylmethacrylate copolymer E, polyvinylpyrrolidone and the like; and polysaccharides such as pullulan and the like. In some embodiments, the water-soluble film coating base is hydroxypropyl methylcellulose (e.g., hypromellose 2910, TC-5). In some embodiments, the film former/film coating base is hydroxypropyl methylcellulose (HPMC). In some embodiments, the hydroxypropyl methylcellulose is hypromellose 2910.

In some embodiments, the film former/film coating base comprises cellulose polymers such as hydroxypropylmethylcellulose phthalate, ethylcellulose, hydroxypropylmethylcellulose acetate succinate, carboxymethylethylcellulose, cellulose acetate phthalate and the like; acrylic acid polymers such as methacrylic acid copolymer L, methacrylic acid copolymer LD, methacrylic acid copolymer S, aminoalkylmethacrylate copolymer RS, ethyl acrylate-methyl methacrylate copolymer suspension, and the like; and naturally occurring substances such as shellac and the like.

In some embodiments, the flow aid/polishing agent is carnauba wax.

In some embodiments, colorants for use herein include, but are not limited to, ferric oxide. In some embodiments, the colorant is red ferric oxide. In some embodiments, the colorant is yellow ferric oxide. In some embodiments, the colorant is a combination of yellow ferric oxide and red ferric oxide.

In some embodiments, the plasticizers for use herein include, but are not limited to, polyethylene glycol (e.g., macrogol 6000), triethyl citrate, castor oil, polysorbates, and the like.

In some embodiments, the organic acids for use herein include, but are not limited to, citric acid, tartaric acid, malic acid, ascorbic acid, and the like.

In some embodiments, the oral formulations of the disclosure, comprise at least one excipient that improves stability while maintaining load capacity. Oral formulations provided by this disclosure that include sodium starch glycolate may have improved stability and greater load capacity of Compound 1, or a pharmaceutically acceptable salt thereof.

Tablets of various doses of Compound 1 may be formulated in a dose-proportional manner. That is, the weight ratio of all excipients to Compound 1 in the dosage form is the same for each of the doses (e.g., a 10 mg dose contains 50 mg of a first excipient and 1 mg of a second excipient, and a 20 mg dose contains 100 mg of the first excipient and 2 mg of the second excipient). In one embodiment, tablets containing 10 mg to 60 mg of Compound 1 can be formulated to be dose-proportional to the 40 mg high-bioavailability tablet. In some embodiments, tablet comprising a corresponding amount of a pharmaceutically acceptable salt of Compound 1 are prepared in a dose-proportional manner.

D. Illustrative Formulations

In an embodiment of treating uterine fibroids or endometriosis, an illustrative oral dosage form can be used in an amount that includes from 10 mg to 60 mg of Compound 1. In an embodiment for treating adenomyosis or heavy menstrual bleeding, an illustrative oral dosage form can be used in an amount that includes from 10 mg to 60 mg of Compound 1. In certain embodiments, a corresponding amount of a pharmaceutically acceptable salt thereof is used. Further, the oral dosage form can further include: from 30.5 mg to 183 mg of mannitol (including D-mannitol); from 10 mg to 60 mg of microcrystalline cellulose; from 1.5 mg to 9 mg of hydroxypropyl cellulose; from 2.5 mg to 15 mg of croscarmellose sodium; from 0.5 mg to 3 mg of magnesium stearate; from 1.78 mg to 10.68 mg of hypromellose 2910; from 0.2 mg to 1.2 mg of titanium dioxide; and optionally, from 0.02 mg to 0.12 mg of ferric oxide. Water is removed during processing.

In an embodiment, an illustrative oral dosage form includes: 17.54 wt % of Compound 1; 53.51 wt % of mannitol; 17.54 wt % of microcrystalline cellulose; 2.63 wt % of hydroxypropyl cellulose; 4.39 wt % of croscarmellose sodium; 0.88 wt % of magnesium stearate; 3.12 wt % of hypromellose 2910; 0.35 wt % of titanium dioxide; and 0.04 wt % of ferric oxide.

In another embodiment of treating uterine fibroids or endometriosis, this disclosure provides a preferred oral dosage form for such treatment. In still another embodiment of treating adenomyosis or heavy menstrual bleeding, this disclosure provides a preferred oral dosage form for such treatment. The oral dosage form provided by this disclosure may be in an amount that includes from 10 mg to 60 mg of Compound 1. Further, the oral dosage form can further include: from 12.75 mg to 76.5 mg of mannitol (including D-mannitol); from 1.25 mg to 7.5 mg of sodium starch glycolate (Type A); from 0.75 mg to 4.5 mg of hydroxypropyl cellulose; from 0.25 mg to 1.5 mg of magnesium stearate; from 0.89 mg to 5.34 mg of hypromellose 2910; from 0.1 mg to 0.6 mg of titanium dioxide; and optionally, from 0.01 mg to 0.06 mg of ferric oxide; and a sufficient quantity of carnauba wax. Water may be removed during processing.

In an embodiment, an oral dosage form provided by this disclosure includes: 38.46 wt % of Compound 1; 49.04 wt % of mannitol; 4.81 wt % of sodium starch glycolate; 2.88 wt % of hydroxypropyl cellulose; 0.96 wt % of magnesium stearate; 3.42 wt % of hypromellose 2910; 0.38 wt % of titanium dioxide; 0.04 wt % of ferric oxide; and a sufficient quantity of carnauba wax.

An illustrative oral dosage form includes: 10 mg of Compound 1, 30.5 mg of mannitol (including D-mannitol), 10 mg of microcrystalline cellulose, 1.5 mg of hydroxypropyl cellulose, 2.5 mg of croscarmellose sodium, 0.5 mg of magnesium stearate, 1.78 mg of hypromellose 2910, 0.2 mg of titanium dioxide, and optionally, 0.02 mg of ferric oxide. Water may be removed during processing of this illustrative oral dosage form.

In another embodiment, an oral dosage form includes: 40 mg of Compound 1, 122 mg of mannitol (including D-mannitol) (filler/diluent), 40 mg of microcrystalline cellulose (filler/diluent), 6 mg of hydroxypropyl cellulose (binder), 10 mg of croscarmellose sodium (disintegrant), 2 mg of magnesium stearate (lubricant), 7.12 mg of hypromellose 2910 (film coating agent), 0.8 mg of titanium dioxide (pigment), and optionally, 0.08 mg of ferric oxide (colorant). Water may be removed during processing.

Yet another illustrative oral dosage form includes: 60 mg of Compound 1, 183 mg of mannitol (including D-mannitol), 60 mg of microcrystalline cellulose, 9 mg of hyroxypropyl cellulose, 15 mg of croscarmellose sodium, 3 mg of magnesium stearate, 10.68 mg of hypromellose 2910, 1.2 mg of titanium dioxide, and optionally, 0.12 mg of ferric oxide. Water may be removed during processing.

Still another illustrative dosage form includes: 10 mg of Compound 1, 12.75 mg of mannitol (including D-mannitol), 1.25 mg of sodium starch glycolate (Type A), 0.75 mg of hydroxypropyl cellulose, 0.25 mg of magnesium stearate, 0.89 mg of hypromellose 2910, 0.1 mg of titanium dioxide, and optionally, 0.01 mg of ferric oxide, and a sufficient quantity of carnauba wax. Water may be removed during processing.

Still yet another preferred oral dosage form includes: 40 mg of Compound 1, 51 mg of mannitol (including D-mannitol) (filler/diluent), 5 mg of sodium starch glycolate (Type A) (disintegrant), 3 mg of hydroxypropyl cellulose (binder), 1 mg of magnesium stearate (lubricant), 3.56 mg of hypromellose 2910 (film coating agent), 0.4 mg of titanium dioxide (pigment), and optionally, 0.04 mg of ferric oxide (colorant), and a sufficient quantity of carnauba wax (tablet flow aid/polishing agent). Water may be removed during processing.

A further illustrative dosage form includes 60 mg of Compound 1, 76.5 mg of mannitol (including D-mannitol), 7.5 mg of sodium starch glycolate (Type A), 4.5 mg of hydroxypropyl cellulose, 1.5 mg of magnesium stearate, 5.34 mg of hypromellose 2910, 0.6 mg of titanium dioxide, and optionally, 0.06 mg of ferric oxide, and a sufficient quantity of carnauba wax. Water may be removed during processing.

Yet another illustrative oral dosage form provided by this disclosure includes: 10 mg of Compound 1; 12.75 mg of mannitol; 1.25 mg of sodium starch glycolate; 0.75 mg of hydroxypropyl cellulose; 0.25 mg of magnesium stearate; 0.89 mg of hypromellose 2910; 0.1 mg of titanium dioxide; 0.01 mg of ferric oxide; and a sufficient quantity of carnauba wax. Water may be removed during processing.

Another preferred oral dosage form provided by this disclosure includes: 40 mg of Compound 1; 51 mg of mannitol (filler/diluent); 5 mg of sodium starch glycolate (disintegrant); 3 mg of hydroxypropyl cellulose (binder); 1 mg of magnesium stearate (lubricant); 3.56 mg of hypromellose 2910 (film coating agent); 0.4 mg of titanium dioxide (pigment); 0.04 mg of ferric oxide (colorant); and a sufficient quantity of carnauba wax (tablet flow aid/polishing agent). Solvent (such as water) may be removed during processing.

Still another illustrative oral dosage form provided by this disclosure includes: 60 mg of Compound 1; 76.5 mg of mannitol; 7.5 mg of sodium starch glycolate; 4.5 mg of hydroxypropyl cellulose; 1.5 mg of magnesium stearate; 5.34 mg of hypromellose 2910; 0.6 mg of titanium dioxide; 0.06 mg of ferric oxide; and a sufficient quantity of carnauba wax. Water may be removed during processing.

Any of the illustrative oral dosage forms may be used in any of the methods provided herein. These methods may include treating one or more of uterine fibroids, endometriosis, adenomyosis; heavy menstrual bleeding; or pain associated with uterine fibroids, endometriosis, or adenomyosis in a pre-menopausal woman. The methods may also include maintaining bone mineral density; treating hot flashes, night sweats, or other vasomotor symptoms; maintaining one or both of lipid profile or blood glucose range; treating one or both of vulvovaginal atrophy or vaginal dryness; treating fatigue or malaise; treating headache; or a method of contraception in a pre-menopausal woman being treated for one or more of uterine fibroids, endometriosis, adenomyosis, or heavy menstrual bleeding. The methods may further include achieving amenorrhea, preventing miscarriage, improving fertility, or treating anemia.

It has been found that for the treatment of uterine fibroids, endometriosis, adenomyosis, or heavy menstrual bleeding, the above oral dosage forms provided by this disclosure that include sodium starch glycolate improves storage stability and provides greater load capacity of Compound 1 or a pharmaceutically acceptable salt thereof so that the dosage of Compound 1 can be as low as 40 mg. In some embodiments, a corresponding amount of a pharmaceutically acceptable salt of Compound 1 is used. This greater load capacity permits a smaller dosage form and may improve dosing compliance.

While Compound 1 can be administered in an amount of 10 mg, 20 mg, 40 mg or 60 mg per day, it is preferably administered at 40 mg. Further, the excipient base may optimize stability in the composition, and the 40 mg amount of Compound 1 may maintain an efficacious dose for treatment of the symptoms of uterine fibroids. In some embodiments, a corresponding amount of a pharmaceutically acceptable salt of Compound 1 is administered.

E. Dosage Pack

The present disclosure provides for dosage packs comprising an oral formulation comprising Compound 1, or a pharmaceutically acceptable salt thereof. The present disclosure also provides for dosage packs comprising an oral formulation comprising Compound 1, or a pharmaceutically acceptable salt thereof; and an oral formulation comprising a hormone replacement medicament. In some embodiments, the dosage pack comprises a single oral formulation comprising Compound 1, or pharmaceutically acceptable salt thereof, and a hormone replacement medicament. In other embodiments, the dosage pack comprises separate oral formulations, for example an oral formulation comprising Compound 1, or a pharmaceutically acceptable salt thereof, and a separate oral formulation comprising the hormone replacement medicament. The dosage pack may comprise any of the illustrative formulations described herein.

In certain embodiments, the dosage pack is used for treating endometriosis; uterine fibroids; adenomyosis; heavy menstrual bleeding; pain associated with uterine fibroids, endometriosis, or adenomyosis; or one or more other symptoms associated with endometriosis, uterine fibroids, adenomyosis; or one or more side effects of GnRH antagonist administration. In some embodiments, the dosage pack comprises two or more oral formulations, wherein at least one oral formulation has a different color, shape, and/or size than at least one other oral formulation.

In some embodiments, the dosage pack provided by this disclosure includes: an oral formulation comprising excipients and from about 10 mg to about 60 mg of Compound 1, or a corresponding amount of a pharmaceutically acceptable salt thereof; and an oral formulation comprising about 0.5 mg to about 2 mg of estradiol or a corresponding amount of estradiol equivalent; and about 0.01 mg to about 5 mg of a progestin. In certain embodiments, the oral formulations are the same formulation, while in other embodiments the oral formulations are two or more separate formulations.

In some embodiments, the dosage pack provided by this disclosure includes: an oral formulation comprising excipients and from about 65 mg to about 140 mg of Compound 1, or a corresponding amount of a pharmaceutically acceptable salt thereof; and an oral formulation comprising about 1.5 mg to about 5.0 mg of estradiol or a corresponding amount of estradiol equivalent; and about 0.5 mg to about 2.0 mg norethindrone acetate or other progestin. In certain embodiments, the oral formulations are the same formulation, while in other embodiments the oral formulations are two or more separate formulations. In some embodiments, the oral formulation comprises about 65 mg to about 120 mg of Compound 1, or a corresponding amount of a pharmaceutically acceptable salt thereof.

In some embodiments, the dosage pack provided by this disclosure includes: an oral formulation comprising excipients and from about 10 mg to about 60 mg of Compound 1, or a corresponding amount of a pharmaceutically acceptable salt thereof. In other embodiments, the dosage pack provided by this disclosure includes: an oral formulation comprising excipients and from about 65 mg to about 140 mg of Compound 1, or a corresponding amount of a pharmaceutically acceptable salt thereof. In some embodiments, the oral formulation comprises about 65 mg to about 120 mg of Compound 1, or a corresponding amount of a pharmaceutically acceptable salt thereof.

In certain such embodiments, the one or more formulations independently comprise excipients such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the one or more oral formulations further independently comprise one or more film formers/film coating bases, one or more pigments, one or more colorants, one or more flow aids/polishing agents, or combinations thereof. In certain such embodiments, the film former/film coating base comprises hypromellose 2910, the pigment comprises titanium dioxide, the colorant comprises ferric oxide, and the flow aid/polishing agent comprises carnauba wax.

In certain aspects of the disclosure, the one or more oral formulations of the dosage pack include at least one excipient that improves stability while maintaining load capacity. In some embodiments, the sodium starch glycolate in the oral formulation of the dosage pack of the disclosure improves stability and load capacity of Compound 1 or a pharmaceutically acceptable salt thereof in the oral dosage formulation.

In some embodiments, the one or more oral formulations of the dosage pack of the disclosure comprise one or more tablets. In some embodiments, the one or more oral formulations of the dosage pack of the disclosure have an immediate release profile.

IX. Timing of Administration

The administration mode of Compound 1, and the hormone replacement medicament are not particularly limited, provided that the compound of this disclosure and the hormone replacement medicament are orally administered as a combination or co-administered. In some embodiments, an administration mode can, for example, be (1) an administration of a single formulation obtained by formulating Compound 1 and the hormone replacement medicament, (2) a simultaneous administration via an identical route of two formulations obtained by formulating Compound 1, and a hormone replacement medicament separately, and (3) a sequential and intermittent administration via an identical route of two formulations obtained by formulating Compound 1 and a hormone replacement medicament separately. In some embodiments, a pharmaceutically acceptable salt of Compound 1 is co-administered with the hormone replacement medicament. Co-administration of separate dosage forms may include administration at the same time, or close in time, for example administration of separate dosage forms within 30 min or less of each other, within 20 min or less of each other, within 15 min or less of each other, within 10 min or less of each other, or within 5 min or less of each other.

In certain embodiments, Compound 1 or a pharmaceutically acceptable salt thereof is administered once-daily without a hormone replacement medicament for a period of time prior to beginning administration of a combination of Compound 1, or pharmaceutically acceptable salt thereof, and a hormone replacement medicament.

A combination of Compound 1, or a pharmaceutically acceptable salt thereof, and a hormone replacement medicament according to any of the methods described above may be administered once-daily preprandial. For example, the combination may be administered at least 1 hour before the eating or at least 2 hours after eating. In some embodiments, the combination is administered at least 30 minutes before eating, or while the subject is fasting.

In some embodiments, the methods provided herein do not include administering Compound 1 or a pharmaceutically acceptable salt thereof (alone or in combination with a hormone replacement medicament) within 6 hours of administering a P-glycoprotein (P-gp) inhibitor, CYP3A inducer, or a P-gp inducer, or any combinations thereof. P-gp mediates the export of drugs from certain cells, such as those located in the small intestine, blood-brain barrier, hepatocytes, and kidney proximal tube. P-gp may be affected by P-gp inducers or inhibitors, which impair P-gp mediated uptake or efflux, or enhance P-gp activity, respectively. CYP3A is a subfamily of monooxygenases which may be involved in drug metabolism. P-gp or CYP3A inducers may include carbamazepine, rifampin, St. John's wort, bosentan, efavirenz, mitotane, modafinil, or nafcillin. P-gp inhibitors may include amiodarone, azithromycin, captopril, carvedilol, clarithromycin, conivaptan, cyclosporine, diltiazem, dronedarone, eliglustat, erythromycin, felodipine, itraconazole, ketoconazole, lapatinib, lopinavir/ritonavir, propafenone, quercetin, quinidine, reserpine, ranolazine, saquinavir, telaprevir, tipranavir, ticagrelor, tacrolimus, and verapamil. A discussion of the P-gp transport system may be found in J. D. Wesslery, et al. JACC (2013) 61(25): 2495–502. In some embodiments, Compound 1 or a pharmaceutically acceptable salt thereof is administered no less than 6 hours, no less than 8 hours, no less than 10 hours, or no less than 12 hours before a P-gp inhibitor, CYP3A inducer, or a P-gp inducer, or any combinations thereof is administered. In some embodiments, Compound 1 or a pharmaceutically acceptable salt thereof is administered no less than 6 hours, no less than 8 hours, no less than 10 hours, or no less than 12 hours after a P-gp inhibitor, CYP3A inducer, or a P-gp inducer, or any combinations thereof is administered. In certain embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours before a P-gp inhibitor, CYP3A inducer, or a P-gp inducer, or any combinations thereof is administered. In other embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours after a P-gp inhibitor, CYP3A inducer, or a P-gp inducer, or any combinations thereof is administered.

In some embodiments, the combination of Compound 1 or a pharmaceutically acceptable salt thereof and a hormone replacement medicament is orally administered once-daily for at least 4 consecutive weeks, at least 8 consecutive weeks, at least 12 consecutive weeks, at least 16 consecutive weeks, at least 20 consecutive weeks, or at least 24 consecutive weeks, at least 36 consecutive weeks, at least 48 consecutive weeks, at least 72 consecutive weeks, or at least 96 consecutive weeks. In some embodiments, the combination is orally administered daily for at least 4 consecutive weeks and up to 24 consecutive weeks. The combination may be administered as a single dosage form, or as two separate dosage forms co-administered.

Daily administration for a prolonged period of time, for example, for consecutive day periods of 48 weeks or greater, consecutive day periods of 52 weeks or greater, consecutive day periods of 76 weeks or greater, consecutive day periods of 104 weeks or greater, or consecutive day periods of 128 weeks or greater, may achieve long term therapy.

When an oral dosage form is administered to a subject, the period of daily administration can vary. Daily administration may be for 7 consecutive days, 14 consecutive days, 28 consecutive days, 56 consecutive days, 84 consecutive days or 168 consecutive days. Longer periods of daily administration may include consecutive day periods of at least 48 weeks which can be consecutive day periods of at least two separate 24 week periods. Other longer periods of administration may include consecutive day periods of 48 weeks or greater, consecutive day periods of 76 weeks or greater, consecutive day periods of 104 weeks or greater, or consecutive day periods of 128 weeks or greater. In some embodiments, the period of daily administration is at least 24 weeks to not greater than 48 weeks. In one embodiment, the administration is chronic, for example not limited to a treatment period.

In some embodiments, for long term administration, the first and second oral dosage forms are administered for: consecutive day periods of 48 weeks or greater, consecutive day periods of 76 weeks or greater, consecutive day periods of 104 weeks or greater, or consecutive day periods of 128 weeks or greater. In some embodiments, the first oral dosage form is a tablet or capsule, and the second oral dosage form is a tablet or capsule.

In some embodiments, this therapy has the potential to enable a woman to avoid surgical intervention that can result in postoperative complications or complications with future pregnancy or even preclude the potential for future pregnancy. In particular, the fixed combination, oral dosage form, which may be a once-daily, single pill having both Compound 1 and low-dose estrogen and progestogen, can be used longer-term, unlike the currently approved GnRH agonist therapies. This low dose may be used to minimize bone mineral density loss in a hypoestrogenic state, and also other hypoestrogenic symptoms such as hot flashes, commonly associated with GnRH agonists and antagonists.

In some embodiments, for example, the treatment periods for treating endometriosis in a subject, reducing pain associated with endometriosis in a subject including non-menstrual pelvic pain, dysmenorrhea and dyspareunia, reducing menstrual bleeding associated with endometriosis in a subject, suppressing sex hormone in a subject, reducing bone mineral density loss in a subject caused by administering a GnRH antagonist to a subject, reducing vasomotor symptoms or hot flashes in a subject; and reducing symptoms of decreased libido in a subject, can be, for example, consecutive day periods of 48 weeks or greater, consecutive day periods of 76 weeks or greater, consecutive day periods of 104 weeks or greater, or consecutive day periods of 128 weeks or greater.

In some embodiments, the combination is administered daily for 24 consecutive weeks or greater, or 48 consecutive weeks or greater, or 96 consecutive weeks or greater. In some embodiments, the combination is administered for: consecutive day periods of 48 weeks or greater, consecutive day periods of 52 weeks or greater, consecutive day periods of 76 weeks or greater, consecutive day periods of 104 weeks or greater, or consecutive day periods of 128 weeks or greater.

X. Pharmacokinetic Parameters

Bioavailability and the pharmacokinetic (PK) profile or parameters, such as mean maximum plasma concentration ($C_{max}$), mean time to maximum plasma concentration ($T_{max}$) and mean area under the plasma concentration vs. time curve (AUC) after oral administration, may, in some embodiments, be positively or negatively impacted by the formulation, the type of the excipients selected and the specific excipients. The safety and efficacy of Compound 1 in an oral dosage form may depend on these PK parameters being in the appropriate range. Thus, in some embodiments, the type and specifics of the excipients are carefully selected so as to achieve the target PK parameters for Compound 1. In some embodiments, the combination used in the methods discussed above comprises a pharmaceutically acceptable salt of Compound 1, and the safety and efficacy of the pharmaceutically acceptable salt of Compound 1 in an oral dosage form depends on pharmacokinetic parameters being in the appropriate range. In some embodiments, pharmacokinetic parameters can be determined in healthy subjects after single or repeat-dose administration (once per day, until pharmacokinetic steady-state is reached, at least as long as 5 half-lives). The effect of food or meals may be determined, for example, after a single-dose administration, where the pharmacokinetics of Compound 1 before/with/after food is compared to administration in the fasted state (such as no food for at least 8 hours prior to dosing and for 4 hours after dosing). In some embodiments, after administration of Compound 1, blood samples at pre-specified intervals are collected, plasma is harvested, and the concentration of Compound 1 is determined using analytical methods such as high-performance liquid chromatography with tandem mass-spectometry. Pharmacokinetic parameters (such as $C_{max}$, AUC and half-life) may be determined from plasma concentration-time data for each individual subject using noncompartmental analysis methods, as implemented in software such as Phoenix® WinNonlin®. These parameters may then be summarized or compared using statistical methods.

The PK profile of Compound 1 or a pharmaceutically acceptable salt thereof may or may not be affected by food intake. In another embodiment, differences in Compound 1, or a pharmaceutically acceptable salt thereof, mean $C_{max}$ and mean plasma AUC values for fed and fasted administration of a fixed combination oral dosage form embodiment, having Compound 1 in an amount of 40 mg (or a corresponding amount of a pharmaceutically acceptable salt thereof) and a hormone replacement medicament in an immediate release formulation may be shown to be clinically significant based on dose-response (exposure-response) and/or pharmacokinetic-pharmacodynamic relationships of Compound 1 in human studies.

In some embodiments, the administration of Compound 1 in an amount of 40 mg, and a hormone replacement medicament in an immediate release formulation and administered orally in a fasted state, i.e., at least 2 hours after a meal and no less than 30 minutes before the next meal, may have a mean plasma $T_{1/2}$ for Compound 1 between about 37 hours and about 42 hours. In some embodiments, a corresponding amount of a pharmaceutically acceptable salt of Compound 1 is administered with the hormone replacement medicament.

Several benefits may result from preprandial administration. For example, mean $C_{max}$ may be higher with preprandial administration than with postprandial administration. Also, mean plasma $AUC_{(0-tau)}$ may be higher with preprandial administration than with postprandial administration.

In an embodiment of this disclosure, a method is provided for treating uterine fibroids that includes administering to the subject, once-daily for a 2 consecutive week or greater treatment period from 10 mg to 60 mg per day of Compound 1, so that mean plasma half-life ($T_{1/2}$) is at least 18 hours measured at the end of treatment. In an embodiment of this disclosure, a method is provided for treating endometriosis, uterine fibroids, or heavy menstrual bleeding that includes administering to the subject, once-daily for a 2 consecutive week or greater treatment period from 10 mg to 60 mg per day of Compound 1, so that mean plasma half-life ($T_{1/2}$) is at least 18 hours measured at the end of treatment. In some embodiments, a corresponding amount of a pharmaceutically acceptable salt of Compound 1 is co-administered with the hormone replacement medicament.

In some embodiments, for treatment of uterine fibroids, Compound 1 is preferably administered orally, as formulated with pharmaceutically acceptable excipients. In some embodiments, the oral dose is in the form of a solid preparation. Further, in some embodiments, the oral dosage form preferably has an immediate release profile. However, the oral dosage form can have other release profiles including, for example, sustained release, controlled release, delayed release, extended release, and the like. Immediate release dosage forms may include those for which ≥85% of labeled amount dissolves within 30 minutes. In particular, for immediate release products, the drug release rate and/or the absorption of the drug is neither appreciably nor intentionally delayed due to galenic methods. In some embodiments, a the oral dosage form comprises a pharmaceutically acceptable salt of Compound 1.

In some embodiments, Compound 1 is formulated to achieve effective drug plasma levels for treatment with a low dose of Compound 1. In one embodiment, a 40 mg high-bioavailability formulation single fixed combination dosage form of Compound 1 and a hormone replacement medicament taken preprandially, provides a blood plasma concentration of at least about 7.56 ng/mL at 1 hour after dose administration. In some embodiments, it provides a median blood plasma concentration of about 16.2 ng/mL at 1 hour after dose administration. In another embodiment, it provides a blood plasma concentration of about 28 ng/mL at 1 hour after dose administration. The high-bioavailability formulation may achieve the same average drug exposure in subjects as Compound 1 and the hormone replacement medicament when separately co-administered. In some embodiments, a the oral dosage form comprises a pharmaceutically acceptable salt of Compound 1.

In some embodiments, Compound 1 is formulated to achieve a low variability of pharmacokinetic and pharmacodynamic effects in subjects. In an embodiment, a 40 mg "low-variability formulation" dosage form of Compound 1 taken orally preprandially provides pharmacokinetic and pharmacodynamic effects that are less subject to variation in subjects, yet achieves the same average drug exposure in subjects as the other embodiments described herein. In some embodiments, a the oral dosage form comprises a pharmaceutically acceptable salt of Compound 1.

In an embodiment, a 40 mg tablet is formulated that is both high-bioavailability and food-independent, and provides the desired pharmacokinetic and pharmacodynamic effects that are less subject to variation in subjects.

In some embodiments, a patient may take Compound 1 before or after a meal, which may require that consuming a meal has a minimal effect on the mean plasma AUC relative to the fasting state. In one embodiment, when a 40 mg "food-independent formulation" dosage form of Compound 1 is taken orally, the ratio of the AUC for fed-state administration relative to fasted-state administration [mean plasma $AUC_{(fed)}$/mean plasma $AUC_{(fasted)}$] is 0.8 to 1.25, preferably 0.95 to 1.05, more preferably 1.0. In an embodiment, the 90% confidence interval of the ratio is within the bounds of 0.8 to 1.25. In some embodiments, the formulation comprises a corresponding amount of a pharmaceutically acceptable salt of Compound 1.

As described herein, in some embodiments, the absorption of Compound 1 in plasma may be decreased and delayed following a single dose administered 30 minutes after the start of a standard U.S. Food and Drug Administration (FDA) high fat, high-calorie breakfast (approx. 800–1000 calories, 50% from fat) compared to fasting conditions. Median $T_{max}$ may increase under fed conditions. Mean $C_{max}$ and mean plasma $AUC_\infty$ may be reduced under fed conditions compared with fasted conditions, indicating a clinically meaningful effect of food on the oral bioavailability of Compound 1. In some embodiments, when Compound 1 is administered daily 30 minutes prior to ingestion of a standardized morning meal (approx. 600 calories, 27% from fat), systemic exposure to Compound 1 is reduced to a lesser extent and no obvious changes in the rate of absorption are observed when compared to fasting conditions. In some embodiments, subjects may take Compound 1 upon arising in the morning, on an empty stomach, and start eating approximately 30 minutes after dosing whenever possible. In some embodiments, a pharmaceutically acceptable salt of Compound 1 is co-administered with the hormone replacement medicament.

In an embodiment, Compound 1 is administered preprandial, at least 1 hour before eating or at least 2 hours after eating. Administration can also be at least 30 minutes before eating or while the subject is fasting.

In one embodiment, subjects may take Compound 1 upon arising in the morning, on an empty stomach, and start eating approximately 60 minutes after dosing whenever possible. Several benefits may result from preprandial administration. For example, in one embodiment, maximum plasma drug concentration ($C_{max}$) of Compound 1 is higher with preprandial administration than with postprandial administration. Also, for the same embodiment, area under the plasma concentration-time curve ($AUC_{(0-tau)}$) for Compound 1 is higher with preprandial administration than with postprandial administration. In some embodiments, a pharmaceutically acceptable salt of Compound 1 is co-administered with the hormone replacement medicament.

In one embodiment, the administration is without any fasting or eating schedule requirement. The administration of the oral dosage form can be food independent.

For a food independent oral dosage form, the dosage of Compound 1 may be increased without altering the dosage of the hormone replacement medicament. For example, the food independent oral dosage can be from 80 to 160 mg per day, or from 100 mg to 140 mg per day, of Compound 1, and from 0.01 mg to 5 mg per day of the hormone replacement medicament. In an embodiment of the present disclosure, the food independent oral dosage can be 120 mg per day of Compound 1, 1 mg estradiol, and 0.5 mg of NETA. In some embodiments, at such a higher dose, Compound 1 may significantly suppress estrogen levels (whether taken on an empty stomach or on a full stomach, and whether taken with or without food). In some embodiments, the hormone replacement medicament (e.g., estradiol and NETA) is food independent and brings the patient's estrogen levels to the needed range to protect against bone mineral density loss. Thus, a higher dose of Compound 1 with a normal dose of the hormone replacement medicament, may provide a once-daily (anytime) dosage form, that is food independent, and which further differentiates it from other conventional options such as elagolix. In some embodiments, a corresponding amount of a pharmaceutically acceptable salt of Compound 1 is co-administered with the hormone replacement medicament.

In an embodiment, the weight ratio of the fixed combination, oral dosage of Compound 1 to the hormone replacement medicament (e.g., estradiol and NETA) is increased in order to provide food independent dosing. While 40 mg of Compound 1 may be food dependent, higher dosing of Compound 1 may still (fully) suppress estrogen in patients with uterine fibroids or endometriosis, whether taken with or without food. Further, while 40 mg of Compound 1 may be food dependent, higher dosing of Compound 1 may still (fully) suppress estrogen in patients with adenomyosis or heavy menstrual bleeding, whether taken with or without food. The hormone replacement medicament (e.g., estradiol and NETA) may increase the level of estrogen in order to protect against bone mineral density loss and mitigate other possible side-effects. The hormone replacement medicament, estradiol and NETA, may be a food independent ingredient. Thus, in some embodiments, to be food independent in a fixed combination, oral dosage, Compound 1 can be increased to higher amounts (higher than 40 mg) and the hormone replacement medicament of estradiol and NETA can remain at the same level (e.g., 1 mg estradiol and 0.5 mg of NETA). It may be desirable to provide patients with a once-daily oral medication for treatment of uterine fibroids or endometriosis that can be taken at any time of day in order to increase compliance and reduction of symptoms. It may also be desirable to provide patients with a once-daily oral medication for treatment of adenomyosis or heavy menstrual bleeding that can be taken at any time of day in order to increase compliance and reduction of symptoms. It may further be desirable for such a food independent drug to be a fixed dose with Compound 1 and the hormone replacement medicament, in order to mitigate long term side-effects, such as protecting against bone mineral density loss. In some embodiments, a corresponding amount of a pharmaceutically acceptable salt of Compound 1 is co-administered with the hormone replacement medicament.

Several benefits may result from treating uterine fibroids, endometriosis, adenomyosis, or heavy menstrual bleeding by administering Compound 1 to a subject in need of treatment. For example, for a 14 consecutive day treatment period of 10 mg to 60 mg per day of Compound 1, Compound 1 mean plasma half-life ($T_{1/2}$) may be at least 18 hours measured at the end of the treatment period. Also, for the 14 consecutive day treatment period of 10 mg to 60 mg per day of Compound 1, area under the plasma drug concentration-time curve ($AUC_{(0-tau)}$) may increase at least 1.5 fold (150%), and preferably 2 fold (200%) or greater, from day 1 to day 14. In one embodiment, a subject with uterine fibroids is treated. In another embodiment, a subject with endometriosis is treated. In still a further embodiment, a subject with adenomyosis is treated. In yet another embodiment, a subject with heavy menstrual bleeding is treated. In some embodiments, a corresponding amount of a pharmaceutically acceptable salt of Compound 1 is co-administered with the hormone replacement medicament.

In accordance with this disclosure, the mean plasma half-life of Compound 1 may be at least 18 hours, preferably at least about 30 hours, and more preferably at least about 35 hours, measured at the end of the treatment period. In an even more preferred embodiment, the mean plasma half-life ($T_{1/2}$) of Compound 1 is about 37 hours to about 42 hours. In some embodiments, a pharmaceutically acceptable salt of Compound 1 is co-administered with the hormone replacement medicament.

Compound 1 may have a higher potency and a longer mean plasma half-life than elagolix, another GnRH antagonist. Near complete estrogen suppression (median less than 10 pg/mL) may be achieved with a lower total daily dose of Compound 1 compared with elagolix. In particular, Compound 1 may achieve near complete estrogen suppression with a dosage of 40 mg once per day in a fasted state, whereas elagolix may requires 200 mg or higher, twice per day (BID) in a fasted state to achieve similar estrogen suppression. This high rate of estrogen suppression may be clinically important, since the hormone replacement medicament may provide a controlled exposure of estrogen and/or progestogen. Compound 1 may be given once-daily due to its longer mean plasma half-life of about 37 hours to about 42 hours compared to approximately 2 to 6 hours for elagolix. In some embodiments, a pharmaceutically acceptable salt of Compound 1 is co-administered with the hormone replacement medicament.

Suppressing estrogen to low levels may provide a consistent baseline upon which to add back low-dose estrogen and progestogen in a controlled fashion. This hormone add-back therapy may achieve estradiol levels above 20 pg/mL, the level thought to protect women from bone mineral density loss. This strategy of estrogen suppression coupled with adding back low-dose estrogen and progestogen may preserve Compound 1's clinical benefit while minimizing bone mineral density loss and improving tolerability, thereby potentially enabling longer-term use.

As discussed above, in certain populations of women, it may be preferred to administer a dose of hormone replacement medicament that results in average daily circulating estrogen level average of about 55 pg/mL to about 150 pg/mL, such as about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, about 100 pg/mL, about 105 pg/mL, about 110 pg/mL, about 115 pg/mL, about 120 pg/mL, about 125 pg/mL, about 130 pg/mL, about 135 pg/mL, about 140 pg/mL, about 145 pg/mL, or about 150 pg/mL. It should be understood that the peaks and troughs accompanying daily hormone replacement medicament (such as one comprising estradiol) administration may result in concentrations above and below an average value, for example 150 pg/mL.

In some embodiments, for all methods of the present disclosure that include administration of both Compound 1 in an amount of 40 mg, and a hormone replacement medicament, in a fasted state, e.g., at least 2 hours after a meal and no less than 30 minutes before the next meal, the mean maximum plasma concentration, or $C_{max}$, for Compound 1 may be in the range of 5 ng/mL to 35 ng/mL. Preferably, the mean $C_{max}$ may be in the range from 10 ng/mL to 30 ng/mL, and more preferably from 15 ng/mL to 25 ng/mL. In some embodiments, a corresponding amount of a pharmaceutically acceptable salt of Compound 1 is co-administered with the hormone replacement medicament.

Further, in some embodiments, for all methods of the present disclosure that include oral administration of both Compound 1 in an amount of 40 mg, and a hormone replacement medicament, in a fasted state, e.g., at least 2 hours after a meal and no less than 30 minutes before the next meal, the mean concentration under the plasma vs. time curve from 0 to 24 hours for Compound 1, or $AUC_{0-24}$, may be in the range of from 50 to 200 ng h/mL, and more preferably in the range of from 75 to 150 ng h/mL. In some embodiments, a corresponding amount of a pharmaceutically acceptable salt of Compound 1 is co-administered with the hormone replacement medicament.

EXAMPLES

The following non-limiting examples are provided to illustrate the present disclosure.

Example 1: Production of Compound 1

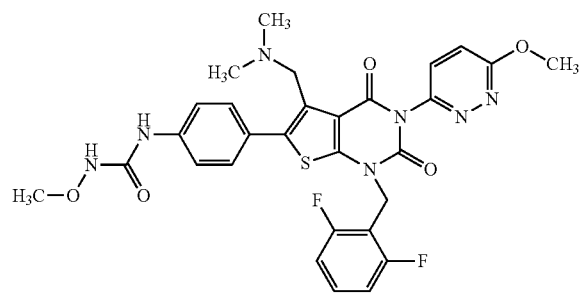

N-(4-(1-(2,6-difluorobenzyl)-3-(6-methoxy-3-pyridazinyl)-5-((methylamino) methyl)-2,4-dioxo-1,2,3,4-tetrahydrothieno[2,3-d]pyrimidin-6-yl)phenyl)-N'-methoxyurea (150 mg, 0.259 mmol) was dissolved in DMF (4 ml), and methyl iodide (0.010 ml, 0.164 mmol) was added thereto. The reaction mixture was stirred at room temperature for 1 hour, combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent:ethyl acetate/methanol=40/1), and recrystallized from dichloromethane/methanol/diethyl ether to give the title compound (17.3 mg, 17%) as colorless crystals. $^1$H-NMR (CDCl$_3$) δ: 2.15 (6H, s), 3.6-3.8 (2H, m), 3.82 (3H, s), 4.18 (3H, s), 5.35 (2H), 6.92 (2H, t, J=8.2 Hz), 7.12 (1H, d, J=8.8 Hz), 7.2–7.65 (7H, m), 7.69 (1H, s).

Example 2: Production of Film Coated Tablets of Compound 1

Film coated tablets were prepared by using the compound obtained in Example 1 (40 mg), mannitol (preferably D-mannitol) (122 mg), microcrystalline cellulose (40 mg), hydroxypropyl cellulose (6 mg), croscarmellose sodium (10 mg), magnesium stearate (2 mg), and sufficient quantity of purified water. Water was removed during processing. In a fluid bed dryer granulator (LAB-1, Powrex Corporation), the compound obtained in Example 1, D-mannitol, and microcrystalline cellulose were preheated and mixed, an aqueous solution of hydroxypropyl cellulose was sprayed, and the mixture was dried to give a granulated powder. To the obtained granulated powder was added croscarmellose sodium and magnesium stearate, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (7.12 mg), titanium dioxide (0.8 mg), and ferric oxide (0.08 mg) was sprayed to give film coated tablets. The obtained film coated tablets were placed in a glass bottle, which was tightly sealed and preserved at 60° C. for 2 weeks.

Example 3: Production of Film Coated Tablets of Compound 1

Film coated tablets were prepared by using the compound obtained in Example 1 (40 mg), mannitol (including D-mannitol) (51 mg), sodium starch glycolate (Type A) (5 mg), hydroxypropyl cellulose (3 mg), magnesium stearate (1 mg), and a sufficient quantity of purified water. Water was removed during processing. In a fluid bed dryer granulator (LAB-1, Powrex Corporation), the compound obtained in Example 1, mannitol, and sodium starch glycolate were preheated and mixed, an aqueous solution of hydroxypropyl cellulose was sprayed, and the mixture was dried to give a granulated powder. To the obtained granulated powder was added magnesium stearate, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (3.56 mg), titanium dioxide (0.4 mg), ferric oxide (0.0.04 mg), and a sufficient quantity of carnauba wax, was sprayed to give film coated tablets. The obtained film coated tablets were placed in a glass bottle, which was tightly sealed and preserved at 60° C. for 2 weeks.

Example 4: A Double Blind, Randomized, Placebo-Controlled, Sequential-Panel, Ascending Single- and Multiple-Dose Study to Evaluate the Effect of Compound 1 on Safety, Tolerability, Pharmacokinetics and Pharmacodynamics in Healthy Premenopausal Women The study was a phase 1, double-blind, randomized, placebo-controlled, sequential-panel, ascending single- and multiple-dose study in healthy premenopausal women. Ten groups, each of 12 healthy premenopausal, adult women, participated in the study (Cohorts 1 to 10). The dose escalation scheme for Cohorts 1–10 is shown in FIG. 4 and explained below.

Cohorts 1 to 6 were referred to as the single-rising dose (SRD) portion of the study, where cohorts were dosed in an escalating fashion. All subjects in a given cohort received their dose of study medication on the same day with the exception of subjects in Cohort 1, which were split into 2 subcohorts (Cohorts 1a and 1b). Dosing between these 2 subcohorts was separated by a minimum of 2 days. Dosing between subsequent cohorts was separated by a minimum of 7 days. The decision to proceed to Cohort 1b was made by the investigator after a minimum 48-hour evaluation of subjects in Cohort 1a. The decision to escalate the dose for the remaining cohorts in the SRD portion was based on review of the safety and pharmacokinetic data for all subjects in the previous cohort.

In Cohorts 1 to 6, subjects were randomized to receive a single dose of Compound 1 (10 subjects per cohort) or placebo (2 subjects per cohort). Subjects were required to fast overnight (minimum 10 hours) prior to dosing and continued to fast for 4 hours following dosing. Subjects were given a menu for the dosing period to include 2 meals and an evening snack, each containing approximately 25% fat content. Six ascending dose groups were planned: 1.0 mg (Cohort 1), 5.0 mg (Cohort 2), 10 mg (Cohort 3), 20 mg (Cohort 4), 40 mg (Cohort 5), and 80 mg (Cohort 6). Subjects in each of Cohorts 1a, 1b, 2, 3, 4, 5 and 6 received drug dosing on a single day only.

Cohorts 1 to 7 were each composed of 12 healthy premenopausal women aged 18 to 49 years, inclusive. Subjects in Cohort 7 were equally randomized into 1 of 2 sequences, both consisting in opposite order of a single dose of Compound 1 (40 mg or one-half of the maximum tolerated dose (MTD) established from the SRD portion). In one sequence, dosing was under fasting conditions (minimum 10 hours). In the other sequence, dosing was approximately 30 minutes after the start of a high-fat, high calorie breakfast (provided approximately 1000 calories, with 50% of the calories from fat). Thus, all 12 subjects in Cohort 7 received Compound 1 in both dosing periods, and all subjects received drug dosing for 2 days (Days 1 and 7). Subjects had a washout period before crossing over to the other dosing period on Day 7.

Cohorts 8 to 10 were each composed of 12 healthy premenopausal women aged 18 to 45 years, inclusive. Cohorts 8 to 10 were referred to as the multiple-rising dose (MRD) portion of the study, where cohorts were dosed in escalating fashion. The MRD portion was not started until all the blinded safety and pharmacokinetic data from the SRD cohorts had been assessed by the investigator and the sponsor. Subjects in Cohorts 8 to 10 were randomized to receive multiple daily doses of Compound 1 (9 subjects per cohort) or multiple daily doses of placebo (3 subjects), under fasted conditions approximately 35 minutes before a standard breakfast. Subjects received the first dose of study medication (Day 1) within 2 to 7 days following the onset of their menstrual cycle. Three ascending dose groups were planned: 10 mg once-daily (QD) (Cohort 8), 20 mg QD (Cohort 9), and 40 mg QD (Cohort 10). Subjects in each of Cohorts 8 to 10 received drug dosing on 14 days (Days 1 to 14). The highest dose in the MRD portion did not exceed 50% of the MTD established in the SRD portion of the study.

Each dose of Compound 1 or placebo was administered to subjects with 240 mL of water. Subjects had to drink all of the water provided with the dose of study drug. Subjects were able to consume water ad libitum with the exception of 1 hour prior to and 1 hour after drug administration, not including the 240 mL of water taken with dosing.

The PK evaluation of unchanged Compound 1 in plasma and urine was performed by calculation of: area under the plasma drug concentration-time curve from time 0 to time of the last quantifiable concentration (mean plasma $AUC_{[0-tlqc]}$), area under the plasma drug concentration-time curve from time 0 to infinity (mean plasma $AUC_{[0-inf]}$), area under the plasma drug concentration-time curve from time 0 to time tau where tau is the length of the dosing interval (i.e., 24 hours) (mean plasma $AUC_{[0-tau]}$), mean $C_{max}$, $C_{min}$, $T_{max}$, plasma drug concentration rate constant, mean plasma $T_{1/2}$, apparent oral clearance (CL/F), apparent volume of distribution (Vz/F), renal clearance (CLr), total amount of drug excreted in the urine (Ae), fraction of the dose excreted unchanged in urine (Fe) where appropriate, and the terminal elimination rate constant (lamda-z).

The plasma PK profile of Compound 1 for Cohorts 1–6 are shown in FIGS. 5A-C following administering the above-described dosages of Compound 1. In particular, FIG. 5A shows mean $AUC_{[0-tlqc]}$ and mean $AUC_{[0-inf]}$ of Compound 1; FIG. 5B shows mean $C_{max}$, $T_{max}$ and Lamba_z of Compound 1; and FIG. 5C shows mean plasma $T_{1/2}$, CL/F and Vz/F of Compound 1.

The plasma PK profile of Compound 1 for Cohort 7 is shown in FIGS. 6A-C following administering the above-described dosage of Compound 1. In particular, FIG. 6A shows mean $AUC_{[0-tlqc]}$ and mean $AUC_{[0-inf]}$ of Compound 1; FIG. 6B shows $C_{max}$, $T_{max}$ and lamba_z of Compound 1; and FIG. 6C shows mean plasma $T_{1/2}$, CL/F and Vz/F of Compound 1.

The plasma PK profiles of Compound 1 for Cohorts 8–10 are shown in FIGS. 7A-F following administering the above-described dosage of Compound 1. In particular, FIG. 7A shows mean $C_{max}$ of Compound 1 on Day 1; FIG. 7B shows $T_{max}$, CL/F and Vz/F on Day 1; FIG. 7C shows mean plasma $AUC_{[0-tau]}$ on Day 1; FIG. 7D shows mean $C_{max}$ and $T_{max}$ on Day 14; FIG. 7E shows CL/F, $C_{min}$ and Vz/F on Day 14; and FIG. 7F shows mean plasma $AUC_{[0-tau]}$ on Day 14.

FIGS. 8-13 are tables of plasma and urine PK parameters following different doses of Compound 1. In particular, FIG. 8 shows PK parameters for Cohorts 1 to 6; FIGS. 9 and 10 show various PK parameters for Cohort 7; FIG. 11 shows PK parameters for Cohorts 8 to 10 on Days 1 and 14; FIG. 12 shows detailed PK parameters for Cohorts 8 to 10 on Day 1; and FIG. 13 shows detailed PK parameters for Cohorts 8 to 10 on Day 14.

Descriptive statistics were used to summarize pharmacodynamic parameters: serum concentrations of estradiol ($E_2$), FSH, LH, progesterone, growth hormone (GH), prolactin (PRL), thyrotropin, adrenocorticotropic hormone (ACTH) and urine 60-hydroxycortisol to cortisol ratios (Q).

To assess the dose proportionality following single dosing in Cohorts 1 to 6, regression analysis of natural logarithm (log) transformed mean $C_{max}$, mean plasma $AUC_{(0-tlqc)}$, and mean $AUC_{(0-inf)}$ was performed on log(dose).

To assess the food effect, an analysis of variance was performed using Cohort 7 log(mean $C_{max}$), log(area under the plasma drug concentration-time curves [mean plasam AUCs]) as dependent variable; treatment, sequence, period as fixed effects; and subject (seq) as a random effect. The least squares means ratio of Compound 1 fed (test) to Compound 1 fasted (reference) and the corresponding 90% CI was presented for mean $C_{max}$, mean plasma $AUC_{(0-tlqc)}$, and mean plasma $AUC_{(0-inf)}$. FIG. 14 shows a statistical analysis of plasma pharmacokinetic parameters for 40 mg of Compound 1 in fed compared with fasted states.

To assess the dose proportionality following multiple dosing in Cohorts 8 to 10, regression analysis of log transformed mean $C_{max}$, $C_{min}$, and mean plasma $AUC_{(0-tau)}$ was performed on log(dose).

After single and multiple doses, Compound 1 was absorbed rapidly with median $T_{max}$ ranging from 0.78 to 1.75 hours for both single and multiple doses up to 40 mg. The median $T_{max}$ following a single dose of 80 mg was 4 hours. All subjects had a $T_{max}$ within 6 hours.

Mean Compound 1 $C_{max}$, $C_{min}$, and AUC parameters increased supra-proportionally to dose when Compound 1 was given as either single doses (1 to 80 mg) or as multiple QD doses (10 to 40 mg QD). This non-proportionality was confirmed by separate statistical analyses of the single- and multiple-dose pharmacokinetic parameters. The degree of non-proportionality was deemed moderate as represented graphically by comparison of dose normalized mean $C_{max}$ and mean plasma AUC. For single doses of Compound 1, between-subject variability was generally moderate to high with % CVs up to 130% at the highest dose. For multiple doses of Compound 1, between-subject variability was moderate to high with % CVs up to 91%. Mean $C_{max}$ and mean plasma AUC values for all dose levels were higher on Day 14 compared with Day 1.

Figure 15B:
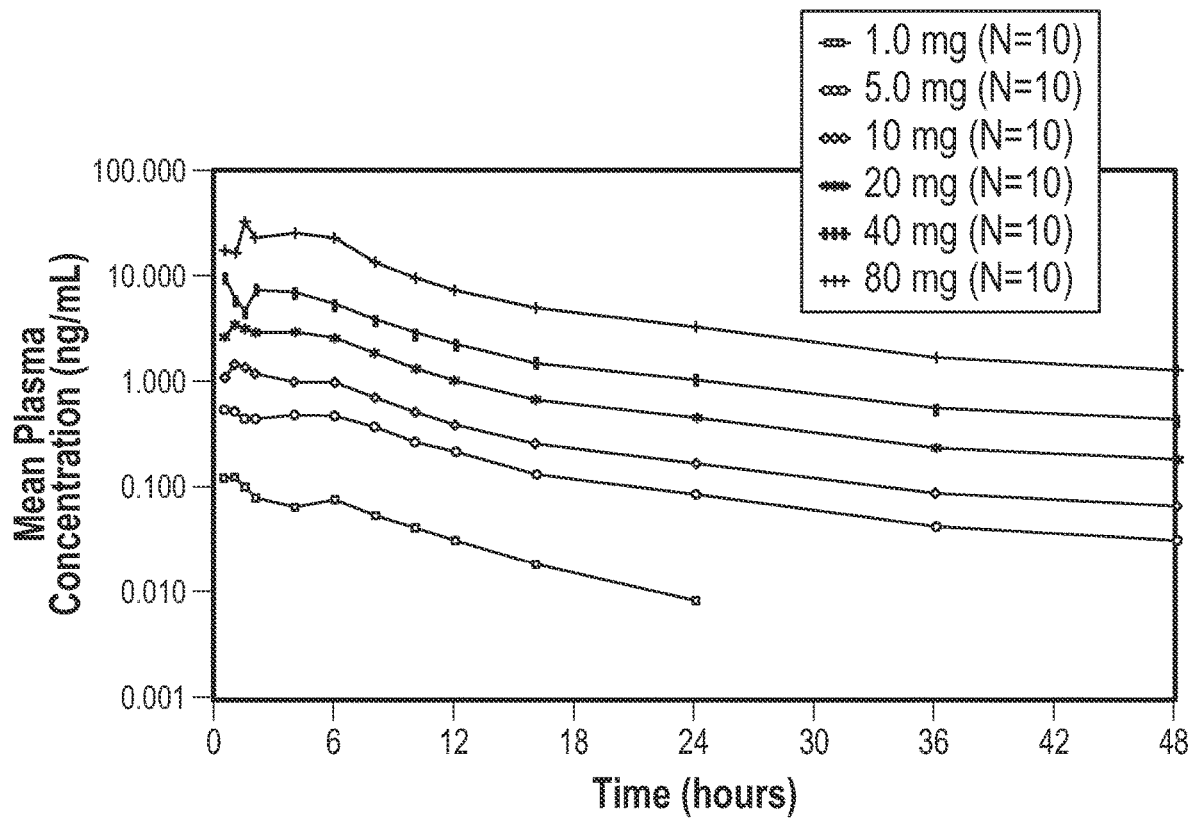

FIGS. 15A (linear scale) and 15B (log-linear scale) graphically depict mean plasma concentrations versus time profiles following single doses of Compound 1. As shown in FIGS. 15A and 15B, mean plasma concentrations of Compound 1 increased with dose of Compound 1. All subjects in Cohort 1 (Compound 1 1.0 mg) had plasma concentrations that were below the lower limit of quantitation (BLQ) (0.0100 ng/mL) by 36 hours postdose. All subjects in the other cohorts (Cohorts 2–6) had detectable plasma concentrations of Compound 1 at all measured time points (i.e., up to 48 hours postdose). Inspection of the individual plasma concentration profiles shown in FIGS. 15A and 15B demonstrated that most subjects had more than 1 peak (usually 2 peaks, but occasionally more). The second peak occurred most commonly around 2 to 6 hours postdose. Disposition of Compound 1 appeared to be biphasic with a moderate distribution phase followed by a much longer elimination phase. This second peak was not apparent in the MRD portion of the study either on Day 1 or Day 14.

Mean plasma $T_{1/2}$ of Compound 1 did not appear to be dependent on dose and was approximately 14 to 16 hours following doses of 5 to 80 mg and would appear to support a QD dosing regimen. The mean plasma $T_{1/2}$ following the lowest dose (1 mg) was approximately 6 hours and was lower than mean plasma $T_{1/2}$ for other doses.

The amount of Compound 1 excreted in the urine (Ae and Fe) was low relative to dose, with mean Fe being less than 3% of the dose at all observations indicating that CLr was therefore a negligible component of Compound 1 elimination. Mean CLr was independent of dose or time and ranged from 5.7 to 8.3 L/hr.

CL/F and Vz/F decreased with increasing dose of Compound 1, and with increasing duration of dosing (i.e., between Day 1 and Day 14) indicating a possible change in bioavailability.

At all doses, steady state was reached within 6 to 7 days. FIG. 16 shows a steady-state assessment of plasma concentrations (ng/mL) of Compound 1 for Cohorts 8 to 10. The tabulated data in FIG. 16 was analyzed based on an analysis of variance (ANOVA) model with fixed effect for day and random effect for subject. Day 15, as referred to in FIG. 16, is 24 hours post Day 14 dose. The geometric mean (a) was obtained by taking the anti-log of the natural logarithms of concentration values. The % ratio (b) was obtained by taking the anti-log of the difference between the means on the natural logarithmic scale. The 90% Confidence Interval Ratio (c) was obtained by taking the anti-log of the 90% confidence interval of the difference between the means on the natural logarithmic scale, obtained as a percentage.

Figure 17:
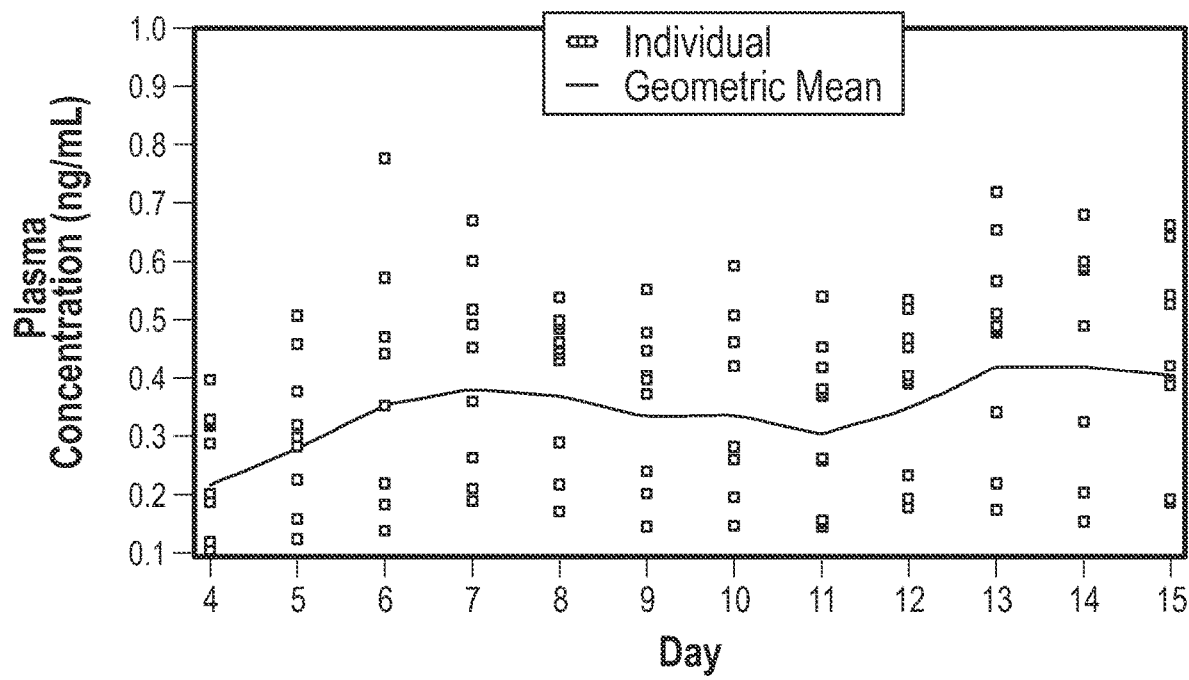
FIG. 17 graphically depicts mean trough concentrations of 10 mg Compound 1 v. day of treatment in the Multiple Rising Dose portion in accordance with Example 4.
Figure 18:
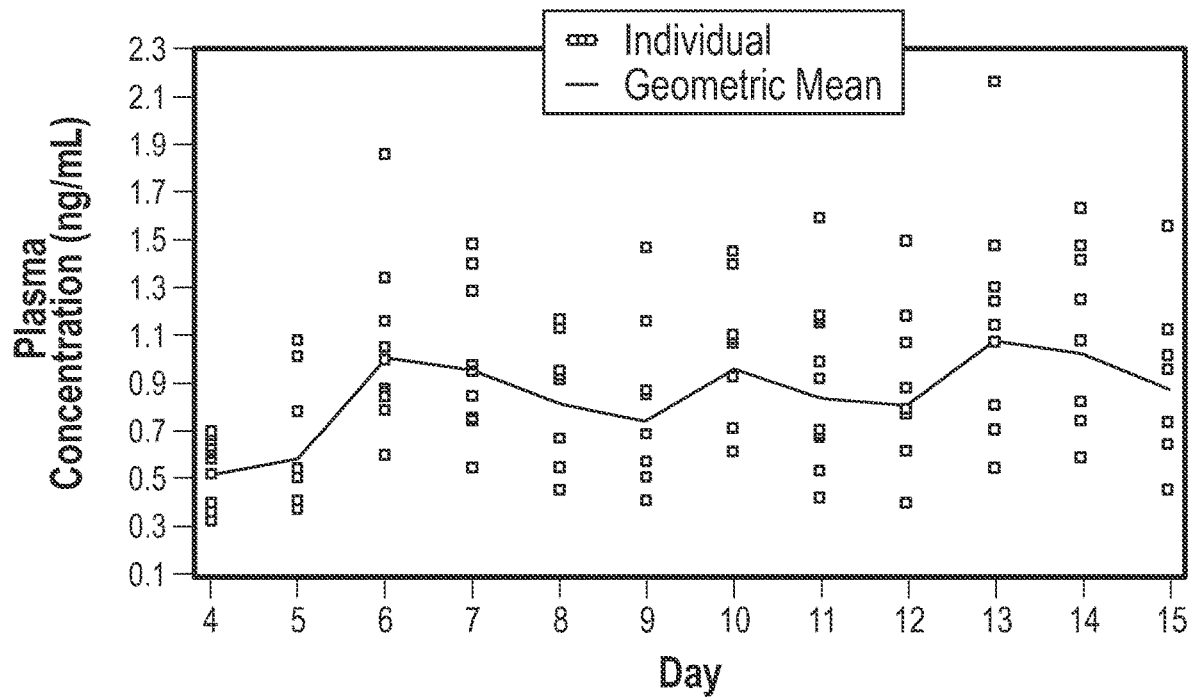
FIG. 18 graphically depicts mean trough concentrations of 20 mg Compound 1 v. day of treatment in the Multiple Rising Dose portion in accordance with Example 4.
Figures 19, 20:
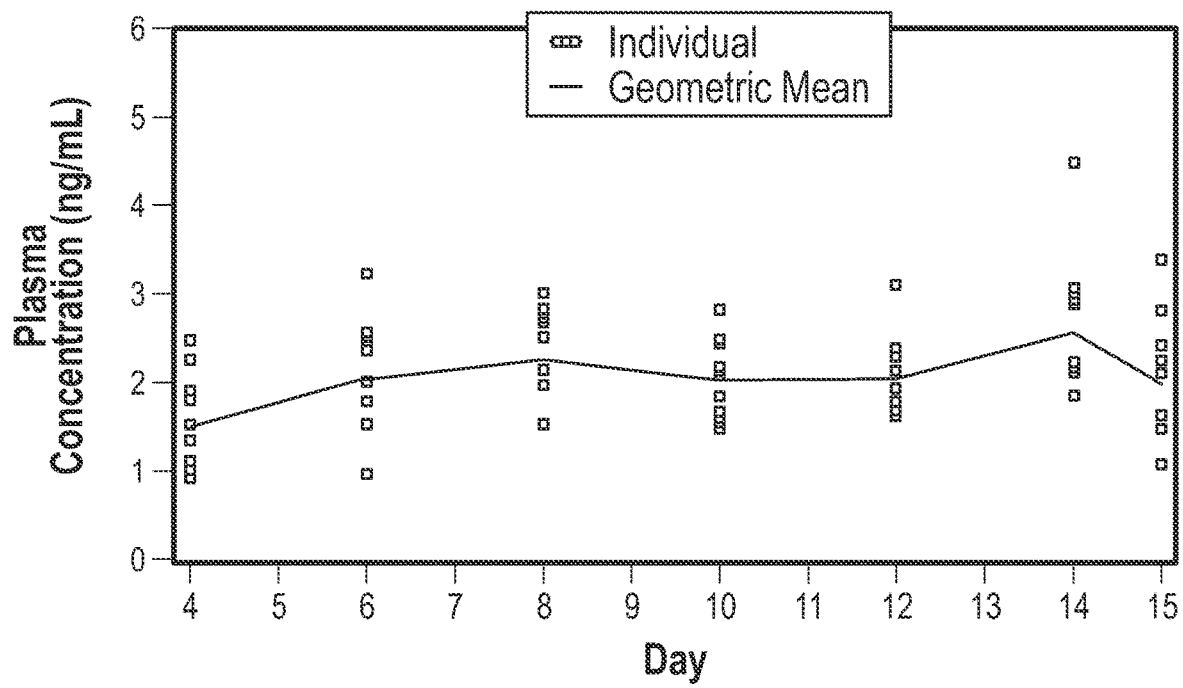
FIG. 19 graphically depicts mean trough concentrations of 40 mg Compound 1 v. day of treatment in the Multiple Rising Dose portion in accordance with Example 4.
FIG. 20 shows a statistical analysis of the time independence of Compound 1 in accordance with Example 4.

FIGS. 17-19 show mean trough concentrations of Compound 1 vs. Day (Days 1 to 15) in the MRD portion. FIG. 17 shows results for 10 mg of Compound 1, FIG. 18 shows results for 20 mg of Compound 1, and FIG. 19 shows results for 40 mg of Compound 1.

Following both single and multiple dosing of Compound 1, mean plasma $AUC_{(0-tau)}$ doubled between Day 1 and Day 14. Median $T_{max}$ of Compound 1 was approximately 1 to 1.48 hours and did not appear to alter with dose or from Day 1 to Day 14. $T_{max}$ occurred within 2 hours for all subjects in the MRD portion.

Statistical analyses comparing mean plasma $AUC_{(0-tau)}$ Day 14 from the MRD portion to mean plasma $AUC_{(0-inf)}$ from the SRD portion suggest that the pharmacokinetics of Compound 1 are time-independent (i.e., no autoinduction or autoinhibition of its metabolism). FIG. 20 shows a statistical analysis of the time independence of Compound 1.

Analysis of mean $C_{max}$, $C_{min}$ and mean plasma $AUC_{(0-tau)}$ suggest that the multiple dose pharmacokinetics of Compound 1 are not dose-proportional over the dose range 10 to 40 mg. Following both single and multiple doses, Compound 1 concentrations appeared to increase supra-proportionally to dose.

Figure 21:
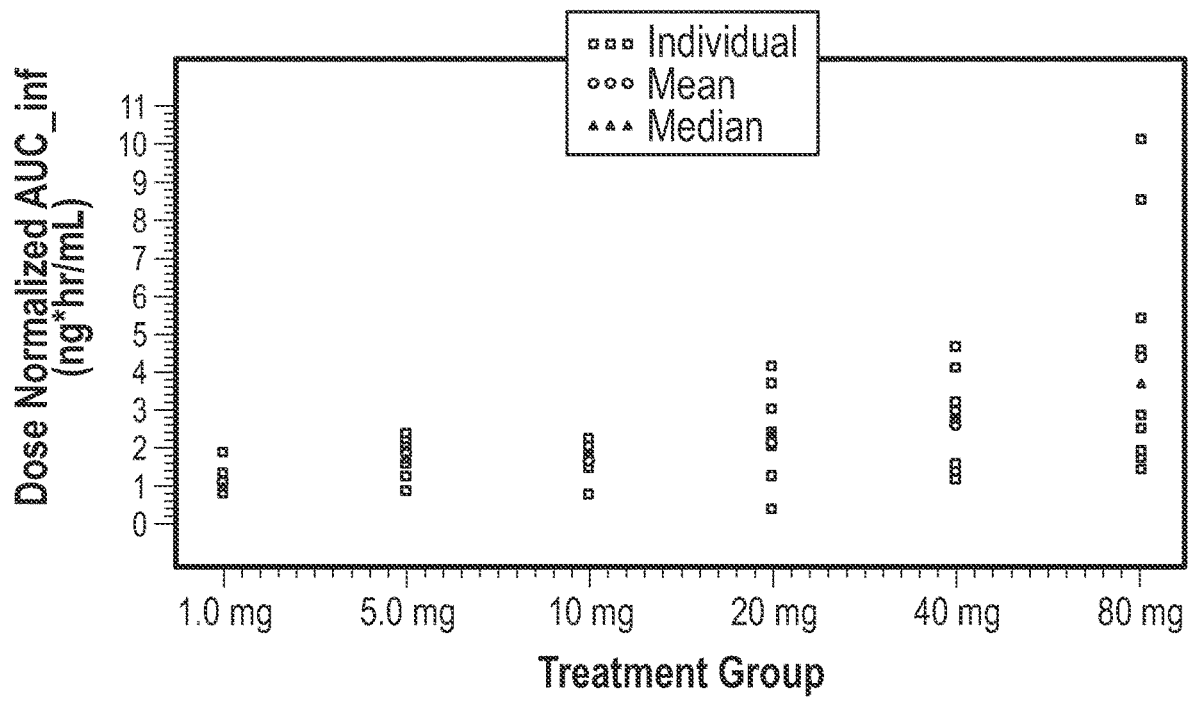
FIG. 21 graphically depicts individual dose normalized $AUC_{(0-inf)}$ from the Single Rising Dose portion in accordance with Example 4.
Figure 22:
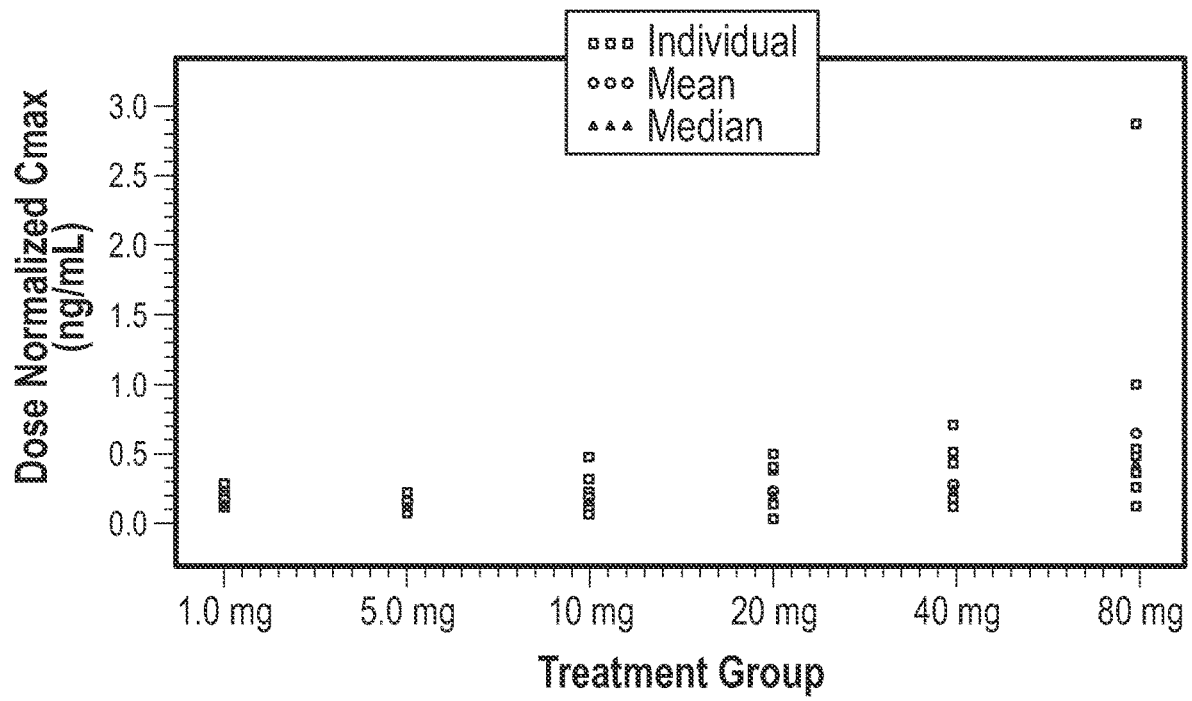
FIG. 22 graphically depicts individual dose normalized $C_{max}$ from the Single Rising Dose portion in accordance with Example 4.
Figure 23:
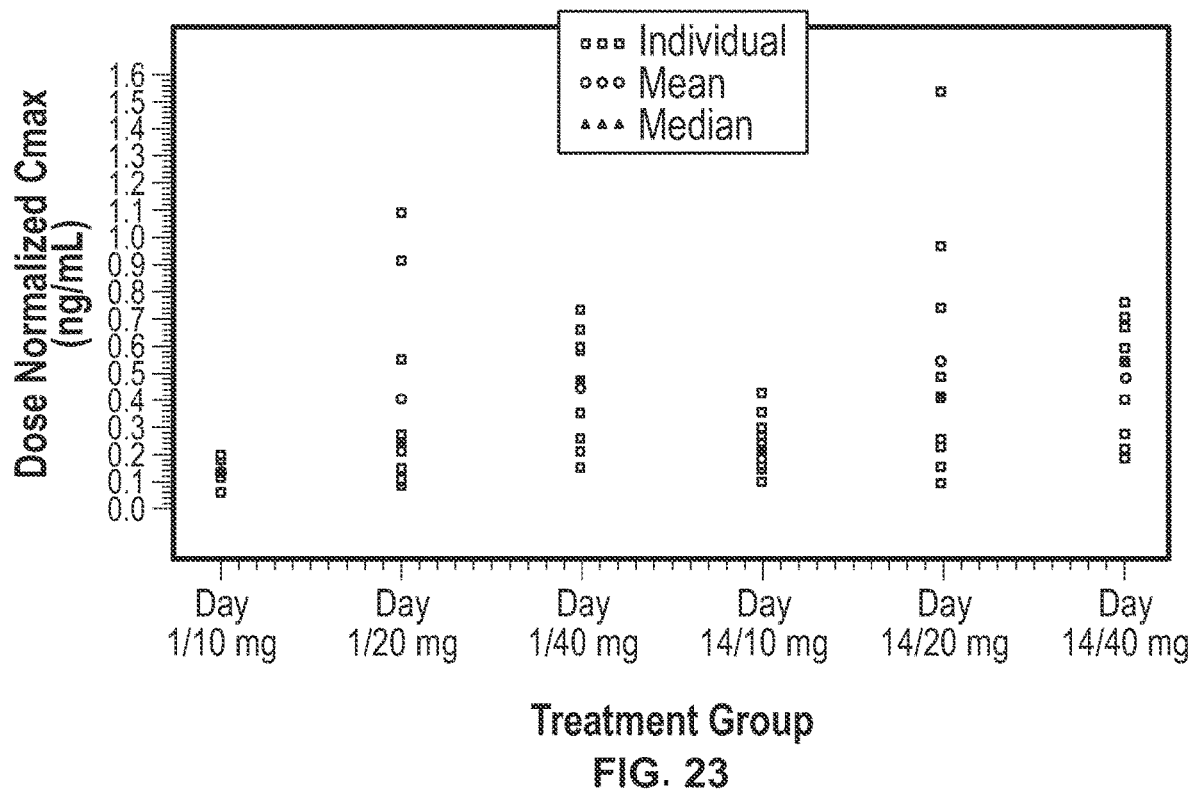
FIG. 23 graphically depicts individual dose normalized $C_{max}$ from the Multiple Rising Dose portion in accordance with Example 4.
Figure 24:
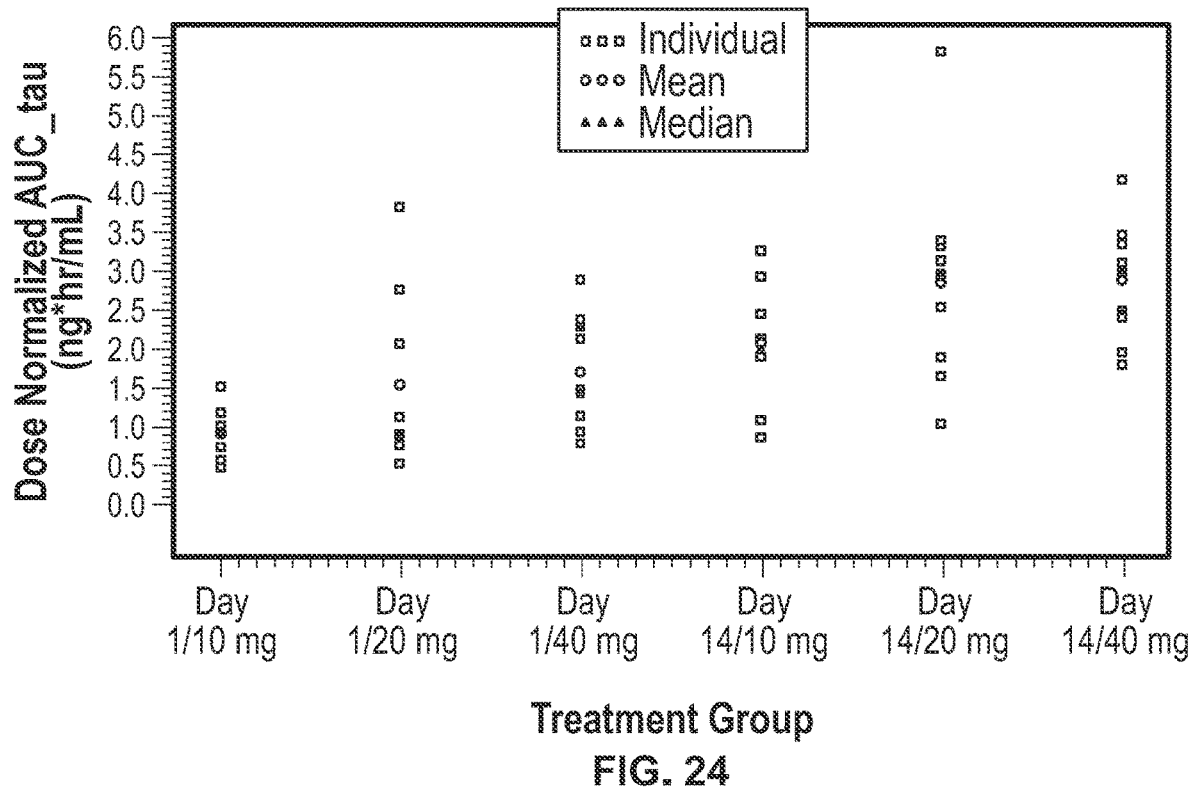
FIG. 24 graphically depicts individual dose normalized $AUC_{(0-tau)}$ from the Multiple Rising Dose portion in accordance with Example 4.

Individual dose normalized mean plasma $AUC_{(0-inf)}$ from the SRD portion is shown in FIG. 21. Individual dose normalized mean $C_{max}$ from the SRD and MRD portions are shown in FIGS. 22 and 23, respectively. Individual dose normalized mean $AUC_{(0-tau)}$ from the MRD portion is shown in FIG. 24. An increase in dose normalized mean plasma $AUC_{(0-inf)}$ with increasing dose occurs in the SRD portion as well as the MRD portion. For both the SRD portion and the MRD portion, the degree of nonproportionality is moderate and appeared more marked from 40 mg onward. The dose normalized mean $C_{max}$ figures for both SRD and MRD portions show a similar trend, although subject variability was generally high.

Mean plasma concentrations for Compound 1 increased with dose and were generally higher on Day 14 compared with Day 1. All subjects in all cohorts had detectable plasma concentrations of Compound 1 at all measured time points. Inspection of the individual plasma concentration profiles suggested that the multiple peaks seen in Cohort 1 to 6 were not as apparent in Cohorts 8 to 10 on either Day 1 or Day 14. This observation may be due to the different conditions between the SRD and MRD portions of the study. Subjects in the SRD portion were fasted at least 10 hours before and for 4 hours following dosing, whereas subjects in the MRD portion were dosed 35 minutes prior to a standard breakfast.

Figure 25A:
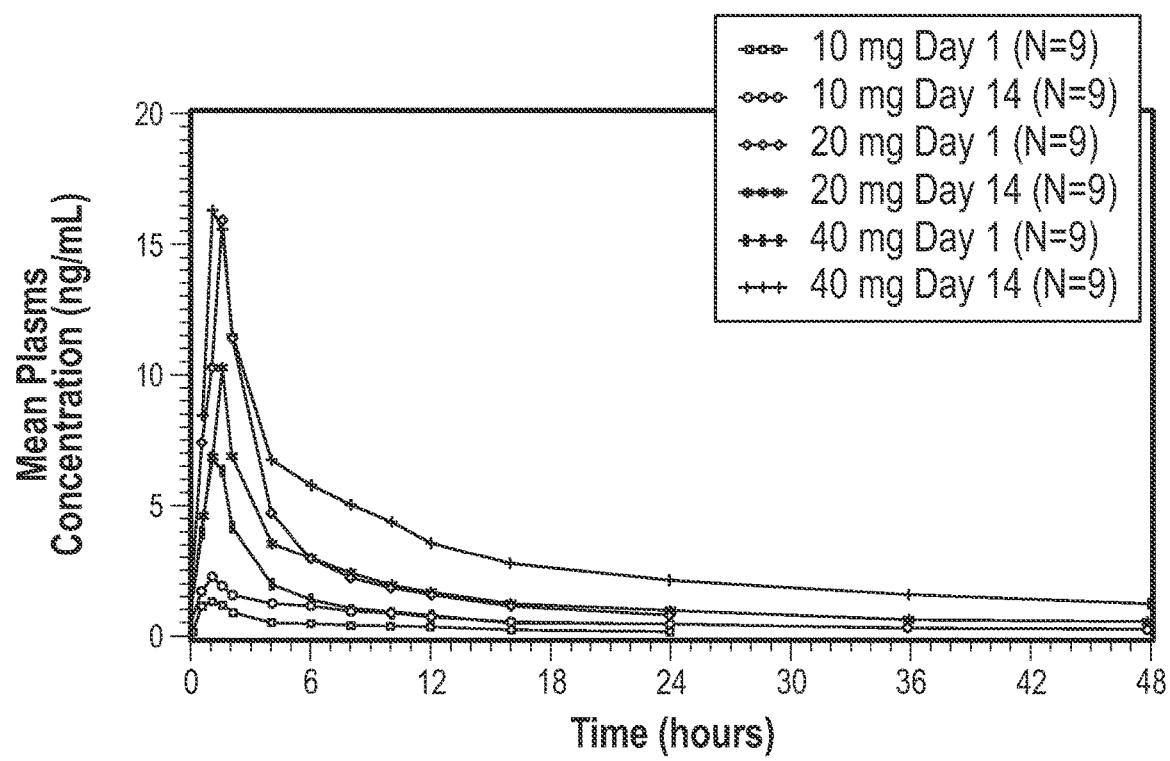
FIGS. 25A and 25B graphically depict mean plasma concentrations following multiple doses of Compound 1 in accordance with Example 4.
Figure 25B:
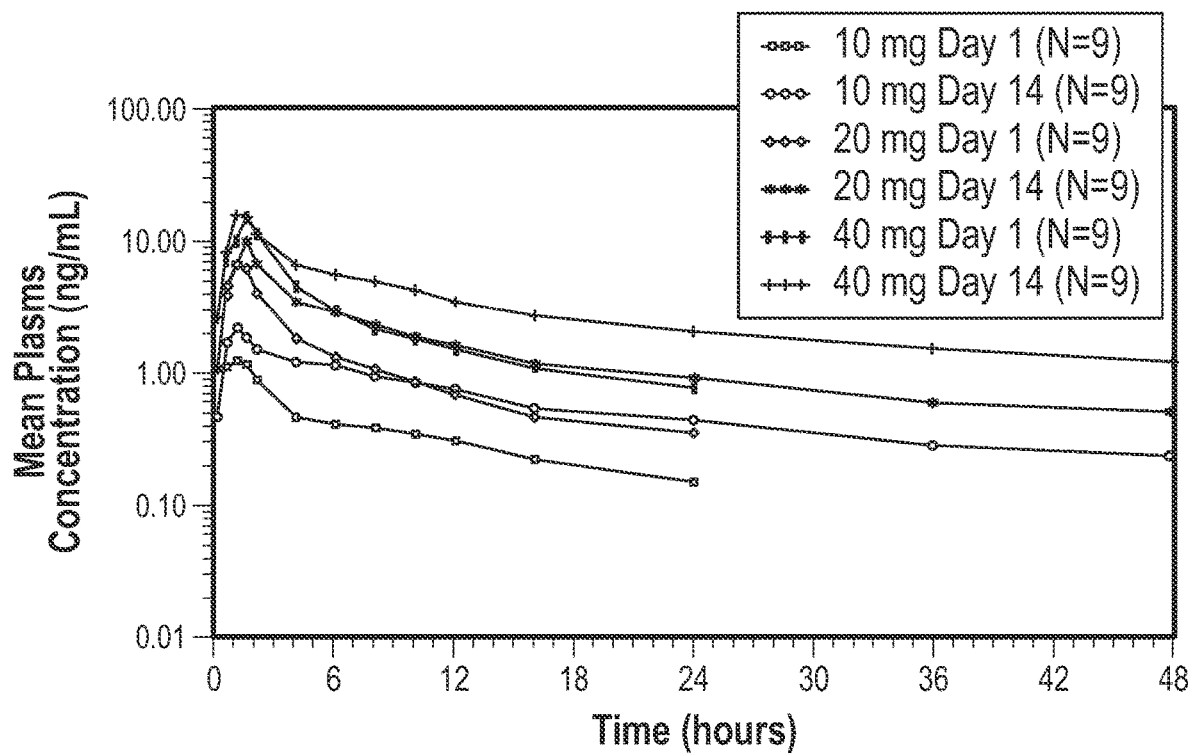

FIGS. 25A (linear scale) and 25B (log-linear scale) graphically depict mean plasma concentrations following multiple doses of Compound 1.

Figure 26A:
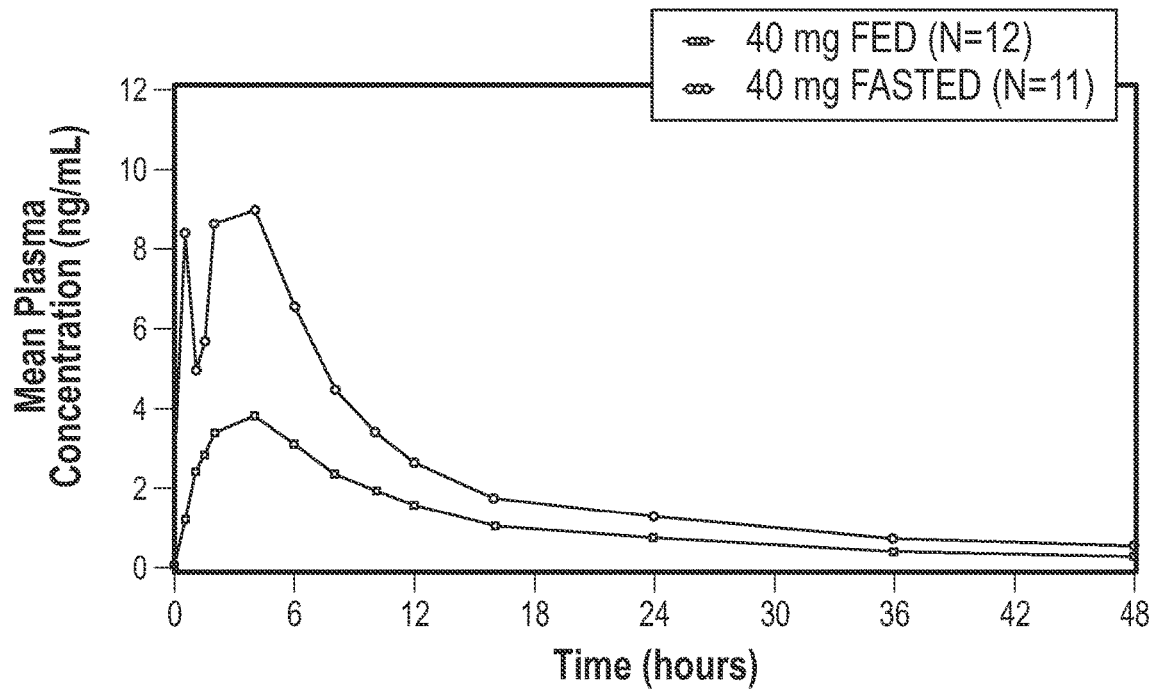
FIGS. 26A and 26B graphically depict mean plasma concentrations of Compound 1 under fed and fasted conditions in accordance with Example 4.
Figure 26B:
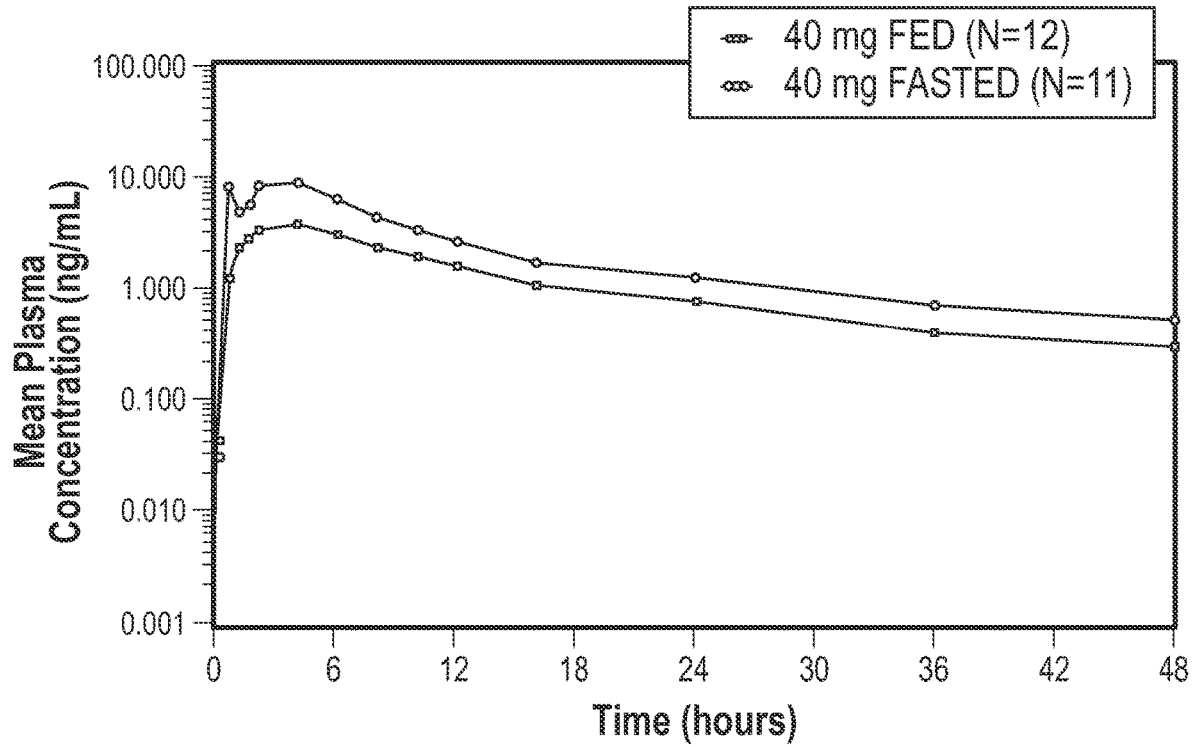

Comparison of the pharmacokinetics of Compound 1 when given as a single 40 mg dose under fed conditions compared with fasted conditions, demonstrated a marked food effect. In particular, mean plasma concentrations of Compound 1 were lower when administered with food compared with fasted conditions, and the plasma concentration-time profiles appeared to be smoother, with little evidence of secondary peaking, when fed. The comparison showed that food intake prior to dosing reduced mean $C_{max}$ and mean plasma AUC parameters by approximately 60% and 45%, respectively. FIGS. 26A (linear scale) and 26B (log-linear scale) graphically depict mean plasma concentrations of Compound 1 under fed and fasted conditions. Median $T_{max}$ occurred approximately 1 hour earlier under fed compared with fasted conditions, while $T_{1/2}$ was similar under both fed and fasted conditions (~17 hours). CL/F and Vz/F were higher under fed compared with fasted conditions, while the amount of Compound 1 excreted in the urine (Ae and Fe) was lower under fed compared with fasted conditions. CLr was unaffected by the presence of food. Future dosing regimens are expected to consider the food effect to maximize a patient's exposure to Compound 1.

Figure 27:
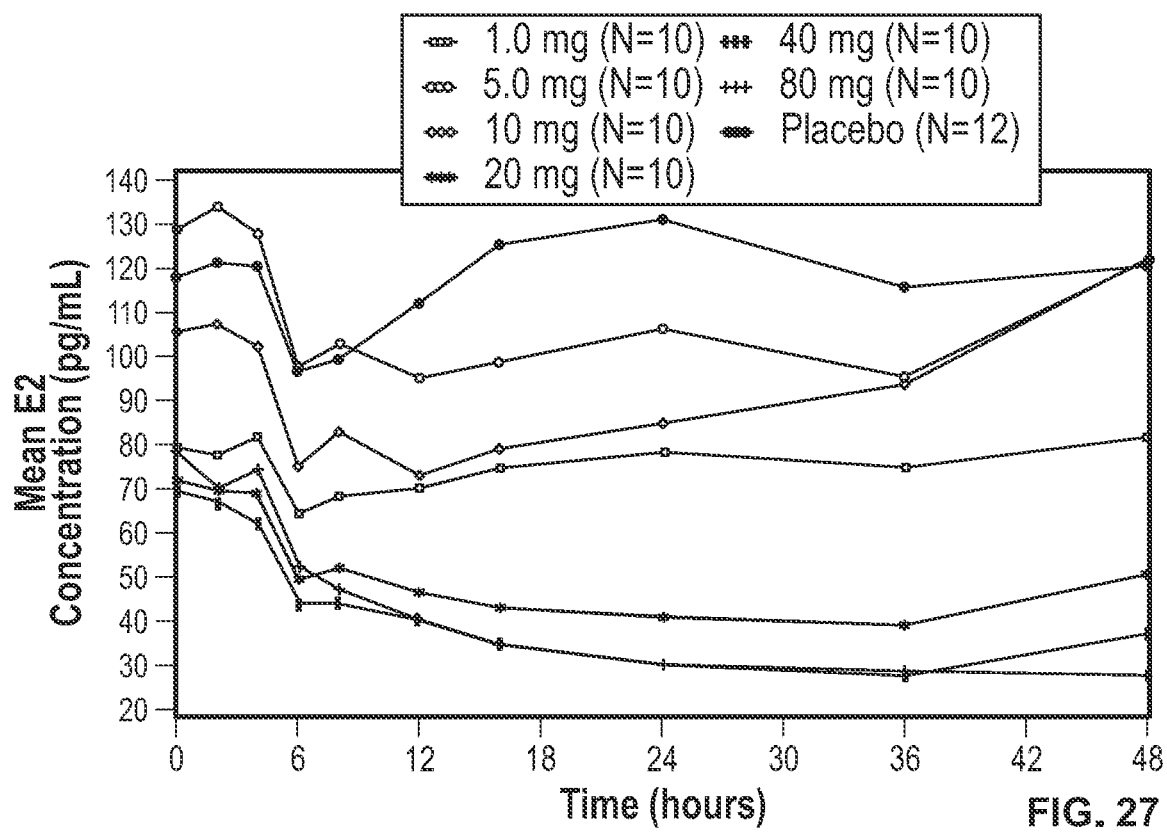
FIG. 27 is a linear scale graph of mean serum estradiol ($E_2$) concentrations following single doses of Compound 1 in accordance with Example 4.

Mean estradiol ($E_2$), LH, and FSH concentrations were suppressed compared with placebo for subjects receiving single doses of Compound 1, and the duration of suppression appeared to increase with increasing dose of Compound 1. Mean $E_2$, LH, and FSH concentrations remained suppressed for 24 to 48 hours dependent on the dose of Compound 1. Following a single dose of placebo, mean estradiol ($E_2$) concentrations decreased at 6 hours postdose, but then increased again, until they had returned to baseline values by approximately 12 to 16 hours postdose. Following single doses of 1 to 80 mg of Compound 1, mean estradiol ($E_2$) concentrations initially decreased to a similar extent compared with placebo, but then stayed suppressed. The duration of suppression increased with increasing dose of Compound 1, such that mean estradiol ($E_2$) concentrations were still fully suppressed at 36 hours postdose following 20 and 40 mg Compound 1 (with concentrations increasing only slightly at 48 hours postdose). Following 80 mg of Compound 1, mean estradiol ($E_2$) concentrations were still fully suppressed at 48 hours postdose. FIG. 27 is a linear scale graph of mean estradiol ($E_2$) concentrations following single doses of Compound 1.

Figure 28:
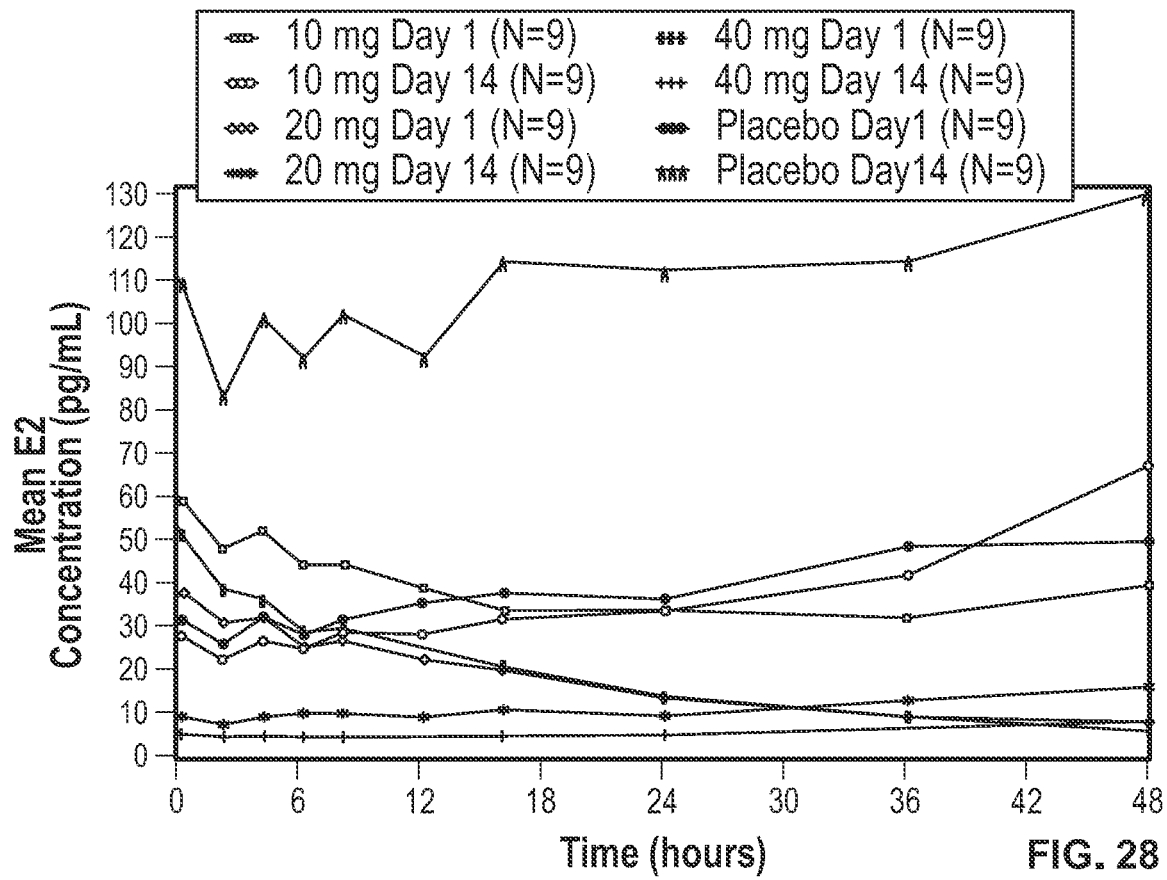
FIG. 28 is a linear scale graph of mean serum estradiol ($E_2$) concentrations following multiple doses of Compound 1 in accordance with Example 4.
Figure 29:
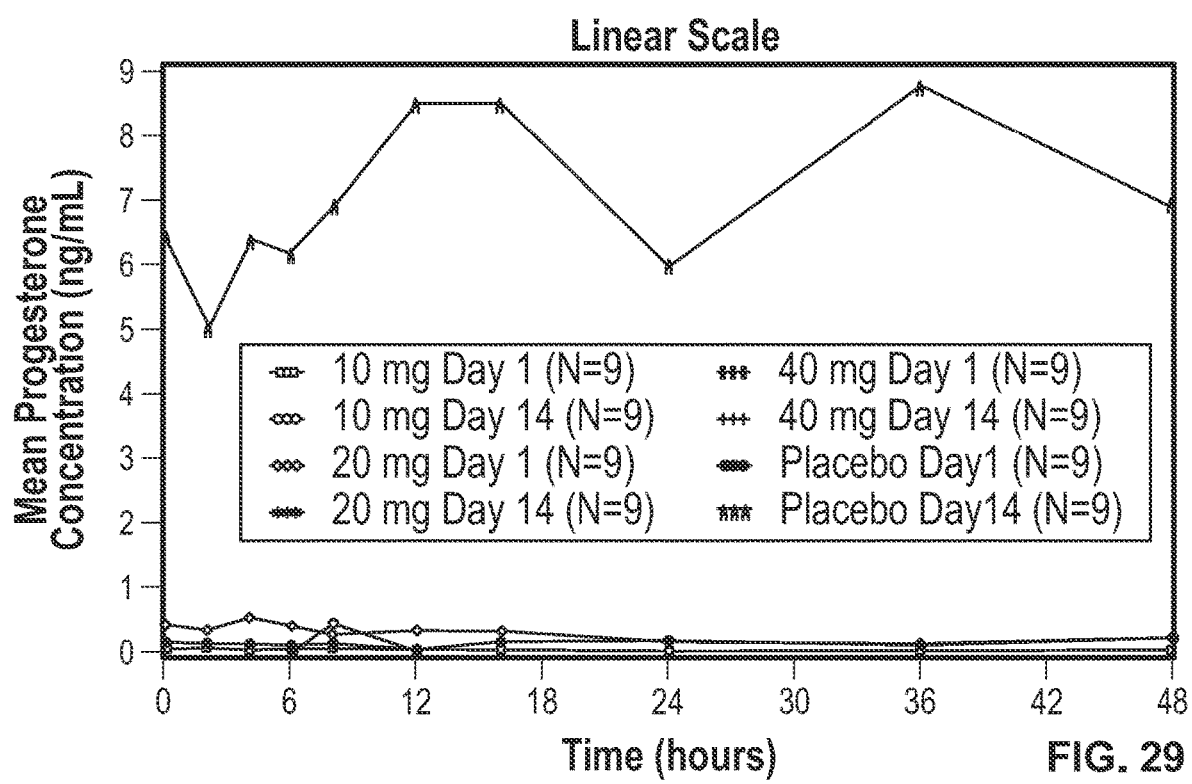
FIG. 29 is a linear scale graph of mean serum progesterone concentrations following multiple doses of Compound 1 in accordance with Example 4.

Multiple doses of Compound 1 also suppressed estradiol ($E_2$), LH, and FSH and progesterone (P) concentrations in a dose-related manner. In the MRD portion of the study, mean $E_2$ concentrations were significantly higher on Day 14 compared with Day 1 in subjects receiving placebo. This increase is consistent with that expected during mid to late cycle in these premenopausal women. However this increase in $E_2$ was not observed in subjects receiving multiple doses of Compound 1 (10 to 40 mg QD), suggesting that $E_2$ suppression was maintained with continued Compound 1 dosing. Likewise, the mid-cycle peak in LH and FSH observed in the placebo group (Days 8-12), was not apparent in subjects receiving the 40 mg Compound 1 QD. While a dose of 5.0 mg of Compound 1 was found to show some $E_2$ suppression in the SRD evaluation, variability in the recorded data was large. Therefore, a 10 mg dose of Compound 1 was chosen as the lowest dose in the MRD evaluation in order to ensure demonstrable suppression of $E_2$ at this level. FIGS. 28 and 29 are linear scale graphs of mean $E_2$ and progesterone concentrations, respectively, following multiple doses of Compound 1.

The natural endogenous increase in progesterone expected post-ovulation, was observed in subjects receiving placebo QD, but not in subjects receiving Compound 1 from 10 mg to 40 mg QD. This suggests that Compound 1 QD prevented ovulation.

There was no apparent effect of Compound 1 on endogenous GH, PRL, thyrotropin, and ACTH.

Urinary 6β-hydroxycortisol to cortisol ratios were similar to baseline values in the SRD and MRD portion of the study, suggesting that Compound 1 at single doses up to 80 mg, and multiple doses up to 40 mg QD, does not inhibit or induce CYP34A.

A total of 68% of subjects experienced one or more adverse event during the study, with no apparent difference between Compound 1 groups and placebo or dose relationship. The majority of adverse events were considered to be of mild intensity. The most common adverse event was headache, and the overall frequency of headache was similar following placebo and Compound 1. Based on these results, Compound 1 was found to appear safe and well tolerated following use of Compound 1 at single doses up to 80 mg and multiple doses up to 40 mg QD for 14 days, in healthy premenopausal women.

Overall, the frequency of adverse events was similar between the placebo and Compound 1 dose groups in both the single dosing and multiple dosing portions of the study with no apparent dose relationship. However, the frequency of drug-related adverse events were higher after the highest single dose (80 mg) and the highest multiple dosing dose (40 mg QD) than in the comparable dose groups, with the increased frequency being spread over several system organ classes.

Mean plasma $T_{1/2}$ was not dependent on dose and was approximately 14 to 16 hours supporting a QD dosage regimen.

CLr was not a substantial pathway of the Compound 1 elimination since less than 3% of the dose was excreted in the urine. CLr was independent of dose or time.

A marked food effect was observed. Food intake prior to dosing reduced mean $C_{max}$ and mean plasma AUC by approximately 60% and 45%, respectively. Notably, the increased exposure associated with fasted dosing was an important finding for the clinical development program overall. Following consideration of the food effect data, dosage regimens will be based upon dosing prior to food intake, so as to ensure that Compound 1 safety evaluation includes circumstances in which potential exposure was maximized for the study subjects.

Serum chemistry, hematology, urinalysis, vital signs, and ECGs were monitored during the study up to 1 week after the last dose. There were no meaningful changes in these parameters in the Compound 1 dose groups compared with placebo. QT and corrected QT interval (QTc) intervals >450 msec and 500 msec were seen across all dose groups, including the placebo group.

Example 5A: A Randomized, Double-Blind, Placebo-Controlled Study of the Efficacy and Safety of Compound 1 in the Treatment of Uterine Fibroids This was a randomized, double-blind, study to evaluate the efficacy and safety of 3 dose levels (10 mg, 20 mg and 40 mg) of 12-week oral administration of the Compound 1 formulation compared with placebo in pre-menopausal (aged ≥20 years) women with uterine fibroids. Study participants were Japanese women with HMB (heavy menstrual bleeding) associated with UF (uterine fibroids).

The primary endpoint was the proportion of patients with a total Pictorial Blood Loss Assessment Chart (PBAC) score 4 of <10 from Week 6 to 12. Secondary endpoints included amenorrhea (PBAC score of 0), myoma and uterine volumes, hemoglobin (Hb), Numerical Rating Scale (NRS) score, Uterine Fibroid Symptom and Quality of Life (UFS-QOL) scores. Serum levels of luteinizing hormone (LH), follicle-stimulating hormone (FSH), estradiol ($E_2$) and progesterone (P) were evaluated as pharmacodynamics endpoints. Safety endpoints included adverse events (AEs), vital signs, weight, 12-lead electrocardiogram (ECG), clinical laboratory tests, bone mineral density (BMD) and recovery of menstruation.

This study consisted of a Pretreatment Period of 4 to 12 weeks, a Treatment Period of 12 weeks, a Follow-Up Period of 4 weeks, and the total period of study participation was 20 to 28 weeks.

To enter the Pre-Treatment Period, subjects had to have been diagnosed with uterine fibroids confirmed by transvaginal ultrasound, abdominal ultrasound, magnetic resonance imaging, computed tomography, or laparoscopy. Additionally, to enter the Pretreatment Period (at Visit 1) and the Treatment Period (at Visit 3), subjects had one or more measureable non-calcified myomas with a longest diameter of >3 cm confirmed by transvaginal ultrasound. Only the largest myomas among those measurable at Visit 1 were measured throughout the study.

All subjects must have experienced one or more regular menstrual cycles immediately prior to Visit 1. Regular menstrual cycles are defined in this application as being 25 to 38 days and including menstrual bleeding of at least 3 consecutive days. Similarly, all subjects had also experienced regular menstrual cycles immediately prior to Visit 2.

Subjects started recording in the patient diary on the day of Visit 1 to the day before Visit 7 (or until early termination). The study drug (placebo) was administered under single-blind conditions from the day of Visit 2 to the day before Visit 3. Visit 2 was on Days 1 to 5 of the first menstruation after Visit 1.

During the period between Visit 2 and 3, in which subjects must have experienced at least 1 regular menstrual cycle, the baseline values concerning efficacy evaluation, including PBAC scores and pain symptoms, were collected. The baseline PBAC score is the total PBAC score for the entire menstrual cycle immediately before Visit 3. A table of demographic and baseline characteristics for the analyses in this example is set forth in FIGS. 30A-H.

To enter the Treatment Period (at Visit 3), subjects must have been diagnosed with heavy menstrual bleeding, and must have had a total PBAC score of ≥120 (corresponding to a blood loss of more than 80 mL) in one menstrual cycle just before Visit 3. Visit 3 was on Days 1 to 5 of the second menstrual cycle after Visit 1. From Visits 3 to 7, subjects tried to visit the clinics in a fasted state and before taking the study drug.

At Visit 3, subjects were randomized to either placebo (57 subjects), or one of the following Compound 1 formulations: 10-mg (48 subjects), 20-mg (56 subjects), and 40-mg (55 subjects). The Compound 1 formulations (10 mg, 20 mg or 40 mg) or placebo were administered from the day of Visit 3 to the day before Visit 7 (or until discontinuation of treatment) under double-blind conditions. Either the Compound 1 formulation or placebo was administered daily as a single oral dose every morning 30 minutes before breakfast. When a dose was missed before breakfast, subjects took the study drug 30 minutes before either dinner or lunch on the same day.

During the course of this study, patients visited the clinic every other week for a month after the start of study drug administration under double-blind conditions (Visit 3), and monthly thereafter. Designated examinations and evaluations were performed at each visit.

At Visit 3, blood was drawn twice, at 0.5 to 1.5 hours postdose and at 2 to 5 hours postdose, from each evaluable subject. At Visits 4, 5 and 6, blood was drawn once immediately prior to the dose for each day, and again at 0.5 to 1.5 hours postdose and at 2 to 5 hours postdose, from each evaluable subject. Blood was drawn only once for patients who took the study drug for the day before visiting the investigational site. At Visit 7, blood was drawn only once at the visit.

Patients: Of 307 screened patients, 216 were randomized and included in the full analysis set and safety analysis set (n=57, placebo group; n=48, Compound 1 10 mg group; n=56, Compound 1 20 mg group; and n=55, Compound 1 40 mg group). Overall, there were no clinically significant differences between the treatment groups in demographic and baseline characteristics (Table 1). There were no apparent differences among the uterine volumes or myoma volumes and the mean baseline PBAC score was slightly higher in the placebo group, compared to the Compound 1 groups.

to 24.6 hours. The AUC from time 0 to infinity ($AUC_{(0-inf)}$) and $C_{max}$ of Compound 1 generally increased in a dose-proportional manner. The $AUC_{(0-tau)}$ and $C_{max}$ on Day 1, and the $C_{max}$ on Day 14 roughly increased in a dose-dependent manner, but the $AUC_{(0-tau)}$ on Day 14 exhibited an increase in a slightly greater than dose-proportional manner. The plasma drug concentration reached steady state by Day 7 of multiple dosing, and the AUC and $C_{max}$ on Day 14 were both higher than the values on Day 1. The AUC after a single dose was higher after fasted dosing than after postprandial or preprandial dosing. The AUC and $C_{max}$ with multiple dosing were higher with preprandial than with postprandial dosing. These findings suggest that, in one embodiment, food affects the pharmacokinetics of the Compound 1 formulation. However, in a preferred embodiment, the pharmacokinetics of the Compound 1 formulation are not affected by food intake.

Blood LH, FSH, $E_2$, and P concentrations roughly decreased in a dose-proportional manner following a single dose of the Compound 1 formulation (10 to 40 mg) in comparison to placebo. The LH and $E_2$ concentrations showed a rapid decrease after each dose in all subjects (except one), and kept decreasing throughout the treatment period. The plasma P concentrations showed a rapid decrease after dosing with all dose levels and regimens, and suppression was maintained throughout the treatment period. The plasma FSH concentrations also showed a rapid decrease after dosing with all dose levels and regimens, and

TABLE 1

Demographic and Baseline Characteristics

| Characteristic | Placebo (n = 57) | Relugolix 10 mg (n = 48) | Relugolix 20 mg (N = 56) | Relugolix 40 mg (n = 55) |
|---|---|---|---|---|
| Age (years) | 42 (5.0) | 43 (4.6) | 43 (5.3) | 41 (4.4) |
| BMI (kg/m$^2$) | 24 (4.2) | 23 (2.7) | 22 (2.8) | 22 (2.8) |
| Birth experience | 30 (52.6) | 25 (52.1) | 29 (51.8) | 20 (36.4) |
| Type of uterine fibroid | | | | |
| Subserosal fibroid | 23 (40.4) | 22 (45.8) | 25 (44.6) | 17 (30.9) |
| Intramural fibroid | 42 (73.7) | 39 (81.3) | 44 (78.6) | 45 (81.8) |
| Submucosal fibroid | 12 (21.1) | 11 (22.9) | 11 (19.6) | 11 (20.0) |
| Cervical fibroid | 1 (1.8) | 1 (2.1) | 1 (1.8) | 2 (3.6) |
| Myoma volume (cm$^3$) | 136 (159.1) | 116 (127.4) | 119 (117.4) | 138 (199.8) |
| Uterine volume (cm$^3$) | 367 (276.6) | 322 (285.0) | 363 (304.6) | 407 (361.8) |
| PBAC score | 328 (292.1) | 269 (160.8) | 276 (165.9) | 260 (190.5) |
| NRS score | 0.8 (0.80) | 0.7 (1.13) | 0.8 (0.93) | 0.6 (0.60) |
| UFS-QOL score | | | | |
| Symptom severity | 28 (17.7) | 29 (17.3) | 26 (14.4) | 25 (14.0) |
| HRQL total | 16 (18.8) | 14 (11.9) | 13 (11.5) | 12 (15.5) |
| Hemoglobin (g/dL) | 12.1 (1.50) | 12.2 (1.16) | 12.2 (1.41) | 12.0 (1.70) |

Mean (SD) or number of patients (%)

The plasma drug concentration after a single dose of the Compound 1 formulation at 1 to 80 mg reached a peak ($C_{max}$) at 0.5 to 4.0 hours postdose (maximum drug concentration time [$T_{max}$]), with a mean plasma half-life ($T_{1/2}$) of 7.1 to 19.8 hours. The AUC and $C_{max}$ exhibited an increase in a slightly greater than dose-proportional manner. The plasma drug concentration on Day 14 of multiple doses of 10 to 40 mg reached a peak ($C_{max}$) at 1 to 1.5 hours postdose ($T_{max}$), with a mean plasma half-life ($T_{1/2}$) of 19.2 remained suppressed throughout the treatment period in the groups given 40 mg of Compound 1 preprandially or postprandially.

The most common treatment-emergent adverse events (occurring >10% and more than placebo) include hot flash, metrorrhagia (irregular menstrual bleeding), menorrhagia (or HMB), headache, genital hemorrhage. No serious treatment-emergent adverse event considered related to study drug was observed. The adverse event rates are summarized in Table 2.

TABLE 2

AE Summary

| Variables, n (%) | Placebo (n = 57) | Relugolix 10 mg (n = 48) | Relugolix 20 mg (N = 56) | Relugolix 40 mg (n = 55) |
|---|---|---|---|---|
| Any AEs | 40 (70.2) | 41 (85.4) | 54 (96.4) | 49 (89.1) |
| Mild | 34 (59.6) | 36 (75.0) | 47 (83.9) | 46 (83.6) |
| Moderate | 6 (10.5) | 5 (10.4) | 7 (12.5) | 2 (3.6) |
| Severe | 0 (0.0) | 0 (0.0) | 0 (0.0) | 1 (1.8) |
| AEs related to study drug | 23 (40.4) | 33 (68.8) | 51 (91.1) | 45 (81.8) |
| AEs leading to study drug discontinuation | 1 (1.8) | 0 (0.0) | 1 (1.8) | 0 (0.0) |
| Serious AEs | 1 (1.8) | 0 (0.0) | 1 (1.8) | 1 (1.8) |
| Common AEs (≥10% of patients in any group) | | | | |
| Nasopharyngitis | 16 (28.1) | 9 (18.8) | 4 (7.1) | 7 (12.7) |
| Hot flush | 2 (3.5) | 2 (4.2) | 1.6 (28.6) | 21 (38.2) |
| Metrorrhagia | 10 (17.5) | 13 (27.1) | 17 (30.4) | 15 (27.3) |
| Menorrhagia | 4 (7.0) | 6 (12.5) | 13 (23.2) | 12 (21.8) |
| Headache | 1 (1.8) | 1 (2.1) | 8 (14.3) | 8 (14.5) |
| Genital haemorrhage | 2 (3.5) | 2 (4.2) | 6 (10.7) | 6 (10.9) |
| Menstruation irregular | 0 (0.0) | 12 (25.0) | 8 (14.3) | 3 (5.5) |

FIG. 31 shows total PBAC scores, and FIG. 32 shows change from baseline in total PBAC scores, from Weeks 6 to 12 following administering placebo or one of the three Compound 1 formulations (10 mg, 20 mg and 40 mg) to a subject for the treatment period of 12 weeks.

The proportion of subjects with a total PBAC score of <10 from Week 6 to 12 was evaluated as the primary endpoint. FIG. 33 shows the proportion of subjects that met this primary endpoint based on uterine volumes at baseline. The proportion of subjects with a total PBAC score of <10 from Week 6 to 12 was 0% in placebo, 20.8% in the Compound 1 formulation 10-mg group, 43.6% in the Compound 1 formulation 20-mg group, and 83.6% in the Compound 1 formulation 40-mg group. Thus, a higher proportion of subjects achieved the primary endpoint of the study in the Compound 1 formulation 40-mg group, suggesting a dose-response relationship. A statistically significant difference in proportion of the subjects with a total PBAC score of <10 from Week 6 to 12 between each Compound 1 formulation group and placebo was observed, and the superiority of each Compound 1 formulation group to placebo was demonstrated. A dose-dependent decrease in myoma and uterine volumes were observed. The incidence of headache, metrorrhagia, menorrhagia, and hot flash were more than 10% higher in Compound 1 20-mg and 40-mg groups than in placebo group; these AEs were mild or moderate in severity.

The proportion of subjects with a total PBAC score of <10 from Week 2 to 6 and Week 2 to 12 were evaluated as secondary endpoints. The proportion of subjects with a total PBAC score of <10 from Week 2 to 6 was 0% in placebo, 16.7% in the Compound 1 formulation 10-mg group, 42.9% in the Compound 1 formulation 20-mg group, and 65.5% in the Compound 1 formulation 40-mg group. The proportion of subjects with a total PBAC score of <10 from Week 2 to 12 was 0% in placebo, 12.5% in Compound 1 10-mg, 32.1% in the Compound 1 formulation 20-mg group, and 61.8% in the Compound 1 formulation 40-mg group.

The proportion of subjects who achieved amenorrhea (had a total PBAC score equal to 0) from Week 6 to 12, from Week 2 to 6, and from Week 2 to 12 were evaluated as secondary endpoints. The proportion of subjects who achieved amenorrhea from Week 6 to 12 was 0% in placebo, 16.7% in the Compound 1 formulation 10-mg group, 38.2% in the Compound 1 formulation 20-mg group, and 72.7% in the Compound 1 formulation 40-mg group. The proportion of subjects who achieved amenorrhea from Week 2 to 6 was 0% in placebo, 12.5% in the Compound 1 formulation 10-mg group, 33.9% in the Compound 1 formulation 20-mg group, and 54.5% in the Compound 1 formulation 40-mg group. The proportion of subjects who achieved amenorrhea from Week 2 to 12 was 0% in placebo, 10.4% in the Compound 1 formulation 10-mg group, 28.6% in the Compound 1 formulation 20-mg group, and 52.7% in the Compound 1 formulation 40-mg group.

The total PBAC score (mean±SD) from week 6 to 12 was 405.2±353.71 in placebo, 268.0±276.37 in the Compound 1 formulation 10-mg group, 126.0±188.55 in the Compound 1 formulation 20-mg group, and 21.3±56.11 in the Compound 1 formulation 40-mg group. The change of total PBAC score from baseline was 77.3±255.54 in placebo, −1.4±222.94 in the Compound 1 formulation 10-mg group, −153.0±194.83 in the Compound 1 formulation 20-mg group, and −238.7±203.34 in the Compound 1 formulation 40-mg group.

Myoma volume was evaluated as a secondary endpoint. Referring to FIG. 34, the myoma volumes at Weeks 0, 2, 4, 8 and 12 (mean±SD) were 136.13±159.111 $cm^3$, 134.42±140.559 $cm^3$, 136.44±159.095 $cm^3$, 132.79±140.825 $cm^3$, and 128.26±130.414 $cm^3$, respectively, in placebo; 115.57±127.396 $cm^3$, 116.68±152.833 $cm^3$, 90.89±108.009 $cm^3$, 97.47±117.339 $cm^3$, and 97.09±126.578 $cm^3$, respectively, in the Compound 1 formulation 10-mg group; 118.68±117.364 $cm^3$, 98.63±112.118 $cm^3$, 101.51±132.419 $cm^3$, 86.34±103.084 $cm^3$, and 75.09±89.699 $cm^3$, respectively, in the Compound 1 formulation 20-mg group, and 138.00±199.758 $cm^3$, 109.29±132.534 $cm^3$, 100.04±139.060 $cm^3$, 86.01±120.639 $cm^3$, and 77.88±110.873 $cm^3$, respectively, in the Compound 1 formulation 40-mg group. The percent change of myoma volume at Week 12 from baseline was 10.19±47.159% in placebo, −22.63±29.539% in the Compound 1 formulation 10-mg group, −36.69±32.631% in the Compound 1 formulation 20-mg group, and −38.59±34.197% in the Compound 1 formulation 40-mg group. The myoma volumes showed almost no changes during the treatment period in placebo group. However, in the Compound 1 formulation groups, these volumes tended to decrease from Week 2 and thereafter continued to decrease depending on the duration of treatment and dose levels of the Compound 1 formulation.

Uterine volume was also evaluated as a secondary endpoint. Referring to FIG. 35, the uterine volumes at Weeks 0, 2, 4, 8 and 12 (mean±SD) were 366.51±276.607 cm$^3$, 384.88±313.354 cm$^3$, 381.17±298.220 cm$^3$, 380.19±289.302 cm$^3$, and 379.38±300.058 cm$^3$, respectively, in placebo; 322.12±285.002 cm$^3$, 305.07±265.810 cm$^3$, 258.10±171.703 cm$^3$, 259.64±190.452 cm$^3$, and 252.93±175.064 cm$^3$ in the Compound 1 formulation 10-mg group; 363.33±304.622 cm$^3$, 294.81±269.990 cm$^3$, 291.73±327.844 cm$^3$, 290.93±413.549 cm$^3$, and 259.44±322.759 cm$^3$ in the Compound 1 formulation 20-mg group; and 406.63±361.814 cm$^3$, 293.51±288.596 cm$^3$, 267.74±275.256 cm$^3$, 224.91±227.442 cm$^3$, and 208.03±209.312 cm$^3$ in the Compound 1 formulation 40-mg group. The percent change of uterine volume at Week 12 from baseline was 9.75±57.946% in placebo, −12.10±29.936% in the Compound 1 formulation 10-mg group, −27.70±28.787% in the Compound 1 formulation 20-mg group, and −40.90±37.233% in the Compound 1 formulation 40-mg group. The uterine volumes showed almost no changes during the treatment period in placebo group. However, in the Compound 1 formulation groups, these volumes tended to decrease from Week 2 and thereafter decreased depending on the duration of treatment and dose of the Compound 1 formulation.

Figure 38:
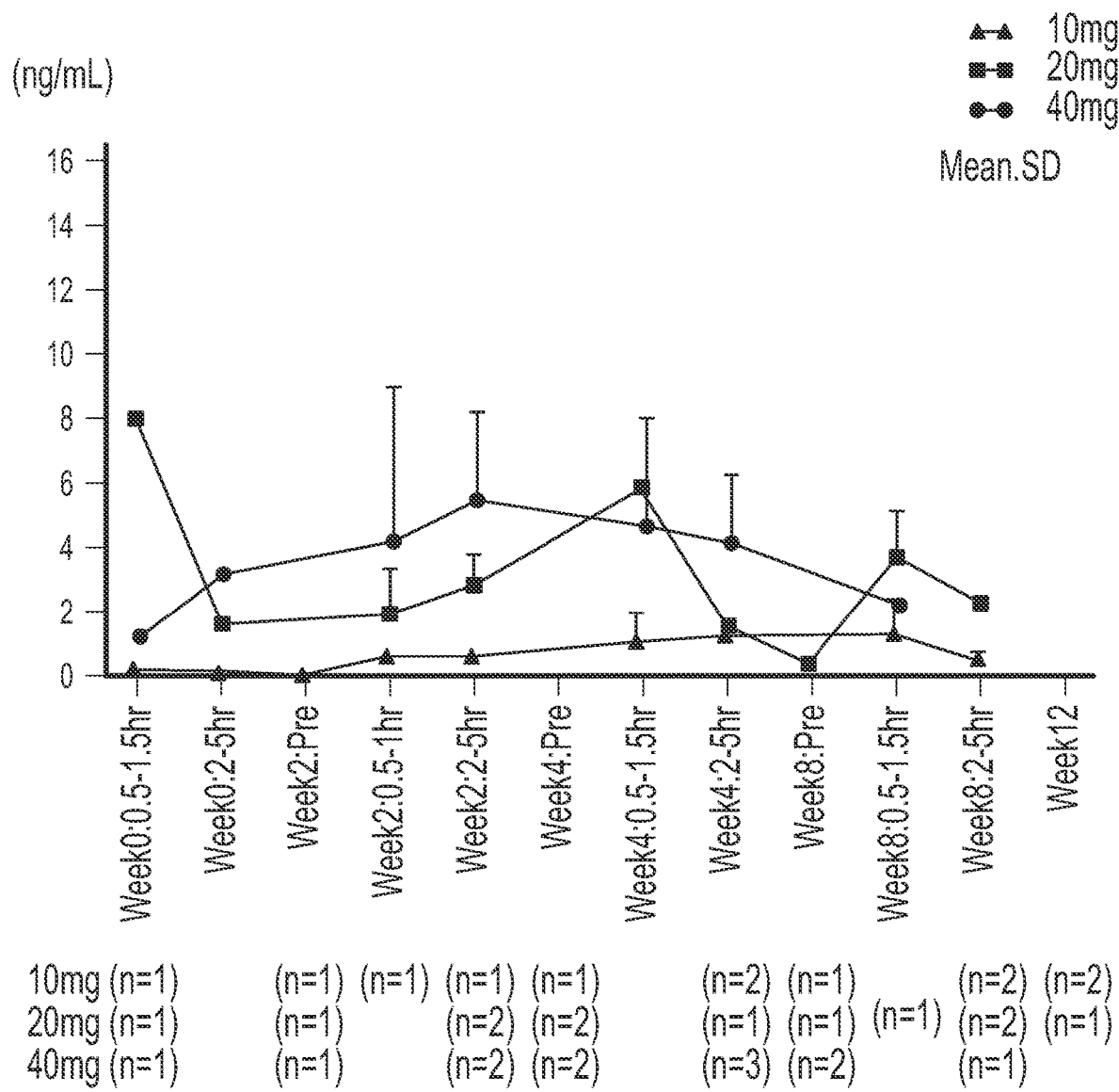
FIG. 38 graphically depicts plasma concentrations of unchanged Compound 1 for a treatment period of 12 weeks in accordance with Example 5A.
Figure 56A:
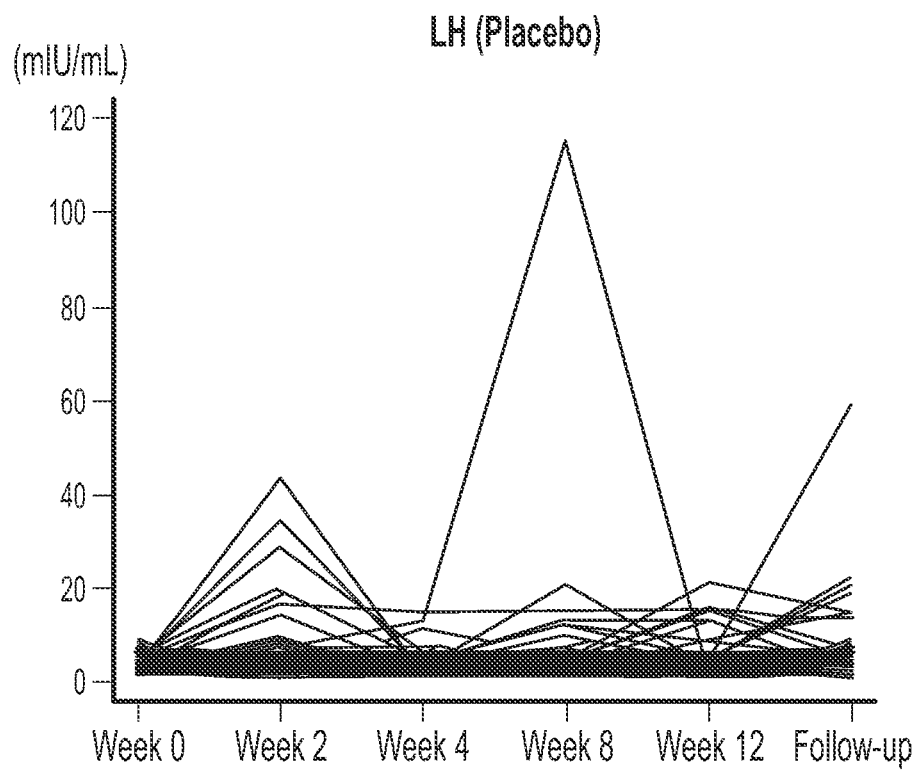
FIGS. 56A-D are plots depicting serum LH concentrations for a treatment period of 12 weeks in accordance with Example 5A.
Figure 56B:
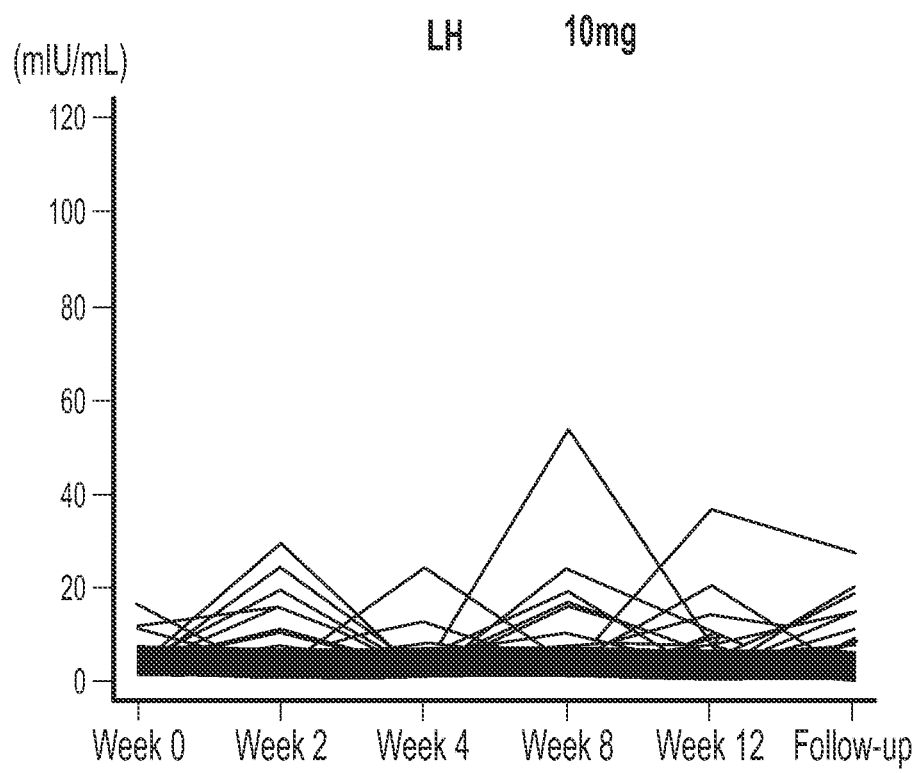
Figure 56C:
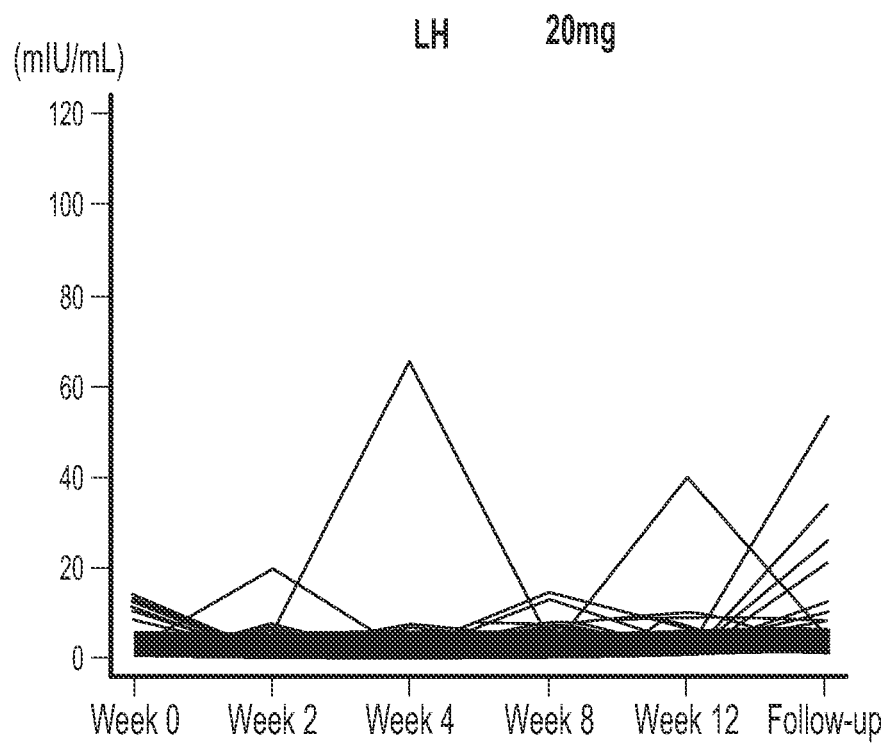
Figure 56D:
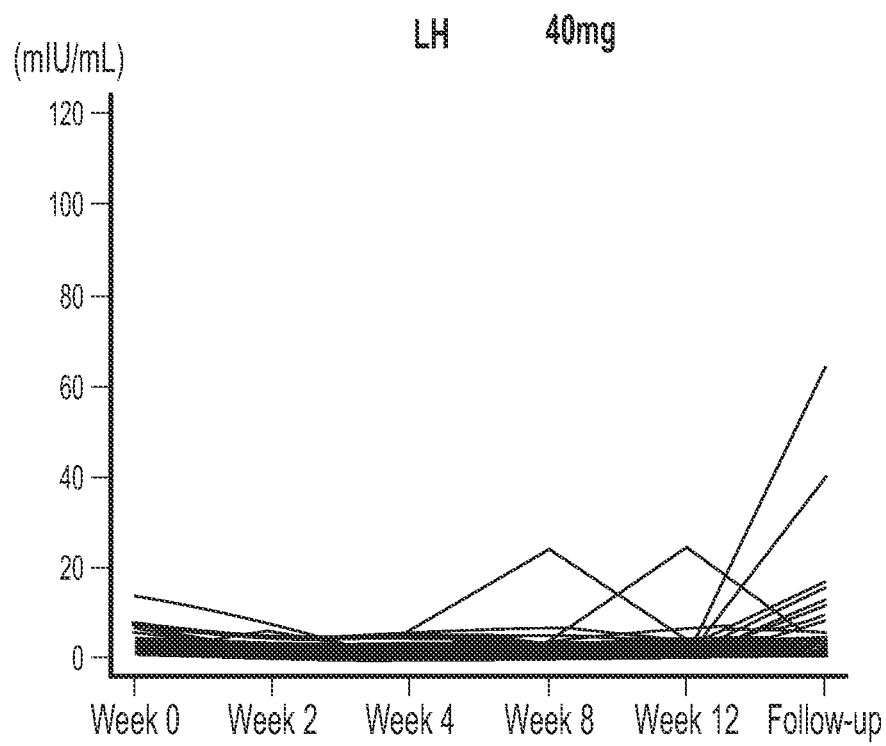
Figure 58A:
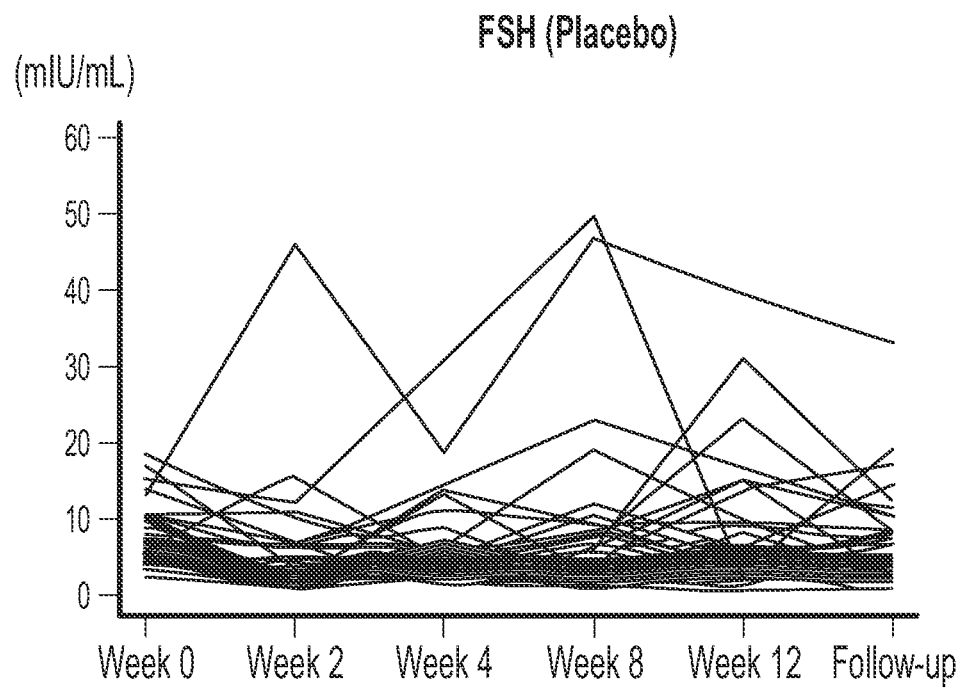
FIGS. 58A-D are plots depicting serum FSH concentrations for a treatment period of 12 weeks in accordance with Example 5A.
Figure 58B:
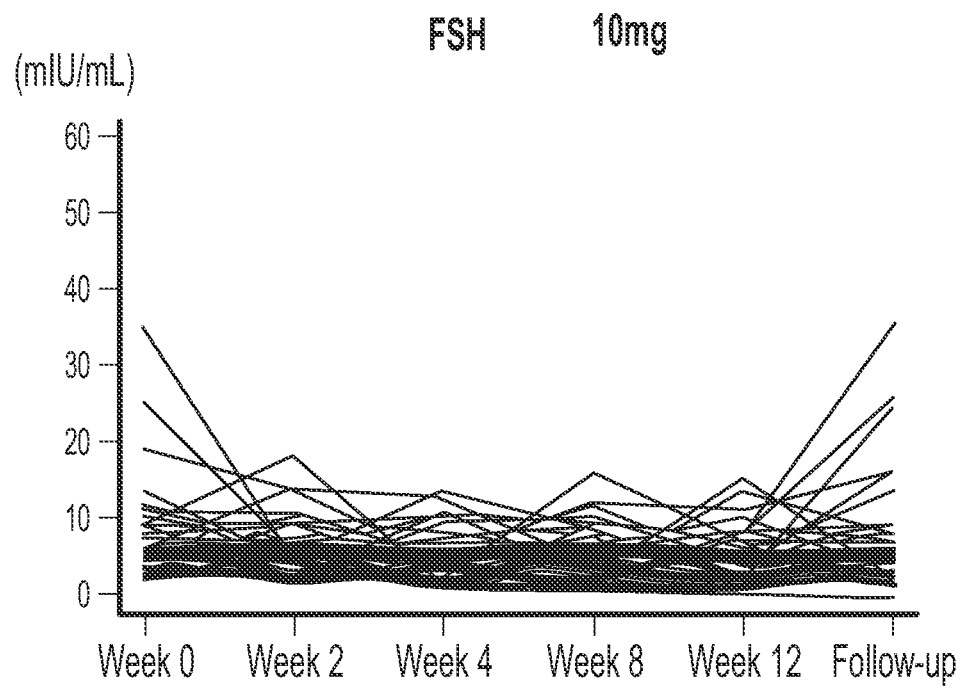
Figure 58C:
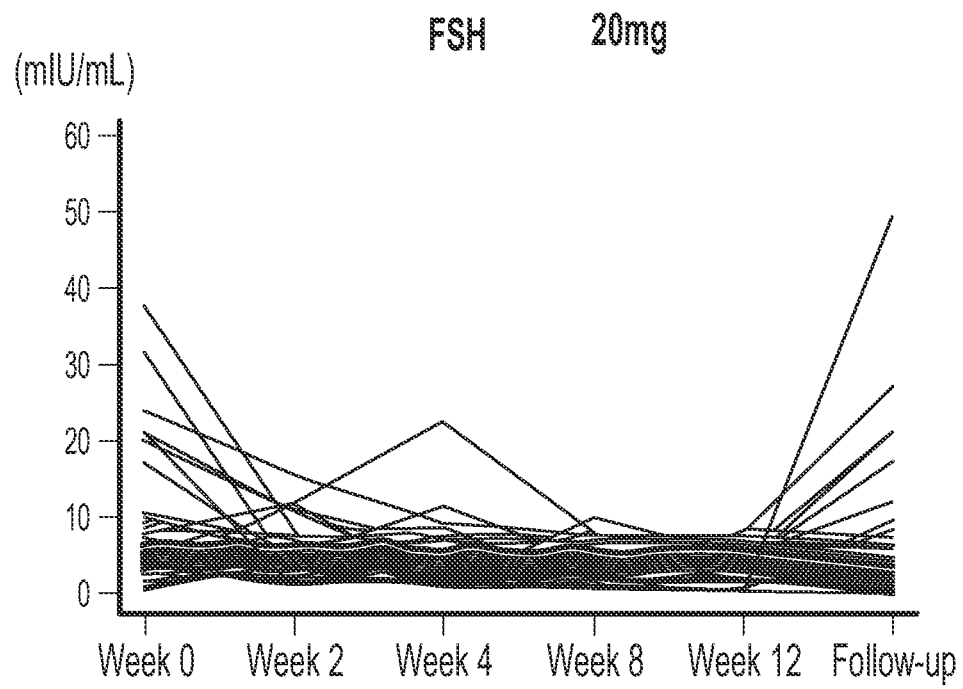
Figure 58D:
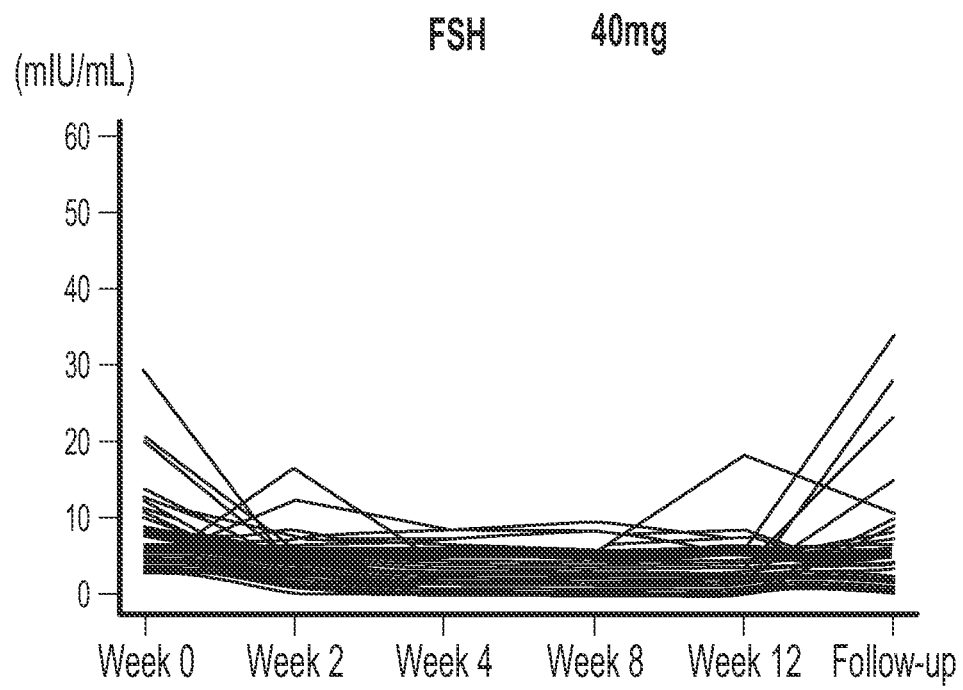
Figure 60A:
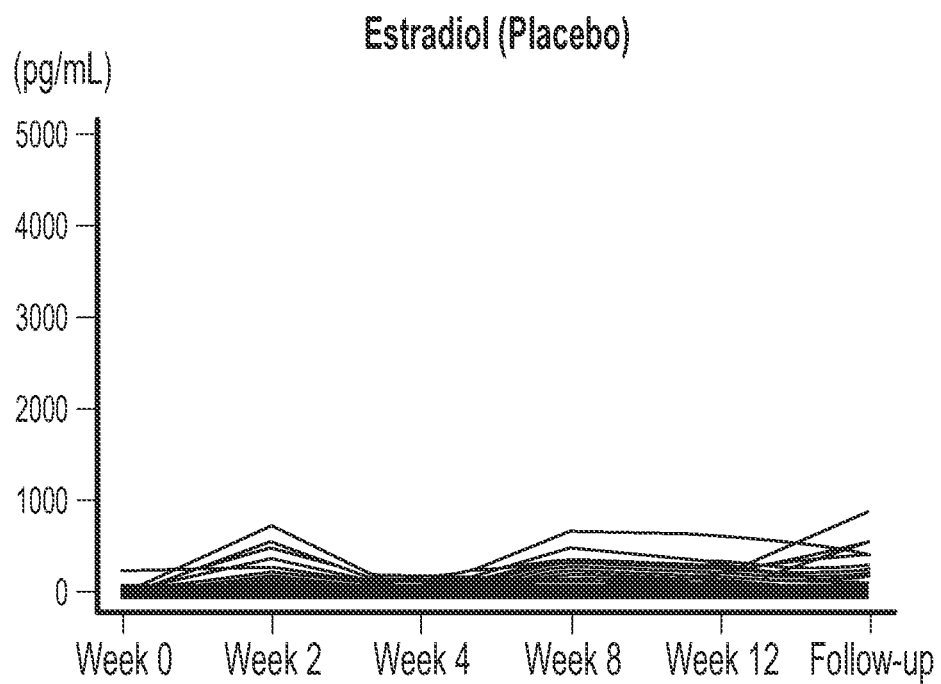
FIGS. 60A-D are plots depicting serum $E_2$ concentrations for a treatment period of 12 weeks in accordance with Example 5A.
Figure 60B:
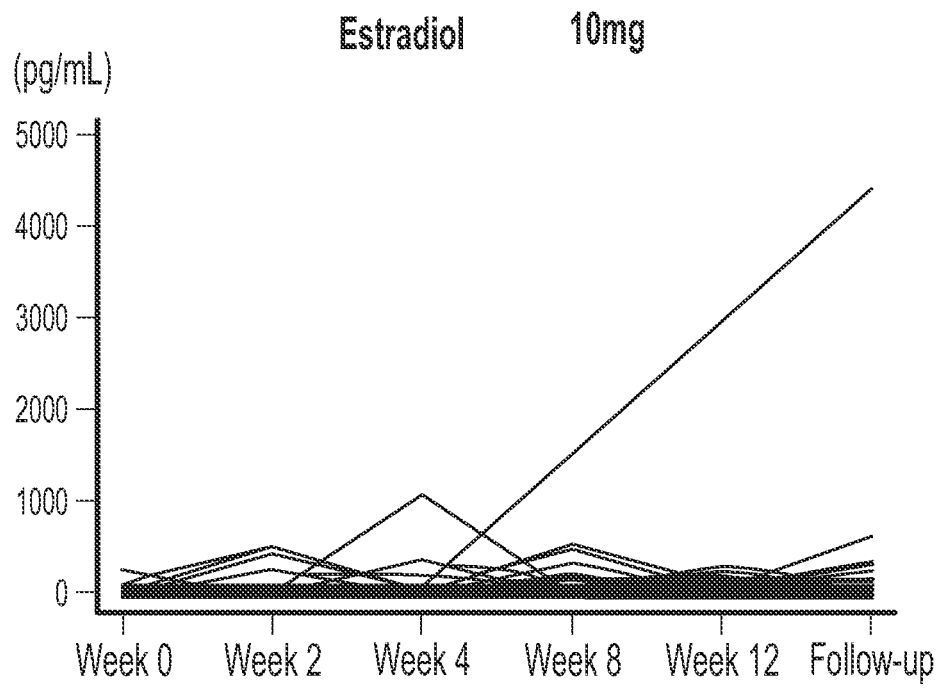
Figure 60C:
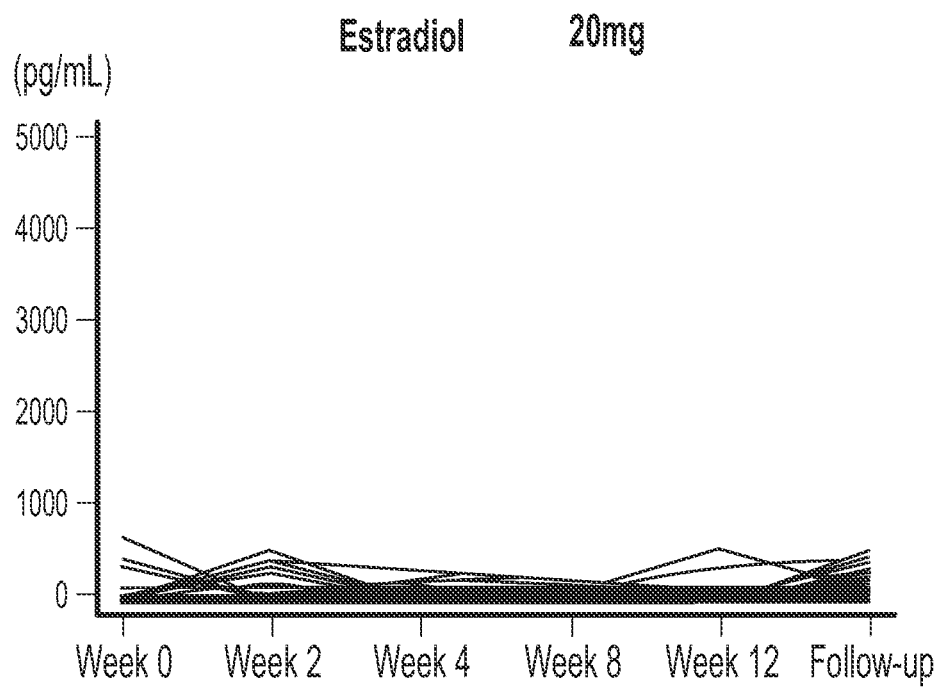
Figure 60D:
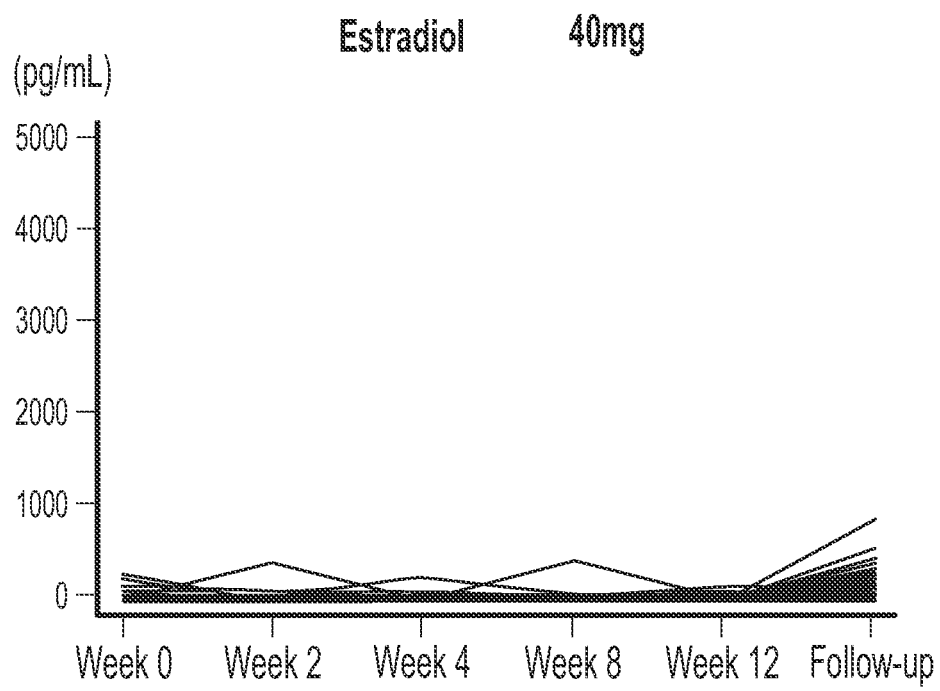
Figure 62A:
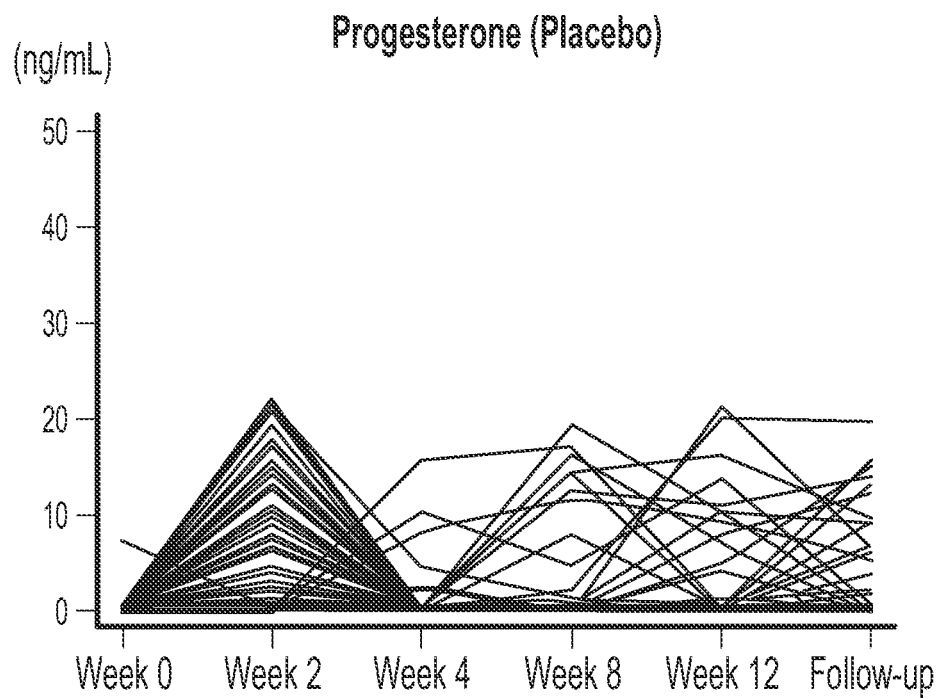
FIGS. 62A-D are plots depicting serum P concentrations for a treatment period of 12 weeks in accordance with Example 5A.
Figure 62B:
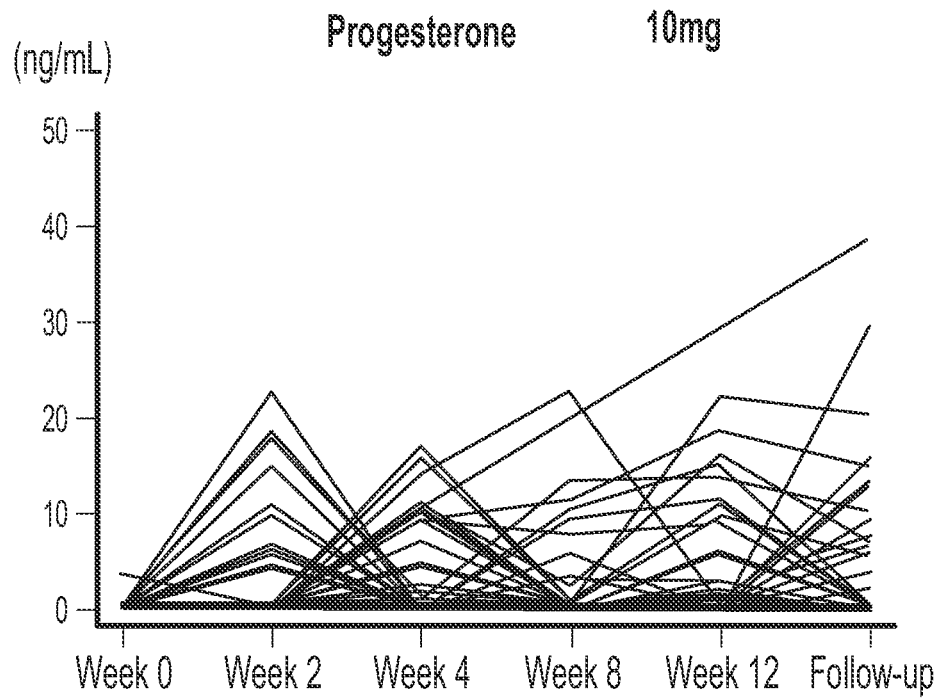
Figure 62C:
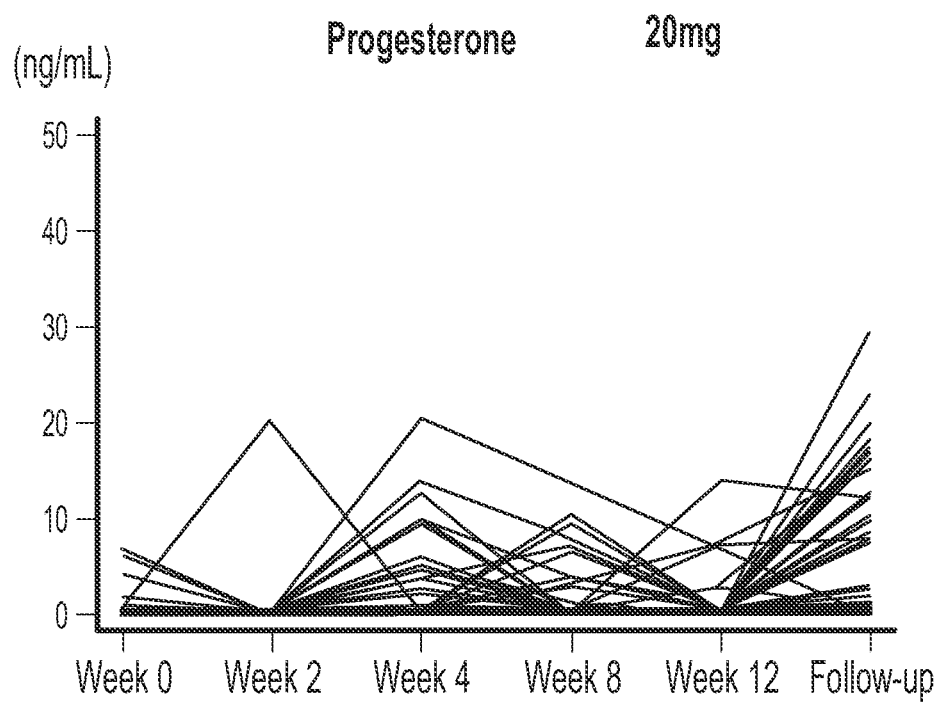
Figure 62D:
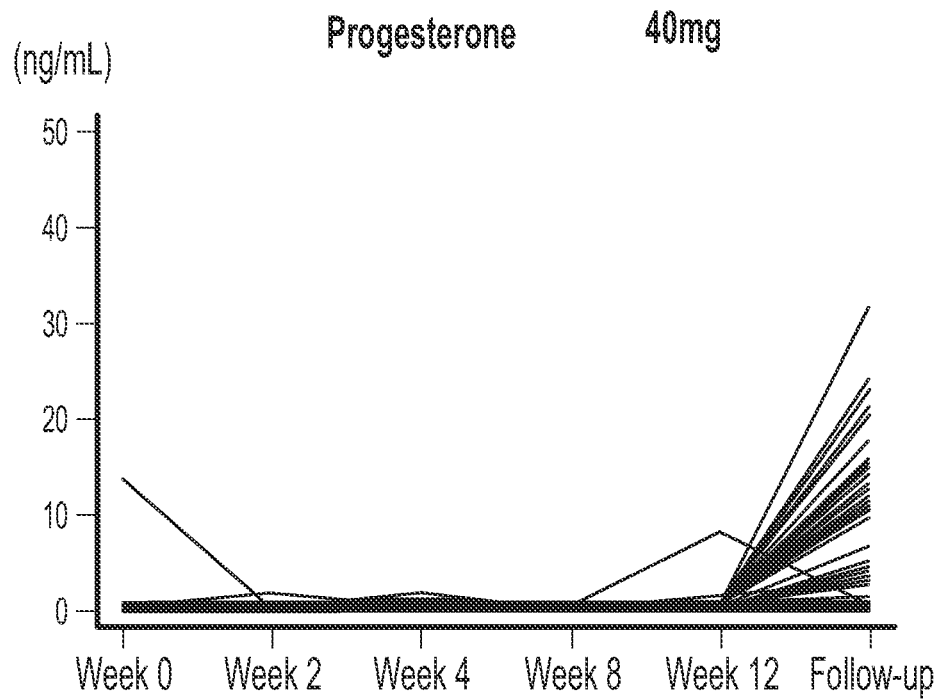

Among the 10 mg, 20 mg and 40 mg of Compound 1 formulations, the plasma drug concentrations of unchanged Compound 1 were highest at 0.5 to 1.5 hours after administration in all treatment groups. The plasma drug concentrations prior to administration in each visit (the trough values) were comparable in each treatment group, showing that the steady state had already been reached by 2 weeks after administration of the Compound 1 formulation. Population PK analysis revealed that the observed profiles of plasma concentrations of unchanged Compound 1 formulation were adequately described by a 2-compartmental model with first-order elimination (fed condition) and dose dependence of relative bioavailability, and no covariates were identified to effect the pharmacokinetics of the Compound 1 formulations. FIG. 38 graphically depicts plasma concentrations of unchanged Compound 1 for a treatment period of 12 weeks in accordance with Example 5A. FIG. 37 is a table of plasma concentrations of unchanged Compound 1 depicted in FIG. 38.

Figure 36:
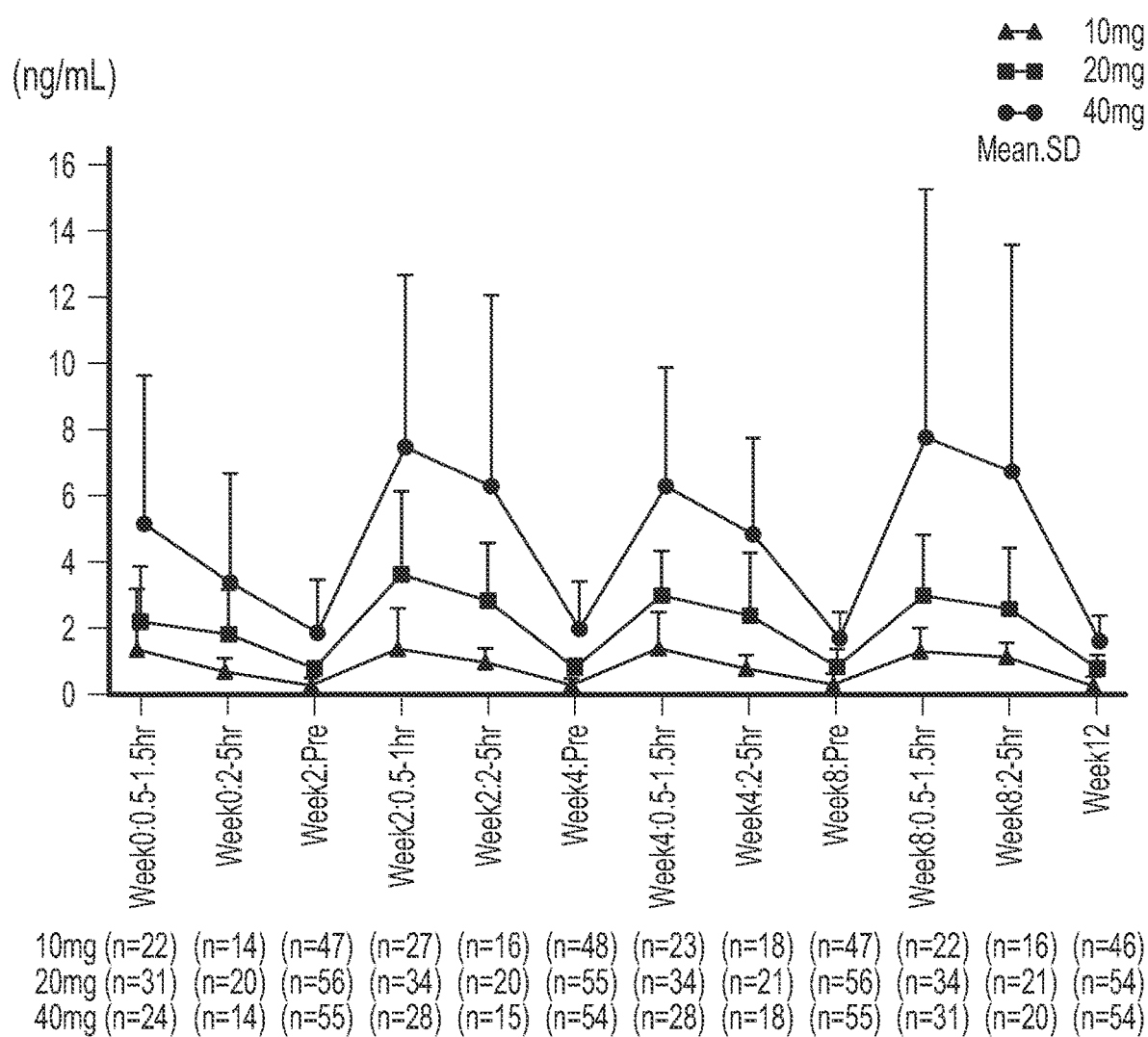
FIG. 36 graphically depicts plasma concentrations of unchanged Compound 1 for a treatment period of 12 weeks in which Compound 1 was administered 30 minutes before a meal in accordance with Example 5A.

The plasma drug concentrations of unchanged Compound 1 were lower in subjects when the study drug was administered 30 minutes before a meal. Plasma drug concentrations of unchanged Compound 1 for the treatment period of 12 weeks in which Compound 1 was administered 30 minutes before a meal are graphically depicted in FIG. 36 and tabulated in FIG. 39. Plasma drug concentrations of unchanged Compound 1 for the treatment period of 12 weeks in which Compound 1 was not administered 30 minutes before a meal are tabulated in FIG. 40.

Relative bioavailability was found to be 30.9% higher in the Compound 1 formulation 40-mg compared with the Compound 1 formulation 10-mg. Considerable variability in the absorption profiles among subjects was observed. The first order absorption rate constant (ka) was estimated only for subjects who had at least one sample collected in the absorption phase. The estimated population values for the absorption rate constant (ka) and apparent oral clearance (CL/F) were 0.416 h$^{-1}$ (CV % 21.5) and 198 L/hr (CV % 7.83).

Pain symptoms, other clinical symptoms and QOL were measured as secondary endpoints. Pain symptoms were evaluated in the patient diary from Visit 1 to the day before Visit 7 using the NRS score. The UFS-QOL score was used to evaluate other clinical symptoms and the QOL of subjects. Subjects completed the UFS-QOL questionnaire at Visits 3, 5, 6 and 7.

The NRS scores are tabulated in FIG. 41. The NRS score from Week 6 to 12 (mean SD) was 0.82±0.989 in placebo, 0.61±1.235 in the Compound 1 formulation 10-mg group, 0.35±0.618 in the Compound 1 formulation 20-mg group, and 0.25±0.542 in the Compound 1 formulation 40-mg group. The NRS score from Week 2 to 6 (mean±SD) was 0.82±1.045 in placebo, 0.67±1.228 in the Compound 1 formulation 10-mg group, 0.48±0.970 in the Compound 1 formulation 20-mg group, and 0.29±0.564 in the Compound 1 formulation 40-mg group. The NRS score from Week 2 to 12 (mean±SD) was 0.82±0.992 in placebo, 0.63±1.217 in the Compound 1 formulation 10-mg group, 0.44±0.855 in the Compound 1 formulation 20-mg group, and 0.27±0.535 in the Compound 1 formulation 40-mg group.

FIGS. 42-49 show UFS-QOL scores following administering placebo and one or more of the three Compound 1 formulations (10 mg, 20 mg and 40 mg) to a subject for a treatment period of 12 weeks. In particular, FIG. 42 tabulates UFS-QOL scores measuring symptom severity; FIG. 43 tabulates the UFS-QOL HRQL total score; FIG. 44 tabulates the UFS-QOL score measuring concern of the subject; FIG. 45 tabulates the UFS-QOL score measuring effect on activities of the subject; FIG. 46 tabulates the UFS-QOL score measuring effect on energy/mood of the subject; FIG. 47 tabulates the UFS-QOL score measuring effect on control of the subject; FIG. 48 tabulates the UFS-QOL score measuring effect on self-consciousness of the subject; and FIG. 49 tabulates the UFS-QOL score measuring effect on sexual function of the subject.

Referring to FIG. 42, the UFS-QOL scores measuring symptom severity (mean±SD) at Weeks 0, 4, 8 and 12 were 27.64±17.726, 25.01±16.990, 25.68±17.291, and 23.48±17.226, respectively, in placebo; 29.31±17.291, 23.78±14.736, 24.55±16.105, and 23.28±16.053 in the Compound 1 formulation 10-mg group; 25.84±14.431, 23.12±14.327, 18.53±13.304, and 16.56±14.024 in the Compound 1 formulation 20-mg group, and 25.29±13.989, 24.10±16.141, 18.08±15.187, and 14.05±15.272 in the Compound 1 formulation 40-mg group. The change (mean±SD) at Week 12 from baseline was −3.58±13.325 in placebo, −6.51±18.122 in the Compound 1 formulation 10-mg group, −8.97±15.530 in the Compound 1 formulation 20-mg group, and −11.25±17.274 in the Compound 1 formulation 40-mg group.

Referring to FIG. 43, the UFS-QOL scores measuring total health-related quality of life (HRQL total) (mean±SD) at Weeks 0, 4, 8 and 12 were 16.06±18.797, 14.19±17.284, 13.32 18.601, and 14.19±18.797, respectively, in placebo; 14.35±11.914, 11.28±10.342, 13.39±13.179, and 13.01±13.270 in the Compound 1 formulation 10-mg group; 12.79±11.510, 11.10±13.829, 9.54±10.904, and 9.63±12.735 in the Compound 1 formulation 20-mg group; and 15.04±15.536, 11.31±12.082, 11.20±12.279, and 9.52±10.885 in the Compound 1 formulation 40-mg group. The change (mean±SD) at Week 12 from baseline was −2.20±11.555 in placebo, −1.61±10.586 in the Compound 1 formulation 10-mg group, −2.11±10.529 in the Compound 1 formulation 20-mg group, and −5.52±15.871 in the Compound 1 formulation 40-mg group.

Assessment in the bleeding profile was evaluated by measuring anemia-related parameters, including hemoglobin (Hb), hematocrit (Ht), ferrum (Fe), and ferritin following administering placebo or one of the Compound 1 formulations (10 mg, 20 mg and 40 mg) to a subject for a treatment period of 12 weeks. In particular, FIGS. 50-52 tabulate hemoglobin concentrations; FIG. 53 tabulates hematocrit percentages; FIG. 54 tabulates serum iron concentrations; and FIG. 55 tabulates ferritin concentrations. Specifically, FIG. 51 shows subjects who took iron drug concomitant medications, and FIG. 52 shows subjects who did not take iron drug concomitant medications.

Referring to FIG. 50, the blood concentrations of Hb (mean±SD) at Weeks 0, 4, 8 and 12 were 12.11±1.504 g/dL, 12.15±1.518 g/dL, 12.33±1.554 g/dL, and 12.42±1.353 g/dL, respectively, in placebo; 12.18±1.159 g/dL, 12.56±1.191 g/dL, 12.55±1.164 g/dL, and 12.55±1.350 g/dL in the Compound 1 formulation 10-mg group; 12.15±1.407 g/dL, 12.79±1.495 g/dL, 12.88±1.379 g/dL, and 12.94±1.225 g/dL in the Compound 1 formulation 20-mg group; and 11.99±1.699 g/dL, 12.45±1.644 g/dL, 12.81±1.543 g/dL, and 12.91±1.380 g/dL in the Compound 1 formulation 40-mg group. The change of blood concentration of Hb at Week 12 from baseline was 0.20±1.003 g/dL in placebo, 0.35±1.055 g/dL in the Compound 1 formulation 10-mg group, 0.83±1.161 g/dL in the Compound 1 formulation 20-mg group, and 0.92±1.183 g/dL in the Compound 1 formulation 40-mg group. Thus, the blood concentrations of Hb increased in the Compound 1 formulations 20-mg and 40-mg as compared with placebo. Referring to FIGS. 51-52, the blood concentrations of Hb in the Compound 1 formulation groups, there is shown an increasing tendency irrespective of presence or absence of iron preparation.

Referring to FIG. 53, the Ht values (mean±SD) at Weeks 0, 4, 8 and 12 were 38.36±3.739%, 38.31±3.985%, 38.79±3.932%, and 39.13±3.324%, respectively, in placebo; 38.50±3.128%, 39.48±3.327%, 39.43±3.154%, and 39.37±3.639% in the Compound 1 formulation 10-mg group; 38.30±3.882%, 40.06±3.773%, 40.39±3.389%, and 40.54±3.003% in the Compound 1 formulation 20-mg group; and 38.06±4.275%, 39.44±4.012%, 40.23±3.620%, and 40.53±3.307% in the Compound 1 formulation 40-mg group. The change of Ht value at Week 12 from baseline was 0.51±2.583% in placebo, 0.77±2.792% in the Compound 1 formulation 10-mg group, 2.31±3.522% in the Compound 1 formulation 20-mg group, and 2.46±3.445% in the Compound 1 formulation 40-mg group. The Ht value showed little change in placebo and the Compound 1 formulation 10-mg group during the treatment period, but an increasing tendency was observed in the Compound 1 formulation 20-mg and 40-mg groups.

Referring to FIG. 54, the Fe values (mean±SD) at Weeks 0, 4, 8 and 12 were 64.0±45.85 μg/dL, 68.1±55.53 μg/dL, 68.3±54.24 μg/dL, and 68.1±49.17 μg/dL, respectively, in placebo; 63.8±40.05 μg/dL, 72.8±40.58 μg/dL, 67.3±34.74 μg/dL, and 75.3±46.94 μg/dL in the Compound 1 formulation 10-mg group; 62.6±43.00 μg/dL, 77.4±49.74 μg/dL, 84.2±49.42 μg/dL, and 85.7±44.40 μg/dL in the Compound 1 formulation 20-mg group; and 56.5±34.85 μg/dL, 77.6±44.81, 78.2±41.91, and 82.0±36.93 μg/dL in the Compound 1 formulation 40-mg group. The change of Fe value at Week 12 from baseline was 2.3±57.87 g/dL in placebo, 11.0±42.94 μg/dL in the Compound 1 formulation 10-mg group, 24.7±53.53 μg/dL in the Compound 1 formulation 20-mg group, and 25.5±44.43 μg/dL in the Compound 1 formulation 40-mg group. The Fe value showed no apparent increasing tendency in placebo and the Compound 1 formulation 10-mg group during the treatment period, but clinically significant increase was observed in the Compound 1 formulation 20-mg and 40-mg groups.

Referring to FIG. 55, the ferritin values (mean±SD) at Weeks 0, 4, 8 and 12 were 13.93±12.463 ng/mL, 11.37±9.325 ng/mL, 11.37±8.497 ng/mL, and 11.01±9.349 ng/mL, respectively, in placebo; 13.17±12.217 ng/mL, 14.71±16.372 ng/mL, 12.43±11.117 ng/mL, and 10.81±9.489 ng/mL in the Compound 1 formulation 10-mg group; 14.79±11.396 ng/mL, 14.77±11.536 ng/mL, 16.34±15.659 ng/mL, and 18.03±14.427 ng/mL in the Compound 1 formulation 20-mg group; and 12.94±12.384 ng/mL, 15.14±15.133 ng/mL, 18.10±16.177 ng/mL, and 21.84±21.509 ng/mL in the Compound 1 formulation 40-mg group. The change of ferritin value at Week 12 from baseline was −3.30±7.110 ng/mL in placebo, −2.56±6.833 ng/mL in the Compound 1 formulation 10-mg group, 3.50±10.229 ng/mL in the Compound 1 formulation 20-mg group, and 8.91±13.131 ng/mL in the Compound 1 formulation 40-mg group. The ferritin value decreased gradually during the treatment period in placebo and the Compound 1 formulation 10-mg group, but it tended to increase gradually in the Compound 1 formulation 20-mg and 40-mg groups.

The serum LH concentrations, following administration of either placebo or one of the three Compound 1 formulations (10 mg, 20 mg and 40 mg) for the treatment period of 12 weeks, are graphically depicted in FIGS. 56A-D, respectively, and tabulated in FIG. 57. In particular, the medians of LH concentrations at Weeks 0, 2, 4, 8 and 12 were 3.280 mIU/mL, 4.530 mIU/mL, 3.600 mIU/mL, 3.565 mIU/mL, and 4.130 mIU/mL, respectively, in placebo and respectively: 3.480 mIU/mL, 3.815 mIU/mL, 2.565 mIU/mL, 3.460 mIU/mL, and 3.550 mIU/mL in the Compound 1 formulation 10-mg group; 3.485 mIU/mL, 2.520 mIU/mL, 1.750 mIU/mL, 2.260 mIU/mL, and 2.685 mIU/mL in the Compound 1 formulation 20-mg group; and 3.520 mIU/mL, 0.720 mIU/mL, 0.550 mIU/mL, 0.570 mIU/mL, and 0.650 mIU/mL in the Compound 1 formulation 40-mg group. The median change in serum LH concentrations at Week 12 from baseline was 0.590 mIU/mL in placebo, 0.420 mIU/mL in the Compound 1 formulation 10-mg group, −0.895 mIU/mL in the Compound 1 formulation 20-mg group, and −2.760 mIU/mL in the Compound 1 formulation 40-mg group. Thus, the serum LH concentrations tended to decrease in the Compound 1 formulation 20-mg and 40-mg groups during the treatment period.

The serum FSH concentrations, following administration of either placebo or one of the three Compound 1 formulations (10 mg, 20 mg and 40 mg) for the treatment period of 12 weeks, are graphically depicted in FIGS. 58A-D, respectively, and tabulated in FIG. 59. In particular, the medians of serum FSH concentrations at Weeks 0, 2, 4, 8 and 12 were 6.580 mIU/mL, 3.570 mIU/mL, 5.280 mIU/mL, 5.080 mIU/mL, and 5.140 mIU/mL, respectively, in placebo and respectively: 6.645 mIU/mL, 5.990 mIU/mL, 5.225 mIU/mL, 6.150 mIU/mL, and 6.200 mIU/mL in the Compound 1 formulation 10-mg group; 6.125 mIU/mL, 5.705 mIU/mL, 4.660 mIU/mL, 4.840 mIU/mL, and 5.710 mIU/mL in the Compound 1 formulation 20-mg group; and 6.140 mIU/mL, 4.280 mIU/mL, 3.710 mIU/mL, 3.210 mIU/mL, and 2.950 mIU/mL in the Compound 1 formulation 40-mg group. The median change in serum FSH concentrations at Week 12 from baseline was −1.040 mIU/mL in placebo, −1.060 mIU/mL in the Compound 1 formulation 10-mg group, −0.720 mIU/mL in the Compound 1 formulation 20-mg group, and −3.180 mIU/mL in the Compound 1 formulation 40-mg group. Thus, the serum FSH concentrations tended to be lower in the Compound 1 formulation 40-mg group during the treatment period.

The serum $E_2$ concentrations, following administration of either placebo or one of the three Compound 1 formulations (10 mg, 20 mg and 40 mg) for the treatment period of 12 weeks, are graphically depicted in FIGS. 60A-D, respectively, and tabulated in FIG. 61. In particular, the medians of serum $E_2$ concentrations at Weeks 0, 2, 4, 8 and 12 were 41.0 pg/mL, 142.0 pg/mL, 55.0 pg/mL, 91.5 pg/mL, and 110.0 pg/mL, respectively, in placebo and respectively: 46.5 pg/mL, 82.5 pg/mL, 58.0 pg/mL, 52.0 pg/mL, and 57.0 pg/mL in the Compound 1 formulation 10-mg group; 44.0 pg/mL, 25.0 pg/mL, 23.5 pg/mL, 16.0 pg/mL, and 13.0 pg/mL in the Compound 1 formulation 20-mg group; and 40.0 pg/mL, 0.0 pg/mL, 0.0 pg/mL, 0.0 pg/mL, and 0.0 pg/mL in the Compound 1 formulation 40-mg group. The median change in serum $E_2$ concentrations at Week 12 from baseline was 59.0 pg/mL in placebo, 0.0 pg/mL in the Compound 1 formulation 10-mg group, −18.5 pg/mL in the Compound 1 formulation 20-mg group, and −35.0 pg/mL in the Compound 1 formulation 40-mg group. In the Compound 1 formulation 40-mg group, the median of serum $E_2$ concentrations decreased to 0.0 pg/mL (less than the quantitation limit) at Week 2 and was maintained until Week 12. The serum $E_2$ concentrations tended to be lower in the Compound 1 40 mg group during the treatment period.

FIG. 172 depicts the percentage of subjects with serum $E_2$ concentration of less than 10 pg/mL, as a function of dose. FIG. 173 depicts the serum $E_2$ concentration for individual subjects as a function of plasma Compound 1 (relugolix) concentration. These figures demonstrate that the dosage of Compound 1 may be important for achieving effective $E_2$ suppression with low variability between subjects.

The serum P concentrations, following administration of either placebo or one of the three Compound 1 formulations (10 mg, 20 mg and 40 mg) for the treatment period of 12 weeks, are graphically depicted in FIGS. 62A-D, respectively, and tabulated in FIG. 63. In particular, the medians of serum P concentrations at Weeks 0, 2, 4, 8 and 12 were 0.290 ng/mL, 7.740 ng/mL, 0.320 ng/mL, 0.300 ng/mL, and 0.360 ng/mL, respectively, in placebo and respectively: 0.270 ng/mL, 0.315 ng/mL, 0.440 ng/mL, 0.360 ng/mL, and 0.410 ng/mL in the Compound 1 formulation 10-mg group; 0.325 ng/mL, 0.235 ng/mL, 0.270 ng/mL, 0.250 ng/mL, and 0.250 ng/mL in the Compound 1 formulation 20-mg group; and 0.300 ng/mL, 0.230 ng/mL, 0.240 ng/mL, 0.220 ng/mL, and 0.250 ng/mL in the Compound 1 formulation 40-mg group. The median change in serum P concentrations at Week 12 from baseline was 0.050 ng/mL in placebo, 0.080 ng/mL in the Compound 1 formulation 10-mg group, −0.090 ng/mL in the Compound 1 formulation 20-mg group, and −0.060 ng/mL in the Compound 1 formulation 40-mg group. The serum P concentrations did not increase in the Compound 1 formulation 20-mg and 40-mg groups during the treatment period.

The bone mineral density (BMD) of the second to fourth lumbar vertebra (L2 to L4) was measured using dual X-ray absorptiometry (DXA). The bone mineral density values at Weeks 0 and 12 (mean±SD) were 1.1207±0.16933 and 1.1188±0.17186 g/cm$^2$, respectively, in placebo and respectively: 1.0792±0.13998 and 1.0757±0.13907 g/cm$^2$ in the Compound 1 formulation 10-mg group, 1.0880±0.15287 and 1.0665±0.15479 g/cm$^2$ in the Compound 1 formulation 20-mg group, and 1.0924±0.15355 and 1.0677±0.15306 g/cm$^2$ in the Compound 1 formulation 40-mg group. The percent change of bone mineral density from baseline was −0.24±2.218% in placebo, −0.75±2.350% in the Compound 1 formulation 10-mg group, −2.01±2.334% in the Compound 1 formulation 20-mg group, and −2.28±2.194% in the Compound 1 formulation 40-mg group. As for other GnRH agonists, it has been reported that bone mineral density decreased −2.21±1.709% following administration of leuprolide acetate to subjects having uterine fibroids. The percent change of bone mineral density in this study was considered to be the same level or less compared to this result for the leuprolide acetate group.

Biochemical bone metabolism markers (serum NTx and BAP) were also assessed as a supplementary marker of bone metabolism.

FIG. 173 shows the percentage of subjects with a PBAC score of 0 from week 6 to 12, and the mean percentage change from baseline in bone mineral density at week 12, as functions of dose. This graph demonstrates the improvement of symptoms (PBAC=0) with increasing dose of Compound 1. Bone mineral density loss also increased with higher doses of Compound 1, but the difference between higher doses was less than the difference between lower doses.

FIG. 64 shows the return of menstrual cycles following administering of placebo or one of the three Compound 1 formulations (10 mg, 20 mg and 40 mg) for a treatment period of 12 weeks. The period from the last dose of study drug to return of menstrual cycles (mean±SD) was 18.6±8.75 days in placebo, 19.8±9.26 days in the Compound 1 formulation 10-mg group, 31.0±17.65 days in the Compound 1 formulation 20-mg group, and 36.4±7.63 days in the Compound 1 formulation 40-mg group. Overall, it was determined that there were no clinically significant issues regarding the recovery of menstruation, with the menstruation recovery period being 20 to 35 days after the last dose in the Compound 1 groups (Table 3).

TABLE 3

Other Safety Endpoints

| Endpoint | | Placebo | Relugolix | | |
|---|---|---|---|---|---|
| | | | 10 mg | 20 mg | 40 mg |
| BMD, (%) | n | 55 | 47 | 56 | 55 |
| | mean | −0.2 | −0.7 | −2.0 | −2.3 |
| | (SD) | (2.22) | (2.35) | (2.33) | (2.19) |
| Menstruation recovery period, days | n | 57 | 47 | 55 | 52 |
| | mean | 19 | 20 | 31 | 36 |
| | (SD) | (8.8) | (9.3) | (17.6) | (7.6) |

Figure 68:
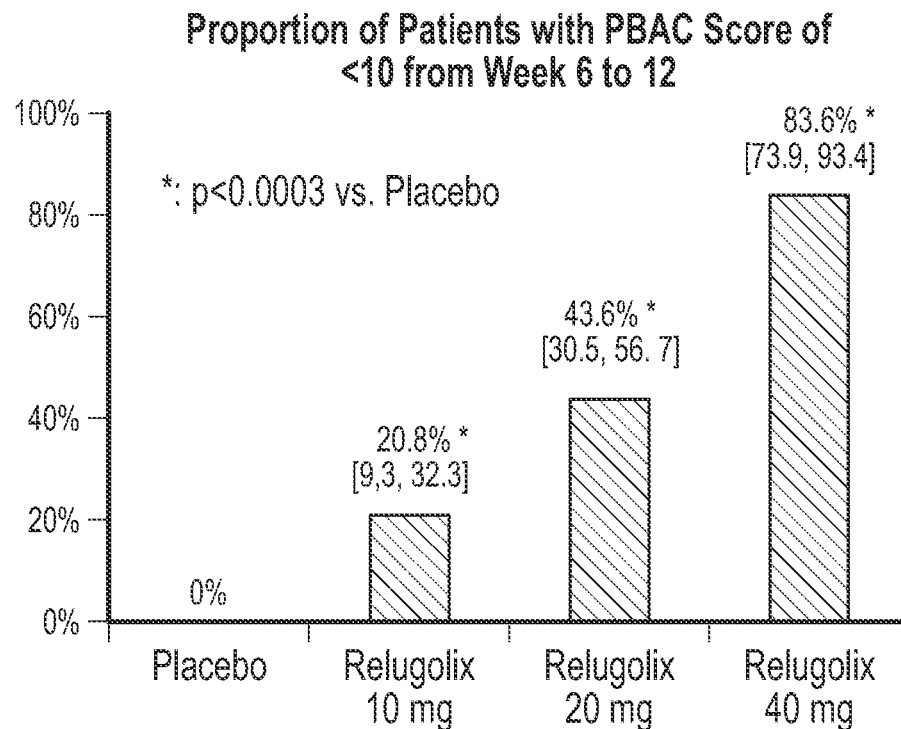
FIG. 68 summarizes the proportion of patients with a Pictorial Blood Loss Assessment Chart (PBAC) score of <10 from Week 6 to 12 in accordance with Example 5A.

In summary, for secondary endpoints, the achievement of amenorrhea (total PBAC score equal to 0) from Week 6 to 12 was 73% in the Compound 1 (relugolix) 40 mg group vs 0% in the placebo group (Table 4, below). Myoma volumes and uterine volumes for the placebo group increased by week 12, whereas those volumes in all the Compound 1 groups decreased from Week 2 and continued to decrease by Week 4, 8, and 12 with a trend for the largest decrease in volumes observed in the 40 mg group (Table 4). At week 12 uterine and myoma volumes were reduced ~40% in the Compound 1 40 mg group, but the placebo group increased ~10%, resulting in ~50% changes from baseline for the 40 mg group, compared to placebo. By week 12, there was an elevation in Hb levels in the Compound 1 20- and 40-mg groups with the highest increase in Hb observed in the 40 mg group (Table 4). Patient-reported NRS assessments indicated that, compared with the placebo group, patients who received Compound 1 treatment had a lower NRS score (i.e.

less pain symptoms from Week 6 to Week 12) and the group administered Compound 1 40 mg had the greatest pain reduction benefit (Table 4). Compared with placebo, the Compound 1 40 mg group had a lower UFS-QOL symptom severity score and a lower UFS-QOL HRQL total score, indicating a trend for greater improvement for patients in the highest Compound 1 dose group (40 mg) (Table 4). All of the relugolix doses significantly reduced menstrual blood loss from Week 6 to 12, compared with placebo in a dose-dependent manner with the highest proportion of patients in the 40 mg group (P<0.0003 for each comparison). Point estimate [95% CI] *: Each relugolix group was statistically significant vs. placebo, p<0.0003. Chi-square test was performed according to the closed testing procedure. (FIG. 68).

TABLE 4

Secondary Endpoints

|  | Placebo (n = 57) | Relugolix 10 mg (n = 48) | Relugolix 20 mg (n = 56) | Relugolix 40 mg (n = 55) |
|---|---|---|---|---|
| Variable | | | | |
| Amenorrhea*, n (%) | 0 (0.0) | 8 (16.7) | 21 (38.2) | 40 (72.7) |
| Change from baseline at Week 12, mean (SD) | | | | |
| Myoma volumes (%) | 10 (47.2) | −23 (29.5) | −37 (32.6) | −39 (34.2) |
| Uterine volumes (%) | 10 (57.9) | −12 (29.9) | −28 (28.8) | −41 (37.2) |
| Hemoglobin (g/dL) | 0.2 (1.00) | 0.3 (1.05) | 0.8 (1.16) | 0.9 (1.18) |
| UFS-QOL score | | | | |
| Symptom severity | −4 (13.3) | −7 (18.1) | −9 (15.5) | −11 (17.3) |
| HRQL total | −2 (11.6) | −2 (10.6) | −2 (10.5) | −6 (15.9) |
| NRS score**, mean (SD) | 0.8 (0.99) | 0.6 (1.23) | 0.4 (0.62) | 0.2 (0.54) |

*PBAC from Week 6 to 12 was 0
**mean from Week 6 to 12

Figure 69:
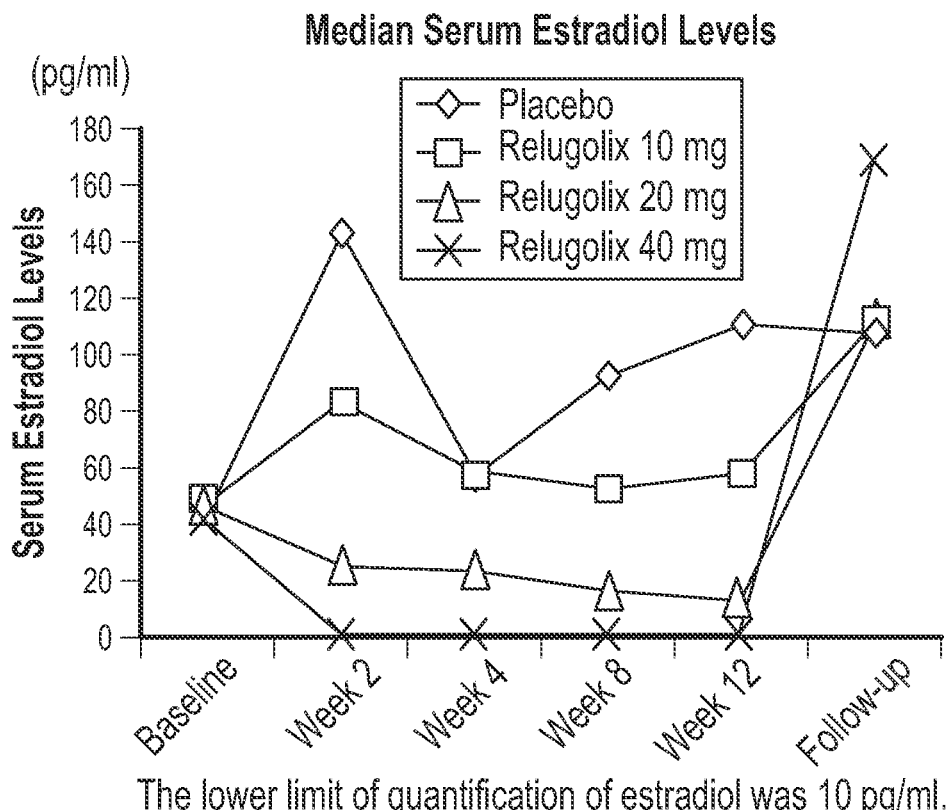
FIG. 69 shows median serum estradiol levels.

Additionally, with respect to pharmacodynamics, median serum estradiol ($E_2$) levels decreased to <10 pg/mL (less than lower limit of quantification) at Week 2 in the Compound 1 (relugolix) 40 mg group and these very low concentrations were maintained until Week 12 (FIG. 69). The 40 mg dose of Compound 1 resulted in the greatest change from baseline in LH, FSH and P.

On the basis of the efficacy and safety findings in this study, it was considered that there were no clinically significant issues in the safety of the Compound 1 formulation. Further, on the basis of the efficacy and safety findings in this study, 40 mg of the Compound 1 formulation was considered to be an effective dose for treating the symptoms associated with uterine fibroids.

Example 5B: Summary of Example 5A

This Example summarizes some of the findings as described above for Example 5A.

PBAC scores were used in Example 5A, and provide an estimate of menstrual blood loss volume. The PBAC score was evaluated by having subjects record details related to menstrual blood loss on a PBAC score sheet distributed by the sponsor during the treatment period. FIG. 1 shows an illustrative PBAC score sheet that includes two items (tampon and towel) across three pictographic ranges (1: lightly stained; 5: moderately stained; 10: saturated). These items represent the level of stained sanitary materials over the course of a menstrual cycle, with a total score ranging from 0 (none) to infinity. Higher scores indicate heavier blood loss. The PBAC score sheet also allows subjects to indicate: whether they experienced bleeding between periods that required sanitary protection; whether they passed clots, and if so, approximate size of the clots; whether they experienced episodes of flooding; and whether they required double protection (used both a pad and tampon simultaneously). As used in the PBAC score sheet of Example 5A, flooding is defined as overflowing, or staining, of clothing or underwear due to menstrual bleeding.

Subjects were instructed to complete the PBAC score sheet by assigning scores as follows: 1, 5 or 10 points were added for each lightly stained, moderately stained, or completely saturated feminine hygiene product, respectively, 1 or 5 points were added for each blood clot of smaller than 1 cm or for each blood clot of 1 cm or larger in the longest diameter, respectively, and 5 points were added for each episode of flooding. This scoring differs slightly from the scoring listed on the illustrative PBAC score sheet shown in FIG. 1. The total PBAC score was derived by summing points for each of the above.

Following administering, once-daily, doses of 40 mg per day for 12 consecutive weeks of Compound 1 in a formulation ("Compound 1 formulation") having the following excipients: 122 mg of mannitol, 40 mg of microcrystalline cellulose, 6 mg of hydroxypropyl cellulose, 10 mg of croscarmellose sodium, 2 mg of magnesium stearate, 7.12 mg of hypromellose 2910, 0.8 mg of titanium dioxide, and optionally, 0.08 mg of ferric oxide, and without a hormone replacement medicament, the change from baseline in the mean total Pictorial Blood Loss Assessment Chart (PBAC) score from weeks 6 to 12, was 77.3±255.54 in the placebo and −238.7±203.34 in the 40 mg Compound 1 formulation.

All myoma and uterine volumes referred to herein were evaluated using transvaginal ultrasound. Specifically, the myoma volumes were calculated using the following formula: $D1 \times D2 \times D3 \times 7\pi/6$, where D1 is the longest diameter of the myoma; D2 is the longest diameter of the myoma at an angle perpendicular to D1; and D3 is the diameter of the myoma crossing the intersection of D1 and D2 perpendicular to the D1/D2 plane.

Following administering once-daily doses of 40 mg per day for 12 consecutive weeks of the Compound 1 formulation, the percent change from baseline in mean myoma volume at the end of 12 consecutive weeks was 10.19±47.159% in the placebo and −38.59±34.197% in the 40 mg Compound 1 formulation.

Following administering once-daily doses of 40 mg per day for 12 consecutive weeks of the Compound 1 formulation, the percent change from baseline in mean uterine volume at the end of 12 consecutive weeks was 9.75±57.946% in the placebo and −40.90±37.233% in the 40 mg Compound 1 formulation.

Numerical Rating Scale (NRS) is an 11-item self-reported instrument for assessing pain. As shown in FIG. 2, it includes 11 items ranging from 0 (No Pain) to 10 (Worst Pain Possible). Higher NRS scores reflect greater levels of pain.

Following administering once-daily doses of 40 mg per day for 12 consecutive weeks of the Compound 1 formulation, the mean Numerical Rating Scale (NRS) score from weeks 6 to 12 was 0.82±0.989 in the placebo and 0.25±0.542 in the 40 mg Compound 1 formulation.

The Uterine Fibroid Symptom Quality of Life (UFS-QOL) questionnaire is a 37-item self-reported instrument assessing differences in symptom severity and health-related quality of life. It includes eight symptom-related questions and 29 health-related quality of life questions across eight subscales (symptom severity, concern, activities, energy/mood, control, self-consciousness, sexual function, and health-related quality of life total score), with subscale and total score ranging from 37 (not at all/none of the time) to 116 (a very great deal/all of the time). The UFS-QOL questionnaire used in Example 5A is shown in FIGS. 3A-C. Higher UFS-QOL scores reflect greater symptom severity and symptom impact on health-related quality of life.

Following administering once-daily doses of 40 mg per day for 12 consecutive weeks of the Compound 1 formulation, the change from baseline in mean Uterine-Fibroid Symptom Quality-Of-Life (UFS-QOL) score measuring symptom severity at the end of 12 consecutive weeks was −3.58±13.325 in the placebo and −11.25±17.274 in the 40 mg Compound 1 formulation.

Following administering once-daily doses of 40 mg per day for 12 consecutive weeks of the Compound 1 formulation, the change from baseline in mean Uterine Fibroid Symptom Quality of Life score (HRQL total) at the end of 12 consecutive weeks was −2.20±11.555 in the placebo and −5.52±15.871 in the 40 mg Compound 1 formulation.

Following administering once-daily doses of 40 mg per day for 12 consecutive weeks of the Compound 1 formulation, the change from baseline in mean blood concentration of hemoglobin (Hb) at the end of 12 consecutive weeks was 0.20±1.003 g/dL in the placebo and 0.92±1.183 g/dL in the 40 mg Compound 1 formulation.

Following administering once-daily doses of 40 mg per day for 12 consecutive weeks of the Compound 1 formulation, the change from baseline in mean hematocrit (Ht) value at the end of 12 consecutive weeks was 0.51±2.583% in the placebo and 2.46±3.445% in the 40 mg Compound 1 formulation.

Following administering once-daily doses of 40 mg per day for 12 consecutive weeks of the Compound 1 formulation, the change from baseline in mean ferrum (Fe) value at the end of 12 consecutive weeks was 2.3±57.87 µg/dL in the placebo and 25.5±44.43 µg/dL in the 40 mg Compound 1 formulation.

Following administering once-daily doses of 40 mg per day for 12 consecutive weeks of the Compound 1 formulation, the change from baseline in mean ferritin value at the end of 12 consecutive weeks was −3.30±7.110 ng/mL in the placebo and 8.91±13.131 ng/mL in the 40 mg Compound 1 formulation.

Following administering once-daily doses of 40 mg per day for 12 consecutive weeks of the Compound 1 formulation, the change from baseline in median luteinizing hormone concentrations at the end of 12 consecutive weeks was 0.590 mIU/mL in the placebo and −2.760 mIU/mL in the 40 mg Compound 1 formulation.

Following administering once-daily doses of 40 mg per day for 12 consecutive weeks of the Compound 1 formulation, the change from baseline in median FSH concentration was −1.040 mIU/mL in the placebo and −3.180 mIU/mL in the 40 mg Compound 1 formulation.

Following administering once-daily doses of 40 mg per day for 12 consecutive weeks of the Compound 1 formulation, the change from baseline in median $E_2$ concentrations at the end of 12 consecutive weeks was 59.0 pg/mL in the placebo and −35.0 pg/mL in the 40 mg Compound 1 formulation.

Following administering once-daily doses of 40 mg per day for 12 consecutive weeks of the Compound 1 formulation, the change in median progesterone (P) concentrations from baseline at the end of 12 consecutive weeks was 0.050 ng/mL in the placebo and −0.060 ng/mL in the 40 mg Compound 1 formulation.

Following administering once-daily doses of 40 mg per day for at least 2 consecutive weeks of Compound 1, and from 0.05 mg to 2.5 mg per day of an estrogen and/or a progestogen, bone mineral density loss is minimized.

Example 6: International Phase 3 Randomized, Double-Blind, Placebo-Controlled Efficacy and Safety Studies to Evaluate Compound 1 Co-Administered with Low-Dose Estradiol and Progestin in Women with Heavy Menstrual Bleeding (HMB) Associated with Uterine Fibroids This will be randomized, double-blind study to evaluate the safety and efficacy of 40 mg of the Compound 1 formulation administered orally once-daily with a hormone replacement medicament that includes 1 mg estradiol and 0.5 mg norethindrone acetate, compared with placebo, in women with heavy menstrual bleeding associated with uterine fibroids. The study described in this example is intended to form the basis for an upcoming phase III clinical program in support of approval of Compound 1 as a treatment for women with uterine fibroids.

The study will include both an initial study and a separate extension study. The initial study will include a screening period of approximately 10 weeks, a drug treatment period of 24 weeks, and a follow-up period of one month. The extension study will allow those subjects from the initial study to extend the treatment period. In particular, the extension study will permit those subjects from the initial study on the placebo treatment to be administered Compound 1 for a period of 24 weeks, and for those on the Compound 1 drug treatment in the initial study to extend the same treatment for an additional 24 weeks. Subjects will only be permitted to enter the extension study if their bone mineral density loss does not exceed −8.0%.

It is planned that approximately 390 subjects will enter the study. Of those 390 subjects, approximately 260 women be randomized to Compound 1 plus hormone replacement medicament therapy, and approximately 130 women will be randomized to placebo.

To enter the study, subjects must be women aged 18–50 years, inclusive, who have been diagnosed with heavy menstrual bleeding associated with uterine fibroids demonstrated over 2 cycles during the screening period, as measured by the alkaline hematin method. Heavy menstrual bleeding, as defined under the alkaline hematin method, refers to an average menstrual blood loss ≥80 mL, with a minimum menstrual blood loss of 70 mL per cycle, for the entire menstrual cycle immediately before Visit 3. Visit 3 will be at approximately 8–12 weeks after commencement of the study. The diagnosis of heavy menstrual bleeding can be confirmed by a transabdominal or transvaginal pelvic ultrasound performed with saline or gel contrast.

Subjects will start recording in the patient diary from the day of Visit 1. During the period between Visit 2 and 3, in which subjects must experience at least 2 menstrual cycles, the baseline values for the efficacy evaluation, including total menstrual blood loss, pain symptoms and QOL, will be collected. Subjects will record in the patient diary every day until the end of study drug administration (Visit 9).

Visit 2 will be between Days 1 to 5 of the first menstruation after Visit 1. Visit 3 will be between Days 1 to 5 of the second menstruation after Visit 1. From Visit 3 to Visit 9, subjects will receive the study drug once-daily (amongst the Compound 1 formulation with the hormone replacement medicament, the Compound 1 formulation placebo and the hormone replacement medicament placebo) in a double-blind manner, along with daily calcium (up to 1300 mg) and vitamin D (up to 1000 Units). Women with iron-deficient anemia will also be treated with oral or parenteral iron replacement if the hemoglobin is less than 10 g/dL and the mean corpuscular volume is below the lower limit of normal. All women will have an assessment of bone mineral density with dual-energy X-ray absorptiometry and an endometrial biopsy at baseline and at Week 24.

Since previous studies have demonstrated that the plasma drug exposure of Compound 1 can be reduced when administered with a high-fat, high-calorie meal, the study drug is intended to be administered in a fasted state for this study, namely at least 1 hour before or 2 hours after a meal.

During the course of this study, subjects will visit the study site to undergo the designated examinations and evaluations at each visit monthly after randomization and the initiation of study drug administration (Visit 3) under double-blind conditions.

At Visit 3, the study drug will be administered in a double-blind, double-dummy method from the day of Visit 3 to the day before Visit 9 (or until early termination) under double-blind conditions. The study drug will be taken once-daily as a single oral dose in the morning under fasted conditions: at least one hour before or at least two hours after a meal. If dosing is missed in the morning, the dose can be taken later in the day at least 1 hour before eating the next meal and 2 hours after eating the prior meal.

Subjects will fill out a patient diary every day. Subjects will record, in the patient diary, pain symptoms experienced in the past 24 hours due to uterine fibroids, which will be used to calculate the NRS score; and information related to clinical trial medication, menstrual bleeding, and use of pain medication and supplements. The specific questions to be included in the patient diary are shown in FIG. 2 and in FIGS. 65A-C.

The primary endpoint of this study is to evaluate the percent of subjects who achieve a menstrual blood loss volume of less than 80 mL and a 50% or greater reduction from baseline to last month of treatment in menstrual blood loss as measured by the alkaline hematin (AH) method. Subjects will return used feminine sanitary products for a quantitation of menstrual blood loss via the AH method. The AH method measures volume of menstrual blood loss in milliliters by pummeling used feminine products in a solution and measuring the resulting hematin absorbance against calibration curves. The method is validated in accordance with current FDA Guidance for Method Validations and is an accepted quantitative endpoint for the assessment of heavy menstrual bleeding. Feminine products will be dispensed at Screening Visit 1 and collected at each visit until the patient completes treatment or terminates participation from the study prior to completing treatment. Each time the patient submits her feminine products from a menstrual cycle for analysis, a venous blood sample will be collected and sent to the laboratory.

Secondary endpoints of this study are intended to include: 1) the percent of subjects achieving sustained amenorrhea from week 5 to the last month of treatment; 2) time to amenorrhea; 3) change in menstrual blood loss from baseline to last month of treatment; 4) change in hemoglobin concentration from baseline to last month of treatment; 5) Numerical Rating Scale (NRS) score for uterine fibroid related pain; 6) change in fibroid volume from baseline to last month of treatment; 7) change in uterine volume from baseline to last month of treatment; 8) change in bone mineral density from baseline to week 24 (assessed by DXA); and 9) endometrial biopsy, e.g., percent of patients with endometrial thickness greater than 4 mm at the end of treatment.

Subjects will complete various questionnaires to evaluate the impact of uterine fibroids on QOL. In particular, subjects will complete the UFS-QOL questionnaire, described in Example 5A, once the Treatment Period begins. Subjects will also complete the Change in Work Productivity and Activity Impairment Questionnaire: General Health Version 2.0 (WPAI: GH), which consists of six questions that measure the effects of general health and specific symptoms on work productivity and life outside of work. Questions from the WPAI: GH are shown in FIGS. 66A-B. Subjects are also expected to complete the EuroQol, the Patient Global Impression of Change (shown in FIG. 67), and the Menorrhagia Impact Questionnaire (MIQ). Although not intended to be part of the present study, it is also possible to have subjects complete the Resource Utilization Questionnaire to provide an additional tool for evaluating QOL of patients having uterine fibroids.

This study will also evaluate the pharmacokinetic and pharmacodynamics effects of Compound 1 with the hormonal add-back therapy. Particular parameters that will be analyzed include: 1) concentrations of estradiol, luteinizing hormone, follicle stimulating hormone and progesterone; 2) $C_{max}$, CT and $AUC_{(0-tau)}$; and 3) plasma drug trough concentrations for Compound 1, ethinyl estradiol and norethindrone acetate.

Example 7: A Randomized, Double-Blind, Placebo-Controlled Study of the Efficacy of Compound 1 in the Treatment of Endometriosis This was a randomized, double-blind, study to evaluate the efficacy of 3 dose levels (10 mg, 20 mg, and 40 mg) of 12-week oral administration of the Compound 1 formulation compared with placebo in premenopausal Japanese women aged ≥20 years with endometriosis. The efficacy of this drug was also comparatively assessed using leuprolide acetate (Leuplin®; also known as leuprorelin) injection (once every 4 weeks, 3.75 mg per dose) as a reference drug.

Subjects were diagnosed with endometriosis within the 5 years before screening and had dysmenorrhea and pelvic pain, of which either 1 or both was at least "moderate" as determined by the investigator using the Biberoglu & Behrman (B&B) scale. The primary endpoint was change from baseline in mean visual analogue scale (VAS) score for overall pelvic pain at the end of treatment period (VAS "0=no pain"; "100=pain as bad as you can imagine"). Secondary endpoints included VAS score for pelvic pain, dysmenorrhea, and dyspareunia during the treatment period. Safety endpoints included bone mineral density (BMD), adverse events (AEs), vital signs, weight, 12-lead electrocardiogram (ECG), clinical laboratory tests, and biochemical bone metabolism markers (serum type I collagen cross-linked N-telopeptide and bone-specific alkaline phosphatase). A summary of demographic and baseline characteristics for the groups is provided in Table 5.

study, patients visited the clinic every other week for a month after the start of study drug administration under double-blind conditions (Visit 3), and monthly thereafter. Designated examinations and evaluations were performed at each visit.

The plasma Compound 1 concentration after a single dose of the Compound 1 formulation at 1 to 80 mg reached a peak mean $C_{max}$ at 0.5 to 4.0 hours postdose ($T_{max}$), with a mean plasma $T_{1/2}$ of 7.1 to 19.8 hours. The mean plasma AUC and mean $C_{max}$ exhibited an increase in a slightly greater than dose-proportional manner. The plasma Compound 1 concentration on Day 14 of multiple doses of 10 to 40 mg reached a peak mean $C_{max}$ at 1 to 1.5 hours postdose ($T_{max}$),

TABLE 5

Demographic and Baseline Characteristics

| | | Relugolix | | | |
| --- | --- | --- | --- | --- | --- |
| Characteristics<br>Mean (SD) | Placebo<br>(N = 99) | 10 mg<br>(N = 103) | 20 mg<br>(N = 100) | 40 mg<br>(N = 103) | Leuprorelin<br>(N = 82) |
| Age [yrs] | 35.7 (6.06) | 35.3 (6.22) | 35.1 (6.78) | 35.6 (6.04) | 36.1 (6.13) |
| BMI [kg/m$^2$][1] | 21.1 (3.01) | 21.5 (3.35) | 20.4 (2.46) | 21.6 (3.14) | 21.8 (3.40) |
| Disease duration [yrs] | 3.9 (4.65) | 3.8 (5.04) | 3.2 (3.84) | 4.3 (5.47) | 2.9 (3.78) |
| | | Mean VAS score [mm] | | | |
| Overall pelvic pain[1] | 15.6 (14.32) | 14.6 (11.99) | 15.6 (15.06) | 15.3 (11.99) | 15.2 (15.10) |
| Dysmenorrhea[1] | 28.4 (16.59) | 28.2 (17.64) | 27.7 (18.94) | 30.4 (17.04) | 27.1 (19.78) |
| Dyspareunia[2] | 11.0 (14.25) | 8.8 (14.24) | 12.5 (16.48) | 9.4 (15.42) | 9.5 (10.71) |
| | | Modified (patient) B&B score | | | |
| Non-menstrual pelvic pain[1] | 0.6 (0.45) | 0.7 (0.46) | 0.6 (0.47) | 0.7 (0.44) | 0.7 (0.55) |
| Dysmenorrhea[1] | 1.2 (0.44) | 1.2 (0.47) | 1.2 (0.48) | 1.2 (0.47) | 1.2 (0.47) |
| Dyspareunia[2] | 0.6 (0.45) | 0.6 (0.60) | 0.6 (0.55) | 0.5 (0.48) | 0.6 (0.45) |
| Proportion of days with usage of analgesics [%][1] | 10.0 (11.55) | 12.5 (12.32) | 13.3 (16.43) | 12.0 (14.53) | 11.6 (13.84) |

[1]Placebo: N = 97, Compound 1 (relugolix) 10 mg: N = 103, 20 mg: N = 100, 40 mg: N = 103, leuprorelin: N = 81, total: N = 484
[2]Placebo: N = 41, Compound 1 10 mg: N = 46, 20 mg: N = 47, 40 mg: N = 44, leuprorelin: N = 26, total: N = 204

Subjects started recording in the patient diary on the day of Visit 1. During the period between Visit 2 and 3, in which subjects must have experienced at least 1 menstrual cycle, the baseline values concerning efficacy evaluation including quality of life (QOL) and pain symptoms were collected. Subjects recorded in the patient diary every day until the end of treatment. Visit 2 was on Days 1 to 5 of the first menstrual cycle after Visit 1. The study drug (Compound 1 formulation placebo and Leuplin placebo) was administered under single-blind conditions from the day of Visit 2 to the day before Visit 3. Visit 3 was on Days 1 to 5 of the second menstrual cycle after Visit 1. From Visits 3 to 7, subjects were instructed to visit the clinics in a fasted state and before taking the study drug. At Visit 3, subjects were randomized to either the Compound 1 formulations: 10 mg, 20 mg, 40 mg, and placebo, or Leuplin groups at a ratio of 2:2:2:2:1, respectively. The Compound 1 formulation (10 mg, 20 mg, or 40 mg)+Leuplin placebo, the Compound 1 formulation placebo+Leuplin placebo, or the Compound 1 formulation placebo+Leuplin were administered from the day of Visit 3 to the day before Visit 7 (or until discontinuation of treatment) under double-blind conditions. The Compound 1 formulation or the Compound 1 formulation placebo was administered daily as a single oral dose every morning 30 minutes before breakfast, and Leuplin (or Leuplin placebo) was administered subcutaneously once every 4 weeks. The study consisted of a Pretreatment Period of 4 to 12 weeks, a treatment period of 12 weeks, and the total period of study participation was 16 to 24 weeks. During the course of this with a mean plasma $T_{1/2}$ of 19.2 to 24.6 hours. The mean plasma $AUC_{(0-inf)}$ and mean $C_{max}$ of Compound 1 generally increased in a dose-proportional manner. The mean plasma $AUC_{(0-tau)}$ and mean $C_{max}$ on Day 1, and the mean $C_{max}$ on Day 14 roughly increased in a dose-dependent manner, but the mean plasma $AUC_{(0-tau)}$ on Day 14 exhibited an increase in a slightly greater than dose-proportional manner. The plasma Compound 1 concentration reached steady state by Day 7 of multiple dosing, and the mean plasma AUC and mean $C_{max}$ on Day 14 were both higher than the values on Day 1. The mean plasma AUC after a single dose was higher after fasted dosing than after postprandial or preprandial dosing. The mean plasma AUC and mean $C_{max}$ with multiple dosing were higher with preprandial than with postprandial dosing. These findings suggest that food affects the pharmacokinetics of the Compound 1 formulation.

Blood LH, FSH, estradiol ($E_2$), and progesterone (P) concentrations roughly decreased in a dose-proportional manner following a single dose of Compound 1 (10 to 80 mg) in comparison to placebo. The LH and estradiol concentrations showed a rapid decrease after each dose in all subjects, and kept decreasing throughout the treatment period. The plasma progesterone concentrations showed a rapid decrease after dosing with all dose levels and regimens, and suppression was maintained throughout the treatment period. The plasma FSH concentrations also showed a rapid decrease after dosing with all dose levels and regimens, and remained suppressed throughout the treatment period in the groups given 40 mg of Compound 1 preprandially or postprandially.

TABLE 6

Additional Endpoints

| Variables Mean (SD) | Placebo | Relugolix 10 mg | Relugolix 20 mg | Relugolix 40 mg | Leuprorelin |
|---|---|---|---|---|---|
| Modified (patient) B&B | | | | | |
| Non-menstrual pelvic pain | −0.18 (0.361) | −0.21 (0.300) | −0.22 (0.440) | −0.33 (0.414) | −0.41 (0.44) |
| Dysmenorrhea | −0.17 (0.538) | −0.48 (0.645) | −0.76 (0.673) | −1.16 (0.487) | −1.16 (0.480) |
| Deep dyspareunia | −0.07 (0.363) | −0.08 (0.485) | −0.10 (0.566) | −0.07 (0.492) | −0.36 (0.520) |
| Physician B&B | | | | | |
| Non-menstrual pelvic pain | −0.5 (0.75) | −0.6 (0.76) | −0.8 (0.94) | −0.9 (0.84) | −1.1 (0.73) |
| Dysmenorrhea | −0.4 (0.76) | −1.0 (0.93) | −1.5 (0.91) | −2.0 (0.51) | −2.1 (0.49) |
| Dyspareunia | −0.2 (0.72) | −0.2 (0.68) | −0.2 (0.81) | −0.1 (0.60) | −0.6 (0.68) |
| Change from baseline in EHP-30 scores | | | | | |
| Pain | −5.6 (18.99) | −18.3 (19.76) | −17.8 (20.36) | −25.3 (20.87) | −23.2 (20.41) |
| Control and powerlessness | −8.2 (18.74) | −13.7 (18.71) | −14.6 (23.59) | −17.2 (22.48) | −19.6 (23.27) |
| Emotional well-being | −6.3 (14.48) | −8.3 (16.44) | −8.9 (18.62) | −10.4 (17.77) | −8.8 (17.25) |
| Social support | −3.2 (14.59) | −6.6 (10.29) | −8.4 (16.95) | −6.8 (15.19) | −6.8 (16.36) |
| Self-image | −3.9 (16.42) | −5.5 (11.56) | −6.3 (14.90) | −8.4 (16.18) | −6.1 (16.35) |
| Change from baseline in proportion of days with usage of analgesics | −2.0 (10.38) | −6.6 (10.80) | −6.3 (14.00) | −10.1 (13.44) | −8.3 (12.69) |
| Patients who achieved amenorrhea [N (%)] | 2 (2.1) | 26 (25.2) | 54 (54.0) | 95 (92.2) | 79 (97.5) |

Note:
Physician B&B and change from baseline in EHP-30 scores are the results at Week 12.
Other additional endpoints are the results at the end of treatment.

All adverse events considered related to the study drug were mild or moderate in severity, and recovered during or after completion of study drug administration. The major adverse events were headaches, but the incidence of headaches was similar between the Compound 1 formulation and placebo groups.

With regard to efficacy results, the change from baseline in mean of VAS score for pelvic pain at the end of treatment period in the full analysis set (FAS) was evaluated as the primary endpoint. The changes from baseline in mean of VAS score (mean±SD) were −3.753±10.5018 mm in placebo, −6.168±9.1411 mm in the Compound 1 formulation 10 mg, −8.070±13.3707 mm in the Compound 1 formulation 20 mg, −10.418±11.0171 mm in the Compound 1 formulation 40 mg, and −10.460±10.3013 mm in leuprolide acetate groups, respectively. A statistically significant difference was observed between each Compound 1 formulation treatment group and placebo group in the change from baseline in mean of VAS score for pelvic pain at the end of treatment period. The change from baseline in mean of VAS score in the Compound 1 formulation 40 mg group was comparable with that in leuprolide acetate group.

The VAS scores of pelvic pain, dysmenorrhea, and dyspareunia during the treatment period were evaluated as the secondary endpoints. As for the pelvic pain, the changes from baseline in mean of VAS score at Day 1–28, Day 29–56, Day 57–84, and at the end of treatment period in the Compound 1 formulation 40 mg group were −3.761 mm±7.8831, −8.960±9.8226 mm, −10.464±11.0995 mm, and −10.418±11.0171 mm, respectively. Those at the end of treatment period were −3.753±10.5018 mm in placebo, −6.168±9.1411 mm in the Compound 1 formulation 10 mg, −8.070±13.3707 mm in the Compound 1 formulation 20 mg, −10.418±11.0171 mm in the Compound 1 formulation 40 mg, and −10.460±10.3013 mm in leuprolide acetate groups.

The changes from baseline of VAS scores were larger in higher dose levels of Compound 1, and the changes from baseline in mean of VAS scores increased in a time-dependent-manner. The profile of VAS score in the Compound 1 formulation 40 mg group was similar to that in leuprolide acetate group.

The percent change of bone mineral density decrease from the baseline (mean±SD) were −0.07±1.727%, −0.95±1.875%, −1.34±2.087%, and −2.08±2.220% in placebo, the Compound 1 formulation 10 mg, 20 mg, and 40 mg groups, respectively. A similar effect was observed in the Compound 1 formulation 40 mg group as that in leuprolide acetate group (−2.21±1.709%) in this study.

As for the dysmenorrhea, the changes from baseline in mean of VAS scores were larger in higher dose levels of Compound 1 and the VAS scores decreased in a time-dependent manner. However, those for dyspareunia showed no clear trend of changes at any dose levels of Compound 1.

Among the 10 mg, 20 mg and 40 mg Compound 1 formulations, the plasma concentrations of unchanged Compound 1 were higher levels at 0.5 to 1.5 hours or at 2 to 5 hours after administration in all treatment groups. The plasma drug concentrations prior to administration at each visit (the trough values) were comparable in each treatment group, and were proportional to dose levels of Compound 1. Population PK analysis revealed that the observed profiles of plasma concentrations of unchanged Compound 1 formulations were adequately described by a 2-compartmental model with first-order elimination (fed condition) and dose dependence of relative bioavailability, and no covariates were identified to affect the pharmacokinetics of the Compound 1 formulations.

The median serum concentrations of LH, FSH and progesterone in Compound 1 formulation 40 mg group decreased persistently from the early stage of treatment throughout the treatment period with manner comparable to that of leuprolide acetate group. The median of serum estradiol concentration decreased to below the lower limit of quantitation (LLQ) from Week 2 in Compound 1 formulation 40 mg group and decreased persistently throughout the treatment period. In leuprolide acetate group, the median of serum estradiol concentration decreased to below LLQ from Week 4 and decreased persistently throughout the treatment period.

The percent change from the baseline in serum CA125 concentration increased in accordance with the increasing levels of Compound 1. The percent change in the Compound 1 formulation 40 mg group was comparable with that in leuprolide acetate or leuprorelin group.

In this study, the efficacy and safety of orally administered Compound 1 formulation were investigated in patients with endometriosis at doses of 10 mg, 20 mg and 40 mg for 12 weeks, compared with an administration of placebo, and of leuprolide acetate or leuprorelin as an active reference.

In the efficacy evaluation, with respect to the primary endpoint in this study, the change from baseline in mean of VAS score for pelvic pain at the end of the treatment period, a statistically significant difference was observed between each Compound 1 formulation treatment group and placebo group. The change from baseline in mean of VAS score in the Compound 1 formulation 40 mg group was comparable with that in leuprolide acetate group.

The change from the baseline in mean of VAS score by visit for pelvic pain and dysmenorrhea increased in a time-dependent course of scores from the early stage of treatment in higher dose levels of Compound 1. The proportion of days using pain killer and the amount of menstrual bleeding decreased, and the proportion of subjects who achieved amenorrhea increased in a time-dependent manner, depending on the dose levels of Compound 1. The concentration of CA125, a biochemical endometriosis marker, decreased as the Compound 1 dose was increased, and the concentration in the Compound 1 formulation 40 mg group was approximately the same as in leuprolide acetate group.

The decrease in overall pelvic pain upon treatment with Compound 1 for 12 weeks is illustrated in FIG. 157. The mean percent change from baseline of VAS for overall pelvic pain at the end of the treatment period is illustrated in FIG. 158. The mean percent change from baseline of VAS for overall pelvic pain and dysmenorrhea at the end of the treatment period is illustrated in FIG. 159. The change from baseline of VAS for overall pelvic pain, non-menstrual pelvic pain, dysmenorrhea, and dyspareunia by visit is illustrated in FIG. 160. The serum concentration (median) of pharmacodynamic markers as determined in this example is illustrated in FIG. 161. The rapid onset and rapid offset of effect on serum estradiol on Compound 1 is demonstrated in FIG. 162.

On the basis of the efficacy and safety findings in this study, it was considered that there were no clinically significant issues in the safety of the Compound 1 formulation. Further, on the basis of the efficacy and safety findings in this study, 40 mg of Compound 1 was considered to be an effective dose for treating endometriosis.

Example 8A: An Extension Study of the Safety of Compound 1 in the Treatment of Endometriosis This was an open-label extension study of the study conducted in Example 7 to evaluate the safety and efficacy of 3 dose levels (10 mg, 20 mg and 40 mg) of the Compound 1 formulation administered orally once-daily for a total of 24 weeks compared with placebo in women with endometriosis. The objective of this phase 2 study was to evaluate the safety of Compound 1 when administered for 24 weeks in women with EM-associated pain. In addition, the pharmacokinetic and pharmacodynamic effects of the Compound 1 formulation were assessed. Leuprolide acetate (Leuplin®; or leuprorelin) was used as a reference to explore the clinical context of the Compound 1 formulation.

Study participants were premenopausal (≥20 years) Japanese women with endometriosis (EM)-associated pain who completed a preceding 12-week study and were eligible to continue for an additional 12-week treatment were enrolled. The participants has confirmed normal regular menstrual cycles (25 to 38 days per cycle) and diagnosed to have EM and EM-related dysmenorrhea and pelvic pain of at least moderate severity as determined by the physician B&B scale. The primary endpoint was the safety including assessment of change in bone mineral density (BMD) using dual energy x-ray absorptiometry, adverse events, vital signs, weight, 12-lead electrocardiograms, and clinical laboratory tests. Analysis sets were defined as all patients who were administered Compound 1. Secondary endpoint was assessment of efficacy through 24 weeks including visual analogue scale (VAS) scores for pelvic pain, dysmenorrhea and dyspareunia at the end of treatment defined as the 28 days prior to the end of treatment (VAS "0=no pain"; "100=pain as bad as you can imagine". Data from the preceding phase 2 study were combined with data from the present extension study to analyze the safety, efficacy and pharmacodynamics of 24-weeks of administration of Compound 1. Among the randomized patients in the preceding study (N=487), 397 were enrolled in this extension study; 77 to placebo, 78 to 89 to Compound 1 groups, and 69 to leuprorelin. Baseline characteristics were similar between randomized patients and all patients who entered the extension study. Overall, there were no significant differences in the demographic and baseline characteristics among the treatment groups (Table 7).

TABLE 7

Demographic and Baseline Characteristics

| Characteristic | Placebo (N = 99) | Relugolix 10 mg (N = 103) | Relugolix 20 mg (N = 100) | Relugolix 40 mg (N = 103) | Leuproreiin (N = 82) |
|---|---|---|---|---|---|
| Age (yrs) | 35.7 (6.06) | 35.3 (6.22) | 35.1 (6.78) | 35.6 (6.04) | 36.1 (6.13) |
| BMI (kg/m$^2$)[1] | 21.1 (3.01) | 21.5 (3.35) | 20.4 (2.46) | 21.6 (3.14) | 21.8 (3.40) |
| Disease Duration (y) | 3.9 (4.65) | 3.8 (5.04) | 3.2 (3.84) | 4.3 (5.47) | 2.9 (3.78) |
| Mean VAS score (mm)[2] | | | | | |
| Pelvic Pain (Overall)[1] | 15.6 (14.32) | 14.6 (11.99) | 15.6 (15.06) | 15.3 (11.99) | 15.2 (15.10) |
| Dysmenorrhea[1] | 28.4 (16.59) | 28.2 (17.64) | 27.7 (18.94) | 30.4 (17.04) | 27.1 (19.78) |
| Dyspareunia[3] | 11.0 (14.25) | 8.8 (14.24) | 12.5 (16.48) | 9.4 (15.42) | 9.5 (10.71) |

TABLE 7-continued

| | Demographic and Baseline Characteristics | | | | |
|---|---|---|---|---|---|
| | | Relugolix | | | |
| Characteristic | Placebo (N = 99) | 10 mg (N = 103) | 20 mg (N = 100) | 40 mg (N = 103) | Leuprorelin (N = 82) |
| Mean Modified (Patient) B&B Score | | | | | |
| Non-menstrual Pelvic Pain[1] | 0.6 (0.45) | 0.7 (0.46) | 0.6 (0.47) | 0.7 (0.44) | 0.7 (0.55) |
| Dysmenorrhea[1] | 1.2 (0.44) | 1.2 (0.47) | 1.2 (0.48) | 1.2 (0.47) | 1.2 (0.47) |
| Dyspareunia[3] | 0.6 (0.45) | 0.6 (0.60) | 0.6 (0.55) | 0.5 (0.48) | 0.6 (0.45) |
| Proportion of Days with Usage of Analgesics [%][1] | 10.0 (11.55) | 12.5 (12.32) | 13.3 (16.43) | 12.0 (14.53) | 11.6 (13.84) |

Note:
Mean (SD) or number of patients (%).
[1]N = 103, N = 100, and N = 103 in the relugolix 10-, 20-, and 40-mg groups, respectively, and N = 81 in the leuprorelin group and N = 97 in the placebo group.
[2]Mean VAS score at baseline: Mean VAS score during the placebo run-in period.
[3]N = 46, N = 47, and N = 44 in the relugolix 10-, 20- and 40-mg groups, respectively, and N = 26 in the leuprorelin group and N = 41 in the placebo group.

As noted in Example 7, (the preceding phase 2 study) consisted of a pretreatment period of 4 to 12 weeks with a placebo run-in that was initiated during the first menstruation cycle and continued until randomization and a treatment period of 12 weeks. The present extension study consisted of an additional treatment period of 12 weeks and a follow-up period of 4 weeks. Overall treatment duration was 24 weeks from the beginning of the preceding phase 2 study. Patients were assigned to the same treatment group as the preceding phase 2 study. Study groups included Compound 1 10-, 20-, 40-mg, placebo once-daily orally, or leuprorelin 3.75 mg (injection, once/4 weeks).

The incidences of adverse events including metrorrhagia, menorrhagia, and hot flash in the Compound 1 40 mg group were similar to those in the leuprorelin group. Dose-dependent bone mineral density loss was observed with Compound 1 treatment, with the Compound 1 40 mg result consistent with the leuprorelin result. The change from baseline in mean visual analogue scale score for pelvic pain (in mm) during the last 4 weeks of treatment period was −3.222 in the placebo group, −6.849, −9.032, and −11.924 in Compound 1 10 mg, 20 mg and 40 mg groups, respectively, and −12.552 in the leuprorelin group. Estradiol levels decreased with increasing dose of Compound 1 and were maintained below the postmenopausal levels throughout the 24-week Compound 1 40 mg treatment period. Treatment with Compound 1 for 24 weeks was generally well tolerated and demonstrated similar pelvic pain reduction as leuprorelin in women with EM. Compound 1, a once-daily oral nonpeptide GnRH receptor antagonist, demonstrated similar benefit to injectable leuprorelin in this phase 2 study. Treatment with the Compound 1 10-, 20-, or 40-mg for 12 weeks resulted in significant reductions in pelvic pain and dysmenorrhea, compared with placebo treatment, and was generally well tolerated consistent with its mechanism of action (Table 8).

TABLE 8

| | Adverse Event (AE) Summary | | | | |
|---|---|---|---|---|---|
| | | Relugolix | | | |
| Variables, N (%) | Placebo (N = 97) | 10 mg (N = 103) | 20 mg (N = 100) | 40 mg (N = 103) | Leuprorelin (N = 81) |
| Any TEAEs | 79 (81.4) | 89 (86.4) | 96 (96.0) | 98 (95.1) | 79 (97.5) |
| Mild | 68 (70.1) | 83 (80.6) | 82 (82.0) | 83 (80.6) | 65 (80.2) |
| Moderate | 9 (9.3) | 6 (5.8) | 14 (14.0) | 15 (14.6) | 14 (17.3) |
| Severe | 2 (2.1) | 0 (0.0) | 0 (0.0) | 0 (0.0) | 0 (0.0) |
| TEAEs Related to Study Drug | 38 (39.2) | 68 (66.0) | 88 (88.0) | 91 (88.3) | 73 (90.1) |
| TEAEs Leading to Study Drug Discontinuation | 6 (6.2) | 1 (1.0) | 7 (7.0) | 2 (1.9) | 9 (11.1) |
| Serious TEAEs | 5 (5.2) | 0 (0.0) | 2 (2.0) | 0 (0.0) | 0 (0.0) |
| Common TEAEs (≥10% of Patients in anyGroup) | | | | | |
| Nasopharyngitis | 32 (33.0) | 31 (30.1) | 31 (31.0) | 31 (30.1) | 26 (32.1) |
| Headache | 10 (10.3) | 5 (4.9) | 12 (12.0) | 11 (10.7) | 11 (13.6) |
| Metrorrhagia | 8 (8.2) | 28 (27.2) | 36 (36.0) | 30 (29.1) | 32 (39.5) |
| Menstruation Irregular | 5 (5.2) | 21 (20.4) | 21 (21.0) | 7 (6.8) | 5 (6.2) |
| Menorrhagia | 5 (5.2) | 11 (10.7) | 16 (16.0) | 15 (14.6) | 9 (11.1) |
| Oligomenorrhea | 2 (2.1) | 12 (11.7) | 12 (12.0) | 1 (1.0) | 0 (0.0) |

TABLE 8-continued

Adverse Event (AE) Summary

| Variables, N (%) | Placebo (N = 97) | Relugolix 10 mg (N = 103) | Relugolix 20 mg (N = 100) | Relugolix 40 mg (N = 103) | Leuprorelin (N = 81) |
|---|---|---|---|---|---|
| Hyperhidrosis | 1 (1.0) | 4 (3.9) | 11 (11.0) | 10 (9.7) | 11 (13.6) |
| Hot flush | 8 (8.2) | 12 (11.7) | 23 (23.0) | 55 (53.4) | 38 (46.9) |

Note:
An adverse event was defined as any untoward medical occurrence that started on or after the first dose through the end of study. A patient was counted once if the patient reported one or more events.

The incidence of TEAEs including metrorrhagia, menorrhagia, and hot flash (hot flush) in the Compound 1 (relugolix) 40 mg group was similar to those in the leuprorelin group. For the Compound 1 groups, there was a time- and dose-dependent decrease in bone mineral density from baseline. The reduction in bone mineral density in the Compound 1 40 mg group was similar to that in the leuprorelin group (Table 9). The menstruation recovery period was 21 to 37 days after the last dose in the Compound 1 groups, and the recovery period in the leuprorelin group was approximately twice as long as that in the Compound 1 40 mg group (Table 9). There were no clinically significant changes among the treatment groups for laboratory test results, vital signs, weight or ECG parameters and no pregnancies occurred during the study.

TABLE 9

Other Safety Endpoints

| Endpoint | | Placebo | Compound 1 10 mg | Compound 1 20 mg | Compound 1 40 mg | Leuprorelin |
|---|---|---|---|---|---|---|
| Change from Baseline in BMD at Week 24 (%) | N | 75 | 81 | 77 | 88 | 64 |
| | Mean | −0.2 | −1.6 | −2.6 | −4.9 | −4.4 |
| | (SD) | (1.99) | (2.34) | (2.94) | (2.91) | (2.16) |
| Menstruation Recovery Period (Days) | N | 93 | 103 | 95 | 97 | 72 |
| | Mean | 17 | 21 | 26 | 37 | 73 |
| | (SD) | (8.5) | (12.3) | (13.0) | (9.5) | (21.2) |

BMD: bone mineral density;
SD: standard deviation

Figure 70:
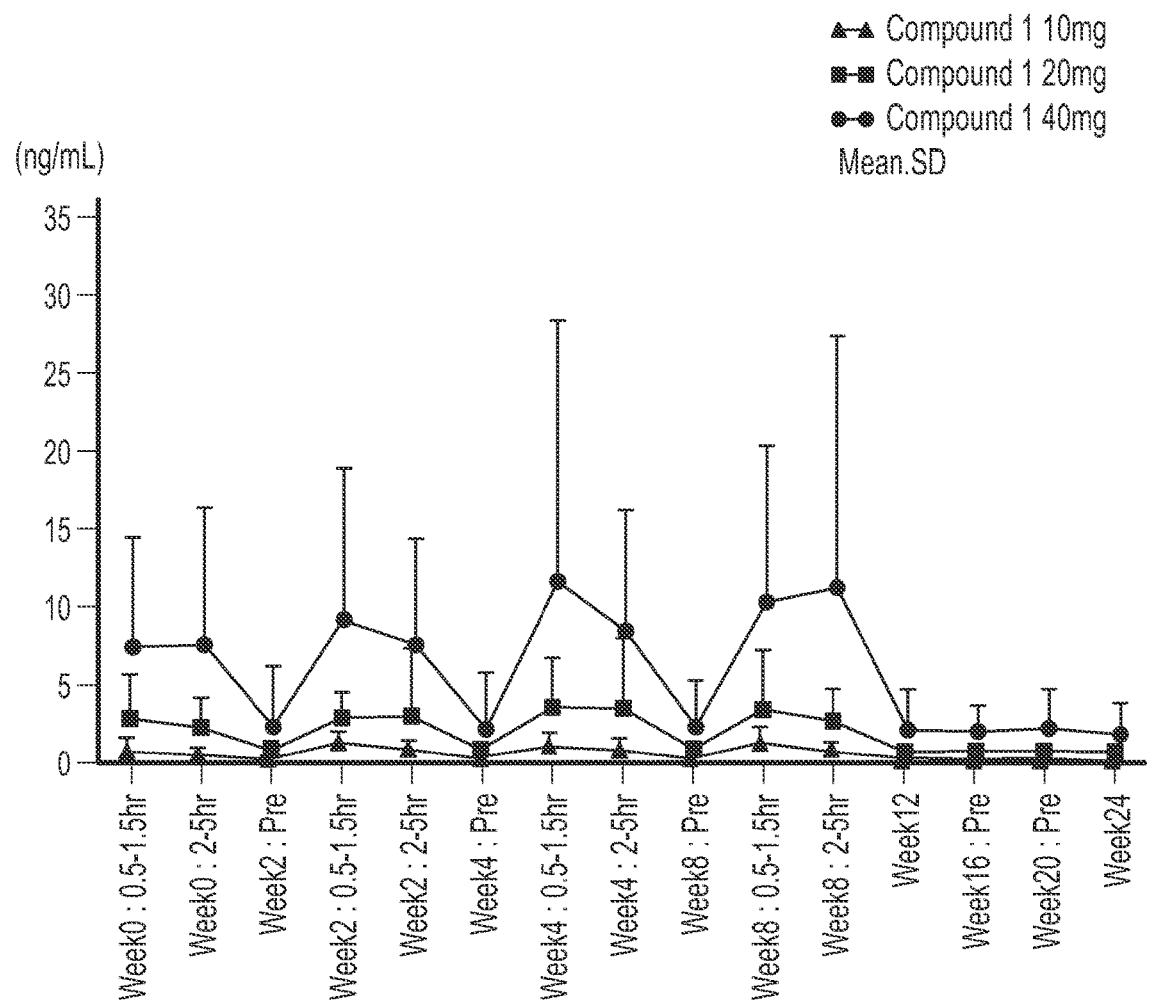
FIG. 70 graphically depicts plasma concentrations of unchanged Compound 1 for a treatment period of 24 weeks in accordance with Example 8.

The plasma concentrations of unchanged Compound 1 were higher levels at 0.5 to 1.5 or at 2 to 5 hours after administration in all treatment groups and increased with dose escalation among the 10, 20, and 40 mg of Compound 1. The plasma drug concentrations prior to administration at each Visit (trough values) corresponded to the dose levels of Compound 1 and were comparable in each treatment group throughout the treatment period for 24 weeks, showing the dose-proportional tendency of Compound 1 in plasma concentrations after oral administration, that the steady state had already been reached by 2 weeks after administration, and that there was no alteration in PK aspects from long-term administration of the Compound 1 formulation for 24 weeks. Plasma concentrations of unchanged Compound 1 for the treatment period of 24 weeks are graphically depicted in FIG. 70 and tabulated in FIG. 71.

Figure 72:
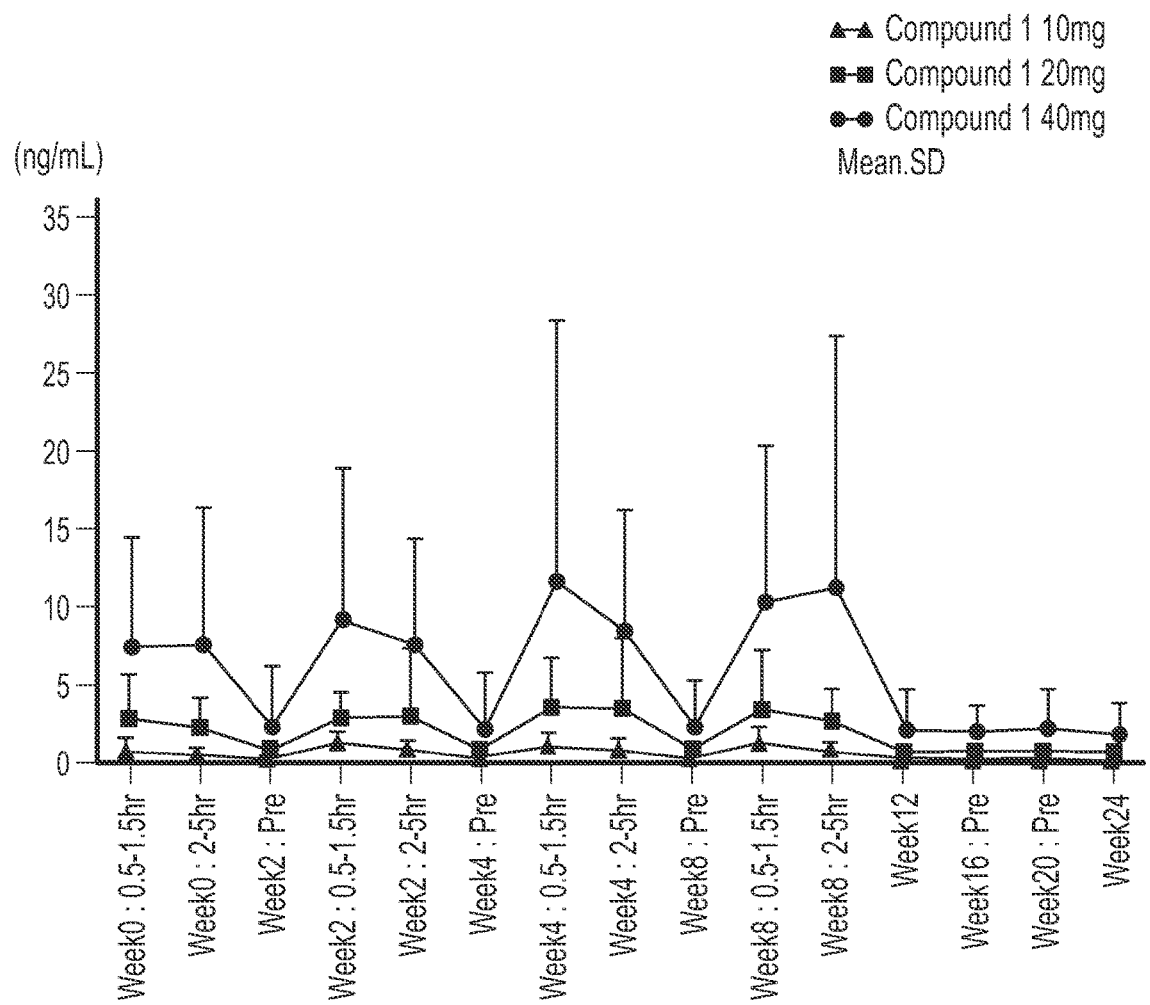
FIG. 72 graphically depicts plasma concentrations of unchanged Compound 1 for a treatment period of 24 weeks in which the Compound 1 was administered 30 minutes before a meal in accordance with Example 8.
Figure 74:
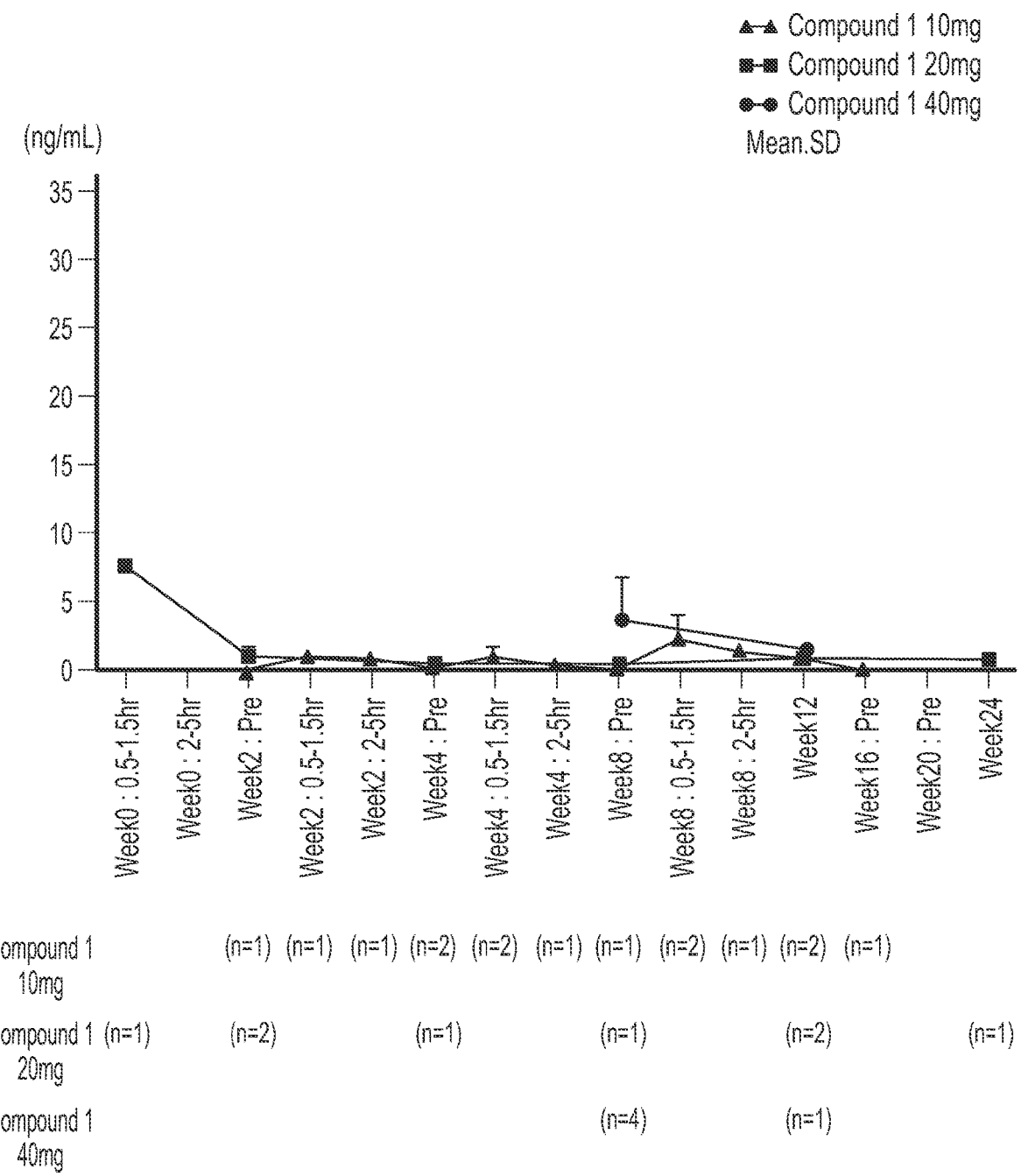
FIG. 74 graphically depicts plasma concentrations of unchanged Compound 1 for a treatment period of 24 weeks in which the Compound 1 was not administered 30 minutes before a meal in accordance with Example 8.

When the plasma concentrations of unchanged Compound 1 were separately tabulated for subjects in whom the study drug could not be administered at 30 minutes before meal, the plasma concentrations of unchanged Compound 1 were lower than in the subjects in which the study drug was administered at 30 minutes before meal. Plasma concentrations of unchanged Compound 1, for the treatment period of 24 weeks, in which Compound 1 was administered 30 minutes before a meal are graphically depicted in FIG. 72 and tabulated in FIG. 73, and in which Compound 1 was not administered 30 minutes before a meal are graphically depicted in FIG. 74 and tabulated in FIG. 75.

The absorption of Compound 1 in plasma was decreased and delayed following a single dose administered 30 minutes after the start of a standard U.S. Food and Drug Administration (FDA) high fat, high-calorie breakfast (approx. 800–1000 calories, 50% from fat) compared to fasting conditions. Median $T_{max}$ increased under fed conditions. Mean $C_{max}$ and mean plasma $AUC_\infty$ were reduced under fed conditions compared with fasted conditions, indicating a clinically meaningful effect of food on the oral bioavailability of the Compound 1 formulation. In this study, the Compound 1 formulation was administered daily 30 minutes prior to ingestion of a standardized morning meal (approx. 600 calories, 27% from fat). Under these conditions, systemic exposure to the Compound 1 formulation was reduced to a lesser extent and no obvious changes in the rate of absorption were observed when compared to fasting conditions. Consequently, in the studies, subjects were instructed to take the Compound 1 formulation upon arising in the morning, on an empty stomach, and start eating approximately 30 minutes after dosing whenever possible.

Figure 77:
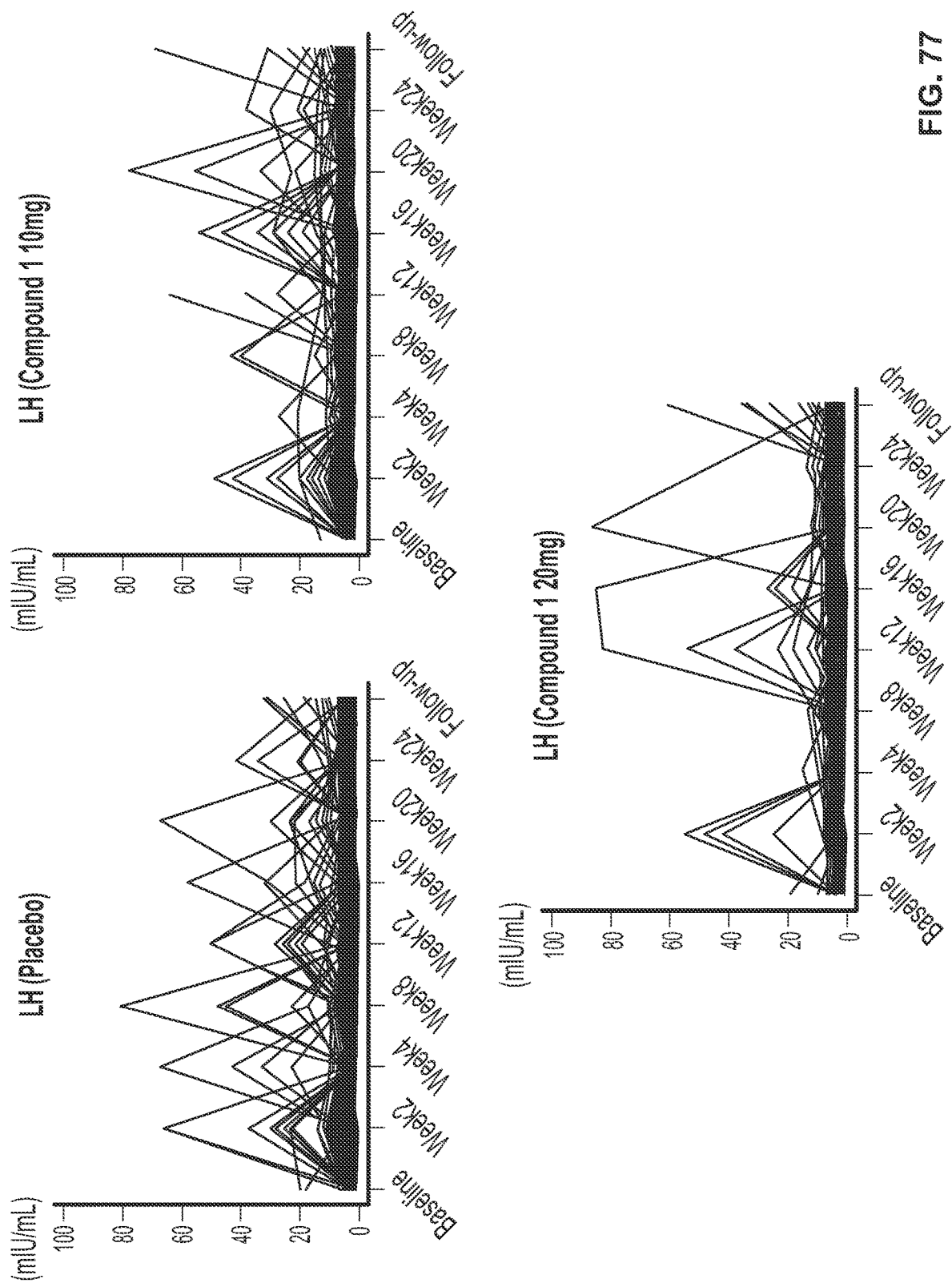
FIG. 77 graphically depicts serum luteinizing hormone (LH) concentrations for a treatment period of 24 weeks in accordance with Example 8.
Figure 77:
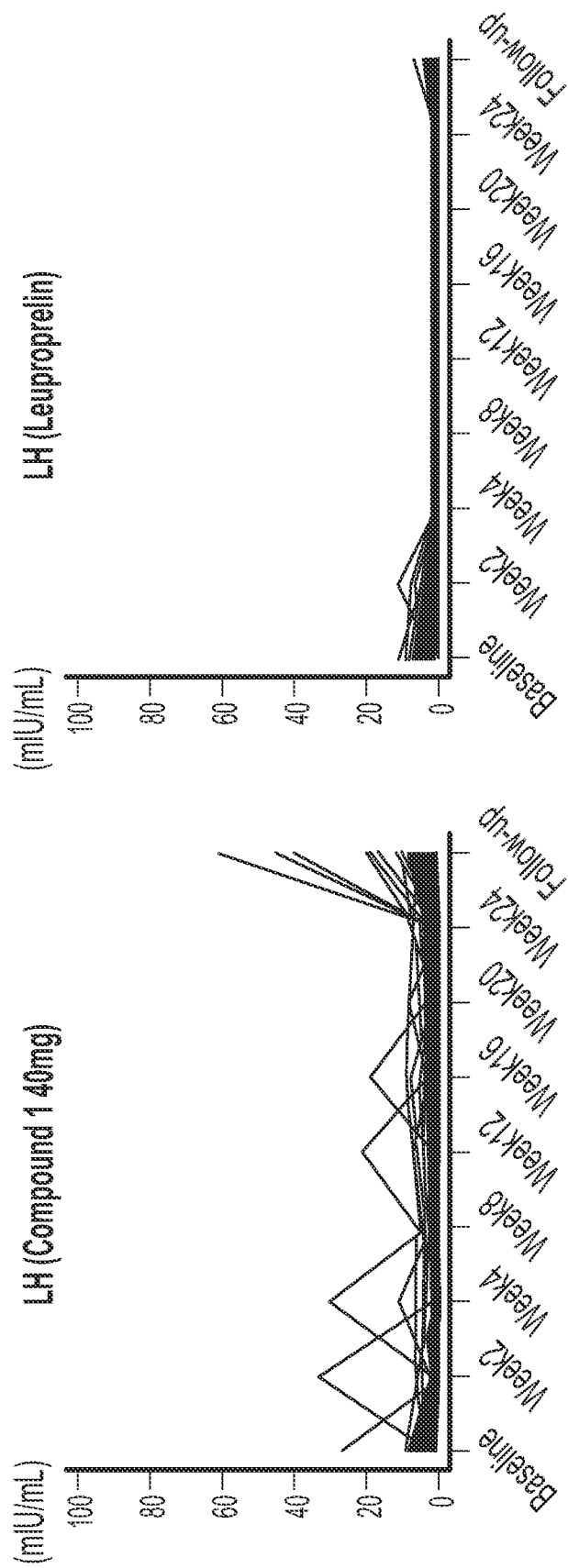

Serum LH concentrations for the treatment period of 24 weeks are graphically depicted in FIG. 77 and tabulated in FIGS. 78A-B. A table of demographic and baseline characteristics for the analyses in this example is set forth in FIGS. 76A-C. The median change in serum LH concentrations at Week 24 from baseline was 0.945 mIU/mL in placebo, 0.300 mIU/mL in the Compound 1 formulation 10 mg, −0.785 mIU/mL in the Compound 1 formulation 20 mg, −2.480 mIU/mL in the Compound 1 formulation 40 mg, and −3.140 mIU/mL in leuprolide acetate groups. The serum LH concentrations were lower in the Compound 1 formulation 40 mg groups during the treatment period as in leuprolide acetate group.

Figure 79:
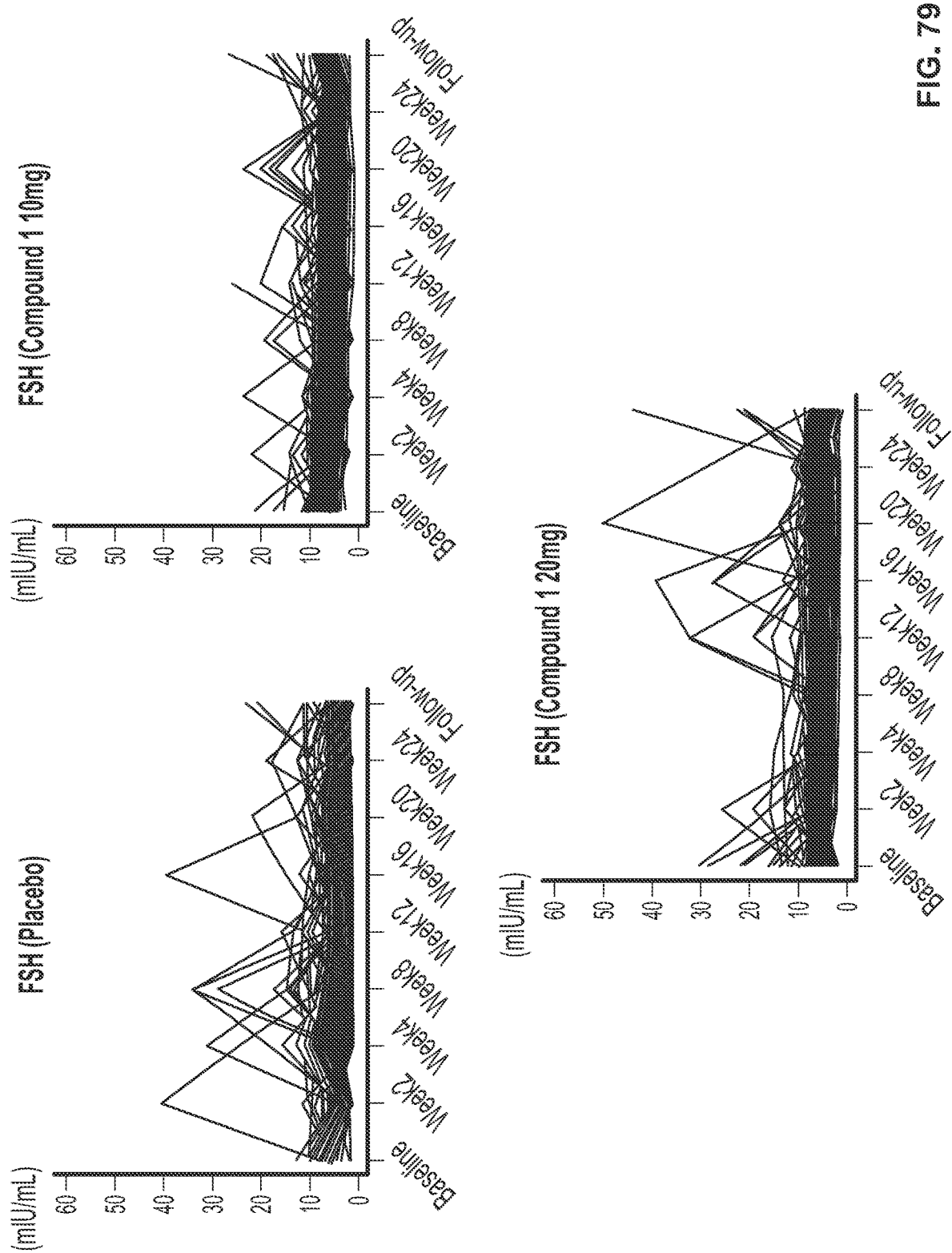
FIG. 79 graphically depicts serum follicle stimulating hormone (FSH) concentrations for a treatment period of 24 weeks in accordance with Example 8.
Figure 79:
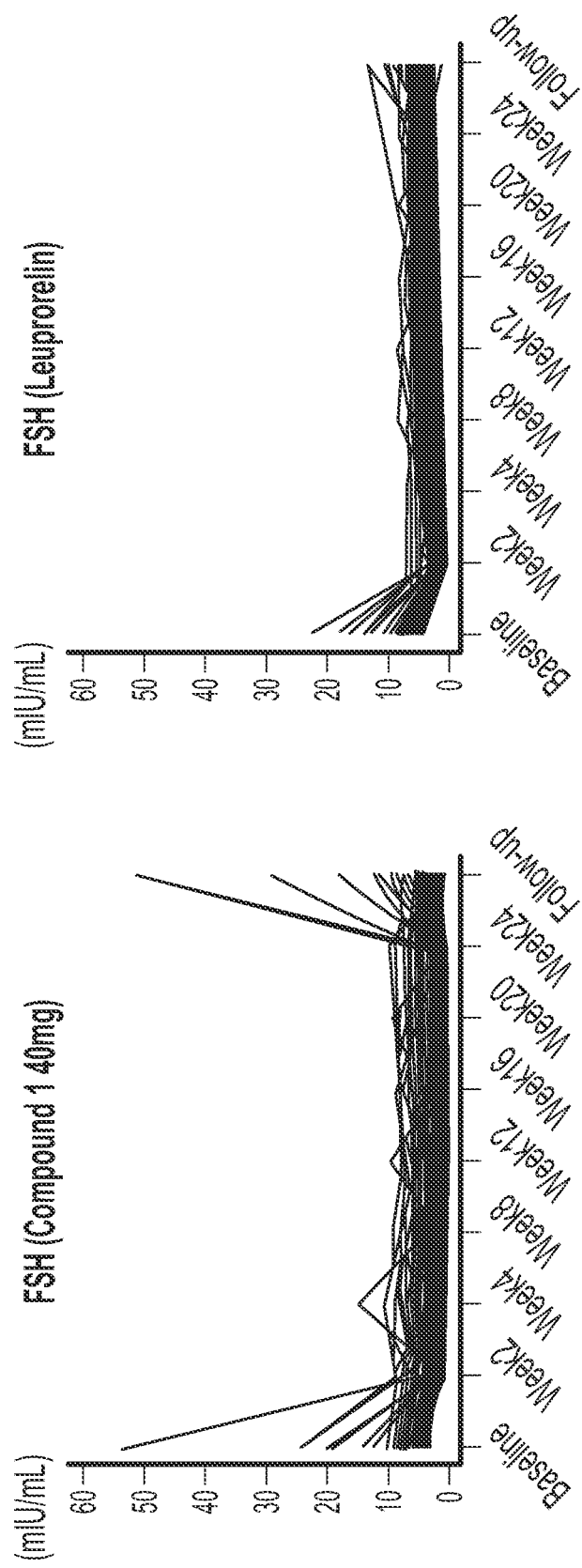

Serum FSH concentrations for the treatment period of 24 weeks are graphically depicted in FIG. 79 and tabulated in FIG. 80A-B. The median change in serum FSH concentrations at Week 24 from baseline was −0.985 mIU/mL in placebo, −0.630 mIU/mL in the Compound 1 formulation 10 mg, −0.990 mIU/mL in the Compound 1 formulation 20 mg, and −3.550 mIU/mL in the Compound 1 formulation 40 mg, and −2.730 mIU/mL in leuprolide acetate groups. The serum FSH concentrations were lower in the Compound 1 formulation 40 mg group during the treatment period. Leuprolide acetate group showed a similar but slightly higher profile than that in the Compound 1 formulation 40 mg group.

Figure 81:
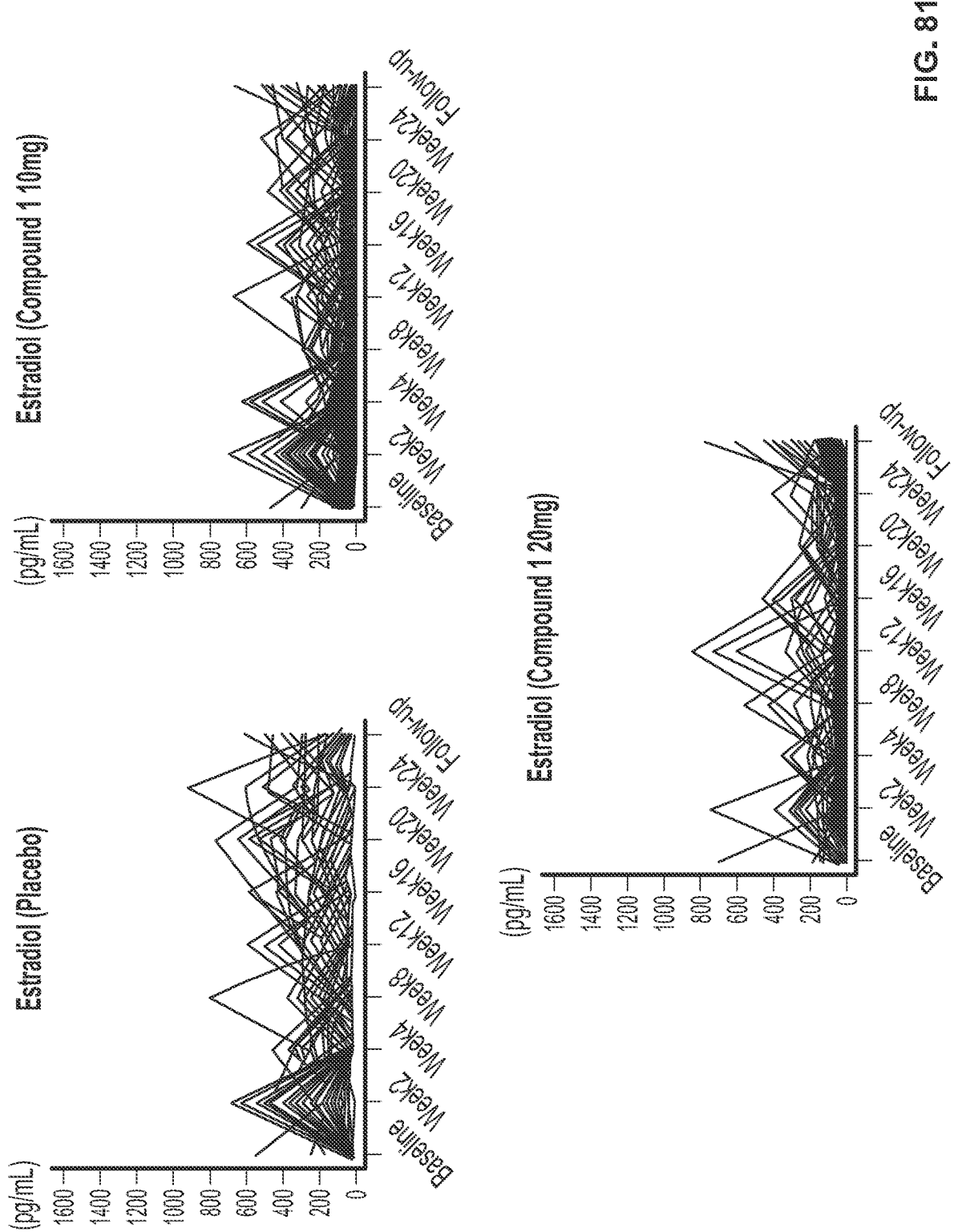
FIG. 81 graphically depicts serum estradiol ($E_2$) concentrations for a treatment period of 24 weeks in accordance with Example 8.
Figure 83:
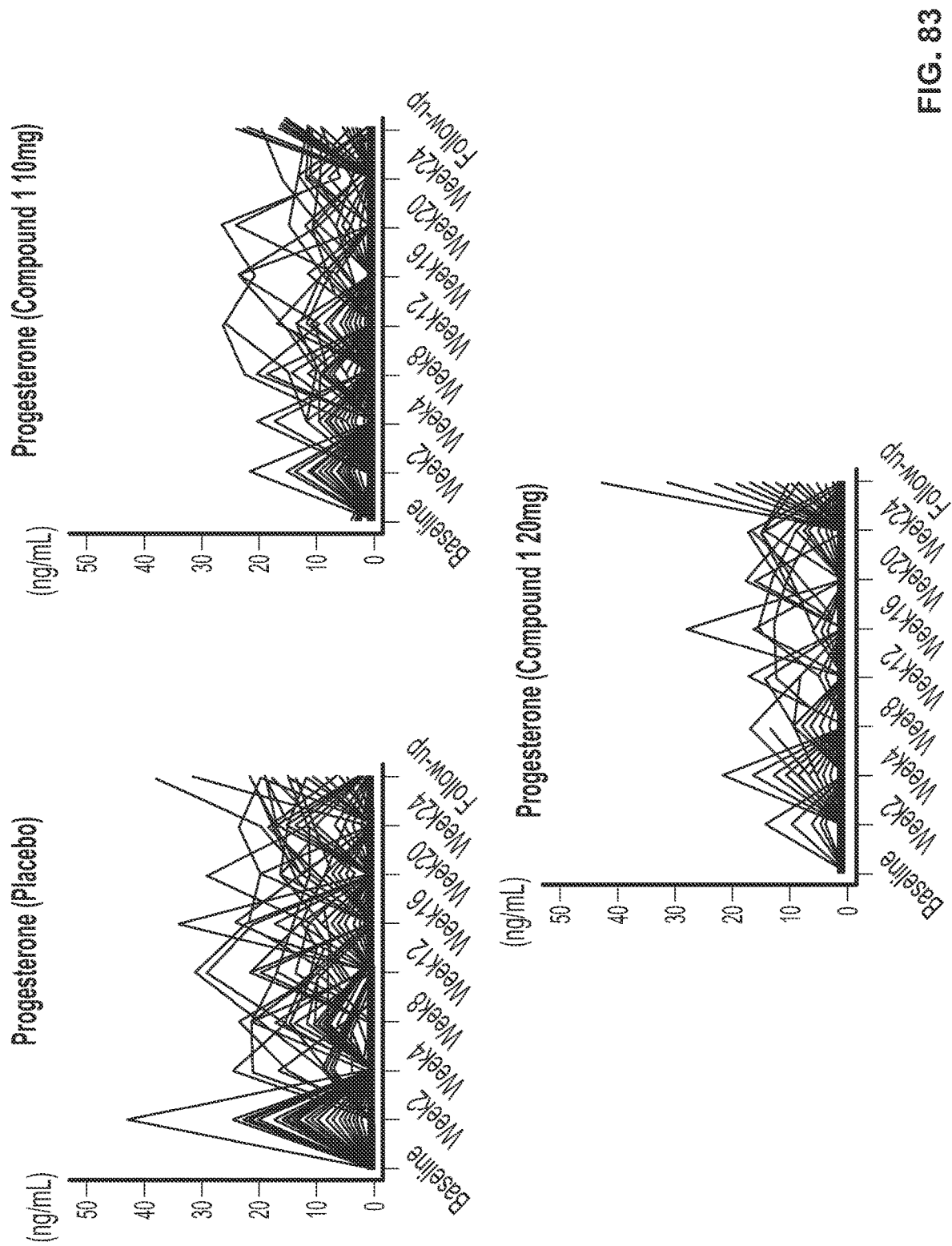
FIG. 83 graphically depicts serum progesterone concentrations for a treatment period of 24 weeks in accordance with Example 8.
Figure 83:
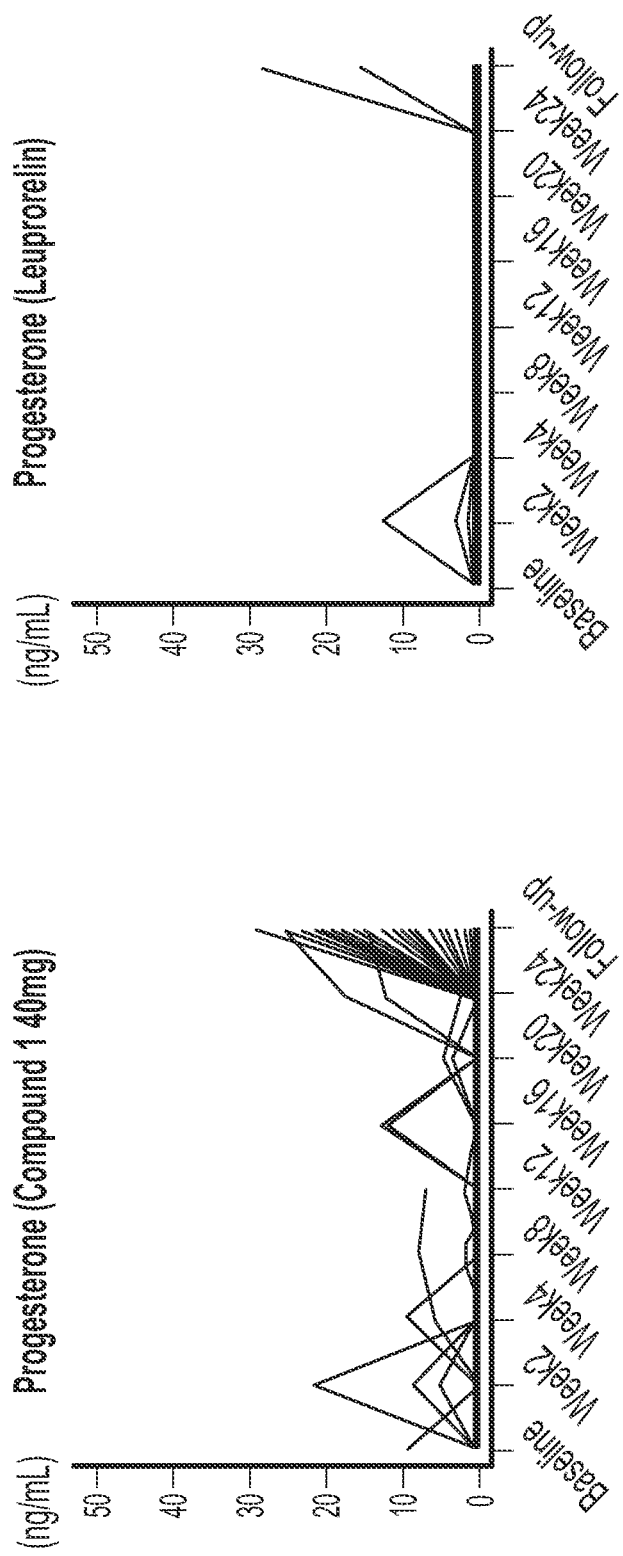

Serum estradiol ($E_2$) concentrations for the treatment period of 24 weeks are graphically depicted in FIG. 81 and tabulated in FIGS. 82A-B. The median change in serum $E_2$ concentrations at Week 24 from baseline was 56.0 pg/mL in placebo, 1.0 pg/mL in the Compound 1 formulation 10 mg, −9.0 pg/mL in the Compound 1 formulation 20 mg, −39.0 pg/mL in the Compound 1 formulation 40 mg, and −40.0 pg/mL in leuprolide acetate groups. The serum $E_2$ concentrations were lower with dose-dependent manner of the Compound 1 formulation during the treatment period. In the Compound 1 formulation 40 mg group, the median of serum $E_2$ concentration decreased to 0.0 pg/mL (less than the lower limit of quantification: LLQ) at Week 2 and thereafter maintained below the lower limit of quantitation (LLQ) until Week 24. In the leuprolide acetate group, the median of serum $E_2$ concentration decreased to LLQ at Week 4 and thereafter maintained LLQ until Week 24. Serum P concentrations for the treatment period of 24 weeks are graphically depicted in FIG. 83 and tabulated in FIGS. 84A-B. The median change in serum progesterone (P) concentrations at Week 24 from baseline was 0.110 ng/mL in placebo, 0.000 ng/mL in the Compound 1 formulation 10 mg, 0.005 ng/mL in the Compound 1 formulation 20 mg, and −0.080 ng/mL in the Compound 1 formulation 40 mg, and −0.070 ng/mL in leuprolide acetate groups. The serum P concentrations were slightly lower in the Compound 1 formulation groups than in placebo group during the treatment period as in leuprolide acetate group.

Percent change from baseline in biochemical endometriosis marker (CA125) concentrations for the treatment period of 24 weeks are tabulated in FIG. 86. The percent changes from baseline in biochemical endometriosis efficacy biomarker (CA125) concentration at Week 24 (mean±SD) were −14.01±55.858% in placebo, −39.08±41.893% in the Compound 1 formulation 10 mg, −46.24±33.099% in the Compound 1 formulation 20 mg, −56.69±45.139% in the Compound 1 formulation 40 mg, and −54.15±46.359% in leuprolide acetate groups, respectively. Larger changes of CA125 concentration at higher dose levels of the Compound 1 formulation were seen from the early stage of administration. The change in the Compound 1 formulation 40 mg group was also comparable to that in leuprolide acetate group. The proportion of subjects whose CA125 concentration being less than or equal to 35 U/mL at Week 24 were 54.8%, 75.3%, 81.1%, 88.5%, and 88.9% in placebo, the Compound 1 formulation 10 mg, the Compound 1 formulation 20 mg, the Compound 1 formulation 40 mg, and leuprolide acetate groups, respectively. Biochemical endometriosis marker (CA125) concentrations for the treatment period of 24 weeks are tabulated in FIG. 85.

The changes from baseline in mean of VAS scores for pelvic pain at the end of treatment period were −3.222±12.1616 mm in placebo, −6.849±10.5616 mm in Compound 1 formulation 10 mg, −9.032±11.8432 mm in Compound 1 formulation 20 mg, −11.924±11.2609 mm in Compound 1 formulation 40 mg, and −12.552±12.5609 mm in leuprolide acetate groups, and were larger in higher dose levels of the Compound 1 formulation in a time-dependent manner throughout the treatment period for 24 weeks. Those for dysmenorrhea were also larger in higher dose levels of the Compound 1 formulation in a time-dependent manner throughout the treatment period. The changes and profiles of VAS score for pelvic pain and dysmenorrhea in the Compound 1 formulation 40 mg group were similar to those in leuprolide acetate group.

Figure 87:
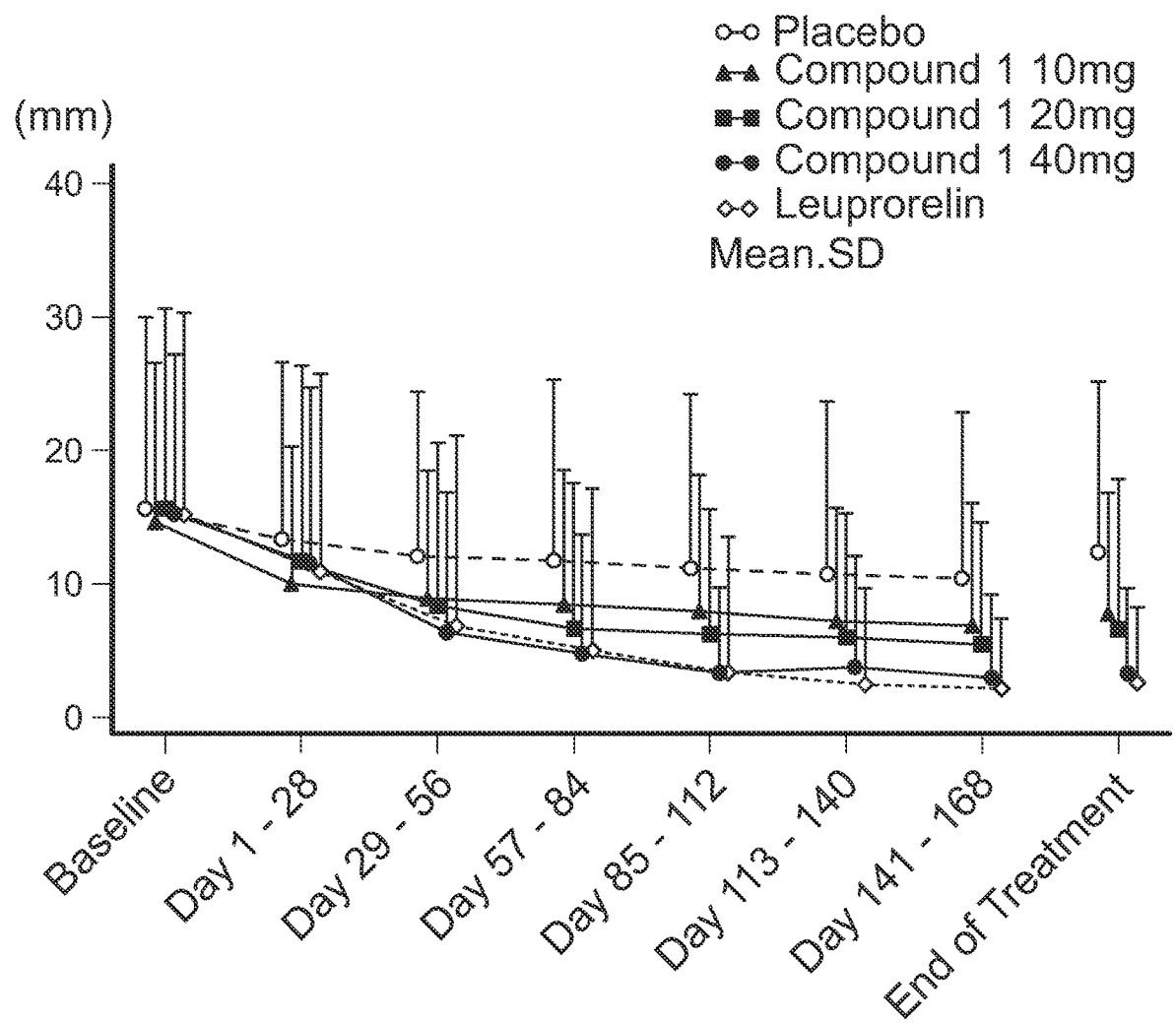
FIG. 87 graphically depicts the mean of visual analogue scale (VAS) scores by visit for pelvic pain for a treatment period of 168 days in accordance with Example 8.

The mean of VAS scores by visit for pelvic pain for the treatment period of 168 days are graphically depicted in FIG. 87 and tabulated in FIG. 88. Also, while the mean of VAS scores for pelvic pain at baseline were around 15 mm in each treatment group, the mean of VAS score (mean±SD) at Day 1–28, Day 57–84, Day 141–168 and the end of treatment period were 13.315±13.1953 mm, 11.776±13.5443 mm, 10.444±12.3696 mm, and 12.387±12.7540 mm, respectively, in placebo group; 9.988±10.3249 mm, 8.400±10.1329 mm, 6.861±9.2099 mm, and 7.746±9.0900 mm in the Compound 1 formulation 10 mg group; 11.627±14.7324 mm, 6.675±10.8072 mm, 5.486±9.1562 mm, and 6.557±11.2902 mm in the Compound 1 formulation 20 mg group; 11.498±13.2341 mm, 4.785±8.9162 mm, 2.979±6.1704 mm, and 3.335±6.4059 mm in the Compound 1 formulation 40 mg group; and 10.899±14.8866 mm, 5.013±12.0454 mm, 2.167±5.1999 mm, and 2.629±5.5783 mm in leuprolide acetate group.

Figure 89:
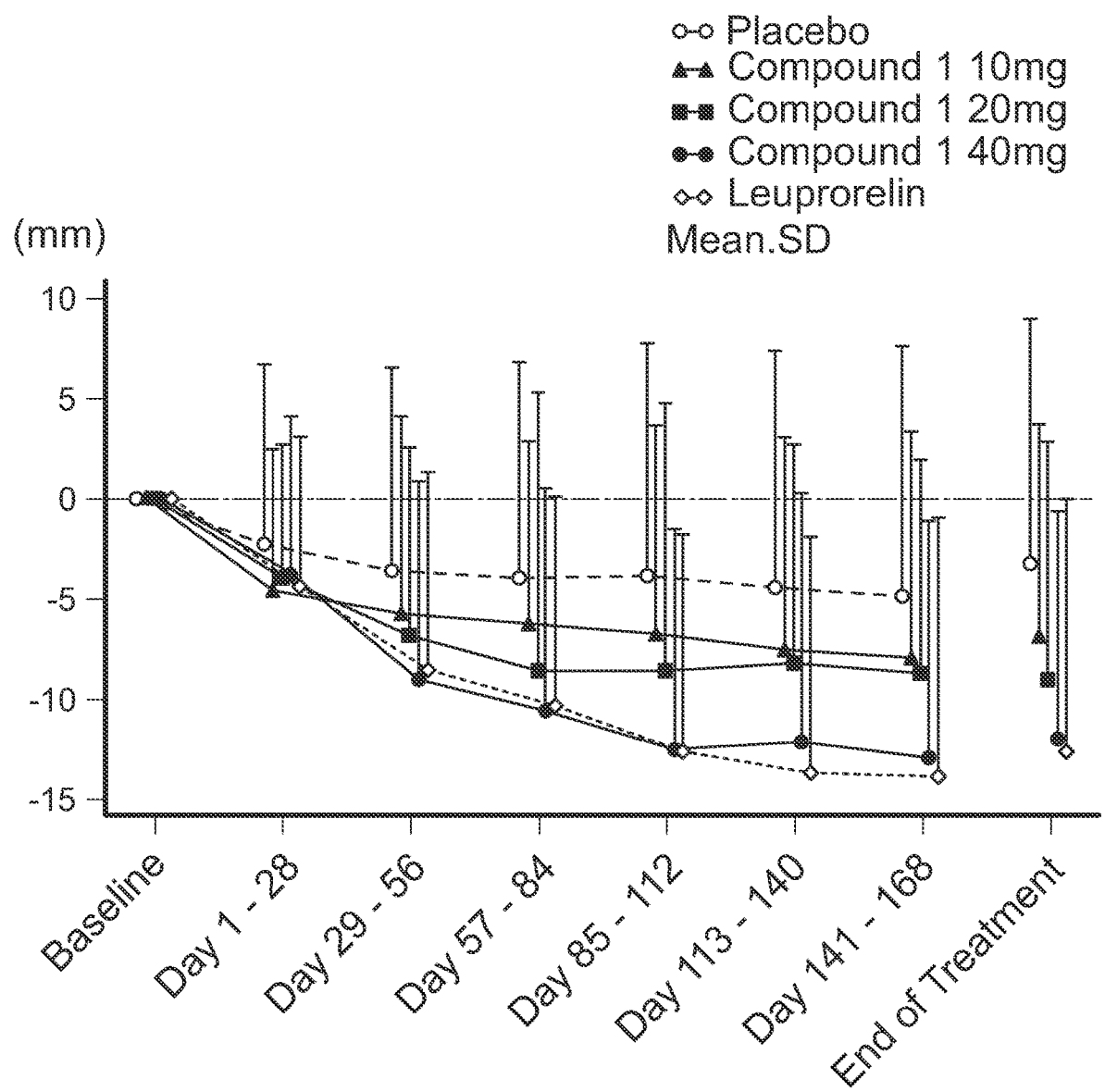
FIG. 89 graphically depicts the change from baseline in mean of VAS scores by visit for pelvic pain for a treatment period of 168 days in accordance with Example 8.

The changes from baseline in mean of VAS score for pelvic pain at Day 1–28, Day 57–84, Day 141–168 and the end of treatment period were −2.294±8.9903 mm, −3.945±10.7499 mm, −4.866±12.4477 mm, and −3.222±12.1616 mm, respectively, in placebo group; −4.606±7.1304 mm, −6.282±9.1659 mm, −7.872±11.2457 mm, and −6.849±10.5616 mm in the Compound 1 formulation 10 mg group; −3.962±6.6751 mm, −8.547±13.8568 mm, −8.678±10.6479 mm, and −9.032±11.8432 mm in the Compound 1 formulation 20 mg group; −3.761±7.8831 mm, −10.537±11.0516 mm, −12.919±11.8210 mm, and −11.924±11.2609 mm in the Compound 1 formulation 40 mg group; and −4.282±7.3628 mm, −10.364±10.4428 mm, −13.804±12.8288 mm, and −12.552±12.5609 mm in leuprolide acetate group. The changes from baseline in mean of VAS scores by visit for pelvic pain for the treatment period of 168 days are graphically depicted in FIG. 89 and tabulated in FIG. 90. The changes from baseline in mean of VAS scores by visit (comparison with leuprolide acetate) for pelvic pain for the treatment period of 168 days are tabulated in FIG. 91.

The changes from baseline in mean of VAS scores for pelvic pain were larger in higher dose levels of the Compound 1 formulation in a time-dependent manner throughout the treatment period. The profile of VAS scores for pelvic pain in the Compound 1 formulation 40 mg group was similar to that in leuprolide acetate group.

Figure 92:
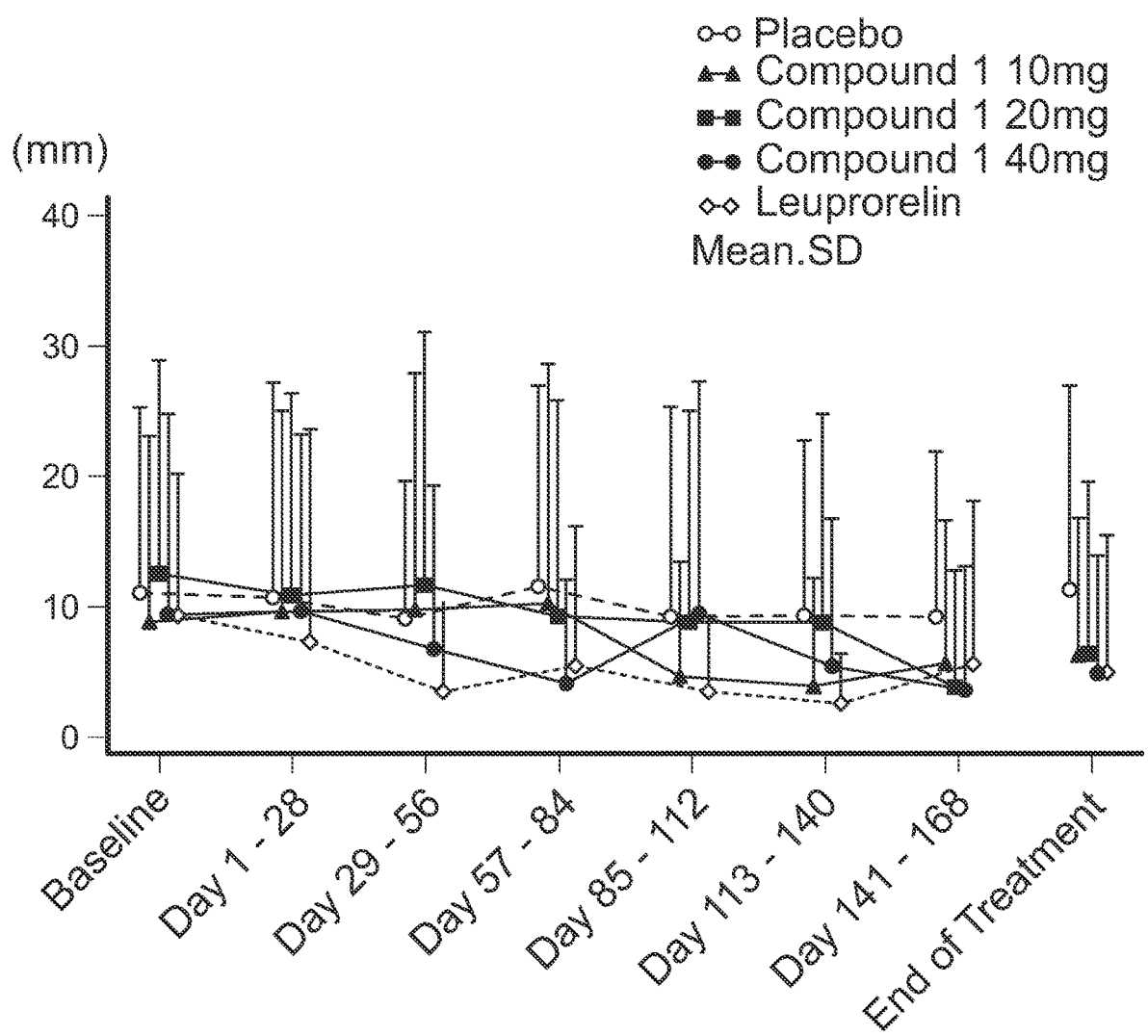
FIG. 92 graphically depicts the mean of VAS scores by visit for dyspareunia for a treatment period of 168 days in accordance with Example 8.

The mean of VAS scores by visit for dyspareunia for the treatment period of 168 days are graphically depicted in FIG. 92 and tabulated in FIG. 93. While the mean of VAS scores for dyspareunia at baseline were 8.8 to 12.5 mm in each treatment group, the mean of VAS score (mean SD) at Day 1–28, Day 57–84, Day 141–168, and the end of treatment period were 10.676±16.5317 mm, 11.445±15.5573 mm, 9.192±12.7469 mm, and 11.318±15.7393 mm, respectively, in placebo group;

9.608±15.4027 mm, 10.110±18.5404 mm, 5.550±11.1157 mm, and 6.218±10.6280 mm in the Compound 1 formulation 10 mg group; 10.809±15.5738 mm, 9.229±16.6530 mm, 3.806±8.9781 mm, and 6.363±13.1847 mm in the Compound 1 formulation 20 mg group; 9.522±13.6408 mm, 4.126±7.9652 mm, 3.531±9.6053 mm, and 4.842±9.1145 mm in the Compound 1 formulation 40 mg group; and 7.288±16.2960 mm, 5.478±10.7612 mm, 5.565±12.5556 mm, and 4.913±10.6249 mm in leuprolide acetate group.

Figure 94:
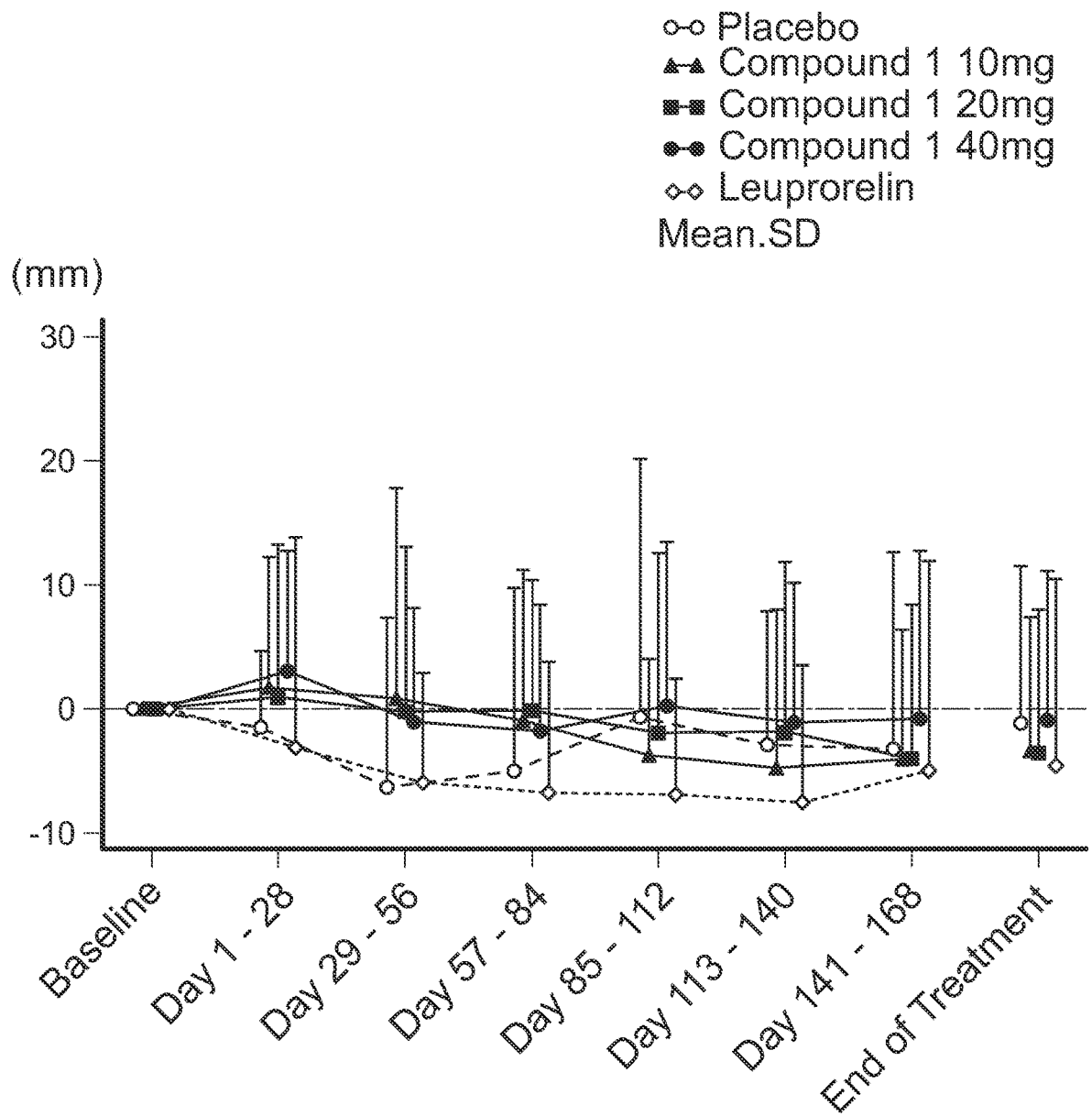
FIG. 94 graphically depicts the changes from baseline in mean of VAS scores by visit for dyspareunia for a treatment period of 168 days in accordance with Example 8.

The changes from baseline in mean of VAS score for dyspareunia at Day 1-28, Day 57-84, Day 141-168, and the end of treatment period were −1.464±6.1084 mm, −5.018±14.8372 mm, −3.256±15.8951 mm, and −1.145±12.6625 mm, respectively, in placebo group; 1.642±10.6212 mm, −1.033±12.2047 mm, −4.124±10.5641 mm, and −3.454±10.8509 mm in the Compound 1 formulation 10 mg group; 0.953±12.3795 mm, −0.191±10.6032 mm, −4.012±12.5050 mm, and −3.553±11.5544 mm in the Compound 1 formulation 20 mg group; 2.995±9.7916 mm, −1.860±10.3161 mm, −0.830±13.6774 mm, and −0.925±12.0373 mm in the Compound 1 formulation 40 mg group; and −3.126±17.0520 mm, −6.752±10.5824 mm, −4.953±16.9523 mm, and −4.593±15.0878 mm in leuprolide acetate group. The changes from baseline in mean of VAS scores by visit for dyspareunia for the treatment period of 168 days are graphically depicted in FIG. 94 and tabulated in FIG. 95. The changes from baseline in mean of VAS scores by visit (comparison with leuprolide acetate) for dyspareunia for the treatment period of 168 days are tabulated in FIG. 96.

Figure 97:
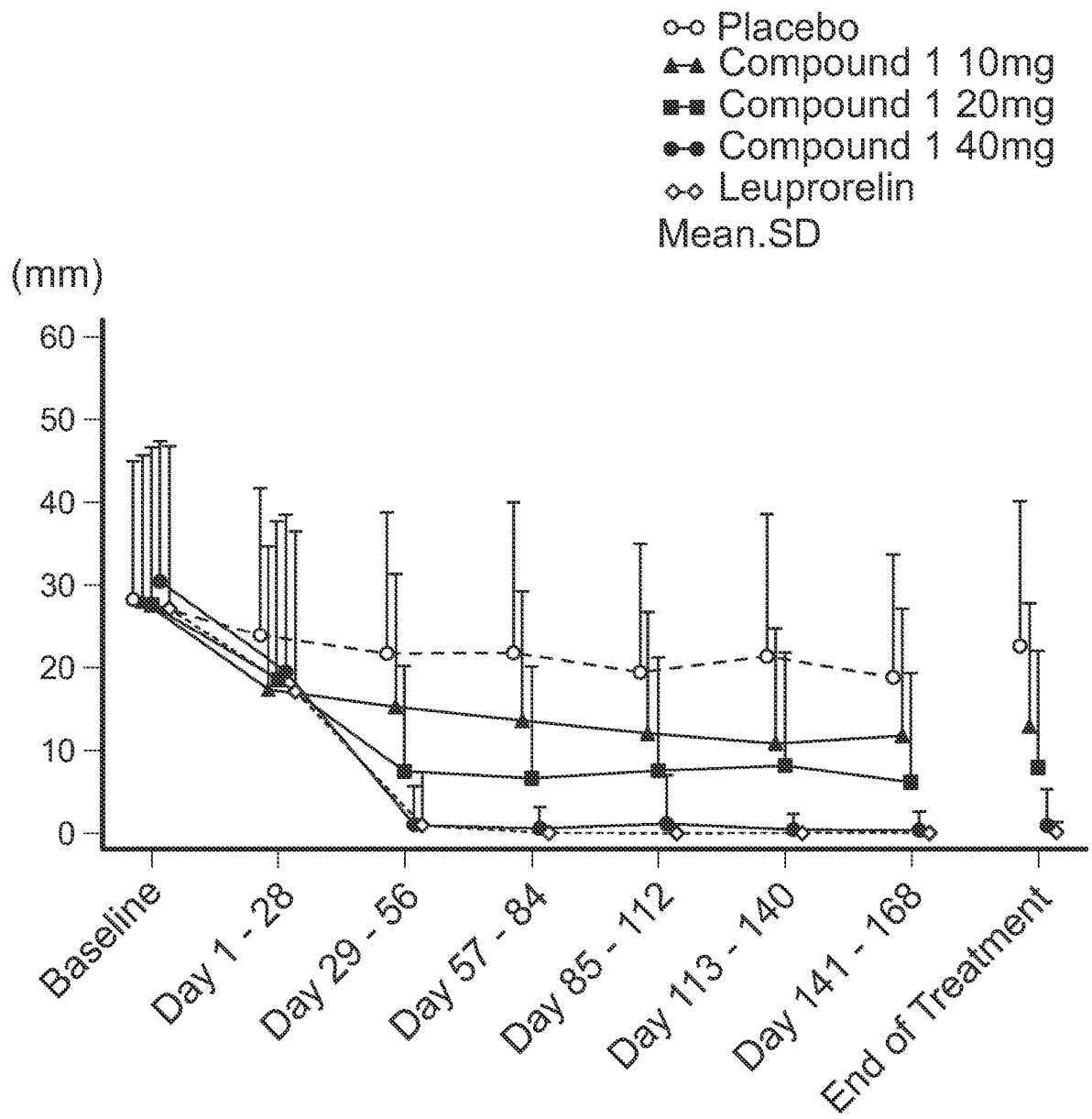
FIG. 97 graphically depicts the mean of VAS scores by visit for dysmenorrhea for a treatment period of 168 days in accordance with Example 8.

The mean of VAS scores by visit for dysmenorrhea for the treatment period of 168 days are graphically depicted in FIG. 97 and tabulated in FIG. 98. While the mean of baseline VAS scores for dysmenorrhea were 27 to 30 mm in each treatment group, the mean of VAS score (mean±SD) at Day 1-28, Day 57-84, Day 141-168, and the end of treatment period were 23.832±17.8381 mm, 21.728±18.3520 mm, 18.797±14.8825 mm, and 22.607±17.5557 mm, respectively, in placebo group; 17.556±17.0427 mm, 13.568±15.5954 mm, 11.758±15.4431 mm, and 12.857±15.0429 mm in the Compound 1 formulation 10 mg group; 18.545±19.2141 mm, 6.626±13.5146 mm, 6.132±13.2012 mm, and 7.878±14.2406 mm in the Compound 1 formulation 20 mg group; 19.452±19.1065 mm, 0.569±2.5367 mm, 0.430±2.3141 mm, and 0.918±4.3438 mm in the Compound 1 formulation 40 mg group; and 17.133±19.4179 mm, 0.000±0.0000 mm, 0.000±0.0000 mm, and 0.174±1.1623 mm in leuprolide acetate group.

Figure 99:
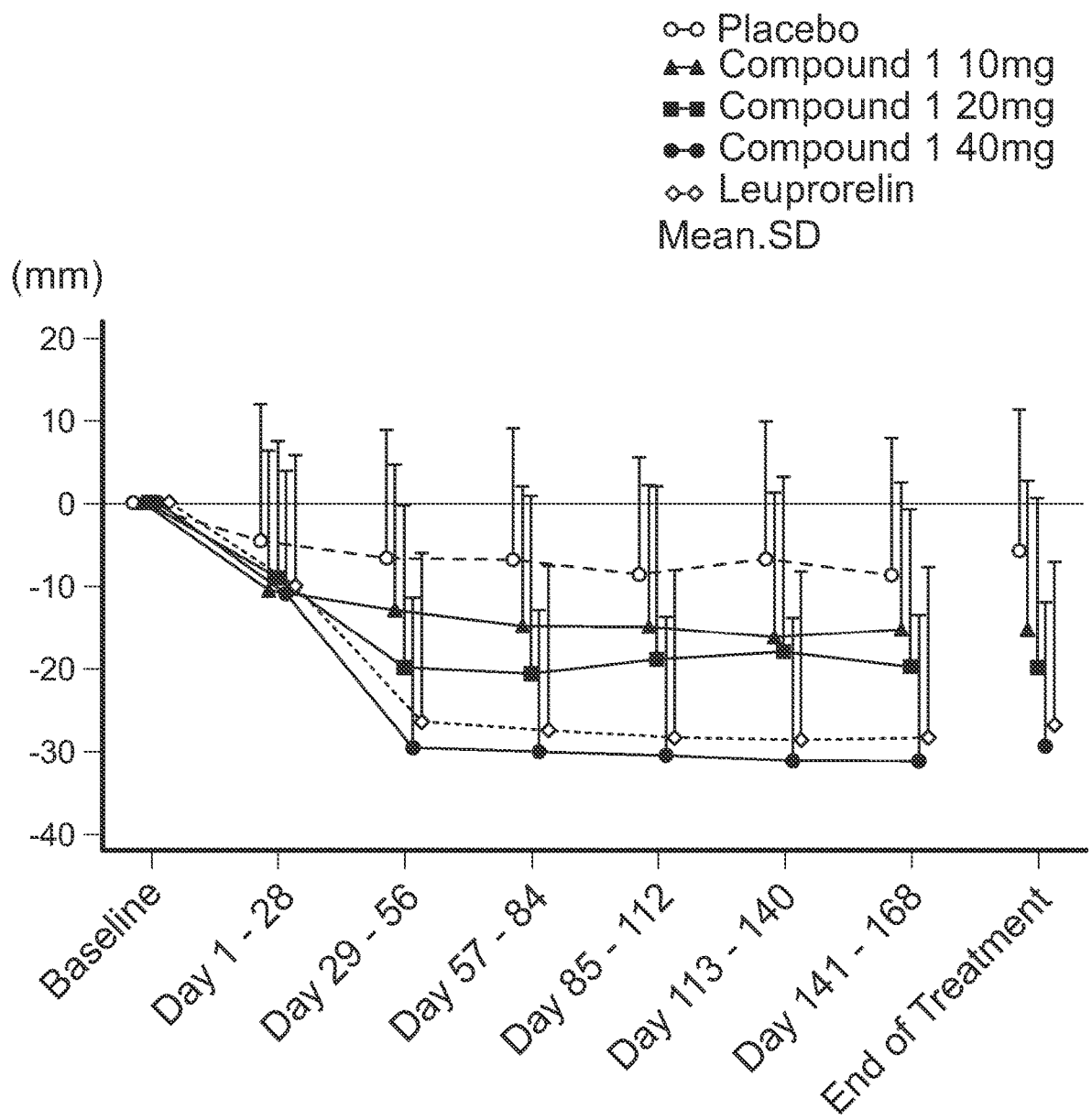
FIG. 99 graphically depicts the change from baseline in mean of VAS scores by visit for dysmenorrhea for a treatment period of 168 days in accordance with Example 8.
Figure 147M:
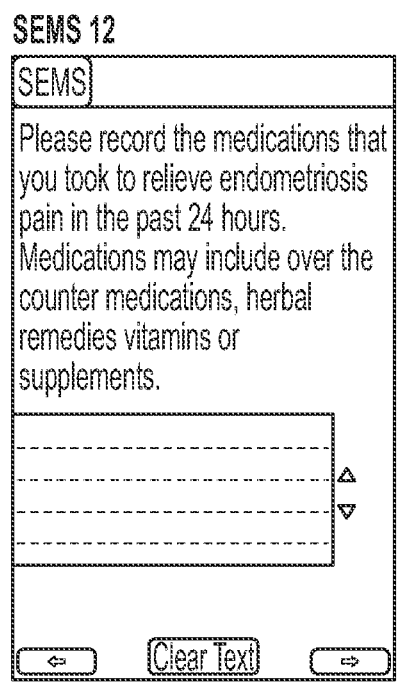

The changes from baseline in mean of VAS score for dysmenorrhea at Day 1-28, Day 57-84, Day 141-168, and the end of treatment period were −4.547±16.4741 mm, −6.857±15.8099 mm, −8.676±16.4615 mm, and −5.772±17.1295 mm, respectively, in placebo group; −10.657±17.0824 mm, −14.747±16.8648 mm, −15.191±17.6754 mm, and −15.356±18.0506 mm in the Compound 1 formulation 10 mg group; −9.158±16.6375 mm, −20.689±21.4387 mm, −19.860±19.1617 mm, and −19.825±20.4332 mm the Compound 1 formulation 20 mg group; −10.979±14.8545 mm, −30.094±17.2623 mm, −31.210±17.7668 mm, and −29.513±17.5379 mm in the Compound 1 formulation 40 mg group; and −9.985±15.7027 mm, −27.558±19.9878 mm, −28.373±20.7287 mm, and −26.944±19.9212 mm in leuprolide acetate group. The changes from baseline in mean of VAS scores by visit for dysmenorrhea for the treatment period of 168 days are graphically depicted in FIG. 99 and tabulated in FIG. 100. The changes from baseline in mean of VAS scores by visit (comparison with leuprolide acetate) for dysmenorrhea for the treatment period of 168 days are tabulated in FIG. 101.

As observed, in pelvic pain, the changes from baseline in mean of VAS scores for dysmenorrhea were larger in higher dose levels of Compound 1 in a time-dependent manner throughout the treatment period. The profile of VAS scores for dysmenorrhea in the Compound 1 formulation 40 mg group was also comparable to that in leuprolide acetate group.

For pelvic pain, the changes from baseline in maximum of VAS score (mean±SD) at the end of treatment period were −8.1±27.50 mm in placebo, −24.0±27.54 mm in the Compound 1 formulation 10 mg, −33.3±30.14 mm in the Compound 1 formulation 20 mg, −49.7±26.47 mm in the Compound 1 formulation 40 mg, and −46.8±26.29 mm in leuprolide acetate groups. Those for dysmenorrhea were −9.3±30.27 mm in placebo, −26.4±27.37 mm in the Compound 1 formulation 10 mg, −39.1±34.29 mm in the Compound 1 formulation 20 mg, −57.1±25.00 mm in the Compound 1 formulation 40 mg, and −51.8±27.01 mm in leuprolide acetate groups. The changes from baseline for pelvic pain and dysmenorrhea were larger in higher dose levels of the Compound 1 throughout the treatment period. The profile of VAS scores in the Compound 1 formulation 40 mg group was also comparable to that in leuprolide acetate group.

The changes from baseline in maximum of VAS score for dyspareunia at the end of treatment period were −5.1±16.63 mm in placebo, −4.2±16.30 mm in the Compound 1 formulation 10 mg, −7.0±15.29 mm in the Compound 1 formulation 20 mg, −2.5±17.17 mm in the Compound 1 formulation 40 mg, and −10.3±19.76 mm in leuprolide acetate groups.

For pelvic pain, the changes from baseline in proportion of days without pain in VAS score (mean±SD) at the end of treatment period were 12.82±26.535% in placebo, 17.90±24.924% in the Compound 1 formulation 10 mg, 21.50±28.859% in the Compound 1 formulation 20 mg, 36.59±34.849% in the Compound 1 formulation 40 mg, and 40.70±33.342% in leuprolide acetate groups. Those for dysmenorrhea were 13.48±34.975% in placebo, 29.28±43.277% in the Compound 1 formulation 10 mg, 50.91±42.602% in the Compound 1 formulation 20 mg, 78.45±29.838% in the Compound 1 formulation 40 mg, and 82.09±24.051% in leuprolide acetate groups.

The changes from baseline in proportion of days without pain in VAS score for pelvic pain were larger in higher dose levels of Compound 1 in a time-dependent manner throughout the treatment period. The profile of VAS scores for pelvic pain in the Compound 1 formulation 40 mg group was similar to that in leuprolide acetate group.

In comparison with the cases of dysmenorrhea and/or pelvic pain, the changes from baseline in proportion of days without pain in VAS score for dyspareunia at the end of treatment period were 6.29±36.617% in placebo, 9.72±38.401% in the Compound 1 formulation 10 mg, 15.14±47.793% in the Compound 1 formulation 20 mg, 4.50±40.796% in the Compound 1 formulation 40 mg, and 21.76±43.266% in leuprolide acetate groups.

For pelvic pain, the percentage of subjects without pain in VAS score at the end of treatment period were 0.0%, 6.8%, 20.0%, 49.5%, and 56.8% in placebo, the Compound 1 formulations of 10 mg, 20 mg, 40 mg, and leuprolide acetate groups, respectively. The higher percentage of subjects was seen at higher dose levels of the Compound 1 formulation.

The profile of percentages in the Compound 1 formulation 40 mg group was comparable to that in leuprolide acetate group.

The percentage of subjects without pain in VAS score for dysmenorrhea at the end of treatment period were 5.2%, 27.2%, 59.0%, 93.2%, and 97.5%, respectively. The higher percentage of subjects was seen at higher dose levels of the Compound 1 formulation throughout the treatment period. The profile of percentages in the Compound 1 formulation 40 mg group was also similar to that in leuprolide acetate group.

The percentage of subjects without pain in VAS score for dyspareunia at the end of treatment period were 38.9%, 48.0%, 47.5%, 48.7%, and 56.5%, respectively.

For pelvic pain, the changes from baseline in mean of M-B&B score (mean±SD) at the end of treatment period were −0.172±0.3851 in placebo, −0.260±0.3624 in the Compound 1 formulation 10 mg, −0.268±0.3913 in the Compound 1 formulation 20 mg, −0.400±0.4491 in the Compound 1 formulation 40 mg, and −0.483±0.4860 in leuprolide acetate groups, respectively. Those for dysmenorrhea were −0.185±0.5491 in placebo, −0.509±0.6675 in the Compound 1 formulation 10 mg, −0.795±0.6490 in the Compound 1 formulation 20 mg, −1.144±0.5014 in the Compound 1 formulation 40 mg, and −1.160±0.4802 in leuprolide acetate groups, respectively, and those for deep dyspareunia were −0.003±0.3796 in placebo, −0.171±0.4683 in the Compound 1 formulation 10 mg, −0.210±0.4936 in the Compound 1 formulation 20 mg, −0.097±0.4325 in the Compound 1 formulation 40 mg, and −0.208±0.5604 in leuprolide acetate groups, respectively.

The mean of M-B&B scores for the treatment period of 168 days are tabulated in FIG. 102 for pelvic pain, in FIG. 103 for dysmenorrhea, and in FIG. 104 for deep dyspareunia.

The changes from baseline in mean of M-B&B scores for the treatment period of 168 days are tabulated: in FIG. 105 for pelvic pain, in FIG. 106 for dysmenorrhea, and in FIG. 107 for deep dyspareunia.

The changes from baseline in mean of M-B&B scores (comparison with leuprolide acetate) for the treatment period of 168 days is tabulated: in FIG. 108 for pelvic pain, in FIG. 109 for dysmenorrhea, and in FIG. 110 for deep dyspareunia.

As observed in VAS scores, the changes from baseline of M-B&B for pelvic pain and dysmenorrhea were larger in higher dose levels of the Compound 1 formulation in a time-dependent manner throughout the treatment period. The change and profile of M-B&B scores in the Compound 1 formulation 40 mg group was also comparable to that in leuprolide acetate group.

The changes from baseline in maximum of M-B&B score (mean±SD) for pelvic pain at the end of treatment period were −0.4±0.87 in placebo, −0.7±0.94 in the Compound 1 formulation 10 mg, −0.7±0.79 in the Compound 1 formulation 20 mg, −1.0±0.89 in the Compound 1 formulation 40 mg, and −1.3±0.82 in leuprolide acetate groups, respectively. Those for dysmenorrhea were −0.2±0.86 in placebo, −0.7±1.01 in the Compound 1 formulation 10 mg, −1.4±1.12 in the Compound 1 formulation 20 mg, −2.0±0.76 in the Compound 1 formulation 40 mg, and −1.9±0.69 in leuprolide acetate groups, respectively. A comparable response was observed in the Compound 1 formulation 40 mg group to that in leuprolide acetate group. The changes from baseline in maximum of M-B&B score at the end of treatment period for dyspareunia were 0.0±0.57 in placebo, −0.2±0.69 in the Compound 1 formulation 10 mg, −0.3±0.59 in the Compound 1 formulation 20 mg, −0.1±0.54 in the Compound 1 formulation 40 mg, and −0.4±0.78 in leuprolide acetate groups.

For pelvic pain, the changes from baseline in proportion of days without pain in M-B&B score (mean±SD) at the end of treatment period were 12.98±27.490% in placebo, 17.18±26.101% in the Compound 1 formulation 10 mg, 17.75±30.339% in the Compound 1 formulation 20 mg, 31.00±36.746% in the Compound 1 formulation 40 mg, and 33.42±34.007% in leuprolide acetate groups. Those for dysmenorrhea were 13.75±34.741% in placebo, 29.55±42.700% in the Compound 1 formulation 10 mg, 50.92±41.641% in the Compound 1 formulation 20 mg, 73.98±29.567% in the Compound 1 formulation 40 mg, and 80.29±23.327% in leuprolide acetate groups.

The changes from baseline in proportion of days without pain in M-B&B score for dysmenorrhea were larger in higher dose levels of the Compound 1 formulation in a time-dependent manner throughout the treatment period. Those for pelvic pain were also larger at higher dose levels of the Compound 1 formulation, but were smaller than those for dysmenorrhea. The change and profile of M-B&B scores in the Compound 1 formulation 40 mg group was similar to those in leuprolide acetate group.

In comparison with the cases of dysmenorrhea and pelvic pain, the changes from baseline in proportion of days without pain in M-B&B score for deep dyspareunia at the end of treatment period were 1.69±35.861% in placebo, 8.32±35.972% in the Compound 1 formulation 10 mg, 18.04±47.892% in the Compound 1 formulation 20 mg, 8.15±43.207% in the Compound 1 formulation 40 mg, and 21.76±43.266% in leuprolide acetate groups.

For pelvic pain, the percentage of subjects without pain in M-B&B score at the end of treatment period were 18.6%, 24.3%, 34.0%, 52.4%, and 63.8% in placebo, the Compound 1 formulation 10 mg, the Compound 1 formulation 20 mg, the Compound 1 formulation 40 mg, and leuprolide acetate groups, respectively. Those for dysmenorrhea were 6.2%, 27.2%, 61.0%, 93.2%, and 97.5%, respectively.

For dysmenorrhea, the percentage of subjects without pain in M-B&B score at the end of treatment period were higher in the higher dose levels of the Compound 1 formulation. The profile of percentages in the Compound 1 formulation 40 mg group was comparable to that in leuprolide acetate group. Those for pelvic pain were also higher at higher dose levels of the Compound 1 formulation, but were lower than those for dysmenorrhea.

The percentage of subjects without pain in M-B&B score for dyspareunia at the end of treatment period were 38.9%, 56.0%, 52.5%, 51.3%, and 56.5%, respectively.

The changes from baseline in mean of B&B score (mean±SD) for dysmenorrhea at Week 24 were −0.3±0.64 in placebo, −1.0±0.87 in the Compound 1 formulation 10 mg, −1.5±0.94 in the Compound 1 formulation 20 mg, −2.0±0.61 in the Compound 1 formulation 40 mg, and −2.1±0.49 in leuprolide acetate groups, respectively. Those in placebo, the Compound 1 formulation 10 mg, the Compound 1 formulation 20 mg, the Compound 1 formulation 40 mg, and leuprolide acetate groups were −0.2±0.83, −0.3±0.67, −0.4±0.70, −0.1±0.43, and −0.5±0.88, respectively, for dyspareunia, −0.6±0.85, −0.8±0.79, −0.9±0.85, −1.0±0.86, and −1.2±0.72 for pelvic pain, −0.6±0.74, −0.7±0.83, −0.8±0.79, −1.0±0.92, and −1.1±0.78 for pelvic tenderness, and −0.5±0.72, −0.6±0.81, −0.7±0.85, −0.8±0.81, and −0.8±0.82 for induration.

The mean of B&B scores by visit for the treatment period of 24 weeks are tabulated: in FIG. 111 for dysmenorrhea, in FIG. 112 for dyspareunia, in FIG. 113 for pelvic pain, in FIG. 114 for pelvic tenderness and in FIG. 115 for induration.

The changes from baseline in mean of B&B scores by visit for the treatment period of 24 weeks are tabulated: in FIG. 116 for dysmenorrhea, in FIG. 117 for dyspareunia for dyspareunia, in FIG. 118 for pelvic pain, in FIG. 119 for pelvic tenderness, and in FIG. 120 for induration.

The proportion of subjects without pain in B&B score for dysmenorrhea at Week 24 were 1.5% in placebo, 27.8% in the Compound 1 formulation 10 mg, 64.9% in the Compound 1 formulation 20 mg, 94.3% in the Compound 1 formulation 40 mg, and 100% in leuprolide acetate groups, respectively. The higher percentage of subjects was seen at higher dose levels of the Compound 1 formulation throughout the treatment period. The profile of percentages in the Compound 1 formulation 40 mg group was also similar to that in leuprolide acetate group.

The proportion of subjects without pain in B&B score for pelvic pain were 27.9%, 30.4%, 39.2%, 58.6%, and 68.9%, respectively, and 42.9%, 63.9%, 53.6%, 56.7%, and 70.6% for dyspareunia, 30.9%, 35.4%, 37.8%, 57.5%, and 70.5% for pelvic tenderness, and 33.8%, 53.2%, 44.6%, 57.5%, and 75.4% for induration. There seemed to be no clear dose-related or time-dependent changes of percentage to the Compound 1 formulation.

The changes from baseline in proportion of days with usage of pain killer at the end of treatment period (mean±SD) were −0.60±10.251% in placebo, −6.32±9.817% in the Compound 1 formulation 10 mg, −7.36±14.585% in the Compound 1 formulation 20 mg, −9.95±14.214% in the Compound 1 formulation 40 mg, and −10.06±13.063% in leuprolide acetate groups. The lower percentage of days with usage of pain killer from the early stage of administration was seen with dose-related decreasing profiles. The profile of percentages in the Compound 1 formulation 40 mg group was comparable to that in leuprolide acetate group. The proportion of days with usage of a pain killer for the treatment period of 168 days are tabulated in FIG. 121. The changes from baseline in proportion of days with usage of a pain killer for the treatment period of 168 days are tabulated in FIG. 122. The changes from baseline in proportion of days with usage of a pain killer (comparison with leuprolide acetate) for the treatment period of 168 days are tabulated in FIG. 123.

The changes from baseline in mean score of amount of bleeding (a self-reporting amount scored with a range from 0 to 5) at the end of treatment period (mean±SD) were −0.056±0.7274 in placebo, −0.529±1.2185 in the Compound 1 formulation 10 mg, −1.264±1.3280 in the Compound 1 formulation 20 mg, −2.207±0.8149 in the Compound 1 formulation 40 mg, and −2.320±0.7281 in leuprolide acetate groups. The larger changes of bleeding amount at higher dose levels of the Compound 1 formulation were seen throughout the treatment period. The profile of percentages in the Compound 1 formulation 40 mg group was similar to that in leuprolide acetate group. The mean of amount of bleeding for the treatment period of 168 days are tabulated in FIG. 124. The changes from baseline in mean of amount of bleeding for the treatment period of 168 days are tabulated in FIG. 125. The changes from baseline in mean of amount of bleeding (comparison with leuprolide acetate) for the treatment period of 168 days are tabulated in FIG. 126.

The percentage of subjects who achieved amenorrhea at the end of treatment period were 4.1%, 22.3%, 54.0%, 91.3%, and 97.5% in placebo, the Compound 1 formulation 10 mg, the Compound 1 formulation 20 mg, the Compound 1 formulation 40 mg, and leuprolide acetate groups, respectively. The higher percentage of subjects who achieved amenorrhea was seen in higher dose levels of the Compound 1 formulation. The profile of percentages in the Compound 1 formulation 40 mg group was comparable to that in leuprolide acetate group. The number of subjects who achieved amenorrhea for the treatment period of 168 days are tabulated in FIGS. 127A-B. The proportion of subjects who achieved amenorrhea (comparison with leuprolide acetate) for the treatment period of 168 days are tabulated in FIG. 128.

Subjects assessed and recorded their own quality of life (QOL) using the EHP-30 once a month during the study visit.

The changes from baseline in EHP-30 score for pain at Week 24 (mean±SD) were −5.41±18.421 in placebo, −16.98±20.286 in the Compound 1 formulation 10 mg, −20.58±19.650 in the Compound 1 formulation 20 mg, −25.94±19.902 in the Compound 1 formulation 40 mg, and −26.38±20.341 in leuprolide acetate groups, respectively. Larger change of EHP-30 scores at all dose levels of the Compound 1 formulation compared to placebo group was seen throughout the treatment period. The profile of EHP-30 scores in the Compound 1 formulation 40 mg group was comparable to that in leuprolide acetate group.

The changes from baseline in EHP-30 score for control & powerlessness were −6.92±15.848 in placebo, −13.97±17.502 in the Compound 1 formulation 10 mg, −20.04±21.880 in the Compound 1 formulation 20 mg, −20.88±21.676 in the Compound 1 formulation 40 mg, and −24.80±23.839 in leuprolide acetate groups, respectively. Larger change of EHP-30 scores at higher dose levels of the Compound 1 formulation was seen throughout treatment period. The profile of EHP-30 scores in the Compound 1 formulation 40 mg group was comparable to that in leuprolide acetate group.

In contrast, the changes from baseline in EHP-30 score in placebo, the Compound 1 formulation 10 mg, the Compound 1 formulation 20 mg, the Compound 1 formulation 40 mg, and leuprolide acetate groups were −6.74±17.669, −8.38±15.918, −15.37±17.858, −13.26±16.316, and −12.37±18.332, respectively, for emotional well-being, −3.21±16.612, −7.52±10.840, −13.44±17.055, −10.28±17.109, and −10.46±17.923 for social support, and −5.39±15.421, −5.91±12.811, −10.59±15.256, −9.68±17.744, and −9.42±15.553 for self-image.

Statistics for QOL (EHP-30), for the treatment period of 24 weeks, are tabulated: with respect to pain in FIG. 129; with respect to control & powerlessness in FIG. 130; with respect to emotional well-being in FIG. 131; with respect to social support in FIG. 132; and with respect to self-image in FIG. 133.

Statistics for change from baseline in QOL (EHP-30), for the treatment period of 24 weeks, are tabulated: with respect to pain in FIG. 134; with respect to control & powerlessness in FIG. 135; with respect to emotional well-being in FIG. 136; with respect to social support in FIG. 137; and with respect to self-image in FIG. 138.

Statistics for change from baseline in QOL (EHP-30) (comparison with leuprolide acetate), for the treatment period of 24 weeks, are tabulated: with respect to pain in FIG. 139; with respect to control & powerlessness in FIG. 140; with respect to emotional well-being in FIG. 141; with respect to social support in FIG. 142; and with respect to self-image in FIG. 143.

The results of other endpoints related to VAS score (maximum value, proportion of days without pain, proportion of subjects without pain) for pelvic pain, dysmenorrhea and dyspareunia were comparable to those of the mean of VAS scores.

The plasma concentrations of unchanged Compound 1 prior to administration at each Visit (trough values) corresponded to the dose levels of Compound 1 and were comparable in each treatment group throughout the treatment period for 24 weeks, showing the dose-proportional tendency of Compound 1 in plasma concentrations. This indicated that the steady state had already been reached by 2 weeks after administration, and that there was no alteration in PK aspects from long-term administration of the Compound 1 formulation for 24 weeks.

The serum LH, FSH, and progesterone (P) concentrations tended to be lower at higher dose levels of the Compound 1 formulation during the treatment period for 24 weeks. Profiles in the Compound 1 formulation 40 mg group were similar to those in leuprolide acetate group. The median of serum $E_2$ concentration decreased below the lower limit of quantification (LLQ) from Week 2 in the Compound 1 formulation 40 mg group and decreased persistently throughout the treatment period for 24 weeks, while in the leuprolide acetate group, the median of serum $E_2$ concentration decreased to LLQ from Week 4, and then decreased persistently throughout the treatment period for 24 weeks. The serum CA125 concentration decreased along with an increase in the Compound 1 dose, and the results in the Compound 1 formulation 40 mg group were similar to those in the leuprolide acetate group.

In this study, the efficacy and safety of orally administered Compound 1 formulation were investigated in patients with endometriosis at doses of 10 mg, 20 mg and 40 mg for 24 weeks, compared with an administration of placebo, and of leuprolide acetate or leuprorelin as an active reference.

With regard to efficacy, in patients with endometriosis, the effects of the Compound 1 formulation on pelvic pain and dysmenorrhea after administration for 12 weeks in the Example 5A study were maintained for extended 12 weeks (24 weeks in total), and were approximately the same in the Compound 1 formulation 40 mg and leuprolide acetate or leuprorelin groups. The $E_2$ values were suppressed throughout the study period.

In summary, the reductions in mean VAS score from baseline for overall pelvic pain (FIG. 152A-B), dysmenorrhea (FIG. 153A-B), and non-menstrual pelvic pain (FIG. 154A-B) in the Compound 1 groups were dose-dependent with the largest decrease in the Compound 1 40 mg group throughout the treatment period. The reductions in mean VAS score from baseline for overall pelvic pain, non-menstrual pelvic pain, and dysmenorrhea in the Compound 1 40 mg group were similar to those in the leuprorelin group. No clear trend was observed in mean VAS scores from baseline across the dosing groups for dyspareunia (FIG. 155A-B) although there was a trend for lower scores over time for the Compound 1 40 mg and leuprorelin groups. The sample size for these dyspareunia analyses was small as not all women enrolled experienced dyspareunia at baseline or were sexually active. The proportion of patients without pain in the VAS score for overall pelvic pain at the end of the treatment were 0%, 20%, 50% and 57% for the placebo, Compound 1 10-, 20-, 40-mg and leuprorelin groups, respectively. The reduction from baseline in mean VAS scores was greatest for dysmenorrhea with the Compound 1 40 mg group showing results similar to that of leuprorelin during the end of treatment period (FIG. 156A). A dose-dependent reduction from baseline in mean VAS scores was also observed for non-menstrual pelvic pain (FIG. 156A).

Overall, similar results were obtained in mean modified (patient) B&B (FIG. 156B) and physician B&B scores for pelvic pain, dysmenorrhea, and dyspareunia. Consistently, dose-dependent reductions were observed with Compound 1 compared with placebo and Compound 1 40 mg consistently demonstrated the greatest pain reduction. The proportion of patients without pain in the VAS score for overall pelvic pain at the end of treatment were 0%, 7%, 20%, 50% and 57% for the placebo, Compound 1 10-, 20-, 40-mg and leuprorelin groups, respectively.

On the basis of the efficacy and safety findings in this study, it was considered that there were no clinically significant issues in the safety of the Compound 1 formulation. Further, on the basis of the efficacy and safety findings in this study, 40 mg of Compound 1 was considered to be an effective dose for treating endometriosis.

In this study, the therapeutic effect of the Compound 1 formulation in the extended administration period of 24 consecutive weeks was assessed in patients with endometriosis. The changes from baseline in mean of VAS scores for pelvic pain at the end of treatment period were −3.222±12.1616 mm in placebo, −6.849±10.5616 mm in the Compound 1 formulation 10 mg, −9.032±11.8432 mm in the Compound 1 formulation 20 mg, −11.924±11.2609 mm in the Compound 1 formulation 40 mg, and −12.552±12.5609 mm in leuprolide acetate groups.

The changes from baseline in mean of VAS scores for pelvic pain were larger in higher dose levels of the Compound 1 formulation in a time-dependent manner throughout the treatment period for 24 weeks. The changes from baseline in mean of VAS scores for dysmenorrhea (the mean of VAS score for pelvic pain on "days with menstruation" in the evaluation period) were also larger in higher dose levels of the Compound 1 formulation in a time-dependent manner throughout the treatment period for 24 weeks. The changes and profiles of VAS score for pelvic pain and dysmenorrhea in the Compound 1 formulation 40 mg group were similar to those in leuprolide acetate group.

The results of other endpoints related to VAS score (maximum value, proportion of days without pain, proportion of subjects without pain) for pelvic pain, dysmenorrhea and dyspareunia were comparable to those of the mean of VAS scores.

The mean of M-B&B score (a self-reporting tool for evaluating pain symptoms) for pelvic pain, dysmenorrhea and deep dyspareunia decreased in a time-dependent manner in higher dose levels of the Compound 1 formulation throughout the treatment period for 24 weeks.

The B&B score (a tool for evaluating pain symptoms through interviews by an investigator) decreased in a time-dependent manner depending on the dose level of the Compound 1 formulation for dysmenorrhea.

In addition, the proportion of days with usage of a pain killer and the amount of menstrual bleeding decreased, and the proportion of subjects who achieved amenorrhea increased in a time dependent manner in accordance with the dose level of the Compound 1 formulation, with that in the Compound 1 formulation 40 mg group being approximately the same as in the leuprolide acetate group.

To assess the QOL of subjects, an evaluation with EHP-30 was carried out. The EHP-30 scores for "pain" and "control & powerlessness" decreased from baseline at higher dose levels of the Compound 1 formulation, in a time-dependent manner throughout the treatment period for 24 weeks. The profile of EHP-30 scores in the Compound 1 formulation 40 mg group was comparable to that in the leuprolide acetate group.

The plasma concentrations of unchanged Compound 1 prior to administration at each visit (trough values) corresponded to the dose levels of the Compound 1 formulation and were comparable in each treatment group throughout the treatment period for 24 weeks, showing the dose-proportional tendency of Compound 1 in plasma concentrations, that the steady state had already been reached by 2 weeks after administration, and that there was no alteration in PK aspects from long-term administration of the Compound 1 formulation for 24 weeks.

The serum LH, FSH, and progesterone (P) concentrations were lower at higher dose levels of the Compound 1 formulation during the treatment period for 24 weeks. Profiles in the Compound 1 formulation 40 mg group were similar to those in leuprolide acetate group. In contrast, the median of serum $E_2$ concentration decreased below the LLQ from Week 2 in the Compound 1 formulation 40 mg group and decreased persistently throughout the treatment period for 24 weeks, while in the leuprolide acetate group, the median of serum $E_2$ concentration decreased to LLQ from Week 4, and then decreased persistently throughout the treatment period for 24 weeks.

The serum CA125 concentration decreased along with an increase in the Compound 1 formulation dose, and the results in the Compound 1 formulation 40 mg group were similar to those in the leuprolide acetate group. The results after administration for 24 weeks were similar to those after administration for 12 weeks.

All adverse events considered related to the study drug were mild or moderate in severity after 24 weeks, and recovered during or after completion of study drug administration. The major adverse events were headaches, but the incidence of headaches was similar between the Compound 1 formulation and placebo groups.

A variety of questionnaires, grading scales, and the like were used in the assessment of subjects. FIG. 144 is an illustrative endometriosis pain questionnaire used for psychometric analyses. FIG. 145 is an illustrative M-B&B grading scale used for dysmenorrhea, pelvic pain and deep dyspareunia. FIGS. 146A-C are an illustrative Symptoms of Endometriosis Scale (SEMS) used for psychometric analyses. FIG. 147-A-M are an illustrative electronic Symptoms of Endometriosis Scale (SEMS) used for psychometric analyses. FIGS. 148A-C are an illustrative mood states form used for psychometric analyses. FIGS. 149A-C are an illustrative baseline clinical questionnaire used for psychometric analyses. FIGS. 150A-B are an illustrative final clinical questionnaire used for psychometric analyses. FIGS. 151A-E are an illustrative Endometriosis Health Profile (EHP-30) questionnaire used for quality of life analyses.

Example 8B: Summary of Examples 7 and 8A

This Example summarizes some of the findings as described above for Examples 7 and 8A.

As used in the examples, the VAS score was evaluated using a 100 mm scale. For pain intensity, the scale was anchored by "no pain" (score of 0) and "pain as bad as you can imagine" (score of 100). The VAS assessment of pelvic pain included: presence or absence of menstruation, amount of bleeding (if menstruating); whether the subject had sexual intercourse; VAS assessment of dyspareunia (if the subject had sexual intercourse); study Compound 1 compliance; and the use of analgesics. The above items were evaluated using a patient diary that was distributed by the sponsor. Subjects filled out the patient diary every day during the treatment period or until early termination. If taking prohibited analgesics, subjects recorded this fact in the patient diary along with the accompanying pain symptoms before use of analgesics.

As used in the examples, pain during menstruation and pelvic pain unrelated to menstruation were evaluated using scores on the M-B&B and B&B. The M-B&B scores were recorded by subjects on the patient diary supplied by the sponsor. Subjects filled out the patient diary every day during the treatment period or until early termination. If taking prohibited analgesics, subjects recorded this fact in the patient diary along with the accompanying pain symptoms before use of analgesics. The investigator or subinvestigator assessed each patient's pain through interviews and filled out a B&B once a month. The items that were assessed are shown below. The M-B&B score included: dysmenorrhea (severe, moderate, mild, no pain, or no menstruation); pelvic pain (severe, moderate, mild, or no pain); deep dyspareunia (severe, moderate, mild, no pain, or no intercourse). The B&B score included: dysmenorrhea (severe, moderate, mild, none, or not applicable); dyspareunia (severe, moderate, mild, none, or not applicable); pelvic pain (severe, moderate, mild, or none); pelvic tenderness (severe, moderate, mild, or none); and induration (severe, moderate, mild, or none).

For M-B&B, a Symptoms of Endometriosis Scale (SEMS) was used for psychometric analyses. Illustrative scales, electronic diary formats, questionnaires, forms, and the like used in the generation of M-B&B scores include, for example: endometriosis pain questionnaire (see FIG. 144); M-B&B grading scale (see FIG. 145); SEMS as tested in subjects (see FIGS. 146A-C); electronic SEMS as tested in subjects (see FIGS. 147A-M); mood states form (see FIGS. 148A-C); baseline clinical questionnaire (see FIGS. 149A-C); and final clinical questionnaire (See FIGS. 150A-B).

A typical method used to evaluate quality of life (QOL) associated with endometriosis includes an Endometriosis Health Profile (EHP-30) score. An exemplary EHP-30 questionnaire is provided in FIGS. 151A-E, comprising 30 questions each with 5 answer choices.

Following administering doses of 40 mg per day for 28 consecutive days of Compound 1 in a formulation ("Compound 1 formulation") having the following excipients: 122 mg of mannitol, 40 mg of microcrystalline cellulose, 6 mg of hydroxypropyl cellulose, 10 mg of croscarmellose sodium, 2 mg of magnesium stearate, 7.12 mg of hypromellose 2910, 0.8 mg of titanium dioxide, and 0.08 mg of ferric oxide, and without a hormone replacement medicament, the change from baseline in the mean of visual analogue scale (VAS) score (mean±SD) for pelvic pain at the end of 28 consecutive days was −2.294±8.9903 mm in the placebo and −3.761±7.8831 mm in the 40 mg Compound 1 formulation. The change from baseline in the VAS score can result in a 1.2 to 2.0 fold (200%), particularly a 1.4 to 1.8 fold (140 to 180%), and more particularly a 1.5 to 1.7 fold (150 to 170%), reduction in pelvic pain.

Following administering doses of 40 mg per day for 84 consecutive days of the Compound 1 formulation, the change from baseline in proportion of days without pelvic pain in the mean of VAS score at the end of 84 consecutive days was 12.82±26.535% in the placebo and 36.59±34.849% in the 40 mg Compound 1 formulation.

Following administering doses of 40 mg per day for 12 consecutive weeks of the Compound 1 formulation, the change from baseline in the mean of VAS score for pelvic pain at the end of 12 consecutive weeks was −3.753±10.5018 mm in the placebo and −10.418±11.0171 mm in the 40 mg Compound 1 formulation.

Following administering doses of 40 mg per day for 84 consecutive days of the Compound 1 formulation, the change from baseline in the mean of modified Biberoglu & Behrman (M-B&B) score for pelvic pain at the end of 84 consecutive days was −0.172±0.3851 in the placebo and −0.400±0.4491 in the 40 mg Compound 1 formulation.

Following administering doses of 40 mg per day for 84 consecutive days of the Compound 1 formulation, the change from baseline in proportion of days without pelvic pain in the mean of M-B&B score at the end of 84 consecutive days was −12.98±27.490% in the placebo and 31.00±36.746% in the 40 mg Compound 1 formulation.

Following administering doses of 40 mg per day for 28 consecutive days of the Compound 1 formulation, the change from baseline in dysmenorrhea in the mean of VAS score at the end of 28 consecutive days was −4.547±16.4741 mm in the placebo and −10.979±14.8545 mm in the 40 mg Compound 1 formulation.

Following administering doses of 40 mg per day for 84 consecutive days of the Compound 1 formulation, the change from baseline in proportion of days without dysmenorrhea in the mean of VAS score at the end of 84 consecutive days was 13.48±34.975% in the placebo and 78.45±29.838% in the 40 mg Compound 1 formulation.

Following administering doses of 40 mg per day for 84 consecutive days of the Compound 1 formulation, the change from baseline in dysmenorrhea in the mean of M-B&B score at the end of 84 consecutive days was −0.185±0.5491 in the placebo and −1.144±0.5014 in the 40 mg Compound 1 formulation.

Following administering doses of 40 mg per day for 28 consecutive days of the Compound 1 formulation, the change from baseline in proportion of days without dysmenorrhea in the mean of M-B&B score at the end of 28 consecutive days was 13.75±34.741% in the placebo and 73.98±29.567% in the 40 mg Compound 1 formulation.

Following administering doses of 40 mg per day for 84 consecutive days of the Compound 1 formulation, the change from baseline in subjects without dysmenorrhea in the mean of Biberoglu & Behrman (B&B) score at the end of 84 consecutive days was 1.5% in the placebo and 94.3% in the 40 mg Compound 1 formulation.

As used in the examples, the EHP-30 score was obtained by subjects assessing and recording their own QOL using the EHP-30 questionnaire. The EHP-30 questionnaire comprised 30 questions, each with 5 answer choices, as set forth in FIGS. 151A-E.

Following administering doses of 40 mg per day for 84 consecutive days of the Compound 1 formulation, the change from baseline in the mean of Endometriosis Health Profile (EHP-30) score at the end of 84 consecutive days was −5.41±18.421 in the placebo and −25.94±19.902 in the 40 mg Compound 1 formulation.

Following administering doses of 40 mg per day for 84 consecutive days of the Compound 1 formulation, the change from baseline in pelvic pain, dysmenorrhea, and dyspareunia in the mean of VAS was −3.753±10.5018 mm in the placebo and −10.418±11.0171 mm in the 40 mg Compound 1 formulation.

Following administering doses of 40 mg per day for 84 consecutive days of the Compound 1 formulation, the change from baseline in subjects without dyspareunia in the mean of M-B&B score at the end of 84 consecutive days was 38.9% in the placebo and 51.3% in the 40 mg Compound 1 formulation.

Following administering doses of 40 mg per day for 84 consecutive days of the Compound 1 formulation, the change from baseline in proportion of days without deep dyspareunia in the mean of M-B&B score at the end of 84 consecutive days was 1.69±35.861% in the placebo and 8.15±43.20% in the 40 mg Compound 1 formulation.

Following administering doses of 40 mg per day for 84 consecutive days of the Compound 1 formulation, the change from baseline in deep dyspareunia in the mean of M-B&B score at the end of 84 consecutive days was −0.003±0.3796 in the placebo and −0.097±0.4325 in the 40 mg Compound 1 formulation.

Example 9: Study of the Pharmacokinetics, Pharmacodynamics, and Safety of Compound 1 with or without Low-Dose Estradiol/Norethindrone Acetate in Healthy Pre-Menopausal Women This was a randomized, open-label, repeat dose study of once-daily Compound 1 alone or Compound 1 combined with hormonal add-back therapy (combination $E_2$/NETA) to assess safety, including markers of bone resorption, pharmacokinetic, and pharmacodynamic endpoints.

Compound 1 (40 mg once-daily) significantly reduced heavy menstrual bleeding associated with UFs in a phase 2 study: 83.6% of patients achieved a PBAC score <10 over 12 weeks of treatment, compared to 0% receiving placebo (Hoshiai. Presented at ACOG. Obstet Gynecol, 2017; May 1, 87S:29).

In this study, PK, PD, and safety data were collected during a 6-week treatment with Compound 1 40 mg or Compound 1 plus low-dose $E_2$/norethindrone acetate ([$E_2$/NETA] 1 mg/0.5 mg) add-back therapy in healthy premenopausal women.

Methods: This was a 6-week phase 1, randomized, open-label, parallel-group, study conducted at 4 sites in the US. Women were randomized to receive Compound 1 40 mg or Compound 1 40 mg plus add-back ($E_2$/NETA 1 mg/0.5 mg) once-daily for 6 weeks. The first day of dosing occurred on Day 1 to 6 of the menstrual cycle. Hormonal preparations were prohibited for at least 3 months prior to screening. Pharmacokinetic (Compound 1, $E_2$, estrone, NETA) and pharmacodynamic including N- and C-telopeptide samples were collected throughout the study. Vasomotor symptoms were captured using a daily diary (from screening until follow-up).

Demographics: Forty-eight healthy premenopausal women were enrolled and 46 completed the study. One withdrew consent on Day 53 and one was lost to follow up on Day 64. Most subjects were White (73%) or African American (17%), 20 to 47 years of age, with body mass index ranging from 19.9 to 33.7 kg/m$^2$.

Pharmacokinetics: Compound 1 plasma exposure was not significantly impacted by estradiol/norethindrone acetate (Table 6).

The observed $E_2$ and NETA exposures (AUCs) in this study (1080 pg*h/mL and 25.1 ng*h/mL at Week 3, respectively) were not greater than those observed in healthy postmenopausal women receiving the same dose of combination $E_2$/NETA in a historic study (1621 pg*h/mL and 47.7 ng*h/mL, respectively). (Activella NDA 20–970 available at www.accessdata.fda.gov. Accessed 6 Jun. 2017).

Estradiol exposure was 3.3-fold higher during treatment with Compound 1 and add-back compared to Compound 1 alone (Table 10). These higher exposures may have the potential to minimize effects on bone loss.

TABLE 10

Geometric mean (CV %) Week 6 Pharmacokinetic Parameters

| | Analyte: | | | | | |
|---|---|---|---|---|---|---|
| | Compound 1 | | Estradiol | | Norethindrone | |
| PK parameter | Cmpd. 1 | Cmpd. 1 + add-back | Cmpd. 1 | Cmpd. 1 + add-back | Cmpd. 1 | Cmpd. 1 + add-back |
| $C_{max}$ (ng/mL) | 17.6 (48.3%) | 18.7 (101%) | 11.7 (185%) | 43.1 (46.7%) | NA | 5.00 (30.7%) |
| $AUC_{0-24}$ (ng · hr/mL) | 116 (42.3%) | 130 (72.9%) | 229 (144%) | 727 (46.4%) | NA | 23.2 (48.2%) |

Pharmacodynamics: Rapid suppression of FSH, LH, estradiol ($E_2$), and progesterone (P) were observed after initiation of Treatment A (Compound 1 40 mg). Serum estradiol and estrone ($E_1$) concentrations were consistently higher in the subjects who received Treatment B (Compound 1 40 mg with co-administration of $E_2$/NETA [1 mg/0.5 mg]) compared to Compound 1 alone (median pre-dose concentration on Day 43 of 27 pg/mL compared to 5.46 pg/mL, respectively). A scatter plot of Compound 1 $AUC_{0-24}$ compared to $C_{avg}$ estradiol concentration at Week 6 is shown in FIG. 168. All subjects were administered the same dosage of Compound 1 (40 mg once-daily), but due to individual metabolism there can be some variation in $AUC_{0-24}$ of the compound. As can be seen in the graph, a higher $AUC_{0-24}$ of Compound 1 correlated with lower estradiol $C_{avg}$ concentration in subjects which were not co-administered hormonal add-back therapy. However, surprisingly, in subjects that were administered add-back therapy, there was not the same correlation between higher $AUC_{0-24}$ and lower estradiol $C_{avg}$. Rather, the estradiol levels in subjects administered the add-back therapy was relatively flat, even when the $AUC_{0-24}$ was different. Full suppression of estrogen via Compound 1 administration coupled with co-administration of $E_2$/NETA led to greater consistency in $E_2$ levels, compared to administration of Compound 1 alone.

This higher estradiol concentration reduces bone resorption, and is reflected in the resorption markers N-telopeptide (NTx) and C-telopeptide (CTx), that were significantly reduced with the addition of $E_2$/NETA 1 mg/0.5 mg compared to Compound 1 40 mg alone. The addition of estradiol/norethindrone significantly mitigated the rise in C-telopeptide and N-telopeptide resulting from treatment with Compound 1, an indication of reduced bone resorption (FIG. 165). FIG. 169 provides a scatter plot of $C_{avg}$ estradiol compared to change from baseline of N-telopeptide at Week 6. This figure shows that in the group administered Compound 1 without add-back therapy, lower estradiol was correlated to a higher change from baseline N-telopeptide, indicating higher bone turnover. However, in the group that was co-administered add-back therapy, the $C_{avg}$ estradiol level exhibited a narrower range across subjects, and the change from baseline N-telopeptide was not as great, indicating lower bone turnover. A similar trend is shown in FIG. 170, depicting $C_{avg}$ estradiol compared to change from baseline of C-telopeptide at Week 6. FIG. 171 depicts a box plot graph of degree of subject-reported menstrual bleeding vs. $C_{avg}$ estradiol at Week 6. As seen in the figure, a higher estradiol level was correlated with higher degree of subject-reported menstrual bleeding in the group receiving Compound 1, where no such trend was evident in subjects receiving Compound 1 and $E_2$/NETA.

Subjects who received exogenous treatment with $E_2$/NETA had higher estradiol and estrone exposures compared to those who received Compound 1 alone. Following multiple doses of Treatment A (Compound 1 40 mg) or Treatment B (Compound 1 40 mg and $E_2$/NETA [1 mg/0.5 mg]), the mean serum $E_2$ concentration time profiles at Week 3 and Week 6 were similar in shape within each treatment, with a low peak-to-trough ratio. The absolute estradiol concentrations were higher in Treatment B and followed a typical oral pharmacokinetic profile. The slightly higher concentrations at Week 3 compared to Week 6 within each treatment may be a result of biological variation. Co-administration of Compound 1 and $E_2$/NETA resulted in 3.3-fold higher serum estradiol overall extent of exposure ($C_{max}$ and $AUC_{0-24}$). Median $C_{trough}$ and $C_{max}$ values of approximately 25 and 45 pg/mL, respectively, are similar to the range reported to mitigate the bone resorptive effects of the hypoestrogenic state typically produced by GnRH agonists. Similarly, co-administration of Compound 1 and $E_2$/NETA resulted in approximately 9- to 12-fold higher serum estrone peak and overall extent of exposure ($C_{max}$ and $AUC_{0-24}$). The percentage of subjects whose predose estradiol concentrations were <10 pg/mL or <20 pg/mL was higher following administration of Compound 1 alone than Compound 1 and $E_2$/NETA. Tables 11 and 12 provide pharmacokinetic parameters for the two treatment groups at Weeks 3 and 6. The median ($25^{th}$ quartile, $75^{th}$ quartile) of $C_{avg}$, $C_{max}$, and $C_{trough}$ for estradiol at Week 3 and Week 6 data has been compiled in Table 13.

TABLE 11

Serum Estradiol Noncompartmental Pharmacokinetic Parameters and Summary
Statistics Separated by Treatment and Week (PK Population)

| PK parameter | Treatment A: Compound 1 40 mg | | Treatment B: Compound 1 40 mg and $E_2$/NETA (1 mg/0.5 mg) | |
|---|---|---|---|---|
| | Week 3 (N = 23) | Week 6 (N = 21) | Week 3 (N = 23) | Week 6 (N = 22) |
| $C_{max}$ (pg/mL) | 42.8 (124) | 28.5 (55.3) | 68.6 (94.5) | 46.8 (17.3) |
| $t_{max}$ (hr) | 8 (0.00, 24.00) | 2 (0.00, 24.00) | 6 (0.50, 12.00) | 3 (0.50, 12.00) |
| $AUC_{0-24}$ (pg · hr/mL) | 693 (1900)[a] | 480 (917)[b] | 1080 (1050) | 784 (262) |
| $C_{trough}$ (pg/mL) | 38.3 (124) | 20 (54.3) | 30.2 (23.2) | 20.8 (7.81) |
| $C_{avg}$ (pg/mL) | 28.9 (79.1)[a] | 20.0 (38.2)[b] | 44.9 (43.8) | 32.6 (10.9) |
| $t_{1/2}$ (hr) | NA | 12.5 (3.23)[c] | 19.7 (7.16)[d] | 17.1 (4.03)[e] |

Abbreviations: hr = hour; N = number of subjects; NA = not applicable; SD = standard deviation.
Arithmetic mean (SD) are shown except for $t_{max}$ where median and range (minimum, maximum) are shown.
[a]N = 21. Values for $AUC_{0-24}$ and $C_{avg}$ were not reported for Subjects 1004 and 4008.
[b]N = 19. Values for $AUC_{0-24}$ and $C_{avg}$ were not reported for Subjects 2001 and 2011.
[c]N = 4. Values for $t_{1/2}$ were only reported for 4 subjects (Subjects 2008, 3001, 3005, and 3014).
[d]N = 13. Values for $t_{1/2}$ were not reported for Subjects 1003, 2002, 2003, 2007, 2012, 3002, 3009, 3013, 4005, and 4012.
[e]N = 15. Values for $t_{1/2}$ were not reported for Subjects 1003, 2007, 3004, 3006, 3009, 3011, and 4002.

TABLE 12

Median Serum Estradiol $C_{max}$ and $C_{trough}$ Summary Statistics
Separated by Treatment and Week (PK Population)

| PK parameter | Treatment A: Compound 1 40 mg | | Treatment B: Compound 1 40 mg and $E_2$/NETA (1 mg/0.5 mg) | |
|---|---|---|---|---|
| | Week 3 (N = 23) | Week 6 (N = 21) | Week 3 (N = 23) | Week 6 (N = 22) |
| $C_{max}$ (pg/mL) | 9.55 (4.55, 606) | 7.22 (2.74, 255) | 44.7 (12.2, 487) | 49.2 (13.0, 78.9) |
| $C_{trough}$ (pg/mL) | 6.40 (2.56, 606) | 5.77 (2.50, 255) | 22.6 (3.02, 104) | 21.4 (3.60, 39.0) |

Abbreviations: hr = hour; N = number of subjects.
Median (minimum, maximum) are shown.

TABLE 13

Median (min, max) [25$^{th}$ quartile, 75$^{th}$ quartile] of
$C_{avg}$, $C_{max}$, and $C_{trough}$ for $E_2$ at Week 3 and Week 6

| PK parameter | Treatment A: 40 mg Compound 1 | | Treatment B: 40 mg Compound 1 and $E_2$/NETA (1 mg/0.5 mg) | |
|---|---|---|---|---|
| | Week 3 (N = 23) | Week 6 (N = 21) | Week 3 (N = 23) | Week 6 (N = 22) |
| $C_{avg}$ (pg/mL) | 7.84 (3.91, 371) [4.60, 19.7] | 6.17 (2.89, 170) [4.72 18.0] | 32.8 (6.50, 227) [26.2, 44.2] | 31.5 (7.73, 50.2) [27.2, 42.2] |
| $C_{max}$ (pg/mL) | 9.55 (4.55, 606) [5.41, 33.9] | 7.22 (2.74, 255) [5.10, 35.1] | 44.7 (12.2, 487) [36.7, 56.7] | 49.2 (13.0, 78.9) [34.4, 61.1] |
| $C_{trough}$ (pg/mL) | 6.40 (2.56, 606) [3.94, 29.2] | 5.77 (2.50, 255) [3.66, 11.5] | 22.6 (3.02, 104) [16.5, 29.8] | 21.4 (3.60, 39.0) [16.2, 25.7] |

As seen in Table 13, the Treatment B group had a $C_{avg}$ (pg/mL) of estradiol at Week 3 of 32.8, with a minimum of 6.50, maximum of 227, 25$^{th}$ quartile of 26.2, and 75$^{th}$ quartile of 44.2. At Week 6, the Treatment B group had a $C_{avg}$ (pg/mL) of estradiol of 31.5, with a minimum of 7.73, maximum of 50.2, 25$^{th}$ quartile of 27.2, and 75$^{th}$ quartile of 42.2. These $E_2$ ranges are narrower than those that have been reported for a titration-type treatment with elagolix, wherein estrogen is not fully suppressed but rather the GnRH antagonist (elagolix) is administered to decrease endogenous estrogen until it falls within the therapeutic window. Administration of 150 mg elagolix (not a full suppression dose) was reported to achieve a median estradiol level of 30.3, pg/mL, but with 25$^{th}$ and 75$^{th}$ quartiles of 17.8 and 64.1, respectively. (See Diamond et al., Reprod. Sci. March 2014, 21(3):363–371) In a separate study, administration of 150 mg elagolix over 12 weeks was found to achieve a median (min, max) estradiol concentration of 36.40 (4.5, 247.0), 39.60 (6.8, 182.00), and 36.70 (2.5, 521.00) at weeks 4, 8, and 12, respectively. (See N. Acs, et al., Journal of Endometriosis and Pelvic Pain Disorders (2015), 7(2):56–62) Greater consistency of estradiol levels was achieved with full suppression of estrogen by Compound 1 administration, along with co-administration of hormonal add-back therapy.

on Days 1 and 2 of their menstrual cycle (Days 1 through 6) with 42 of 48 subjects (87.5%) and 32 of 48 subjects (66.7%) reporting bleeding on Days 1 and 2, respectively. Day 1 of dosing was scheduled to coincide with Day 1–6 of the subject's menstrual cycle. Following Day 2, the number of subjects who reporting bleeding decreased and generally ≤10 of 48 subjects (20.8%) reported bleeding each day for the duration of the study (Days 3 through 58). Following Day 28, the number of subjects who reporting bleeding was generally 5 of 48 subjects (10.4%). A generally higher

TABLE 14

Plasma Compound 1 Noncompartmental Pharmacokinetic Parameters and Summary Statistics Separated by Treatment and Week (PK Population)

| PK parameter | Treatment A: Compound 1 40 mg | | Treatment B: Compound 1 40 mg and E$_2$/NETA (1 mg/0.5 mg) | |
|---|---|---|---|---|
| | Week 3 (N = 25) | Week 6 (N = 25) | Week 3 (N = 23) | Week 6 (N = 22) |
| $C_{max}$ (ng/mL) | 21.8 (14.7) | 19.5 (10) | 23.8 (17) | 26 (21.4) |
| $t_{max}$ (hr) | 2.02 (0.48, 4.05) | 2 (0.5, 4) | 3 (0.5, 4) | 3 (0.5, 6) |
| $AUC_{0-24}$ (ng · hr/mL) | 133 (61.2) | 125 (43.3) | 148 (87) | 157 (94.7) |
| $C_{trough}$ (ng/mL) | 2.57 (1.08) | 2.45 (0.935) | 2.8 (1.56) | 2.96 (1.74) |
| $C_{avg}$ (ng/mL) | 5.53 (2.55) | 5.2 (1.8) | 6.17 (3.62) | 6.53 (3.94) |
| $t_{1/2}$ (hr) | 16.7 (4.88)$^a$ | 17.1 (6.16)$^b$ | 15.4 (5.56)$^c$ | 17.6 (5.83)$^c$ |

Abbreviations: hr = hour; N = number of subjects; SD = standard deviation.
Arithmetic mean (SD) are shown except for $t_{max}$ where median and range (minimum, maximum) are shown.
$^a$N = 22. Values for $t_{1/2}$ were not reported for Subjects 2006, 4001, and 4011.
$^b$N = 23. Values for $t_{1/2}$ were not reported for Subjects 1001 and 3014.
$^c$N = 18. Values for $t_{1/2}$ were not reported for Subjects 1003, 2003, 2007, 3004, and 3009 for Week 3 and Subjects 2002, 3002, 3013, and 4002 for Week 6.

Table 14 summarizes some pharmacokinetic parameters of the two treatment groups at week 3 and week 6. Following multiple doses of Treatment A (Compound 1 40 mg) or Treatment B (Compound 1 40 mg and E$_2$/NETA [1 mg/0.5 mg]), within each treatment the mean plasma Compound 1 concentration time profiles at Week 3 and Week 6 were visually similar. The plasma pharmacokinetic parameters of Compound 1 following treatment with Treatment A (Compound 1 40 mg) and Treatment B (Compound 1 40 mg and E$_2$/NETA [1 mg/0.5 mg]) had a similar peak and overall extent of exposure ($C_{max}$ and $AUC_{0-24}$). In general, steady-state was achieved within 1 to 2 weeks of QD Compound 1 administration. Compound 1 exposure was not impacted by the addition of E$_2$/NETA, which was consistent with the low drug-drug interaction potential of E$_2$/NETA. There was no relationship between body mass index and Compound 1 pharmacokinetics, as demonstrated by FIG. 175.

incidence of bleeding was observed following Treatment B (Compound 1 40 mg and E$_2$/NETA [1 mg/0.5 mg]) than Treatment A (Compound 1 40 mg). Over the last 28 days of treatment, the majority of subjects reported no light, normal, or heavy bleeding (33 of 48 subjects [68.8%]) and no normal or heavy bleeding (37 of 48 subjects [77.1%]) and these numbers were greater following Treatment A (Compound 1 40 mg) (22 of 25 subjects [88.0%] and 23 of 25 subjects [92.0%], respectively) than Treatment B (Compound 1 40 mg and E$_2$/NETA [1.0 mg/0.5 mg]) (11 of 23 subjects [47.8%] and 14 of 23 subjects [60.9%], respectively).

FIG. 163 further provides two graphs demonstrating the effect on serum estradiol levels of the two different treatments. As is shown in the graph on the left, administration of Compound 1 once-daily results in a serum estradiol concentration that is consistently below 10 pg/mL over multiple weeks. Subjects that were administered E$_2$/NETA

TABLE 15

Summary of Menstruation Over the Last 28 Days of Treatment

| Category | Treatment A: Compound 1 40 mg (N = 25) n (%) | Treatment B: Compound 1 40 mg and E$_2$/NETA (1 mg/0.5 mg) (N = 23) n (%) | Overall (N = 48) n (%) |
|---|---|---|---|
| No bleeding | 18 (72.0%) | 9 (39.1%) | 27 (56.3%) |
| No light/normal/heavy bleeding (i.e., no bleeding except spotting) | 22 (88.0%) | 11 (47.8%) | 33 (68.8%) |
| No normal/heavy bleeding | 23 (92.0%) | 14 (60.9%) | 37 (77.1%) |

Abbreviations: n = number of non-missing observations; N = number of subjects.

Table 15 summarizes menstruation for the subjects over 28 days of treatment. Overall, the majority of subjects reported the greatest incidence of events of uterine bleeding add-back also had a consistent trough serum estradiol concentration as measured at each study visit, but above the 20 pg/mL threshold. As shown in the right graph, the median estradiol concentration during the week 3 visit remained between 20 pg/mL to 50 pg/mL during the 24 hours following administration of Compound 1 and E$_2$/NETA. Administration of Compound 1 without a hormone replacement medicament resulted in serum estradiol levels of below 10 pg/mL over the subsequent 24 hours.

Safety: The most commonly (≥10%) reported adverse events were hot flash, headache, nausea, and events of uterine bleeding (delayed, irregular). The majority of adverse events were mild in severity.

One subject experienced 2 serious adverse events (syncope and chest pain) unrelated to study drug and related to viral illness. There were no deaths, withdrawals due to adverse events, or reported pregnancies.

Hot Flash Diary: Subjects reported both a decrease in the frequency (FIG. 166) and severity of hot flash with the addition of add-back therapy. Each of the study treatments (Treatment A [Compound 1 40 mg] or Treatment B [Compound 1 40 mg and E$_2$/NETA, 1 mg/0.5 mg]) was observed to have mitigated the incidence of menstrual bleeding during the study; the proportions of subjects reporting no menstrual bleeding (except spotting) over the last 28 days of treatment were 88.0% and 47.8% after treatment with Compound 1 alone or Compound 1 and E$_2$/NETA, respectively. During week 6 of treatment, the addition of add-back therapy: (1) reduced the proportion of subjects reporting hot flash from 60% to 17%; (2) reduced the average number of hot flash per subject (any severity) from 72.6 to 12.6; and (3) in subjects reporting severe hot flash, the number was reduced from 63.2 (n=5 subjects) to 9.0 (n=2 subjects).

Overall, Treatment A (Compound 1 40 mg) administered once-daily, alone and Treatment B (Compound 1 40 mg in combination with hormonal add-back therapy with E$_2$/NETA [1 mg/0.5 mg]), was generally well tolerated in this study population of healthy premenopausal women treated for 6 weeks. The pharmacokinetic and pharmacodynamic data for the combination of Compound 1 and E$_2$/NETA, including median estradiol C$_{trough}$ values of approximately 25 pg/mL and C$_{max}$ values of approximately 45 pg/mL, the range associated with reduced bone resorption, support the use of this combination in Phase 3 studies evaluating heavy menstrual bleeding associated with uterine fibroids and endometriosis-associated pain.

The data presented here demonstrate that Compound 1 at 40 mg once-daily reliably suppresses estradiol to low levels in women of reproductive age, but may result in hot flashes and vasomotor symptoms, as well as an increase in markers of bone turnover such as N-telopeptide and C-telopeptide. Co-administration of hormonal add-back therapy consisting of 1.0 mg estradiol and 0.5 mg norethindrone acetate with Compound 1 decreased hot flashes and vasomotor symptoms in the majority of women.

However, some women continue to have clinically relevant hot flashes despite add-back therapy with 1.0 mg estradiol. These data suggests that contrary to what one might expect, higher doses, specifically 1.5 mg-5 mg of estradiol, such as 2.0 mg-4.0 mg estradiol, combined with up to 2.0 mg, such as 1.5-2 mg or 1.25 mg-2 mg, 1.5 mg-2 mg, or 1.75-2 mg, norethindrone acetate, co-administered with Compound 1 20 mg-120 mg, for example 40 mg once-daily, may be used without affecting Compound 1's effectiveness in reducing the symptoms of uterine fibroids or endometriosis in some women. Moreover, the higher amount of hormonal add-back may be able to ameliorate hot flashes even in women who experience clinically meaningful vasomotor symptoms while on Compound 1 and a lower dose hormone replacement medicament.

Assessment of markers of bone turnover may indicate that the co-administration of 1.0 mg estradiol and 0.5 mg norethindrone acetate hormonal add-back therapy with Compound 1, for example, 40 mg once-daily does not completely mitigate bone turnover to baseline in all women. The bone turnover marker data indicate that doses higher than 1.0 mg of estradiol co-administered with Compound 1 may be required in some women.

As seen in FIG. 164, co-administration of Compound 1 and E$_2$/NETA add-back resulted in mean serum estradiol was within the 20–50 pg/mL therapeutic window. However, as indicated by the error bars for each time point (standard deviation), the serum estradiol level of some subjects fell outside this window. This may result from differences in absorption or metabolism. Thus, in certain populations of women, it may be beneficial to increase the dose of Compound 1 or pharmaceutically acceptable salt thereof (for example, for those who are above the 50 pg/mL upper limit), or to increase the dose of estradiol or estradiol equivalent (for example, for those who are below the 20 pg/mL lower limit).

If the serum estradiol is too high one might expect reduced efficacy for treating the symptoms of uterine fibroids (UF) and endometriosis. If serum estradiol is too low, one might expect increased bone mineral density loss and vasomotor symptoms/hot flashes. Thus, it may be expected that while increasing the hormonal add-back therapy would help boost the serum estradiol (better preventing bone mineral density loss/vasomotor symptoms/hot flash), the higher the estradiol beyond the therapeutic window, the less effective the impact on reducing the symptoms of uterine fibroids and endometriosis. With hormonal add-back therapy, one might predict the efficacy of Compound 1 to diminish. This was seen in phase 2 efficacy data when hormonal add-back therapy was co-administered with elagolix, another GnRH antagonist, versus elagolix alone. Increasing the add-back dose might lead to a higher estradiol level, and lower the efficacy for reducing bleeding associated with uterine fibroids or endometriosis-associated pain. However, contrary to these expectations, it was surprisingly discovered in this phase 1 study that efficacy of Compound 1 with and without add-back worked to ameliorate the symptoms of a hypoestrogenic state in most but not all women. These results may suggest that treatment of uterine fibroids, adenomyosis, heavy menstrual bleeding, and/or endometriosis with Compound 1 together with add back is a preferable treatment method over a Compound 1 monotherapy.

Further, these data also suggest that it may be possible to increase the dose of hormonal add-back therapy even more to reduce side effects of GnRH antagonist therapy without losing the efficacy of the treatment, e.g., the reduction in the symptoms of uterine fibroids, adenomyosis, heavy menstrual bleeding, or endometriosis.

Hormonal add-back therapy resulted in estradiol plasma concentrations that mitigated bone resorption and vasomotor symptoms associated with administration of Compound 1 alone. This study further suggests evaluation of Compound 1 in combination with add-back therapy. A description of Phase 3 studies of Compound 1 40 mg co-administered with hormonal add-back therapy in women with uterine fibroids and endometriosis can be found at ClinicalTrials.gov; NCT03049735, NCT03103087, NCT03204318 and NCT03204331.

Example 10: Multicenter, Randomized, Double-Blind, Parallel-Group, Phase 3 Study to Evaluate the Efficacy and Safety of Oral Compound 1 (40 mg) Compared with Leuprorelin in the Treatment of Uterine Fibroids This was a phase 3, multicenter, randomized, double-blind, parallel-group, non-inferiority study to evaluate the efficacy and safety of Compound 1 administered orally in daily dosing 40 mg for 24 weeks, compared with leuprorelin injection (once/4 weeks, 1.88 mg or 3.75 mg subcutaneous [SC]/time) in premenopausal subjects ≥20 years of age with symptomatic uterine fibroids. The primary objective of this study was to evaluate the efficacy of Compound 1 40 mg administered orally once-daily for 12 weeks.

Subjects were aged 20 years or older inclusive, with uterine fibroids. 281 subjects total were randomized and split into a Compound 1 group (139 subjects) and a leuprorelin group (142 subjects). The number of sites for this study was approximately 40.

The Compound 1 group subjects were orally administered either 40 mg of Compound 1 or placebo once-daily before breakfast. The leuprorelin subjects were administered 1.88 mg leuprorelin, 3.75 mg leuprorelin, or placebo subcutaneously once every 4 weeks. The duration of treatment for both groups was 24 weeks, and the follow-up period was 4 weeks.

Assessment included answers to the uterine fibroid symptom and quality of life questionnaire provided in FIGS. 3A-3C; answers to the work productivity and activity impairment questionnaire: general health provided in FIGS. 66A-66B; clinical laboratory tests for hematology, chemistries, urinalysis, hormone, and biochemical bone metabolism markers.

The primary endpoint for this study was the proportion of subjects with a total PBAC score of <10 from Week 6 to 12. Secondary endpoints for this study included: the proportion of subjects with a total PBAC score of <10 (from Week 2 to 6, from Week 18 to 24, and for 6 weeks before the final dose of study drug); myoma volumes (Week 2, 4, 8, 12 and 24) (Only the largest myoma among those measurable at VISIT 1 was measured throughout the study; uterine volumes (Week 2, 4, 8, 12 and 24); hemoglobin (HGB) (Week 4, 8, 12, 16, 20, 24 and Follow-up); Numerical Rating Scale (NRS) score (from Week 6 to 12, from Week 2 to 6, from Week 18 to 24, and for 6 weeks before the final dose); and uterine fibroid symptom and QOL (UFS-QOL) score (Week 4, 8, 12, 16, 20, 24 and Follow-up). Secondary endpoints for safety included: Adverse events (AEs), vital signs, weight, standard 12-lead electrocardiogram (ECG), clinical laboratory tests, BMD, biochemical bone metabolism markers (serum N-telopeptide [NTELOP] and bone specific alkaline phosphatase [BAP])

Other endpoints related to efficacy included: Hematocrit (HCT), serum iron (Fe), and serum ferritin (Week 4, 8, 12, 16, 20, 24 and Follow-up); use of analgesic medications during the Treatment (from Week 6 to 12, from Week 2 to 6, from Week 18 to 24, and for 6 weeks before the final dose); and Work Productivity and Activity Impairment Questionnaire: General Health (WPAI:GH) (Week 2, 4, 8, 12 and 24).

Other endpoints related to safety included: Period from the last dose of study drug to return of menstrual cycles, and pharmacodynamic effects included: LH, FSH, estradiol and progesterone (Week 2, 4, 8, 12, 16, 20, 24 and Follow-up).

Table 16 summarizes the disposition of subjects in this study. Table 17 summarizes subject demographics. Table 18 provides a summary of adverse events. Table 19 is a summary of adverse events reported in greater than or equal to 5% of subjects in any treatment group. Table 20 summarizes adverse events that lead to discontinuation. Table 21 is a summary of subjects with markedly abnormal liver function tests.

TABLE 16

Subject Disposition

| | Number of Subjects (%) | | |
|---|---|---|---|
| | Compound 1 40 mg (N = 139) | Leuprorelin (N = 142) | Total (N = 281) |
| Completed Study Drug | 122 (87.8) | 131 (92.3) | 253 (90.0) |
| Prematurely Discontinued Study Drug | 16 (11.5) | 11 (7.7) | 27 (9.6) |
| Death | 0 (0.0) | 0 (0.0) | 0 (0.0) |
| Adverse Event | 10 (62.5) | 7 (63.6) | 17 (63.0) |
| Protocol Deviation | 2 (12.5) | 0 (0.0) | 2 (7.4) |
| Lost to Follow-up | 0 (0.0) | 0 (0.0) | 0 (0.0) |
| Withdrawal by Subject | 1 (6.3) | 2 (18.2) | 3 (11.1) |
| Study Terminated by Sponsor | 0 (0.0) | 0 (0.0) | 0 (0.0) |
| Pregnancy | 0 (0.0) | 0 (0.0) | 0 (0.0) |
| Lack of Efficacy | 0 (0.0) | 1 (9.1) | 1 (3.7) |
| Bone Mineral Density Loss | 0 (0.0) | 0 (0.0) | 0 (0.0) |
| Recovery Leading to Surgery | 2 (12.5) | 1 (9.1) | 3 (11.1) |
| Reduction of HGB Concentration | 1 (6.3) | 0 (0.0) | 1 (3.7) |
| Other | 0 (0.0) | 0 (0.0) | 0 (0.0) |

TABLE 17

Subject Demographics

| | Compound 1 (N = 139) | Leuprorelin (N = 142) |
|---|---|---|
| Age (years) | | |
| Mean | 43.2 | 42.6 |
| SD | 4.98 | 5.27 |
| BMI (kg/m$^2$) at Baseline | | |
| Mean | 22.78 | 23.43 |
| SD | 3.506 | 3.657 |
| Birth Experience (N[%]) | 74 (53.2) | 75 (52.8) |
| Disease Duration (years) | | |
| Mean | 4.36 | 4.72 |
| SD | 5.037 | 5.073 |

TABLE 17-continued

Subject Demographics

| | Compound 1 (N = 139) | Leuprorelin (N = 142) |
|---|---|---|
| Type of Uterine Fibroid | | |
| Subserosal Fibroid (N[%]) | 54 (38.8) | 53 (37.3) |
| Intramural Fibroid (N[%]) | 117 (84.2) | 112 (78.9) |
| Submucosal Fibroid (N[%]) | 13 (9.4) | 20 (14.1) |
| Cervical Fibroid (N[%]) | 0 (0.0) | 0 (0.0) |
| Volume of Myoma at Baseline (cm³) | | |
| Mean | 117.41 | 122.25 |
| SD | 126.533 | 124.270 |
| Volume of Uterus at Baseline (cm³) | | |
| Mean | 406.25 | 379.07 |
| SD | 392.354 | 331.568 |
| PBAC Score at Baseline | | |
| Mean | 254.3 | 263.7 |
| SD | 155.28 | 171.33 |
| UFS-QOL Score at Baseline Symptom Severity | | |
| Mean | 28.4 | 29.7 |
| SD | 14.38 | 15.18 |
| Health related QOL (HRQL) Total | | |
| Mean | 80.2 | 76.8 |
| SD | 16.73 | 19.57 |
| HGB at Baseline (g/dL) | | |
| Mean | 11.49 | 11.62 |
| SD | 1.368 | 1.377 |
| Dosage of leuprorelin vial (N[%]) | | |
| 1.88 mg | 121 (87.7) | 124 (87.3) |
| 3.75 mg | 17 (12.3) | 18 (12.7) |

TABLE 18

Summary of adverse events

| | Compound 1 40 mg (N = 138) | Leuprorelin (N = 142) |
|---|---|---|
| Treatment-Emergent AEs | 131(94.9) | 139(97.9) |
| Not Related | 11(8.0) | 5(3.5) |
| Related | 120(87.0) | 134(94.4) |
| Leading to Study Drug Discontinuation | 9(6.5) | 7(4.9) |
| Serious Treatment-Emergent AEs | 0(0.0) | 2(1.4) |
| Not Related | 0(0.0) | 2(1.4) |
| Related | 0(0.0) | 0(0.0) |
| SAEs Leading to Study Drug Discontinuation | 0(0.0) | 0(0.0) |
| Deaths | 0(0.0) | 0(0.0) |

TABLE 19

Adverse events reported in ≥5% of subjects in any treatment group

| System Organ Class Preferred Term | Compound 1 (N = 138) | Leuprorelin (N = 142) |
|---|---|---|
| General disorders and administration site conditions | | |
| Malaise | 8 (5.8) | 5 (3.5) |
| Infections and infestations | | |
| Viral upper respiratory tract infection | 39 (28.3) | 46 (32.4) |
| Investigations | | |
| Gamma-glutamyl transferase increased | 7 (5.1) | 9 (6.3) |
| Bone density decreased | 6 (4.3) | 8 (5.6) |
| Bone resorption test abnormal | 7 (5.1) | 7 (4.9) |
| Musculoskeletal and connective tissue disorders | | |
| Arthralgia | 8 (5.8) | 9 (6.3) |
| Resorption bone increased | 7 (5.1) | 8 (5.6) |
| Nervous system disorders | | |
| Headache | 21 (15.2) | 14 (9.9) |
| Dizziness | 9 (6.5) | 7 (4.9) |
| Somnolence | 7 (5.1) | 6 (4.2) |
| Reproductive system and breast disorders | | |
| Metrorrhagia | 68 (49.3) | 93 (65.5) |
| Menorrhagia | 34 (24.6) | 22 (15.5) |
| Genital haemorrhage | 7 (5.1) | 7 (4.9) |
| Skin and subcutaneous tissue disorders | | |
| Hyperhidrosis | 13 (9.4) | 15 (10.6) |
| Vascular disorders | | |
| Hot flush | 59 (42.8) | 75 (52.8) |

TABLE 20

Adverse events leading to discontinuation.

| System Organ Class Preferred Term | Compound 1 (N = 138) | Leuprorelin (N = 142) |
|---|---|---|
| Gastrointestinal disorders | | |
| Abdominal pain | 0 (0.0) | 1 (0.7) |
| Nausea | 0 (0.0) | 1 (0.7) |
| General disorders and administration site conditions | | |
| Malaise | 1 (0.7) | 1 (0.7) |
| Fatigue | 1 (0.7) | 0 (0.0) |
| Pyrexia | 0 (0.0) | 1 (0.7) |
| Investigations | | |
| Liver function test increased | 1 (0.7) | 1 (0.7) |
| Blood pressure increased | 0 (0.0) | 1 (0.7) |
| Liver function test abnormal | 0 (0.0) | 1 (0.7) |
| Musculoskeletal and connective tissue disorders | | |
| Arthralgia | 1 (0.7) | 1 (0.7) |
| Back pain | 0 (0.0) | 1 (0.7) |
| Tenosynovitis | 1 (0.7) | 0 (0.0) |
| Tenosynovitis stenosans | 1 (0.7) | 0 (0.0) |
| Nervous system disorders | | |
| Headache | 1 (0.7) | 0 (0.0) |
| Psychiatric disorders | | |
| Depression | 1 (0.7) | 0 (0.0) |
| Skin and subcutaneous tissue disorders | | |
| Drug eruption | 0 (0.0) | 1 (0.7) |

TABLE 20-continued

Adverse events leading to discontinuation.

| System Organ Class<br>Preferred Term | Compound 1<br>(N = 138) | Leuprorelin<br>(N = 142) |
|---|---|---|
| Vascular disorders | | |
| Hot flush | 4 (2.9) | 1 (0.7) |
| Hypertension | 0 (0.0) | 1 (0.7) |

TABLE 21

Subjects with markedly abnormal liver function tests

| Variable | Compound 1<br>(N = 138) | Leuprorelin<br>(N = 142) |
|---|---|---|
| Any Markedly Abnormal LFT | 3 (2.2) | 2 (1.4) |
| ALT > 3xULN | 3 (2.2) | 2 (1.4) |
| ALT > 5xULN | 1 (0.7) | 0 (0.0) |
| AST > 3xULN | 2 (1.4) | 0 (0.0) |
| AST > 5xULN | 0 (0.0) | 0 (0.0) |
| ALT or AST > 3xULN with Tbili > 2xULN | 0 (0.0) | 0 (0.0) |
| ALT and AST > 3xULN | 2 (1.4) | 0 (0.0) |
| ALP > 3xULN | 0 (0.0) | 0 (0.0) |

FIG. 176 is a graph of the proportion of PBAC responders with primary endpoint results. Non-inferiority margin between the two groups was −15%. FIG. 177 is a graph depicting the proportion of responders with secondary endpoint results. The primary endpoint results are also included for context. FIG. 178A depicts a graph of secondary endpoint myoma volume; FIG. 178B depicts a graph of secondary endpoint uterine volume; and FIG. 178C depicts a graph of secondary hemoglobin, for the two different treatment groups. FIG. 179 depicts a graph of bone mineral density over time in the two different treatment groups.

Demographic and baseline characteristics were generally balanced across treatment groups. Similar proportions of subjects with a PBAC <10 between Week 6 and Week 12 were observed with Compound 1 (82.2%) and leuprorelin (83.1%). Compound 1 was statistically non-inferior to leuprorelin meeting the primary study objective. Results for secondary efficacy endpoints were consistent with that of the primary endpoint. Incidence of adverse events was generally similar between treatment groups. Incidence of adverse events related to liver function was low and generally similar between groups. A reduction from baseline in bone mineral density was observed with Compound 1 that was similar to that observed with leuprorelin.

It was found that Compound 1 was efficacious and generally well tolerated in the subjects of the study, who had heavy menstrual bleeding due to uterine fibroids.

Example 11: A Multicenter, Randomized, Double-Blind, Parallel-Group, Placebo-Controlled, Phase 3 Study to Evaluate the Efficacy and Safety of Oral Compound 1 (40 mg) in the Treatment of Pain Symptoms Associated with Uterine Fibroids This will be a phase 3, multicenter, randomized, double-blind, parallel-group study to evaluate the efficacy of Compound 1 (40 mg) administered orally once-daily for 12 weeks compared with placebo in subjects having pain symptoms associated with uterine fibroids. To be included, subjects must have been diagnosed to have uterine fibroids confirmed by transvaginal ultrasound or other methods, and experienced pain symptoms associated with uterine fibroids (e.g., lower abdominal pain and low back pain). The total number of subjects to be randomized under double-blind conditions will be 64 (32 subjects each for the Compound 1 40 mg group, or placebo group). The objectives of this study will be to evaluate the efficacy and safety of Compound 1 (40 mg) administered orally once-daily for 12 weeks, compared with placebo in subjects having pain symptoms associated with uterine fibroids. Subjects will be aged 20 years or older inclusive, and had uterine fibroids. The study will be carried out at approximately 15 sites.

Subjects will be orally administered either 40 mg of Compound 1 or placebo once-daily before breakfast. The duration of treatment will be 12 weeks, and the follow-up period will be 4 weeks.

After signing the informed consent form, subjects will start recording in the patient diary from the day of VISIT 1. During the period between VISIT 2 and VISIT 3, in which subjects must have experienced 1 menstrual cycle, the baseline values for the efficacy evaluation of pain symptoms will be collected. Subjects will record in the patient diary every day until the end of study drug administration. VISIT 2 will be between the first and fifth day of the first menstruation after VISIT 1. The study drug (placebo) will be administered under single-blind conditions from the day of first menstruation after VISIT 1 to the day before VISIT 3. VISIT 3 will be between the first and fifth day of the second menstruation after VISIT 1. From VISIT 2 to 6, subjects will visit the study site during the morning in a fasted state and before taking the study drug. Subjects will be randomized in a 1:1 ratio to either Compound 1 40 mg group or placebo group at VISIT 3. Study drug (Compound 1 40 mg or placebo) will be administered from the day of VISIT 3 to the day before VISIT 6 (or until early termination) under double-blind conditions.

This study will consist of Screening of approximately 1 to 6 weeks, a Run-in period of 3 to 6 weeks, a Treatment period of 12 weeks, and a Follow-up period of 4 weeks. The total period of study participation will be approximately 20 to 28 weeks. If the recovery of the first post-treatment menstruation is not observed by the visit at the end of the Follow-up (VISIT 7), the subject will undergo further follow-up using possible means such as by telephone interview, until the recovery of the first post-treatment menstruation is observed. During the course of this study, subjects will visit the study site to undergo the designated examinations and evaluations at each visit.

Example 12: An International Phase 3 Randomized, Double-Blind, Placebo-Controlled Efficacy and Safety Study to Evaluate Compound 1 Administered with and without Low-Dose Estradiol and Norethindrone Acetate in Women with Endometriosis-Associated Pain This study will be an international phase 3 randomized, double-blind, placebo-controlled efficacy and safety study to evaluate oral Compound 1 (relugolix) 40 mg once-daily co-administered with either 12 or 24 weeks of low-dose estradiol and norethindrone acetate compared with placebo (1.0 mg estradiol and 0.5 mg norethindrone acetate). Approximately 600 women with endometriosis-associated pain will be enrolled and randomized 1:1:1 to the Compound 1 plus low dose hormonal add-back therapy group (Group A, N≈200; 24 weeks of oral Compound 1 40 mg once-daily co-administered with 1.0 mg estradiol and 0.5 mg norethindrone acetate), the Compound 1 monotherapy followed by coadministration with low-dose hormonal add-back therapy group (Group B, N≈200; 12 weeks of oral Compound 1 40 mg once-daily followed by 12 weeks of oral Compound 1 40 mg once-daily co-administered with 1.0 mg estradiol and 0.5 mg norethindrone acetate), or the placebo group (Group C, N≈200). Stratification variables will include: geographic region (North America versus Rest of World) and years since surgical endometriosis diagnosis (<5 or ≥5 years). Eligible patients will have endometriosis diagnosed or confirmed by laparoscopy or laparotomy within 10 years of the Screening visit. Additionally, patients will have no history of chronic pelvic pain other than that caused by endometriosis and will not be using opioid analgesics or frequent non-opioid analgesics for chronic pain or recurring pain other than that due to endometriosis. Patients receiving hormonal contraceptives will discontinue these at least 28 days prior to the start of the Run-In Period. An endometrial biopsy will also be performed at Screening. A transvaginal ultrasound (with or without a transabdominal ultrasound) will be performed at Week 24. Endometrial biopsy will be performed at the Week 24 visit only if indicated (endometrial thickness at any location is ≥4 mm or if any other endometrial abnormality is visualized on the Week 24 ultrasound).

Between the Baseline Day 1 and Week 24 visits, patients will attend visits every 4 weeks. During the Run-In Period and at the Week 12 and Week 24 visits, each patient will have an assessment of bone mineral density with dual-energy x-ray absorptiometry (DXA). Patients will complete a daily eDiary from the Screening visit through the Follow-Up visit (including during the up to 7-day window following the Run-In Period) to record study drug treatment, assessment of pain using the NRS, menstrual bleeding, analgesic use, and the functional effects of endometriosis-associated pain (Subject Modified Biberoglu and Behrman [sB&B]). Quality of life questionnaires, Physician's Global Impression of Change (PGIC), and Patient Global Assessment (PGA) will be completed during the visits in an electronic tablet, as specified in the Schedule of Activities. Patients will be permitted to use only protocol-specified rescue analgesic medications as listed in the Study Reference Manual from the start of the Run-In Period through the end of the Follow-Up Period.

Example 13: An International Phase 3 Randomized, Double-Blind, Placebo-Controlled Efficacy and Safety Study to Evaluate Compound 1 Co-Administered with and without Low-Dose Estradiol and Norethindrone Acetate in Women with Heavy Menstrual Bleeding Associated with Uterine Fibroids This study will be an international phase 3 randomized, double-blind, placebo-controlled efficacy and safety study to evaluate 24 weeks of oral Compound 1 40 mg once-daily co-administered with low-dose estradiol and norethindrone acetate and 12 weeks of oral Compound 1 40 mg once-daily followed by 12 weeks of oral Compound 1 40 mg once-daily co-administered with low-dose estradiol and norethindrone acetate compared with 24 weeks of placebo. Approximately 390 women with heavy menstrual bleeding associated with uterine fibroids will be enrolled and randomized 1:1:1 to the Compound 1 plus low-dose hormonal add-back therapy group (Group A; N≈130; 24 weeks of oral Compound 1 40 mg once-daily co-administered with 1.0 mg estradiol and 0.5 mg norethindrone acetate), the Compound 1 monotherapy followed by co-administration with low-dose hormonal add-back therapy group (Group B; N≈130; 12 weeks of oral Compound 1 40 mg once-daily followed by 12 weeks of oral Compound 1 40 mg once-daily co-administered with 1.0 mg estradiol and 0.5 mg norethindrone acetate), or placebo group (Group C; N≈130). Stratification variables will include: geographic region (North America versus Rest of World) and mean screening menstrual blood loss volume (<225 mL versus ≥225 mL) by the alkaline hematin method. The study will consist of a screening period (up to ~13 weeks), a randomized treatment period (24 weeks), and a follow-up period (~30 days). Additionally, unscheduled follow-up visit(s) may be arranged for patients with study-related safety concerns and as needed. A diagnosis of uterine fibroids will be confirmed during the screening period by centrally-reviewed transvaginal (with or without a transabdominal ultrasound). Heavy menstrual bleeding will be defined as menstrual blood loss of ≥80 mL per cycle for 2 cycles or ≥160 mL during 1 cycle during the screening period. During the randomized treatment period, study participants will take blinded study treatment orally once-daily for 24 weeks. Women with iron-deficient microcytic anemia and hemoglobin ≥8 g/dL and ≤10 g/dL at Screening must be treated with oral or parenteral iron replacement therapy. Between the Baseline Day 1 and Week 24 visits, patients will attend visits monthly (i.e., every 4 weeks). At the Screening, Week 12, and Week 24 visits, patients will have an assessment of bone mineral density with dual-energy x-ray absorptiometry (DXA). An endometrial biopsy will also be performed at Screening. A transvaginal ultrasound (with or without a transabdominal ultrasound) will be performed at Week 24, followed by a repeat endometrial biopsy. Patients will have paired baseline and end-of-treatment endometrial biopsies, independent of ultrasound results. Feminine products will be standardized and will be collected and assessed for blood loss by the alkaline hematin method. Complete blood counts and chemistries will be collected monthly and uterine and uterine fibroid volumes will be assessed at the Screening and Week 24 visits. Patients will complete daily electronic diaries (eDiary) including compliance with study treatment, menstrual bleeding, use of feminine products for menstrual bleeding, uterine fibroid-associated pain by the Numerical Rating Scale, and use of pain medication to treat pain caused by uterine fibroids. Exemplary eDiary questions are shown in FIGS. 180A-E. Quality of life questionnaires will be completed according to the Schedule of Activities. Safety will be assessed throughout the study by monitoring adverse events, vital signs, physical examinations including visual acuity, clinical laboratory tests, 12-lead electrocardiograms, endometrial biopsies, and assessments of bone mineral density. Height will be measured at the Screening 1 visit and weight will be measured at specified intervals. Samples will be collected for PK assessment of Compound 1, estradiol, and norethindrone and for the pharmacodynamic assessment of luteinizing hormone (LH), follicle-stimulating hormone (FSH), estradiol, and progesterone. All patients completing the Week 24 visit, including women randomized to placebo, will be offered the opportunity to enroll in an open-label extension study in which all eligible patients will receive Compound 1 co-administered with low-dose estradiol and norethindrone acetate. Patients who do not enroll into the extension study will have a follow-up visit approximately 30 days after the end of treatment (i.e., after the patient's last dose of study medication).

Example 14: An International Phase 3 Randomized, Double-Blind, Placebo-Controlled Efficacy and Safety Study to Evaluate Compound 1 Co-Administered with and without Low-Dose Estradiol and Norethindrone Acetate in Women with Heavy Menstrual Bleeding Associated with Uterine Fibroids This study will be to evaluate 24 weeks of oral Compound 1 (relugolix) 40 mg once-daily co-administered with low-dose estradiol and norethindrone acetate and 12 weeks of oral Compound 1 40 mg once-daily followed by 12 weeks of oral Compound 1 40 mg once-daily co-administered with low-dose estradiol and norethindrone acetate compared with 24 weeks of placebo. Approximately 390 women with heavy menstrual bleeding associated with uterine fibroids will be enrolled and randomized 1:1:1 to the Compound 1 plus low-dose hormonal add-back therapy group (Group A; N≈130; Compound 1 40 mg tablet co-administered with 1.0 mg estradiol/0.5 mg norethindrone acetate capsule for 24 weeks), the Compound 1 monotherapy followed by coadministration with low-dose hormonal add-back therapy group (Group B; N≈130; Compound 1 40 mg tablet co-administered with Compound 1 placebo tablet for 12 weeks followed by Compound 1 40 mg tablet coadministered with 1.0 mg estradiol/0.5 mg norethindrone acetate capsule for 12 weeks), or placebo group (Group C; N≈130). Stratification variables will include: geographic region (North America versus Rest of World) and mean screening menstrual blood loss volume (<225 mL versus ≥225 mL) by the alkaline hematin method. The study will consist of a screening period (up to ~13 weeks), a randomized treatment period (24 weeks), and a follow-up period (~30 days). Additionally, unscheduled follow-up visit(s) may be arranged for patients with study-related safety concerns and as needed. A diagnosis of uterine fibroids will be confirmed during the screening period by centrally-reviewed transvaginal (with or without a transabdominal ultrasound). Heavy menstrual bleeding will be defined as menstrual blood loss of ≥80 mL per cycle for 2 cycles or ≥160 mL during 1 cycle during the screening period. During the randomized treatment period, study participants will take blinded study treatment orally once-daily for 24 weeks. Women with iron-deficient microcytic anemia and hemoglobin ≥8 g/dL and ≤10 g/dL at Screening must be treated with oral or parenteral iron replacement therapy. Between the Baseline Day 1 and Week 24 visits, patients will attend visits monthly (ie, every 4 weeks). At the Screening, Week 12, and Week 24 visits, patients will have an assessment of bone mineral density with dual-energy x-ray absorptiometry (DXA). An endometrial biopsy will also be performed at Screening. A transvaginal ultrasound (with or without a transabdominal ultrasound) will be performed at Week 24. Endometrial biopsy will be performed at the Week 24 visit only if indicated (endometrial thickness at any location is ≥4 mm or if any other endometrial abnormality is visualized on the Week 24 ultrasound). Feminine products will be standardized and will be collected and assessed for blood loss by the alkaline hematin method. Complete blood counts and chemistries will be collected monthly and uterine and uterine fibroid volumes will be assessed at the Screening and Week 24 visits. Patients will complete daily electronic diaries (eDiary) including compliance with study treatment, menstrual bleeding, use of feminine products for menstrual bleeding, uterine fibroid-associated pain by the Numerical Rating Scale, and use of pain medication to treat pain caused by uterine fibroids. Exemplary eDiary questions are shown in FIGS. 180A-E. Quality of life questionnaires will be completed according to the Schedule of Activities. Safety will be assessed throughout the study by monitoring adverse events, vital signs, physical examinations including visual acuity, clinical laboratory tests, 12-lead electrocardiograms, paired endometrial biopsies in a subset of patients, and assessments of bone mineral density. Height will be measured at the Screening 1 visit and weight will be measured at specified intervals. Samples will be collected for PK assessment of Compound 1, estradiol, and norethindrone and for the pharmacodynamic assessment of luteinizing hormone (LH), follicle-stimulating hormone (FSH), estradiol, and progesterone. All patients completing the Week 24 visit, including women randomized to placebo, will be offered the opportunity to enroll in an open-label extension study in which all eligible patients will receive Compound 1 co-administered with low-dose estradiol and norethindrone acetate. Patients who do not enroll into the extension study will have a follow-up visit approximately 30 days after the end of treatment (i.e., after the patient's last dose of study medication).

Example 15: An International Phase 3 Randomized, Double-Blind, Placebo-Controlled Efficacy and Safety Study to Evaluate Compound 1 Administered with and without Low-Dose Estradiol and Norethindrone Acetate in Women with Endometriosis-Associated Pain This study will be an international phase 3 randomized, double-blind, placebo-controlled efficacy and safety study to evaluate oral Compound 1 (relugolix) 40 mg once-daily co-administered with either 12 or 24 weeks of low-dose estradiol (1.0 mg) and norethindrone acetate (0.5 mg) compared with placebo. Approximately 600 women with endometriosis-associated pain will be enrolled and randomized 1:1:1 to the Compound 1 plus low-dose hormonal add-back therapy group (Group A, N≈200; Compound 1 40 mg tablet co-administered with 1.0 mg estradiol/0.5 mg norethindrone acetate capsule for 24 weeks), the Compound 1 monotherapy followed by co-administration with low-dose hormonal add-back therapy group (Group B, N≈200; Compound 1 40 mg tablet co-administered with estradiol/norethindrone acetate placebo capsule for 12 weeks followed by Compound 1 40 mg tablet co-administered with 1.0 mg estradiol/0.5 mg norethindrone acetate capsule for 12 weeks), or the placebo group (Group C, N≈200). Stratification variables will include: geographic region (North America versus Rest of World) and years since surgical endometriosis diagnosis (<5 or ≥5 years).

Eligible patients will have endometriosis diagnosed or confirmed by laparoscopy or laparotomy within 10 years of the Screening visit. Additionally, patients will have no history of chronic pelvic pain other than that caused by endometriosis and will not be using opioid analgesics or frequent non-opioid analgesics for chronic pain or recurring pain other than that due to endometriosis. Patients receiving hormonal contraceptives will discontinue these 28 to 56 days prior to the start of the single-blind Run-In Period. At the Screening visit, patients will answer questions as to the severity of their dysmenorrhea and nonmenstrual pelvic pain (NMPP). Only those whose pain is self-characterized as moderate, severe, or very severe for both dysmenorrhea and NMPP will proceed to additional Screening visit procedures and Run-In procedures. Patients who are not excluded by the results available at the end of the Screening visit will be dispensed an electronic diary (eDiary) and will begin a 35-day Run-In Period on the next day. During the single-blind Run-In Period, in which only patients will be blinded, the patients will take one placebo tablet and one placebo capsule each day and report their pain and analgesic medication use daily in the eDiary. Only study-specific analgesic medications will be allowed starting with the second Screening visit day (if the Screening visit is conducted over more than 1 day), during the Run-In Period, and subsequently. These medications will be taken for control of pain and not prophylactically. Final eligibility will be based on severity of pain determined by the specified Numerical Rating Scale (NRS) scores for dysmenorrhea and NMPP and Patient Global Impression of Change (PGIC) for NMPP obtained during the Run-In Period (Days R1 through R35). A 7-day window period (Days R36 to R42) between the end of the Run-In Period and date of randomization (D1) is allowed for confirmation of eligibility criteria and scheduling the Baseline Day 1 visit to coincide with the first 14 days of the menstrual cycle. The Run-In Period (Days R1 through R35) plus the 7-day window (Days R36 to R42) NRS scores for dysmenorrhea and NMPP will serve as the Baseline pain assessment period for the study. Run-In Day 1 is defined as the day that the first dose of single-blind study drug was taken. Once eligibility has been confirmed, patients will be randomized on Baseline Day 1 and will begin double-blinded study drug treatment on Day 1. During the Randomized Treatment Period, study participants will take the blinded study treatment (1 tablet and 1 capsule) orally once-daily for 24 weeks. The last dose of study drug will be taken on the day prior to the Week 24 visit. An endometrial biopsy will also be performed at Screening. A transvaginal ultrasound (with or without a transabdominal ultrasound) will be performed at Week 24, followed by a repeat endometrial biopsy.

Between the Baseline Day 1 and Week 24 visits, patients will attend visits every 4 weeks. During the Run-In Period and at the Week 12 and Week 24 visits, each patient will have an assessment of bone mineral density with dual-energy x-ray absorptiometry (DXA). Patients will complete a daily eDiary from the day prior to Run-In Day 1 through the Follow-Up visit (including the 7-day window following the Run-In Period) to record study drug treatment, assessment of pain using the NRS, menstrual bleeding and its severity, analgesic use, and the functional effects of endometriosis-associated pain (using Subject Modified Biberoglu and Behrman [sB&B]). Evaluation of function (using Endometriosis Health Profile [EHP]—30), quality of life questionnaires, PGIC, and Patient Global Assessments (PGA) for pain will be completed during the visits in an electronic tablet and a PGA for function will be completed on a paper questionnaire, as specified in the Schedule of Activities. Patients will be permitted to use only protocol-specified rescue analgesic medications as listed in the Study Reference Manual from the second day of the Screening visit, through the Run-In Period, and until the end of the Follow-Up Period.

Safety will be assessed throughout the study by the monitoring of adverse events, vital signs and weight, physical examinations including visual acuity, clinical laboratory tests, 12-lead electrocardiograms (ECGs), and bone mineral density by DXA. Pharmacodynamics samples will be collected for assessment of luteinizing hormone (LH), follicle-stimulating hormone (FSH), estradiol, and progesterone at intervals during the study. Eligible patients, including women randomized to placebo, will be offered the opportunity to enroll in a 28-week open-label extension study where patients will receive Compound 1 co-administered with low-dose estradiol and norethindrone acetate. Patients who do not enroll into the extension study will have a Follow-Up visit approximately 30 days after the patient's last dose of study drug. Patients who are not proceeding to the extension study and who have bone mineral density loss of >2% at the lumbar spine (L1-L4) or total hip relative to the baseline measurement at their Week 24/Early Termination visit will undergo further testing and follow-up to evaluate recovery. Patients whose menses has not resumed as of the Follow-Up visit for unexplained reasons (e.g., not explained by concomitant medications or medical procedures) will be contacted by telephone to determine if menses has resumed. Patients with reductions in visual acuity will be referred for ophthalmology consultation.

Example 16: An International Phase 3 Open-Label, Single-Arm, Long-Term Efficacy and Safety Extension Study to Evaluate Compound 1 Co-Administered with Low-Dose Estradiol and Norethindrone Acetate in Women with Heavy Menstrual Bleeding Associated with Uterine Fibroids This study will be an international phase 3 open-label, single-arm, long-term efficacy and safety extension study that will enroll eligible patients who have completed their participation in one of the phase 3 randomized, double-blind, placebo-controlled parent studies described in Example 13 and Example 14. All patients will receive oral Compound 1 40 mg once-daily co-administered with low-dose estradiol 1.0 mg and norethindrone acetate 0.5 mg for up to 28 weeks. Approximately 600 women with heavy menstrual bleeding associated with uterine fibroids will be enrolled. The objectives of the study will be to evaluate long-term efficacy and safety through up to 52 weeks of treatment (including treatment during the parent study) with Compound 1 co-administered with low-dose estradiol/norethindrone acetate. Eligible patients will have completed participation in one of the parent studies and consented to participate in this extension study. Screening and baseline procedures will be done at the same visit for this extension study (referred to as the "Week 24/Baseline visit" in this study), which coincides with the Week 24 visit from the parent study, and will be defined as the date of completion of the last Week 24 procedure in the parent study. The Week 24/Baseline visit will include vital signs, physical examination, laboratory assessments, a 12-lead electrocardiogram (ECG), bone densitometry, patient-reported outcome assessments, transvaginal ultrasound, and endometrial biopsy (if required). When Week 24 procedures in the parent study have been completed, the investigator will assess patient eligibility for participation in the open-label extension study. The eligibility assessment will be based on data available at the Week 24/Baseline visit. No study procedures will be performed until the consent form for this extension study is signed.

Patients will have received their last dose of study drug in the parent study on the day prior to the Week 24/Baseline visit and will receive their first dose of study drug for this extension study in the clinic after the patient is determined to be eligible for this extension study and has provided informed consent to participate. The administration of the first dose of study drug for this study will define enrollment into this study. Study participants will then take the open-label study treatment (Compound 1) 40 mg co-administered with estradiol 1.0 mg and norethindrone acetate 0.5 mg) orally once-daily for 28 weeks.

At the Week 36 visit and Week 52/Early Termination visit, each patient will have an assessment of bone mineral density via dual-energy x-ray absorptiometry (DXA). Quality of life questionnaires will be completed according to the Schedule of Activities. Safety will be assessed throughout the study by the monitoring of adverse events, vital signs and weight, physical examinations, clinical laboratory tests, 12-lead ECG, bone mineral density with DXA, and transvaginal ultrasound.

Patients with a bone mineral density loss of >3% at the lumbar spine (L1-L4) or total hip at their Week 52/Early Termination visit relative to the parent study Baseline measurement will undergo another bone densitometry scan at 6 (±1) months. Status of menstruation recovery will be documented at the Follow-up visit. Patients whose menses has not resumed as of the Follow-Up visit for whom there is no explanation for the lack of resumption (e.g., medical procedure or medications) will be contacted again by telephone 3 (+0.5) months after the Follow-Up visit to determine if menses has resumed and will be asked about factors that may affect resumption of menses. If the patient enrolls directly into another Compound 1 clinical study upon completion of the Week 52 visit, then the Follow-up visit and the follow-up procedures performed under this protocol, including the follow-up bone densitometry scan at 6 (±1) months and status of menstruation recover, may be waived.

Example 17: A Phase 1, Open-Label, Randomized, Three-Way Crossover Study Evaluating the Relative Bioavailability and Effect of Food on Compound 1 Tablet Formulations in Healthy Subjects This was an open-label, randomized, 3-way crossover, single-dose study designed to evaluate the oral bioavailability of two Compound 1 tablet formulation candidates (T4 Formulation B and T4 Formulation C) relative to a third Compound 1 tablet formulation (T2 Formulation), and the effect of food on the PK of Compound 1 following oral administration of the T4 Formulations B and C. There were five single-dose treatment regimens:

Regimen A: Compound 1, 120 mg dose T2 Formulation under fasted conditions.
Regimen B: Compound 1, 120 mg T4 Formulation B under fasted conditions.
Regimen C: Compound 1, 120 mg T4 Formulation B under fed conditions (standard US Food and Drug Administration [FDA] high-fat, high-calorie breakfast).
Regimen D: Compound 1, 120 mg T4 Formulation C under fasted conditions.
Regimen E: Compound 1, 120 mg T4 Formulation C under fed conditions (standard US FDA high-fat, high-calorie breakfast).

Screening assessments were performed within 28 days before the Day 1 dose of Compound 1. Following confirmation of eligibility, subjects were randomly assigned to a sequence in one of two treatment arms:

Arm 1: T2 Formulation (Regimen A to serve as a reference group) and T4 Formulation B (Regimens B and C).
Arm 2: T2 Formulation (Regimen A to serve as a reference group) and T4 Formulation C (Regimens D and E).

In each study arm, each subject participated in 3 treatment periods with a 10-day washout interval between each dose. Subjects received a single 120 mg oral dose of Compound 1 on Day 1, Day 11, and Day 21, per the assigned arm and sequence, followed by serial blood sampling for PK assessments at predetermined time points up to 120 hours postdose. During each of the 3 treatment periods, subjects were confined to the clinical site for a total of 4 days. Each eligible subject was to check into the clinical site on the evening of Day −1 and undergo baseline safety assessments.

Subjects were confined to the clinical site from Day −1 through Day 4. Following the Day 4 (72 hours postdose) PK blood sampling, subjects were discharged from the clinical site. Subjects were instructed to return to the study clinic on the morning of Day 5 for the 96-hour PK assessment and on the morning of Day 6 for the 120-hour PK assessment. Subjects were to return to the study clinic on the evening of Day 10 and were confined from Day 10 through Day 14. Following the Day 14 (72 hours postdose) PK blood sampling, subjects were discharged from the clinical site. Subjects were instructed to return to the study clinic on the morning of Day 15 for the 96-hour PK assessment and the morning of Day 16 for the 120-hour PK assessment. Subjects were to return to the study clinic on the evening of Day 20 and were confined from Day 20 through Day 24. Following the Day 24 (72 hours postdose) PK blood sampling, subjects were discharged from the clinical site. Subjects were instructed to return to the study clinic on the morning of Day 25 for the 96-hour PK assessment on the morning of Day 26 for the 120-hour PK assessment. Study drug was administered in the morning of Days 1, 11, and 21 in either the fed or fasted state. During confinement, subjects received standardized meals scheduled at the same time each day. For each subject, vital signs, physical examinations, adverse event (AE) assessments, laboratory values (chemistry, hematology, and urinalysis), and 12-lead electrocardiograms (ECGs) were obtained to evaluate the safety and tolerability of Compound 1. Subjects were considered to have completed the study if they completed each of the 3 treatment periods and the End-of-Study (EOS) assessment (30 days after the last dose of study drug). Subjects could discontinue participation in the study at any time. Each subject must have been a healthy adult male, aged 18–55 years (inclusive) to be included in this study. Tables 22 and 23 summarize treatment Arm 1 and treatment Arm 2 of the study.

TABLE 22

Treatment period sequences for Arm 1

| Sequence | Period[a] 1 | Period[a] 2 | Period[a] 3 |
|---|---|---|---|
| 1 | Regimen A[b] | Regimen B[c] | Regimen C[d] |
| 2 | Regimen A | Regimen C | Regimen B |
| 3 | Regimen B | Regimen A | Regimen C |
| 4 | Regimen B | Regimen C | Regimen A |
| 5 | Regimen C | Regimen A | Regimen B |
| 6 | Regimen C | Regimen B | Regimen A |

[a]The length of each treatment period was 10 days. Subjects received single doses of Compound 1 on the first day of each treatment period (i.e., Day 1, Day 11, and Day 21).
[b]Regimen A: Compound 1, 120 mg dose (80 mg + 40 mg tablets) T2 Formulation under fasted conditions.
[c]Regimen B: Compound 1, 120 mg (1 × 120 mg tablet) T4 Formulation B under fasted conditions.
[d]Regimen C: Compound 1, 120 mg (1 × 120 mg tablet) T4 Formulation B under fed conditions (standard US FDA high-fat, high-calorie breakfast).

TABLE 23

Treatment period sequences for Arm 2

| Sequence | Period[a] 1 | Period[a] 2 | Period[a] 3 |
|---|---|---|---|
| 1 | Regimen A[b] | Regimen D[c] | Regimen E[d] |
| 2 | Regimen A | Regimen E | Regimen D |
| 3 | Regimen D | Regimen A | Regimen E |
| 4 | Regimen D | Regimen E | Regimen A |
| 5 | Regimen E | Regimen A | Regimen D |
| 6 | Regimen E | Regimen D | Regimen A |

[a]The length of each treatment period was 10 days. Subjects received single doses of Compound 1 on the first day of each treatment period (i.e., Day 1, Day 11, and Day 21).
[b]Regimen A: Compound 1, 120 mg dose (80 mg + 40 mg tablets) T2 Formulation under fasted conditions.
[c]Regimen D: Compound 1, 120 mg (1 × 120 mg tablet) T4 Formulation C under fasted conditions.
[d]Regimen E: Compound 1, 120 mg (1 × 120 mg tablet) T4 Formulation C under fed conditions (standard US FDA high-fat, high-calorie breakfast).

A total of 54 subjects enrolled in and completed the study. There were 27 subjects in each arm of the study. All 54 subjects were included in the safety population and the PK-evaluable population. No major protocol deviations occurred for any subject during this study. One subject had a minor protocol deviation related to a dose administration interval that occurred greater than 30 minutes after the start of breakfast. In Period 3, the subject was administered the T4 Formulation B under fed conditions; the starting time of Compound 1 dose administration following the start of breakfast was 31 minutes and 3 seconds. All of the PK parameters for this subject following oral administration of T4 Formulation B under fed conditions were generally similar to the mean values of PK parameters in this treatment group; therefore, the PK parameters of this subject were included in the descriptive and ANOVA statistical analyses. Tables 24 and 25 below provide summaries of some pharmacokinetic parameters following administration of the different formulations.

TABLE 24

Summary Statistics of Plasma Pharmacokinetic Parameters of Compound 1 Following Single Oral Administration of 120 mg Compound 1 as T4 Formulation B or C Tablet Compared to T2 Formulation Tablets Under Fasted Conditions

| Parameter (unit) | Arm 1 | | Arm 2 | |
|---|---|---|---|---|
| Statistic | T2 Form. | T4 Form. B | T2 Form. | T4 Form. C |
| N | 27 | 26 | 27 | 27 |
| $t_{max}$ (h) | | | | |
| Median | 2.01 | 3.00 | 3.00 | 3.00 |
| Min, Max | 0.500, 6.00 | 0.502, 12.0 | 0.499, 6.02 | 0.499, 12.0 |
| $C_{max}$ (ng/mL) | | | | |
| GM | 46.7 | 42.0 | 52.0 | 43.5 |
| CV % | 115 | 153 | 93.3 | 147 |
| $AUC_{120}$ (ng · h/mL) | | | | |
| GM | 447 | 440 | 532 | 415 |
| CV % | 64.7 | 83.3 | 55.4 | 85.1 |
| $AUC_{\infty}$ (ng · h/mL) | | | | |
| GM | 476 | 467 | 563 | 440 |
| CV % | 63.5 | 82.8 | 55.1 | 84.8 |
| $t_{1/2z}$ (h) | | | | |
| Mean | 36.3 | 36.1[a] | 34.9 | 35.5 |
| SD | 4.40 | 4.90 | 4.13 | 4.22 |
| Min, Max | 28.8, 46.5 | 27.4, 44.7 | 29.2, 44.8 | 25.4, 46.0 |

CV = geometric coefficient of variation; GM = geometric mean.
[a] N = 27.

TABLE 25

Summary Statistics of Plasma Pharmacokinetic Parameters of Compound 1 Following Single Oral Administration of 120 mg Compound 1 as T4 Formulation B or C Tablet Under Fed Conditions

| Parameter (unit) Statistic | T4 Formulation B | T4 Formulation C |
|---|---|---|
| N | 27 | 27 |
| $t_{max}$ (h) | | |
| Median | 3.00 | 3.00 |
| Min, Max | 0.500, 8.00 | 1.00, 8.00 |
| $C_{max}$ (ng/mL) | | |
| GM | 33.0 | 41.2 |
| CV % | 116 | 106 |
| $AUC_{120}$ (ng · h/mL) | | |
| GM | 350 | 386 |
| CV % | 65.0 | 52.4 |
| $AUC_{\infty}$ (ng · h/mL) | | |
| GM | 372 | 409 |
| CV % | 64.1 | 51.8 |
| $t_{1/2z}$ (h) | | |
| Mean | 35.1 | 35.4 |
| SD | 4.11 | 2.97 |
| Min, Max | 29.9, 45.7 | 29.9, 42.2 |

CV = geometric coefficient of variation; GM = geometric mean.

All subjects included in this study were healthy men, a majority of who were white (81%) and Hispanic or Latino (65%). The overall mean (SD) age of study subjects was 38.9 (10.8) years, with an age range from 19 to 55 years. The overall mean (SD) weight and BMI of subjects was 83.4 (12.7) kg and 27.2 (3.2) kg/m², respectively. Demographic characteristics were similar between treatment arms. No subjects were excluded from the PK-evaluable population; therefore, the demographics for this population were the same as the safety population. The formulation information for various formulations used in this example, and other exemplary formulations, is provided in Table 26.

TABLE 26

Exemplary formulations

| | Function | 1-20 mg (T1) | 40 mg (T2) | 40 mg (T3) | 40 mg (T4-B) | 120 mg (T4-B) | 120 mg (T4-C) |
|---|---|---|---|---|---|---|---|
| Compound 1 | DS | 1-20 | 40 | 40 | 40 | 120 | 120 |
| Mannitol | Diluent | 80-61 | 122 | 122 | 51 | 153 | 234 |
| Microcrystalline cellulose | Diluent | 10 | 20 | 40 | — | — | 30 |
| Polyethylene Glycol 8000 | Lubricant | — | — | — | — | — | 1.8 |
| Hydroxypropyl cellulose | Binder | 3 | 6 | 6 | 3 | 9 | 11.4 |
| Croscarmellose sodium | Disintegrant | 5 | 10 | 10 | — | — | 19.05 |
| Sodium starch glycolate | Disintegrant | — | — | — | 5 | 15 | — |

TABLE 26-continued

Exemplary formulations

| | Function | 1-20 mg (T1) | 40 mg (T2) | 40 mg (T3) | 40 mg (T4-B) | 120 mg (T4-B) | 120 mg (T4-C) |
|---|---|---|---|---|---|---|---|
| Magnesium stearate | Lubricant | 1 | 2 | 2 | 1 | 3 | 3.75 |
| Purified water* | solvent | q.s | q.s | q.s | q.s | q.s | q.s |
| Sub total (Core tablets) | | 100 | 220 | 220 | 100 | 300 | 420 |
| Hypromellose 2910 | Film coating | 2.93 | 7.12 | 7.12 | 3.56 | 10.68 | 13.5 |
| Polyethylene glycol 8000 | plasticizer | 0.67 | — | — | — | — | — |
| Titanium dioxide | Pigment | 0.33 | 0.8 | 0.8 | 0.4 | 1.2 | 1.5 |
| Ferric oxide, red | Colorant | 0.07 | 0.02 | 0.02 | 0.04 | 0.12 | 0.15 |
| Ferric oxide, yellow | Colorant | — | — | 0.06 | — | — | — |
| Purified water* | | q.s | q.s | q.s | q.s | q.s | q.s |
| Sub total (FC layer) | | 4 | 8 | 8 | 4 | 12 | 15.15 |
| Total | | 104 | 228 | 228 | 104 | 312 | 435.15 |
| Carnauba Wax | | — | — | 0.012 | 0.004 | 0.008 | q.s |

Example 18: Content Confirmation of a Symptoms of Endometriosis Scale (SEMS)

This qualitative study was conducted in 15 women with endometriosis and at least mild pain associated with endometriosis to evaluate the understandability of a SEMS scale. The subjects represented a range different races, ethnicities, and educational levels, including 7 (470%) with a high school level-only educational attainment. Overall, the majority of subjects demonstrated correct interpretation of instructions, items and response options across all measures tested. Specifically, the primary endpoint measures NRS for severity of dysmenorrhea and NRS for severity of NMPP were correctly interpreted by 10000 of subjects. Additionally, all concepts measured by the SEMS were reported as relevant by 11 or more subjects (>730%); the following three concepts were experienced by all 15 subjects (100.0%): "pelvic pain," "heavy bleeding," and "taking medications for pelvic pain." For the concept of pelvic pain, the most meaningful dimension of improvement to subjects was reduction in severity (73% of subjects). Overall, subjects found that it was easy to think about their symptoms over the past 24 hours (n=14, 93.3%), the recall period for the NRS used for the co-primary endpoints. The potential anchors for the co-primary endpoints PGIC for dysmenorrhea, PGIC for NMPP and PGA for pain were also interpreted as intended by 100% of subjects. Of the 14 subjects debriefed on the PGIC, 11 (79%) expressed no difficulty in distinguishing between the 7 categories, suggesting that the majority were able to distinguish 1-category differences. Similarly, the majority (~93%) of subject expressed no difficulty in distinguishing between the 5-categories of the PGA for pain. The usability of both of the ePRO devices (phone and tablet) was rated very highly across subjects. The content and understandability of the patient-reported outcomes instruments, in particular, the measures for the co-primary endpoints and key secondary endpoint, the EHP-30 pain domain was confirmed, with no major gaps identified in the concepts included in the EHP-30 pain domain.

FIG. 181 presents a summary of the cognitive debriefing findings for each unique set of response options. In order to assess the relevance of the concepts included in the SEMS, subjects were asked or spontaneously reported if they experienced symptoms included in the SEMS. FIG. 182 presents a summary of each of the concepts measured by the SEMS evaluated in this example, along with the number of subjects that reported relevance of that concept. FIGS. 183A-C present a comparison of subject-reported symptoms with patient-reported outcomes (PRO), such as endpoints that may be used to evaluate the efficacy of one or more treatments. Table 27 summarizes the self-reported demographic information of the subjects in this study.

TABLE 27

Demographic information

| Characteristic | Total sample (N = 15) n (%) |
|---|---|
| Age (in years) | |
| Range | 25-49 |
| Average (SD) | 33.87 (7.74) |
| Gender | |
| Female | 15 (100.0%) |
| Race (all that apply selected) | |
| White | 11 (73.3%) |
| Black or African American | 4 (26.7%) |
| Ethnicity | |
| Not Hispanic or Latino | 13 (86.7%) |
| Hispanic or Latino | 2 (13.3%) |
| Highest level of education | |
| High school graduate (or equivalent) | 7 (46.7%) |

Enumerated Embodiments

Embodiment I-1. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6- yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in the treatment of one or more of uterine fibroids, endometriosis, adenomyosis, heavy menstrual bleeding, or pain associated with uterine fibroids, endometriosis, or adenomyosis in a pre-menopausal woman.

Embodiment I-2. The combined preparation for use according to Embodiment I-1, wherein the treatment comprises orally administering the combined preparation to the pre-menopausal woman once-daily for at least 24 consecutive weeks.

Embodiment I-3. The combined preparation for use according to Embodiment I-1 or Embodiment I-2, wherein the progestin is norethindrone or a salt thereof in an amount of about 0.1 mg to about 0.5 mg.

Embodiment I-4. The combined preparation for use according to any one of Embodiments I-1 to I-3, wherein the combined preparation comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-5. The combined preparation for use according to any one of Embodiments I-1 to I-4, wherein the combined preparation comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-6. The combined preparation for use according to any one of Embodiments I-1 to I-5, wherein the combined preparation comprises about 1 mg of estradiol or a corresponding amount of estradiol equivalent.

Embodiment I-7. The combined preparation for use according to any one of Embodiments I-1 to I-6, wherein the progestin is norethindrone acetate (NETA) and the combined preparation comprises about 0.5 mg NETA.

Embodiment I-8. The combined preparation for use according to any one of Embodiments I-1 to I-7, wherein the combined preparation comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-9. The combined preparation for use according to any one of Embodiments I-1 to I-8, wherein the combined preparation is a single dosage form.

Embodiment I-10. The combined preparation for use according to any one of Embodiments I-1 to I-8, wherein the combined preparation comprises separate dosage forms that are co-administered.

Embodiment I-11. The combined preparation for use according to any one of Embodiments I-1 to I-10, wherein prior to administration of the combined preparation, the treatment further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

Embodiment I-12. The combined preparation for use according to any one of Embodiments I-1 to I-11, wherein the combined preparation is for use in the treatment of endometriosis.

Embodiment I-13. The combined preparation for use according to any one of Embodiments I-1 to I-12, wherein the combined preparation is for use in the treatment of adenomyosis.

Embodiment I-14. The combined preparation for use according to any one of Embodiments I-1 to I-13, wherein the combined preparation is for use in the treatment of uterine fibroids.

Embodiment I-15. The combined preparation for use according to any one of Embodiments I-1 to I-14, wherein the combined preparation is for use in the treatment of heavy menstrual bleeding.

Embodiment I-16. The combined preparation for use according to Embodiment I-15, wherein the heavy menstrual bleeding is associated with a non-malignant etiology.

Embodiment I-17. The combined preparation for use according to Embodiment I-15 or I-16, wherein the heavy menstrual bleeding is associated with one or more of uterine fibroids, endometriosis, or adenomyosis.

Embodiment I-18. The combined preparation for use according to any one of Embodiment I-1 to I-17, wherein the combined preparation is for use in the treatment of pain associated with uterine fibroids, endometriosis, or adenomyosis.

Embodiment I-19. The combined preparation for use according to Embodiment I-18, wherein the pain is associated with endometriosis.

Embodiment I-20. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent, and about 0.01 mg to about 5 mg of a progestin; for simultaneous or sequential use in a method of maintaining bone mineral density in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-21. The combined preparation for use according to Embodiment I-20, wherein the method comprises orally administering the combined preparation to the pre-menopausal woman once-daily for at least 24 consecutive weeks.

Embodiment I-22. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in the treatment of one or more of hot flashes, night sweats and other vasomotor symptoms in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-23. The combined preparation for use according to Embodiment I-22, wherein the treatment comprises orally administering the combined preparation to the pre-menopausal woman once-daily for at least 24 consecutive weeks.

Embodiment I-24. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in a method for maintaining one or both of lipid profile or blood glucose range in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-25. The combined preparation for use according to Embodiment I-24, wherein the method comprises orally administering the combined preparation to the pre-menopausal woman once-daily for at least 24 consecutive weeks.

Embodiment I-26. The combined preparation for use according to Embodiment I-24 or I-25, wherein one or more of the pre-menopausal woman's lipid profile or blood glucose range does not change in a clinically meaningful way after or during treatment as compared to the lipid profile or blood glucose range prior to treatment.

Embodiment I-27. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in a method for treating one or both of vulvovaginal atrophy or vaginal dryness in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-28. The combined preparation for use according to Embodiment I-27, wherein the method comprises orally administering the combined preparation to the pre-menopausal woman once-daily for at least 24 consecutive weeks.

Embodiment I-29. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in the treatment of headache in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-30. The combined preparation for use according to Embodiment I-29, wherein the treatment comprises orally administering the combined preparation to the pre-menopausal woman once-daily for at least 24 consecutive weeks.

Embodiment I-31. The combined preparation for use according to Embodiment I-29 or I-30, wherein the headache is a migraine associated with the menstrual cycle.

Embodiment I-32. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in a method of contraception in a pre-menopausal woman.

Embodiment I-33. The combined preparation for use according to Embodiment I-32, wherein the method comprises orally administering the combined preparation to the pre-menopausal woman once-daily for at least 24 consecutive weeks.

Embodiment I-34. The combined preparation for use according to any one of Embodiments I-20 to I-33, wherein the progestin is norethindrone or a salt thereof in an amount of about 0.1 mg to about 0.5 mg.

Embodiment I-35. The combined preparation for use according to any one of Embodiments I-20 to I-34, wherein the combined preparation comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-36. The combined preparation for use according to any one of Embodiments I-20 to I-35, wherein the combined preparation comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-37. The combined preparation for use according to any one of Embodiments I-20 to I-36, wherein the combined preparation is a single dosage form.

Embodiment I-38. The combined preparation for use according to any one of Embodiments I-20 to I-36, wherein the combined preparation comprises separate dosage forms that are co-administered.

Embodiment I-39. The combined preparation for use according to any one of Embodiments I-20 to I-38, wherein the combined preparation comprises about 1 mg of estradiol or a corresponding amount of estradiol equivalent.

Embodiment I-40. The combined preparation for use according to any one of Embodiments I-20 to I-39, wherein the progestin is norethindrone acetate (NETA) and the combination comprises about 0.5 mg NETA.

Embodiment I-41. The combined preparation for use according to any one of Embodiments I-20 to I-40, wherein the combined preparation comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-42. The combined preparation for use according to any one of Embodiments I-20 to I-41, wherein prior to administration of the combined preparation, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

Embodiment I-43. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in a method of achieving amenorrhea in a pre-menopausal woman for at least 12 or at least 24 weeks.

Embodiment I-44. The combined preparation for use according to Embodiment I-43, wherein the method comprises orally administering the combined preparation to the pre-menopausal woman once-daily for at least 12 or at least 24 consecutive weeks.

Embodiment I-45. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in a method of improving fertility or preventing miscarriages in a pre-menopausal woman, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-46. The combined preparation for use according to Embodiment I-45, wherein the method comprises orally administering the combined preparation to the pre-menopausal woman once-daily for at least 12 or at least 24 consecutive weeks, and discontinuing the treatment for at least 4 weeks while the woman attempts or re-attempts conception.

Embodiment I-47. A combined preparation comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; for simultaneous or sequential use in the treatment of anemia in a pre-menopausal woman.

Embodiment I-48. The combined preparation for use according to Embodiment I-47, wherein the method comprises orally administering the combined preparation to the pre-menopausal woman once-daily for at least 12 or at least 24 consecutive weeks.

Embodiment I-49. The combined preparation for use according to any one of Embodiments I-43 to I-48, wherein the pre-menopausal woman is experiencing heavy menstrual bleeding.

Embodiment I-50. The combined preparation for use according to Embodiment I-49, wherein the heavy menstrual bleeding is associated with a non-malignant etiology.

Embodiment I-51. The combined preparation for use according to any one of Embodiments I-43 to I-50, wherein the pre-menopausal woman has one or more of uterine fibroids, endometriosis, adenomyosis, heavy menstrual bleeding, or symptoms related to one or more of uterine fibroids, endometriosis, or adenomyosis.

Embodiment I-52. The combined preparation for use according to any one of Embodiments I-1 to I-51, wherein administration of the combined preparation is once-daily for at least 48 consecutive weeks, at least 72 consecutive weeks, or at least 96 consecutive weeks.

Embodiment I-53. The combined preparation for use according to any one of Embodiments I-1 to I-52, wherein administration of the combined preparation is suspended for conception and pregnancy.

Embodiment I-54. The combined preparation for use according to Embodiment I-53, wherein administration is resumed after delivery.

Embodiment I-55. The combined preparation for use according to any one of Embodiments I-1 to 154, wherein the combined preparation is administered pre-prandial.

Embodiment I-56. The combined preparation for use according to any one of Embodiments I-1 to I-55, wherein the administering is at least 30 minutes before eating or while subject is fasting.

Embodiment I-57. The combined preparation for use according to any one of Embodiments I-1 to I-56, wherein the combined preparation is administered at least 1 hour before eating or at least 2 hours after eating.

Embodiment I-58. The combined preparation for use according to any one of Embodiments I-1 to I-57, wherein the combined preparation is administered as one or more immediate release dosage forms.

Embodiment I-59. A combined preparation of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.5 mg to about 5.0 mg of estradiol or a corresponding amount of estradiol equivalent; and about 0.5 mg to about 2.0 mg norethindrone acetate or other progestin; for simultaneous or sequential use in the treatment of symptomatic uterine fibroids or endometriosis in a pre-menopausal woman.

Embodiment I-60. The combined preparation for use according to Embodiment I-59, wherein the treatment comprises administering the combined preparation to said woman once-daily.

Embodiment I-61. The combined preparation for use according to Embodiment I-59 or I-60, wherein administration of the combined preparation suppresses the endometrium.

Embodiment I-62. The combined preparation for use according to any one of Embodiments I-59 to I-61, wherein the combined preparation is in a single dosage form.

Embodiment I-63. A combined preparation of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a pharmaceutically acceptable salt thereof, about 1.5 mg to about 5 mg estradiol or a corresponding amount of estradiol equivalent; and about 0.5 mg to about 2.0 mg norethindrone acetate or other progestin; for simultaneous or sequential use in the treatment of one or more of hot flashes, night sweats, vasomotor symptoms other than hot flashes or night sweats, and bone mineral density loss in a pre-menopausal woman who continues to have one or more of hot flashes and other vasomotor symptoms and bone mineral density loss when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, wherein the treatment comprises administering the combined preparation to said pre-menopausal woman.

Embodiment I-64. The combined preparation for use according to Embodiment I-63, where administration of the combined preparation suppresses endometrial tissue.

Embodiment I-65. A method for treating one or more of uterine fibroids, endometriosis or adenomyosis in a pre-menopausal woman in need thereof, the method comprising orally administering to the pre-menopausal woman once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-66. The method of Embodiment I-65, wherein the progestin is norethindrone or a salt thereof in an amount of about 0.1 mg to about 0.5 mg.

Embodiment I-67. The method of Embodiment I-65 or I-66, wherein the combination comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-68. The method of any one of Embodiments I-65 to I-67, wherein the combination comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-69. The method of any one of Embodiments I-65 to I-68, wherein the combination comprises about 1 mg of estradiol or a corresponding amount of estradiol equivalent.

Embodiment I-70. The method of any one of Embodiments I-65 to I-69, wherein the progestin is norethindrone acetate (NETA) and the combination comprises about 0.5 mg NETA.

Embodiment I-71. The method of any one of Embodiments I-65 to I-70, wherein the combination comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-72. The method of any one of Embodiments I-65 to I-71, wherein the combination is a single dosage form.

Embodiment I-73. The method of any one of Embodiments I-65 to I-71, wherein the combination comprises separate dosage forms that are co-administered.

Embodiment I-74. The method of any one of Embodiments I-65 to I-73, wherein the treatment results in one or both of contraception and amenorrhea during treatment.

Embodiment I-75. The method of any one of Embodiments I-65 to I-74, wherein after at least 4 consecutive weeks of administration of the combination, the pre-menopausal woman's ovarian estrogen production is suppressed.

Embodiment I-76. The method of any one of Embodiments I-65 to I-75, wherein after at least 4 consecutive weeks of administration of the combination, the pre-menopausal woman's serum estradiol concentration is between about 20 pg/ml and about 50 pg/ml between daily doses of the combination.

Embodiment I-77. The method of any one of Embodiments I-65 to I-76, wherein after at least 4 consecutive weeks of administration of the combination, the pre-menopausal woman's ovarian progesterone production is suppressed.

Embodiment I-78. The method of any one of Embodiments I-65 to I-77, wherein after at least 4 consecutive weeks of administration of the combination, the pre-menopausal woman's serum progesterone concentration is less than about 5 ng/ml between daily doses of the combination.

Embodiment I-79. The method of any one of Embodiments I-65 to I-78, wherein prior to administration of the combination, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

Embodiment I-80. The method of any one of Embodiments I-65 to I-79, wherein during and/or after treatment, the pre-menopausal woman experiences an improvement in one or more of the following symptoms, which are selected from the group consisting of anemia, heavy menstrual bleeding, irregular periods, spotting, inflammation, pain, fatigue, urinary obstruction, urinary frequency, incontinence, constipation, anxiety, sleep disturbance, quality of life, activities of daily living, female sexual dysfunction and depression.

Embodiment I-81. The method of any one of Embodiments I-65 to I-80, wherein the pre-menopausal woman is treated for endometriosis.

Embodiment I-82. The method of any one of Embodiments I-65 to I-81, wherein the pre-menopausal woman is treated for adenomyosis.

Embodiment I-83. The method of any one of Embodiments I-65 to I-82, wherein the pre-menopausal woman is treated for uterine fibroids.

Embodiment I-84. The method of any one of Embodiments I-65 to I-83, wherein one or both of the number and size of the uterine fibroids are reduced during and/or after treatment compared to one or both of the number and size of the uterine fibroids prior to treatment.

Embodiment I-85. A method for treating heavy menstrual bleeding in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-86. The method of Embodiment I-85, wherein the heavy menstrual bleeding is associated with a non-malignant etiology.

Embodiment I-87. The method of Embodiment I-85 or I-86, wherein the heavy menstrual bleeding is associated with one or more of uterine fibroids, endometriosis, or adenomyosis.

Embodiment I-88. The method of any one of Embodiments I-85 to I-87, wherein, for a pre-menopausal woman with uterine fibroids, one or both of the number and size of the uterine fibroids are reduced during and/or after treatment compared to one or both of the number and size of the uterine fibroids prior to treatment.

Embodiment I-89. A method for treating pain associated with uterine fibroids, endometriosis, or adenomyosis in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

Embodiment I-90. The method of Embodiment I-89, wherein the pain is associated with endometriosis.

Embodiment I-91. The method of any one of Embodiments I-85 to I-90, wherein the progestin is norethindrone or a salt thereof in an amount of about 0.1 mg to about 0.5 mg.

Embodiment I-92. The method of any one of Embodiments I-85 to I-91, wherein the combination comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-93. The method of any one of Embodiments I-85 to I-92, wherein the combination comprises about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-94. The method of any one of Embodiments I-85 to I-93, wherein the combination is a single dosage form.

Embodiment I-95. The method of any one of Embodiments I-85 to I-93, wherein the combination comprises separate dosage forms that are co-administered.

Embodiment I-96. The method of any one of Embodiments I-85 to I-95, wherein the combination comprises about 1 mg of estradiol or a corresponding amount of estradiol equivalent.

Embodiment I-97. The method of any one of Embodiments I-85 to I-96, wherein the progestin is norethindrone acetate (NETA) and the combination comprises about 0.5 mg NETA.

Embodiment I-98. The method of any one of Embodiments I-85 to I-97, wherein the combination comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-99. The method of any one of Embodiments I-85 to I-98, wherein the treatment results in one or both of contraception and amenorrhea during treatment.

Embodiment I-100. The method of any one of Embodiments I-85 to I-99, wherein after at least 4 consecutive weeks of administration of the combination, the pre-menopausal woman's ovarian estrogen production is suppressed.

Embodiment I-101. The method of any one of Embodiments I-21 to I-100, wherein after at least 4 consecutive weeks of administration of the combination, the pre-menopausal woman's serum estradiol concentration is between 20 pg/ml and 50 pg/ml between daily doses of the combination.

Embodiment I-102. The method of any one of Embodiments I-85 to I-101, wherein after at least 4 consecutive weeks of administration of the combination, the pre-menopausal woman's ovarian progesterone production is suppressed.

Embodiment I-103. The method of any one of Embodiments I-85 to I-102, wherein after at least 4 consecutive weeks of administration of the combination, the pre-menopausal woman's serum progesterone concentration is less than about 5 ng/ml between daily doses of the combination.

Embodiment I-104. The method of any one of Embodiments I-85 to I-103, wherein prior to administration of the combination, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

Embodiment I-105. The method of any one of Embodiments I-85 to I-104, wherein during and/or after treatment, the pre-menopausal woman experiences an improvement in one or more of the following symptoms, which are selected from the group consisting of anemia, irregular periods, spotting, inflammation, pain, fatigue, urinary obstruction, urinary frequency, incontinence, constipation, anxiety, sleep disturbance, quality of life, activities of daily living, female sexual dysfunction and depression.

Embodiment I-106. The method of any one of Embodiments I-65 to I-105, wherein after treatment is discontinued, said pre-menopausal woman conceives or gives birth.

Embodiment I-107. The method of Embodiment I-106, wherein prior to treatment the pre-menopausal women experienced one or more miscarriages or an inability to conceive or a combination thereof.

Embodiment I-108. A method for maintaining bone mineral density in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent, and about 0.01 mg to about 5 mg of a progestin.

Embodiment I-109. A method for treating one or more of hot flashes, night sweats, or vasomotor symptoms other than hot flashes or night sweats in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-110. A method for maintaining one or both of lipid profile or blood glucose range in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; wherein one or more of the pre-menopausal woman's lipid profile or blood glucose range does not change in a clinically meaningful way after or during treatment as compared to the lipid profile or blood glucose range prior to treatment.

Embodiment I-111. A method for treating one or both of vulvovaginal atrophy or vaginal dryness in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-112. A method for treating headache in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-113. The method of Embodiment I-112, wherein the headache is a migraine associated with the menstrual cycle.

Embodiment I-114. A method of contraception in a pre-menopausal woman in need thereof, the method comprising orally administering to the pre-menopausal woman in need thereof once-daily for at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

Embodiment I-115. The method of any one of Embodiments I-108 to I-114, wherein the progestin is norethindrone or a salt thereof in an amount of about 0.1 mg to about 0.5 mg.

Embodiment I-116. The method of any one of Embodiments I-108 to I-115, wherein the combination comprises about 20 mg to about 50 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-117. The method of any one of Embodiments I-108 to I-116, wherein the combination comprises about 40 mg of N-(4-(1-(2,6-difluorobenzyl)-5-((dimethylamino)methyl)-3-(6-methoxy-3-pyridazinyl)-2,4-dioxo-1,2, 3,4-tetrahydrothieno[2,3-d]pyrimidin-6-yl)phenyl)-N'-methoxyurea, or a corresponding amount of a pharmaceutically acceptable salt thereof.

Embodiment I-118. The method of any one of Embodiments I-108 to I-117, wherein the combination is a single dosage form.

Embodiment I-119. The method of any one of Embodiments I-108 to I-117, wherein the combination comprises separate dosage forms that are co-administered.

Embodiment I-120. The method of any one of Embodiments I-108 to I-119, wherein the combination comprises about 1 mg of estradiol or a corresponding amount of estradiol equivalent.

Embodiment I-121. The method of any one of Embodiments I-108 to I-120, wherein the progestin is norethindrone acetate (NETA) and the combination comprises about 0.5 mg NETA.

Embodiment I-122. The method of any one of Embodiments I-108 to I-121, wherein the combination comprises about 0.5 mg NETA, about 1 mg estradiol and about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-123. The method of any one of Embodiments I-108 to I-122, wherein the treatment results in one or both of contraception and amenorrhea during treatment.

Embodiment I-124. The method of any one of Embodiments I-108 to I-123, wherein after at least 4 consecutive weeks of administration of the combination, the pre-menopausal woman's ovarian estrogen production is suppressed.

Embodiment I-125. The method of any one of Embodiments I-108 to I-124, wherein after at least 4 consecutive weeks of administration of the combination, the pre-menopausal woman's serum estradiol concentration is between 20 pg/ml and 50 pg/ml between daily doses of the combination.

Embodiment I-126. The method of any one of Embodiments I-108 to I-125, wherein after at least 4 consecutive weeks of administration of the combination, the pre-menopausal woman's ovarian progesterone production is suppressed.

Embodiment I-127. The method of any one of Embodiments I-108 to I-126, wherein after at least 4 consecutive weeks of administration of the combination, the pre-menopausal woman's serum progesterone concentration is less than about 5 ng/ml between daily doses of the combination.

Embodiment I-128. The method of any one of Embodiments I-108 to I-127, wherein, for a pre-menopausal woman with uterine fibroids, one or both of the number and size of the uterine fibroids are reduced during and/or after treatment compared to one or both of the number and size of the uterine fibroids prior to treatment.

Embodiment I-129. The method of any one of Embodiments I-108 to I-128, wherein prior to administration of the combination, the method further comprises oral administration once-daily of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for at least 4 consecutive weeks and up to 24 consecutive weeks.

Embodiment I-130. The method of any one of Embodiments I-108 to I-129, wherein during and/or after treatment, the pre-menopausal woman experiences an improvement in one or more of the following symptoms, which are selected from the group consisting of anemia, irregular periods, spotting, inflammation, pain, fatigue, urinary obstruction, urinary frequency, incontinence, constipation, anxiety, sleep disturbance, quality of life, activities of daily living, female sexual dysfunction and depression.

Embodiment I-131. A method of achieving amenorrhea in a pre-menopausal woman in need thereof for at least 12 or at least 24 weeks, the method comprising orally administering to the pre-menopausal woman in need thereof once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin.

Embodiment I-132. A method for preventing miscarriages in a pre-menopausal woman need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, the method comprising administering to the pre-menopausal woman in need thereof once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 0.5 mg to about 2 mg of estradiol or a corresponding amount of estradiol equivalent; and about 0.01 mg to about 5 mg of a progestin; and discontinuing the treatment for at least 4 weeks while the woman re-attempts conception.

Embodiment I-133. A method for improving fertility in a pre-menopausal woman in need thereof, treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, the method comprising orally administering to the pre-menopausal woman in need thereof once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin; and discontinuing the treatment for a time period of at least 4 weeks while the pre-menopausal woman attempts conception.

Embodiment I-134. The method of Embodiment I-133, wherein after treatment is discontinued, said pre-menopausal woman conceives or gives birth.

Embodiment I-135. The method of Embodiment I-133 or I-134, wherein prior to treatment the pre-menopausal women experienced one or more miscarriages, an inability to conceive, or a combination thereof.

Embodiment I-136. A method of treating anemia in a pre-menopausal woman in need thereof, the method comprising orally administering to the pre-menopausal woman in need thereof once-daily for at least 12 or at least 24 consecutive weeks a combination comprising about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; about 0.5 mg to about 2 mg of estradiol or a corresponding amount of estradiol equivalent; and about 0.01 mg to about 5 mg of a progestin.

Embodiment I-137. The method of any one of Embodiments I-131 to I-136, wherein the pre-menopausal woman is experiencing heavy menstrual bleeding.

Embodiment I-138. The method of Embodiment I-137, wherein the heavy menstrual bleeding is associated with a non-malignant etiology.

Embodiment I-139. The method of any one of Embodiments I-67 to I-138, wherein the pre-menopausal woman has one or more of uterine fibroids, endometriosis, adenomyosis, heavy menstrual bleeding, or symptoms related to one or more of uterine fibroids, endometriosis, or adenomyosis.

Embodiment I-140. The method of any one of Embodiments I-65 to I-139, wherein administration of the combination is once-daily for at least 48 consecutive weeks, at least 72 consecutive weeks, or at least 96 consecutive weeks.

Embodiment I-141. The method of any one of Embodiments I-65 to I-140, wherein administration of the combination is suspended for conception and pregnancy.

Embodiment I-142. The method of Embodiment I-141, wherein administration is resumed after delivery.

Embodiment I-143. The method of any one of Embodiments I-65 to I-142, wherein the combination is administered pre-prandial.

Embodiment I-144. The method of any one of Embodiments I-65 to I-143, wherein the administering is at least 30 minutes before eating or while subject is fasting.

Embodiment I-145. The method of any one of Embodiments I-65 to I-144, wherein the combination is administered at least 1 hour before eating or at least 2 hours after eating.

Embodiment I-146. The method of any one of Embodiments I-65 to I-145, wherein the combination is administered as one or more immediate release dosage forms.

Embodiment I-147. The method of any one of Embodiments I-65 to I-146, wherein the pre-menopausal woman's bone mineral density during and/or after treatment is within ±2% of the pre-menopausal woman's bone mineral density prior to treatment.

Embodiment I-148. A method of treating a pre-menopausal woman with symptomatic uterine fibroids or endometriosis, the method comprising administering to said woman once-daily a combination of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.5 mg to about 5.0 mg of estradiol or a corresponding amount of estradiol equivalent; and about 0.5 mg to about 2.0 mg norethindrone acetate or other progestin, and wherein administration of the combination suppresses the endometrium.

Embodiment I-149. The method of Embodiment I-148, wherein the combination is effective in treating the symptoms of the uterine fibroids or endometriosis and reducing one or more side effects including one or more of hot flashes, night sweats, bone mineral density loss, or vasomotor symptoms other than hot flashes or night sweats.

Embodiment I-150. The method of Embodiment I-148 or I-149, wherein the combination is in a single dosage form.

Embodiment I-151. A method of treating a pre-menopausal woman who continues to have one or more of hot flashes, night sweats, vasomotor symptoms other than hot flashes or night sweats, or bone mineral density loss when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, the method comprising administering to said pre-menopausal woman a combination of about 65 mg to about 140 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a pharmaceutically acceptable salt thereof, about 1.5 mg to about 5 mg estradiol or a corresponding amount of estradiol equivalent; and about 0.5 mg to about 2.0 mg norethindrone acetate or other progestin, and where administration of the combination suppresses endometrial tissue.

Embodiment I-152. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or more of uterine fibroids, endometriosis or adenomyosis in a pre-menopausal woman.

Embodiment I-153. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of heavy menstrual bleeding in a pre-menopausal woman.

Embodiment I-154. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and a progestin for the manufacture of a medicament for the treatment of pain associated with uterine fibroids, endometriosis, or adenomyosis in a pre-menopausal woman.

Embodiment I-155. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for maintaining bone mineral density in a pre-menopausal woman.

Embodiment I-156. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or more of hot flashes, night sweats, or vasomotor symptoms other than hot flashes or night sweats in a pre-menopausal woman.

Embodiment I-157. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for maintaining one or both of lipid profile or blood glucose range in a pre-menopausal woman.

Embodiment I-158. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of one or both of vulvovaginal atrophy or vaginal dryness in a pre-menopausal woman.

Embodiment I-159. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of headache in a pre-menopausal woman.

Embodiment I-160. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for contraception in a pre-menopausal woman.

Embodiment I-161. Use according to any one of Embodiments I-155 to I-160, wherein the pre-menopausal woman has been treated with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea for one or more of uterine fibroids, endometriosis, adenomyosis or heavy menstrual bleeding.

Embodiment I-163. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for achieving amenorrhea in a pre-menopausal woman.

Embodiment I-164. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for preventing miscarriages in a pre-menopausal woman.

Embodiment I-165. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for improving fertility in a pre-menopausal woman.

Embodiment I-166. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament for the treatment of anemia in a pre-menopausal woman.

Embodiment I-167. Use according to any one of Embodiments I-152 to I-166, wherein the medicament contains about 10 mg to about 60 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof, about 0.5 mg to about 2 mg of the estradiol or a corresponding amount of the estradiol equivalent; and about 0.01 mg to about 5 mg of the progestin.

Embodiment I-168. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and norethindrone acetate or other progestin for the manufacture of a medicament for treating symptomatic uterine fibroids or endometriosis in a pre-menopausal woman.

Embodiment I-169. Use according to Embodiment I-168, wherein the medicament contains about 65 mg to about 140 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof, about 1.5 mg to about 5.0 mg of the estradiol or a corresponding amount of the estradiol equivalent; and about 0.5 mg to about 2.0 mg of the norethindrone acetate or other progestin.

Embodiment I-170. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and norethindrone acetate or other progestin for the manufacture of a medicament for treating a pre-menopausal woman who continues to have one or more of hot flashes, night sweats, bone mineral density loss, or vasomotor symptoms other than hot flashes or night sweats when orally administered once-daily a combination of about 10 mg to about 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, about 1.0 mg estradiol, and about 0.5 mg norethindrone acetate, wherein the medicament contains about 65 mg to about 140 mg of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a corresponding amount of the pharmaceutically acceptable salt thereof; about 1.5 mg to about 5.0 mg of the estradiol or a corresponding amount of the estradiol equivalent; and about 0.5 mg to about 2.0 mg of the norethindrone acetate or other progestin.

Embodiment I-171. The combined preparation for simultaneous or sequential use of any one of Embodiments I-1 to I-11, I-14 to I-18, or I-20 to I-64; or the method of any one of Embodiments I-65 to I-80, I-83 to I-89, or I-91 to I-151; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-170, wherein the pre-menopausal woman has a menstrual blood loss volume of less than 80 mL during treatment; or has at least a 50% reduction from baseline in menstrual blood loss volume during treatment, as compared to before beginning treatment; or has a PBAC score of less than 10 during treatment; or any combinations thereof.

Embodiment I-172. The combined preparation for simultaneous or sequential use of Embodiment I-171; or the method of Embodiment I-171; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-171, wherein the pre-menopausal woman has a menstrual blood loss volume of less than 80 mL during treatment; or has at least a 50% reduction from baseline in menstrual blood loss volume during treatment, as compared to before beginning treatment; or has a PBAC score of less than 10 during treatment; or any combinations thereof, within at least 30 weeks, within at least 24 weeks, or within at least 12 weeks of beginning treatment.

Embodiment I-173. The combined preparation for simultaneous or sequential use of any one of Embodiments I-1 to I-11, I-14 to 1–18, 1–20 to 1–64, 1–171, or I-172; or the method of any one of Embodiments I-65 to 1–80, 1–83 to 1–89, 1–91 to 1–151, 1–171, or I-172; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-170, I-171, or I-172, wherein the pre-menopausal woman has a maximum NRS score of 1 or less for uterine fibroid pain after beginning treatment; or has an increase in the number of days with an NRS score of 0 after beginning treatment, compared to before beginning treatment; or has a mean NRS score over 35 days during treatment reduced by at least 30% after beginning treatment.

Embodiment I-174. The combined preparation for simultaneous or sequential use of Embodiment I-173; or the method of Embodiment I-173; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-173, wherein the pre-menopausal woman has a maximum NRS score of 1 or less for uterine fibroid pain 6 weeks, 8 weeks, or 10 weeks, after beginning treatment; or has an increase in the number of days with an NRS score of 0 within 6 weeks, 8 weeks, or 10 weeks after beginning treatment, compared to the 6 weeks, 8 weeks, or 10 weeks immediately before beginning treatment; or has a mean NRS score over 35 days during treatment reduced by at least 30% within 6 weeks, 8 weeks, or 10 weeks after beginning treatment.

Embodiment I-175. The combined preparation for simultaneous or sequential use of Embodiment I-174; or the method of Embodiment I-174; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-174, wherein the pre-menopausal woman had a maximum NRS score for uterine fibroid associated pain of ≥4 during the 6 weeks, 8 weeks, or 10 weeks immediately before beginning treatment.

Embodiment I-176. The combined preparation for simultaneous or sequential use of any one of Embodiments I-1 to I-11, I-14 to I-18, I-20 to I-64, or I-171 to I-175; or the method of any one of Embodiments I-65 to I-80, I-83 to I-89, I-91 to I-151, or I-171 to I-175; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-169, or I-171 to I-175, wherein the pre-menopausal woman has a hemoglobin increase of ≥1 g/dL during treatment, compared to before beginning treatment.

Embodiment I-177. The combined preparation for simultaneous or sequential use of Embodiment I-176; or the method of Embodiment I-176; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-176, wherein the increase in hemoglobin is within 20 weeks, 24 weeks, or 28 weeks of beginning treatment.

Embodiment I-178. The combined preparation for simultaneous or sequential use of any one of Embodiments I-1 to I-11, I-14 to I-18, I-20 to I-64, or I-171 to I-177; or the method of any one of Embodiments I-65 to I-80, I-83 to I-89, I-91 to I-151, or I-171 to I-177; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-169, or I-171 to I-177, wherein the pre-menopausal woman has a decrease in impact of uterine fibroids as measured by the UFS-QOL; a decrease in in the interference of uterine fibroids with physical activities as measured by the UFS-QOL activities domain; a decrease in the interference of uterine fibroids with social activities as measured by the UFS-QOL; a decrease in embarrassment caused by uterine fibroids as measured by the UFS-QOL; a decrease in uterine fibroid-related symptoms as measured by UFS-QOL Symptom Severity; a decrease in uterine fibroid-related quality of life problems as measured by UFS-QOL Health-related Quality of Life; a change from baseline in uterine fibroid related function based on the Patient Global Assessment (PGA); a decrease in uterine fibroid symptoms based on the PGA; a change from baseline for physical activities as measured by the Menorrhagia Impact Questionnaire Score; a change from baseline for social and leisure activities as measured by the Menorrhagia Impact Questionnaire Score; a reduction in uterine volume; or a reduction in uterine fibroid volume.

Embodiment I-179. The combined preparation for simultaneous or sequential use of Embodiment I-178; or the method of Embodiment I-178; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-178, wherein the decrease or change is at least 10%, at least 20%, at least 30%, at least 40%, at least 50%, at least 60%, at least 70%, at least 80%, at least 90%, at least 100%, or more.

Embodiment I-180. The combined preparation for simultaneous or sequential use of Embodiment I-178 or I-179; or the method of Embodiment I-178 or I-179; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-178 or I-179, wherein the decrease or change occurs within 6 weeks, within 12 weeks, within 18 weeks, within 24 weeks, or within 30 weeks of beginning treatment.

Embodiment I-181. The combined preparation for simultaneous or sequential use of any one of Embodiments I-1 to I-12, or I-15 to I-64; or the method of any one of Embodiments I-65 to I-81, I-85 to I-87, I-89 to I-127, or I-129 to I-151; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-169, or I-171 to I-177, wherein the pre-menopausal woman has a decrease of dysmenorrhea as measured by a change from baseline in dysmenorrhea NRS score; a decrease of pain as measured by a change from baseline in NMPP NRS score; a decrease of dyspareunia as measured by a change from baseline in dyspareunia NRS score; a decrease of dyspareunia functional impairment as measured by a change from baseline on the sB&B scale; a decrease of pain as measured by a change from baseline in severity score on the PGA for pain; a decrease of function impairment as measured by a change from baseline on the PGA for function; has an improvement as measured by a change from baseline in each of the non-pain EHP-30 domains (Control and Powerlessness, Social Support, Emotional Well-Being, and Self-Image); a decrease of dysmenorrhea functional impairment as measured by a change from baseline on the sB&B scale; a decrease of NMPP functional impairment as measured by a change from baseline on the sB&B scale; or a decrease of pain as measured by a change from baseline in EHP-30 Pain Domain score, wherein the baseline is determined within the 6 weeks, 8 weeks, or 10 weeks immediately before beginning treatment.

Embodiment I-182. The combined preparation for simultaneous or sequential use of any one of Embodiments I-1 to I-12, or I-15 to I-64; or the method of any one of Embodiments I-65 to I-81, I-85 to I-87, I-89 to I-127, or I-129 to I-151; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-152 to I-169, or I-171 to I-177, wherein the pre-menopausal woman is better or much better on the PGIC for dysmenorrhea; is better or much better on the PGIC for NMPP; is better or much better on the PGIC for dyspareunia, as compared to the 6 weeks, 8 weeks, or 10 weeks, immediately before beginning treatment.

Embodiment I-183. The combined preparation for simultaneous or sequential use of Embodiment I-181 or I-182; or the method of Embodiment I-181 or I-182; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-181 or I-182, wherein the decrease or change is at least 10%, at least 20%, at least 30%, at least 40%, at least 50%, at least 60%, at least 70%, at least 80%, at least 90%, at least 100%, or more.

Embodiment I-184. The combined preparation for simultaneous or sequential use of any one of Embodiments I-181 to I-183; or the method of any one of Embodiments I-181 to I-183; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to any one of Embodiments I-181 to I-183, wherein the decrease or change occurs within 6 weeks, within 12 weeks, within 18 weeks, within 24 weeks, or within 30 weeks of beginning treatment.

Embodiment I-185. The combined preparation for simultaneous or sequential use of any one of Embodiments I-1 to I-11, I-18, or I-19; or the method of any one of Embodiments I-80, 1–89 to I-107, or I-130; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-154, wherein the pain is chronic pain.

Embodiment I-186. The combined preparation for simultaneous or sequential use of any one of Embodiments I-1 to I-11, I-18, or I-19; or the method of any one of Embodiments I-80, 1–89 to I-107, or I-130; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-154, wherein the pain is dyspareunia.

Embodiment I-187. The combined preparation for simultaneous or sequential use of any one of Embodiments I-1 to I-11, I-18, or I-19; or the method of any one of Embodiments I-80, 1–89 to I-107, or I-130; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-154, wherein the pain is pain with defecation.

Embodiment I-188. The combined preparation for simultaneous or sequential use of any one of Embodiments I-1 to I-11, I-18, or I-19; or the method of any one of Embodiments I-80, 1–89 to I-107, or I-130; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-154, wherein the pain is pain with urination.

Embodiment I-189. The combined preparation for simultaneous or sequential use of any one of Embodiments I-32 to I-42; or the method of any one of Embodiments I-114 to I-130; or the use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof, estradiol or an estradiol equivalent, and progestin for the manufacture of a medicament according to Embodiment I-160, wherein the pre-menopausal woman is treated for one or more of uterine fibroids, endometriosis, adenomyosis, or heavy menstrual bleeding with N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment II-1. A method for treating uterine fibroids in a subject, the method comprising administering to the subject at least one daily for 2 consecutive weeks (14 days) or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-2. A method for reducing menstrual blood loss in a subject, the method comprising administering to the subject at least once-daily for 2 consecutive weeks (14 days) or greater for a treatment period, from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-3. A method for suppressing sex hormones in a subject, the method comprising administering to the subject at least once-daily for 2 consecutive weeks (14 days) or greater for a treatment period, from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-4. A method for reducing bone mineral density loss in a subject caused by administering a GnRH antagonist to the subject, the method comprising administering to the subject at least once-daily for 2 consecutive weeks (14 days) or greater for a treatment period, from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-5. A method for reducing vasomotor symptoms or hot flashes in a subject, the method comprising administering to the subject at least once-daily for 2 consecutive weeks (14 days) or greater for a treatment period, from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-6. A method for reducing vasomotor symptoms or hot flashes in a subject, the method comprising administering to the subject, at least once-daily for 2 consecutive weeks (14 days) or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of an additional compound selected from the group consisting of gabapentin, pregabalin, venlafaxine, fluoxetine, paroxetine, and aspirin. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-7. A method for reducing symptoms of decreased libido in a subject, the method comprising administering to the subject, at least once-daily for 2 consecutive weeks (14 days) or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of at least one $5\text{-HT}_{1a}$ receptor agonist. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-8. The method of Embodiments II-1 through II-7, wherein a PK profile is achieved in which mean plasma $AUC_{(0-tau)}$ increases at least 1.5 fold (150%) when measured from the first to last day of the treatment period.

Embodiment II-9. The method of Embodiment II-8, wherein the at least 1.5 fold is 2 fold or greater.

Embodiment II-10. The method of Embodiments II-1 through II-7, wherein the treatment period is 4 consecutive weeks (28 days) or greater.

Embodiment II-11. The method of Embodiments II-1 through II-7, wherein the treatment period is 8 consecutive weeks (56 days) or greater.

Embodiment II-12. The method of Embodiments II-1 through II-7, wherein the treatment period is 12 consecutive weeks (84 days) or greater.

Embodiment II-13. The method of Embodiments II-1 through II-7, wherein the treatment period is 24 weeks (168 days) or greater.

Embodiment II-14. The method of Embodiments II-1 through II-7, wherein the treatment period is 52 weeks (364 days) or greater.

Embodiment II-15. The method of Embodiments II-1 through II-7, wherein the administering is daily and continuously for at least 48 weeks to achieve a chronic status.

Embodiment II-16. The method of Embodiments II-1 through II-13, wherein the administering is preprandial.

Embodiment II-17. The method of Embodiments II-1 through II-13, wherein the administering is at least 1 hour before eating or at least 2 hours after eating.

Embodiment II-18. The method of Embodiments II-1 through II-13, wherein the administering is at least 30 minutes before eating or while the subject is fasting.

Embodiment II-19. The method of Embodiments II-1 through II-13, wherein the administering is without any fasting requirement.

Embodiment II-20. The method of Embodiments II-1 through II-18, wherein when administered in a fasted state, a mean $C_{max}$ is in the range of from 5 ng/mL to 35 ng/mL.

Embodiment II-21. The method of Embodiments II-1 through II-18, wherein when administered in a fasted state, mean plasma $AUC_{(0-24)}$ is from 50 ng h/mL to 200 ng h/mL.

Embodiment II-22. The method of Embodiments II-1 through II-7, wherein the administering is at least twice per day.

Embodiment II-23. The method of Embodiments II-1 through II-7, wherein mean plasma half-life ($T_{1/2}$) is about 37 to about 42 hours measured at the end of the treatment period.

Embodiment II-24. The method of Embodiments II-1 through II-7, wherein the hormone replacement medicament is in an amount up to about 5 mg.

Embodiment II-25. The method of Embodiments II-1 through II-7, wherein the hormone replacement medicament is in an amount from 0.05 mg to 2.5 mg per day.

Embodiment II-26. The method of Embodiments II-1 through II-7, wherein the hormone replacement medicament is selected from the group consisting of an estrogen, a progestogen, and a combination of same.

Embodiment II-27. The method of Embodiments II-1 through II-7, wherein the hormone replacement medicament is a combination of 1 mg estradiol and 0.5 mg of NETA.

Embodiment II-28. The method of Embodiments II-1 through II-7, wherein the hormone replacement medicament is a combination of 1.5 mg estradiol and 0.5 mg of NETA.

Embodiment II-29. The method of Embodiments II-1 through II-7, wherein the hormone replacement medicament is a combination of 2 mg estradiol and 0.5 mg of NETA.

Embodiment II-30. The method of Embodiments II-1 through II-7, wherein the hormone replacement medicament is 5 mg of NETA.

Embodiment II-31. The method of Embodiments II-1 through II-7, wherein the hormone replacement medicament is a progestin.

Embodiment II-32. The method of Embodiments II-1 through II-7, wherein the administering is orally.

Embodiment II-33. The method of Embodiments II-1 through II-7, wherein the administering is by a transdermal patch, a spray, or an implant.

Embodiment II-34. The method of Embodiment II-7, wherein the at least one $5\text{-}HT_{1a}$ receptor agonist comprises flibanserin.

Embodiment II-35. The method of Embodiment II-5, wherein the amount of the hormone replacement medicament administered to the subject decreases over the treatment period.

Embodiment II-36. The method of Embodiments II-1 through II-7, wherein the subject is a premenopausal woman.

Embodiment II-37. The method of Embodiment II-32, wherein the administering is by a tablet, a capsule, a caplet, a pill, a granule, a powder, a lozenge, gum, or an oral dissolving film.

Embodiment II-38. A method for treating uterine fibroids in a subject, the method comprising administering to the subject at least once-daily for 2 consecutive weeks (14 days) or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0\text{-}tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-39. A method for reducing menstrual blood loss in a subject, the method comprising administering to the subject at least once-daily for 2 consecutive weeks (14 days) or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0\text{-}tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-40. A method for suppressing sex hormones in a subject, the method comprising the method comprising administering to the subject at least once-daily for 2 consecutive weeks (14 days) or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0\text{-}tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-41. A method for reducing bone mineral density loss in a subject, caused by administering a GnRH antagonist to the subject, the method comprising administering to the subject at least once-daily for 2 consecutive weeks (14 days) or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and a hormone replacement medicament, wherein the oral dosage has a PK profile in which mean plasma $AUC_{(0\text{-}tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-42. A method for reducing vasomotor symptoms or hot flashes in a subject, the method comprising administering to the subject, at least once-daily for 2 consecutive weeks (14 days) or greater for a treatment period, an oral dosage having from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-43. The method of Embodiment II-42, wherein the oral dosage further comprises from 0.05 mg to 10 mg of an additional compound selected from the group consisting of gabapentin, pregabalin, venlafaxine, fluoxetine, paroxetine, and aspirin.

Embodiment II-44. A method for reducing symptoms of decreased libido in a subject, the method comprising administering to the subject, at least once-daily for 2 consecutive weeks (14 days) or greater for a treatment period, an oral dosage having from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of at least one $5\text{-HT}_{1a}$ receptor agonist, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment II-45. The method of Embodiments II-38 through II-44, wherein the at least 1.5 fold is 2 fold or greater.

Embodiment II-46. The method of Embodiments II-38 through II-44, wherein the treatment period is 4 consecutive weeks (28 days) or greater.

Embodiment II-47. The method of Embodiments II-38 through II-44, wherein the treatment period is 8 consecutive weeks (56 days) or greater.

Embodiment II-48. The method of Embodiments II-38 through II-44, wherein the treatment period is 12 consecutive weeks (84 days) or greater.

Embodiment II-49. The method of Embodiment II-38 through II-44, wherein the treatment period is 24 weeks (168 days) or greater.

Embodiment II-50. The method of Embodiments II-38 through II-44, wherein the treatment period is 52 weeks (364 days) or greater.

Embodiment II-51. The method of Embodiments II-38 through II-44, wherein the administering is preprandial.

Embodiment II-52. The method of Embodiments II-38 through II-44, wherein the administering is at least 1 hour before eating or at least 2 hours after eating.

Embodiment II-53. The method of Embodiments II-38 through II-44, wherein the administering is at least 30 minutes before eating or while the subject is fasting.

Embodiment II-54. The method of Embodiments II-38 through II-44, wherein the administering is without any fasting requirement.

Embodiment II-55. The method of Embodiments II-38 through II-44, wherein the mean plasma $AUC_{(0-tau)}$ is higher with preprandial administration than with postprandial administration after at least 30 minutes.

Embodiment II-56. The method of Embodiments II-38 through II-44, wherein mean $C_{max}$ is higher with preprandial than with postprandial administration.

Embodiment II-57. The method of Embodiments II-38 through II-44, wherein the oral dosage is a fixed combination oral dosage form that comprises from 0.01 mg to 5 mg of a hormone replacement medicament.

Embodiment II-58. The method of Embodiments II-38 through II-44, wherein the administering is at least twice per day.

Embodiment II-59. The method of Embodiments II-38 through II-44, wherein the oral dosage is a solid oral dosage.

Embodiment II-60. The method of Embodiments II-38 through II-44, wherein the oral dosage has an immediate release profile.

Embodiment II-61. The method of Embodiments II-38 through II-44, wherein the mean plasma $T_{1/2}$ is about 37 to about 42 hours measured at the end of the treatment period.

Embodiment II-62. The method of Embodiments II-38 through II-44, further comprising co-administering to the subject, a hormone replacement medicament.

Embodiment II-63. The method of Embodiments II-38 through II-44, wherein following administering of 40 mg per day for 2 consecutive weeks or greater for the treatment period, the subject has a menstrual blood loss Pictorial Blood Loss Assessment Chart (PBAC) score of less than 10 when measured at the end of the treatment period.

Embodiment II-64. The method of Embodiments II-38 through II-44, wherein following administering of 40 mg per day for 12 consecutive weeks, change from baseline in mean of total PBAC score from weeks 6 to 12 is at least a 3 fold reduction.

Embodiment II-65. The method of Embodiments II-38 through II-44, wherein following administering of 40 mg per day for 12 consecutive weeks, change from baseline in mean of total PBAC score from weeks 6 to 12 is at least a 3.5 fold reduction.

Embodiment II-66. The method of Embodiments II-38 through II-44, wherein following administering of 40 mg per day for 12 consecutive weeks, change from baseline in mean of total PBAC score from weeks 6 to 12 is at least a 5 fold reduction.

Embodiment II-67. The method of Embodiments II-38 through II-44, wherein following administering of 40 mg per day for 12 consecutive weeks, change from baseline in mean of total PBAC score from weeks 6 to 12 is from a 3.0 to 5.0 fold reduction.

Embodiment II-68. The method of Embodiments II-38 through II-44, wherein following administering of 40 mg per day for 12 consecutive weeks, the subject has a total PBAC score of zero at the end of the treatment period.

Embodiment II-69. The method of Embodiments II-38 through II-44, wherein following administering of 40 mg per day for 12 consecutive weeks, the subject has a total PBAC score of zero measured from one of more of: weeks 2 to 6, weeks 6 to 12, and weeks 2 to 12 of the treatment period.

Embodiment II-70. The method of Embodiments II-38 through II-44, wherein following administering of 40 mg per day for 12 consecutive weeks, the subject has a decreased myoma volume after treatment for 14, 28, 56, 84, 168 or 364 consecutive days.

Embodiment II-71. The method of Embodiments II-38 through II-44, wherein following administering 40 mg per day for 12 consecutive weeks, change from baseline in mean myoma volume is at least a 3.5 fold reduction when measured from first to last day of the treatment period.

Embodiment II-72. The method of Embodiments II-38 through II-44, wherein following administering of 40 mg per day for 12 consecutive weeks, change from baseline in mean myoma volume is at least a 4 fold reduction when measured from first to last day of the treatment period.

Embodiment II-73. The method of Embodiments II-38 through II-44, wherein following administering of 40 mg per day for 12 consecutive weeks, change from baseline in mean myoma volume is from a 3.5 to 6.5 fold reduction when measured from first to last day of the treatment period.

Embodiment II-74. The method of Embodiments II-38 through II-44, wherein following administering 40 mg per day for 12 consecutive weeks, change from baseline in mean uterine volume is at least a 4 fold reduction when measured from first to last day of the treatment period.

Embodiment II-75. The method of Embodiments II-38 through II-44, wherein following administering 40 mg per day for 12 consecutive weeks, change from baseline in mean uterine volume is at least a 4.5 fold reduction when measured from first to last day of the treatment period.

Embodiment II-76. The method of Embodiments II-38 through II-44, wherein following administering 40 mg per day for 12 consecutive weeks, change from baseline in mean uterine volume is from a 4.0 to 7.0 fold reduction when measured from first to last day of the treatment period.

Embodiment II-77. The method of Embodiments II-38 through II-44, wherein following administering 40 mg per day for 12 consecutive weeks, change in mean of Numerical Rating Scale (NRS) score from weeks 6 to 12 is a 0.1 fold reduction in pain symptoms associated with uterine fibroids.

Embodiment II-78. The method of Embodiments II-38 through II-44, wherein following administering 40 mg per day for 12 consecutive weeks, change in mean of NRS score from weeks 6 to 12 is a 0.1 to 2.0 fold reduction in pain symptoms associated with uterine fibroids.

Embodiment II-79. The method of Embodiments II-38 through II-44, wherein following administering 40 mg per day for 12 consecutive weeks, change in mean of Uterine Fibroid Symptom Quality of Life (UFS-QOL) score is at least a 1 fold reduction in symptom severity when measured from first to last day of the treatment period.

Embodiment II-80. The method of Embodiments II-38 through II-44, wherein following administering 40 mg per day for 12 consecutive weeks, change in mean of UFS-QOL score is at least a 2 fold reduction in symptom severity when measured from first to last day of the treatment period.

Embodiment II-81. The method of Embodiments II-38 through II-44, wherein following administering 40 mg per day for 12 consecutive weeks, change in mean of UFS-QOL score is at least a 2.5 fold reduction in symptom severity when measured from first to last day of the treatment period.

Embodiment II-82. The method of Embodiments II-38 through II-44, wherein following administering 40 mg per day for 12 consecutive weeks, change in mean of UFS-QOL score is at from a 1.0 fold to 6.0 fold reduction in symptom severity when measured from first to last day of the treatment period.

Embodiment II-83. The method of Embodiments II-38 through II-44, wherein following administering 40 mg per day for 12 consecutive weeks, change from baseline in mean blood concentration of hemoglobin is at least a 3 fold increase when measured from first to last day of the treatment period.

Embodiment II-84. The method of Embodiments II-38 through II-44, wherein following administering 40 mg per day for 12 consecutive weeks, change from baseline in mean blood concentration of hemoglobin is at least a 3.5 fold increase when measured from first to last day of the treatment period.

Embodiment II-85. The method of Embodiments II-38 through II-44, wherein following administering 40 mg per day for 12 consecutive weeks, change from baseline in mean blood concentration of hemoglobin is at least a 3.8 fold increase when measured from first to last day of the treatment period.

Embodiment II-86. The method of Embodiments II-38 through II-44, wherein following administering 40 mg per day for 12 consecutive weeks, change from baseline in mean blood concentration of hemoglobin is from a 3.0 to 6.0 fold increase when measured from first to last day of the treatment period.

Embodiment II-87. The method of Embodiments II-38 through II-44, wherein following administering 40 mg per day for 12 consecutive weeks, change from baseline in mean hematocrit concentration is at least a 3.0 fold increase when measured from first to last day of the treatment period.

Embodiment II-88. The method of Embodiments II-38 through II-44, wherein following administering 40 mg per day for 12 consecutive weeks, change from baseline in mean hematocrit concentration is at least a 3.5 fold increase when measured from first to last day of the treatment period.

Embodiment II-89. The method of Embodiments II-38 through II-44, wherein following administering 40 mg per day for 12 consecutive weeks, change from baseline in mean hematocrit concentration is at least a 4.2 fold increase when measured from first to last day of the treatment period.

Embodiment II-90. The method of Embodiments II-38 through II-44, wherein following administering 40 mg per day for 12 consecutive weeks, change from baseline in mean hematocrit concentration is from a 3.0 to 7.0 fold increase when measured from first to last day of the treatment period.

Embodiment II-91. The method of Embodiments II-38 through II-44, wherein following administering 40 mg per day for 12 consecutive weeks, change from baseline in mean ferrum concentration is at least a 6.0 fold increase when measured from first to last day of the treatment period.

Embodiment II-92. The method of Embodiments II-38 through II-44, wherein following administering 40 mg per day for 12 consecutive weeks, change from baseline in mean ferrum concentration is at least a 8.0 fold increase when measured from first to last day of the treatment period.

Embodiment II-93. The method of Embodiments II-38 through II-44, wherein following administering 40 mg per day for 12 consecutive weeks, change from baseline in mean ferrum concentration is at least a 9.0 fold increase when measured from first to last day of the treatment period.

Embodiment II-94. The method of Embodiments II-38 through II-44, wherein following administering 40 mg per day for 12 consecutive weeks, change from baseline in mean ferrum concentration is from a 6.0 to 16.0 fold increase when measured from first to last day of the treatment period.

Embodiment II-95. The method of Embodiments II-38 through II-44, wherein following administering 40 mg per day for 12 consecutive weeks, change from baseline in mean ferritin concentration is at least a 2.0 fold increase when measured from first to last day of the treatment period.

Embodiment II-96. The method of Embodiments II-38 through II-44, wherein following administering 40 mg per day for 12 consecutive weeks, change from baseline in mean ferritin concentration is at least a 2.5 fold increase when measured from first to last day of the treatment period.

Embodiment II-97. The method of Embodiments II-38 through II-44, wherein following administering 40 mg per day for 12 consecutive weeks, change from baseline in mean ferritin concentration is at least a 3.0 fold increase when measured from first to last day of the treatment period.

Embodiment II-98. The method of Embodiments II-38 through II-44, wherein following administering 40 mg per day for 12 consecutive weeks, change from baseline in mean ferritin concentration is from a 2.0 to 6.0 fold increase when measured from first to last day of the treatment period.

Embodiment II-99. The method of Embodiments II-38 through II-44, wherein following administering 40 mg per day for 12 consecutive weeks, change from baseline in median serum luteinizing hormone (LH) concentration is at least a 3.0 fold reduction when measured from first to last day of the treatment period.

Embodiment II-100. The method of Embodiments II-38 through II-44, wherein following administering 40 mg per day for 12 consecutive weeks, change from baseline in median LH concentration is at least a 4.0 fold reduction when measured from first to last day of the treatment period.

Embodiment II-101. The method of Embodiments II-38 through II-44, wherein following administering 40 mg per day for 12 consecutive weeks, change from baseline in median LH concentration is at least a 4.7 fold reduction when measured from first to last day of the treatment period.

Embodiment II-102. The method of Embodiments II-38 through II-44, wherein following administering 40 mg per day for 12 consecutive weeks, change from baseline in median LH concentration is from a 3.0 to 9.0 fold reduction when measured from first to last day of the treatment period.

Embodiment II-103. The method of Embodiments II-38 through II-44, wherein following administering 40 mg per day for 12 consecutive weeks, change from baseline in median follicle stimulating hormone (FSH) concentration is at least a 1.0 fold reduction when measured from first to last day of the treatment period.

Embodiment II-104. The method of Embodiments II-38 through II-44, wherein following administering 40 mg per day for 12 consecutive weeks, change from baseline in median FSH concentration is at least a 1.5 fold reduction when measured from first to last day of the treatment period.

Embodiment II-105. The method of Embodiments II-38 through II-44, wherein following administering 40 mg per day for 12 consecutive weeks, change from baseline in median FSH concentration is at least a 2.1 fold reduction when measured from first to last day of the treatment period.

Embodiment II-106. The method of Embodiments II-38 through II-44, wherein following administering 40 mg per day for 12 consecutive weeks, change from baseline in median FSH concentration is from a 1.0 to 5.0 fold reduction when measured from first to last day of the treatment period.

Embodiment II-107. The method of Embodiments II-38 through II-44, wherein following administering 40 mg per day for 12 consecutive weeks, change from baseline in median estradiol ($E_2$) concentration is at least a 0.2 fold reduction when measured from first to last day of the treatment period.

Embodiment II-108. The method of Embodiments II-38 through II-44, wherein following administering 40 mg per day for 12 consecutive weeks, change from baseline in median $E_2$ concentration is at least a 0.8 fold reduction when measured from first to last day of the treatment period.

Embodiment II-109. The method of Embodiments II-38 through II-44, wherein following administering 40 mg per day for 12 consecutive weeks, change from baseline in median $E_2$ concentration is at least a 1.0 fold reduction when measured from first to last day of the treatment period.

Embodiment II-110. The method of Embodiments II-38 through II-44, wherein following administering 40 mg per day for 12 consecutive weeks, change from baseline in median $E_2$ concentration is from a 0.2 to 3.2 fold reduction when measured from first to last day of the treatment period.

Embodiment II-111. The method of Embodiments II-38 through II-44, wherein following administering 40 mg per day for 12 consecutive weeks, change from baseline in median progesterone (P) concentration is at least a 0.5 fold reduction when measured from first to last day of the treatment period.

Embodiment II-112. The method of Embodiments II-38 through II-44, wherein following administering 40 mg per day for 12 consecutive weeks, change from baseline in median P concentration is at least a 0.8 fold reduction when measured from first to last day of the treatment period.

Embodiment II-113. The method of Embodiments II-38 through II-44, wherein following administering 40 mg per day for 12 consecutive weeks, change from baseline in median P concentration is at least a 1.2 fold reduction when measured from first to last day of the treatment period.

Embodiment II-114. The method of Embodiments II-38 through II-44, wherein following administering 40 mg per day for 12 consecutive weeks, change from baseline in median P concentration is from a 0.5 to 4.0 fold reduction when measured from first to last day of the treatment period.

Embodiment II-115. The method of Embodiments II-38 through II-44, wherein following administering of 40 mg per day for at least 2 consecutive weeks, and co-administering of from 0.01 mg to 5 mg per day of at least one of an estrogen and a progestogen, bone mineral density loss is less than 5% from first to last day of the treatment period.

Embodiment II-116. The method of Embodiments II-38 through II-44, wherein following administering of 40 mg per day for at least 2 consecutive weeks, and co-administering of from 0.01 mg to 5 mg per day of at least one of an estrogen and a progestogen, bone mineral density loss is less than 2% from first to last day of the treatment period.

Embodiment II-117. The method of Embodiments II-38 through II-44, wherein following administering 40 mg per day for at least 2 consecutive weeks, and co-administering of from 0.01 mg to 5 mg per day of at least one of an estrogen and a progestogen, bone mineral density loss is reduced at least 50% in comparison with no co-administering of from 0.01 mg to 5 mg per day of at least one of an estrogen and a progestogen.

Embodiment II-118. The method of Embodiments II-38 through II-44, wherein the oral dosage is selected from the group consisting of a tablet, a capsule, a caplet, a pill, a granule, a powder, a lozenge, gum, and an oral dissolving film.

Embodiment II-119. The method of Embodiment II-44, wherein the at least one 5-$HT_{1a}$ receptor agonist comprises flibanserin.

Embodiment II-120. The method of Embodiments II-1 through II-7 and II-41 through II-44, wherein the administering of the hormone replacement medicament is by a separate dosage form.

Embodiment II-121. The method of Embodiments II-41 through II-44, wherein the oral dosage is a fixed combination, oral dosage form.

Embodiment III-1. A method for treating endometriosis in a subject, the method comprising administering to the subject, at least once-daily for 7 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-2. A method for reducing pain associated with endometriosis in a subject, the method comprising administering to the subject, at least once-daily for 7 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-3. A method for reducing menstrual bleeding associated with endometriosis in a subject, the method comprising administering to the subject, at least once-daily for 7 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-4. A method for suppressing sex hormone in a subject, the method comprising administering to the subject, at least once-daily for 7 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-5. A method for reducing bone mineral density loss in a subject, caused by administering a GnRH antagonist to the subject, the method comprising administering to the subject, at least once-daily for 7 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-6. A method for reducing vasomotor symptoms or hot flashes in a subject, the method comprising administering to the subject, at least once-daily for 14 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-7. A method for reducing vasomotor symptoms or hot flashes in a subject, the method comprising administering to the subject, at least once-daily for 14 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of at least one additional compound selected from the group consisting of gabapentin, pregabalin, venlafaxine, fluoxetine, paroxetine, and aspirin. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-8. A method for reducing symptoms of decreased libido in a subject, the method comprising administering to the subject, at least once-daily for 14 consecutive days or greater for a treatment period, from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of at least one 5-$HT_{1a}$ receptor agonist. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-9. The method of Embodiments III-1 through III-8, wherein when measured from the first to last day of the treatment period, a PK profile is achieved in which the mean plasma $AUC_{(0-tau)}$ increases at least 1.5 fold.

Embodiment III-10. The method of Embodiment III-9, wherein the at least 1.5 fold is 2 fold or greater.

Embodiment III-11. The method of Embodiments III-1 through III-8, wherein the treatment period is 14 days or greater.

Embodiment III-12. The method of Embodiments III-1 through III-8, wherein the treatment period is 28 days or greater.

Embodiment III-13. The method of Embodiments III-1 through III-8, wherein the treatment period is 56 days or greater.

Embodiment III-14. The method of Embodiments III-1 through III-8, wherein the treatment period is 12 weeks (84 days) or greater.

Embodiment III-15. The method of Embodiments III-1 through III-8, wherein the treatment period is 24 weeks (168 days) or greater.

Embodiment III-16. The method of Embodiments III-1 through III-8, wherein the treatment period is 52 weeks (364 days) or greater.

Embodiment III-17. The method of Embodiments III-1 through III-8, wherein the administering is daily and continuously for at least 48 weeks to achieve a chronic status.

Embodiment III-18. The method of Embodiments III-1 through III-8, wherein the administering is preprandial.

Embodiment III-19. The method of Embodiments III-1 through III-8, wherein the administering is at least 1 hour before eating or at least 2 hours after eating.

Embodiment III-20. The method of Embodiments III-1 through III-8, wherein the administering is at least 30 minutes before eating or while subject is fasting.

Embodiment III-21. The method of Embodiments III-1 through III-8, wherein the administering is without any fasting requirement.

Embodiment III-22. The method of Embodiments III-1 through III-8, wherein when administered in a fasted state, a mean $C_{max}$ is in the range of from 5 ng/mL to 35 ng/mL.

Embodiment III-23. The method of Embodiments III-1 through III-8, wherein when administered in a fasted state, the mean plasma $AUC_{(0-24)}$ is from 50 ng·h/mL to 200 ng·h/mL.

Embodiment III-24. The method of Embodiments III-1 through III-8, wherein the administrating is at least twice per day.

Embodiment III-25. The method of Embodiments III-1 through III-8, wherein the mean plasma half-life ($T_{1/2}$) is about 37 to about 42 hours measured at the end of the treatment period.

Embodiment III-26. The method of Embodiments III-1 through III-8, wherein the hormone replacement medicament is selected from the group consisting of an estrogen, a progestogen, and a combination of same.

Embodiment III-27. The method of Embodiments III-1 through III-8, wherein the hormone replacement medicament is present in an amount up to about 5 mg.

Embodiment III-28. The method of Embodiments III-1 through III-8, wherein the hormone replacement medicament is from 0.05 mg to 2.5 mg per day.

Embodiment III-29. The method of Embodiments III-1 through III-8, wherein the hormone replacement medicament is a combination of 1 mg estradiol and 0.5 mg of NETA.

Embodiment III-30. The method of Embodiments III-1 through III-8, wherein the hormone replacement medicament is a combination of 1.5 mg estradiol and 0.5 mg of NETA.

Embodiment III-31. The method of Embodiments III-1 through III-8, wherein the hormone replacement medicament is a combination of 2 mg estradiol and 0.5 mg of NETA.

Embodiment III-32. The method of Embodiments III-1 through III-8, wherein the hormone replacement medicament is NETA alone.

Embodiment III-33. The method of Embodiment III-32, wherein the hormone replacement medicament is 5 mg of NETA.

Embodiment III-34. The method of Embodiments III-1 through III-8, wherein the hormone replacement medicament is a progestin.

Embodiment III-35. The method of Embodiments III-1 through III-8, wherein the administering is orally.

Embodiment III-36. The method of Embodiments III-1 through III-8, wherein the administering is by a transdermal patch, a spray, or an implant.

Embodiment III-37. The method of Embodiment III-2, wherein the pain associated with endometriosis is at least one of nonmenstrual pelvic pain, dysmenorrhea and dyspareunia.

Embodiment III-38. The method of Embodiment III-8 wherein the at least one $5\text{-HT}_{1a}$ receptor agonist comprises flibanserin.

Embodiment III-39. The method of Embodiment III-6 wherein the amount of hormone replacement medicament administered to the subject decreases over the treatment period.

Embodiment III-40. The method of Embodiments III-1 through III-8, wherein the subject is a premenopausal woman.

Embodiment III-41. The method of Embodiment III-35, wherein the administering is in a dosage form selected from the group consisting of a tablet, a capsule, a caplet, a pill, a granule, a powder, a lozenge, a gum, and an oral film.

Embodiment III-42. A method for treating endometriosis in a subject, the method comprising administering to the subject at least once-daily for 7 consecutive days or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-43. A method for reducing pain associated with endometriosis in a subject, the method comprising administering to the subject at least once-daily for 7 consecutive days or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-44. A method for reducing menstrual bleeding associated with endometriosis in a subject, the method comprising administering to the subject at least once-daily for 7 consecutive days or greater for a treatment period, an oral dosage having from 10 mg to 60 mg per day of N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-45. A method for suppressing sex hormone in a subject, the method comprising administering to the subject at least once-daily for 7 consecutive days or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-46. A method for reducing bone mineral density loss in a subject, caused by administering a GnRH antagonist to the subject, the method comprising administering to the subject at least once-daily for 7 consecutive days or greater for a treatment period, an oral dosage having from 10 mg to 60 mg per day of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-47. A method for reducing vasomotor symptoms or hot flashes in a subject, the method comprising administering to the subject, at least once-daily for 7 consecutive days or greater for a treatment period, an oral dosage having from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, and from 0.01 mg to 5 mg of a hormone replacement medicament, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-48. The method of Embodiment III-47, wherein the oral dosage further comprises from 0.05 mg to 10 mg of an additional compound selected from the group consisting of gabapentin, pregabalin, venlafaxine, fluoxetine, paroxetine, and aspirin.

Embodiment III-49. A method for reducing symptoms of decreased libido in a subject, the method comprising administering to the subject, at least once-daily for 7 consecutive days or greater for a treatment period, an oral dosage having from 10 mg to 60 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea; from 0.01 mg to 5 mg of a hormone replacement medicament; and from 0.05 mg to 10 mg of at least one $5\text{-HT}_{1a}$ receptor agonist, wherein the oral dosage has a PK profile in which mean plasma $AUC_{(0-tau)}$ increases at least 1.5 fold when measured from the first to last day of the treatment period. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is administered.

Embodiment III-50. The method of Embodiments III-42 through III-49, wherein the at least 1.5 fold is 2 fold or greater.

Embodiment III-51. The method of Embodiments III-42 through III-49, wherein the treatment period is 14 days or greater.

Embodiment III-52. The method of Embodiments III-42 through III-49, wherein the treatment period is 28 days or greater.

Embodiment III-53. The method of Embodiments III-42 through III-49, wherein the treatment period is 56 days or greater.

Embodiment III-54. The method of Embodiments III-42 through III-49, wherein the treatment period is 12 weeks (84 days) or greater.

Embodiment III-55. The method of Embodiments III-42 through III-49, wherein the treatment period is 24 weeks (168 days) or greater.

Embodiment III-56. The method of Embodiments III-42 through III-49, wherein the treatment period is 52 weeks (364 days) or greater.

Embodiment III-57. The method of Embodiments III-42 through III-49, wherein the administering is preprandial.

Embodiment III-58. The method of Embodiments III-42 through III-49, wherein the administering is at least 1 hour before eating or at least 2 hours after eating.

Embodiment III-59. The method of Embodiments III-42 through III-49, wherein the administering is at least 30 minutes before eating or while subject is fasting.

Embodiment III-60. The method of Embodiments III-42 through III-49, wherein the administering is without any fasting requirement.

Embodiment III-61. The method of Embodiments III-42 through III-49, wherein the mean plasma $AUC_{(0-tau)}$ is higher with preprandial administration than with postprandial administration after at least 30 minutes.

Embodiment III-62. The method of Embodiments III-42 through III-49, wherein mean $C_{max}$ is higher with preprandial administration than with postprandial administration.

Embodiment III-63. The method of Embodiments III-42 through III-45, wherein the oral dosage is a fixed combination, oral dosage form that comprises from 0.01 mg to 5 mg of a hormone replacement medicament.

Embodiment III-64. The method of Embodiments III-46 through III-49, wherein the oral dosage is a fixed combination, oral dosage form.

Embodiment III-65. The method of Embodiments III-42 through III-49, wherein the administrating is at least twice per day.

Embodiment III-66. The method of Embodiments III-42 through III-49, wherein the oral dosage is a solid oral dosage.

Embodiment III-67. The method of Embodiments III-42 through III-49, wherein the oral dosage has an immediate release profile.

Embodiment III-68. The method of Embodiments III-42 through III-49, wherein the mean plasma $T_{1/2}$ is about 37 to about 42 hours measured at the end of the treatment period Embodiment III-69. The method of Embodiments III-42 through III-45, further comprising co-administering to the subject, a hormone replacement medicament.

Embodiment III-70. The method of Embodiments III-46 through III-49, wherein the hormone replacement medicament is co-administered to the subject.

Embodiment III-71. The method of Embodiment III-48, wherein the additional compound is co-administered to the subject.

Embodiment III-72. The method of Embodiment III-49, wherein the at least one 5-$HT_{1a}$ receptor agonist is co-administered to the subject.

Embodiment III-73. The method of Embodiment III-43, wherein the pain associated with endometriosis is at least one of nonmenstrual pelvic pain, dysmenorrhea and dyspareunia.

Embodiment III-74. The method of Embodiments III-42 through III-49, wherein there is a change from baseline in mean of visual analogue scale (VAS) score of at least a 1.4 fold reduction in pelvic pain when measured from the first to last day of the treatment period.

Embodiment III-75. The method of Embodiments III-42 through III-49, wherein there is a change from baseline in mean of VAS score of at least 2 fold increase in proportion of days without pelvic pain when measured from the first to last day of the treatment period.

Embodiment III-76. The method of Embodiments III-42 through III-49, wherein there is a change from baseline in the mean of modified Biberoglu & Behrman (M-B&B) score of at least a 1.5 fold reduction in pelvic pain when measured from the first to last day of the treatment period.

Embodiment III-77. The method of Embodiments III-42 through III-49, wherein there is a change from baseline in the mean of M-B&B score of at least a 1.5 fold increase in proportion of days without pelvic pain when measured from the first to last day of the treatment period.

Embodiment III-78. The method of Embodiments III-42 through III-49, wherein there is a change from baseline in mean of VAS score of at least a 1.5 fold reduction in dysmenorrhea when measured from the first to last day of the treatment period.

Embodiment III-79. The method of Embodiments III-42 through III-49, wherein following administering of 40 mg per day for 84 consecutive days, change from baseline in mean of VAS score is a 4 to 8 fold increase in proportion of days without dysmenorrhea when measured from the first to last day of the treatment period.

Embodiment III-80. The method of Embodiments III-42 through III-49, wherein following administering of 40 mg per day for 84 consecutive days, change from baseline in the mean of M-B&B score is a 5 to 9 fold reduction in dysmenorrhea when measured from the first to last day of the treatment period.

Embodiment III-81. The method of Embodiments III-42 through III-49, wherein following administering of 40 mg per day for 28 consecutive days, change from baseline in M-B&B score is a 3.5 to 7.5 fold increase in proportion of days without dysmenorrhea when measured from the first to last day of the treatment period.

Embodiment III-82. The method of Embodiments III-42 through III-49, wherein following administering of 40 mg per day for 84 consecutive days, change from baseline in M-B&B score is a 50 to 75 fold increase in proportion of days without dysmenorrhea when measured from the first to last day of the treatment period.

Embodiment III-83. The method of Embodiments III-42 through III-49, wherein following administering of 40 mg per day for 84 consecutive days, change from baseline in mean of M-B&B score is a 1.1 to 1.5 fold increase in proportion of days without dyspareunia when measured from the first to last day of the treatment period.

Embodiment III-84. The method of Embodiments III-42 through III-49, wherein following administering of 40 mg per day for 84 consecutive, change from baseline in mean of M-B&B score is a 20 to 40 fold reduction in deep dyspareunia when measured from the first to last day of the treatment period.

Embodiment III-85. The method of Embodiments III-42 through III-49, wherein following administering of 40 mg per day for 84 consecutive days, change from baseline in mean of VAS score is a 1.5 to 4.0 fold reduction in pelvic pain, dysmenorrhea and dyspareunia when measured from the first to last day of the treatment period.

Embodiment III-86. The method of Embodiments III-42 through III-49, wherein following administering of 40 mg per day for 84 consecutive days, change from baseline in mean of Endometriosis Health Profile (EHP-30) score is a 2.5 to 6.5 fold increase in quality of life when measured from the first to last day of the treatment period.

Embodiment III-87. The method of Embodiments III-42 through III-49, wherein following administering of 40 mg per day for 28 consecutive days, and co-administering of from 0.01 mg to 5 mg per day of at least one of an estrogen and a progestogen, bone mineral density loss is less than 5% from initiation of treatment.

Embodiment III-88. The method of Embodiments III-42 through III-49, wherein following administering of 40 mg per day for 28 consecutive days, and co-administering of from 0.01 mg to 5 mg per day of at least one of an estrogen and a progestogen, bone mineral density loss is less than 2% from initiation of treatment.

Embodiment III-89. The method of Embodiments III-42 through III-49, wherein following administering of 40 mg per day for 28 consecutive days, and co-administering of from 0.01 mg to 5 mg per day of at least one of an estrogen and a progestogen, bone mineral density loss is reduced at least 50% in comparison with no co-administering of from 0.01 mg to 5 mg per day of at least one of an estrogen and a progestogen.

Embodiment III-90. The method of Embodiments III-42 through III-49, wherein the oral dosage is selected from the group consisting of a tablet, a capsule, a caplet, a pill, a granule, a powder, a lozenge, a gum, and an oral film.

Embodiment III-91. The method of Embodiment III-49, wherein the at least one 5-$HT_{1a}$ receptor agonist comprises flibanserin.

Embodiment III-92. The method of Embodiments III-1 through III-8 and III-46 through II-49, wherein the administering of the hormone replacement medicament is by a separate dosage form.

Embodiment IV-1. A method for maintaining bone mineral density in a female being treated for endometriosis or uterine fibroids comprising: concomitant once-daily oral administration of an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and between 0.05 mg and 2.5 mg (or 0.05 mg and 5 mg) of a hormone replacement medicament. In some embodiments, the salt is a pharmaceutically acceptable salt.

Embodiment IV-2. A method for treating endometriosis-associated pain in a female with endometriosis-associated pain comprising: concomitant once-daily oral administration of an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and between 0.05 mg and 2.5 mg (or 0.05 mg and 5 mg) of a hormone replacement medicament. In some embodiments, the salt is a pharmaceutically acceptable salt.

Embodiment IV-3. A method for reducing heavy menstrual bleeding in a female with uterine fibroids comprising: concomitant once-daily oral administration of an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and between 0.05 mg and 2.5 mg (or 0.05 mg and 5 mg) of a hormone replacement medicament. In some embodiments, the salt is a pharmaceutically acceptable salt.

Embodiment IV-4. A method for reducing the side effects of estradiol suppression, in a female being treated with an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, comprising: concomitant once-daily oral administration of an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and between 0.05 mg and 2.5 mg (or 0.05 mg and 5 mg) of a hormone replacement medicament. In some embodiments, the salt is a pharmaceutically acceptable salt.

Embodiment IV-5. A method for reducing the side effects of estradiol suppression, in a female being treated with an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, comprising: once-daily oral administration of between 0.05 mg and 2.5 mg (or 0.05 mg and 5 mg) of a hormone replacement medicament, wherein the hormone replacement medicament is administered within about 30 minutes (or 5, 10, 15, 20 or 25 minutes) of administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof. In some embodiments, the salt is a pharmaceutically acceptable salt.

Embodiment IV-6. A method for maintaining estradiol levels, in a female being treated with an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, comprising: once-daily oral administration of between 0.05 mg and 2.5 mg (or 0.05 mg and 5 mg) of a hormone replacement medicament, wherein the hormone replacement medicament is administered within about 30 minutes (or 5, 10, 15, 20 or 25 minutes) of administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof. In some embodiments, the salt is a pharmaceutically acceptable salt.

Embodiment IV-7. A method for administering an estradiol-suppressing amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and between 0.05 mg and 2.5 mg (or 0.05 mg and 5 mg) of a hormone replacement medicament. In some embodiments, the salt is a pharmaceutically acceptable salt.

Embodiment IV-8. The method of any of Embodiments IV-1 to IV-7, further comprising administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, without the administration of a hormone replacement medicament for up to 12 weeks prior to the concomitant once-daily administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, and hormone replacement medicament. In some embodiments, the salt is a pharmaceutically acceptable salt.

Embodiment IV-9. The method of any of Embodiments IV-1 to IV-8, wherein the hormone replacement medicament comprises between 0.1 mg and 0.5 mg norethindrone acetate (NETA), and between 0.5 mg and 2 mg estradiol.

Embodiment IV-10. The method of any of Embodiments IV-1 to IV-8, wherein the amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a salt thereof, is between 20 mg and 50 mg. In some embodiments, a corresponding amount of a pharmaceutically acceptable salt of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is used.

Embodiment V-1. A method of treating a woman with symptomatic uterine fibroids or endometriosis, the method comprising administering to said woman once a daily dose of 20–140 mg, for example, 25, 30, 35, 40, 45, 50, 55, 60, 65, 70, 75, 80, 85, 90, 95, 100, 105, 110, 115, 120, 125, 130, 135 mg of Compound 1 with estradiol at 1.5–5.0 mg, for example, 2.0 mg-4.0 mg of estradiol in combination with 0.5–2.0 mg norethindrone acetate or other progestin to suppress the endometrium. In some embodiments, a corresponding amount of a pharmaceutically acceptable salt of Compound 1 is administered.

Embodiment V-2. The method of Embodiment V-1, wherein the combination is effective in treating the symptoms of the uterine fibroids or endometriosis and reducing side effects of hot flashes and/or other vasomotor symptoms and/or bone mineral density loss.

Embodiment V-3. The method of Embodiment V-1 or V-2, wherein the daily dose of 20–140 mg, for example 40 of Compound 1 comprises 1.5–5.0 mg, for example 2–4 mg of estradiol and 0.5–2.0 mg of norethindrone in a single dosage form. In some embodiments, a corresponding amount of a pharmaceutically acceptable salt of Compound 1 is administered.

Embodiment V-4. A method of treating a woman who continues to have hot flashes and/or other vasomotor symptoms and/or bone mineral density loss when administered Compound 1 at a dose of 20–140 mg, for example, 40 mg, once a day orally with 1.0 mg estradiol and norethindrone acetate, 0.5 mg, the method comprising administering to said woman Compound 1 at 20–140 mg, for example 40 mg orally once-daily or higher co-administered with 1.5–5 mg, for example, 2.0–4.0 mg estradiol in combination with 0.5–2.0 mg norethindrone acetate or other progestin to suppress endometrial tissue. In some embodiments, a corresponding amount of a pharmaceutically acceptable salt of Compound 1 is administered.

Embodiment V-5. The method of Embodiment V-4, wherein the hot flashes and/or other vasomotor symptoms and/or bone mineral density loss are reduced while not affecting the effectiveness of the treatment of the symptoms of uterine fibroids or endometriosis.

Embodiment V-6. The method of Embodiment V-4 or V-5, wherein the daily dose of 20–140 mg, for example 40 mg of Compound 1 comprises 1.5–5.0 mg, for example 2–4 mg of estradiol and 0.5–2.0 mg of norethindrone in a single dosage form. In some embodiments, a corresponding amount of a pharmaceutically acceptable salt of Compound 1 is administered.

Embodiment V-7. A method of treating uterine fibroids and endometriosis in a woman, the method comprising administering to said woman a once a daily dosage of Compound 1 in an amount of 20–140 mg, for example 40 mg, and further administering a combination of estradiol and norethindrone acetate or other progestin to suppress endometrial tissue in an amount that results in estradiol levels no more than an average daily concentration of 150 pg/mL in said woman. In some embodiments, a corresponding amount of a pharmaceutically acceptable salt of Compound 1 is administered.

Embodiment V-8: A method of any of the described methods and uses, wherein administration of the combination of Compound 1 and the estradiol or estradiol equivalent and progestin is suspended for conception or pregnancy.

What is claimed is:

1. A method for treating pain associated with endometriosis in a pre-menopausal woman in need thereof, the method comprising orally administering to the pre-menopausal woman, once-daily, a combination comprising
   about 40 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;
   about 1.0 mg of estradiol; and
   about 0.5 mg of norethindrone acetate;
   wherein the pre-menopausal woman's ovarian estrogen production is suppressed, as demonstrated by prevention of ovulation;
   wherein the pre-menopausal woman's bone mineral density during treatment is within ±3% of the pre-menopausal woman's bone mineral density prior to treatment; and
   wherein the method reduces said pain.

2. The method of claim 1, wherein the pre-menopausal woman's bone mineral density during treatment is within ±2% of the pre-menopausal woman's bone mineral density prior to treatment.

3. The method of claim 1, wherein the pre-menopausal woman's daily serum estradiol concentration is between 20 pg/ml and 50 pg/ml between daily doses of the combination.

4. The method of claim 1, wherein the pre-menopausal woman is a peri-menopausal woman.

* * * * *